United States Patent
Biagetti et al.

(10) Patent No.: US 9,527,869 B2
(45) Date of Patent: Dec. 27, 2016

(54) INDOLIZINE DERIVATIVES AS PHOSHOINOSITIDE 3-KINASES INHIBITORS

(71) Applicant: CHIESI FARMACEUTICI S.P.A., Parma (IT)

(72) Inventors: Matteo Biagetti, Parma (IT); Alessandro Accetta, Parma (IT); Anna Maria Capelli, Parma (IT); Matilde Guala, Parma (IT); Michele Retini, Parma (IT)

(73) Assignee: CHIESI FARMACEUTICI S.p.A., Parma (IT)

(*) Notice: Subject to any disclaimer, the term of this patent is extended or adjusted under 35 U.S.C. 154(b) by 0 days.

(21) Appl. No.: 14/741,965

(22) Filed: Jun. 17, 2015

(65) Prior Publication Data
US 2015/0361100 A1 Dec. 17, 2015

(30) Foreign Application Priority Data
Jun. 17, 2014 (EP) .................................. 14172764

(51) Int. Cl.
| | | |
|---|---|---|
| *C07D 487/04* | (2006.01) | |
| *C07D 471/04* | (2006.01) | |
| *C07D 473/02* | (2006.01) | |
| *C07D 519/00* | (2006.01) | |
| *A61K 31/519* | (2006.01) | |
| *A61K 31/5377* | (2006.01) | |
| *A61K 31/53* | (2006.01) | |
| *A61K 31/52* | (2006.01) | |
| *A61K 31/506* | (2006.01) | |
| *A61K 31/497* | (2006.01) | |
| *A61P 19/02* | (2006.01) | |
| *A61P 11/00* | (2006.01) | |
| *A61P 11/02* | (2006.01) | |

(52) U.S. Cl.
CPC ........... *C07D 519/00* (2013.01); *A61K 31/497* (2013.01); *A61K 31/506* (2013.01); *A61K 31/519* (2013.01); *A61K 31/52* (2013.01); *A61K 31/5377* (2013.01); *C07D 471/04* (2013.01); *C07D 473/02* (2013.01); *C07D 487/04* (2013.01)

(58) Field of Classification Search
CPC ... C07D 471/04; C07D 487/04; C07D 473/02; C07D 519/00; A61K 31/4353; A61K 31/519; A61K 31/5377; A61K 31/52; A61K 31/497; A61K 31/506
USPC ......... 546/112; 514/299, 231.5, 241, 255.05, 514/258.1, 263.2, 265.1; 544/118, 180, 242, 544/253, 264, 280, 405
See application file for complete search history.

(56) References Cited

U.S. PATENT DOCUMENTS

2012/0232081 A1* 9/2012 Steinhagen .......... C07D 487/04
514/248

FOREIGN PATENT DOCUMENTS

| WO | 2005/121147 | 12/2005 |
|---|---|---|
| WO | 2011/075643 | 6/2011 |

OTHER PUBLICATIONS

Klempner et al.Cancer Discov. Dec. 2013;3(12):1345-54.*
Massacesi et al. Ann. N.Y. Acad. Sci. 1280 (2013) 19-23.*
Gautschi et al., Clin. Cancer Res., 14(6), 1639-1648, 2008.*
Mountzios et al., Cancer Treatments Reviews, 34, 175-182, 2008.*
Mass, R. D., Int. J. Radiation Oncology Bio. Phys.vol. 58(3): 932-940, 2004.*
Fabbro et al. Pharmacology & therapeutics 93, 79-98, 2002.*
Cecil Textbook of Medicine, edited by Bennet, J.C., and Plum F., 20th edition,vol. 1, 1004-101 O, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Kovalenko et al., Zhurnal Organichnoi to Farmatsevtichnoi Khimii (2006), 4(3), 35-39; CA 148:191808, 2006. CAPLUS Abstract provided.*
Miki et al., Heterocycles (2000), 53(10), 2123-2125; CA 134:17416, 2000. CAPLUS Abstract provided.*
Buu-Hoi et al., Journal of the Chemical Society (1957) 2593-6; CA 57:9068, 2000. CAPLUS Abstract provided.*
Kotraiah et al., Journal of Enzyme Inhibition and Medicinal Chemistry (2013), 28(3),489-494; CA 158:493766, 2013. CAPLUS Abstract provided.*
Bedjeguelal et al., WO 2004108722; CA 142: 56369, 2004. CAPLUS Abstract is also provided.*
Pan Y., CN 103641827; CA 160: 457845, 2014. CAPLUS Abstract provided.*
European Search Report in Application No. 14172764.4 issued Oct. 21, 2014.
Tereschchenko A. et al., Synthesis, vol. 2006, No. 2, (2005) pp. 349-353.
Katritzky A. et al., Journal of Organic Chemistry, vol. 65, (2000) pp. 8059-8062.
Wang X. et al., Organic Letters, vol. 16, (2014) pp. 580-583.

* cited by examiner

*Primary Examiner* — Venkataraman Balasubramanian
(74) *Attorney, Agent, or Firm* — Oblon, McClelland, Maier & Neustadt, L.L.P.

(57) ABSTRACT

Compounds of formula (I), defined herein, inhibit phosphoinositide 3-kinases (PI3K) and are useful for the treatment of disorders associated with PI3K enzymes.

21 Claims, No Drawings

INDOLIZINE DERIVATIVES AS PHOSHOINOSITIDE 3-KINASES INHIBITORS

CROSS REFERENCES TO RELATED APPLICATIONS

This application is claims priority to European Patent Application No. 14172764.4 filed on Jun. 17, 2014, which is incorporated herein by reference in its entirety.

BACKGROUND OF THE INVENTION

Field of the Invention

The present invention relates to compounds which inhibit phoshoinositide 3-kinases (hereinafter PI3K). More particularly, the present invention relates to compounds that are indolizine derivatives, methods of preparing such compounds, pharmaceutical compositions containing such a compound, and therapeutic uses of such a compound.

More particularly, the compounds of the present invention are inhibitors of the activity or function of the Class I of PI3K, and more specifically, they are inhibitors of the activity or function of PI3K$\alpha$, PI3K$\beta$, PI3K$\delta$ and/or PI3K$\gamma$ isoforms of the Class I PI3K.

Therefore, the compounds of the present invention may be usefed in the treatment of many disorders associated with PI3K enzymes mechanisms, such as respiratory diseases including asthma, chronic obstructive pulmonary disease (COPD), idiopathic pulmonary fibrosis (IPF) and cough; allergic diseases including allergic rhinitis and atopic dermatitis; autoimmune diseases including systemic lupus erythematous, rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; organ transplantation and in particular in transplant rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain, trigeminal neuralgia, central pain and respiratory infections, airways damage, treatment and/or prevention of airway injury in patients with PI3K$\delta$ mutations.

Discussion of the Background

In biochemistry, a kinase is a type of enzyme that transfers phosphate groups from high-energy donor molecules, such as ATP, to specific substrates, a process referred to as phosphorylation. Specifically, PI3K enzymes are lipid enzyme kinases that can phosphorylate phosphoinositides (PIs) at the 3'-hydroxyl group of the inositol ring (Panayotou et al, Trends Cell Biol 2:358-60 (1992) which is incorporated herein by reference in its entirety). It is well known that PIs, localized in the plasma membranes, can act as second messengers in signaling cascades by docking proteins containing pleckstrin-homology (PH), FYVE, PX and other phospholipid-binding domains (Vanhaesebroeck B et al, Annu. Rev. Biochem 70, 535-602, 2001; Katso R et al, Annu. Rev. Cell Dev. Biol. 17, 615-675, 2001, which are incorporated herein by reference in their entireties).

Therefore, PIs can act as second messengers in many cellular processes including signal transduction, regulation of membrane trafficking and transport, cytoskeleton organization, cell survival and death, and many other functions.

PIs may be bound to the lipid bilayer of the cell membrane via two fatty acids that are attached to the cytosolic inositol ring via a glycerol phosphate linker. PIs inositol ring can be phosphorylated by PI3K enzymes, leading to the regulation of cellular growth, survival and proliferation. For this reason, PIs phosphorylation by PI3K enzymes is one of the most relevant signal transduction events associated with mammalian cell surface receptor activation (Cantley L C, Science 296, 1655-7, 2002; Vanhaesebroeck B et al, Annu. Rev. Biochem 70, 535-602, 2001, which are incorporated herein by reference in their entireties).

The PI3K enzymes have been divided into three classes: Class I PI3K, Class II PI3K, and Class III PI3K, on the basis of sequence homology, structure, binding partners, mode of activation, and substrate preference (Vanhaesebroeck B et al, Exp. Cell Res. 253(1), 239-54, 1999; and Leslie N R et al, Chem. Rev. 101(8), 2365-80, 2001, which are incorporated herein by reference in their entireties).

Class I PI3K convert phosphoinositide-(4,5)-diphosphate (PI(4,5)P2) to phosphoinositide-(3,4,5)-triphosphate (PI(3,4,5)P3), which functions as a second messenger. The signaling cascade activated by the increase in intracellular levels of PI(3,4,5)P3 is negatively regulated through the action of 5'-specific and 3'-specific phosphatases (Vanhaesebroeck B et al., Trends Biochem. Sci. 22(7), 267-72, 1997; Katso R et al, Annu. Rev. Cell Dev. Biol. 17, 615-75, 2001; and Toker A, Cell. Mol. Life Sci. 59(5), 761-79, 2002, which are incorporated herein by reference in their entireties).

Class II PI3K enzymes are the most recently identified class of PI3K and their exact function is still unclear.

Class III PI3K enzymes consists of a single family member which is structurally related to Class I PI3K enzymes and appears to be important in endocytosis and vesicular trafficking. However, there are some evidences showing that Class III PI3K may be relevant in immune cell processes, such as phagocytosis and Toll-like receptor (TLR) signaling.

Class I PI3K enzymes can be further divided in class IA and class IB on the basis of their activation mechanisms.

In more detail, Class IA PI3K enzymes comprises three closely related isoforms: PI3K$\alpha$, PI3K$\beta$ and PI3K$\delta$, while Class IB comprises only the PI3K$\gamma$ isoform. These enzymes are heterodimers composed of a catalytic subunit known as p110, with four types: alpha ($\alpha$), beta ($\beta$), delta ($\delta$) and gamma ($\gamma$) isoforms, constitutively associated with a regulatory subunit. The first two p110 isoforms ($\alpha$ and $\beta$) are ubiquitously expressed and involved in cellular differentiation and proliferation. Consequently, PI3K$\alpha$ and PI3K$\beta$ enzymes have been extensively studied as targets for the development of new chemotherapeutic agents.

Otherwise, p110$\delta$ and p110$\gamma$ isoforms are mainly expressed in leukocytes and are important in the activation of the immune response, such as leukocytes migration, B and T cells activation and mast cells degranulation. Therefore, PI3K$\delta$ and PI3K$\gamma$ isoforms are very relevant in inflammatory respiratory diseases and in cancer.

Presently, the inhibitor derivatives of PI3K enzymes known in the art could generally inhibit said isoforms (alpha $\alpha$, beta $\beta$, delta $\delta$ and gamma $\gamma$ isoforms) and they could act on the individual roles played in various diseases by said specific isoforms.

Many genetic variants of the PI3K$\delta$ isoform have been described in the literature (Angulo et al., Science 2013, 342, 866-871; Kracker et al. J. Clinic. Immunol. 2014, 134, 233-234; Lucas et al. Nature Immunology 2014, 15, 88-97, which are incorporated herein by reference in their entireties). Some of them involve the catalytic domain (e.g.

E1021K) whereas others take place in different enzyme regions (e.g. N334K of the C2 domain). Considering that PI3K activation seems to depend on domain-domain interactions or interactions with other proteins, these mutations might lead to a change in the enzyme stability and affect enzyme activation. Furthermore, the role of PI3K mutations in immunodeficiency has been described (see references above). Patients with these mutations may develop respiratory infections, damage to the airway wall and lung parenchyma.

Therefore, specific activity assays of Class IA inhibitors for one specific PI3Kα, PI3Kβ, PI3K δ and PI3Kγ isoform over another have been extensively developed in order to discern the suitable profile for the treatment of disorders associated with PI3K enzymes mechanisms. Such disorders could, for example, include respiratory diseases selected from idiopathic chronic cough, cough-variant asthma, cough associated with thoracic tumour or lung cancer, viral or post-viral cough, upper airways cough syndrome (UACS) or post nasal drip cough, or cough associated with gastro-oesophageal reflux disease both acid and non-acid, asthma, chronic bronchitis, chronic obstructive pulmonary disease (COPD), interstitial lung disease, idiopathic pulmonary fibrosis (IPF), congestive heart disease, sarcoidosis, infections (such as whooping cough), viral infections including viral respiratory tract infections and viral exacerbation of respiratory diseases; non-viral respiratory infections including aspergillosis and leishmaniasis; allergic diseases including allergic rhinitis and atopic dermatitis; autoimmune diseases including systemic lupus erythematous, rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In view of the number of pathological responses which are mediated by PI3K enzymes, there is a continuing need for inhibitors of PI3K enzymes which can be useful in the treatment of many disorders.

SUMMARY OF THE INVENTION

Accordingly, it is one object of the present invention to provide novel compounds which inhibit phosphoinositide 3-kinases (hereinafter PI3K).

It is another object of the present invention to provide novel methods of preparing such a compound.

It is another object of the present invention to provide novel pharmaceutical compositions which contain such a compound.

It is another object of the present invention to provide novel methods of preventing and/or treating certain diseases and conditions by administering such a compound.

These and other objects, which will become apparent during the following detailed description, have been achieved by the inventors' discovery of the compounds of formula (I):

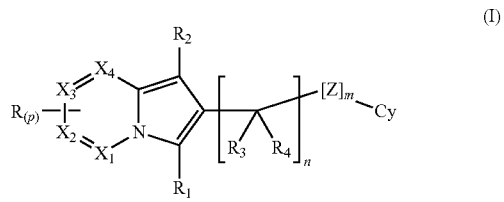

wherein $X_1$, $X_2$, $X_3$ and $X_4$, R, $R_1$, $R_2$, $R_3$, $R_4$, Cy, Z, m, n and p are as described below in the detailed description of the invention, which act as inhibitors of phosphoinositide 3-kinases; processes for the preparation of such a compound; and pharmaceutical compositions which contain such a compound either alone or in combination with one or more active ingredient, in admixture with one or more pharmaceutically acceptable carrier.

In one aspect, the present invention provides the use of a compound of the present invention for the manufacture of a medicament.

In a further aspect, the present invention provides the use of a compound of the present invention for the preparation of a medicament for the prevention and/or treatment of any disease characterized by phosphoinositide-3-kinase (PI3K) enzyme overactivity and/or wherein an inhibition of PI3K activity is desirable and in particular through the selective inhibition of the delta or of both the delta and the gamma enzyme isoforms over the alpha and beta ones.

Moreover, the present invention provides a method for prevention and/or treatment of any disease wherein a PI3K enzyme inhibition is desirable, said method comprises administering to a patient in need of such treatment a therapeutically effective amount of a compound of the present invention.

In particular the compounds of the present invention alone or combined with other active ingredients may be administered for the prevention and/or treatment of a disease of the respiratory tract characterized by inflammatory airway obstruction such as, for example, cough, asthma, COPD and IPF.

Thus, the present invention relates to novel compounds which are inhibitors of PI3Kα, PI3Kβ, PI3Kδ and PI3Kγ isoforms of Class I PI3K enzymes that, for the above reasons, may often have therapeutically desirable characteristics. Particularly, compounds of the invention may have much more selectivity for the δ isoform or for both the γ and the δ isoforms of PI3K enzyme over other isoforms of the same enzyme.

DETAILED DESCRIPTION OF THE PREFERRED EMBODIMENTS

The invention is directed to a class of compounds acting as inhibitors of Phosphoinositide 3 Kinases (PI3K). Said class of compounds inhibits the activity or function of the Class I of PI3K and more specifically, they are inhibitors derivatives of the activity or function of PI3Kα, PI3Kβ, PI3Kγ, and/or PI3Kδ isoforms of the Class I PI3K. The present invention relates to compounds of formula (I):

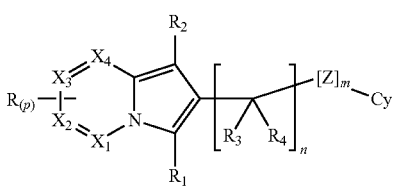

(I)

wherein $X_1$, $X_2$, $X_3$ and $X_4$ are all CH groups or at least one of $X_1$, $X_2$, $X_3$ and $X_4$ is a nitrogen atom and the others are CH groups;

each R, when present, is selected from the group consisting of: $-OR_5$, $-SR_5$, $-S(O)_q-R_7$, halogen, $-NR_{10}R_{11}$, $(C_1-C_6)$ alkyl, $(C_1-C_6)$ haloalkyl, $(C_1-C_6)$ hydroxyalkyl, $(C_1-C_6)$ aminoalkyl, $(C_3-C_7)$ cycloalkyl, $(C_2-C_6)$ alkenyl, $(C_5-C_7)$ cycloalkenyl, $(C_2-C_6)$ alkynyl, and $(C_2-C_6)$ hydroxyalkynyl, or by a group selected from aryl, heteroaryl and $(C_3-C_6)$ heterocycloalkyl each of which being in his turn optionally and independently substituted with one or more groups selected from halogen, $-OH$, $(C_1-C_6)$ alkyl, $(C_1-C_6)$ haloalkyl, $(C_1-C_6)$ hydroxyalkyl, $(C_1-C_6)$ aminoalkyl, $(C_3-C_7)$ cycloalkyl, $(C_2-C_6)$ alkenyl, $(C_5-C_7)$ cycloalkenyl, $(C_2-C_6)$ alkynyl, and $(C_2-C_6)$ hydroxyalkynyl;

$R_1$ is selected from the group consisting of $-H$, $-OR_6$, $-SR_6$, $-S(O)_q-R_8$, halogen, $-NR_{12}R_{13}$, $-CN$, $-C(O)NR_{12}R_{13}$, $-C(O)OR_{16}$, $(C_1-C_6)$ alkyl, $(C_1-C_6)$ haloalkyl, $(C_1-C_6)$ hydroxyalkyl, $(C_1-C_6)$ aminoalkyl, $(C_3-C_7)$ cycloalkyl, $(C_2-C_6)$ alkenyl, $(C_5-C_7)$ cycloalkenyl, $(C_2-C_6)$ alkynyl, $(C_2-C_6)$ hydroxyalkynyl, and $(C_2-C_6)$ aminoalkynyl or by a group selected from aryl, heteroaryl and $(C_3-C_6)$ heterocycloalkyl each of which being in his turn optionally and independently substituted with one or more groups selected from halogen, $-NR_{22}R_{23}$, $-(CH_2)_nNR_{22}R_{23}$, $(C_1-C_6)$ alkyl, $(C_1-C_6)$ alkoxyl, $(C_1-C_6)$ aminoalkoxyl, $(C_3-C_6)$ heterocycloalkyloxyl or $(C_3-C_6)$ heterocycloalkyl $(C_1-C_6)$ alkoxyl, $(C_1-C_6)$ haloalkyl, $(C_1-C_6)$ hydroxyalkyl, $(C_2-C_6)$ alkenyl, $(C_2-C_6)$ alkynyl, $(C_2-C_6)$ hydroxyalkynyl;

$R_2$ is selected from the group consisting of $-H$, $-OR_9$, $-SR_9$, $-S(O)_q-R_{17}$, halogen, $-NR_{14}R_{15}$, $-CN$, $-C(O)NR_{14}R_{15}$, $-C(O)OR_{18}$, $-(C_1-C_6)$ alkyl, $-(C_1-C_6)$ haloalkyl, $-(C_1-C_6)$ hydroxyalkyl, $(C_1-C_6)$ aminoalkyl, $(C_3-C_7)$ cycloalkyl, $(C_5-C_7)$ cycloalkenyl, $(C_2-C_6)$ alkenyl, $(C_2-C_6)$ alkynyl, and $(C_2-C_6)$ hydroxyalkynyl, or by a group selected from aryl, heteroaryl and $(C_3-C_6)$ heterocycloalkyl each of which being in his turn optionally and independently substituted with one or more groups selected from halogen; $-NR_{24}R_{25}$, $-(CH_2)_nNR_{24}R_{25}$, $(C_1-C_6)$ alkyl, $(C_1-C_6)$ haloalkyl, $(C_1-C_6)$ hydroxyalkyl, $(C_2-C_6)$ alkenyl, $(C_2-C_6)$ alkynyl, and $(C_2-C_6)$ hydroxyalkynyl;

$R_3$ and $R_4$, the same or different, are selected from the group consisting of $-H$, $(C_1-C_6)$ alkyl, $(C_1-C_6)$ haloalkyl;

Cy is selected from the group consisting of aryl, heteroaryl, and $(C_3-C_6)$ heterocycloalkyl; each of which being optionally and independently substituted by one or more groups selected from halogen, $-OH$, $-NR_{19}R_{20}$, $-CH_2NR_{19}R_{20}$; $-CN$, $-CH(O)$, $-CH=NOH$, $-C(O)NR_{19}R_{20}$, $-C(O)OR_{21}$, $(C_1-C_6)$ alkyl, $(C_1-C_6)$ haloalkyl, $(C_1-C_6)$ hydroxyalkyl, $(C_2-C_6)$ alkenyl, $(C_2-C_6)$ alkynyl, $(C_2-C_6)$ hydroxyalkynyl, or by a group selected from aryl, heteroaryl and $(C_3-C_6)$ heterocycloalkyl each of which being in his turn optionally and independently substituted with one or more groups selected from $-OH$, halogen, $-CN$, $-S(O)_2NR^IR^{III}$, $-NR^{III}S(O)_2R^{II}$, $-NR^IR^{III}$, $(C_1-C_6)$ alkyl, $(C_1-C_6)$ haloalkyl, $(C_1-C_6)$ hydroxyalkyl, $(C_1-C_6)$ alkoxy, aryl, heteroaryl, and $(C_3-C_6)$ heterocycloalkyl;

wherein $R^IR^{II}$ and $R^{III}$ the same or different, are independently selected from the group consisting of $-H$, $(C_1-C_6)$ alkyl and alkanoyl;

$R_5$, $R_6$, $R_9$, $R_{16}$, $R_{18}$, and $R_{21}$ the same or different, are independently selected from the group consisting of $-H$, $(C_1-C_6)$ alkyl, $(C_1-C_6)$ haloalkyl, $(C_1-C_6)$ hydroxyalkyl, $(C_1-C_6)$ aminoalkyl, alkanoyl, and aryl alkanoyl;

$R_7$, $R_8$ and $R_{17}$, the same or different, are independently selected from the group consisting of $NR_{12}R_{13}$, $(C_1-C_6)$ alkyl, $(C_1-C_6)$ haloalkyl, $(C_1-C_6)$ hydroxyalkyl, $(C_1-C_6)$ aminoalkyl, or by a group selected from aryl, heteroaryl and $(C_3-C_6)$ heterocycloalkyl each of which being in his turn optionally and independently substituted with one or more groups selected from halogen, $-NR_{22}R_{23}$, $-CH_2NR_{22}R_{23}$, $(C_1-C_6)$ alkyl, $(C_1-C_6)$ haloalkyl, $(C_1-C_6)$ hydroxyalkyl, $(C_2-C_6)$ alkenyl, $(C_2-C_6)$ alkynyl, and $(C_2-C_6)$ hydroxyalkynyl;

$R_{10}$, $R_{11}$, $R_{12}$, $R_{13}$, $R_{14}$, $R_{15}$, $R_{19}$, $R_{20}$, $R_{22}$, $R_{23}$, $R_{24}$ and $R_{25}$, the same or different, are independently selected from the group consisting of $-H$, $(C_1-C_6)$ alkyl $(C_1-C_6)$ hydroxyalkyl and alkanoyl or, taken together with the nitrogen atom they are linked to, anyone of $R_{10}$ and $R_{11}$, $R_{12}$ and $R_{13}$, $R_{14}$ and $R_{15}$, $R_{19}$ and $R_{20}$, $R_{22}$ and $R_{23}$, $R_{24}$ and $R_{25}$ may form a 5 to 6 membered heterocycle optionally containing one additional heteroatom or heteroatomic group selected from O, S, N, NH;

Z, when present, is an atom or a group selected from $-O-$, $-NH-$, $-C(O)-$, $-NHC(O)-$, $-C(O)NH-$, $-S-$, $-S(O)-$, and $-S(O)_2-$;

m is zero or 1;

n is 1 or 2, p is zero or an integer ranging from 1 to 3 q is an integer ranging from 1 to 2 or pharmaceutically acceptable salts thereof.

The term "pharmaceutically acceptable salts," as used herein, refers to derivatives of compounds of formula (I) wherein the parent compound is suitably modified by converting any of the free acid or basic group, if present, into the corresponding addition salt with any base or acid conventionally intended as being pharmaceutically acceptable. Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen atoms" as used herein includes fluorine, chlorine, bromine, and iodine, preferably chlorine or fluorine.

The term "$(C_1-C_6)$ alkyl" refers to straight-chained or branched alkyl groups wherein the number of constituent carbon atoms is in the range 1 to 6. Particular alkyl groups are methyl, ethyl, n-propyl, isopropyl, and t-butyl.

The expressions "$(C_1-C_6)$ haloalkyl" refer to the above defined "$(C_1-C_6)$alkyl" groups wherein one or more hydrogen atoms are replaced by one or more halogen atoms, which can be the same or different from each other.

Examples of said ($C_1$-$C_6$) haloalkyl groups may thus include halogenated, poly-halogenated and fully halogenated alkyl groups wherein all of the hydrogen atoms are replaced by halogen atoms, e.g. trifluoromethyl or difluoro methyl groups.

By way of analogy, the terms "($C_1$-$C_6$) hydroxyalkyl" or "($C_1$-$C_6$) aminoalkyl" refer to the above defined "($C_1$-$C_6$) alkyl" groups wherein one or more hydrogen atoms are replaced by one or more hydroxy (OH) or amino group respectively.

In the present description, unless otherwise provided, the definition of aminoalkyl encompasses alkyl groups substituted by one or more ($NR_{10}R_{11}$).

With reference to the substituent $R_{10}$, $R_{11}$, $R_{12}$, $R_{13}$, $R_{14}$, $R_{15}$, $R_{19}$, $R_{20}$, $R_{22}$, $R_{23}$, $R_{24}$ and $R_{25}$ as above defined, it is here further explained that when either $R_{10}$ and $R_{11}$ or $R_{12}$ and $R_{13}$ etc. are taken together with the nitrogen atom they are linked to form a 5 to 6 membered heterocyclic radical, at least one further ring carbon atom in the said heterocyclic radical may be replaced by at least one heteroatom or hetero-group (e.g. N, NH, S, or O) and/or may bear an -oxo (=O) substituent group. The said heterocyclic radical might be further optionally substituted on the available points in the ring, namely on a carbon atom, or on a heteroatom or hetero-group available for substitution. Substitution on a carbon atom includes spiro disubstitution as well as substitution on two adjacent carbon atoms, in both cases thus form an additional 5 to 6 membered heterocylic ring. Thus, Examples of said heterocycle radicals are 1-pyrrolidinyl, 1-piperidinyl, 1-piperazinyl, 4-morpholinyl, piperazin-4yl-2-one, 4-methylpiperazine-1-yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3 aR,6aS)-5-methyl-octahydropyrrolo[3,4-c]pyrrol-2-yl.

The term "($C_3$-$C_7$) cycloalkyl" refers to saturated cyclic hydrocarbon groups containing from 3 to 7 ring carbon atoms. Non-limiting examples include cyclopropyl, cyclobutyl, cyclopentyl, cyclohexyl, and cycloheptyl.

The term "($C_2$-$C_6$) alkenyl" refers to straight or branched carbon chains with one or more double bonds, conjugated or not conjugated, in cis or trans configuration, wherein the number atoms is in the range 2 to 6.

By way of analogy, the term "($C_5$-$C_7$) cycloalkenyl" refers to cyclic hydrocarbon groups containing from 5 to 7 ring carbon atoms and one or two double bonds.

The term "($C_2$-$C_6$) alkynyl" refers to straight or branched carbon chains with one or more triple bonds wherein the number of atoms is in the range 2 to 6.

The term "($C_2$-$C_6$) hydroxyalkynyl" refers to the above defined "($C_1$-$C_6$) alkynyl" groups wherein one or more hydrogen atoms are replaced by one or more hydroxy (OH) group.

The term "($C_2$-$C_6$) aminoalkynyl" refers to the above defined "($C_1$-$C_6$) alkynyl" groups wherein one or more hydrogen atoms are replaced by one or more ($NR_{10}R_{11}$) groups.

The expression "aryl" refers to mono, bi- or tri-cyclic carbon ring systems which have 6 to 20, preferably from 6 to 15 ring atoms, wherein at least one ring is aromatic. The expression "heteroaryl" refers to mono-, bi- or tri-cyclic ring systems with 5 to 20, preferably from 5 to 15 ring atoms, in which at least one ring is aromatic and in which at least one ring atom is a heteroatom or heteroaromatic group (e.g. N, NH, S or O).

Examples of suitable aryl or heteroaryl monocyclic ring systems include, for instance, phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl radicals, and the like.

Examples of suitable aryl or heteroaryl bicyclic ring systems include naphthalenyl, biphenylenyl, purinyl, pteridinyl, pyrazolopyrimidinyl, benzotriazolyl, quinolinyl, isoquinolinyl, indolyl, isoindolyl, benzothiophenyl, benzodioxinyl, dihydrobenzodioxinyl, indenyl, dihydro-indenyl, dihydrobenzodioxepinyl, benzooxazinyl radicals, and the like.

Examples of suitable aryl or heteroaryl tricyclic ring systems include fluorenyl radicals as well as benzocondensed derivatives of the aforementioned heteroaryl bicyclic ring systems.

The derived expression "($C_3$-$C_6$) heterocycloalkyl" refers to saturated or partially unsaturated monocyclic ($C_3$-$C_6$) cycloalkyl groups in which at least one ring carbon atom is replaced by at least one heteroatom or hetero-group (e.g. N, NH, S or O) or may bear an -oxo (=O) substituent group. The said heterocyclic radical might be further optionally substituted on the available points in the ring, namely on a carbon atom, or on an heteroatom or hetero-group available for substitution. Substitution on a carbon atom includes spiro disubstitution as well as substitution on two adjacent carbon atoms, in both cases thus form an additional 5 to 6 membered heterocylic ring. Thus, examples of said heterocycle radicals are 1-pyrrolidinyl, 1-methyl-2-pyrrolidinyl, 1-piperidinyl, 1-piperazinyl, 4-morpholinyl, piperazin-4yl-2-one, 4-methylpiperazine-1-yl, 1-methylpiperidin-4yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3aR,6aS)-5-methyl-octahydropyrrolo[3,4-c]pyrrol-2-yl.

Non-limiting examples of ($C_3$-$C_6$) heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl, pyrrolidin-2-one-yl radicals and the like.

The term "aryl ($C_1$-$C_6$) alkyl" refers to an aryl ring linked to a straight-chained or branched alkyl groups wherein the number of constituent carbon atoms is in the range from 1 to 6, e.g. phenylmethyl, phenylethyl or phenylpropyl.

The term "alkanoyl", refers to HC(O)— or to alkylcarbonyl groups (e.g. ($C_1$-$C_6$)alkylC(O)— wherein the group "alkyl" has the meaning above defined. Non-limiting examples include formyl, acetyl, propanoyl, and butanoyl.

The term "alkoxy" refers to a straight or branched hydrocarbon of the indicated number of carbons, attached through an oxygen bridge.

By analogy, derived expressions ($C_3$-$C_6$) heterocycloalkyloxyl and ($C_3$-$C_6$) heterocycloalkyl ($C_1$-$C_6$) alkoxyl refer to heterocycloalkyl groups attached through an oxygen bridge and chained heterocycloalkyl-alkoxyl groups. Non-limiting examples of such ($C_3$-$C_6$) heterocycloalkyloxyl and ($C_3$-$C_6$) heterocycloalkyl ($C_1$-$C_6$) alkoxyl groups are respectively (piperidin-4-yl)oxy, 1-methylpiperidin-4-yl)oxy, 2-(piperidin-4-yl)ethoxyl, 2-(1-methylpiperidin-4-yl)ethoxy, and 2-(4-morpholino)ethoxy.

Likewise derived expression "($C_1$-$C_6$) aminoalkoxyl" refers to ($C_1$-$C_6$) aminoalkyl groups as above defined attached through an oxygen bridge, non-limiting example is (2-(dimethylamino)ethoxy.

The term "aryl alkanoyl" refers to an arylC(O) or arylalkylcarbonyl group (e.g. Aryl($C_1$-$C_6$)alkylC(O)—) wherein aryl and alkyl have the meaning above defined. Non-limiting examples are represented by benzoyl, phenylacetyl, phenylpropanoyl or phenylbutanoyl radicals.

The expression "saturated, partially unsaturated or aromatic, five or six membered cycloalkane-diyl, arylene-diyl or heterocycle-diyl" refers to suitable vicinal disubstituted cycloalkane or heterocycle residue with five or six elements including 1,2-phenylene-diyl; 2,3-, 3,4-, 4,5- or 5,6-pyridine-diyl; 3,4-, 4,5- or 5,6-pyridazine-diyl; 4,5- or 5,6-pyrimidine-diyl; 2,3-pyrazinediyl; 2,3-, 3,4- or 4,5-thiophene-diyl/furane-diyl/pyrrole-diyl; 4,5-imidazole-diyl/oxazole-diyl/thiazolediyl; 3,4- or 4,5-pyrazole-diyl/isoxazolediyl/isothiazole-diyl their saturated or partially unsaturated analogues and the like.

As used herein, the expression "ring system" refers to mono- or bicyclic ring systems which may be saturated, partially unsaturated or unsaturated, such as aryl, ($C_3$-$C_7$) cycloalkyl, ($C_3$-$C_6$) heterocycloalkyl or heteroaryl.

As used herein the terms "group", "radical" or "fragment" or "substituent" are synonymous and are intended to indicate functional groups or fragments of molecules attachable to a bond or other fragments or molecules. A dash ("-") that is not between two letters or symbols is meant to represent the point of attachment for a substituent. When graphically represented the point of attachment in a cyclic functional group (e.g. formulae I-1 to I-9) is indicated with a dot ("•") localized in one of the available ring atoms where the functional group is attachable to a bond or other fragment of molecules.

As used herein an oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general the bracketed group is a lateral group, not included into the chain, and brackets are used, when deemed useful, to help disambiguating linear chemical formulas; e.g. the sulfonyl group —$SO_2$— might be also represented as —$S(O)_2$— to disambiguate e.g. with respect to the sulfinic group —S(O)O—.

Whenever basic amino or quaternary ammonium groups are present in the compounds of formula I, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate may be present. Likewise, in the presence of acidic groups such as COOH groups, corresponding physiological cation salts may be present as well, for instance including alkaline or alkaline earth metal ions.

It will be apparent to those skilled in the art that compounds of formula (I) can at least contain one stereogenic center, namely represented in formula (IA) by the carbon atom (*) with an asterisk, and therefore may exist as optical stereoisomers.

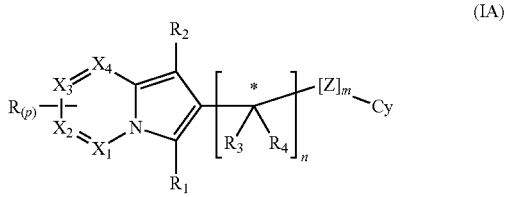

(IA)

Where the compounds according to the present invention have at least one stereogenic center, they may accordingly exist as enantiomers. Where the compounds according to the present invention possess two or more stereogenic centers, they may additionally exist as diastereoisomers. It is to be understood that all such single enantiomers, diastereoisomers and mixtures thereof in any proportion are encompassed within the scope of the present invention. The absolute configuration (R) or (S) for carbon (*) is assigned on the basis of Cahn-Ingold-Prelog nomenclature rules based on groups' priorities.

Atropisomers are stereoisomers resulting from hindered rotation about single bonds where the steric strain barrier to rotation is high enough to allow for the isolation of the conformers (Bringmann G et al, Angew. Chemie Int. Ed. 44 (34), 5384-5427, 2005. doi:10.1002/anie.200462661, which is incorporated herein by reference in its entirety).

Oki defined atropisomers as conformers that interconvert with a half-life of more than 1000 seconds at a given temperature (Oki M, Topics in Stereochemistry 14, 1-82, 1983, which is incorporated herein by reference in its entirety).

Atropisomers differ from other chiral compounds in that in many cases they can be equilibrated thermally whereas in the other forms of chirality isomerization is usually only possible chemically.

Separation of atropisomers is possible by chiral resolution methods such as selective crystallization. In an atropoenantioselective or atroposelective synthesis one atropisomer is formed at the expense of the other. Atroposelective synthesis may be carried out by use of chiral auxiliaries like a Corey Bakshi Shibata (CBS) catalyst, an asymmetric catalyst derived from proline, or by approaches based on thermodynamic equilibration when an isomerization reaction favors one atropisomer over the other.

Racemic forms of compounds of formula (I) as well as the individual atropisomers (substantially free of its corresponding enantiomer) and stereoisomer-enriched atropisomers mixtures are included in the scope of the present invention.

It is to be understood that all preferred groups or embodiments described herebelow for compounds of formula I may be combined among each other and apply as well mutatis mutandis.

In a preferred embodiment, the present invention is directed to compounds of formula (I) as above defined wherein n=1, $R_3$ has the same significance as above except H, $R_4$ is H and the absolute configuration of the chiral carbon (*) is (R).

In another embodiment the preferred configuration of the carbon (*) is (S).

In a preferred embodiment, the compounds of formula (I) described in the present invention are present as mixtures of diastereoisomers.

A first preferred group of compounds is that of formula (I) wherein:

$R_3$ is selected from H and ($C_1$-$C_6$) alkyl;
$R_4$ is H;
R, $R_1$, $R_2$, m, n, p, Z, Cy and $X_{14}$ are as defined above.

A more preferred group of compounds is that of formula (I) wherein:

$R_3$ is selected from H and ($C_1$-$C_6$) alkyl;
$R_4$ is H;
Cy is an heteroaryl selected from the group consisting of I-1 to I-9 wherein (I-1) is 3H-purin-3-yl, (I-2) is 9H-purin-9-yl, (I-3) is 9H-purin-6-yl, (I-4) is 1H-pyrazolo[3,4-d]pyrimidin-1-yl, (I-5) is 6-oxo-5H,6H,7H-pyrrolo[2,3-d]pyrimidin-4-yl, (I-6) is pyrimidin-4-yl, (I-7) is pyrimidin-2-yl, (I-8) is pyrazin-2-yl, (I-9) is 1,3,5-triazin-2-yl; each of which being optionally and independently substituted by one or more groups selected from halogen, —OH, —NR$_{19}$R$_{20}$, —CH$_2$NR$_{19}$R$_{20}$, —CN, —CH(O), —CH=NOH, —C(O)NR$_{19}$R$_{20}$, —C(O)OR$_{21}$, (C$_1$-C$_6$) alkyl, (C$_1$-C$_6$) haloalkyl, (C$_1$-C$_6$) hydroxyalkyl, (C$_2$-C$_6$) alkenyl, (C$_2$-C$_6$) alkynyl, (C$_2$-C$_6$) hydroxyalkynyl or by a group selected from aryl, heteroaryl and (C$_3$-C$_6$) heterocycloalkyl each of which being in his turn optionally and independently substituted with one or more groups selected from —OH, halogen, —CN, —S(O)$_2$NR′R$^{III}$, —NR$^{III}$S(O)$_2$R$^{II}$, (C$_1$-C$_6$) alkyl, (C$_1$-C$_6$) haloalkyl, (C$_1$-C$_6$) hydroxyalkyl, (C$_1$-C$_6$)alkoxy, aryl, heteroaryl, (C$_3$-C$_6$) heterocycloalkyl; all the other variables being as defined above, and pharmaceutically acceptable salt thereof.

I-1 to I-9 can be graphically represented as follows

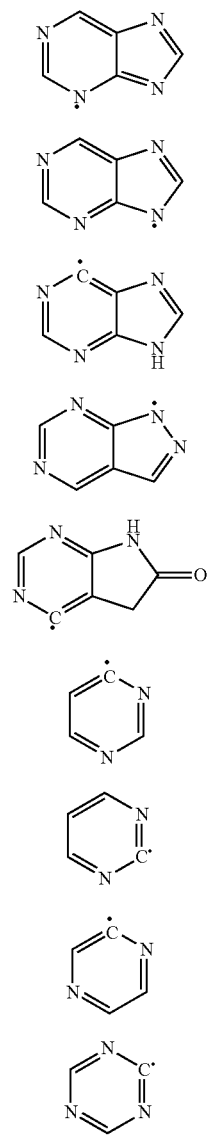

I-1
I-2
I-3
I-4
I-5
I-6
I-7
I-8
I-9

As above explained when graphically represented the monoradical symbol "•" is localized in one of the available ring atom indicating where the functional group is attachable to a bond or other fragment of molecules. This is not limiting the scope solely to the graphically represented structures; the invention is including also other chemically acceptable localization of the point of attachment in the functional group.

Examples of preferred aryl, heteroaryl, (C$_3$-C$_6$) heterocycloalkyl groups are phenyl, pyridinyl, thiazolyl and tetrazolyl groups, some particularly preferred are 3-fluoro-5-hydroxyphenyl, 2-amino-1,3-thiazol-5-yl, 5-hydroxypyridin-3yl, 1-methyl-1,2,3,6-tetrahydropyridin-4yl; corresponding to the below reported structures (CHEMAXON 6.0.4 name to structure tool).

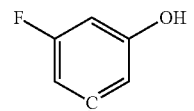

3-fluoro-5-hydroxyphenyl

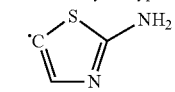

2-amino-1,3-thiazol-5-yl

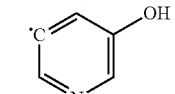

5-hydroxypyridin-3yl

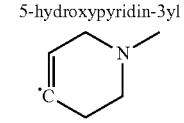

1-methyl-1,2,3,6-tetrahydropyridin-4yl

In one embodiment:
X$_1$, X$_2$, X$_3$ and X$_4$ are all CH groups;
R is selected from the group consisting of C$_1$-C$_6$ alkyl, such as methyl, C$_1$-C$_6$ haloalky such as trifluoromethyl, and halogen, more preferably fluoro, chloro and bromo;
R$_1$ is selected in the group consisting of hydrogen, C$_2$-C$_6$ alkynyl such as 3-pent-1-yn-1-yl, C$_2$-C$_6$ aminoalkynyl such as 3-dimethylaminoprop-1-yn-1-yl, and C$_2$-C$_6$ hydroxyalkynyl such as 3-hydroxyprop-1-yn-1-yl, aryl, such as phenyl, heteroaryl, such as pyridyl, pyrazinyl, thienyl and thiazolyl, C$_3$-C$_6$ heterocycloalkyl such as 3,6-dihydro-2H-pyran-4-yl, 1,2,3,6-tetrahydropyridin-4-yl, pyrrolidin-1-yl-2-one, and 4-methylpiperazin-1-yl-2-one, a group —(CH$_2$)$_n$N$_{22}$N$_{23}$ such as 4-morpholinomethyl, 2-methyl-2,9-diazaspiro[5.5]undecan-9-ylmethyl, 9-methyl-3,9-diazaspiro[5.5]undecan-3-yl}methyl, 7-methyl-2,7-diazaspiro[3.5]nonan-2-yl}methyl, and 5-methyl-octahydropyrrolo[3,4-c]pyrrol-2-yl]methyl, wherein each aryl and heteroaryl may be optionally substituted by one or two groups independently selected from halogen such as chlorine and fluorine, cyano, (C$_1$-C$_6$) alkyl such as methyl, —C(O)NR$_{12}$R$_{13}$ such as 4-morpholinocarbonyl, (C$_3$-C$_6$) heterocycloalkyl such as 1-methylpyrrolidin-1-yl, —NR$_{22}$R$_{23}$ such as dimenthlamino, —(CH$_2$)nR$_{22}$R$_{23}$ such as 2-dimethylaminomethyl, N,N-bis(2-hydroxyethyl)amino, 4-morpholinomethyl, 2-(4-morpholino)ethyl, 1-pyrrolidinomethyl, and (4-methylpiperazin-i-yl)methyl, (C$_3$-C$_6$) heterocycloalkoxyl such as 1-methylpiperidin-4-yl-oxyl, (C$_3$-C$_6$) heterocycloalkyl (C$_1$-C$_6$) alkoxyl such as 2-(4-methylpiperazin-1yl)ethoxyl, 2-(4-morpholino)ethoxyl, 2-dimethylaminoethoxyl and 2-(1-methylpiperidin-4-yl)ethoxyl;

R₂ is selected in the group consisting of hydrogen, cyano, ($C_1$-$C_6$) haloalkyl such as trifluoromethyl, aryl such as phenyl which is optionally substituted by halogen such as fluoro and methyl, heteroaryl such as pyridinyl;

R₃ is selected from the group consisting of H and ($C_1$-$C_6$) alkyl such as methyl and ethyl;

R₄ is H;

Cy is an heteroaryl selected from the following group: 9H-purine-6-amine-9-yl, 3H-purine-6-amine-3-yl, 9H-purin-6-yl, 4-amino-5-cyanopyrimidine-6-yl, 4-amino-5-formylpyrimidin-6-yl, 4-amino-5-bromopyrimidin-6-yl, 4-amino-5-trifluoromethylpyrimidin-6-yl, 4-amino-5-methylpyrimidin-6-yl, 4-amino-5-(N-methylcarbamoyl)pyrimidin-6-yl, 4-amino-5-carbamoylpyrimidin-6-yl, 4-amino-5-carboxypyrimidin-6-yl, 2-amino-3-pyrazinyl, 4-amino-5-hydroxymethylpyrimidin-6-yl, 4-amino-5-(4-morpholinomethyl)pyrimidin-6-yl, 4-amino-5-(hydroxyiminomethyl)pyrimidin-6-yl, 4-amino-5-(3-hydroxypropyn-1-yl)pyrimidin-6-yl, 4-amino-3-(3-fluoro-5-methoxyphenyl)-1H-pyrazolo[3,4-d]pyrimidin-1-yl, 4-amino-3-(3-acetylaminophenyl)-1H-pyrazolo[3,4-d]pyrimidin-1-yl, 4-amino-3-(3-hydroxymethylphenyl)-1H-pyrazolo[3,4-d]pyrimidin-1-yl, 4-amino-3-(5-hydroxy-3-trifluoromethylphenyl)-1H-pyrazolo[3,4-d]pyrimidin-1-yl, 4-amino-3-(3-fluorophenyl)-1H-pyrazolo[3,4-d]pyrimidin-1-yl, 4-amino-3-(3-methanesulphonylaminophenyl)-1H-pyrazolo[3,4-d]pyrimidin-1-yl, 4-amino-3-(3-pyridyl)-1H-pyrazolo[3,4-d]pyrimidin-1-yl, 4-amino-3-(5-hydroxy-3-pyridyl)-1H-pyrazolo[3,4-d]pyrimidin-1-yl, 4-amino-3-(3-fluoro-4-hydroxyphenyl)-1H-pyrazolo[3,4-d]pyrimidin-1-yl, 4-amino-3-(4-fluoro-3-hydroxyphenyl)-1H-pyrazolo[3,4-d]pyrimidin-1-yl, 4-amino-3-(3-chloro-5-hydroxyphenyl)-1H-pyrazolo[3,4-d]pyrimidin-1-yl, 4-amino-3-(3-aminosulphonylphenyl)-1H-pyrazolo[3,4-d]pyrimidin-1-yl, 4-amino-3-(3-sulphonylamino-5-fluorophenyl)-1H-pyrazolo[3,4-d]pyrimidin-1-yl, 4-amino-3-(3-aminosulphonyl-5-fluorophenyl)-1H-pyrazolo[3,4-d]pyrimidin-1-yl, 4-amino-3-(3-amino-5-fluorophenyl)-1H-pyrazolo[3,4-d]pyrimidin-1-yl, 4-amino-3-(3-cyano-5-hydroxyphenyl)-1H-pyrazolo[3,4-d]pyrimidin-1-yl, 4-amino-3-(3-fluoro-5-(1H-1,2,3,4-tetrazol-5-yl)phenyl)-1H-pyrazolo[3,4-d]pyrimidin-1-yl, 4-amino-3-(3-fluoro-5-hydroxyphenyl)-1H-pyrazolo[3,4-d]pyrimidin-1-yl, 4-amino-3-(3-hydroxypropyn-1-yl)-1H-pyrazolo[3,4-d]pyrimidin-1-yl, and 4-amino-3-(2-aminothiazol-5-yl)-1H-pyrazolo[3,4-d]pyrimidin-1-yl.

m is 1;

n is 1;

p is 1;

Z is absent or is selected from —NH— or —NHC(O)—; and all the other variables are as defined above.

A second preferred group of compounds is that of formula (I) wherein:

R₃ is methyl;

R₄ is H;

Cy is 1H-pyrazolo[3,4-d]pyrimidin-1-yl, which is optionally and independently substituted by one or more groups selected from —NR₁₉R₂₀ and aryl which is optionally substituted by one or more groups selected from OH and halogen; and pharmaceutically acceptable salt thereof.

A more preferred group of compounds is that of formula (I) wherein:

R₁ is selected from the group consisting of 4-morpholinomethyl, 2-methyl-2,9-diazaspiro[5.5]undecan-9-yl}methyl, 9-methyl-3,9-diazaspiro[5.5]undecan-3-yl}methyl, 7-methyl-2,7-diazaspiro[3.5]nonan-2-yl}methyl, and 5-methyl-octahydropyrrolo[3,4-c]pyrrol-2-yl]methyl;

R₃ is methyl;

R₄ is H;

Cy is 1H-pyrazolo[3,4-d]pyrimidin-1-yl (I-4), which is substituted in the position 4 by —NH₂ and in the position 3 by 3-fluoro-5-hydroxyphenyl; and a pharmaceutically acceptable salt thereof.

According to specific embodiments, the present invention provides the compounds listed in the table below: and pharmaceutical acceptable salts thereof

| Example | Chemical name - Chemaxon |
| --- | --- |
| 1 | 9-[(3-phenylindolizin-2-yl)methyl]-9H-purin-6-amine |
| 2 | 3-[(3-phenylindolizin-2-yl)methyl]-3H-purin-6-amine |
| 3 | 9-{[3-(pyridin-2-yl)indolizin-2-yl]methyl}-9H-purin-6-amine |
| 4 | 9-{[3-(3-fluorophenyl)indolizin-2-yl]methyl}-9H-purin-6-amine |
| 5 | 3-{[3-(3-fluorophenyl)indolizin-2-yl]methyl}-3H-purin-6-amine |
| 6 | 9-{[3-(2-fluorophenyl)indolizin-2-yl]methyl}-9H-purin-6-amine |
| 7 | 9-{[3-(2-methylphenyl)indolizin-2-yl]methyl}-9H-purin-6-amine |
| 8 | 3-{[3-(2-methylphenyl)indolizin-2-yl]methyl}-3H-purin-6-amine |
| 9 | 9-(indolizin-2-ylmethyl)-9H-purin-6-amine |
| 10 | 9-[(1-phenylindolizin-2-yl)methyl]-9H-purin-6-amine |
| 11 | 9-{[1-(3-fluorophenyl)indolizin-2-yl]methyl}-9H-purin-6-amine |
| 12 | 9-{[1-(2-methylphenyl)indolizin-2-yl]methyl}-9H-purin-6-amine |
| 13 | N-[(3-phenylindolizin-2-yl)methyl]-9H-purin-6-amine |
| 14 | N-{[3-(pyridin-2-yl)indolizin-2-yl]methyl}-9H-purin-6-amine |
| 15 | N-{[3-(3-fluorophenyl)indolizin-2-yl]methyl}-9H-purin-6-amine |
| 16 | N-{[3-(2-fluorophenyl)indolizin-2-yl]methyl}-9H-purin-6-amine |
| 17 | N-[(1-phenylindolizin-2-yl)methyl]-9H-purin-6-amine |
| 18 | N-{[1-(3-fluorophenyl)indolizin-2-yl]methyl}-9H-purin-6-amine |
| 19 | N-{[1-(2-methylphenyl)indolizin-2-yl]methyl}-9H-purin-6-amine |
| 20 | N-{[1-(pyridin-2-yl)indolizin-2-yl]methyl}-9H-purin-6-amine |
| 21 | N-(indolizin-2-ylmethyl)-9H-purin-6-amine |
| 22 | 4-amino-6-{[(3-phenylindolizin-2-yl)methyl]amino}pyrimidine-5-carbonitrile |
| 23 | 4-amino-6-({[3-(pyridin-2-yl)indolizin-2-yl]methyl}amino)pyrimidine-5-carbonitrile |
| 24 | 4-amino-6-({[3-(3-fluorophenyl)indolizin-2-yl]methyl}amino)pyrimidine-5-carbonitrile |
| 25 | 4-amino-6-({[3-(2-fluorophenyl)indolizin-2-yl]methyl}amino)pyrimidine-5-carbonitrile |
| 26 | 4-amino-6-({[3-(2-methylphenyl)indolizin-2-yl]methyl}amino)pyrimidine-5-carbonitrile |

-continued

| Example | Chemical name - Chemaxon |
|---|---|
| 27 | 4-amino-6-{[(1-phenylindolizin-2-yl)methyl]amino}pyrimidine-5-carbonitrile |
| 28 | 4-amino-6-({[1-(3-fluorophenyl)indolizin-2-yl]methyl}amino)pyrimidine-5-carbonitrile |
| 29 | 4-amino-6-({[1-(2-methylphenyl)indolizin-2-yl]methyl}amino)pyrimidine-5-carbonitrile |
| 30 | 4-amino-6-({[1-(pyridin-2-yl)indolizin-2-yl]methyl}amino)pyrimidine-5-carbonitrile |
| 31 | 4-amino-6-[(indolizin-2-ylmethyl)amino]pyrimidine-5-carbonitrile |
| 32 | 4-amino-6-{[1-(3-phenylindolizin-2-yl)ethyl]amino}pyrimidine-5-carbonitrile |
| 33 | 4-amino-6-({1-[3-(pyridin-2-yl)indolizin-2-yl]ethyl}amino)pyrimidine-5-carbonitrile |
| 34 | 4-amino-6-({1-[3-(pyridin-3-yl)indolizin-2-yl]ethyl}amino)pyrimidine-5-carbonitrile |
| 35 | 4-amino-6-({1-[3-(pyrazin-2-yl)indolizin-2-yl]ethyl}amino)pyrimidine-5-carbonitrile |
| 36 | 4-amino-6-({1-[3-(pyridin-4-yl)indolizin-2-yl]ethyl}amino)pyrimidine-5-carbonitrile |
| 37 | 4-amino-6-({1-[3-(thiophen-2-yl)indolizin-2-yl]ethyl}amino)pyrimidine-5-carbonitrile |
| 38 | 4-amino-6-({1-[3-(thiophen-3-yl)indolizin-2-yl]ethyl}amino)pyrimidine-5-carbonitrile |
| 39 | 4-amino-6-({1-[8-fluoro-3-(pyridin-2-yl)indolizin-2-yl]ethyl}amino)pyrimidine-5-carbonitrile |
| 40 | 4-amino-6-({1-[5-methyl-3-(pyridin-2-yl)indolizin-2-yl]ethyl}amino)pyrimidine-5-carbonitrile |
| 41 | 4-amino-6-({1-[8-methyl-3-(pyridin-2-yl)indolizin-2-yl]ethyl}amino)pyrimidine-5-carbonitrile |
| 42 | 4-amino-6-({1-[3-(3,6-dihydro-2H-pyran-4-yl)indolizin-2-yl]ethyl}amino)pyrimidine-5-carbonitrile |
| 43 | 4-amino-6-({1-[3-(pent-1-yn-1-yl)indolizin-2-yl]ethyl}amino)pyrimidine-5-carbonitrile |
| 44 | 4-amino-6-({1-[3-(pyridin-2-yl)indolizin-2-yl]propyl}amino)pyrimidine-5-carbonitrile |
| 45 | 4-amino-6-({1-[3-(1,2,3,6-tetrahydropyridin-4-yl)indolizin-2-yl]ethyl}amino)pyrimidine-5-carbonitrile |
| 46 | 4-amino-6-({1-[3-(3-hydroxyprop-1-yn-1-yl)indolizin-2-yl]ethyl}amino)pyrimidine-5-carbonitrile |
| 47 | 4-amino-6-({1-[3-(pyridin-2-yl)indolizin-2-yl]ethyl}amino)pyrimidine-5-carbaldehyde (A/1106/33/1) |
| 48 | 5-bromo-4-N-{1-[3-(pyridin-2-yl)indolizin-2-yl]ethyl}pyrimidine-4,6-diamine |
| 49 | 4-N-{1-[3-(pyridin-2-yl)indolizin-2-yl]ethyl}-5-(trifluoromethyl)pyrimidine-4,6-diamine |
| 50 | 5-methyl-4-N-{1-[3-(pyridin-2-yl)indolizin-2-yl]ethyl}pyrimidine-4,6-diamine |
| 51 | 4-amino-N-methyl-6-({1-[3-(pyridin-2-yl)indolizin-2-yl]ethyl}amino)pyrimidine-5-carboxamide |
| 52 | 4-amino-6-({1-[3-(pyridin-2-yl)indolizin-2-yl]ethyl}amino)pyrimidine-5-carboxamide |
| 53 | 4-amino-6-({1-[3-(pyridin-2-yl)indolizin-2-yl]ethyl}amino)pyrimidine-5-carboxylic acid |
| 54 | 3-amino-N-{1-[3-(pyridin-2-yl)indolizin-2-yl]ethyl}pyrazine-2-carboxamide |
| 55 | 3-amino-N-{[1-(pyridin-2-yl)indolizin-2-yl]methyl}pyrazine-2-carboxamide |
| 56 | [4-amino-6-({1-[3-(pyridin-2-yl)indolizin-2-yl]ethyl}amino)pyrimidin-5-yl]methanol |
| 57 | 5-(morpholin-4-ylmethyl)-4-N-{1-[3-(pyridin-2-yl)indolizin-2-yl]ethyl}pyrimidine-4,6-diamine |
| 58 | 5-[(1E)-(hydroxyimino)methyl]-4-N-{1-[3-(pyridin-2-yl)indolizin-2-yl]ethyl}pyrimidine-4,6-diamine |
| 59 | 3-[4-amino-6-({1-[3-(pyridin-2-yl)indolizin-2-yl]ethyl}amino)pyrimidin-5-yl]prop-2-yn-1-ol |
| 60 | 3-phenyl-1-{1-[3-(pyridin-2-yl)indolizin-2-yl]ethyl}-1H-pyrazolo[3,4-d]pyrimidin-4-amine |
| 61 | 3-(4-amino-1-{1-[3-(pyridin-2-yl)indolizin-2-yl]ethyl}-1H-pyrazolo[3,4-d]pyrimidin-3-yl)phenol |
| 62 | 3-(3-fluoro-5-methoxyphenyl)-1-{1-[3-(pyridin-2-yl)indolizin-2-yl]ethyl}-1H-pyrazolo[3,4-d]pyrimidin-4-amine |
| 63 | N-[3-(4-amino-1-{1-[3-(pyridin-2-yl)indolizin-2-yl]ethyl}-1H-pyrazolo[3,4-d]pyrimidin-3-yl)phenyl]acetamide |
| 64 | [3-(4-amino-1-{1-[3-(pyridin-2-yl)indolizin-2-yl]ethyl}-1H-pyrazolo[3,4-d]pyrimidin-3-yl)phenyl]methanol |

-continued

| Example | Chemical name - Chemaxon |
|---|---|
| 65 | 3-(4-amino-1-{1-[3-(pyridin-2-yl)indolizin-2-yl]ethyl}-1H-pyrazolo[3,4-d]pyrimidin-3-yl)-5-(trifluoromethyl)phenol |
| 66 | 3-(3-fluorophenyl)-1-{1-[3-(pyridin-2-yl)indolizin-2-yl]ethyl}-1H-pyrazolo[3,4-d]pyrimidin-4-amine |
| 67 | N-[3-(4-amino-1-{1-[3-(pyridin-2-yl)indolizin-2-yl]ethyl}-1H-pyrazolo[3,4-d]pyrimidin-3-yl)phenyl]methanesulfonamide |
| 68 | 1-{1-[3-(pyridin-2-yl)indolizin-2-yl]ethyl}-3-(pyridin-3-yl)-1H-pyrazolo[3,4-d]pyrimidin-4-amine |
| 69 | 5-(4-amino-1-{1-[3-(pyridin-2-yl)indolizin-2-yl]ethyl}-1H-pyrazolo[3,4-d]pyrimidin-3-yl)pyridin-3-ol |
| 70 | 4-(4-amino-1-{1-[3-(pyridin-2-yl)indolizin-2-yl]ethyl}-1H-pyrazolo[3,4-d]pyrimidin-3-yl)-2-fluorophenol |
| 71 | 5-(4-amino-1-{1-[3-(pyridin-2-yl)indolizin-2-yl]ethyl}-1H-pyrazolo[3,4-d]pyrimidin-3-yl)-2-fluorophenol |
| 72 | 3-(4-amino-1-{1-[3-(pyridin-2-yl)indolizin-2-yl]ethyl}-1H-pyrazolo[3,4-d]pyrimidin-3-yl)-5-chlorophenol |
| 73 | 3-(4-amino-1-{1-[3-(pyridin-2-yl)indolizin-2-yl]ethyl}-1H-pyrazolo[3,4-d]pyrimidin-3-yl)benzene-1-sulfonamide |
| 74 | N-[3-(4-amino-1-{1-[3-(pyridin-2-yl)indolizin-2-yl]ethyl}-1H-pyrazolo[3,4-d]pyrimidin-3-yl)-5-fluorophenyl]methanesulfonamide |
| 75 | 3-(4-amino-1-{1-[3-(pyridin-2-yl)indolizin-2-yl]ethyl}-1H-pyrazolo[3,4-d]pyrimidin-3-yl)-5-fluorobenzene-1-sulfonamide |
| 76 | 3-(3-amino-5-fluorophenyl)-1-{1-[3-(pyridin-2-yl)indolizin-2-yl]ethyl}-1H-pyrazolo[3,4-d]pyrimidin-4-amine |
| 77 | 3-(4-amino-1-{1-[3-(pyridin-2-yl)indolizin-2-yl]ethyl}-1H-pyrazolo[3,4-d]pyrimidin-3-yl)-5-hydroxybenzonitrile |
| 78 | 3-[3-fluoro-5-(1H-1,2,3,4-tetrazol-5-yl)phenyl]-1-{1-[3-(pyridin-2-yl)indolizin-2-yl]ethyl}-1H-pyrazolo[3,4-d]pyrimidin-4-amine |
| 79 | 3-(4-amino-1-{1-[3-(pyridin-2-yl)indolizin-2-yl]ethyl}-1H-pyrazolo[3,4-d]pyrimidin-3-yl)-5-fluorophenol |
| 80 (enantiomer 1) and 81 (enantiomer 2) | 3-(4-amino-1-{1-[3-(pyridin-2-yl)indolizin-2-yl]ethyl}-1H-pyrazolo[3,4-d]pyrimidin-3-yl)-5-fluorophenol single enantiomers |
| 82 | 3-(4-amino-1-{1-[3-(pyridin-4-yl)indolizin-2-yl]ethyl}-1H-pyrazolo[3,4-d]pyrimidin-3-yl)-5-fluorophenol |
| 83 (enantiomer 1) and 84 (enantiomer 2) | 3-(4-amino-1-{1-[3-(pyridin-4-yl)indolizin-2-yl]ethyl}-1H-pyrazolo[3,4-d]pyrimidin-3-yl)-5-fluorophenol single enantiomers |
| 85 | 3-{4-amino-1-[1-(3-phenylindolizin-2-yl)ethyl]-1H-pyrazolo[3,4-d]pyrimidin-3-yl}-5-fluorophenol |
| 86 | 3-(4-amino-1-{1-[3-(2-fluorophenyl)indolizin-2-yl]ethyl}-1H-pyrazolo[3,4-d]pyrimidin-3-yl)-5-fluoro-phenol |
| 87 | 3-(4-amino-1-{1-[6-methyl-3-(pyridin-2-yl)indolizin-2-yl]ethyl}-1H-pyrazolo[3,4-d]pyrimidin-3-yl)-5-fluorophenol |
| 88 | 3-(4-amino-1-{1-[3-(pyridin-2-yl)-6-(trifluoromethyl)indolizin-2-yl]ethyl}-1H-pyrazolo[3,4-d]pyrimidin-3-yl)-5-fluorophenol |
| 89 | 3-(4-amino-1-{1-[1-methyl-3-(pyridin-2-yl)indolizin-2-yl]ethyl}-1H-pyrazolo[3,4-d]pyrimidin-3-yl)-5-fluorophenol |
| 90 | 3-[4-amino-1-1-{3-[5-(morpholin-4-ylmethyl)thiophen-2-yl]indolizin-2-yl}ethyl)-1H-pyrazolo[3,4-d]pyrimidin-3-yl]-5-fluorophenol |
| 91 | 3-[4-amino-1-(1-{3-[4-(morpholin-4-ylmethyl)phenyl]indolizin-2-yl}ethyl)-1H-pyrazolo[3,4-d]pyrimidin-3-yl]-5-fluorophenol |
| 92 | 3-{4-amino-1-[1-(3-{4-[(dimethylamino)methyl]phenyl}indolizin-2-yl)ethyl]-1H-pyrazolo[3,4-d]pyrimidin-3-yl}-5-fluorophenol |
| 93 | 3-{4-amino-1-[1-(3-{3-[(dimethylamino)methyl]phenyl}indolizin-2-yl)ethyl]-1H-pyrazolo[3,4-d]pyrimidin-3-yl}-5-fluorophenol |
| 93a (enantiomer 1) and 93b (enantiomer 2) | 3-{4-amino-1-[1-(3-{3-[(dimethylamino)methyl]phenyl}indolizin-2-yl)ethyl]-1H-pyrazolo[3,4-d]pyrimidin-3-yl}-5-fluorophenol |
| 94 | 3-(4-amino-1-{1-[3-(1,3-thiazol-5-yl)indolizin-2-yl]ethyl}-1H-pyrazolo[3,4-d]pyrimidin-3-yl)-5-fluorophenol |
| 95 | 1-(2-{1-[4-amino-3-(3-fluoro-5-hydroxyphenyl)-1H-pyrazolo[3,4-d]pyrimidin-1-yl]ethyl}indolizin-3-yl)pyrrolidin-2-one |
| 96 | 3-(4-amino-1-{1-[7-(pyridin-2-yl)pyrrolo[1,2-b]pyridazin-6-yl]ethyl}-1H-pyrazolo[3,4-d]pyrimidin-3-yl)-5-fluorophenol |
| 97 | 3-(4-amino-1-{[3-(pyridin-2-yl)indolizin-2-yl]methyl}-1H-pyrazolo[3,4-d]pyrimidin-3-yl)-5-fluorophenol |
| 98 | 3-(4-amino-1-{[3-(pyridin-3-yl)indolizin-2-yl]methyl}-1H-pyrazolo[3,4-d]pyrimidin-3-yl)-5-fluorophenol |
| 99 | 3-(4-amino-1-{[3-(pyridin-4-yl)indolizin-2-yl]methyl}-1H-pyrazolo[3,4-d]pyrimidin-3-yl)-5-fluorophenol |
| 100 | 3-(4-amino-1-{[7-(pyridin-2-yl)pyrrolo[1,2-b]pyridazin-6-yl]methyl}-1H-pyrazolo[3,4-d]pyrimidin-3-yl)-5-fluorophenol |

-continued

| Example | Chemical name - Chemaxon |
|---|---|
| 101 | 3-(4-amino-1-{1-[3-(1,2,3,6-tetrahydropyridin-4-yl)indolizin-2-yl]ethyl}-1H-pyrazolo[3,4-d]pyrimidin-3-yl)-5-fluorophenol |
| 102 | 3-(4-amino-1-{1-[3-(pyridin-2-yl)indolizin-2-yl]ethyl}-1H-pyrazolo[3,4-d]pyrimidin-3-yl)prop-2-yn-1-ol |
| 103 | 5-(4-amino-1-{1-[3-(pyridin-2-yl)indolizin-2-yl]ethyl}-1H-pyrazolo[3,4-d]pyrimidin-3-yl)-1,3-thiazol-2-amine |
| 104 | 3-(4-amino-1-{1-[7-chloro-3-(pyridin-2-yl)indolizin-2-yl]ethyl}-1H-pyrazolo[3,4-d]pyrimidin-3-yl)-5-fluorophenol |
| 105 | 3-(4-amino-1-{1-[7-methyl-3-(pyridin-2-yl)indolizin-2-yl]ethyl}-1H-pyrazolo[3,4-d]pyrimidin-3-yl)-5-fluorophenol |
| 106 | 3-(4-amino-1-{1-[3-(2-methylpyridin-4-yl)indolizin-2-yl]ethyl}-1H-pyrazolo[3,4-d]pyrimidin-3-yl)-5-fluorophenol |
| 107 | 5-(4-amino-1-{1-[3-(2-methylpyridin-4-yl)indolizin-2-yl]ethyl}-1H-pyrazolo[3,4-d]pyrimidin-3-yl)pyridin-3-ol |
| 108 | 3-[4-amino-1-(1-{3-[5-(morpholin-4-ylmethyl)pyridin-2-yl]indolizin-2-yl}ethyl)-1H-pyrazolo[3,4-d]pyrimidin-3-yl]-5-fluorophenol |
| 108a (enantiomer 1) and 108b (enantiomer 2) | 3-[4-amino-1-(1-{3-[5-(morpholin-4-ylmethyl)pyridin-2-yl]indolizin-2-yl}ethyl)-1H-pyrazolo[3,4-d]pyrimidin-3-yl]-5-fluorophenol |
| 109 | 3-{4-amino-1-[1-(3-{5-[(dimethylamino)methyl]pyridin-2-yl}indolizin-2-yl)ethyl]-1H-pyrazolo[3,4-d]pyrimidin-3-yl}-5-fluorophenol |
| 110 | 3-[4-amino-1-(1-{3-[6-(morpholin-4-ylmethyl)pyridin-2-yl]indolizin-2-yl}ethyl)-1H-pyrazolo[3,4-d]pyrimidin-3-yl]-5-fluorophenol |
| 111 | 3-[4-amino-1-(1-{3-[4-(morpholin-4-ylmethyl)pyridin-2-yl]indolizin-2-yl}ethyl)-1H-pyrazolo[3,4-d]pyrimidin-3-yl]-5-fluorophenol |
| 112 | 3-{4-amino-1-[1-(3-{4-[(dimethylamino)methyl]pyridin-2-yl}indolizin-2-yl)ethyl]-1H-pyrazolo[3,4-d]pyrimidin-3-yl}-5-fluorophenol |
| 113 | 3-[4-amino-1-(1-{3-[5-(pyrrolidin-1-ylmethyl)pyridin-2-yl]indolizin-2-yl}ethyl)-1H-pyrazolo[3,4-d]pyrimidin-3-yl]-5-fluorophenol |
| 114 | 3-{4-amino-1-[1-(3-{5-[(4-methylpiperazin-1-yl)methyl]pyridin-2-yl}indolizin-2-yl)ethyl]-1H-pyrazolo[3,4-d]pyrimidin-3-yl}-5-fluorophenol |
| 114a (enantiomer 1) and 114b (enantiomer 2) | 3-{4-amino-1-[1-(3-{5-[(4-methylpiperazin-1-yl)methyl]pyridin-2-yl}indolizin-2-yl)ethyl]-1H-pyrazolo[3,4-d]pyrimidin-3-yl}-5-fluorophenol |
| 115 | 3-{4-amino-1-[1-(3-{6-[(4-methylpiperazin-1-yl)methyl]pyridin-2-yl}indolizin-2-yl)ethyl]-1H-pyrazolo[3,4-d]pyrimidin-3-yl}-5-fluorophenol |
| 116 | 3-{4-amino-1-[1-(3-{4-[(4-methylpiperazin-1-yl)methyl]pyridin-2-yl}indolizin-2-yl)ethyl]-1H-pyrazolo[3,4-d]pyrimidin-3-yl}-5-fluorophenol |
| 117 | 3-(4-amino-1-{1-[3-(5-{[bis(2-hydroxyethyl)amino]methyl}pyridin-2-yl)indolizin-2-yl]ethyl}-1H-pyrazolo[3,4-d]pyrimidin-3-yl)-5-fluorophenol |
| 117a (enantiomer 1) and 117b (enantiomer 2) | 3-(4-amino-1-{1-[3-(5-{[bis(2-hydroxyethyl)amino]methyl}pyridin-2-yl)indolizin-2-yl]ethyl}-1H-pyrazolo[3,4-d]pyrimidin-3-yl)-5-fluorophenol |
| 118 | 3-[4-amino-1-(1-{3-[3-(1-methylpyrrolidin-2-yl)phenyl]indolizin-2-yl}ethyl)-1H-pyrazolo[3,4-d]pyrimidin-3-yl]-5-fluorophenol |
| 119 | 3-{4-amino-1-[1-(3-{5-[2-(morpholin-4-yl)ethoxy]pyridin-2-yl}indolizin-2-yl)ethyl]-1H-pyrazolo[3,4-d]pyrimidin-3-yl}-5-fluorophenol |
| 120 | 5-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one |
| 121 | 4-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one |
| 121a (enantiomer 1) and 121b (enantiomer 2) | 4-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one |
| 122 | 4-(2-{1-[4-amino-3-(5-hydroxypyridin-3-yl)-1H-pyrazolo[3,4-d]pyrimidin-1-yl]ethyl}indolizin-3-yl)-1-[2-(morpholin-4-yl)ethyl]-1,2-dihydropyridin-2-one |
| 123 | 2-(2-{1-[4-amino-3-(3-fluoro-5-hydroxyphenyl)-1H-pyrazolo[3,4-d]pyrimidin-1-yl]ethyl}indolizin-3-yl)benzonitrile |
| 124 | 3-(4-amino-1-{1-[3-(pyridin-2-yl)-1-(trifluoromethyl)indolizin-2-yl]ethyl}-1H-pyrazolo[3,4-d]pyrimidin-3-yl)-5-fluorophenol |
| 125 | 3-[4-amino-1-(1-{3-[5-(morpholine-4-carbonyl)pyridin-2-yl]indolizin-2-yl}ethyl)-1H-pyrazolo[3,4-d]pyrimidin-3-yl]-5-fluorophenol |

| Example | Chemical name - Chemaxon |
|---|---|
| 126 | 2-{1-[4-amino-3-(3-fluoro-5-hydroxyphenyl)-1H-pyrazolo[3,4-d]pyrimidin-1-yl]ethyl}-3-(pyridin-2-yl)indolizine-1-carbonitrile |
| 127 | 2-{1-[4-amino-3-(3-fluoro-5-hydroxyphenyl)-1H-pyrazolo[3,4-d]pyrimidin-1-yl]ethyl}-3-{3-[(dimethylamino)methyl]phenyl}indolizine-1-carbonitrile |
| 127a (enantiomer 1) and 127b (enantiomer 2) | 2-{1-[4-amino-3-(3-fluoro-5-hydroxyphenyl)-1H-pyrazolo[3,4-d]pyrimidin-1-yl]ethyl}-3-{3-[(dimethylamino)methyl]phenyl}indolizine-1-carbonitrile |
| 128 | 3-{4-amino-1-[1-(7-{3-[(dimethylamino)methyl]phenyl}pyrrolo[1,2-b]pyridazin-6-yl)ethyl]-1H-pyrazolo[3,4-d]pyrimidin-3-yl}-5-fluorophenol |
| 129 | 3-(4-amino-1-{1-[3-(1,3-thiazol-4-yl)indolizin-2-yl]ethyl}-1H-pyrazolo[3,4-d]pyrimidin-3-yl)-5-fluorophenol |
| 130 | 3-[4-amino-1-(1-{3-[2-(morpholin-4-ylmethyl)-1,3-thiazol-4-yl]indolizin-2-yl}ethyl)-1H-pyrazolo[3,4-d]pyrimidin-3-yl]-5-fluorophenol |
| 131 | 3-[4-amino-1-(1-{3-[3-(dimethylamino)prop-1-yn-1-yl]indolizin-2-yl}ethyl)-1H-pyrazolo[3,4-d]pyrimidin-3-yl]-5-fluorophenol |
| 132 | 1-(2-{1-[4-amino-3-(3-fluoro-5-hydroxyphenyl)-1H-pyrazolo[3,4-d]pyrimidin-1-yl]ethyl}indolizin-3-yl)-4-methylpiperazin-2-one |
| 133 | 4-(2-{1-[4-amino-3-(3-fluoro-5-hydroxyphenyl)-1H-pyrazolo[3,4-d]pyrimidin-1-yl]ethyl}indolizin-3-yl)-1-[2-(dimethylamino)ethyl]-1,2-dihydropyridin-2-one |
| 133a (enantiomer 1) and 133b (enantiomer 2) | 4-(2-{1-[4-amino-3-(3-fluoro-5-hydroxyphenyl)-1H-pyrazolo[3,4-d]pyrimidin-1-yl]ethyl}indolizin-3-yl)-1-[2-(dimethylamino)ethyl]-1,2-dihydropyridin-2-one |
| 134 | 6-(2-{1-[4-amino-3-(3-fluoro-5-hydroxyphenyl)-1H-pyrazolo[3,4-d]pyrimidin-1-yl]ethyl}indolizin-3-yl)-2-[2-(pyrrolidin-1-yl)ethyl]-2,3-dihydropyridazin-3-one |
| 135 | 6-(2-{1-[4-amino-3-(3-fluoro-5-hydroxyphenyl)-1H-pyrazolo[3,4-d]pyrimidin-1-yl]ethyl}indolizin-3-yl)-2-[2-(4-methylpiperazin-1-yl)ethyl]-2,3-dihydropyridazin-3-one |
| 136 | 6-(2-{1-[4-amino-3-(3-fluoro-5-hydroxyphenyl)-1H-pyrazolo[3,4-d]pyrimidin-1-yl]ethyl}indolizin-3-yl)-2-[2-(morpholin-4-yl)ethyl]-2,3-dihydropyridazin-3-one |
| 137 | 3-{4-amino-1-[1-(3-{6-[2-(4-methylpiperazin-1-yl)ethoxy]pyridazin-3-yl}indolizin-2-yl)ethyl]-1H-pyrazolo[3,4-d]pyrimidin-3-yl}-5-fluorophenol |
| 138 | 3-{4-amino-1-[1-(3-{6-[2-(dimethylamino)ethoxy]pyridazin-3-yl}indolizin-2-yl)ethyl]-1H-pyrazolo[3,4-d]pyrimidin-3-yl}-5-fluorophenol |
| 139 | 3-{4-amino-1-[1-(3-{6-[(1-methylpiperidin-4-yl)oxy]pyridazin-3-yl}indolizin-2-yl)ethyl]-1H-pyrazolo[3,4-d]pyrimidin-3-yl}-5-fluorophenol |
| 140 | 3-{4-amino-1-[1-(3-{6-[2-(1-methylpiperidin-4-yl)ethoxy]pyridazin-3-yl}indolizin-2-yl)ethyl]-1H-pyrazolo[3,4-d]pyrimidin-3-yl}-5-fluorophenol |
| 141 | 3-(4-amino-1-{1-[3-(morpholin-4-ylmethyl)indolizin-2-yl]ethyl}-1H-pyrazolo[3,4-d]pyrimidin-3-yl)-5-fluorophenol |
| 142 | 3-(4-amino-1-{1-[3-({2-methyl-2,9-diazaspiro[5.5]undecan-9-yl}methyl)indolizin-2-yl]ethyl}-1H-pyrazolo[3,4-d]pyrimidin-3-yl)-5-fluorophenol |
| 143 | 3-(4-amino-1-{1-[3-({9-methyl-3,9-diazaspiro[5.5]undecan-3-yl}methyl)indolizin-2-yl]ethyl}-1H-pyrazolo[3,4-d]pyrimidin-3-yl)-5-fluorophenol |
| 144 | 3-(4-amino-1-{1-[3-({7-methyl-2,7-diazaspiro[3.5]nonan-2-yl}methyl)indolizin-2-yl]ethyl}-1H-pyrazolo[3,4-d]pyrimidin-3-yl)-5-fluorophenol |
| 145 | 3-{1-[1-(3-{[(3aR,6aS)-5-methyl-octahydropyrrolo[3,4-c]pyrrol-2-yl]methyl}indolizin-2-yl)ethyl]-4-amino-1H-pyrazolo[3,4-d]pyrimidin-3-yl}-5-fluorophenol |
| 146 | 2-{1-[4-amino-3-(3-fluoro-5-hydroxyphenyl)-1H-pyrazolo[3,4-d]pyrimidin-1-yl]ethyl}-3-(morpholin-4-ylmethyl)indolizine-1-carbonitrile |
| 147 | 3-{4-amino-1-[1-(3-{1-[2-(dimethylamino)ethyl]-1H-pyrazol-3-yl}indolizin-2-yl)ethyl]-1H-pyrazolo[3,4-d]pyrimidin-3-yl}-5-fluorophenol |
| 148 | 3-{4-amino-1-[1-(3-{1-[2-(4-methylpiperazin-1-yl)ethyl]-1H-pyrazol-3-yl}indolizin-2-yl)ethyl]-1H-pyrazolo[3,4-d]pyrimidin-3-yl}-5-fluorophenol |
| 149 | 3-(4-amino-1-{1-[3-(1-{2-[bis(2-hydroxyethyl)amino]ethyl}-1H-pyrazol-3-yl)indolizin-2-yl]ethyl}-1H-pyrazolo[3,4-d]pyrimidin-3-yl)-5-fluorophenol |
| 150 | 3-{4-amino-1-[1-(3-{1-[2-(morpholin-4-yl)ethyl]-1H-pyrazol-3-yl}indolizin-2-yl)ethyl]-1H-pyrazolo[3,4-d]pyrimidin-3-yl}-5-fluorophenol |

The compounds of formula (I) including all the compounds here above listed can be generally prepared according to the procedure outlined in the following Schemes shown below using generally known methods or following slightly modified procedures that the skilled person can easily apply.

Processes of preparation described below and reported in the following Schemes should not be viewed as limiting the scope of the synthetic methods available for the preparation of the compounds of the invention.

Schemes 1-4 together with schemes 5-11 hereinbelow cover the synthetic procedure for the compounds according to the invention in general terms. The processes described are particularly advantageous as they are susceptible of being properly modulated, through any proper variant known to the skilled person, so as to obtain any of the desired compounds of the invention. Such variants are comprised within the scope of the present invention. Where a specific detail or step differs from the general Schemes it has been detailed in the specific examples and/or in additional schemes.

This scheme provides a synthetic route for the preparation of a compound of formula (4a), where $X_1=X_2=X_3=X_4=CH$, R(p) is variable as defined herein above and Alkyl is a $(C_1-C_6)$ alkyl.

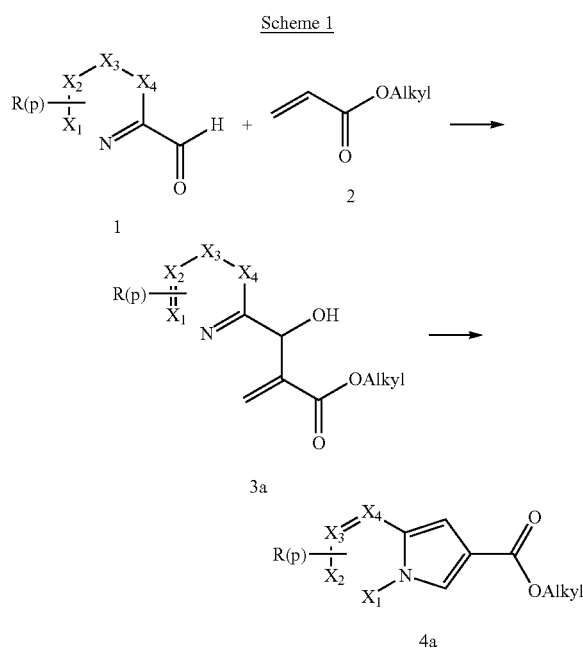

A compound of formula (3a), where $X_1=X_2=X_3=X_4=CH$, may be prepared according to Scheme 1 by reaction of a compound of formula (1) with an alkyl acrylate (2). Typical reaction conditions comprise reacting a pyridine-2-carbaldehyde of formula (1), where $X_1=X_2=X_3=X_4=CH$, with an alkyl acrylate (2), such as ethyl acrylate, in the presence of a base, such as DABCO, in a mixture of solvents, such as dioxane and water, at an appropriate temperature, for example, at RT. Aldehydes of formula (1) are commercially available or prepared following the well-known procedures described in the literature.

A compound of formula (4a), where $X_1=X_2=X_3=X_4=CH$, may be prepared according to Scheme 1 by reaction of a compound of formula (3a) with acetic anhydride. Typical reaction conditions comprise reacting a compound of formula (3a), where $X_1=X_2=X_3=X_4=CH$, in acetic anhydride heating at an appropriate temperature, for example at 130° C., under thermal or microwave heating conditions.

This scheme provides a synthetic route for the preparation of compound of formula (4c), wherein $X_1=N$, $X_2=X_3=X_4=CH$, R(p) is variable as defined herein above and Alkyl is a $(C_1-C_6)$ alkyl.

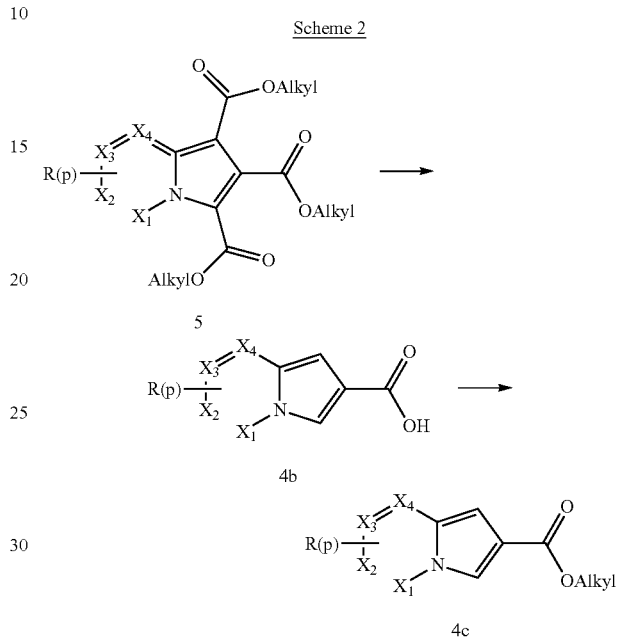

A compound of formula (4b), where $X_1=N$, $X_2=X_3=X_4=CH$, may be prepared by hydrolysis of a compound of formula (5), where $X_1=N$, $X_2=X_3=X_4=CH$. Typical hydrolysis conditions comprise reacting a compound of formula (5), with a solution of a metal hydroxide, such as KOH in water at an appropriate temperature, such as, for example, at 60° C., and then addition of HCl heating at an appropriate temperature, such as at 80° C. A compound of formula 5 could be prepared accordingly to the procedure reported in *J. Mat. Chem.*, 1999, 9, 2183-2188, which is incorporated herein by reference in its entirety.

A compound of formula (4c), where $X_1=N$, $X_2=X_3=X_4=CH$ could be prepared by reaction of a compound of formula (4b) with a suitable alcohol. Typical reaction conditions comprise reacting a compound of formula (4b) with an alcohol such as MeOH, in the presence of a catalytic amount of sulfuric acid, at an appropriate temperature, such as heating at 80° C.

This scheme provides a synthetic route for the preparation of a compound of formula (6) wherein $X_1=X_2=X_3=X_4=CH$, and R(p) is variable as defined herein above.

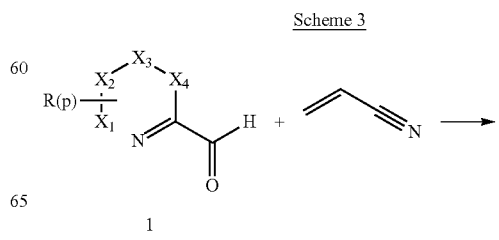

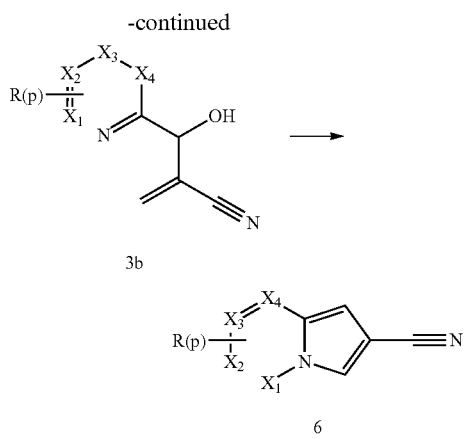

A compound of formula (3b), where $X_1=X_2=X_3=X_4=CH$, may be prepared according to Scheme 3 by reaction of a compound of formula (1), where $X_1=X_2=X_3=X_4=CH$, with acrylonitrile. Typical reaction conditions comprise reacting a pyridine-2-carbaldehyde of formula (1) with acrylonitrile in the presence of a base, such as DABCO, at an appropriate temperature, for example, at 0° C. Aldehydes of formula (1) are commercially available or prepared following the well-known procedures described in the literature. A compound of formula (6), where $X_1=X_2=X_3=X_4=CH$, may be prepared according to Scheme 3 by reaction of a compound of formula (3b) with acetic anhydride. Typical reaction conditions comprise reacting a compound of formula (3b) in acetic anhydride heating at an appropriate temperature, for example at 130° C., under microwave heating conditions.

This scheme provides a synthetic route for the preparation of a compound of formula (10a, b, c, d) and (13a, b, c, d) wherein all the variables are described herein above and Hal is an halogen atom.

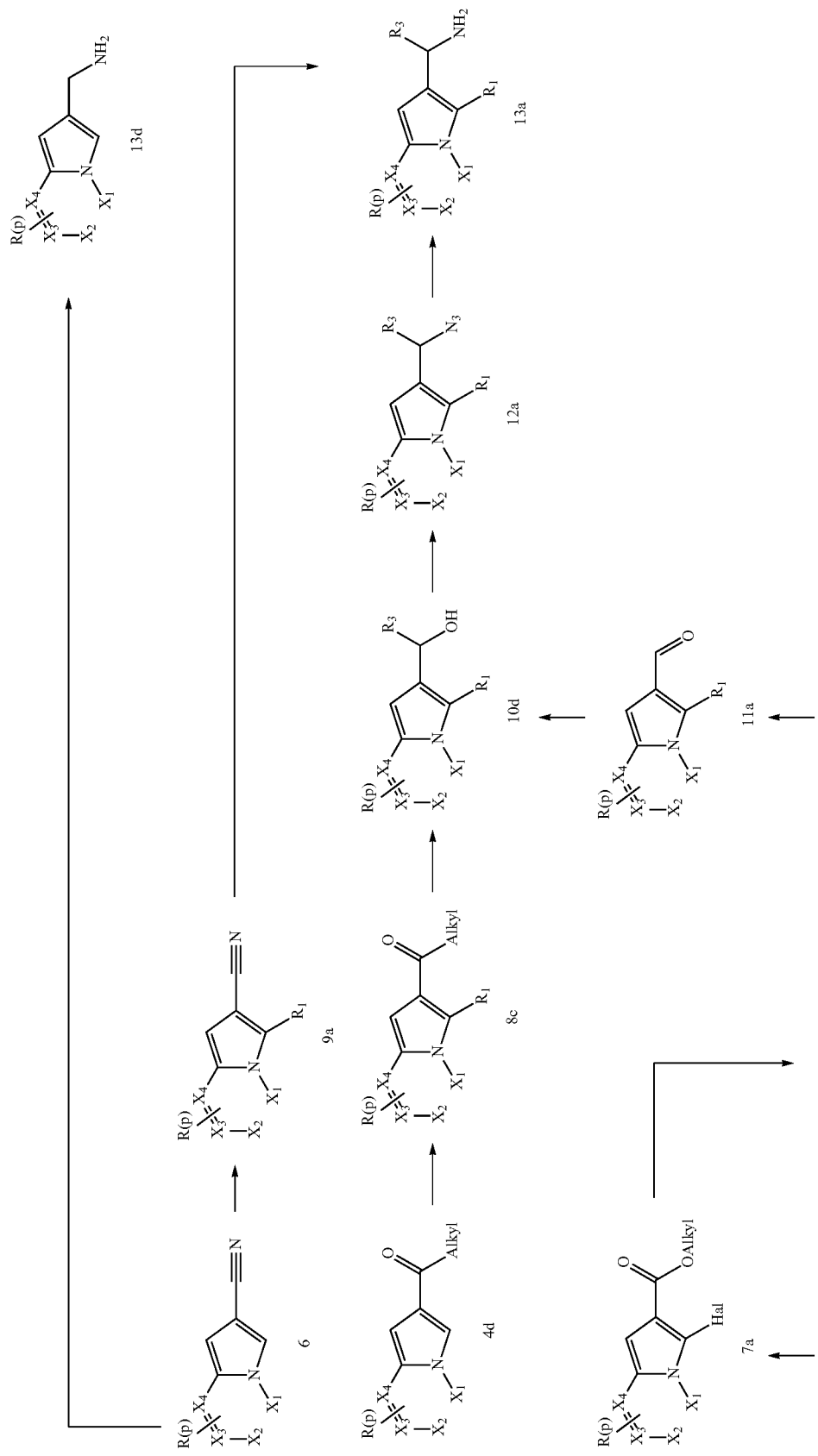

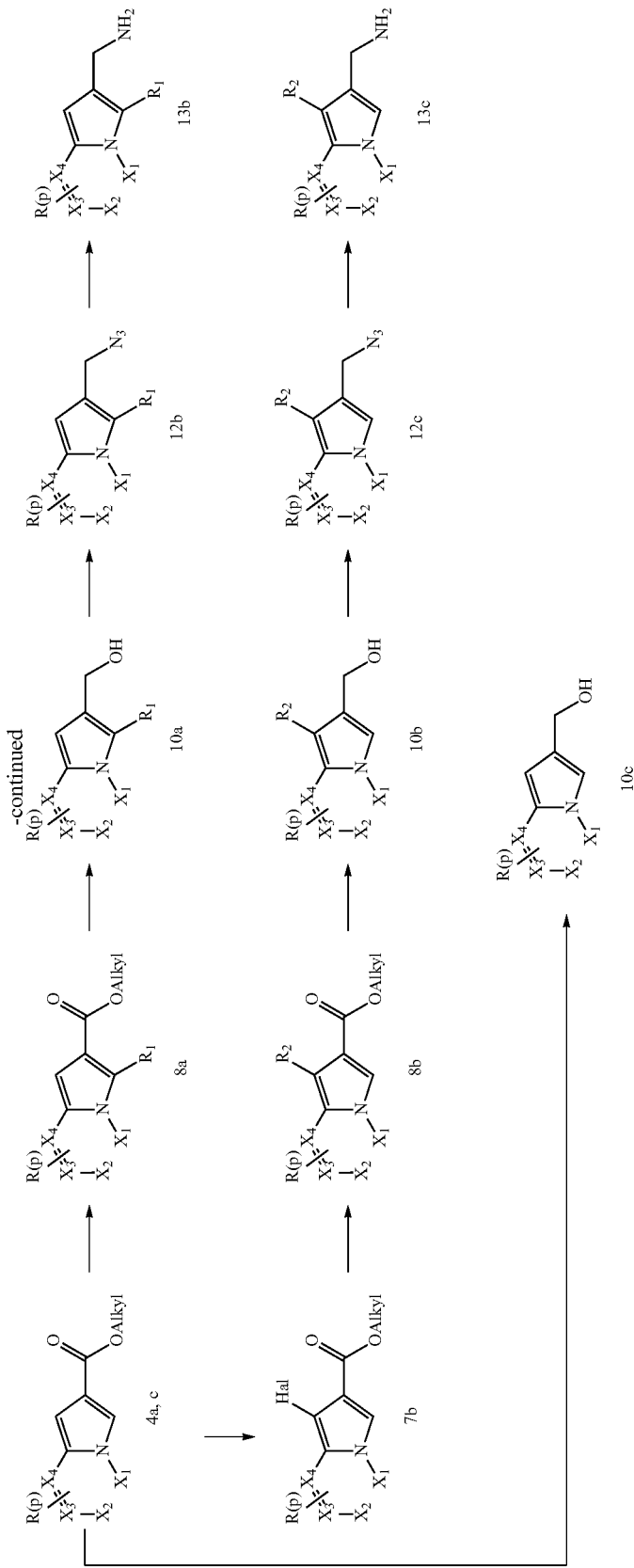

A compound of formula (4a), where $X_1=X_2=X_3=X_4=CH$, or (4c), where $X_1=N$, $X_2=X_3=X_4=CH$, may be converted into a compound of formula (7a) by reaction with an appropriate N-halo succinimide, such as N-chlorosuccinimide, or N-iodosuccinimide, or N-bromosuccinimide in a polar solvent, such as acetonitrile, at an appropriate temperature, such as, for example, ranging from 0° C. to RT.

A compound of formula (4a) may be converted into a compound of formula (7b) for example by reaction with bromine in a polar aprotic solvent, such as DCM, at an appropriate temperature, such as, for example, at −78° C.

A compound of formula (8a) may be prepared reacting a compound of formula (4a), where $X_1=X_2=X_3=X_4=CH$ or (4c), where $X_1=N$, $X_2=X_3=X_4=CH$, with a suitable aryl halide or heteroaryl halide under Heck cross coupling conditions. Typical Heck reaction conditions comprise reacting a compound of formula (4a) with an aryl halide or heteroaryl halide in the presence of a Pd catalyst, such as $Pd(OAc)_2$ with a trialkyl phosphine ligand, for example tricyclopentylphosphine tetrafluoborate, or $PdCl_2(PPh_3)_2$, using a base, such as $Cs_2CO_3$ or potassium acetate, in a suitable solvent, such as toluene or NMP with water, at an appropriate temperature, such as, for example, ranging from 100° C. to 130° C.

Alternatively a compound of formula (8a) may be prepared reacting a compound of formula (7a) in a cross coupling reaction, such as a Suzuki cross coupling, or a Stille cross coupling, or an Ullmann cross coupling, or a Sonogashira cross coupling. Typical Suzuki cross coupling conditions comprise reacting a compound of formula (7a) with a suitable boronic acid, or boronic ester, in the presence of a Pd catalyst, such as [1,1'-bis(di-tert-butylphosphino)ferrocene]dichloropalladium(II), using a base, such as potassium phosphate monobasic and potassium phosphate tribasic, in a mixture of water and an organic solvent, such as dioxane, at an appropriate temperature, such as, for example, at 65° C. Typical Stille cross-coupling conditions comprise reacting a compound of formula (7a) with a suitable organo-tin reagent, in the presence of Pd catalyst, such as $PdCl_2(PPh_3)_2$, in a polar solvent, such as dioxane, at an appropriate temperature, such as, for example, ranging from 65° C. to 90° C. Typical Ullmann conditions comprise reacting a compound of formula (7a) with a suitable amide in the presence of CuI, with a ligand, such as N,N'-dimethylethylenediamine, and a base, such as cesium carbonate or $K_3PO_4$, in a polar solvent, such as DMF, at an appropriate temperature, such as, for example, at 65° C. Typical Sonogashira cross coupling conditions comprise reacting a compound of formula (7a) with an appropriate terminal alkyne in the presence of CuI and a Pd catalyst such as $PdCl_2(PPh_3)_2$, in a mixture of a polar solvent, such as DMF, with an alkyl amine, such as diethylamine, at an appropriate temperature, such as at RT. A further protection step could be performed to introduce a protective group on OH or NH or $NH_2$ moieties following the general protocols reported in *Greene's Protective Groups in Organic Synthesis*, which is incorporated herein by reference in its entirety.

A compound of formula (8b) may be prepared reacting a compound of formula (7b) in a cross coupling reaction, such as a Suzuki cross coupling or a Stille cross-coupling. Typical Suzuki cross coupling conditions comprise reacting a compound of formula (7b) with a suitable boronic acid, or boronic ester, or boroxine, in the presence of a Pd catalyst, such as [1,1'-bis(di-tert-butylphosphino)ferrocene]dichloropalladium(II), or $Pd(PPh_3)_4$, using a base, such as potassium phosphate monobasic and potassium phosphate tribasic, or potassium carbonate, in a mixture of water and an organic solvent, such as dioxane, at an appropriate temperature, such as ranging from 65° C. to 110° C. Typical Stille cross-coupling conditions comprise reacting a compound of formula (7b) with a suitable organo-tin reagent in the presence of a Pd catalyst, such as $Pd(PPh_3)_4$, in a suitable solvent or a mixture of solvents, such as toluene and methanol, at an appropriate temperature, such as, for example, ranging from 80° C. to 110° C.

A compound of formula (8c) may be prepared reacting commercially available compound of formula (4d) where $X_1=X_2=X_3=X_4=CH$, with a suitable aryl halide or heteroaryl halide under Heck cross coupling conditions. Typical Heck reaction conditions comprise reacting a compound of formula (4d) with an aryl halide or heteroaryl halide in the presence of a Pd catalyst, such as $Pd(OAc)_2$ with a trialkyl phosphine ligand, for example tricyclopentylphosphine tetrafluoborate, using a base, such as $Cs_2CO_3$, in a suitable solvent, such as toluene, at an appropriate temperature, such as, for example, at 130° C.

A compound of formula (9a) may be prepared by reacting a compound of formula (6) with a suitable aryl halide or heteroaryl halide under Heck cross coupling conditions. Typical Heck reaction conditions comprise reacting a compound of formula (6) with an aryl halide or heteroaryl halide in the presence of a Pd(II) catalyst, such as $Pd(OAc)_2$ with a trialkyl phosphine ligand, for example tricyclopentylphosphine tetrafluoborate, using a base, such as $Cs_2CO_3$, in a suitable solvent, such as toluene, at an appropriate temperature, such as, for example, at 130° C.

A compound of formula (10a, b, c, or d) may be prepared by reduction of a compound of formula (8a, b, c) and (4a) respectively. Typical reduction conditions comprise reacting a compound of formula (8a, b, or c) or (4a) with DIBAL in a suitable polar aprotic solvent, such as DCM, at an appropriate temperature, such as at −78° C., or with $LiBH_4$ in a suitable solvent, such as THF with MeOH, at an appropriate temperature, such as at 50° C., or with $NaBH_4$ in a protic solvent such as MeOH, at an appropriate temperature, such as at 0° C.

A compound of formula (10d) may be prepared alternatively by reaction of a compound of formula (11a) with a suitable Grignard reagent. Typical reaction conditions comprise reacting a compound of formula (11a) with a suitable alkylmagnesium halide, such as methylmagnesium bromide in a polar aprotic solvent, such as THF, at an appropriate temperature, such as at 0° C. A compound of formula (11a) may be prepared by oxidation of a compound of formula (10a). Typical oxidation conditions comprise reacting a compound of formula (10a) with an oxidizing system, such as $MnO_2$ in DCM at an appropriate temperature, such as at 50° C.

A compound of formula (12a, b, or c) may be prepared by reaction of a compound of formula (10a, b, d) respectively with diphenylphosphoryl azide. Typical reaction conditions comprise reacting a compound of formula (10a, b, or d) with diphenylphosphorylazide in the presence of a base, such as DBU, in a polar aprotic solvent, such as THF, at an appropriate temperature, such as ranging from 0° C. to RT.

A compound of formula (13a, b, or c) may be prepared by reduction of a compound of formula (12a, b, or c) respectively under Staudinger reduction conditions. Typical reaction conditions comprise reacting a compound of formula (12a, b, c) with a triaryl phosphine, such as triphenylphosphine, in a suitable polar aprotic solvent, such as THF, at an appropriate temperature, such as, for example, at RT, and subsequently adding water and stirring at an appropriate temperature, such as, for example, ranging from RT to 50° C.

A compound of formula (13a) could alternatively be prepared by reaction of a compound of formula (9a) with an appropriate Grignard reagent and reduction of the obtained adduct. Typically a compound of formula (9a) may be reacted with an alkyl magnesium halide, such as MeMgBr, or EtMgBr, in a polar aprotic solvent, such as THF, at an appropriate temperature, such as at 100° C. under microwave heating, then the obtained adduct could be reduced with a suitable hydride, such as NaBH$_4$ in a suitable solvent, such as MeOH, at an appropriate temperature, such as, for example, ranging from 0° C. to RT.

A compound of formula (13d) may be prepared by reduction of a compound of formula (6). Typical reaction conditions comprise reduction of a compound of formula (6) with a hydride reagent, such as LiAlH$_4$, in a polar aprotic solvent, such as THF, at an appropriate temperature.

This scheme provides a synthetic route for the preparation of a compound of formula (8c1) where $X_1=X_2=X_3=X_4=CH$ and alky=Methyl, wherein all the variables are described herein above.

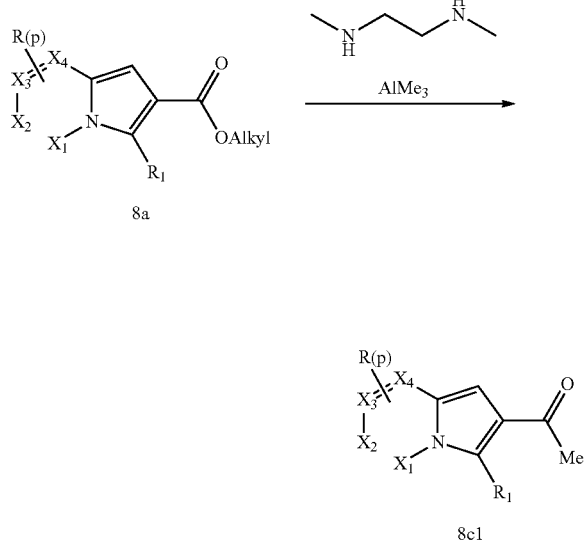

Scheme 4a

8c1

In some cases, a compound of formula (8c1) may be prepared reacting a compound of formula (8a) where $X_1=X_2=X_3=X_4=CH$ and alkyl=Methyl with trimethylaluminum and N,N'-dimethylethylenediamine in a suitable solvent, such as toluene, at an appropriate temperature, such as heating to reflux.

According to Scheme 4, compound of general formula 8c, such as 8c1, may be converted into alcohol 10d by mean of reduction step.

Scheme 4a has been used for the preparation of compounds of example 125.

This scheme provides a synthetic route for the preparation of a compound of formula (8b1) wherein $X_1=X_2=X_3=X_4=CH$ and $R_2=CF_3$ and all the variables are described herein above.

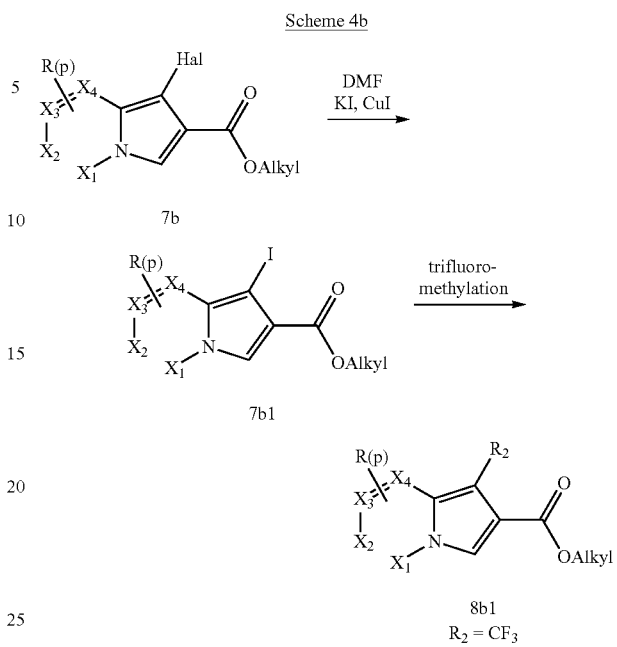

Scheme 4b

7b

7b1

8b1
$R_2 = CF_3$

In some cases, a compound of formula (7b), where $X_1=X_2=X_3=X_4=CH$ and Hal=Br may be converted into a compound of formula (7b1), where $X_1=X_2=X_3=X_4=CH$ and Hal=I for example by reaction with KI and CuI in a polar aprotic solvent, such as DMF, at an appropriate temperature, such as, for example, at 130° C. (step 1).

A compound of formula (8b1), wherein $X_1=X_2=X_3=X_4=CH$ and $R_2=CF_3$, may be prepared by trifluoromethylation reaction of a compound of formula (7b1) with trimethyl(trifluoromethyl)silane in the presence of KF and CuI in a mixture of suitable polar aprotic solvents, such as DMF and NMP, at an appropriate temperature, such as at RT (step 2). According to Scheme 5, compound 8b1, a specific example of general formula 8b, may be converted into alcohol 1 Of by mean of Heck step to 8d, reduction step to alcohol 10e, oxidation step to aldehyde 11b, and finally conversion into alcohol 10f, by mean of reaction with a suitable Grignard reagent.

Scheme 4b has been used for the preparation of compounds of example 124.

This scheme provides a synthetic route for the preparation of a compound of formula (10a1) wherein $X_1=X_2=X_3=X_4=CH$ and $R_1=$—NR$_{12}$R$_{13}$ where R$_{12}$ and R$_{13}$ can be linked to form a ring as above explained, all the other variables are as described above.

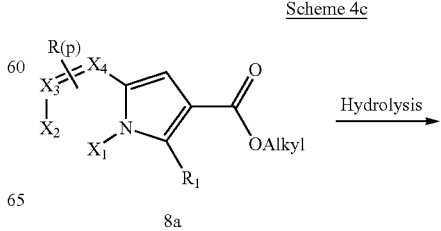

Scheme 4c

8a

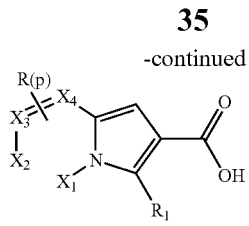

17

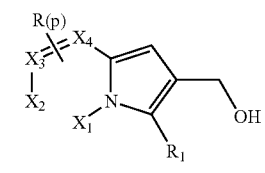

10a1

A compound of formula (17) wherein $X_1=X_2=X_3=X_4=CH$ and $R1=NR_{12}R_{13}$ may be prepared by hydrolysis of a compound of formula (8a). Typical hydrolysis conditions comprise reacting a compound of formula (8a) with a metal hydroxide, such as LiOH, in a mixture of water and a suitable solvent, such as THF, at an appropriate temperature, such as, for example, at 60° C. (step 2).

A compound of formula (10a1) wherein $X_1=X_2=X_3=X_4=CH$ and $R1=NR_{12}R_{13}$ may be prepared by reduction of a compound of formula (17). Typical reduction conditions comprise reacting a compound of formula (17) with a suitable reductive system, such $NaBH_4$ and $BF_3.Et_2O$, in a suitable polar aprotic solvent, such as THF, at an appropriate temperature, such as ranging for 10° C. to RT (step 3).

According to Scheme 4, compound of general formula 10a, such as 10a1, may be converted into alcohol 10d by mean of oxidation to aldehyde 11a, and finally conversion into alcohol 10d, by mean reaction with a suitable Grignard reagent Scheme 4c has been used for the preparation of compounds of example 132.

This scheme provides a synthetic route for the preparation of a compound of formula (8a3) wherein $X_1=X_2=X_3=X_4=CH$ and $R_1$=heteroaryl is 1,2-dihydropyridin-4-yl-2-one N-substituted with, $-(CH_2)_2NR_{22}R_{23}$ and all the variables are described herein above.

Scheme 4d

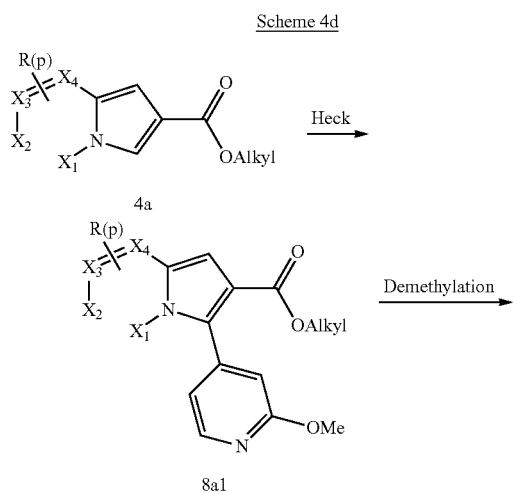

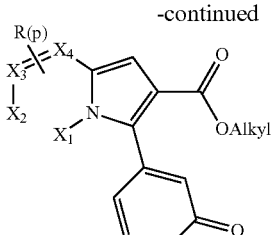

8a2

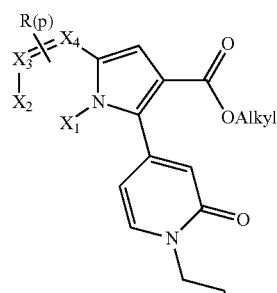

8a3

A compound of formula (8a1) wherein $X_1=X_2=X_3=X_4=CH$ may be prepared from a compound of formula (4a) by means of a Heck cross coupling. Typical conditions comprise reacting a compound of formula (4a) with a suitable aryl or heteroaryl halide like 4-chloro-2-methoxypyridine in the presence of a Pd catalyst, such as $Pd(OAc)_2$ with a trialkyl phosphine ligand, for example tricyclopentylphosphine tetrafluoborate, using a base, such as $Cs_2CO_3$, in a suitable solvent, such as toluene, at an appropriate temperature, such as, for example, at 130° C. (step 1). A compound of formula (8a2) wherein $X_1=X_2=X_3=X_4=CH$ may be prepared from a compound of formula (8a1) with a demethylation reaction. Typical reaction conditions for demethylation step comprise reacting a compound of formula (8a1) with $Me_3SiI$ in a suitable polar aprotic solvent, such as acetonitrile, at an appropriate temperature, such as at 60° C. (step 2). A compound of formula (8a3) wherein $X_1=X_2=X_3=X_4=CH$ may be prepared from a compound of formula (8a2) with an alkylation reaction. Typical reaction conditions for alkylation step comprise reacting a compound of formula (8a3) with suitable aminoalkyl halide, such as 2-chloro-N,N-dimethylethylamine hydrochloride, in the presence of a base, such as $K_2CO_3$ in a suitable polar aprotic solvent, such as acetone, at an appropriate temperature, such as at 50° C. to give compound 8a3 (step 3). According to Scheme 4, compound of general formula 8a, such as 8a3, may be converted into alcohol 10d by mean of reduction step to alcohol 10a, oxidation step to aldehyde 11a, and finally conversion into alcohol 10d, by mean of reaction with a suitable Grignard reagent.

Scheme 4d has been used for the preparation of compounds of examples 121, 122 and 133.

This scheme provides a synthetic route for the preparation of a compound of formula (8a6) wherein $X_1=X_2=X_3=X_4=CH$ and $R_1$=heteroaryl is 2,3-dihydropyridazin-6-yl-3-one N-substituted with $-(CH_2)_2NR_{22}R_{23}$, all the variables are described herein above.

Scheme 4e

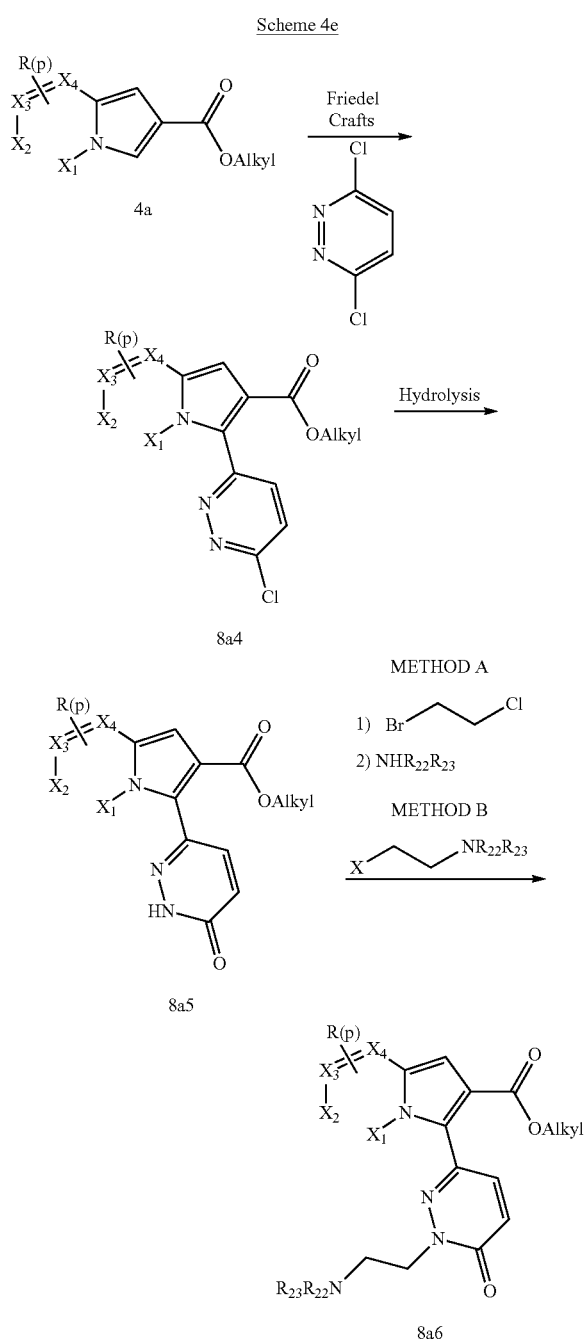

the presence of a base, such as for example $K_2CO_3$, in a suitable polar aprotic solvent, such as DMF, at an appropriate temperature, such as, for example, at 60° C. followed by reaction with a suitable secondary amine such as, for example, pyrrolidine or 1-methyl piperazine in the presence of a base, such as for example $K_2CO_3$, and KI, in a suitable polar aprotic solvent, such as acetonitrile, at an appropriate temperature, such as, for example, at 85° C. Alternatively a compound of formula (8a6) may also be prepared (step 3, method B) by alkylation of a compound of formula (8a5) with a suitable aminoalkyl halide such as for example 4-(2-chloroethyl)morpholine hydrochloride, in the presence of a base, such as for example $K_2CO_3$, in a suitable polar aprotic solvent, such as DMF, at an appropriate temperature, such as, for example, at RT. According to Scheme 4, compound of general formula 8a, such as 8a6, may be converted into alcohol 10d by mean of reduction step to alcohol 10a, oxidation step to aldehyde 11a, and finally conversion into alcohol 10d, by mean reaction with a suitable Grignard reagent.

Scheme 4e has been used for the preparation of compounds of examples 134, 135 and 136.

This scheme provides a synthetic route for the preparation of a compound of formula (8a7) wherein $X_1=X_2=X_3=X_4=CH$ and $R_1$=heteroaryl is pyridazine substituted by a group -OAlkyl selected from ($C_1$-$C_6$) alkoxy, (2-(dimethylamino)ethoxy, ($C_3$-$C_6$) heterocycloalkyloxyl or ($C_3$-$C_6$) heterocycloalkyl($C_1$-$C_6$) alkoxyl further optionally substituted

Scheme 4f

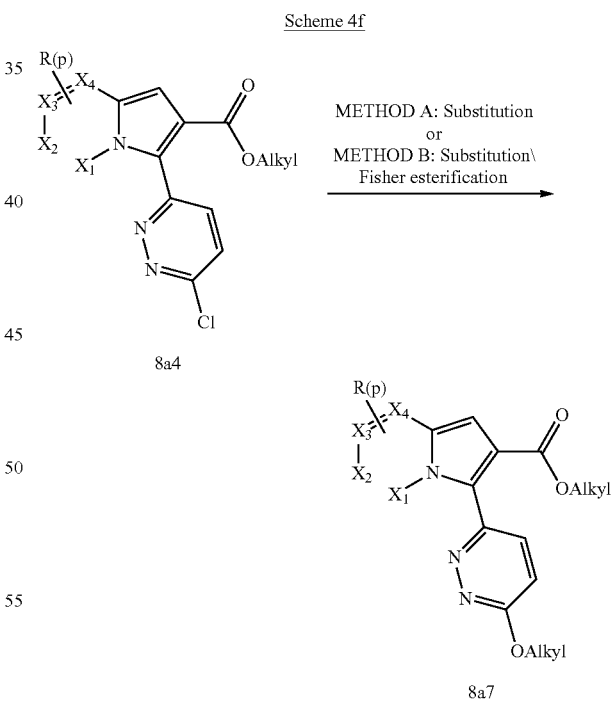

A compound of formula (8a4) where $X_1=X_2=X_3=X_4=CH$ may be prepared by compound of formula (4a) under Friedel Crafts reaction conditions. Typical reaction conditions comprise reacting a compound of formula (4a) with 3,6-dichloropyridazine, in the presence of $AlCl_3$, in a suitable polar aprotic solvent, such as dichloroethane, at an appropriate temperature, such as, for example, at 80° C. (step 1).

A compound of formula (8a5) where $X_1=X_2=X_3=X_4=CH$ may be prepared by hydrolysis of a compound of formula (8a4) with acetic acid and sodium acetate at an appropriate temperature, such as, for example, heating to reflux (step 2).

A compound of formula (8a6) where $X_1=X_2=X_3=X_4=CH$ may be prepared (step 3, method A) by alkylation of a compound of formula (8a5) with 1-bromo-2-chloroethane in A compound of formula (8a7) wherein $X_1=X_2=X_3=X_4=CH$ may be prepared (Method A) by nucleophilic aromatic substitution of a compound of formula (8a4) with a suitable alcohol in the presence of a base, such as potassium tert-butoxide, in a polar aprotic solvent, such as THF, at an appropriate temperature, such as, for example at RT.

Alternatively a compound of formula (8a7) may be prepared (Method B) by nucleophilic aromatic substitution of the carboxylic acid corresponding to a compound of formula (8a4) with a suitable alcohol followed by Fischer esterification with an alcohol, such as MeOH, in the presence of sulfuric acid, at an appropriate temperature, such as, for example, at 80° C. According to Scheme 4, compound of general formula 8a, such as 8a7, may be converted into alcohol 10d by mean of reduction step to alcohol 10a, oxidation step to aldehyde 11a, and finally conversion into alcohol 10d, by mean reaction with a suitable Grignard reagent.

Scheme 4f has been used for the preparation of compounds of examples 137, 138, 139 and 140.

This scheme provides a synthetic route for the preparation of a compounds of formula (8a9) wherein $X_1=X_2=X_3=X_4=CH$ and Y=H or compounds of formula (8d1) (specific example of a compound of formula 8d in scheme 5) wherein $X_1=X_2=X_3=X_4=CH$ and $Y=R_2$, all the variables are as described herein above.

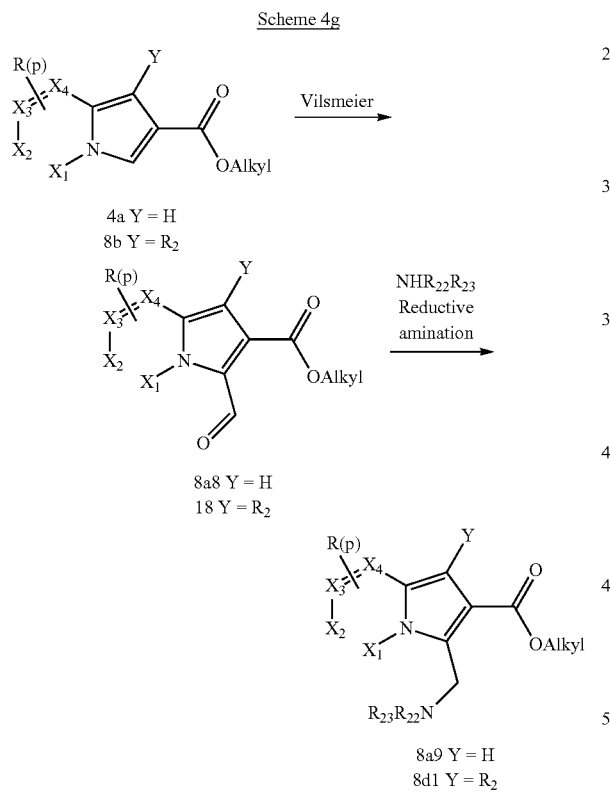

A compound of formula (8a8) wherein $X_1=X_2=X_3=X_4=CH$ and Y=H may be prepared by Vilsmeier formylation of a compound of formula (4a). Similarly a compound of formula (18) wherein $X_1=X_2=X_3=X_4=CH$ and $Y=R_2$ may be prepared by Vilsmeier formylation of a compound of formula (8b). Typical Vilsmeier reaction conditions comprise reacting a compound of formula (4a) or (8b) with DMF and $POCl_3$ in a suitable polar aprotic solvent, such as DCM, at an appropriate temperature, such ranging from 0° C. to RT (step 1).

A compound of formula (8a9) wherein $X_1=X_2=X_3=X_4=CH$ and Y=H may be prepared by reductive amination of a compound of formula (8a8). Similarly a compound of formula (8d1) wherein $X_1=X_2=X_3=X_4=CH$ and $Y=R_2$ may be prepared by reductive amination of a compound of formula (18). Typical reductive amination conditions comprise reacting of formula (8a8) or (18) with a suitable amine and acetic acid in the presence of a reducing reagent, such as sodium triacethoxy borohydride, in a polar solvent, such as DCM, at RT (step 2).

According to Scheme 4, a compound of general formula 8a, such as 8a9 may be converted into alcohol 10d by mean of reduction step to alcohol 10a, oxidation step to aldheide 11a, and finally conversion into alcohol 10d, by mean of reaction with a suitable Grignard reagent. According to Scheme 5, compound of general formula 8d, such as 8d1, may be converted into alcohol 10f by mean of reduction step to alcohol 10e, oxidation step to aldheide 11b, and finally conversion into alcohol 10f, by mean of reaction with a suitable Grignard reagent.

Scheme 4g has been used for the preparation of compounds of examples 141, 142, 143, 144, 145 and 146.

This scheme provides a synthetic route for the preparation of a compound of formula (8a-11) wherein $X_1=X_2=X_3=X_4=H$ and $R_1$=heteroaryl like 1H-pyrazol-3-yl N1-substituted with $-(CH_2)_2NR_{22}R_{23}$, all the variables are described herein above.

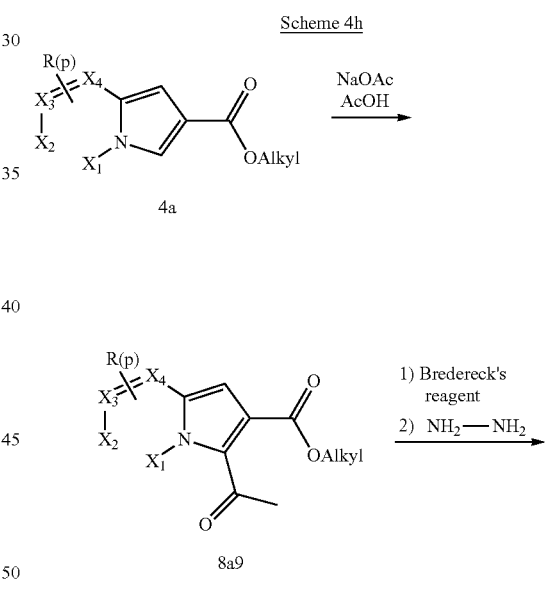

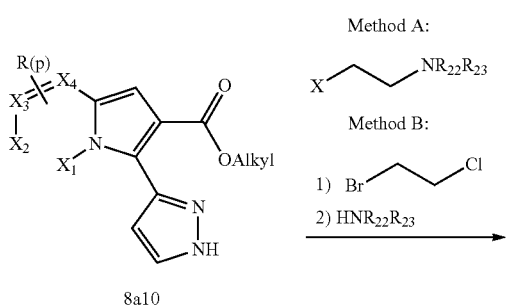

-continued

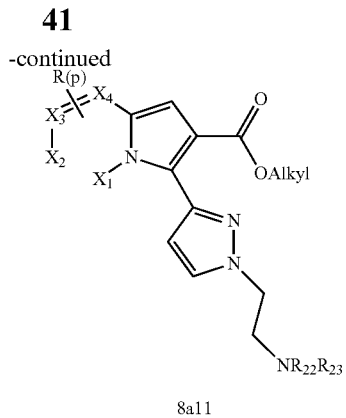

8a11

Scheme 5

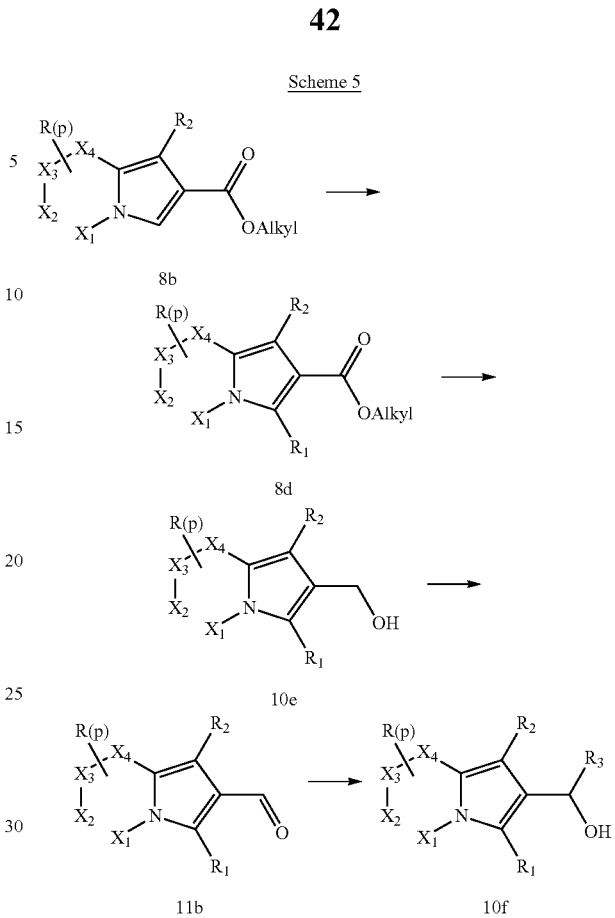

A compound of formula (8a9) wherein $X_1=X_2=X_3=X_4=CH$ may be prepared by acylation of a compound of formula (4a) with sodium acetate in acetic acid, at an appropriate temperature, such at 140° C. (step 1).

A compound of formula (8a10) wherein $X_1=X_2=X_3=X_4=CH$ may be prepared by reaction of a compound of formula (8a9) with Bredereck's reagent in a suitable solvent such as toluene, at an appropriate temperature, such at 110° C. followed by reaction with hydrazine monohydrate, in a suitable solvent such as ethanol, at an appropriate temperature, such at 80° C. (step 2).

A compound of formula (8a11) may be prepared by (step 3, Method A) alkylation of a compound of formula (8a10) with 1-bromo-2-chloroethane in the presence of a base, such as for example $K_2CO_3$, in a suitable polar aprotic solvent, such as DMF, at an appropriate temperature, such as, for example, at 60° C. followed by reaction with a suitable secondary amine in the presence of a base, such as for example $K_2CO_3$, and KI, in a suitable polar aprotic solvent, such as acetonitrile, at an appropriate temperature, such as, for example, at 85° C. In some cases (example 149) a protection step of OH group as TBS was also required: for protection conditions see the general protocols reported in *Greene's Protective Groups in Organic Synthesis*, Peter G. Wuts, Theodora W. Greene; Editor Wiley&Sons, 4th Edition December 2006, which is incorporated herein by reference in its entirety.

Alternatively a compound of formula (8a11) may be prepared (step 3, Method B) by alkylation of a compound of formula (8a10) with a suitable aminoalkyl halide such as for example 4-(2-chloroethyl)morpholine hydrochloride, in the presence of a base, such as for example $K_2CO_3$, in a suitable polar aprotic solvent, such as THF, at an appropriate temperature, such as, for example, at 60° C. According to Scheme 4, a compound of general formula 8a, such as 8a11 may be converted into alcohol 10d by mean of reduction step to alcohol 10a, oxidation step to aldehyde 11a, and finally conversion into alcohol 10d, by mean reaction with a suitable Grignard reagent.

Scheme 4h has been used for the preparation of compounds of examples 147, 148, 149 and 150.

This scheme provides a synthetic route for the preparation of a compound of formula (10f) wherein $X_1=X_2=X_3=X_4=CH$ and R1, R2 and R3 and R(p) and Alkyl are variable as defined herein above. The compound of formula (10f) can be converted to the desired compounds of the invention as provided in Scheme 6 and 10 below.

A compound of formula (8d) wherein R1 is an heteroaryl group, may be prepared reacting a compound of formula (8b) with a suitable heteroaryl halide, such as 2-chloropyridine, under Heck cross coupling conditions. Typical Heck reaction conditions comprise reacting a compound of formula (8b) with (hetero)aryl halide in the presence of a Pd catalyst, such as $Pd(OAc)_2$ with a trialkyl phosphine ligand, for example tricyclopentylphosphine tetrafluoborate, using a base, such as $Cs_2CO_3$, in a suitable solvent, such as toluene, at an appropriate temperature, such as, for example, at 130° C.

A compound of formula (10e) may be prepared by reduction of a compound of formula (8d). Typical reaction conditions comprise reacting a compound of formula (8d) with a reducing reagent, such as DIBAL, in a polar aprotic solvent, such as DCM, at an appropriate temperature, such as, for example, at −78° C.

A compound of formula (11b) may be prepared by oxidation of a compound of formula (10e). Typical oxidation conditions comprise reacting a compound of formula (10e) under Swern oxidation conditions, such as with oxalyl chloride and DMSO in a suitable solvent, such as DCM, at an appropriate temperature, for example at −78° C.

A compound of formula (10f) may be prepared by reaction of a compound of formula (11b) with a suitable Grignard reagent. Typical reaction conditions comprise reacting a compound of formula (11b) with an alkylmagnesium halide such as methylmagnesium bromide, in a polar aprotic solvent, such as THF, at an appropriate temperature, such as at 0° C.

This scheme provides a synthetic route for the preparation of a compound of formula (14a) from a compound of formula (10) wherein $X_1=X_2=X_3=X_4=CH$ or $X_1=N$, $X_2=X_3=X_4=CH$, and $R_1$, $R_2$ and $R_3$ and $R(p)$ are variable as described herein above.

Scheme 6

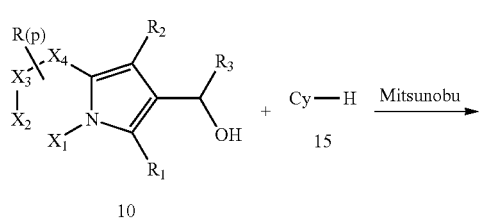

10

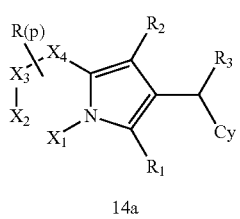

14a

A compound of general formula (14a) may be prepared according to Scheme 6 by reaction of a compound of formula (10) with nitrogen based nucleophile CyH (15), such as adenine under Mitsunobu reaction conditions. Typical reaction conditions comprise reacting a compound of formula (10) with (15), such as adenine, in a polar aprotic solvent, such as THF, in the presence of a dialkyl azodicarboxylate, such as DIAD, and a triaryl phosphine, such as triphenylphosphine, at an appropriate temperature, such as, for example, ranging from RT to 50° C. This scheme provides a synthetic route for the preparation of the compound of example 1 to 12.

In some particular cases, where CyH is 3-(3-((tert-butyldimethylsilyl)oxy)-5-fluorophenyl)-1H-pyrazolo[3,4-d]pyrimidin-4-amine (15a) compounds of formula (14a) may be prepared under Mitsunobu reaction conditions followed by deprotection of the TBS moiety. Typical reaction conditions comprise reacting a compound of formula (10) with 3-(3-((tert-butyldimethylsilyl)oxy)-5-fluorophenyl)-1H-pyrazolo[3,4-d]pyrimidin-4-amine (15a) in an apolar aprotic solvent, such as THF, in the presence of a dialkyl azodicarboxylate, such as DIAD and a triaryl phosphine, such as triphenylphosphine, at an appropriate temperature, such as, for example, at RT. Typical deprotection conditions to remove a TBS group comprise treatment with strong acid, such as HCl, in a suitable solvent, such as EtOH, at an appropriate temperature, such as at RT. For deprotection conditions see the general protocols reported in *Greene's Protective Groups in Organic Synthesis*, Peter G. Wuts, Theodora W. Greene; Editor Wiley&Sons, 4th Edition December 2006, which is incorporated herein by reference in its entirety.

Scheme 6a

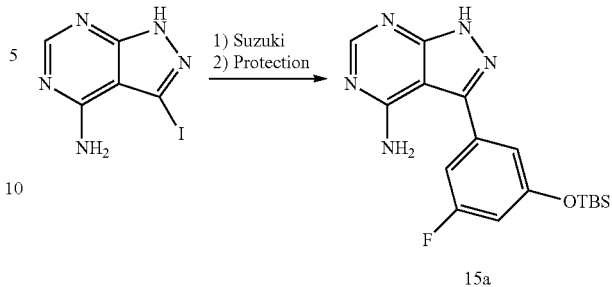

15a

This scheme provides a synthetic route for the preparation of a compound of formula (15a).

A compound of formula (15a) may be prepared by a two-step Suzuki coupling\Protection sequence from commercially available 3-iodo-1H-pyrazolo[3,4-d]pyrimidin-4-amine. Typical Suzuki cross coupling conditions comprise reacting commercially available 3-iodo-1H-pyrazolo[3,4-d]pyrimidin-4-amine with a suitable boronic acid, or boronic ester like (3-fluoro-5-hydroxyphenyl)boronic acid, in the presence of a Pd catalyst, such as $PdCl_2(dppf)$, using a base, such as aqueous potassium phosphate tribasic, in a polar solvent or in a mixture of polar solvents, such as DMF, at an appropriate temperature, such as at 120° C. For protection conditions see the general protocols reported in *Greene's Protective Groups in Organic Synthesis*, Peter G. M Wuts, Theodora W Greene; Editor Wiley&Sons, 4th Edition December 2006, which is incorporated herein by reference in its entirety.

Scheme 6a has been used for the preparation of compounds of example 124.

This scheme provides a synthetic route for the preparation of a compound of formula (14b) from a compound of formula (13) wherein all the variables are described herein above.

Scheme 7

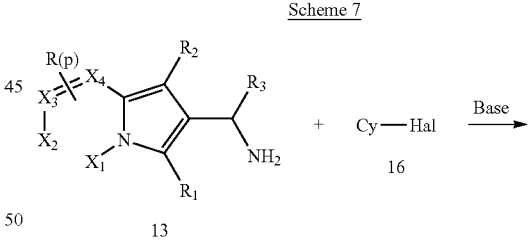

13

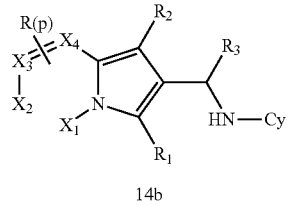

14b

A compound of general formula (14b) may be prepared according to Scheme 7 by reaction of a compound of formula (13) with a suitable halide Cy-Hal (16), where "Cy" has the meaning above defined, such as for example 6-bromopurine, 4-amino-6-chloropyrimidine-5-carbonitrile, 4-amino-6-chloro-5-pyrimidinecarbaldehyde, 6-chloro-5-methylpyrimidin-4-amine. Typical reaction conditions comprise reacting a compound of formula (13) with 6-bromopurine in a polar solvent, such as t-BuOH, in the presence of a base, such as DIPEA, at an appropriate temperature, such as, for example, ranging from 80° C. to 100° C.

This scheme provides a synthetic route for the preparation of the compound of examples 13 to 21 (where Cy-Hal is a purine derivative); and of examples 22 to 44 and 47 to 53 and 59 (where Cy-Hal is a pyrimidine derivative).

This scheme provides a synthetic route for the preparation of a compound of formula (14c) from a compound of formula (13) wherein $X_1=X_2=X_3=X_4=CH$ and R1, R2 and R3 and R(p) are variable as described herein above.

Scheme 8

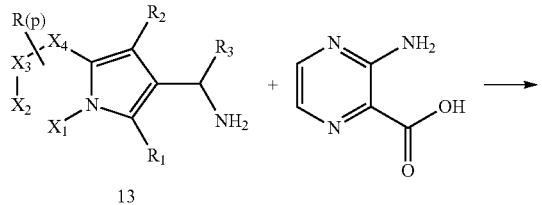

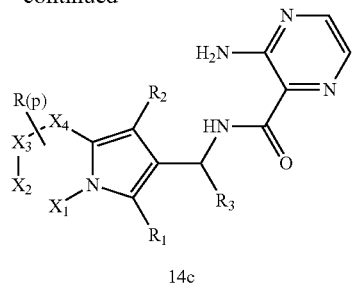

14c

A compound of formula (14c) may be prepared according to Scheme 8 by condensation of a compound of formula (13) with 3-amino-2-pyrazinecarboxylic acid. Typical reaction conditions comprise reacting a compound of formula (13) with 3-amino-2-pyrazinecarboxylic acid in the presence of HOBt and a dialkyl carbodiimide, such as ECD HCl, in a polar aprotic solvent, such as DMF, at an appropriate temperature, such as at RT.

This scheme provides a synthetic route for the preparation of the compound of example 54 and 55.

This scheme provides a synthetic route for the preparation of a compound of formula (14e, f, g) from a compound of formula 14d wherein all the variables are described herein above (e.g. starting from the compound of example 47). Particularly Alkyl may also be H or is a ($C_1$-$C_6$) alkyl, and Alkyl$_1$ and Alkyl$_2$ may form, taken together with the nitrogen atom they are linked to, a 5 to 6 membered heterocyclic radical such as 1-pyrrolidinyl, 1-piperidinyl, 1-piperazinyl, or 4-morpholinyl.

Scheme 9

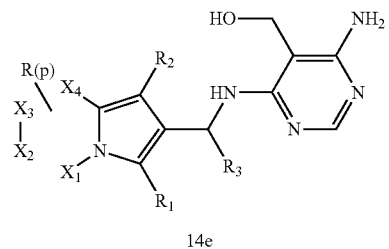

14e

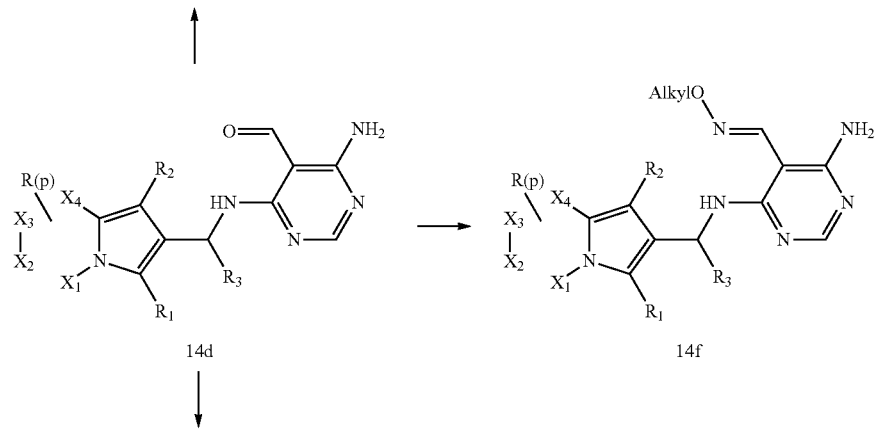

14d                14f

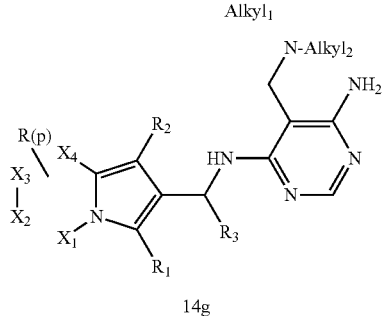

14g

A compound of formula (14e) (e.g. compound of example 56) may be prepared according to Scheme 9 by reduction of a compound of formula (14d). Typical reaction conditions comprise reacting (14d), with a reducing reagent, such as NaBH$_4$, in a polar protic solvent, such as MeOH, at an appropriate temperature, such as at 0° C. Compound of formula (14d) may be prepared as reported in scheme 7, from 13 and CyHal=4-amino-6-chloro-5-pyrimidinecarbaldehyde.

A compound of formula (14g) may be prepared according to Scheme 9 by reacting a compound of formula (14d), under reductive amination conditions. Typical reaction conditions comprise reacting a compound of formula (14d), with a secondary amine, such as morpholine (e.g. in example 57) in the presence of a reducing reagent, such as sodium triacetoxy borohydride, in a polar solvent, such as DCM, at pH~5-6, at an appropriate temperature, such as at RT.

A compound of formula (14f) (e.g. compound of example 58) may be prepared according to scheme 9 by reaction of a compound of formula (14d), with an hydroxylamine salt. Typical reaction conditions comprise reacting a compound of formula (14d), with hydroxylamine salt such as hydroxylamine hydrochloride in the presence of pyridine, in a polar solvent, such as ethanol, at an appropriate temperature, such as at RT.

This scheme provides a synthetic route for the preparation of a compound of formula 14h and 14i from a compound of formula (10) and 3-iodo-1H-pyrazolo[3,4-d]pyrimidin-4-amine wherein all the variables are described herein above.

Scheme 10

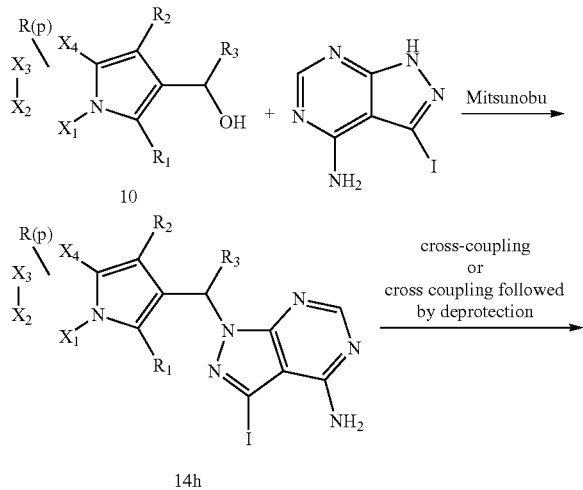

14h

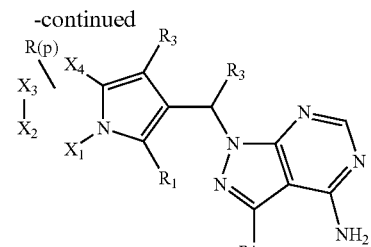

14i

A compound of general formula (14h) may be prepared according to Scheme 10 by reaction of a compound of formula (10) with 3-iodo-1H-pyrazolo[3,4-d]pyrimidin-4-amine under Mitsunobu reaction conditions. Typical reaction conditions comprise reacting a compound of formula (10) with 3-iodo-1H-pyrazolo[3,4-d]pyrimidin-4-amine in an apolar aprotic solvent, such as THF, in the presence of a dialkyl azodicarboxylate, such as DIAD and a triaryl phosphine, such as triphenylphosphine, at an appropriate temperature, such as, for example, at RT.

A compound of general formula (14i) may be prepared according to Scheme 10 by reaction of a compound of formula (14h) in a cross-coupling reaction, such as for example Suzuki cross-coupling, or Sonogashira cross-coupling, or Stille cross-coupling with suitable reagents. Typical Suzuki cross coupling conditions comprise reacting a compound of formula (14h) with a suitable boronic acid, or boronic ester, in the presence of a Pd catalyst, such as Pd(PPh$_3$)$_4$, using a base, such as aqueous sodium bicarbonate, in a polar solvent or in a mixture of polar solvents, such as DME and EtOH, at an appropriate temperature, such as 80° C. Typical Sonogashira cross coupling conditions comprise reacting a compound of formula (14i) with an appropriate terminal alkyne in the presence of CuI and using a catalyst such as PdCl$_2$(PPh$_3$)$_2$, in a mixture of a polar solvent, such as DMF, and an alkyl amine, such as diethylamine, at an appropriate temperature, such as at RT. Typical Stille cross-coupling conditions comprise reacting a compound of formula (14i) with a suitable organo-tin reagent, in the presence of LiCl and a catalyst, such as Pd(PPh$_3$)$_4$, in a polar aprotic solvent, such as dioxane, at an appropriate temperature, such as at 100° C.

This scheme provides a synthetic route for the preparation of the compound of examples 60 to 102.

An additional deprotection step could be required to remove protection group from OH or NH or NH$_2$ moieties. Typical deprotection conditions to remove Boc protecting group comprise treatment with strong acid, such as TFA in a polar solvent, such as DCM, at an appropriate temperature, such as ranging from 0° to RT. Typical deprotection conditions to remove TIPS protecting group comprise treatment with a fluoride salt, such as TBAF, in an apolar solvent, such as THF, at an appropriate temperature, such as, for example, at RT. Typical deprotection conditions to remove a TBS group comprise treatment with stong acid, such as HCl, in a suitable solvent, such as EtOH, at an appropriate temperature, such as at RT. For deprotection conditions see the general protocols reported in *Greene's Protective Groups in Organic Synthesis*, Peter G. Wuts, Theodora W. Greene; Editor Wiley&Sons, 4th Edition December 2006, which is incorporated herein by reference in its entirety. This deprotection step was used for the preparation of example 45, 46 and 103. And 117, 149

In some other particular cases, an additional step was required to transform a Boc protecting group into a methyl group. Typical conditions comprise treatment with a reducing agent such as LiAlH$_4$ in a polar solvent or in a mixture of polar solvents like THF at an appropriate temperature such as 65° C.

This scheme provides a synthetic route for the preparation of a compound of formula (14i1) wherein $X_1=X_2=X_3=X_4=$CH, $R_1=$heteroaryl like 2,3-dihydropyridinyl-2-one N-substituted with —(CH$_2$)$_2$NR$_{22}$R$_{23}$.

Scheme 11

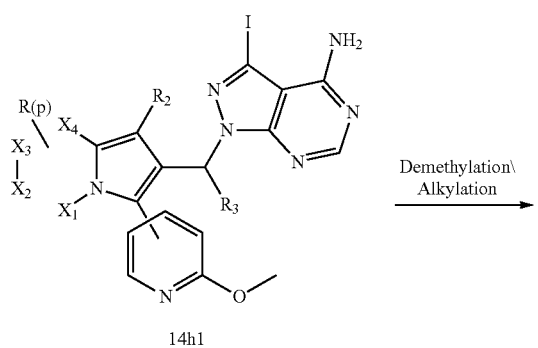

14h1

Demethylation\Alkylation

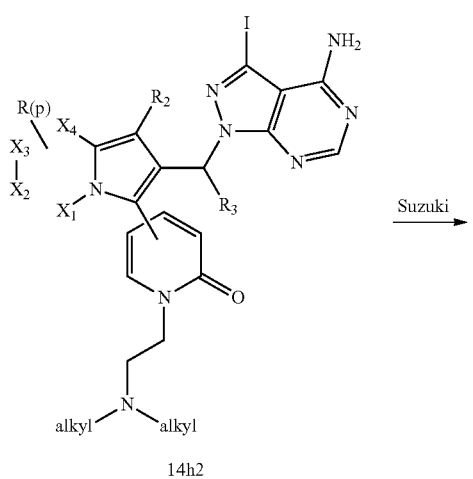

14h2

Suzuki

-continued

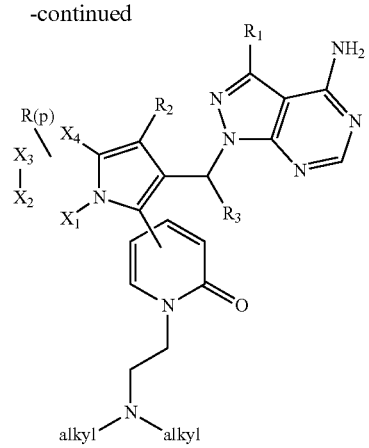

14i1

A compound of formula (14h2) may be prepared from a compound of formula (14h1) wherein $X_1=X_2=X_3=X_4=$C with a demethylation\alkylation sequence. Typical reaction conditions for demethylation step comprise reacting a compound of formula (14h1) with Me$_3$SiI in a suitable polar aprotic solvent, such as acetonitrile, at an appropriate temperature, such as ranging from 50° C. to 60° C. Typical reaction conditions for alkylation step comprise reacting the obtained material with suitable aminoalkyl halide, such as 4-(2-chloroethyl)morpholine hydrochloride, in the presence of a base, such as K$_2$CO$_3$ in a suitable polar aprotic solvent, such as acetone, at an appropriate temperature, such as at 60° C. to give compound (14h2).

A compound of general formula (14i1) may be prepared according to Scheme 11 by reaction of a compound of formula (14h) in a cross-coupling reaction, such as for example Suzuki cross-coupling. Typical Suzuki cross coupling conditions comprise reacting a compound of formula (14h2) with a suitable boronic acid, or boronic ester, in the presence of a Pd catalyst, such as Pd(PPh$_3$)$_4$, using a base, such as aqueous sodium bicarbonate, in a polar solvent or in a mixture of polar solvents, such as DME and EtOH, at an appropriate temperature, such as 80° C.

The compounds of the present invention are inhibitors of kinase activity, in particular PI3-kinase activity. Generally speaking, compounds which are PI3K inhibitors may be useful in the treatment of many disorders associated with PI3K enzymes mechanisms.

In one embodiment, the disorders that can be treated by the compounds of the present invention include respiratory diseases selected from idiopathic chronic cough, cough-variant asthma, cough associated with thoracic tumour or lung cancer, viral or post-viral cough, upper airways cough syndrome (UACS), or post nasal drip cough, or cough associated with gastro-oesophageal reflux disease (both acid and non-acid reflux), asthma, chronic bronchitis, chronic obstructive pulmonary disease (COPD), interstitial lung disease, (such as idiopathic pulmonary fibrosis (IPF)), congestive heart disease, sarcoidosis, infections (such as whooping cough); viral infections (including viral respiratory tract infections and viral exacerbation of respiratory diseases; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In another embodiment, the disorder that can be treated by the compound of the present invention is selected from the group consisting of idiopathic chronic cough, cough-variant asthma, cough associated with thoracic tumour or lung cancer, viral or post-viral cough, upper airways cough syndrome (UACS), post nasal drip cough, cough associated gastro-oesophageal reflux disease (both acid and non-acid reflux), asthma, chronic bronchitis, chronic obstructive pulmonary disease (COPD) and interstitial lung disease (such as idiopathic pulmonary fibrosis (IPF).

In a further embodiment, the disorder is selected from the group of asthma, chronic obstructive pulmonary disease (COPD), idiopathic pulmonary fibrosis (IPF), cough and chronic cough.

The methods of treatment of the present invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A., which is incorporated herein by reference in its entirety.

Administration of the compounds of the present invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the present invention can be administered as the sole active agent or in combination with other pharmaceutical active ingredients including those currently used in the treatment of respiratory disorders, e.g. beta$_2$-agonists, antimuscarinic agents, corticosteroids, mitogen-activated kinases (P38 MAP kinases) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The dosages of the compounds of the invention depend upon a variety of factors including the particular disease to be treated, the severity of the symptoms, the route of administration, the frequency of the dosage interval, the particular compound utilized, the efficacy, toxicology profile, and the pharmacokinetic profile of the compound.

Advantageously, the compounds of formula (I) can be administered for example, at a dosage of 0.001 to 1000 mg/day, preferably 0.1 to 500 mg/day.

When the compounds of formula (I) are administered by inhalation route, they are preferably given at a dosage of 0.001 to 500 mg/day, preferably 0.1 to 200 mg/day.

Other features of the invention will become apparent in the course of the following descriptions of exemplary embodiments which are given for illustration of the invention and are not intended to be limiting thereof.

EXAMPLES

Preparation of Intermediates and Examples

Chemical Names of the compounds were generated with CHEMAXON 6.0.4 tool. solutions of common inorganic salts used in workups are aqueous solutions.

Abbreviations:

| | |
|---|---|
| Et$_2$O | Diethyl ether |
| EtOAc | Ethyl acetate |
| DCM | Dichloromethane |
| MeOH | Methanol |
| DMF | N,N-Dimethylformamide |
| MeCN | Acetonitrile |
| THF | Tetrahydrofuran |
| DMSO | Dimethyl sulfoxide |
| NMP | 1-Methyl-2-pyrrolidinone |
| t-BuOH | tert-Butanol |
| n-BuOH | 1-Butanol |
| EtOH | Ethanol |
| DME | 1,2-Dimethoxyethane |
| DABCO | 1,4-Diazabicyclo[2.2.2]octane |
| TEA | Triethylamine |
| KOAc | Potassium acetate |
| PdCl$_2$(PPh$_3$)$_2$ | Bis(triphenylphosphine)palladium(II) dichloride |
| Pd(OAc)$_2$ | Palladium(II) acetate |
| PdCl$_2$(dtbpf) | [1,1'-Bis(di-tert-butylphosphino)ferrocene]dichloropalladium(II) |
| Pd$_2$(dba)$_3$ | Tris(dibenzylideneacetone)dipalladium(0) |
| Pd(PPh$_3$)$_4$ | Tetrakis(triphenylphosphine)palladium(0) |
| DIBAL | Diisobutylaluminum hydride |
| PPH$_3$ | Triphenylphosphine |
| DPPA | Diphenyl phosphoryl azide |
| DBU | 1,8-Diazabicyclo[5.4.0]undec-7-ene |
| DMAP | 4-(Dimethylamino)pyridine |
| DIPEA | N,N-Diisopropylethylamine |
| MeMgBr | Methylmagnesium bromide |
| EtMgBr | Ethylmagnesium bromide |
| DIAD | Diisopropyl azodicarboxylate |
| HOBt | 1-Hydroxybenzotriazole hydrate |
| EDC HCl | N-(3-Dimethylaminopropyl)-N'-ethylcarbodiimide hydrochloride |
| TFA | Trifluoroacetic acid |
| MW | microwave |
| SCX | Strong cation exchanger |
| Silica-NH | Secondary amine functionalized silica cartridge |
| r.t./RT | Room temperature |
| Rt | Retention time |
| H | hour |
| Min | minutes |
| Conc | concentrated |
| Eq | equivalent |
| Sat | saturated |
| MDAP | mass directed autopurification |
| TBS | tert-butyl-dimethylsilyl group |

General Experimental Details
NMR Characterization:

Proton Magnetic Resonance ($^1$H NMR) spectra were collected using deuterated solvents (DMSO-d$_6$, CDCl$_3$) at 25° C. on Agilent VNMRS-500, Agilent VNMRS-400 and Bruker Avance 400. Chemical shifts are expressed in parts per million (ppm) downfield of tetramethylsilane (δ units). Multiplity is indicated as follows: (s) singlet, (d) doublet, (dd) double doublet, (ddd) triple doublet, (t) triplet, (dt) double triplet, (q) quartet, (m) multiplet, (br s) broad signal. Coupling constants J are expressed in unit of hertz (Hz).

LC/UV/MS Analytical Methods

LCMS may be recorded under the following conditions: diode array detector DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative electron spray ES ionisation mode and/or Fractionlynx system used in analytical mode coupled with ZQ™ single quadrupole operated in positive and/or negative ES ionisation mode. Quality Control methods used were four, two operated under low pH conditions and the other ones operated under high pH conditions:

Method A, low pH conditions: column: Acquity CSH C18, 1.7 μm, 2.1×50 mm, the column temperature was 40° C.; mobile phase solvent A was milliQ water+0.1% HCOOH, mobile phase solvent B MeCN+0.1% HCOOH. The flow rate was 1 ml/min. The gradient table was t=0 min 97% A-3% B, t=1.5 min 0.1% A-99.9% B, t=1.9 min 0.1% A-99.9% B and t=2 min 97% A-3% B. The UV detection range was 210-350 nm and the ES+/ES− range was 100-1000 amu.

Method B, low pH conditions: column: Acquity UPLC BEH C18, 1.7 μm, 50 mm×2.1 mm, the column temperature was 40° C.; mobile phase solvent A was milliQ water+0.1% HCOOH, mobile phase solvent B MeCN+0.1% HCOOH. The flow rate was 1 ml/min. The gradient table was t=0 min 97% A-3% B, t=1.5 min 0.1% A-99.9% B, t=1.9 min 0.1% A-99.9% B and t=2 min 97% A-3% B. The UV detection range was 210-350 nm and the ES+/ES− range was 100-1000 amu.

Method C, high pH conditions: column: Acquity BEH C18, 1.7 μm, 2.1×50 mm the column temperature was 40° C.; mobile phase solvent A was 10 mM aqueous solution of NH$_4$HCO$_3$ adjusted to pH=10 with ammonia, mobile phase solvent B MeCN. The flow rate was 1 ml/min. The gradient table was t=0 min 97% A-3% B, t=1.5 min 0.1% A-99.9% B, t=1.9 min 0.1% A-99.9% B and t=2 min 97% A-3% B. The UV detection range was 210-350 nm and the ES+/ES− range was 100-1000 amu.

Method D, high pH conditions: column: XBridge C18, 5 μm, 50 mm×4.6 mm, the column temperature was 40° C.; mobile phase solvent A was 10 mM aqueous solution of NH$_4$HCO$_3$ adjusted to pH=10 with ammonia, mobile phase solvent B MeCN. The flow rate was 2 ml/min. The gradient table was t=0 min 97% A-3% B, t=6.5 min 0.1% A-99.9% B, t=8.5 min 0.1% A-99.9% B and t=8.6 min 97% A-3% B. The UV detection range was 210-350 nm and the ES+/ES− range was 100-1000 amu.

Method J, high pH conditions: column: Acquity BEH C18, 1.7 μm, 2.1×50 mm the column temperature was 40° C.; mobile phase solvent A was 0.1% v/v ammonia aqueous solution at pH 10, mobile phase solvent B MeCN. The flow rate was 1 ml/min. The gradient table was t=0 min 97% A-3% B, t=1.5 min 0.1% A-99.9% B, t=1.9 min 0.1% A-99.9% B and t=2 min 97% A-3% B. The UV detection range was 210-350 nm and the ES+/ES− range was 100-1000 amu.

Semipreparative mass directed autopurifications (MDAP) were carried out using Waters Fractionlynx™ systems operating under low or high pH chromatographic conditions under the following conditions. The trigger for the collection of the target species was the presence of the target m/z ratio value in the TIC MS signal. All the purifications were carried out with the column kept at room T.

The semi-preparative set of conditions used were three:

Method E, low pH conditions: Stationery phase: XSelect CSH Prep. C18, 5 um, OBD 30×100 mm, at room temperature; mobile phase solvent A was milliQ water+0.1% HCOOH, mobile phase solvent B MeCN; the flow rate was 43 ml/min; the gradient timetables were customised on the Rt behaviour of the target species. The UV detection range was 210-350 nm and the ES+/ES− range was 100-900 amu.

Method F, high pH conditions: Stationary phase: Gemini 5 um C18 110 A AXIA (100×30 mm); mobile phase solvent A was 10 mM aqueous solution of $NH_4HCO_3$ adjusted to pH=10 with ammonia, the flow rate was 43 ml/min; mobile phase solvent B MeCN; the gradient timetables were customized on the Rt behaviour of the target species. The UV detection range was 210-350 nm and the ES+/ES− range was 100-900 amu.

Method G, high pH conditions: Stationary phase: Gemini 5 um C18 110 A AXIA (100×30 mm); mobile phase solvent A was 10 mM aqueous solution of $NH_4HCO_3$ adjusted to pH=10 with ammonia, the flow rate was 40 ml/min; mobile phase solvent B MeCN; the gradient timetable was customized on the Rt behaviour of the target species. The UV detection range was 210-350 nm and the ES+/ES− range was 100-900 amu.

Chiral resolutions were performed using a Semipreparative Waters 600 system or a Semipreparative HPLC Agilent 1100 for semipreparative separations. The conditions are reported in the Examples.

The enantiomeric excess is determined by chiral HPLC analysis on a HPLC Agilent 1100 equipped with 6-position switching valve. It is equipped with DA, and CD detectors. The following methods were used:

Method H: Chiralpak AD-H (25×0.46 cm), 5 um; Mobile phase: n-Hexane/(Ethanol+0.1% isopropylamine) 80/20 v/v; UV detection: 220 nM; Flow Rate: 0.8 mL/min; Loop: 10 uL.

Method I: Column: Chiralpak IC (25×0.46 cm), 5 um; Mobile phase: n-Hexane/(2-Propanol+0.1% isopropylamine) 60/40% v/v; UV detection: 220 nM; Flow Rate: 1.0 mL/min; Loop: 20 uL.

Method K: Column: Chiralpak AD-H (25×0.46 cm), 5 um; Mobile phase: n-Hexane/(Ethanol+0.1% isopropylamine) 85/15% v/v; UV detection: 220 nM; Flow Rate: 0.8 mL/min; Loop: 15 uL.

Method L: Column: Chiralpak AD-H (25×0.46 cm), 5 um; Mobile phase: n-Hexane/(Ethanol+0.1% isopropylamine) 70/30% v/v; UV detection: 220 nM; CD: 240 nM; Flow Rate: 0.8 mL/min; Loop: 3 uL.

Method M: Column: Chiralpak AD-H (25×0.46 cm), 5 um; Mobile phase: n-Hexane/(Ethanol+0.1% isopropylamine) 80/20% v/v; UV detection: 220 nM; Flow Rate: 1.0 mL/min; Loop: 20 uL.

Method N: Column: Chiralpak AD-H (25×0.46 cm), 5 um; Mobile phase: n-Hexane/(Ethanol/Methanol 1/1+0.1% isopropylamine) 75/25% v/v; UV detection: 220 nM; Flow Rate: 1.0 mL/min; Loop: 20 uL.

Method O: Column: Chiralpak IC (25×0.46 cm), 5 um; Mobile phase: n-Hexane/(Ethanol+0.1% isopropylamine) 75/25% v/v; UV detection: 220 nM; Flow Rate: 1.0 mL/min; Loop: 15 uL.

Method P: Column: Chiralpak AD-H (25×0.46 cm), 5 um; Mobile phase: n-Hexane/(Ethanol+0.1% isopropylamine) 75/25% v/v v; UV detection: 220 nM; Flow Rate: 1.0 mL/min; Loop: 20 uL.

Method Q: Column: Chiralpak IC (25×0.46 cm), 5 um; Mobile phase: n-Hexane/(Ethanol+0.1% isopropylamine) 70/30% v/v; UV detection: 220 nM; Flow Rate: 1.0 mL/min; Loop: 15 uL.

The experiments performed under microwave irradiation were carried out using a Biotage Initiator 2.0 system.

Flash chromatography purifications were performed using Biotage Isolera or Biotage SP1 flash chromatography systems, both instruments working with Biotage KP-SIL cartridges and Biotage KP-NH cartridges, or were manually performed using Isolute Flash silica gel pre-packed cartridges, or Varian Bond Elut pre-packed cartridges.

Reverse phase flash chromatography were carried out over pre-packed Biotage C18 SNAP cartridges or Varian Bond Elut C18 cartridges.

SPE-SCX cartridges are ion exchange solid phase extraction columns supplied by Varian.

Many of the compounds described in the following Examples have been prepared from stereochemically pure starting materials, for example 95% ee.

Brine refers to a saturated aqueous solution of NaCl, unless otherwise specified.

Where the preparation of starting materials is not described, these are commercially available, known in the literature, or readily obtainable by those skilled in the art using standard procedures.

The stereochemistry of the compounds in the Examples, where indicated, has been assigned on the assumption that absolute configuration at resolved stereogenic centers of staring materials is maintained throughout any subsequent reaction conditions.

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Preparation of Intermediates

Intermediate A1 of ethyl 2-[hydroxy(pyridin-2-yl)methyl]prop-2-enoate

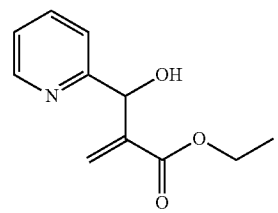

To a solution of pyridine-2-carbaldehyde (commercially available from Sigma Aldrich, 9.0 g, 84 mmol) and ethyl acrylate (27.42 mL, 252 mmol) in a mixture of dioxane/water≈1/1 (840 mL), DABCO (9.42 g, 84 mmol) was added and the resulting mixture was stirred at room temperature for 1 h. The mixture was partitioned between Et₂O and water and the aqueous phase was extracted with Et₂O. The combined organic layers were washed with brine and dried over sodium sulfate. The solvent was removed and the crude was purified by flash chromatography on silica gel Biotage SNAP cartridge (340 g) (cyclohexane to cyclohexane:EtOAc=50:50) yielding title compound as a pale yellow oil (17.9 g, 86.4 mmol, 91.2% yield). MS/ESI⁺ 208.1. [MH]⁺, Rt=0.35 min (Method A).

Intermediate A2 ethyl 2-[hydroxy(5-methylpyridin-2-yl)methyl]prop-2-enoate

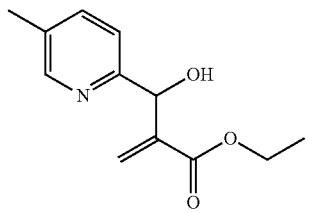 [SMILES: C=C(C(=O)OCC)C(O)c1ccc(C)cn1]

Prepared similarly to intermediate A1 starting from 5-methylpyridine-2-carbaldehyde (1.0 g, 8.25 mmol) in a mixture of dioxane/water 1/1 (70 mL), stirring at RT for 3 h, and purified by flash chromatography on silica gel Biotage SNAP cartridge (cyclohexane:EtOAc=80:20 to 50:50) yielding title compound as a pale yellow solid (0.862 g, 3.89 mmol, 47% yield). MS/ESI⁺ 222.1 [MH]⁺, Rt=0.39 min (Method A).

Intermediate A3 ethyl 2-{hydroxy[5-(trifluoromethyl)pyridin-2-yl]methyl}prop-2-enoate

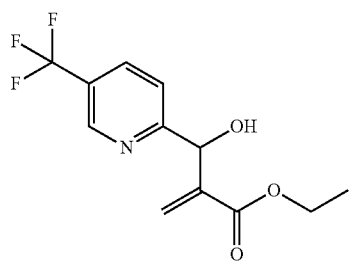 [SMILES: C=C(C(=O)OCC)C(O)c1ccc(C(F)(F)F)cn1]

Prepared similarly to intermediate A1, starting from 5-(trifluoromethyl)pyridine-2-carbaldehyde (3.66 mmol), and stirring at RT overnight, and purified by flash chromatography on silica gel Biotage cartridge (cyclohexane to cyclohexane:EtOAc=70:30) yielding title compound as a pale yellow oil (0.450 g, 1.64 mmol, 45% yield). MS/ESI⁺ 276.1 [MH]⁺, Rt=0.88 min (Method A).

Intermediate A4 ethyl 2-[(3-fluoropyridin-2-yl)(hydroxy)methyl]prop-2-enoate

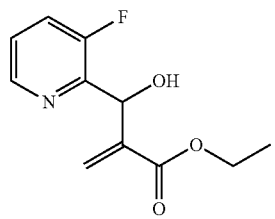 [SMILES: C=C(C(=O)OCC)C(O)c1ncccc1F]

Prepared similarly to intermediate A1 starting from 3-fluoropyridine-2-carbaldehyde (0.5 g, 4.0 mmol) stirring at r.t. for 1.5 h, and purified by flash chromatography on silica gel Biotage SNAP cartridge (cyclohexane:EtOAc=70:30 to 50:50) to afford title compound (0.900 g, 4.00 mmol, quantitative yield). MS/ESI⁺ 226.0 [MH]⁺, Rt=0.62 min (Method A).

Intermediate A5

2-[hydroxy(pyridin-2-yl)methyl]prop-2-enenitrile

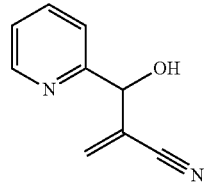

To a solution of pyridine-2-carbaldehyde (4.72 g, 44 mmol) in acrylonitrile (17.4 mL, 264 mmol), DABCO (4.95 g, 44 mmol) was added and the resulting mixture was stirred at 0° C. for 30 minutes. The mixture was partitioned between Et₂O and water and the aqueous phase was extracted with Et₂O. The combined organic layers were dried over sodium sulfate, the solvent was removed and the crude was purified by flash chromatography on silica gel Biotage SNAP cartridge (cyclohexane to cyclohexane:EtOAc=50:50) yielding title compound as a white solid (5.88 g, 4.7 mmol, 83% yield). MS/ESI⁺ 161.0 [MH]⁺, Rt=0.35 min (Method A).

Intermediate A6

2-[hydroxy(6-methylpyridin-2-yl)methyl]prop-2-enenitrile

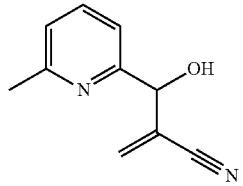

Prepared similarly to intermediate A5, starting from 6-methylpyridine-2-carbaldehyde (1.211 g, 10 mmol), and purified by flash chromatography on silica gel Biotage SNAP cartridge (cyclohexane:EtOAc=80:20 to 50:50) yielding title compound as a white solid (1.0 g, 5.75 mmol, 57% yield). MS/ESI$^+$ 175.0 [MH]$^+$, Rt=0.33 min (Method A).

Intermediate A8 ethyl 2-[(4-chloropyridin-2-yl)(hydroxy)methyl]prop-2-enoate

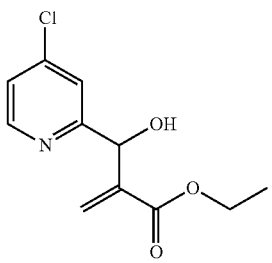 [SMILES: C=C(C(=O)OCC)C(O)c1cc(Cl)ccn1]

Prepared similarly to intermediate A1 starting from 4-chloropyridine-2-carbaldehyde (1.0 g, 7.06 mmol) stirring at r.t. for 2 h, and purified by flash chromatography on silica gel Biotage SNAP cartridge (cyclohexane to cyclohexane:EtOAc=70:30) to afford title compound as a colorless oil (1.75 g, quantitative yield). MS/ESI$^+$ 242.1 [MH]$^+$, Rt=0.74 min (Method A).

Intermediate A9 ethyl 2-[hydroxy(4-methylpyridin-2-yl)methyl]prop-2-enoate

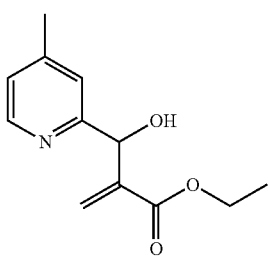 [SMILES: C=C(C(=O)OCC)C(O)c1cc(C)ccn1]

Prepared similarly to intermediate A1 starting from 4-methylpyridine-2-carbaldehyde (1.0 g, 8.26 mmol) stirring at r.t. overnight, and purified by flash chromatography on silica gel Biotage SNAP cartridge (cyclohexane to cyclohexane:EtOAc=50:50) to afford title compound as a yellow oil (0.970 g, 4.38 mmol, 53% yield). MS/ESI$^+$ 222.2 [MH]$^+$, Rt=0.39 min (Method A).

Intermediate A7

2-[hydroxy(3-methylpyridin-2-yl)methyl]prop-2-enenitrile

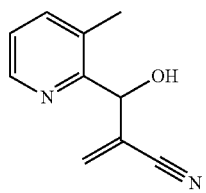

Prepared similarly to intermediate A5, starting from 3-methylpyridine-2-carbaldehyde (0.500 g, 4.12 mmol), and purified by flash chromatography on silica gel Biotage cartridge SNAP (cyclohexane:EtOAc=80:20 to 70:30) yielding title compound as a white solid (0.380 g, 2.18 mmol, 53% yield). MS/ESI$^+$ 175.0 [MH]$^+$, Rt=0.31 min (Method A).

Intermediate B1 ethyl indolizine-2-carboxylate

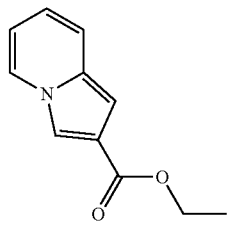

A solution of ethyl 2-[hydroxy(pyridin-2-yl)methyl]prop-2-enoate A1 (17.9 g, 86.4 mmol) in acetic anhydride (150 mL) was split in ten vials and heated under MW irradiation at 130° C. for 45 minutes (each one). The batches were combined, the volatiles were removed under reduced pressure and the crude was partitioned between EtOAc and aqueous sat. NaHCO$_3$. The aqueous phase was extracted with EtOAc and the combined organic layers were washed with brine and dried over sodium sulfate. The solvent was evaporated and the crude was purified by flash chromatography on silica gel (340 g) Biotage SNAP column (cyclohexane to cyclohexane:EtOAc=90:10) to afford title compound as a white-yellow solid (10.91 g, 57.6 mmol, 67% yield). MS/ESI$^+$ 190.1 [MH]$^+$, Rt=0.99 min (Method A).

Intermediate B2 ethyl 6-methylindolizine-2-carboxylate

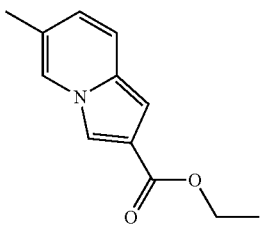

Prepared similarly to intermediate B1, starting from ethyl 2-[hydroxy(5-methylpyridin-2-yl)methyl]prop-2-enoate A2 (0.860 g, 3.88 mmol) and acetic anhydride (6.6 mL), heating under MW irradiation at 130° C. for 1 h. The crude was purified by flash chromatography on silica gel Biotage SNAP cartridge (cyclohexane:EtOAc=95:5 to 80:20) affording title compound as a light-yellow solid (0.410 g, 2.01 mmol, 52% yield). MS/ESI$^+$ 204.1 [MH]$^+$, Rt=1.12 min (Method A).

Intermediate B3 ethyl 6-(trifluoromethyl)indolizine-2-carboxylate

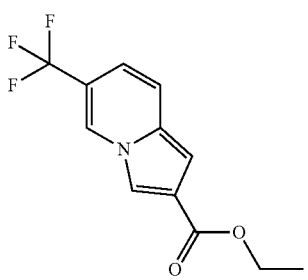 [SMILES: CCOC(=O)c1cc2ccc(C(F)(F)F)cn2c1]

A solution of ethyl 2-{hydroxy[5-(trifluoromethyl)pyridin-2-yl]methyl}prop-2-enoate A3 (0.450 g, 1.64 mmol) in acetic anhydride (5 mL) was heated at 130° C. overnight. The volatiles were removed under reduced pressure and the crude was partitioned between EtOAc and aqueous sat. NaHCO$_3$; the aqueous phase was extracted with EtOAc and the combined organic layers were washed with brine and dried over sodium sulfate. The solvent was removed under reduced pressure. The crude was purified by flash chromatography on Biotage silica gel cartridge (cyclohexane to cyclohexane:EtOAc=85:15) to afford title compound (0.240 g, 0.933 mmol, 60% yield). MS/ESI$^+$ 258.1 [MH]$^+$, Rt=1.19 min (Method A).

Intermediate B4 ethyl 8-fluoroindolizine-2-carboxylate

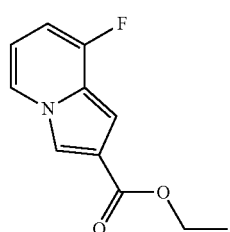

A solution of ethyl 2-[(3-fluoropyridin-2-yl)(hydroxy)methyl]prop-2-enoate A4 (0.900 g, 4.00 mmol) in acetic anhydride (7 mL) was heated under MW irradiation at 130° C. for 45 min. The volatiles were removed under reduced pressure and the crude was partitioned between EtOAc and sat. NaHCO$_3$. The aqueous phase was extracted with EtOAc and the combined organic layers were washed with brine and dried over sodium sulfate. The solvent was evaporated and the crude was purified by flash chromatography on silica gel Biotage SNAP cartridge (cyclohexane:EtOAc=90:10 to 80:20) affording title compound (0.228 g, 1.10 mmol). Crude starting intermediate A4 was recovered and further reacted in acetic anhydride (3 mL) heating under MW irradiation at 130° C. for 45 min. The solvent was removed and the residue was purified by flash chromatography on silica gel (25 g) Biotage SNAP cartridge (cyclohexane:EtOAc=90:10 to 80:20) to afford title compound (0.230 g, 1.11 mmol). The two batches were combined to give the title compound (0.458 g, 2.21 mmol, 55% yield overall). MS/ESI$^+$ 208.0 [MH]$^+$, Rt=1.05 min (Method A).

Intermediate B5 indolizine-2-carbonitrile

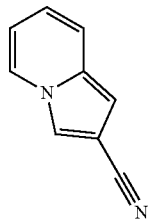 [SMILES: N#Cc1cc2ccccn2c1]

Prepared similarly to intermediate B1, starting from 2-[hydroxy(pyridin-2-yl)methyl]prop-2-enenitrile A5 (5.88 g, 36.7 mmol) in acetic anhydride (62.5 mL), heating under MW irradiation at 130° C. for 1.5 h, and purified by flash chromatography on silica gel Biotage SNAP cartridge (cyclohexane to cyclohexane:EtOAc=90:10) affording title compound as a yellow solid (2.588 g, 18.2 mmol, 50% yield). MS/ESI$^+$ 143.0 [MH]$^+$, Rt=0.88 min (Method A).

Intermediate B6

5-methylindolizine-2-carbonitrile

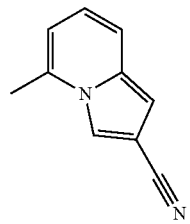

Prepared similarly to intermediate B1, starting from 2-[hydroxy(6-methylpyridin-2-yl)methyl]prop-2-enenitrile A6 (1.0 g, 5.74 mmol) and acetic anhydride (8 mL), heating under MW irradiation at 130° C. for 2.5 h. The crude was purified by flash chromatography on silica gel Biotage SNAP cartridge (cyclohexane:EtOAc=95:5) to afford title compound as a white solid (0.567 g, 3.63 mmol, 63% yield). MS/ESI$^+$ 157.0 [MH]$^+$, Rt=0.98 min (Method A).

Intermediate B7

8-methylindolizine-2-carbonitrile

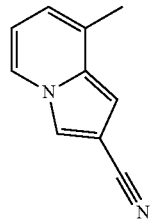

Prepared similarly to intermediate B1, starting from 2-[hydroxy(3-methylpyridin-2-yl)methyl]prop-2-enenitrile A7 (0.380 g, 2.18 mmol) and acetic anhydride (3.8 mL), heating under MW irradiation at 130° C. for 1 h. The crude was purified by flash chromatography on silica gel Biotage SNAP cartridge (cyclohexane:EtOAc=95:5) affording title compound as a white solid (0.245 g, 1.56 mmol, 72% yield). MS/ESI$^+$ 157.0 [MH]$^+$, Rt=0.99 min (Method A).

Intermediate B8 pyrrolo[1,2-b]pyridazine-6-carboxylic acid

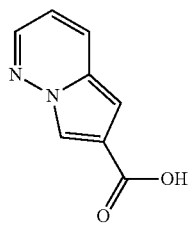 [SMILES: O=C(O)c1cc2cccnn2c1]

7-tert-butyl 5,6-dimethyl pyrrolo[1,2-b]pyridazine-5,6,7-tricarboxylate, prepared accordingly to the procedure reported in *J. Mat. Chem.*, 1999, 9, 2183-2188, which is incorporated herein by reference in its entirety, (3.25 g, 9.72 mmol) was suspended in a solution of KOH (2.727 g, 48.6 mmol) in water (12 mL) and the reaction was heated at 60° C. overnight. The mixture was acidified by addition of aqueous conc. HCl (9.41 mL) until pH=1 and stirred at 80° C. overnight. After cooling to room temperature the precipitated was collected by filtration to afford title compound (1.52 g, 9.37 mmol, 96% yield). MS/ESI$^+$ 163.1 [MH]$^+$, Rt=0.61 min (Method A).

Intermediate B9 methyl pyrrolo[1,2-b]pyridazine-6-carboxylate

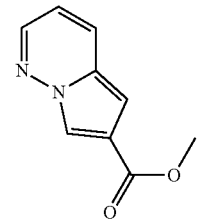

To a solution of pyrrolo[1,2-b]pyridazine-6-carboxylic acid B8 (1.52 g, 9.37 mmol) in MeOH (110 mL), concentrated sulfuric acid (6 drops) was added and the mixture was stirred at 80° C. for 6 h. The solvent was evaporated under reduced pressure and the residue was dissolved in DCM and washed with aqueous sat. NaHCO$_3$. The organic phase was dried over sodium sulfate, the solvent was removed and the crude was purified by flash chromatography on Biotage silica gel SNAP cartridge (cyclohexane:EtOAc=85:15 to 80:20) to afford title compound (1.0 g, 5.67 mmol, 61% yield). MS/ESI$^+$ 177.1 [MH]$^+$, Rt=0.81 min (Method A).

Intermediate B10 ethyl 7-chloroindolizine-2-carboxylate

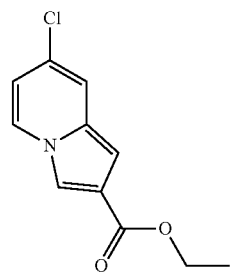

Here and in the following examples when the title compound was obtained by combining crude obtained from more than 1 synthetic batch (e.g. 2 batches), the amount of any precursor in each batch was sometimes indicated as a sum in parenthesis (e.g. amount precursor in batch 1+amount precursor in batch 2).

The crudes from the individual batches were finally mixed in a "combined crude" and a total yield over the two (or more) batches was reported.

A solution of ethyl 2-[(4-chloropyridin-2-yl)(hydroxy)methyl]prop-2-enoate A8 (0.500 g+1.25 g) in acetic anhydride (5 mL+7 mL) was heated at 120° C. for 1 h. The volatiles were removed under reduced pressure and the crude was partitioned between EtOAc and aqueous sat. NaHCO₃; the aqueous phase was extracted with EtOAc and the combined organic layers were washed with brine and dried over sodium sulfate. The solvent was removed under reduced pressure.

Combined crude was purified by flash chromatography on Biotage silica gel cartridge (cyclohexane to cyclohexane: EtOAc=90:10) to afford title compound (1.07 g, 4.78 mmol). MS/ESI⁺ 224.2 [MH]⁺, Rt=1.15 min (Method A).

Intermediate B11 ethyl 7-methylindolizine-2-carboxylate

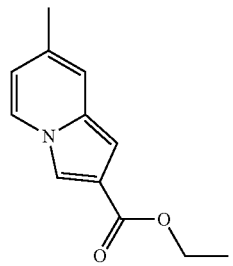

Prepared similarly to intermediate B10 starting from ethyl 2-[hydroxy(4-methylpyridin-2-yl)methyl]prop-2-enoate A9 (0.7500.850 g, 3.393.842 mmol+0.100 g, 0.452 mmol) in acetic anhydride (98 mL+1 mL) and purified by flash chromatography on Biotage silica gel cartridge (cyclohexane to cyclohexane:EtOAc=50:50) to afford title compound as a white solid (0.280 g, 1.38 mmol, 36% yield). MS/ESI⁺ 204.1 [MH]⁺, Rt=1.12 min (Method A).

Intermediate BA1

4-[(6-chloropyridin-2-yl)methyl]morpholine

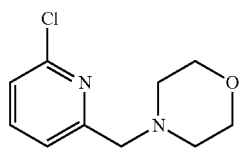

To a solution of 6-chloropyridine-2-carbaldehyde (1.0 g, 7.06 mmol) in DCM (28 mL), morpholine (0.93 mL, 10.59 mmol) and 30 drops of AcOH were added. The mixture was stirred overnight at room temperature and then Na(OAc)₃BH (2.24 g, 10.59 mmol) was added and the mixture was stirred for 6 h. The reaction was quenched with sat. NaHCO₃, the organic layer was separated, washed with brine, dried over sodium sulfate and concentrated to afford title compound as a pale yellow oil (1.45 g, 6.82 mmol, 97%).

¹H NMR (400 MHz, CHLOROFORM-d) δ ppm 7.60-7.76 (m, 1 H), 7.41 (d, 1 H), 7.22 (d, 1 H), 3.70-3.79 (m, 4 H), 3.65 (s, 2 H), 2.49-2.58 (m, 4 H).

Intermediate BA2

4-[(2-chloropyridin-4-yl)methyl]morpholine

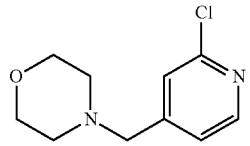 [SMILES: Clc1cc(CN2CCOCC2)ccn1]

Prepared similarly to intermediate BA1 starting from 2-chloropyridine-4-carbaldehyde (1.0 g, 7.06 mmol) and morpholine (0.93 mL, 10.59 mmol) to afford title compound as a pale yellow oil (1.4 g, 6.58 mmol, 93% yield).

1H NMR (400 MHz, CHLOROFORM-d) δ ppm 8.32 (d, 1 H), 7.34-7.37 (m, 1 H), 7.22 (d, 1 H), 3.70-7.77 (m, 4 H), 3.49 (s, 2 H), 2.42-2.50 (m, 4 H)

Intermediate BA3

[(2-chloropyridin-4-yl)methyl]dimethylamine

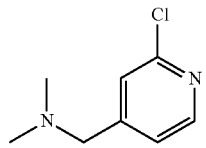

Prepared similarly to intermediate BA1 starting from 2-chloropyridine-4-carbaldehyde (1.0 g, 7.06 mmol) and 2M dimethylamine in THF (5.30 mL, 10.59 mmol) to afford title compound as a pale yellow oil (1.20 g, 7.03 mmol, 99% yiled).

1H NMR (400 MHz, DMSO-d6) δ ppm 8.68 (d, 1 H), 7.75 (s, 1 H), 7.66-7.70 (m, 1 H), 3.78 (s, 2 H), 2.50 (s, 6 H)

Intermediate BA4

2-chloro-5-(pyrrolidin-1-ylmethyl)pyridine

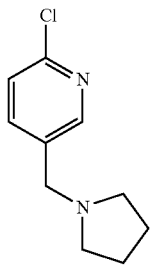 [SMILES: Clc1ccc(CN2CCCC2)cn1]

Prepared similarly to intermediate BA1 starting from 6-chloropyridine-3-carbaldehyde (1.0 g, 7.06 mmol) and pyrrolidine (0.88 mL, 10.59 mmol) and purified by flash chromatography on Biotage silica-NH cartridge (cyclohexane to cyclohexane:EtOAc=90:10) to afford title compound as a colorless oil (0.972 g, 4.94 mmol, 70% yield).

1H NMR (400 MHz, CHLOROFORM-d) δ ppm 8.32 (d, 1 H), 7.70-7.79 (m, 1 H), 7.30 (d, 1 H), 3.65 (s, 2 H), 2.49-2.62 (m, 4 H), 1.77-1.89 (m, 4 H).

Intermediate BA5

1-[(6-chloropyridin-3-yl)methyl]-4-methylpiperazine

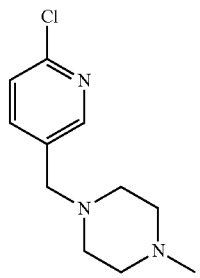

Prepared similarly to intermediate BA1 starting from 6-chloropyridine-3-carbaldehyde (3.0 g, 21.19 mmol) and 1-methylpiperazine (4.7 mL, 42.38 mmol) to afford title compound as an orange oil (4.8 g) which was used without purification.

1H NMR (400 MHz, DMSO-d6) δ ppm 8.30 (d, 1 H), 7.76 (dd, 1 H), 7.47 (d, 1 H), 3.48 (s, 2 H), 2.21-2.44 (m, 8 H), 2.14 (s, 3 H).

Intermediate BA6

1-[(6-chloropyridin-2-yl)methyl]-4-methylpiperazine

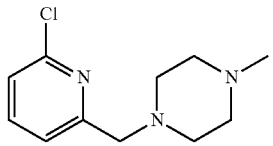

Prepared similarly to intermediate BA1 starting from 6-chloropyridine-2-carbaldehyde (1.0 g, 7.06 mmol) and 1-methylpiperazine (1.18 mL, 10.6 mmol) to afford title compound as a pale yellow oil (1.54 g, 6.82 mmol, 97% yield).

1H NMR (400 MHz, DMSO-d6) δ ppm 7.80-7.85 (m, 1 H), 7.42 (d, 1 H), 7.38 (d, 1 H), 3.54 (s, 2 H), 2.20-2.48 (m, 8 H), 2.15 (s, 3 H).

Intermediate BA7

1-[(2-chloropyridin-4-yl)methyl]-4-methylpiperazine

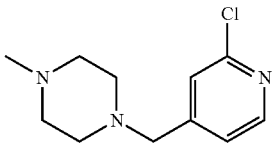

Prepared similarly to intermediate BA1 starting from 2-chloropyridine-4-carbaldehyde (1.0 g, 7.06 mmol) and 1-methylpiperazine (1.18 mL, 10.6 mmol) to afford title compound as a pale yellow oil (1.37 g, 6.07 mmol, 86% yield).

1H NMR (400 MHz, CHLOROFORM-d) δ ppm 8.29-8.33 (m, 1 H), 7.33-7.36 (m, 1 H), 7.18-7.23 (m, 1 H), 3.50 (s, 2 H), 2.33-2.65 (m, 8 H), 2.31 (s, 3 H).

Intermediate BA8

2-chloro-5-[(2,2,3,3,11,11,12,12-octamethyl-4,10-dioxa-7-aza-3,11-disilatridecan-7-yl)methyl]pyridine

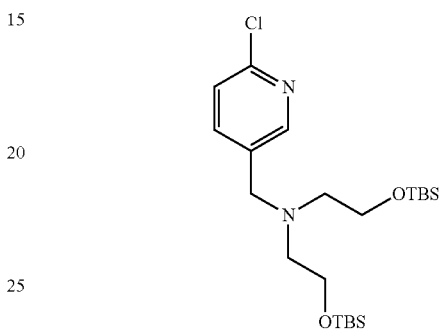

Step 1: 2-{[(6-chloropyridin-3-yl)methyl](2-hydroxyethyl)amino}ethan-1-ol BA8a

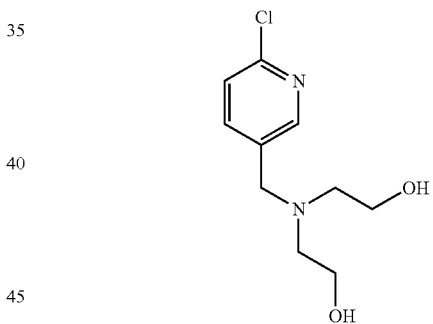

Prepared similarly to intermediate BA1 starting from 6-chloropyridine-3-carbaldehyde (1.2 g, 8.48 mmol) and 2-[(2-hydroxyethyl)amino]ethan-1-ol (1.22 mL, 12.72 mmol) and purified by flash chromatography on Biotage silica-NH cartridge (DCM to DCM:MeOH=98:2) to afford title compound as a colorless oil (0.680 g).

1H NMR (400 MHz, DMSO-d6) δ ppm 8.35 (d, 1 H), 7.83 (dd, 1 H), 7.45 (d, 1 H), 4.37 (t, 2 H), 3.67 (s, 2 H), 3.40-3.48 (m, 4 H), 2.52 (t, 4 H)

Step 2: 2-chloro-5-[(2,2,3,3,11,11,12,12-octamethyl-4,10-dioxa-7-aza-3,11-disilatridecan-7-yl)methyl] pyridine BA8

2-{[(6-Chloropyridin-3-yl)methyl](2-hydroxyethyl) amino}ethan-1-ol BA8a (0.880 g) was dissolved in DCM (10 mL); imidazole (1.3 g, 19.05 mmol) and tert-butyl (chloro)dimethylsilane (1.44 g, 9.53 mmol) were added and the mixture was stirred at r.t. overnight. The mixture was washed with water, then with brine, the organic phase was dried over sodium sulfate and the solvent was removed under reduced pressure. The crude was purified by flash chromatography on silica-NH Biotage column (cyclohexane to cyclohexane:EtOAc=95:5) to afford title compound as a colorless oil (1.3 g). MS/ESI⁺ 459.5 [MH]⁺, Rt=1.24 min (Method A).

Intermediate BA9

2-(3-bromophenyl)-1-methylpyrrolidine

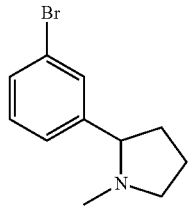

To a solution of 2-(3-bromophenyl)pyrrolidine (4.0 g, 17.69 mmol) in MeOH (120 mL), aqueous formaldehyde solution (37 wt. %) (2.63 mL, 35.38 mmol) and 20 drops of AcOH were added followed by Na(OAc)₃BH (7.5 g, 35.38 mmol) and the mixture was stirred at room temperature for 2 h. The mixture was then quenched with aqueous sat. NaHCO₃ and extracted with DCM; the organic layer was washed with brine, dried over Na₂SO₄ and concentrated to afford title compound as colorless oil (4.06 g, 16.91 mmol, 96% Yield).

1H NMR (400 MHz, DMSO-d6) δ ppm 7.49-7.51 (m, 1 H), 7.40-7.44 (m, 1 H), 7.25-7.34 (m, 2 H), 3.11-3.17 (m, 1 H), 3.07 (t, 1 H), 2.23 (q, 1 H), 2.10-2.20 (m, 1 H), 2.08 (s, 3 H), 1.68-1.88 (m, 2 H), 1.48-1.58 (m, 1 H).

Intermediate BA10

4-{2-[(6-chloropyridin-3-yl)oxy]ethyl}morpholine

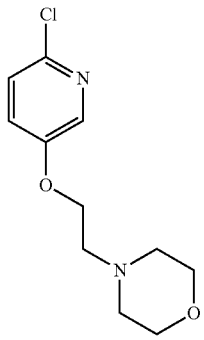 [SMILES: Clc1ccc(OCCN2CCOCC2)cn1]

To a stirred solution of PPh₃ (4.22 g, 16.1 mmol) in THF (55 mL) cooled at 0° C., DEAD 97% (3 mL, 16.1 mmol) was added and the mixture was stirred for 15 min. Then a solution of 4-(2-hydroxyethyl)morpholine (1.96 mL, 16.1 mmol) in THF (16 mL) was added followed by 2-chloro-5-hydroxypyridine (1.5 g, 11.5 mmol). The mixture was allowed to warm to room temperature and stirred for 4 h. The solvent was removed and the residue was purified by flash chromatography on Biotage silica-NH SNAP cartridge (cyclohexane to cyclohexane:EtOAc=70:30) to afford a title compound a pink oil (2.722 g, 11.2 mmol, 97% yield). MS/ESI⁺ 243.3 [MH]⁺, Rt=0.71 min (Method J).

Intermediate BA11

[(3-chlorophenyl)methyl]dimethylamine

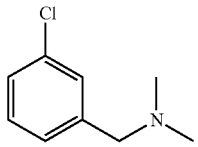

Prepared similarly to intermediate BA1 starting from 3-chlorobenzaldehyde (4.0 mL, 35.28 mmol) and 2M dimethylamine solution in THF (35.28 mL, 70.56 mmol) to afford title compound as a pale yellow oil (5.8 g, 34.18 mmol, 97% yield).

1H NMR (400 MHz, DMSO-d6) δ ppm 7.28-7.37 (m, 3 H), 7.22-7.27 (m, 1 H), 3.38 (s, 2 H), 2.14 (s, 6 H).

Intermediate BB1

4-{[4-(trimethylstannyl)-1,3-thiazol-2-yl]methyl}morpholine

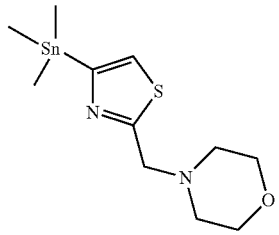 [SMILES: [CH3][Sn]([CH3])([CH3])[c]1csc(CN2CCOCC2)n1]

A mixture of 4-[(4-bromo-1,3-thiazol-2-yl)methyl]morpholine (prepared accordingly to the procedure reported in the patent US2009/143372 A1, which is incorporated herein by reference in its entirety, 2.18 g, 8.28 mmol), hexamethylditin (17.2 mL, 82.8 mmol) and Pd(PPh₃)₄ (0.957 g, 0.828 mmol) in toluene (83 mL) was heated at 100° C. for 3 h. The solvent was removed under reduced pressure and the residue was purified by flash chromatography on silica-NH Biotage cartridge (cyclohexane to cyclohexane:EtOAc=90:10) to afford title compound as a yellow oil (2.18 g, 6.28 mmol, 76% yield). MS/ESI⁺ 349.1 [MH]⁺, Rt=0.59 min (Method A).

Intermediate C ethyl 3-chloroindolizine-2-carboxylate

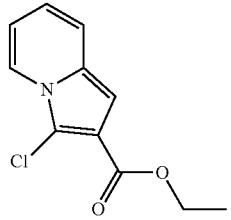

Ethyl indolizine-2-carboxylate B1 (2.00 g, 10.5 mmol) and N-chlorosuccinimide (1.69 g, 12.7 mmol) were dissolved in MeCN (320 mL) and the reaction was stirred for 30 min at room temperature. The mixture was concentrated under reduced pressure, the residue was diluted with water and extracted with EtOAc. The organic layer was dried over sodium sulfate, filtered and concentrated. The crude was purified by flash chromatography on silica gel Biotage SNAP cartridge (cyclohexane to cyclohexane:EtOAc=90:10); a further purification by reverse phase flash chromatography on 60 g Biotage C-18 cartridge. ($H_2O$+0.1% $HCOOH$:$CH_3CN$+0.1% $HCOOH$=95:5 to 50:50) was required to afford title compound as a yellow green oil (1.642 g, 7.34 mmol, 70% yield). MS/ESI$^+$ 224.1 [MH]$^+$, Rt=1.17 min (Method A).

Intermediate D ethyl 3-iodoindolizine-2-carboxylate

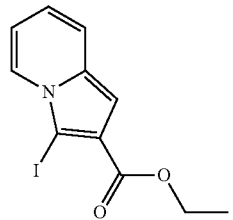

Ethyl indolizine-2-carboxylate B1 (0.400 g, 2.11 mmol) and N-iodosuccinimide (0.523 g, 2.3 mmol) were dissolved in MeCN (65 mL) and the reaction was stirred for 30 min at 0° C. The reaction mixture was diluted with DCM and washed with aqueous sodium thiosulfate. The resulting organic phase was dried over sodium sulfate, filtered and concentrated under reduced pressure. The crude was purified by flash chromatography on silica gel Biotage SNAP cartridge (cyclohexane to cyclohexane:EtOAc=90:10) to afford title compound as a yellow oil (0.626 g, 1.98 mmol, 94% yield). MS/ESI$^+$ 316.1 [MH]$^+$, Rt=1.21 min (Method A).

Intermediate DA1 ethyl 3-formylindolizine-2-carboxylate

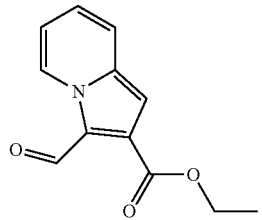 [SMILES: CCOC(=O)c1cc2ccccn2c1C=O]

A solution of POCl$_3$ (4.07 mL, 44.85 mmol) in DMF (146 mL) was stirred at 0° C. for 1 h. To a stirred solution of ethyl indolizine-2-carboxylate B1 (5.000 g, 26.4 mmol) in dry DCM (588 mL), ⅔ of the previously prepared POCl$_3$ solution in DMF (1.1 eq.) was added at 0° C. After being stirred at RT for 1 h, the reaction mixture was quenched with aqueous sat. NaHCO$_3$ (350 mL) and diluted with DCM (200 mL). The organic layer was washed with water (300 mL), dried over sodium sulfate and concentrated under reduced pressure. The residue was purified by flash chromatography on silica gel Biotage SNAP cartridge (cyclohexane to cyclohexane:EtOAc=80:20) to afford title compound as a yellow-green solid (4.342 g, 19.99 mmol, 76% yield). MS/ESI$^+$ 218.0 [MH]$^+$, Rt=0.99 min (Method A).

Intermediate DA2 ethyl 1-cyano-3-formylindolizine-2-carboxylate

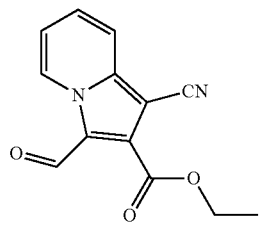 [SMILES: CCOC(=O)c1c(C#N)c2ccccn2c1C=O]

Prepared similarly to intermediate DA1 starting from ethyl 1-cyanoindolizine-2-carboxylate (prepared as reported in Journal of the Chemical Society, 1965, 2948-2951, which is incorporated herein by reference in its entirety, 1.4 g, 6.1 mmol), and purified by flash chromatography on silica gel Biotage SNAP cartridge (cyclohexane to cyclohexane:EtOAc=50:50) to afford title compound as a light-yellow solid (1.21 g, 4.99 mmol, 81% yield). MS/ESI$^+$ 243.2 [MH]$^+$, Rt=0.97 min (Method A).

Intermediate DB ethyl 3-acetylindolizine-2-carboxylate

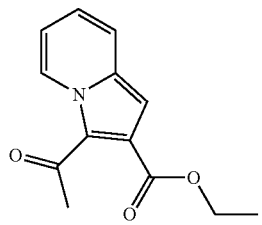 [SMILES: CCOC(=O)c1cc2ccccn2c1C(C)=O]

A solution of ethyl indolizine-2-carboxylate B1 (2.0 g, 10.5 mmol) and sodium acetate (4.3 g, 52.5 mmol) in acetic anhydride (60 mL) was heated at 140° C. overnight. Additional sodium acetate (1 eq) was added and the reaction was stirred at same temperature for further 4 h. The reaction was diluted with EtOAc and washed with water and brine. The aqueous phase was extracted with EtOAc and the combined organic layers were dried over sodium sulfate. The solvent was evaporated and the crude was purified by flash chromatography on silica gel Biotage column (cyclohexane to cyclohexante:EtOAc=90:10) affording title compound as a yellow solid (1.78 g, 7.7 mmol, 73% yield). MS/ESI$^+$ 232.2 [MH]$^+$, Rt=1.03 min (Method A).

Intermediate E methyl 7-bromopyrrolo[1,2-b]pyridazine-6-carboxylate

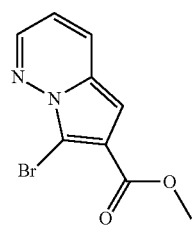

Methyl pyrrolo[1,2-b]pyridazine-6-carboxylate B9 (0.500 g, 2.83 mmol) and N-bromosuccinimide (0.606 g, 3.4 mmol) were dissolved in MeCN (85.5 mL) and the reaction was stirred for 30 min at RT. The mixture was concentrated under reduced pressure, the residue was diluted with water and extracted with EtOAc. The organic layer was washed with a saturated solution of sodium thiosulfate, dried over anhydrous sodium sulfate, filtered and concentrated. The crude was purified by reverse phase flash chromatography on Biotage C18 cartridge (H$_2$O+0.1% HCOOH:MeCN+0.1% HCOOH=90:10 to 50:50) to afford title compound as a pale yellow solid (0.425 g, 1.66 mmol, 58% yield). MS/ESI$^+$ 255.0-257.0 [MH]$^+$, Rt=0.91 min (Method A).

Intermediate F ethyl 1-bromoindolizine-2-carboxylate

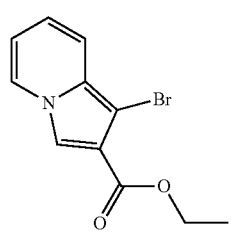

0.5 M Bromine in DCM (9.5 mL, 4.75 mmol) was slowly added to a solution of ethylindolizine-2-carboxylate B1 (1.00 g, 5.28 mmol) in DCM at −78° C. After 0.5 h the reaction was quenched with water; the organic phase was separated, washed with aqueous 10% sodium thiosulfate and dried over sodium sulfate. The volatiles were removed under reduced pressure and the crude mixture was purified by flash chromatography on a silica gel Biotage SNAP cartridge (cyclohexane:EtOAc=95:5) affording title compound as a white-yellow solid (0.908 g, 3.38 mmol, 64% yield). This intermediate was stored at −20° C. under nitrogen atmosphere. MS/ESI$^+$ 268.0-270.0 [MH]$^+$, Rt=1.13 min (Method A).

Intermediate FA ethyl 1-iodoindolizine-2-carboxylate

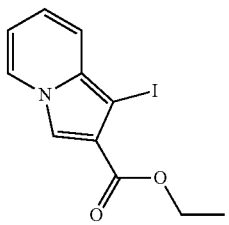

To a solution of ethyl 1-bromoindolizine-2-carboxylate F (0.700 g, 2.61 mmol) in anhydrous DMF (7 ml), KI (1.299 g, 7.84 mmol) and CuI (1.490 g, 7.84 mmol) were added and the mixture was stirred at 130° C. overnight. The mixture was cooled to RT, diluted with EtOAc and washed with aqueous 10% sodium thiosulfate. The organic phase was washed with brine, dried over sodium sulfate and concentrated; the residue was purified by flash chromatography on silica gel Biotage column (cyclohexane:EtOAc=98:2 to 95:5) affording title compound as a white-yellow solid (0.595 g) which was stored at −20° C. under nitrogen atmosphere. MS/ESI$^+$ 316.1 [MH]$^+$, Rt=1.24 min (Method A).

Intermediate G ethyl 1-methylindolizine-2-carboxylate

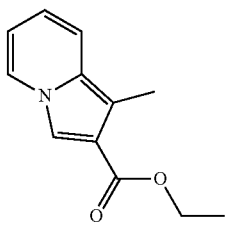

Ethyl 1-bromoindolizine-2-carboxylate F (1.156 g, 4.31 mmol) was split in three vials; trimethylboroxine (0.390 ml, 2.87 mmol), potassium carbonate (0.597 g, 4.32 mmol), Pd(PPh$_3$)$_4$ (0.173 g 0.15 mmol) and 4.4 mL of dioxane/H$_2$O (10/1) were added in each vial at RT, the mixtures were degassed and then heated at 110° C. overnight. The mixtures were combined and extracted with DCM; the organic phase was washed with brine, dried over sodium sulfate, filtered and concentrated under reduced pressure. The crude was purified by flash chromatography on silica gel Biotage SNAP cartridge (cyclohexane to cyclohexane:EtOAc=95:5) to afford title compound (0.396 g, 1.95 mmol, 45% yield). MS/ESI$^+$ 204.1 [MH]$^+$, Rt=1.14 min (Method A).

Intermediate GA ethyl 1-(trifluoromethyl)indolizine-2-carboxylate

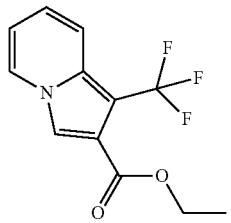 [SMILES: CCOC(=O)c1cn2ccccc2c1C(F)(F)F]

KF (0.369 g, 6.38 mmol) and CuI (1.214 g, 6.38 mmol) were thoroughly mixed in a Schlenk tube and flame heated under gentle shaking at reduced pressure until a greenish color appeared. Ethyl 1-iodoindolizine-2-carboxylate FA (0.670 g), anhydrous DMF (2.7 mL) and NMP (2.7 ml) were added followed by trimethyl(trifluoromethyl)silane (0.943 ml, 6.38 mmol) and the slurry solution was stirred at RT overnight. The mixture was quenched with water and extracted with $Et_2O$, the organic phase was washed with brine, dried over sodium sulphate, filtered and concentrated under reduced pressure. The residue was purified by flash chromatography on silica gel Biotage column (cyclohexane:EtOAc=95:5 to 90:10) to afford title compound (0.360 g, 1.4 mmol). MS/ESI+ 258.2 [MH]+, Rt=1.17 min (Method A).

Intermediate H1 ethyl 3-phenylindolizine-2-carboxylate

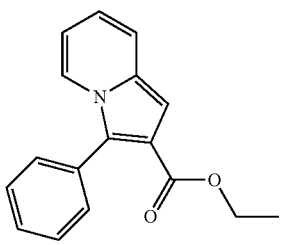 [SMILES: CCOC(=O)c1cc2ccccn2c1-c1ccccc1]

Ethyl indolizine-2-carboxylate B1 (0.500 g, 2.645 mmol), bromobenzene (0.338 mL, 3.175 mmol), KOAc (0.519 g, 5.29 mmol) and $Pd(PPh_3)_2Cl_2$ (0.093 g, 0.132 mmol) in NMP (5.3 mL) were reacted under nitrogen at 100° C. for 10 min, then water (0.095 mL, 5.29 mmol) was added and the reaction was further stirred for 6.5 h. Additional bromobenzene (0.170 mL, 1.59 mmol) was added followed by $Pd(PPh_3)_2Cl_2$ (0.045 g, 0.064 mmol) and the mixture was stirred at that temperature overnight. Further $Pd(PPh_3)_2Cl_2$ (0.045 g, 0.064 mmol) was added and the heating was continued for 3 h. The mixture was cooled to room temperature and then partitioned between EtOAc and brine. The organic phase was washed several times with brine and dried over sodium sulfate. The solvent was removed under reduced pressure and the crude was purified by flash chromatography on Biotage silica gel SNAP column (cyclohexane to cyclohexane:EtOAc=95:5) to afford title compound as a yellow solid (0.477 g, 1.80 mmol, 68% yield). MS/ESI+ 266.1 [MH]+, Rt=1.25 min (Method B).

Intermediate H2 ethyl 3-(pyridin-2-yl)indolizine-2-carboxylate

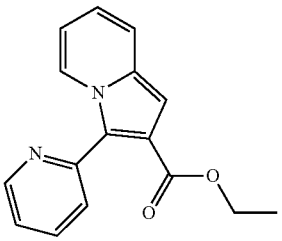 [SMILES: CCOC(=O)c1cc2ccccn2c1-c1ccccn1]

A mixture of ethyl indolizine-2-carboxylate B1 (0.567 g, 3.00 mmol), $Pd(OAc)_2$ (0.034 g, 0.15 mmol), tricyclopentylphosphine tetrafluoroborate (0.098 g, 0.30 mmol) and $Cs_2CO_3$ (2.932 g, 9.00 mmol) was flushed with nitrogen and toluene (5.5 mL) was added followed by 2-chloropyridine (0.568 mL, 6.00 mmol). The mixture was stirred at RT for 10 min and then heated at 130° C. overnight. Additional $Pd(OAc)_2$ (0.034 g, 0.15 mmol) and tricyclopentylphosphine tetrafluoroborate (0.098 g, 0.30 mmol) were added at RT followed by 2-chloropyridine (0.085 mL, 0.9 mmol) and the reaction was heated at 130° C. for further 24 h. The mixture was diluted with DCM and filtered through a celite pad. The filtrate was evaporated to dryness and the crude was purified by flash chromatography on Biotage silica gel SNAP cartridge (cyclohexane to cyclohexane:EtOAc=85:15) yielding title compound as a yellow solid (0.555 g, 2.08 mmol, 69% yield). MS/ESI+ 267.1 [MH]+, Rt=0.91 min (Method A).

Intermediate H3 ethyl 3-(3-fluorophenyl)indolizine-2-carboxylate

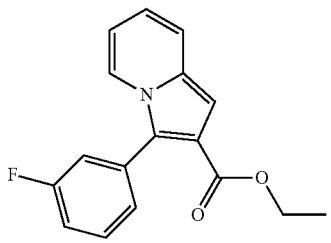 [SMILES: CCOC(=O)c1cc2ccccn2c1-c1cccc(F)c1]

Prepared similarly to intermediate H2 starting from ethyl indolizine-2-carboxylate B1 (0.200 g, 1.06 mmol), $Pd(OAc)_2$ (0.012 g, 0.053 mmol), tricyclopentylphosphine tetrafluoroborate (0.035 g, 0.106 mmol), $Cs_2CO_3$ (1.036 g, 3.18 mmol), toluene (3 mL) and 1-bromo-3-fluorobenzene (0.236 mL, 2.12 mmol), at 130° C. for 20 h. Additional tricyclopentylphosphine tetrafluoroborate (0.035 g, 0.106 mmol), $Pd(OAc)_2$ (0.012 g, 0.053 mmol) and 1-bromo-3-fluorobenzene (0.080 mL, 0.716 mmol) were added and the reaction was heated at the same temperature for further 4 h. After work-up the crude was purified by flash chromatography on silica gel Biotage SNAP cartridge (cyclohexane to cyclohexane:EtOAc=95:5) to afford title compound as a yellow oil (0.255 g, 0.900 mmol, 85% yield). MS/ESI+ 284.1 [MH]+, Rt=1.26 min (Method B).

Intermediate H4 ethyl 3-(2-fluorophenyl)indolizine-2-carboxylate

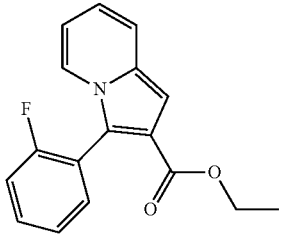 [SMILES: CCOC(=O)c1cc2ccccn2c1-c1ccccc1F]

Prepared similarly to intermediate H2, using ethyl indolizine-2-carboxylate B1 (0.500 g, 2.643 mmol), Pd(OAc)$_2$ (0.030 g, 0.132 mmol), tricyclopentylphosphine tetrafluoroborate (0.086 g, 0.265 mmol), Cs$_2$CO$_3$ (2.583 g, 7.935 mmol), toluene (5.2 mL) and 1-chloro-2-fluorobenzene (0.555 mL, 5.29 mmol), at 130° C. for 40 h. The crude was purified by flash chromatography on Biotage silica gel SNAP cartridge (cyclohexane to cyclohexane:EtOAc=95:5) to give title compound as a pale yellow oil (0.640 g, 2.26 mmol, 85% yield). MS/ESI$^+$ 284.1 [MH]$^+$, Rt=1.22 min (Method A).

Intermediate H5 ethyl 3-(2-methylphenyl)indolizine-2-carboxylate

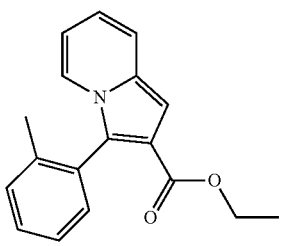 [SMILES: CCOC(=O)c1cc2ccccn2c1-c1ccccc1C]

Prepared similarly to intermediate H2, using ethyl indolizine-2-carboxylate B1 (0.500 g, 2.645 mmol), Pd(OAc)$_2$ (0.030 g, 0.132 mmol), tricyclopentylphosphine tetrafluoroborate (0.086 g, 0.265 mmol), Cs$_2$CO$_3$ (2.583 g, 7.935 mmol), toluene (5.2 mL) and 2-chlorotoluene (0.618 mL, 5.29 mmol), at 130° C. overnight. After work-up the crude was purified by flash chromatography on Biotage silica gel SNAP cartridge (cyclohexane to cyclohexane:EtOAc=90: 10) to give title compound as a pale yellow oil (0.770 g). MS/ESI$^+$ 280.2 [MH]$^+$, Rt=1.32 min (Method A).

Intermediate H6 ethyl 3-(pyridin-3-yl)indolizine-2-carboxylate

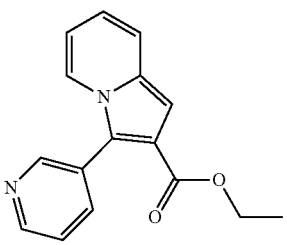 [SMILES: CCOC(=O)c1cc2ccccn2c1-c1cccnc1]

Prepared similarly intermediate H2, using ethyl indolizine-2-carboxylate B1 (0.300 g, 1.585 mmol), Pd(OAc)$_2$ (0.018 g, 0.079 mmol), tricyclopentylphosphine tetrafluoroborate (0.052 g, 0.158 mmol), Cs$_2$CO$_3$ (1.549 g, 4.755 mmol), toluene (1.8 mL) and 3-chloropyridine (0.302 mL, 3.171 mmol), at 130° C. overnight. After work-up the crude was purified by flash chromatography on Biotage silica gel cartridge (cyclohexane:EtOAc=90:10 to 50:50) to afford title compound as a pale yellow oil (0.346 g, 1.299 mmol, 82% yield). MS/ESI$^+$ 267.1 [MH]$^+$, Rt=0.81 min (Method A).

Intermediate H7 ethyl 3-(pyrazin-2-yl)indolizine-2-carboxylate

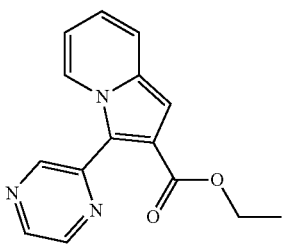 [SMILES: CCOC(=O)c1cc2ccccn2c1-c1cnccn1]

Prepared similarly to intermediate H2, using ethyl indolizine-2-carboxylate B1 (0.300 g, 1.585 mmol), Pd(OAc)$_2$ (0.018 g, 0.079 mmol), tricyclopentylphosphine tetrafluoroborate (0.052 g, 0.158 mmol), Cs$_2$CO$_3$ (1.549 g, 4.755 mmol), toluene (3 mL) and 2-chloropyrazine (0.283 mL, 3.171 mmol), at 130° C. overnight. Additional Pd(OAc)$_2$ (0.018 g, 0.079 mmol), tricyclopentylphosphine tetrafluoroborate (0.052 g, 0.158 mmol) and 2-chloropyrazine (0.283 mL, 3.171 mmol) were added continuing the heating for further 24 h. Additional Pd(OAc)$_2$ (0.018 g, 0.079 mmol), tricyclopentylphosphine tetrafluoroborate (0.052 g, 0.158 mmol) and 2-chloropyrazine (0.283 mL, 3.171 mmol) were added heating at the same temperature for further 48 h. After work-up the crude was purified by flash chromatography on Biotage silica SNAP gel cartridge (cyclohexane:EtOAc=90: 10 to 70:30) to afford title compound as a yellow solid (0.100 g, 0.374 mmol, 24% yield). MS/ESI$^+$ 268.1 [MH]$^+$, Rt=0.98 min (Method A).

Intermediate H8 ethyl 3-(pyridin-4-yl)indolizine-2-carboxylate

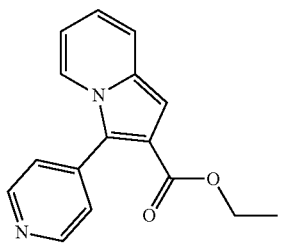 [SMILES: CCOC(=O)c1cc2ccccn2c1-c1ccncc1]

Prepared similarly to intermediate H2, using ethyl indolizine-2-carboxylate B1 (0.250 g, 1.32 mmol), Pd(OAc)$_2$ (0.015 g, 0.066 mmol), tricyclopentylphosphine tetrafluoroborate (0.043 g, 0.132 mmol), Cs$_2$CO$_3$ (1.290 g, 3.96 mmol), toluene (2.5 mL) and 4-chloropyridine (0.300 g, 2.64 mmol), at 130° C. overnight. Additional Pd(OAc)$_2$ (0.015 g, 0.066 mmol) and tricyclopentylphosphine tetrafluoroborate (0.043 g, 0.132 mmol) were added continuing the heating for further 24 h. After work-up the crude was purified by flash chromatography on Biotage silica SNAP gel cartridge (cyclohexane to cyclohexane:EtOAc=50:50) to afford title compound as a yellow solid (0.250 g, 0.939 mmol, 71% yield). MS/ESI$^+$ 267.2 [MH]$^+$, Rt=0.66 min (Method A).

Intermediate H9 ethyl 6-methyl-3-(pyridin-2-yl)indolizine-2-carboxylate

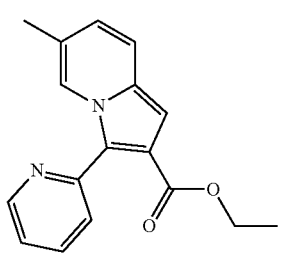 [SMILES: CCOC(=O)c1cc2ccc(C)cn2c1-c1ccccn1]

Prepared similarly to intermediate H2, using ethyl 6-methylindolizine-2-carboxylate B2 (0.410 g, 2.01 mmol), Pd(OAc)$_2$ (0.045 g, 0.201 mmol), tricyclopentylphosphine tetrafluoroborate (0.131 g, 0.402 mmol), Cs$_2$CO$_3$ (1.964 g, 6.03 mmol), toluene (3.5 mL) and 2-chloropyridine (0.380 mL, 4.02 mmol), at 130° C. overnight. Additional Pd(OAc)$_2$ (0.045 g, 0.201 mmol) and tricyclopentylphosphine tetrafluoroborate (0.131 g, 0.402 mmol) were added at RT and the mixture was heated at 130° C. for further 2 h. After work-up, the crude was purified by flash chromatography on Biotage silica-NH cartridge (cyclohexane:EtOAc=95:5 to 90:10) to afford title compound as a light-yellow solid (0.115 g, 0.41 mmol, 20% yield). MS/ESI$^+$ 281.2 [MH]$^+$, Rt=1.00 min (Method A).

Intermediate H10 ethyl 3-(pyridin-2-yl)-6-(trifluoromethyl)indolizine-2-carboxylate

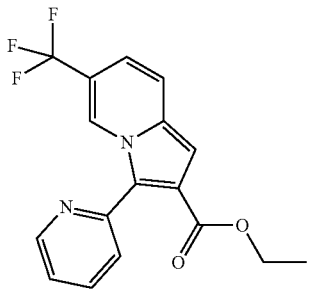 [SMILES: CCOC(=O)c1cc2ccc(C(F)(F)F)cn2c1-c1ccccn1]

Prepared similarly to intermediate H2, using ethyl 6-(trifluoromethyl)indolizine-2-carboxylate B3 (0.240 g, 0.933 mmol), Pd(OAc)$_2$ (0.011 g, 0.047 mmol), tricyclopentylphosphine tetrafluoroborate (0.030 g, 0.093 mmol), Cs$_2$CO$_3$ (0.912 g, 2.800 mmol), toluene (1.5 mL) and 2-chloropyridine (0.177 mL, 1.866 mmol), at 130° C. overnight. After work-up, the crude was purified by flash chromatography on Biotage silica gel cartridge (cyclohexane to cyclohexane:EtOAc=90:10) to afford title compound as a yellow solid (0.255 g, 0.763 mmol, 82% yield). MS/ESI$^+$ 335.2 [MH]$^+$, Rt=1.24 min (Method A).

Intermediate H11 ethyl 8-fluoro-3-(pyridin-2-yl)indolizine-2-carboxylate

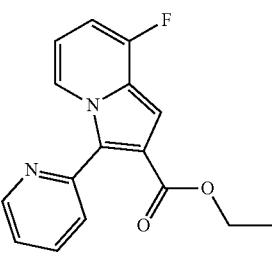 [SMILES: CCOC(=O)c1cc2c(F)cccn2c1-c1ccccn1]

Prepared similarly to intermediate H2, using ethyl 8-fluoroindolizine-2-carboxylate B4 (0.458 g, 2.21 mmol), Pd(OAc)$_2$ (0.025 g, 0.11 mmol), tricyclopentylphosphine tetrafluoroborate (0.073 g, 0.22 mmol), Cs$_2$CO$_3$ (2.160 g, 6.63 mmol), toluene (3 mL) and 2-chloropyridine (0.418 mL, 4.42 mmol), at 130° C. overnight. Additional Pd(OAc)$_2$ (0.050 g, 0.22 mmol) and tricyclopentylphosphine tetrafluoroborate (0.146 g, 0.44 mmol) were added at RT and the mixture was heated at 130° C. for further 24 h. After work-up, the crude was purified by flash chromatography on Biotage silica gel SNAP cartridge (cyclohexane to cyclohexane:EtOAc=85:15); a further purification by flash chromatography on Biotage silica gel SNAP cartridge (DCM: EtOAc=98:2) was required to obtain title compound as a pale yellow solid (0.140 g, 0.49 mmol, 22% yield). MS/ESI$^+$ 285.1 [MH]$^+$, Rt=1.05 min (Method A).

Intermediate H12 ethyl 1-methyl-3-(pyridin-2-yl)indolizine-2-carboxylate

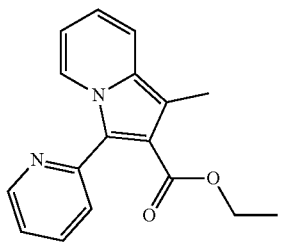 [SMILES: CCOC(=O)c1c(C)c2ccccn2c1-c1ccccn1]

Prepared similarly to intermediate H2, using ethyl 1-methylindolizine-2-carboxylate G (0.206 g, 0.96 mmol), Pd(OAc)$_2$ (0.011 g, 0.048 mmol), tricyclopentylphosphine tetrafluoroborate (0.031 g, 0.096 mmol), Cs$_2$CO$_3$ (0.938 g, 2.88 mmol), toluene (1.76 mL) and 2-chloropyridine (0.181 mL, 1.91 mmol), at 130° C. for 48 h. Additional Pd(OAc)$_2$ (0.011 g, 0.048 mmol) and tricyclopentylphosphine tetrafluoroborate (0.031 g, 0.096 mmol) were added at RT and the mixture was heated at 130° C. for further 48 h. After work-up, the crude was purified by flash chromatography on Biotage silica NH SNAP cartridge (cyclohexane:EtOAc=95:5) to afford title compound as a yellow solid (0.088 g, 0.31 mmol, 32% yield). MS/ESI$^+$ 281.2 [MH]$^+$, Rt=0.98 min (Method A).

Intermediate H13 ethyl 3-[5-(morpholin-4-ylmethyl)thiophen-2-yl]indolizine-2-carboxylate

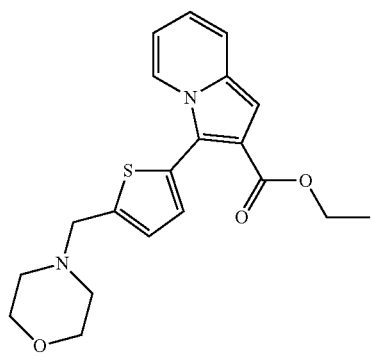 [SMILES: CCOC(=O)c1cc2ccccn2c1-c1ccc(CN2CCOCC2)s1]

To a solution of ethyl 3-chloroindolizine-2-carboxylate C (0.400 g, 1.79 mmol) in dioxane (14 mL) and water (1.79 mL), (5-(morpholinomethyl)-2-thiopheneboronic acid pinacol ester (1.217 g 3.93 mmol), potassium phosphate monobasic (0.487 g, 3.58 mmol), potassium phosphate tribasic (0.759 g, 3.58 mmol) and PdCl$_2$(dtbpf), (0.233 g 0.358 mmol) were added under nitrogen atmosphere at RT, the mixture was degassed and the reaction was heated at 65° C. overnight. The mixture was extracted with DCM, washed with brine, dried over sodium sulfate, filtered and concentrated under reduced pressure. The crude was purified by flash chromatography on silica-NH Biotage cartridge (cyclohexane to cyclohexane:EtOAc=80:20) to afford title compound as an orange oil (0.569 g, 1.53 mmol, 86%). MS/ESI$^+$ 371.2 [MH]$^+$, Rt=0.67 min (Method A).

Intermediate H14 ethyl 3-[4-(morpholin-4-ylmethyl)phenyl]indolizine-2-carboxylate

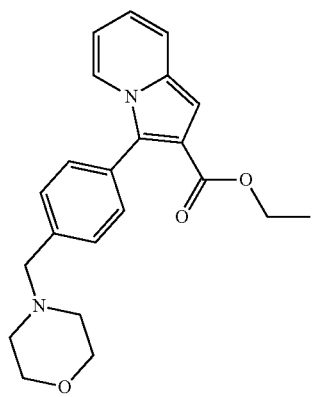 [SMILES: CCOC(=O)c1cc2ccccn2c1-c1ccc(CN2CCOCC2)cc1]

Prepared similarly to intermediate H13, starting from ethyl 3-chloroindolizine-2-carboxylate C (0.300 g, 1.34 mmol) and 4-(4-morpholinomethyl) phenylboronic acid pinacol ester (0.894 g, 2.95 mmol), at 65° C. for 18 h. The crude was purified by flash chromatography on silica gel Biotage SNAP cartridge (cyclohexane to cyclohexane:EtOAc=50:50) to afford title compound as a brown oil (0.488 g, 1.34 mmol, quantitative yield). MS/ESI$^+$ 365.3 [MH]$^+$, Rt=0.66 min (Method A).

Intermediate H15 ethyl 3-{4-[(dimethylamino)methyl]phenyl}indolizine-2-carboxylate

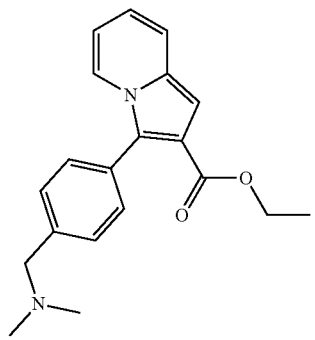 [SMILES: CCOC(=O)c1cc2ccccn2c1-c1ccc(CN(C)C)cc1]

Prepared similarly to intermediate H13, starting from ethyl 3-chloroindolizine-2-carboxylate C (0.300 g, 1.34 mmol) and dimethyl-[4-(4,4,5,5-tetramethyl-[1,3,2]dioxaborolan-2-yl)-benzyl]-amine (0.769 g, 2.95 mmol), at 65° C. overnight. The crude was purified by flash chromatography on silica-NH Biotage SNAP cartridge (cyclohexane to cyclohexane:EtOAc=80:20) to afford title compound as an orange oil (0.421 g, 1.30 mmol, 97%). MS/ESI$^+$ 323.3 [MH]$^+$, Rt=0.65 min (Method A).

Intermediate H16 ethyl 3-{3-[(dimethylamino)methyl]phenyl}indolizine-2-carboxylate

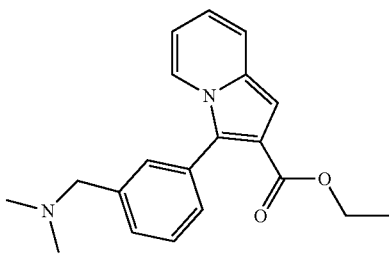 [SMILES: CCOC(=O)c1cc2ccccn2c1-c1cccc(CN(C)C)c1]

Prepared similarly to intermediate H13, starting from ethyl 3-chloroindolizine-2-carboxylate C (0.400 g, 1.79 mmol) and dimethyl({[3-(tetramethyl-1,3,2-dioxaborolan-2-yl)phenyl]methyl})amine (1.027 g, 3.93 mmol), at 65° C. overnight. The crude was purified by flash chromatography on silica-NH Biotage SNAP cartridge (cyclohexane to cyclohexane:EtOAc=80:20) to afford title compound as an orange oil (0.457 g, 1.42 mmol, 79% yield). MS/ESI$^+$ 323.3 [MH]$^+$, Rt=0.67 min (Method A).

Intermediate H17 ethyl 3-(3,6-dihydro-2H-pyran-4-yl)indolizine-2-carboxylate

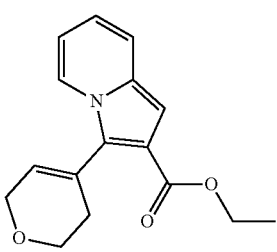 [SMILES: CCOC(=O)c1cc2ccccn2c1C1=CCOCC1]

Prepared similarly to intermediate H13 starting from ethyl 3-chloroindolizine-2-carboxylate C (0.150 g, 0.67 mmol) and 3,6-dihydro-2H-pyran-4-boronic acid pinacol ester (0.309 g 1.47 mmol), at 65° C. overnight. The crude was purified by flash chromatography on silica gel Biotage SNAP cartridge (cyclohexane to cyclohexane:EtOAc=95:5) to afford title compound as a yellow oil (0.106 g, 0.39 mmol, 58%). MS/ESI$^+$ 272.1 [MH]$^+$, Rt=1.10 min (Method A).

Intermediate H18 ethyl 3-{1-[(tert-butoxy)carbonyl]-1,2,3,6-tetrahydropyridin-4-yl}indolizine-2-carboxylate

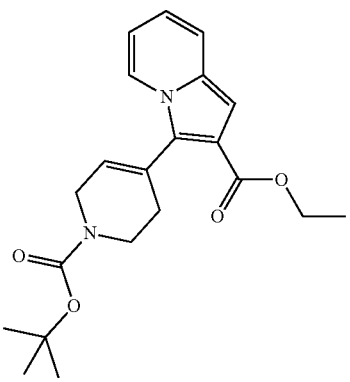 [SMILES: CCOC(=O)c1cc2ccccn2c1C1=CCN(C(=O)OC(C)(C)C)CC1]

Prepared similarly to intermediate H13 starting from 3-chloroindolizine-2-carboxylate C (0.300 g, 1.34 mmol) and N-Boc-1,2,3,6-tetrahydropyridine-4-boronic acid pinacol ester (0.912 g 2.95 mmol), at 65° C. for 18 h. The crude was purified by flash chromatography on silica gel Biotage SNAP cartridge (cyclohexane to cyclohexane:EtOAc=90:10) to afford title compound as a yellow oil (0.254 g, 0.68 mmol, 51%). MS/ESI$^+$ 371.3 [MH]$^+$, Rt=1.34 min (Method A).

Intermediate H19 ethyl 3-(1,3-thiazol-5-yl)indolizine-2-carboxylate

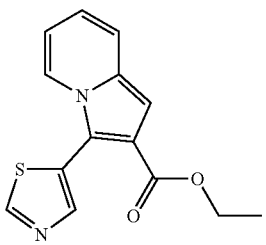 [SMILES: CCOC(=O)c1cc2ccccn2c1-c1cncs1]

To a solution of 3-iodoindolizine-2-carboxylate D (0.346 g, 1.1 mmol) in dioxane (4.1 ml) Pd(PPh$_3$)$_2$Cl$_2$ (0.077 g, 0.11 mmol) and 5-(tributylstannyl)-1,3-thiazole (0.617 g, 1.65 mmol) were added under nitrogen atmosphere and the mixture was heated at 65° C. overnight. Additional Pd(PPh$_3$)$_2$Cl$_2$ (0.077 g, 0.11 mmol) and 5-(tributylstannyl)-1,3-thiazole (0.205 g, 0.55 mmol) were added and the heating was continued at 65° C. for further 6 h. The mixture was cooled to room temperature, diluted with ethyl acetate and filtered through a Celite® pad. The filtrate was concentrated and the residue was purified by flash chromatography on silica gel Biotage SNAP cartridge (cyclohexane to cyclohexane:EtOAc=80:20) affording title compound as a yellow oil (0.169 g, 0.62 mmol, 57%). MS/ESI$^+$ 273.1 [MH]$^+$, Rt=1.04 min (Method A).

Intermediate H20 ethyl 3-(2-oxopyrrolidin-1-yl)indolizine-2-carboxylate

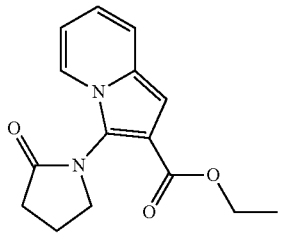 [SMILES: CCOC(=O)c1cc2ccccn2c1N1CCCC1=O]

A sealed tube was charged with CuI (0.010 g, 0.053 mmol), N,N'-dimethylethylenediamine (0.009 g 0.107 mmol), 2-pyrrolidinone (0.127 g 1.49 mmol) and Cs$_2$CO$_3$ (0.488 g, 1.49 mmol); ethyl 3-iodoindolizine-2-carboxylate D (0.337 g, 1.07 mmol) and anhydrous DMF (2.1 mL) were added and the reaction was heated at 65° C. overnight. Additional CuI iodide (0.010 g, 0.053 mmol) and N,N'-dimethylethylenediamine (0.009 g 0.107 mmol) were added and the reaction was heated at 65° C. for further 24 h. The mixture was allowed to cool to room temperature and diluted with DCM and water. The phases were separated, the aqueous phase was extracted with DCM and the combined organic layers were washed with brine, dried over sodium sulfate and evaporated. The crude was purified by flash chromatography on Biotage silica gel SNAP cartridge (cyclohexane to cyclohexane EtOAc=50:50) to afford title compound as a brown oil (0.127 g, 0.47 mmol, 43% yield). MS/ESI$^+$ 273.2 [MH]$^+$, Rt=0.88 min (Method A).

Intermediate H21 ethyl 3-(pent-1-yn-1-yl)indolizine-2-carboxylate

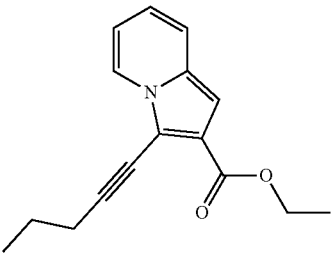 [SMILES: CCCC#Cc1c(C(=O)OCC)cc2ccccn12]

A mixture of ethyl 3-iodoindolizine-2-carboxylate D (0.626 g, 1.98 mmol), 1-pentyne (0.674 g, 9.9 mmol), CuI (0.132 g, 0.693 mmol) and diethylamine (2.23 mL, 21.58 mmol) in DMF (7.9 mL) was degassed, Pd(PPh$_3$)$_2$Cl$_2$ (0.236 g, 0.336 mmol) was added and the reaction was stirred at RT for 1 h. The mixture was diluted with EtOAc and filtered through a Celite® pad; the filtrate was washed with water and brine, then dried over sodium sulfate, filtered and concentrated. The crude was purified by flash chromatography on Biotage silica SNAP cartridge (cyclohexane to cyclohexane:EtOAc=95:5). A further purification by reverse phase flash chromatography on Biotage C18 cartridge (H$_2$O+0.1% HCOOH:CH$_3$CN+0.1% HCOOH=95:5 to 30:70) was required to afford title compound as a yellow oil (0.263 g, 1.03 mmol, 52% yield). MS/ESI$^+$ 256.2 [MH]$^+$, Rt=1.34 min (Method A).

Intermediate H22 ethyl 3-(3-hydroxyprop-1-yn-1-yl)indolizine-2-carboxylate

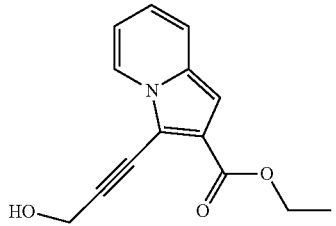 [SMILES: CCOC(=O)c1cc2ccccn2c1C#CCO]

Prepared similarly to intermediate H21, starting from ethyl 3-iodoindolizine-2-carboxylate D (0.688 g, 2.18 mmol) and propargyl alcohol (0.611 g, 10.9 mmol), stirring at RT for 30 minutes. After work-up the crude was purified by flash chromatography on Biotage silica gel cartridge (cyclohexane to cyclohexane:EtOAc=50:50) to afford title compound as a brown oil (0.332 g, 1.36 mmol, 63% yield). MS/ESI$^+$ 243.9 [MH]$^+$, Rt=0.90 min (Method A).

Intermediate H23 ethyl 3-(3-{[tris(propan-2-yl)silyl]oxy}prop-1-yn-1-yl)indolizine-2-carboxylate

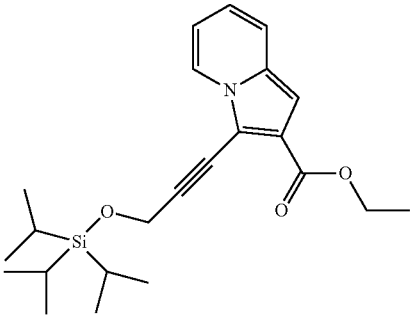 [SMILES: CCOC(=O)c1cc2ccccn2c1C#CCO[Si](C(C)C)(C(C)C)C(C)C]

To a stirred mixture of ethyl 3-(3-hydroxyprop-1-yn-1-yl)indolizine-2-carboxylate H22 (0.332 g, 1.36 mmol) and imidazole (0.231 g, 3.40 mmol) in DMF (1.6 mL), triisopropylsilyl chloride (0.270 g, 1.40 mmol) was added at r.t. and the reaction was stirred overnight. The mixture was diluted with EtOAc and washed with a saturated aqueous solution of NH$_4$Cl. The organic phase was dried over sodium sulfate, filtered and concentrated. The crude was purified by flash chromatography on Biotage silica gel SNAP cartridge (cyclohexane to cyclohexane:EtOAc=90:10) to afford title compound as a yellow oil (0.501 g, 1.25 mmol, 92% yield). MS/ESI$^+$ 400.3 [MH]$^+$, Rt=1.71 min (Method C).

Intermediate H24 ethyl 1-phenylindolizine-2-carboxylate

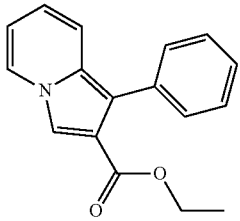 [SMILES: CCOC(=O)c1cn2ccccc2c1-c1ccccc1]

To a solution of ethyl 1-bromoindolizine-2-carboxylate F (0.780 g, 2.9 mmol) in dioxane/$H_2O$=10/1 (22.6 mL), phenylboronic acid (0.780 g, 6.38 mmol), potassium phosphate monobasic (0.790 g, 5.8 mmol), potassium phosphate tribasic (1.23 g, 5.8 mmol) and $PdCl_2$(dtbpf), (0.378 g 0.6 mmol) were added at RT, the mixture was degassed and the reaction was heated at 65° C. for 18 h. The mixture was diluted with DCM, washed with brine and dried over sodium sulfate; the solvent was removed under reduced pressure and the crude was purified by flash chromatography on silica gel Biotage SNAP cartridge (cyclohexane to cyclohexane:EtOAc=95:5) to afford title compound which was used in the next step without any additional purification (0.475 g, 1.79 mmol, 62% yield). MS/ESI$^+$ 266.1 [MH]$^+$, Rt=1.25 min (Method A).

Intermediate H25 ethyl 1-(3-fluorophenyl)indolizine-2-carboxylate

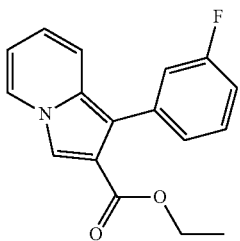 [SMILES: CCOC(=O)c1cn2ccccc2c1-c1cccc(F)c1]

Prepared similarly to intermediate H24, using ethyl 1-bromoindolizine-2-carboxylate F (0.700 g, 2.6 mmol) and (3-fluorophenyl)boronic acid (0.400 g 2.86 mmol), at 65° C. for 18 h. The crude was purified by flash chromatography on Biotage silica gel SNAP cartridge (cyclohexane to cyclohexane:EtOAc=95:15) to give title compound which was used without any additional purification (0.585 g, 2.06 mmol, 70% yield). MS/ESI$^+$ 284.1 [MH]$^+$, Rt=1.25 min (Method A).

Intermediate H26 ethyl 1-(2-methylphenyl)indolizine-2-carboxylate

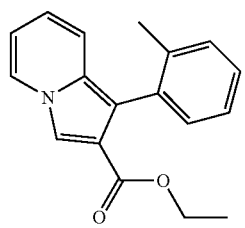 [SMILES: CCOC(=O)c1cn2ccccc2c1-c1ccccc1C]

Prepared similarly to intermediate H24, using ethyl 1-bromoindolizine-2-carboxylate F (0.500 g, 1.86 mmol of intermediate) and (2-methylphenyl)boronic acid (0.556 g 4.09 mmol), at 65° C. for 18 h, and purified by flash chromatography on silica gel Biotage SNAP cartridge (cyclohexane to cyclohexane:EtOAc=95:5) to yield title compound which was used without any additional purification (0.350 g, 1.25 mmol, 67% yield). MS/ESI$^+$ 280.1 [MH]$^+$, Rt=1.30 min (Method A).

Intermediate H27 ethyl 1-(pyridin-2-yl)indolizine-2-carboxylate

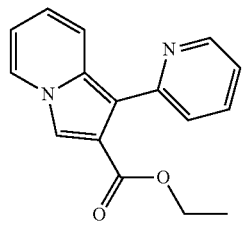 [SMILES: CCOC(=O)c1cn2ccccc2c1-c1ccccn1]

To a solution of ethyl 1-bromoindolizine-2-carboxylate F (1.4 g, 5.22 mmol) in toluene/MeOH=20/1 (25.27 mL), Pd(PPh$_3$)$_4$ (0.090 g, 0.078 mmol) and 2-(tributylstannyl)pyridine (2.53 mL, 7.83 mmol) were added under nitrogen atmosphere and the reaction was refluxed for 24 h. In a different flask, to a solution of ethyl 1-bromoindolizine-2-carboxylate F (0.100 g, 0.37 mmol) in toluene/MeOH=20/1 (1.84 mL), Pd(PPh$_3$)$_4$ (0.0043 g, 0.0037 mmol) and 2-(tributylstannyl)pyridine (0.121 mL, 0.37 mmol) were added under nitrogen atmosphere and the reaction was heated to reflux for 24 h. The two mixtures were cooled to room temperature, diluted with EtOAc, combined and filtered through a Celite® pad. The filtrate was concentrated and the resulting crude was purified by flash chromatography on silica gel Biotage SNAP cartridge (DCM to DCM:MeOH=96:4). A further purification by flash chromatography on silica gel-NH Biotage SNAP cartridge (cyclohexane to cyclohexane:EtOAc=60:40) was required to afford title compound (0.446 g, 1.67 mmol, 32% yield). MS/ESI$^+$ 267.1 [MH]$^+$, Rt=0.49 min (Method A).

Intermediate H28 methyl 7-(pyridin-2-yl)pyrrolo[1,2-b]pyridazine-6-carboxylate

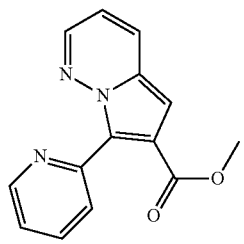 [SMILES: COC(=O)c1cc2cccnn2c1-c1ccccn1]

To a mixture of methyl 7-bromopyrrolo[1,2-b]pyridazine-6-carboxylate E (0.425 g, 1.66 mmol) in dioxane (6.15 mL), Pd(PPh$_3$)$_2$Cl$_2$ (0.116 g, 0.16 mmol) and 2-(tributylstannyl)pyridine (0.806 mL, 2.5 mmol) were added under nitrogen atmosphere and the reaction was heated at 90° C. for 16 h. The mixture was cooled to room temperature, diluted with EtOAc and filtered through a Celite® pad. The filtrate was concentrated and the residue was purified by flash chromatography on silica-NH Biotage cartridge (cyclohexane:EtOAc=80:20 to 50:50) to afford title compound (0.287 g, 1.13 mmol, 68% yield). MS/ESI$^+$ 254.2 [MH]$^+$, Rt=0.52 min (Method A).

Intermediates H29-51 found in the table below may be prepared from suitable intermediates reported below following similar procedures as for compound H2.

| Intermediate | Name and Molecular Structure | | Reagent | Analytical data |
|---|---|---|---|---|
| H29 | ethyl 7-chloro-3-(pyridin-2-yl)indolizine-2-carboxylate | | B10 and 2-chloropyridine | MS/ESI$^+$ 301.1 [MH]$^+$, Rt = 1.17 min (Method A). |
| H30 | ethyl 7-methyl-3-(pyridin-2-yl)indolizine-2-carboxylate | | B11 and 2-chloropyridine | MS/ESI$^+$ 281.2 [MH]$^+$, Rt = 1.03 min (Method A) |
| H31 | ethyl 3-(2-methylpyridin-4-yl)indolizine-2-carboxylate | | B1 and 4-chloro-2-methylpyridine | MS/ESI$^+$ 281.2 [MH]$^+$, Rt = 0.61 min (Method A) |

-continued

| Intermediate | Name and Molecular Structure | | Reagent | Analytical data |
|---|---|---|---|---|
| H32 | ethyl 3-[5-(morpholin-4-ylmethyl)pyridin-2-yl]indolizine-2-carboxylate | 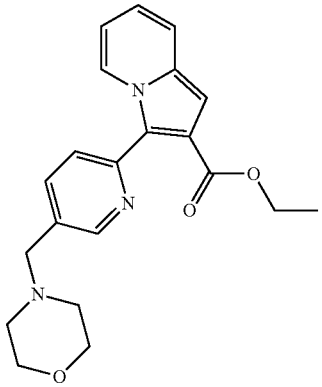 [SMILES: CCOC(=O)c1cc2ccccn2c1-c1ccc(CN2CCOCC2)cn1] | B1 and 4-[(6-chloropyridin-3-yl)methyl]-morpholine | MS/ESI+ 366.3 [MH]+, Rt = 0.58 min (Method A) |
| H33 | ethyl 3-{5-[(dimethylamino)methyl]pyridin-2-yl}indolizine-2-carboxylate | 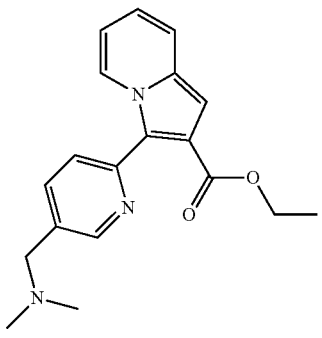 [SMILES: CCOC(=O)c1cc2ccccn2c1-c1ccc(CN(C)C)cn1] | B1 and (6-chloropyridin-3-yl)methyl]-dimethylamine | MS/ESI+ 324.2 [MH]+, Rt = 0.56 min (Method A) |
| H34 | ethyl 3-[6-(morpholin-4-ylmethyl)pyridin-2-yl]indolizine-2-carboxylate | 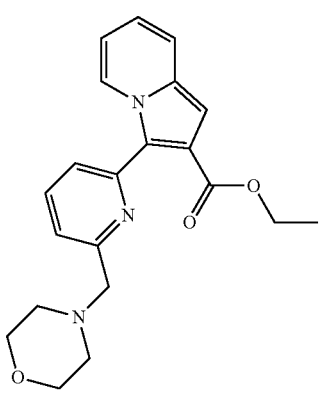 [SMILES: CCOC(=O)c1cc2ccccn2c1-c1cccc(CN2CCOCC2)n1] | B1 and 4-[(6-chloropyridin-2-yl)methyl]-morpholine BA1 | MS/ESI+ 366.4 [MH]+, Rt = 0.61 min (Method A) |
| H35 | ethyl 3-[4-(morpholin-4-ylmethyl)pyridin-2-yl]indolizine-2-carboxylate | 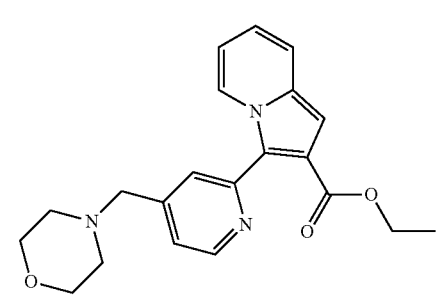 [SMILES: CCOC(=O)c1cc2ccccn2c1-c1cc(CN2CCOCC2)ccn1] | B1 and 4-[(2-chloropyridin-4-yl)methyl]-morpholine BA2 | MS/ESI+ 366.4 [MH]+, Rt = 0.59 min (Method A) |

-continued

| Intermediate | Name and Molecular Structure | Reagent | Analytical data |
|---|---|---|---|
| H36 | ethyl 3-{4-[(dimethylamino)methyl]pyridin-2-yl}indolizine-2-carboxylate | B1 and [(2-chloropyridin-4-yl)methyl]-dimethylamine BA3 | MS/ESI$^+$ 324.4 [MH]$^+$, Rt = 0.55 min (Method A) |
| H37 | ethyl 3-[5-(pyrrolidin-1-ylmethyl)pyridin-2-yl]indolizine-2-carboxylate | B1 and 2-chloro-5-(pyrrolidin-1-ylmethyl)-pyridine BA4 | MS/ESI$^+$ 350.2 [MH]$^+$, Rt = 0.59 min (Method A) |
| H38 | ethyl 3-{5-[(4-methylpiperazin-1-yl)methyl]pyridin-2-yl}indolizine-2-carboxylate | B1 and 1-[(6-chloropyridin-3-yl)methyl]-4-methylpiperazine BA5 | MS/ESI$^+$ 379.4 [MH]$^+$, Rt = 0.57 min (Method A) |
| H39 | ethyl 3-{6-[(4-methylpiperazin-1-yl)methyl]pyridin-2-yl}indolizine-2-carboxylate | B1 and 1-[(6-chloropyridin-2-yl)methyl]-4-methylpiperazine BA6 | MS/ESI$^+$ 379.4 [MH]$^+$, Rt = 0.59 min (Method A) |

-continued

| Intermediate | Name and Molecular Structure | Reagent | Analytical data |
|---|---|---|---|
| H40 | ethyl 3-{4-[(4-methylpiperazin-1-yl)methyl]pyridin-2-yl}indolizine-2-carboxylate | B1 and 1-[(2-chloropyridin-4-yl)methyl]-4-methylpiperazine BA7 | MS/ESI$^+$ 379.2 [MH]$^+$, Rt = 0.54 min (Method A) |
| H41 | ethyl 3-{5-[(2,2,3,3,11,11,12,12-octamethyl-4,10-dioxa-7-aza-3,11-disilatridecan-7-yl)methyl]pyridin-2-yl}indolizine-2-carboxylate | B1 and 2-chloro-5-[(2,2,3,3,11,11,12,12-octamethyl-4,10-dioxa-7-aza-3,11-disilatridecan-7-yl)methyl]-pyridine BA8 | MS/ESI$^+$ 612.6 [MH]$^+$, Rt = 1.29 min (Method A) |
| H42 | ethyl 3-[3-(1-methylpyrrolidin-2-yl)phenyl]indolizine-2-carboxylate | B1 and 2-(3-bromophenyl)-1-methylpyrrolidine BA9 | MS/ESI$^+$ 349.3 [MH]$^+$, Rt = 0.68 min (Method A) |
| H43 | ethyl 3-{5-[2-(morpholin-4-yl)ethoxy]pyridin-2-yl}indolizine-2-carboxylate | B1 and 4-{2-[(6-chloropyridin-3-yl)oxy]ethyl}-morpholine BA10 | MS/ESI$^+$ 396.5 [MH]$^+$, Rt = 1.08 min (Method J). |

-continued

| Intermediate | Name and Molecular Structure | Reagent | Analytical data |
|---|---|---|---|
| H44 | ethyl 3-(6-methoxypyridin-3-yl)indolizine-2-carboxylate | B1 and 5-chloro-2-methoxypyridine | MS/ESI$^+$ 297.3 [MH]$^+$, Rt = 1.17 min (Method A) |
| H45 | ethyl 3-(2-methoxypyridin-4-yl)indolizine-2-carboxylate | B1 and 4-chloro-2-methoxypyridine | MS/ESI$^+$ 297.2 [MH]$^+$, Rt = 1.15 min (Method A) |
| H46 | ethyl 3-(2-cyanophenyl)indolizine-2-carboxylate | B1 and 2-bromobenzonitrile | MS/ESI$^+$ 291.2 [MH]$^+$, Rt = 1.13 min (Method A) |
| H47 | ethyl 3-[5-(morpholine-4-carbonyl)pyridin-2-yl]indolizine-2-carboxylate | B1 and 4-(6-chloropyridine-3-carbonyl)-morpholine | MS/ESI$^+$ 380.4 [MH]$^+$, Rt = 0.93 min (Method A) |
| H48 | ethyl 3-(pyridin-2-yl)-1-(trifluoromethyl)indolizine-2-carboxylate | GA and 2-chloropyridine | MS/ESI$^+$ 335.3 [MH]$^+$, Rt = 1.22 min (Method A) |

| Intermediate | Name and Molecular Structure | Reagent | Analytical data |
|---|---|---|---|
| H49 | ethyl 1-cyano-3-(pyridin-2-yl)indolizine-2-carboxylate | 1-cyanoindolizine-2-carboxylate (prepared as reported in Journal of the Chemical Society, 1965, 2948-2951) and 2-chloropyridine | MS/ESI⁺ 292.2 [MH]⁺, Rt = 0.95 min (Method A) |
| H50 | ethyl 1-cyano-3-{3-[(dimethylamino)methyl]phenyl}indolizine-2-carboxylate | 1-cyanoindolizine-2-carboxylate (prepared as reported in Journal of the Chemical Society, 1965, 2948-2951) and [(3-chlorophenyl)methyl]-dimethylamine BA11 | 1H NMR (400 MHz, DMSO-d6) δ ppm 7.92-7.96 (m, 1 H), 7.73-7.77 (m, 1 H), 7.45-7.54 (m, 2 H), 7.37-7.41 (m, 2 H), 7.30-7.35 (m, 1 H), 6.95-7.00 (m, 1 H), 4.13 (q, 2 H), 3.46 (s, 2 H), 2.17 (s, 6 H), 1.06 (t, 3 H). |
| H51 | methyl 7-{3-[(dimethylamino)methyl]phenyl}pyrrolo[1,2-b]pyridazine-6-carboxylate | B9 and [(3-chlorophenyl)methyl]-dimethylamine BA11 | MS/ES⁺ 310.3 MH]⁺, Rt = 0.54 min (Method A) |

Intermediate H52 ethyl 3-(1,3-thiazol-4-yl)indolizine-2-carboxylate

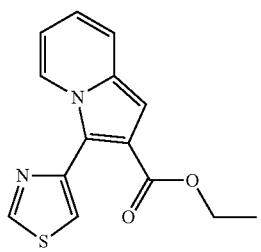 [SMILES: CCOC(=O)c1cc2ccccn2c1-c1cscn1]

Prepared similarly to intermediate H19 starting from 3-iodoindolizine-2-carboxylate D (1.00 g) and 4-(tributylstannyl)-1,3-thiazole (1.78 g, 4.76 mmol) at 65° C. overnight; additional Pd(PPh₃)₂Cl₂ and 4-(tributylstannyl)-1,3-thiazole (0.220 g) were added and the mixture was heated at 65° C. overnight. The crude was purified by flash chromatography on silica-NH Biotage column (cyclohexane to cyclohexane:EtOAc=85:15) to afford title compound (0.200 g, 0.734 mmol) as a brown solid. MS/ESI⁺ 273.3 [MH]⁺, Rt=1.08 min (Method A).

Intermediate H53 ethyl 3-[2-(morpholin-4-ylmethyl)-1,3-thiazol-4-yl]indolizine-2-carboxylate

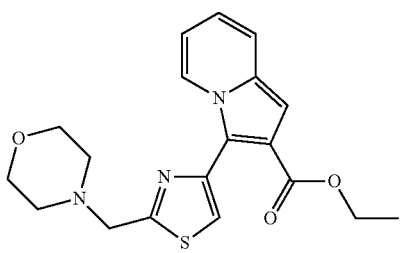 [SMILES: CCOC(=O)c1cc2ccccn2c1-c1csc(CN2CCOCC2)n1]

Prepared similarly to intermediate H19 starting from 3-iodoindolizine-2-carboxylate D (1.097 g+0.236 g) and 4-{[4-(trimethylstannyl)-1,3-thiazol-2-yl]methyl}morpholine BB1 (1.943 g, 5.6 mmol+0.432 g, 1.24 mmol), at 65° C. overnight. Additional Pd(PPh₃)₂Cl₂ and 4-{[4-(trimethylstannyl)-1,3-thiazol-2-yl]methyl}morpholine XX12 (0.230 g, 0.66 mmol) were added and the mixture was heated at 65° C. for further 48 h. The crude was purified by flash chromatography on silica-NH Biotage cartridge (cyclohexane to cyclohexane:EtOAc=90:10); the obtained product was dissolved in EtOAc, KF was added and the mixture was stirred at r.t. for 3 h. The mixture was filtered and the filtrate was concentrated under reduced pressure; the residue was further purified by flash chromatography on silica-NH Biotage cartridge (cyclohexane to cyclohexane:EtOAc=90:10) to afford title compound as a yellow oil (0.485 g). MS/ESI⁺ 372.3 [MH]⁺, Rt=0.76 min (Method A).

Intermediate H54 ethyl 3-[3-(dimethylamino)prop-1-yn-1-yl]indolizine-2-carboxylate

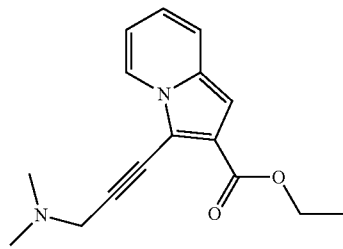 [SMILES: CCOC(=O)c1cc2ccccn2c1C#CCN(C)C]

Prepared similarly to intermediate H21, starting from ethyl 3-iodoindolizine-2-carboxylate D (0.800 g, 2.54 mmol) and 3-dimethylamino-1-propyne (1.37 mL, 12.69 mmol), stirring at RT for 1 h. After work-up the crude was purified by flash chromatography on Biotage silica-NH cartridge (cyclohexane to cyclohexane:EtOAc=50:50) to afford crude title compound as a dark yellow oil (0.687 g) which was used without any additional purification. MS/ESI⁺ 271.2 [MH]⁺, Rt=0.61 min (Method A).

Intermediate H55 ethyl 3-(4-methyl-2-oxopiperazin-1-yl)indolizine-2-carboxylate

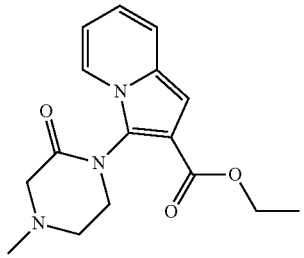 [SMILES: CCOC(=O)c1cc2ccccn2c1N1CCN(C)CC1=O]

A flask was charged with 3-iodoindolizine-2-carboxylate D (1.641 g), 1-methyl-3-oxopiperazine (0.594 g, 5.2 mmol), K₃PO₄ (2.207 g, 10.4 mmol) and Copper (I) iodide (0.050 g, 0.26 mmol), and the flask was purged and back-filled with N₂. Anhydrous DMF (4.9 mL) was added, followed by N,N'-dimethylethylenediamine (0.056 mL, 0.52 mmol) and the suspension was heated at 65° C. overnight. Additional Copper (I) iodide (0.050 g, 0.26 mmol), N,N'-dimethylethylenediamine (0.056 mL, 0.52 mmol) were added and the reaction was heated at 65° C. for further 24 h. The reaction mixture was allowed to cool to room temperature and diluted with EtOAc and water. The aqueous layer was extracted with EtOAc and the combined organic layers were washed with brine, dried over sodium sulfate and evaporated. The crude was purified by flash chromatography on Biotage silica-NH SNAP cartridge (cyclohexane to cyclohexane:EtOAc=50:50) to afford title compound as a yellow solid (0.694 g). MS/ESI⁺ 302.2 [MH]⁺, Rt=0.51 min (Method A).

Intermediate H56 ethyl 3-{1-[2-(dimethylamino)ethyl]-2-oxo-1,2-dihydropyridin-4-yl}indolizine-2-carboxylate and methyl 3-{1-[2-(dimethylamino)ethyl]-2-oxo-1,2-dihydropyridin-4-yl}indolizine-2-carboxylate

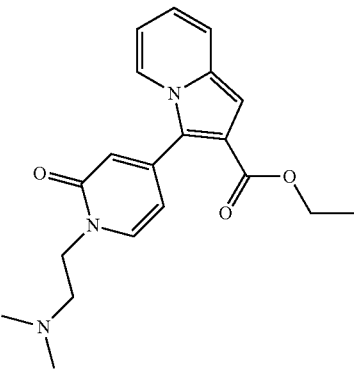

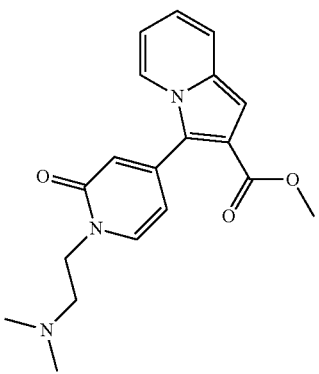

Step 1: ethyl 3-(2-hydroxypyridin-4-yl)indolizine-2-carboxylate H56a

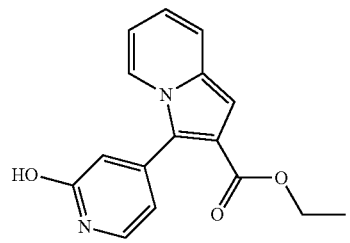 [SMILES: CCOC(=O)c1cc2ccccn2c1-c1ccnc(O)c1]

Iodotrimethylsilane (4.00 mL, 28.6 mmol) was added to a solution of ethyl 3-(2-methoxypyridin-4-yl)indolizine-2-carboxylate H45 (1.00 g, 3.37 mmol) in dry acetonitrile (59 mL) and the resulting mixture was heated at 60° C. for 3 h. Then, at that temperature, MeOH (59 mL) was added and stirring was carried out for further 15 minutes. After cooling to RT, the mixture was diluted with DCM and washed with an aqueous solution of $Na_2S_2O_5$ and then with brine. The organic phase was concentrated under reduce pressure to afford title compound as a yellow solid (0.951 g, 3.37 mmol, 100% yield). MS/ESI$^+$ 283.3 [MH]$^+$, Rt=0.85 min (Method A).

Step 2: ethyl 3-{1-[2-(dimethylamino)ethyl]-2-oxo-1,2-dihydropyridin-4-yl}indolizine-2-carboxylate and methyl 3-{1-[2-(dimethylamino)ethyl]-2-oxo-1,2-dihydropyridin-4-yl}indolizine-2-carboxylate H56

$K_2CO_3$ (1.78 g, 12.88 mmol) was added to a solution of ethyl 3-(2-hydroxypyridin-4-yl)indolizine-2-carboxylate H56a (0.800 g, 2.8 mmol) in acetone (42.0 mL) and the mixture was stirred at 50° C. for 2 h under nitrogen atmosphere. 2-Chloro-N,N-dimethylethylamine hydrochloride (1.209 g, 8.4 mmol) was added and the resulting mixture was stirred overnight at 50° C. Additional $K_2CO_3$ (1.16 g, 8.4 mmol) and 2-chloro-N,N-dimethylethylamine hydrochloride (0.806 g, 5.6 mmol), were added and the reaction was allowed to stir at the same temperature for further 24 h. The reaction mixture was diluted with MeOH and the solvents were removed; water was added and the mixture was extracted with DCM. The combined organic layers were dried over sodium sulfate, filtered and concentrated. The crude was purified by flash chromatography on Biotage silica-NH cartridge (DCM to DCM:EtOAc=80:20) to afford a mixture of ethyl 3-{1-[2-(dimethylamino)ethyl]-2-oxo-1,2-dihydropyridin-4-yl}-indolizine-2-carboxylate and methyl 3-{1-[2-(dimethylamino)ethyl]-2-oxo-1,2-dihydropyridin-4-yl}indolizine-2-carboxylate ($\approx$1:1 ratio) (0.621 g) which was used without any additional purification. MS/ESI$^+$ 354.3 and 340.3 [MH]$^+$, Rt=0.59 min and 0.53 min (Method A).

Intermediate H57 ethyl 3-(6-chloropyridazin-3-yl)indolizine-2-carboxylate

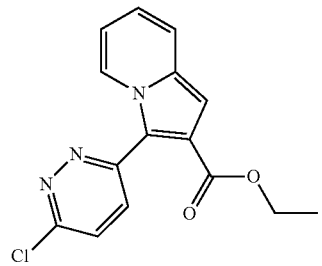 [SMILES: CCOC(=O)c1cc2ccccn2c1-c1ccc(Cl)nn1]

$AlCl_3$ (0.990 g, 7.42 mmol) was added to a solution of 3,6-dichloropyridazine (1.105 g, 7.42 mmol) in 1,2-dichloroethane (10 ml) and the mixture was stirred for 30 minutes at RT, then ethyl indolizine-2-carboxylate B1 (1.00 g, 5.3 mmol) was added and the mixture was stirred at 80° C. for 24 h. The reaction mixture was poured into ice and extracted with DCM. The organic layers were dried over sodium sulfate, the solvent was removed and the crude was purified by flash chromatography on Biotage silica gel cartridge (cyclohexane:EtOAc=95:5 to 80:20) to afford title compound as a pale yellow solid (0.425 g, 1.41 mmol, 26% yield). MS/ESI$^+$ 302.2 [MH]$^+$, Rt=1.09 min (Method A).

Intermediate H58 ethyl 3-(6-oxo-1,6-dihydropyridazin-3-yl)indolizine-2-carboxylate

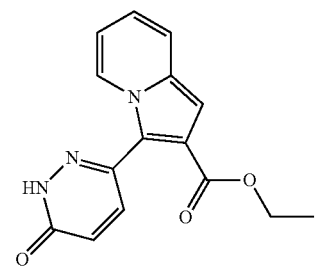 [SMILES: CCOC(=O)c1cc2ccccn2c1-c1ccc(=O)[nH]n1]

To a solution of ethyl 3-(6-chloropyridazin-3-yl)indolizine-2-carboxylate H57 (0.425 g, 1.4 mmol) in 22 ml of acetic acid, sodium acetate (0.231 g, 2.81 mmol) was added and the mixture was heated to reflux under stirring for 3 h. The reaction mixture was poured into cold water and extracted with DCM. The organic layers were dried over sodium sulfate and the solvent was removed to afford title compound as a pale orange solid which was used without any additional purification (0.395 g). MS/ESI$^+$ 284.2 [MH]$^+$, Rt=0.85 min (Method A).

Intermediate H59 ethyl 3-[1-(2-chloroethyl)-6-oxo-1,6-dihydro-pyridazin-3-yl]indolizine-2-carboxylate

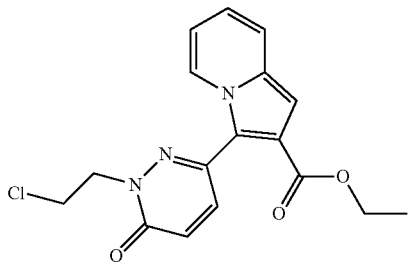 [SMILES: CCOC(=O)c1cc2ccccn2c1-c1ccc(=O)n(CCCl)n1]

Ethyl 3-(6-oxo-1,6-dihydropyridazin-3-yl)indolizine-2-carboxylate H58 (0.175 g) was dissolved in 2 ml of DMF, $K_2CO_3$ (0.389 g, 1.85 mmol) was added followed by 1-bromo-2-chloroethane (0.154 ml, 1.85 mmol) and the mixture was stirred at 60° C. for 2 h. The mixture was diluted with ethyl acetate, the solid was filtered-off and the filtrate was washed with brine. The organic phase was then dried over sodium sulfate, the solvent was removed and the crude was purified by flash chromatography on Biotage silica gel cartridge (cyclohexane:EtOAc=80:20 to 60:40) to afford title compound as a pale yellow solid (0.134 g). MS/ESI$^+$ 346.3 [MH]$^+$, Rt=1.08 min (Method A).

Intermediate H60 ethyl 3-{6-oxo-1-[2-(pyrrolidin-1-yl)ethyl]-1,6-dihydropyridazin-3-yl}indolizine-2-carboxylate

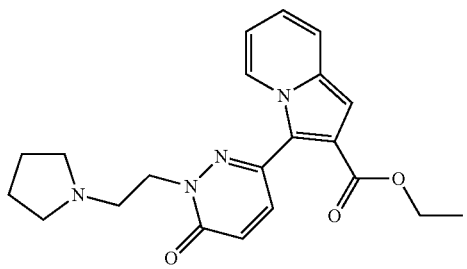 [SMILES: CCOC(=O)c1cc2ccccn2c1-c1ccc(=O)n(CCN2CCCC2)n1]

To a solution of ethyl 3-[1-(2-chloroethyl)-6-oxo-1,6-dihydropyridazin-3-yl]indolizine-2-carboxylate H59 (0.134 g) in acetonitrile (7 mL), KI (69.4 mg, 0.42 mmol) and $K_2CO_3$ (0.157 g, 1.14 mmol) were added followed by pyrrolidine (0.64 ml, 0.77 mmol) and the mixture was stirred at 85° C. for 4 h. The mixture was diluted with ethyl acetate, the solid was filtered-off and the filtrate was evaporated to dryness; the crude was purified by flash chromatography on Biotage silica gel cartridge (DCM to DCM:MeOH=95:5) to afford title compound as a pale yellow oil (0.114 g, 0.3 mmol). MS/ESI$^+$ 381.2 [MH]$^+$, Rt=0.60 min (Method A).

Intermediate H61 ethyl 3-{1-[2-(4-methylpiperazin-1-yl)ethyl]-6-oxo-1,6-dihydropyridazin-3-yl}indolizine-2-carboxylate

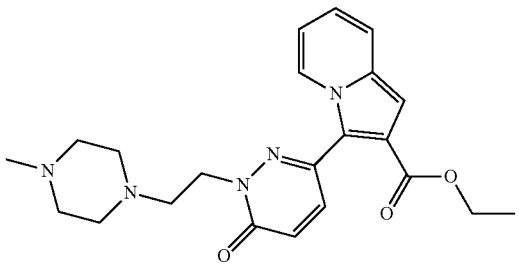 [SMILES: CCOC(=O)c1cc2ccccn2c1-c1ccc(=O)n(CCN2CCN(C)CC2)n1]

Prepared similarly to intermediate H60 starting from ethyl 3-[1-(2-chloroethyl)-6-oxo-1,6-dihydropyridazin-3-yl]indolizine-2-carboxylate H59 (0.193 g) and 1-methyl piperazine (0.125 ml, 1.12 mmol), at 85° C. for 5 h, and purified by flash chromatography on Biotage silica gel cartridge (DCM to DCM:MeOH=95:5) to afford title compound as a pale yellow oil (0.179 g, 0.43 mmol). MS/ESI$^+$ 410.4 [MH]$^+$, Rt=0.59 min (Method A).

Intermediate H62 ethyl 3-{1-[2-(morpholin-4-yl)ethyl]-6-oxo-1,6-dihydropyridazin-3-yl}indolizine-2-carboxylate

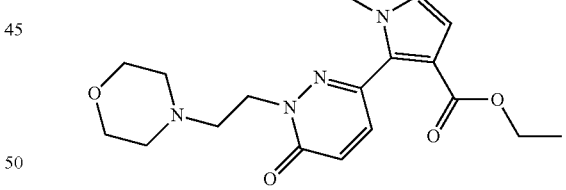

Ethyl 3-(6-oxo-1,6-dihydropyridazin-3-yl)indolizine-2-carboxylate H58 (0.202 g+0.043 g) was dissolved in 9.5 ml (+2 mL) of DMF, $K_2CO_3$ (0.3435 g, 2.48 mmol+0.0725 g, 0.52 mmol) was added followed by 4-(2-chloroethyl)morpholine hydrochloride (0.1725 g, 0.92 mmol+0.0335 g, 0.18 mmol) and the mixture was stirred at room temperature for 48 h. The mixture was diluted with ethyl acetate, the solid was filtered-off and the filtrate was washed with brine. The organic phase was dried over sodium sulfate, the solvent was removed and the crude was purified by flash chromatography on Biotage silica gel cartridge (cyclohexane:EtOAc=70:30 to 30:70) to afford title compound as a pale yellow solid (0.265 g, 0.67 mmol over 2 batches). MS/ESI$^+$ 397.3 [MH]$^+$, Rt=0.60 min (Method A).

Intermediate H63 ethyl 3-{6-[2-(4-methylpiperazin-1-yl)ethoxy]pyridazin-3-yl}indolizine-2-carboxylate

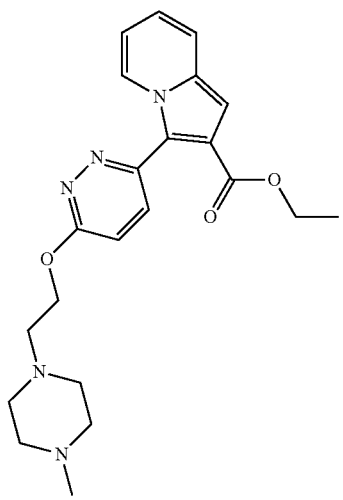 [SMILES: CCOC(=O)c1cc2ccccn2c1-c1ccc(OCCN2CCN(C)CC2)nn1]

2-(4-Methylpiperazin-1-yl)ethan-1-ol (0.2676 g, 1.85 mmol) was dissolved in 5.5 ml of THF, potassium tert-butoxide (0.309 g, 2.76 mmol) was added and the mixture was stirred at room temperature for 30 min. Ethyl 3-(6-chloropyridazin-3-yl)indolizine-2-carboxylate 1157 (0.280 g 0.92 mmol) was added and the mixture was stirred at RT for 5 min. The mixture was diluted with ethyl acetate and washed with brine, the phases were separated and the organic layer was dried over sodium sulphate. The solvent was removed and the residue was purified by flash chromatography on Biotage silica-NH cartridge (DCM to DCM:MeOH=98:2) to afford title compound (0.187 g, 0.45 mmol, 49% yield). MS/ESI$^+$ 410.4 [MH]$^+$, Rt=0.57 min (Method A).

Intermediate H64 ethyl 3-{6-[2-(dimethylamino)ethoxy]pyridazin-3-yl}indolizine-2-carboxylate

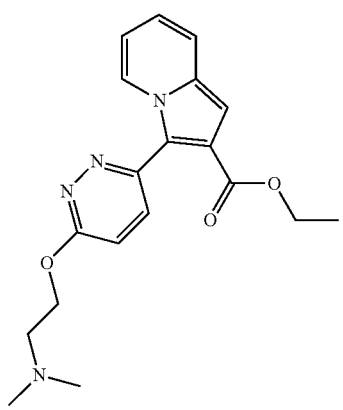 [SMILES: CCOC(=O)c1cc2ccccn2c1-c1ccc(OCCN(C)C)nn1]

Prepared similarly to intermediate H63 starting from ethyl 3-(6-chloropyridazin-3-yl)indolizine-2-carboxylate H57 (0.500 g 1.65 mmol) and 2-dimethylaminoethanol (0.333 ml, 3.30 mmol) and purified by flash chromatography on Biotage silica-NH cartridge (DCM to DCM:MeOH=98:2) to afford title compound (0.341 g). MS/ESI$^+$ 355.3 [MH]$^+$, Rt=0.62 min (Method A).

Intermediate H65 methyl 3-{6-[(1-methylpiperidin-4-yl)oxy]pyridazin-3-yl}indolizine-2-carboxylate

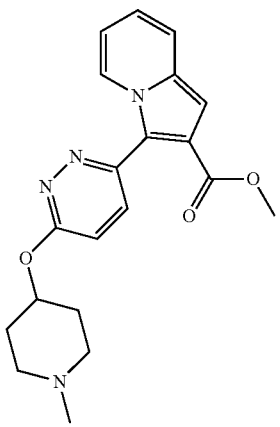 [SMILES: COC(=O)c1cc2ccccn2c1-c1ccc(OC2CCN(C)CC2)nn1]

Ethyl 3-(6-chloropyridazin-3-yl)indolizine-2-carboxylate H57 (0.255 g, 0.84 mmol) and 1-methylpiperidin-4-ol (0.390 g 3.38 mmol) were dissolved in 10.5 ml of THF; potassium tert-butoxide (0.380 g, 3.38 mmol) was added and the mixture was stirred at RT for 30 min. The mixture partitioned between ethyl acetate and water, the phases were separated and the aqueous layer was evaporated. The residue was dissolved in MeOH (25 mL), concentrated sulfuric acid (10 drops) was added and the mixture was stirred at 80° C. for 16 h. The solvent was evaporated and the residue was dissolved in DCM and basified with a saturated solution of NaHCO$_3$ (pH=8). The phases were separated and the aqueous layers was extracted three times with a solution of DCM/MeOH=9/1. The combined organic layers were dried over sodium sulfate, the solvent was evaporated and the residue was purified by flash chromatography on Biotage silica-NH cartridge (DCM to DCM:MeOH=95:5) to afford title compound (0.110 g, 0.3 mmol, 35% yield). MS/ESI$^+$ 367.4 [MH]$^+$, Rt=0.58 min (Method A).

Intermediate H66 methyl 3-{6-[2-(1-methylpiperidin-4-yl)ethoxy]pyridazin-3-yl}indolizine-2-carboxylate

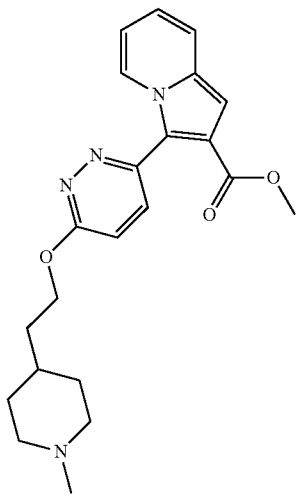 [SMILES: COC(=O)c1cc2ccccn2c1-c1ccc(OCCC2CCN(C)CC2)nn1]

Prepared similarly to intermediate H65 starting from ethyl 3-(6-chloropyridazin-3-yl)indolizine-2-carboxylate H57 (0.510 g, 1.69 mmol) and 2-(1-methylpiperidin-4-yl)ethan-1-ol (0.970 g, 6.77 mmol) and purified by flash chromatography on Biotage silica-NH cartridge (DCM to DCM:MeOH=95:5) to afford title compound (0.140 g). MS/ESI$^+$ 395.4 [MH]$^+$, Rt=0.64 min (Method A).

Intermediate H67 ethyl 3-(morpholin-4-ylmethyl)indolizine-2-carboxylate

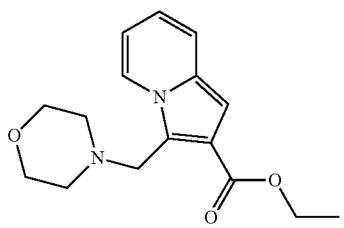 [SMILES: CCOC(=O)c1cc2ccccn2c1CN1CCOCC1]

To a solution of ethyl 3-formylindolizine-2-carboxylate DA1 (1.05 g, 4.83 mmol+0.100 g, 0.46 mmol) in DCM (19.3 mL+1.84 mL), morpholine (0.63 mL, 7.25 mmol+0.060 mL, 0.69 mmol) and 21 drops (+2) of AcOH were added. The mixture was stirred overnight at room temperature and then Na(OAc)$_3$BH (1.536 g, 7.25 mmol+0.146 g, 0.69 mmol) was added. After 6 h the mixture was quenched with sat. NaHCO3 (20 mL+2 mL); the organic layer was separated, washed with brine, dried over sodium sulfate and concentrated. The residue was purified by flash chromatography on Biotage silica-NH cartridge (cycloexane to cycloexane:EtOAc=80:20) to afford title as a pale yellow oil (1.218 g, 4.2 mmol, 79% yield over two batches). MS/ESI$^+$ 289.3 [MH]$^+$, Rt=0.51 min (Method A).

Intermediate H68 ethyl 3-({2-methyl-2,9-diazaspiro[5.5]undecan-9-yl}methyl)indolizine-2-carboxylate

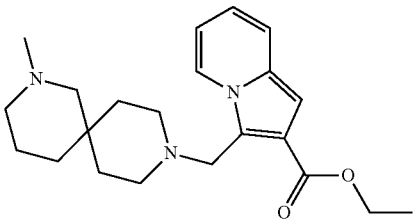 [SMILES: CCOC(=O)c1cc2ccccn2c1CN1CCC2(CCCN(C)C2)CC1]

Prepared similarly to intermediate H67 starting from ethyl 3-formylindolizine-2-carboxylate DA1 (0.786 g, 3.62 mmol) and 2-methyl-2,9-diazaspiro[5.5]undecane (0.730 g, 4.34 mmol, obtained from commercially available dihydrochloride salt after SCX treatment and elution with aqueous ammonia) and purified by flash chromatography on Biotage silica-NH cartridge (cycloexane to cycloexane:EtOAc=50:50) to afford title compound (1.10 g, 2.98 mmol, 82% yield). MS/ESI$^+$ 370.4 [MH]$^+$, Rt=0.39 min (Method A).

Intermediate H69 tert-butyl 9-{[2-(ethoxycarbonyl)indolizin-3-yl]methyl}-3,9-diazaspiro[5.5]undecane-3-carboxylate

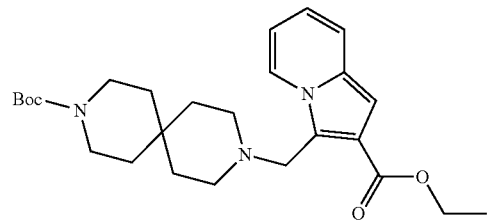 [SMILES: CCOC(=O)c1cc2ccccn2c1CN1CCC2(CC1)CCN(C(=O)OC(C)(C)C)CC2]

Prepared similarly to intermediate H67 starting from ethyl 3-formylindolizine-2-carboxylate DA1 (0.610 g, 2.81 mmol) and tert-butyl 3,9-diazaspiro[5.5]undecane-3-carboxylate (1 g, 3.93 mmol) and purified by flash chromatography on Biotage silica-NH cartridge (cycloexane to cycloexane:EtOAc=90:10) to afford title compound (0.975 g, 2.14 mmol, 76% yield). MS/ESI$^+$ 456.6 [MH]$^+$, Rt=0.79 min (Method A).

Intermediate H70 tert-butyl 2-{[2-(ethoxycarbonyl)indolizin-3-yl]methyl}-2,7-diazaspiro[3.5]nonane-7-carboxylate

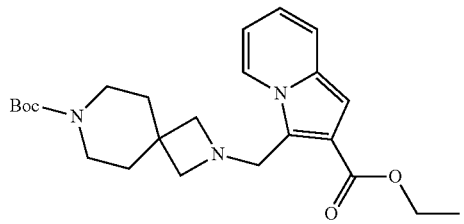 [SMILES: CCOC(=O)c1cc2ccccn2c1CN1CC2(CCN(C(=O)OC(C)(C)C)CC2)C1]

Prepared similarly to intermediate H67 starting from ethyl 3-formylindolizine-2-carboxylate DA1 (0.600 g, 2.72 mmol) and tert-butyl 2,7-diazaspiro[3.5]nonane-7-carboxylate (obtained from 1 g, 3.8 mmol of commercially available hydrochloride salt after filtration through PL-HCO3 cartridges (3×1 g)) and purified by flash chromatography on Biotage silica cartridge (cycloexane:EtOAc=90:10 to 45:55) to afford title compound as an oil (0.537 g, 1.25 mmol, 46%). MS/ESI$^+$ 428.2 [MH]$^+$, Rt=0.74 min (Method A).

Intermediate H71 ethyl 3-{[(3aR,6aS)-5-[(tert-butoxy)carbonyl]-octahydropyrrolo[3,4-c]pyrrol-2-yl]methyl}indolizine-2-carboxylate

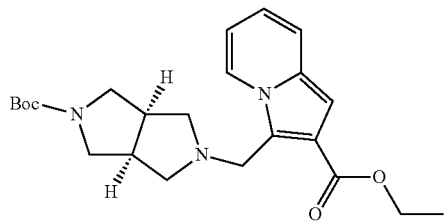 [SMILES: CCOC(=O)c1cc2ccccn2c1CN1C[C@@H]2CN(C(=O)OC(C)(C)C)C[C@@H]2C1]

Prepared similarly to intermediate H67 starting from ethyl 3-formylindolizine-2-carboxylate DA1 (0.500 g, 2.3 mmol) and meso-tert-butyl hexahydropyrrolo[3,4-c]pyrrole-2(1H)-carboxylate (0.733 g, 3.45 mmol) and purified by flash chromatography on Biotage silica-NH cartridge (cyclohexane to cycloexane:EtOAc=70:30) to afford title compound as a pale yellow oil (0.951 g, 2.3 mmol, 100%). MS/ESI$^+$ 414.5 [MH]$^+$, Rt=0.71 min (Method A).

Intermediate H72 ethyl 1-cyano-3-(morpholin-4-ylmethyl)indolizine-2-carboxylate

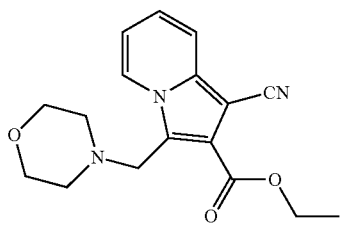 [SMILES: CCOC(=O)c1c(C#N)c2ccccn2c1CN1CCOCC1]

Prepared similarly to intermediate H67 starting from ethyl 1-cyano-3-formylindolizine-2-carboxylate DA2 (0.605 g, 2.49 mmol) and morpholine (0.436 ml, 4.98 mmol) and purified by flash chromatography on Biotage silica-NH cartridge (DCM to DCM:MeOH=99:1) to afford title compound (0.750 g, 2.39 mmol, 96% yield). MS/ESI$^+$ 314.3 [MH]$^+$, Rt=0.54 min (Method A).

Intermediate H73 ethyl 3-(1H-pyrazol-3-yl)indolizine-2-carboxylate

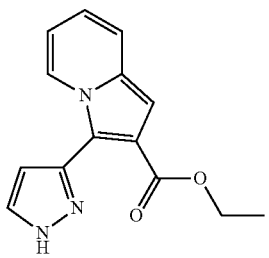 [SMILES: CCOC(=O)c1cc2ccccn2c1-c1cc[nH]n1]

Step 1: ethyl 3-[3-(dimethylamino)prop-2-enoyl]indolizine-2-carboxylate H73a

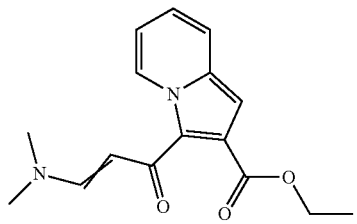 [SMILES: CCOC(=O)c1cc2ccccn2c1C(=O)C=CN(C)C]

To a solution of ethyl 3-acetylindolizine-2-carboxylate DB (1.780 g, 7.7 mmol) in toluene (30 ml), tert-butoxy bis(dimethylamino)methane (3.18 ml, 15.4 mmol) was added and the mixture was stirred at 110° C. for 2 h. The solvent was removed and the crude was purified by flash chromatography on Biotage silica-NH SNAP cartridge (cyclohexane:EtOAc=60:40 to 40:60) to afford title compound as a pale yellow oil (2.120 g, 7.4 mmol, 96% yield). MS/ESI$^+$ 287.3 [MH]$^+$, Rt=0.89 min (Method A).

Step 2: ethyl 3-(1H-pyrazol-3-yl)indolizine-2-carboxylate H73

To a solution of ethyl 3-[3-(dimethylamino)prop-2-enoyl]indolizine-2-carboxylate H73a (1.580 g, 5.5 mmol) in ethanol (14 ml), hydrazine monohydrate (0.267 ml, 5.5 mmol) was added and the mixture was stirred at 80° C. for 1 h. The solvent was removed and the crude was purified by flash chromatography on Biotage silica-NH cartridge (DCM to DCM:MeOH=98:2) to afford title compound as a pale yellow solid (1.165 g, 4.5 mmol, 83% yield). MS/ESI$^+$ 256.2 [MH]$^+$, Rt=0.95 min (Method A).

Intermediate H74 ethyl 3-[1-(2-chloroethyl)-1H-pyrazol-3-yl]indolizine-2-carboxylate

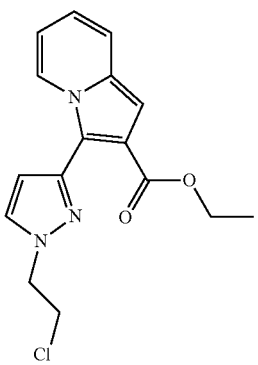 [SMILES: CCOC(=O)c1cc2ccccn2c1-c1ccn(CCCl)n1]

Ethyl 3-(1H-pyrazol-3-yl)indolizine-2-carboxylate H73 (1.165 g, 4.5 mmol) was dissolved in 11 ml of DMF, K$_2$CO$_3$ (1.897 g, 13.5 mmol) was added followed by 1-bromo-2-chloroethane (1.12 ml, 13.5 mmol) and the mixture was stirred at 60° C. for 6 h. The mixture was diluted with ethyl acetate, the solid was filtered off and the filtrate was washed with brine. The organic phase was dried over sodium sulfate, the solvent was removed and the crude was purified by flash chromatography on Biotage silica gel cartridge (DCM to DCM:EtOAc=90:10) to afford title compound as a pale yellow solid (0.995 g, 3.13 mmol, 69% yield). MS/ESI$^+$ 317.9 [MH]$^+$, Rt=1.15 min (Method A).

Intermediate H75 ethyl 3-{1-[2-(dimethylamino)ethyl]-1H-pyrazol-3-yl}indolizine-2-carboxylate

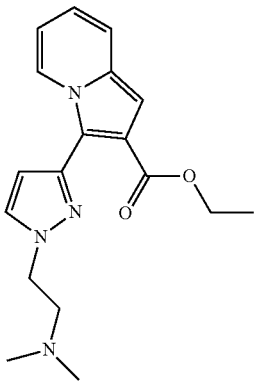 [SMILES: CCOC(=O)c1cc2ccccn2c1-c1ccn(CCN(C)C)n1]

To a solution of ethyl 3-[1-(2-chloroethyl)-1H-pyrazol-3-yl]indolizine-2-carboxylate H74 (0.300 g, 0.94 mmol) acetonitrile (24 mL), KI (0.312 g, 1.88 mmol) and K$_2$CO$_3$ (0.391 g, 2.83 mmol) were added followed by 2M dimethylamine in THF (1.41 ml, 2.83 mmol) and the mixture was stirred at 85° C. for 48 h. The mixture was diluted with ethyl acetate, the solid was filtered off and the filtrate was washed with brine. The organic phase was dried over sodium sulfate, the solvent was removed and the crude was purified by flash chromatography on Biotage silica gel cartridge (DCM: MeOH=99:1 to 90:10) to afford title compound as a pale yellow oil (0.212 g, 0.65 mmol, 70% yield). MS/ESI$^+$ 327.3 [MH]$^+$, Rt=0.61 min (Method A).

Intermediate H76 ethyl 3-{1-[2-(4-methylpiperazin-1-yl)ethyl]-1H-pyrazol-3-yl}indolizine-2-carboxylate

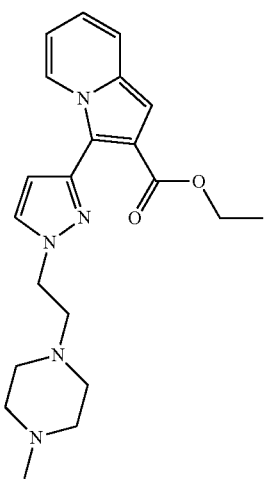 [SMILES: CCOC(=O)c1cc2ccccn2c1-c1ccn(CCN2CCN(C)CC2)n1]

Prepared similarly to intermediate H75 starting from ethyl 3-[1-(2-chloroethyl)-1H-pyrazol-3-yl]indolizine-2-carboxylate H74 (0.300 g, 0.94 mmol+0.025 mg, 0.078 mmol), KI (0.234 g, 1.41 mmol+0.014 g, 0.086 mmol), K$_2$CO$_3$ (0.390 g, 2.82 mmol+0.032 g, 0.234 mmol) and 1-methyl piperazine (0.208 ml, 1.88 mmol+0.017 mL, 0.15 mmol) at 85° C. for 24 h, and purified by flash chromatography on Biotage silica gel cartridge (DCM to DCM:MeOH=95:5) to afford title compound as a pale yellow oil (0.316 g, 0.82 mmol, 81% yield). MS/ESI$^+$ 382.4 [MH]$^+$, Rt=0.61 min (Method A).

Intermediate H77 ethyl 3-{1-[2-(2,2,3,3,11,11,12,12-octamethyl-4,10-dioxa-7-aza-3,11-disilatridecan-7-yl)ethyl]-1H-pyrazol-3-yl}indolizine-2-carboxylate

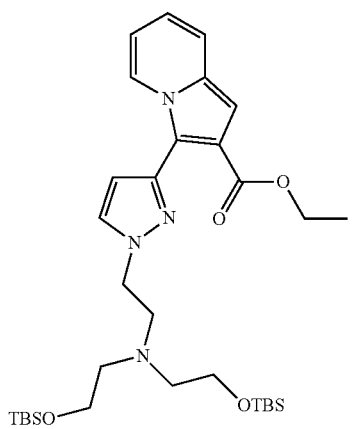 [SMILES: CCOC(=O)c1cc2ccccn2c1-c1ccn(CCN(CCO[Si](C)(C)C(C)(C)C)CCO[Si](C)(C)C(C)(C)C)n1]

Step 1: ethyl 3-(1-{2-[bis(2-hydroxyethyl)amino]
ethyl}-1H-pyrazol-3-yl)indolizine-2-carboxylate
H77a

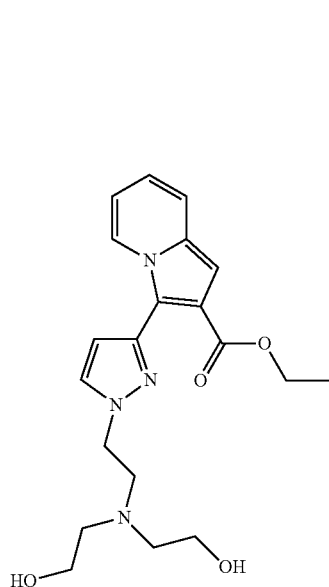 [SMILES: CCOC(=O)c1cc2ccccn2c1-c1ccn(CCN(CCO)CCO)n1]

Prepared similarly to intermediate H75 starting from ethyl 3-[1-(2-chloroethyl)-1H-pyrazol-3-yl]indolizine-2-carboxylate H74 (0.200 g, 0.63 mmol), KI (0.314 g, 1.89 mmol), K$_2$CO$_3$ (0.348 g, 2.52 mmol) and 2-[(2-hydroxyethyl)amino]ethan-1-ol (0.181 ml, 1.89 mmol) at 85° C. for 24 h, and purified by flash chromatography on Biotage silica gel cartridge (DCM to DCM:MeOH=90:10) to afford title compound as a pale yellow oil (0.076 g, 0.19 mmol, 31% yield). MS/ESI$^+$ 387.4 [MH]$^+$, Rt=0.59 min (Method A).

Step 2: ethyl 3-{1-[2-(2,2,3,3,11,11,12,12-octamethyl-4,10-dioxa-7-aza-3,11-disilatridecan-7-yl)ethyl]-1H-pyrazol-3-yl}indolizine-2-carboxylate H77

Ethyl 3-(1-{2-[bis(2-hydroxyethyl)amino]ethyl}-1H-pyrazol-3-yl)indolizine-2-carboxylate H77a (0.121 g, 0.31 mmol) was dissolved in DCM (3 mL); imidazole (0.1055 g, 1.55 mmol) and tert-butyl(chloro)dimethylsilane (0.117 g, 0.77 mmol) were added and the mixture was stirred at room temperature for 2 h. The mixture was washed with water, then with brine, the organic phase was dried over sodium sulphate and the solvent was removed under reduced pressure. The crude was purified by flash chromatography on silica gel Biotage column (DCM to DCM:MeOH=95:5) affording title compound as a yellow oil (0.165 g, 0.27 mmol, 86% yield). MS/ESI$^+$ 615.6 [MH]$^+$, Rt=1.25 min (Method A).

Intermediate H78 ethyl 3-{1-[2-(morpholin-4-yl)ethyl]-1H-pyrazol-3-yl}indolizine-2-carboxylate

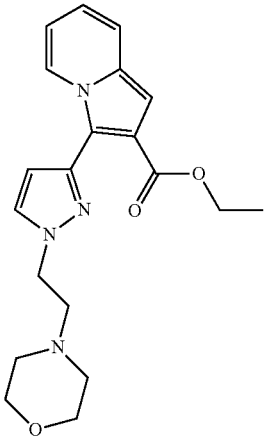 [SMILES: CCOC(=O)c1cc2ccccn2c1-c1ccn(CCN2CCOCC2)n1]

Ethyl 3-(1H-pyrazol-3-yl)indolizine-2-carboxylate H73 (567.4 mg, 1.54 mmol) was dissolved in 8 ml of THF, K$_2$CO$_3$ (0.866 g, 6.16 mmol) was added followed by 4-(2-chloroethyl)morpholine hydrochloride (0.573 g, 3.08 mmol) and the mixture was stirred at 60° C. for 2 h. The mixture was diluted with ethyl acetate, the solid was filtered off and the filtrate was washed with brine. The organic phase was then dried over sodium sulfate, the solvent was removed and the crude was purified by flash chromatography on Biotage silica-NH SNAP cartridge (DCM to DCM:MeOH=95:5) to afford title compound as a pale yellow solid (0.068 g, 0.18 mmol). MS/ESI$^+$ 369.4 [MH]$^+$, Rt=0.65 min (Method A).

Intermediate I1

1-(3-phenylindolizin-2-yl)ethan-1-one

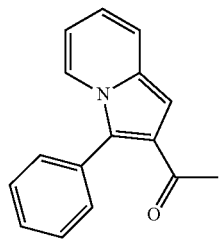 [SMILES: CC(=O)c1cc2ccccn2c1-c1ccccc1]

A mixture of commercially available 1-(indolizin-2-yl)ethan-1-one (0.250 g, 1.57 mmol), Pd(OAc)$_2$ (0.018 g, 0.0785 mmol), tricyclopentylphosphine tetrafluoroborate (0.051 g, 0.157 mmol) and Cs$_2$CO$_3$ (1.530 g, 4.71 mmol) was flushed with nitrogen and toluene (3 mL) was added followed by chlorobenzene (0.320 mL, 3.52 mmol). The reaction was stirred at r.t. for 10 min, then heated at 130° C. for 16 h. The mixture was cooled to RT, diluted with DCM and filtered through a Celite® pad. The filtrate was evaporated to dryness and purified by flash chromatography on silica Biotage SNAP cartridge (cyclohexane to cyclohexane:

EtOAc=93:7) to afford title compound as a yellow oil (0.095 g, 0.40 mmol, 26% yield). MS/ESI⁺ 236.1 [MH]⁺, Rt=1.11 min (Method A).

Intermediate I2

1-[3-(pyridin-2-yl)indolizin-2-yl]ethan-1-one

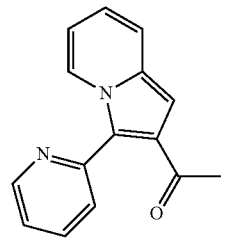 [SMILES: CC(=O)c1cc2ccccn2c1-c1ccccn1]

A mixture of 1-(indolizin-2-yl)ethan-1-one (0.250 g, 1.57 mmol), Pd(Oac)₂ (0.018 g, 0.0785 mmol), tricyclopentylphosphine tetrafluoroborate (0.051 g, 0.157 mmol) and Cs₂CO₃ (1.535 g, 4.71 mmol) was flushed with nitrogen and toluene (3 mL) was added followed by 2-chloropyridine (0.223 mL, 2.36 mmol). The mixture was stirred at RT for 10 minutes, then heated at 130° C. overnight. Additional Pd(Oac)₂ (0.018 g, 0.0785 mmol) and tricyclopentylphosphine tetrafluoroborate (0.051 g, 0.157 mmol) were added at RT followed by 2-chloropyridine (0.148 mL, 1.57 mmol) and the mixture was heated at 130° C. for 24 h. Additional Pd(Oac)₂ (0.018 g, 0.0785 mmol) and tricyclopentylphosphine tetrafluoroborate (0.051 g, 0.157 mmol) were added at RT and the mixture was heated at 130° C. for further 8 h. The mixture was diluted with DCM and filtered through a Celite® pad. The filtrate was evaporated to dryness and the crude was purified by flash chromatography on Biotage silica gel cartridge (cyclohexane to cyclohexane:EtOAc=80:20) to afford title compound as an orange oil (0.055 g, 0.233 mmol, 15% yield). MS/ESI⁺ 237.1 [MH]⁺, Rt=0.66 min (Method A).

Intermediate I3

1-{3-[5-(morpholine-4-carbonyl)pyridin-2-yl]indolizin-2-yl}ethan-1-one

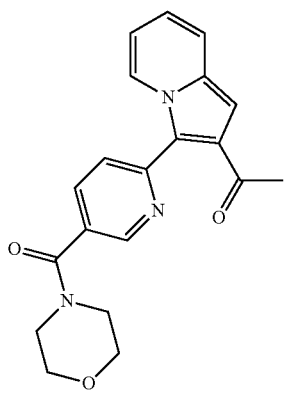 [SMILES: CC(=O)c1cc2ccccn2c1-c1ccc(C(=O)N2CCOCC2)cn1]

To a solution of N,N'-dimethylethylenediamine (0.250 mL, 2.32 mmol+0.062 mL, 0.580 mmol) in toluene (6 mL+1.5 mL) cooled to 0° C. under nitrogen atmosphere, a 2M solution of trimethylaluminum in toluene (3.27 mL, 6.54 mmol+0.817 mL, 1.63 mmol) was added drop-wise and the resulting mixture was stirred at r.t. for 1 h. A solution of ethyl 3-[5-(morpholine-4-carbonyl)pyridin-2-yl]indolizine-2-carboxylate H47 (0.800 g, 2.11 mmol+0.200 g, 0.527 mmol) in toluene (6 mL+1.5 mL) was added and the reaction was heated to reflux for 4 h. The mixture was cooled to room temperature, quenched with 1N aqueous HCl solution and extracted with EtOAc; the organic layer was dried over sodium sulfate, filtered, and concentrated under reduced pressure. Combined crude was purified by flash chromatography on Biotage silica-NH cartridge (cyclohexane to cyclohexane:EtOAc=50:50) to afford title compound as a yellow foam (0.140 g, 0.401 mmol, 15% yield). MS/ESI⁺ 350.2 [MH]⁺, Rt=0.78 min (Method A).

Intermediate J1

3-(pyridin-2-yl)indolizine-2-carbonitrile

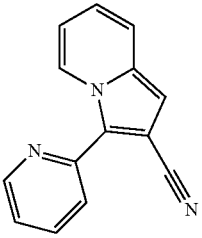 [SMILES: N#Cc1cc2ccccn2c1-c1ccccn1]

A mixture of indolizine-2-carbonitrile B5 (1.3 g, 9.14 mmol), Pd(OAc)₂ (0.102 g, 0.46 mmol), tricyclopentylphosphine tetrafluoroborate (0.298 g, 0.914 mmol) and Cs₂CO₃ (8.93 g, 27.42 mmol) was flushed with nitrogen and toluene (5 mL) was added followed by 2-chloropyridine (1.7 mL, 18.28 mmol). The reaction was heated at 130° C. overnight. The mixture was diluted with DCM and filtered through a Celite® pad; the filtrate was evaporated to dryness and the crude was purified by flash chromatography on Biotage silica gel SNAP cartridge (cyclohexane to cyclohexane:DCM=61:39) to afford title compound as a light yellow solid (1.226 g, 5.59 mmol, 61% yield). MS/ESI⁺ 220.1 [MH]⁺, Rt=1.05 min (Method A).

Intermediate J2

3-(pyridin-4-yl)indolizine-2-carbonitrile

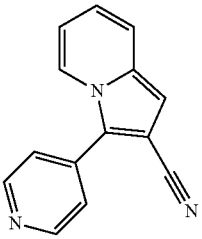 [SMILES: N#Cc1cc2ccccn2c1-c1ccncc1]

Prepared similarly to intermediate J1, starting from indolizine-2-carbonitrile B5 (0.150 g, 1.05 mmol), Pd(OAc)₂ (0.012 g, 0.053 mmol), tricyclopentylphosphine tetrafluoroborate (0.034 g, 0.105 mmol), Cs₂CO₃ (1.026 g, 3.15 mmol), toluene (1.8 mL) and 4-chloropyridine (0.240 g, 2.11 mmol), heating at 130° C. overnight. The crude was purified by flash chromatography on Biotage silica gel SNAP cartridge (DCM to DCM:EtOAc=70:30) to afford title compound as a yellow solid (0.095 g, 0.433 mmol, 41% yield). MS/ESI⁺ 220.1 [MH]⁺, Rt=0.53 min (Method A).

Intermediate J3

3-(thiophen-2-yl)indolizine-2-carbonitrile

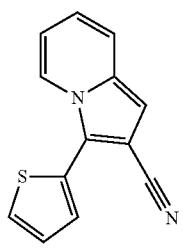 [SMILES: N#Cc1cc2ccccn2c1-c1cccs1]

Prepared similarly to intermediate J1, starting from indolizine-2-carbonitrile B5 (0.150 g, 1.05 mmol), Pd(OAc)₂ (0.012 g, 0.053 mmol), tricyclopentylphosphine tetrafluoroborate (0.034 g, 0.105 mmol), Cs₂CO₃ (1.026 g, 3.15 mmol), toluene (2 mL) and 2-chlorothiophene (0.195 mL, 2.11 mmol), at 130° C. overnight. Additional Pd(OAc)₂ (0.012 g, 0.053 mmol), tricyclopentylphosphine tetrafluoroborate (0.034 g, 0.105 mmol) and 2-chlorothiophene (0.195 mL, 2.11 mmol) were added heating at the same temperature for further 24 h. After work-up, the crude was purified by flash chromatography on Biotage silica gel SNAP cartridge (cyclohexane:EtOAc=95:5); a further purification by flash chromatography on Biotage silica gel SNAP cartridge (cyclohexane:DCM=95:5 to 80:20) was required to afford title compound (0.072 g). MS/ESI⁺ 225.0 [MH]⁺, Rt=1.13 min (Method A).

Intermediate J4

3-(thiophen-3-yl)indolizine-2-carbonitrile

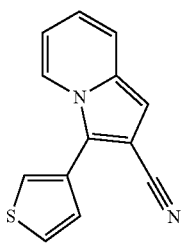 [SMILES: N#Cc1cc2ccccn2c1-c1ccsc1]

Prepared similarly to intermediate J1, starting from indolizine-2-carbonitrile B5 (0.150 g, 1.05 mmol), Pd(OAc)₂ (0.012 g, 0.053 mmol), tricyclopentylphosphine tetrafluoroborate (0.034 g, 0.105 mmol), Cs₂CO₃ (1.026 g, 3.15 mmol), toluene (2 mL) and 3-chlorothiophene (0.196 mL, 2.11 mmol), at 130° C. overnight. Additional Pd(OAc)₂ (0.012 g, 0.053 mmol), tricyclopentylphosphine tetrafluoroborate (0.034 g, 0.105 mmol) and 3-chlorothiophene (0.195 mL, 2.11 mmol) were added heating at the same temperature for further 24 h. After work-up the crude was purified by flash chromatography on Biotage silica gel SNAP cartridge (cyclohexane to cyclohexane:EtOAc=95:5) to afford title compound which was used in the next step without any additional purification (0.097 g). MS/ESI⁺ 225.0 [MH]⁺, Rt=1.12 min (Method A).

Intermediate J5

5-methyl-3-(pyridin-2-yl)indolizine-2-carbonitrile

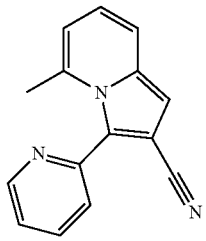 [SMILES: Cc1cccc2cc(C#N)c(-c3ccccn3)n12]

Prepared similarly to intermediate J1, starting from 5-methylindolizine-2-carbonitrile B6 (0.567 g, 3.63 mmol), Pd(OAc)₂ (0.081 g, 0.363 mmol), tricyclopentylphosphine tetrafluoroborate (0.236 g, 0.726 mmol), Cs₂CO₃ (3.55 g, 10.89 mmol), toluene (7 mL) and 2-chloropyridine (0.687 mL, 7.26 mmol), at 130° C. overnight. Additional Pd(OAc)₂ (0.0081 g, 0.363 mmol) and tricyclopentylphosphine tetrafluoroborate (0.236 g, 0.0.726 mmol) were added and the mixture was heated at 130° C. for further 48 h. After work-up the crude was purified by flash chromatography on Biotage silica gel SNAP cartridge (cyclohexane:EtOAc=95:5 to 90:10) to yield title compound as a yellow solid (0.084 g, 0.036 mmol, 10% yield). MS/ESI⁺ 234.1 [MH]⁺, Rt=0.95 min (Method A).

Intermediate J6

8-methyl-3-(pyridin-2-yl)indolizine-2-carbonitrile

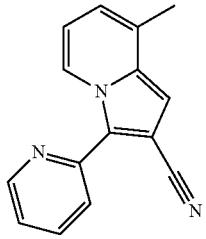 [SMILES: Cc1cccn2c(-c3ccccn3)c(C#N)cc12]

Prepared similarly to intermediate J1, starting from 8-methylindolizine-2-carbonitrile B7 (0.245 g, 1.57 mmol), Pd(OAc)₂ (0.035 g, 0.157 mmol), tricyclopentylphosphine tetrafluoroborate (0.102 g, 0.314 mmol), Cs₂CO₃ (1.530 g, 4.71 mmol) and 2-chloropyridine (0.296 mL, 3.13 mmol), at 130° C. overnight. Additional Pd(OAc)₂ (0.035 g, 0.157 mmol) and tricyclopentylphosphine tetrafluoroborate (0.102 g, 0.314 mmol) were added and the mixture was heated at 130° C. for further 12 h. After work-up, the crude was purified by flash chromatography on Biotage silica gel SNAP cartridge (cyclohexane to cyclohexane:EtOAc=95:5). A further purification by flash chromatography on Biotage silica gel SNAP cartridge (cyclohexane:DCM=50:50 to 100% DCM) was required to yield title compound as a white solid (0.164 g, 0.70 mmol, 45% yield). MS/ESI⁺ 234.1 [MH]⁺, Rt=1.16 min (Method A).

Intermediate K1

(3-phenylindolizin-2-yl)methanol

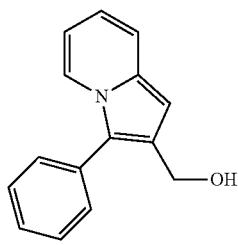 [SMILES: OCc1cc2ccccn2c1-c1ccccc1]

To a solution of ethyl 3-phenylindolizine-2-carboxylate H1 (0.475 g, 1.79 mmol) in DCM (19 mL) cooled at −78° C. under nitrogen, a solution of 1M DIBAL in toluene (5.37 mL, 5.37 mmol) was added drop-wise over 15 minutes and the reaction was stirred at −78° C. for 1.5 h. The reaction mixture was quenched by drop-wise addition of a saturated ammonium chloride solution and gradually warmed up to room temperature. The mixture was extracted several times with DCM and the combined organic layers were filtered through a Phase Separator tube washing with DCM, dried over sodium sulfate and concentrated in vacuo. The crude was purified by flash chromatography on Biotage silica gel SNAP cartridge (cyclohexane to cyclohexane:EtOAc=80:20) to afford title compound as a fluorescent yellow-green solid (0.360 g, 1.61 mmol, 90% yield). MS/ESI⁺ 224.1 [MH]⁺, Rt=0.99 min (Method A).

Intermediate K2

[3-(pyridin-2-yl)indolizin-2-yl]methanol

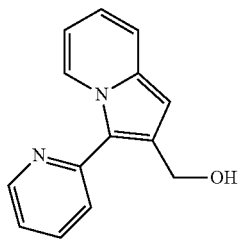 [SMILES: OCc1cc2ccccn2c1-c1ccccn1]

Prepared similarly to intermediate K1, starting from 3-(pyridin-2-yl)indolizine-2-carboxylate H2 (0.554 g, 2.08 mmol), stirring for 1 h, and purified by flash chromatography on silica-NH Biotage SNAP cartridge (cyclohexane to cyclohexane:EtOAc=70:30) to afford title compound as a yellow oil (0.402 g, 1.79 mmol, 86% yield). MS/ESI⁺ 225.1 [MH]⁺, Rt=0.54 min (Method A).

Intermediate K3

[3-(3-fluorophenyl)indolizin-2-yl]methanol

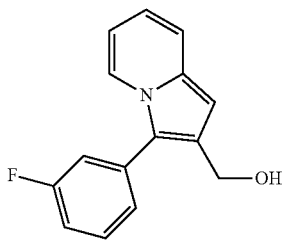 [SMILES: OCc1cc2ccccn2c1-c1cccc(F)c1]

Prepared similarly to intermediate K1, starting from ethyl 3-(3-fluorophenyl)indolizine-2-carboxylate H3 (0.674 g, 2.38 mmol), stirring for 1.5 h, and purified by flash chromatography on silica gel Biotage SNAP cartridge (cyclohexane to cyclohexane:EtOAc=80:20) to afford title compound as a yellow oil (0.400 g, 1.66 mmol, 70% yield). MS/ESI⁺ 242.1 [MH]⁺, Rt=1.01 min (Method A).

Intermediate K4

[3-(2-fluorophenyl)indolizin-2-yl]methanol

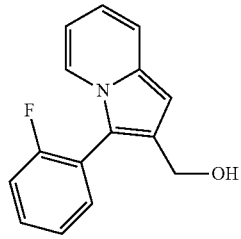 [SMILES: OCc1cc2ccccn2c1-c1ccccc1F]

Prepared similarly to intermediate K1, starting from ethyl 3-(2-fluorophenyl)indolizine-2-carboxylate H4 (0.638 g, 2.25 mmol), stirring for 1 h, and purified by flash chromatography on silica gel Biotage SNAP cartridge (cyclohexane to cyclohexane:EtOAc=90:10) to afford title compound as a pale green oil (0.448 g, 1.857 mmol, 82% yield). MS/ESI⁺ 242.1 [MH]⁺, Rt=0.96 min (Method B).

Intermediate K5

[3-(2-methylphenyl)indolizin-2-yl]methanol

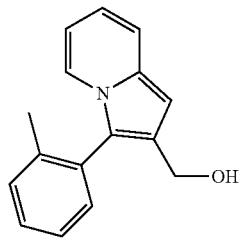 [SMILES: Cc1ccccc1-c1c(CO)cc2ccccn12]

Prepared similarly to intermediate K1, starting from ethyl 3-(2-methylphenyl)indolizine-2-carboxylate H5 (2.65

Intermediate K6

[3-(pyridin-3-yl)indolizin-2-yl]methanol

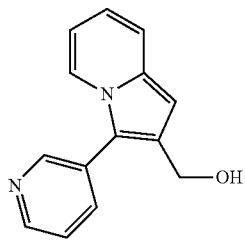 [SMILES: OCc1cc2ccccn2c1-c1cccnc1]

Prepared similarly to intermediate K1, starting from ethyl 3-(pyridin-3-yl)indolizine-2-carboxylate H6 (0.344 g, 1.29 mmol), stirring for 1 h, and purified by flash chromatography on silica gel Biotage SNAP cartridge (cyclohexane:EtOAc=70:30 to 100% EtOAc) to afford title compound as a pale yellow oil (0.234 g, 1.04 mmol, 81% yield). MS/ESI$^+$ 225.1 [MH]$^+$, Rt=0.48 min (Method A).

Intermediate K7

[3-(pyrazin-2-yl)indolizin-2-yl]methanol

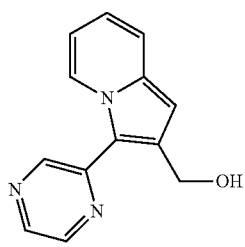 [SMILES: OCc1cc2ccccn2c1-c1cnccn1]

Prepared similarly to intermediate K1, starting from ethyl 3-(pyrazin-2-yl)indolizine-2-carboxylate H7 (0.098 g, 0.367 mmol), stirring for 2 h, and purified by flash chromatography on silica gel Biotage SNAP cartridge (DCM to DCM:EtOAc=40:60) to afford title compound as a yellow solid (0.042 g, 0.186 mmol, 51% yield). MS/ESI$^+$ 226.1 [MH]$^+$, Rt=0.74 min (Method A).

Intermediate K8

[3-(pyridin-4-yl)indolizin-2-yl]methanol

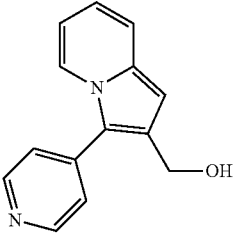 [SMILES: OCc1cc2ccccn2c1-c1ccncc1]

Prepared similarly to intermediate K1, starting from ethyl 3-(pyridin-4-yl)indolizine-2-carboxylate H8 (0.250 g, 0.939 mmol), stirring for 2 h, and the reaction was quenched by drop-wise addition of a saturated solution of potassium and sodium tartrate tetrahydrate; the crude title compound was used without any additional purification (0.200 g, 0.892 mmol, 95% yield). MS/ESI$^+$ 225.1 [MH]$^+$, Rt=0.38 min (Method A).

Intermediate K9

[6-methyl-3-(pyridin-2-yl)indolizin-2-yl]methanol

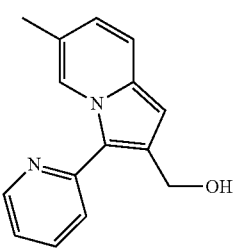 [SMILES: Cc1ccc2cc(CO)c(-c3ccccn3)n2c1]

Prepared similarly to intermediate K1, starting from ethyl 6-methyl-3-(pyridin-2-yl)indolizine-2-carboxylate H9 (0.197 g, 0.70 mmol), stirring for 30 min, and the reaction was quenched by drop-wise addition of a saturated solution of potassium and sodium tartrate tetrahydrate; the crude title compound was used without any additional purification (0.136 g, 0.57 mmol, 81% yield). MS/ESI$^+$ 239.2 [MH]$^+$, Rt=0.63 min (Method A).

Intermediate K10

[3-(pyridin-2-yl)-6-(trifluoromethyl)indolizin-2-yl]methanol

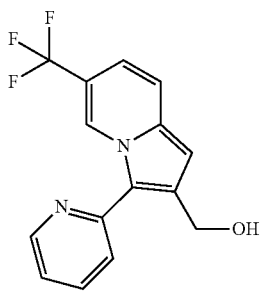 [SMILES: OCc1cc2ccc(C(F)(F)F)cn2c1-c1ccccn1]

Prepared similarly to intermediate K1, starting from ethyl 3-(pyridin-2-yl)-6-(trifluoromethyl)indolizine-2-carboxylate H10 (0.255 g, 0.763 mmol), stirring for 1 h, and the reaction was quenched by drop-wise addition of a saturated solution of potassium and sodium tartrate tetrahydrate; the crude title compound, obtained as a pale yellow solid, was used without any additional purification (0.197 g, 0.674 mmol, 88% yield). MS/ESI$^+$ 239.3 [MH]$^+$, Rt=1.02 min (Method A).

Intermediate K11

[8-fluoro-3-(pyridin-2-yl)indolizin-2-yl]methanol

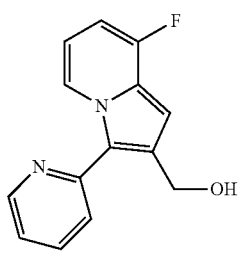 [SMILES: OCc1cc2c(F)cccn2c1-c1ccccn1]

Prepared similarly to intermediate K1, starting from ethyl 8-fluoro-3-(pyridin-2-yl)indolizine-2-carboxylate H11 (0.140 g, 0.49 mmol), stirring for 1 h, and the crude title compound (0.120 g, 0.49 mmol, quantitative yield) was used without any additional purification. MS/ESI$^+$ 243.1 [MH]$^+$, Rt=0.71 min (Method A).

Intermediate K12

[1-methyl-3-(pyridin-2-yl)indolizin-2-yl]methanol

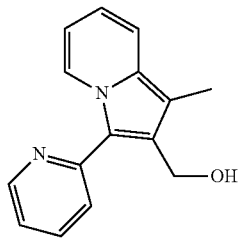 [SMILES: Cc1c(CO)c(-c2ccccn2)n2ccccc12]

Prepared similarly to intermediate K1, starting from ethyl 1-methyl-3-(pyridin-4-yl)indolizine-2-carboxylate H12 (0.088 g, 0.314 mmol), stirring for 2 h, and the reaction was quenched by drop-wise addition of a saturated solution of potassium and sodium tartrate tetrahydrate; the crude title compound was used without any additional purification (0.061 g, 0.256 mmol, 82% yield). MS/ESI$^+$ 239.1 [MH]$^+$, Rt=0.60 min (Method A).

Intermediate K13

{3-[5-(morpholin-4-ylmethyl)thiophen-2-yl]indolizin-2-yl}methanol

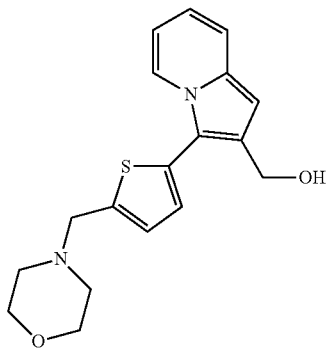 [SMILES: OCc1cc2ccccn2c1-c1ccc(CN2CCOCC2)s1]

Prepared similarly to intermediate K1, starting from ethyl 3-[5-(morpholin-4-ylmethyl)thiophen-2-yl]indolizine-2-carboxylate H13 (0.569 g, 1.53 mmol), stirring for 1 h, and the reaction was quenched by drop-wise addition of a saturated solution of potassium and sodium tartrate tetrahydrate; the crude was purified by flash chromatography on silica-NH Biotage SNAP cartridge (cyclohexane to cyclohexane:EtOAc=50:50) to afford title compound as a yellow oil (0.364 g, 1.11 mmol, 72% yield). MS/ESI$^+$ 328.2 [MH]$^+$, Rt=0.50 min (Method A).

Intermediate K14

{3-[4-(morpholin-4-ylmethyl)phenyl]indolizin-2-yl}methanol

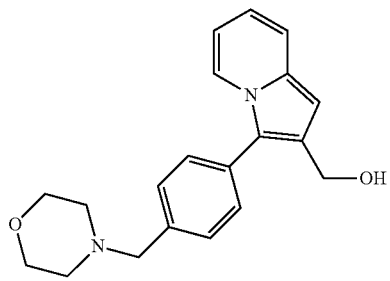

Prepared similarly to intermediate K1, starting from ethyl 3-[4-(morpholin-4-ylmethyl)phenyl]indolizine-2-carboxylate H14 (0.488 g, 1.34 mmol), stirring for 3 h, and the reaction was quenched by drop-wise addition of a saturated solution of potassium and sodium tartrate tetrahydrate; the crude was purified by flash chromatography on Biotage silica gel SNAP cartridge (cyclohexane:EtOAc=100:0 to 0:100) to afford title compound as a dark yellow oil (0.271 g, 0.84 mmol, 63% yield). MS/ESI$^+$ 323.3 [MH]$^+$, Rt=0.50 min (Method A).

Intermediate K15

(3-{4-[(dimethylamino)methyl]phenyl}indolizin-2-yl)methanol

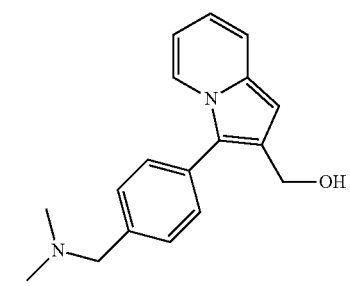 [SMILES: CN(C)Cc1ccc(-c2c(CO)cc3ccccn23)cc1]

Prepared similarly to intermediate K1, starting from ethyl 3-{4-[(dimethylamino)methyl]phenyl}indolizine-2-carboxylate H15 (0.421 g, 1.30 mmol), stirring for 1 h, and the reaction was quenched by drop-wise addition of a saturated solution of potassium and sodium tartrate tetrahydrate; the crude was purified by flash chromatography on Biotage silica-NH SNAP cartridge (cyclohexane to cyclohexane: EtOAc=50:50) to afford title compound as a pale yellow oil (0.235 g, 0.83 mmol, 64% yield). MS/ESI$^+$ 281.2 [MH]$^+$, Rt=0.49 min (Method A).

Intermediate K16

(3-{3-[(dimethylamino)methyl]phenyl}indolizin-2-yl)methanol

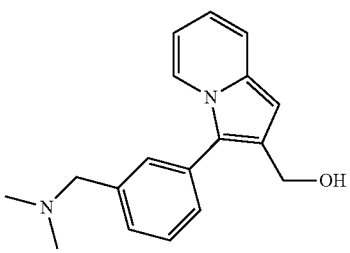 [SMILES: CN(C)Cc1cccc(-c2c(CO)cc3ccccn23)c1]

Prepared similarly to intermediate K1, starting from ethyl 3-{3-[(dimethylamino)methyl]phenyl}indolizine-2-carboxylate H16 (0.457 g, 1.42 mmol), stirring for 1 h, and the reaction was quenched by drop-wise addition of a saturated solution of potassium and sodium tartrate tetrahydrate; the crude was purified by flash chromatography on Biotage silica-NH SNAP cartridge (cyclohexane to cyclohexane: EtOAc=50:50) to afford title compound as a pale yellow oil (0.285 g, 1.02 mmol, 71% yield). MS/ESI$^+$ 281.3 [MH]$^+$, Rt=0.52 min (Method A).

Intermediate K17

[3-(3,6-dihydro-2H-pyran-4-yl)indolizin-2-yl]methanol

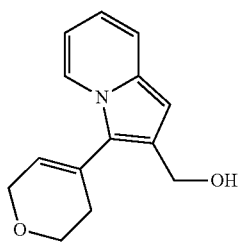 [SMILES: OCc1cc2ccccn2c1C1=CCOCC1]

Prepared similarly to intermediate K1, starting from ethyl 3-(3,6-dihydro-2H-pyran-4-yl)indolizine-2-carboxylate H17 (0.134 g, 0.49 mmol), stirring for 1 h, and the reaction was quenched by drop-wise addition of a saturated solution of potassium and sodium tartrate tetrahydrate; the crude was purified by flash chromatography on silica gel Biotage SNAP cartridge (cyclohexane to cyclohexane:EtOAc=50: 50) to afford title compound as a pale yellow oil (0.078 g, 0.34 mmol, 70% yield). MS/ESI$^+$ 230.1 [MH]$^+$, Rt=0.79 min (Method A).

Intermediate K18 tert-butyl 4-[2-(hydroxymethyl)indolizin-3-yl]-1,2,3,6-tetrahydropyridine-1-carboxylate

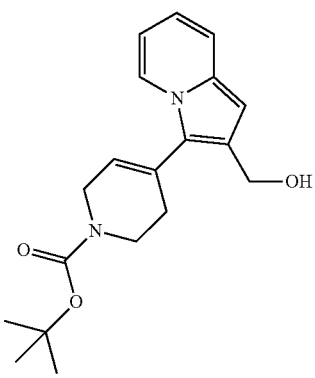 [SMILES: CC(C)(C)OC(=O)N1CC=C(c2c(CO)cc3ccccn23)CC1]

Prepared similarly to intermediate K1, starting from ethyl 3-{1-[(tert-butoxy)carbonyl]-1,2,3,6-tetrahydropyridin-4-yl}indolizine-2-carboxylate H18 (0.370 g, 0.91 mmol), stirring for 1 h, and the reaction was quenched by drop-wise addition of a saturated solution of potassium and sodium tartrate tetrahydrate; the crude was purified by flash chromatography on silica gel Biotage SNAP cartridge (cyclohexane to cyclohexane:EtOAc=50:50) to afford title compound as a yellow oil (0.194 g, 0.59 mmol, 65% yield). MS/ESI$^+$ 329.3 [MH]$^+$, Rt=1.08 min (Method A).

Intermediate K19

[3-(1,3-thiazol-5-yl)indolizin-2-yl]methanol

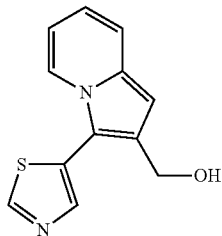 [SMILES: OCc1cc2ccccn2c1-c1cncs1]

Prepared similarly to intermediate K1, starting from ethyl 3-(1,3-thiazol-5-yl)indolizine-2-carboxylate H19 (0.169 g, 0.62 mmol), stirring for 1 h, and the reaction was quenched by drop-wise addition of a saturated solution of potassium and sodium tartrate tetrahydrate; the crude title compound was used without any additional purification (0.143 g, 0.62 mmol, quantitative yield). MS/ESI$^+$ 231.1 [MH]$^+$, Rt=0.75 min (Method A).

Intermediate K20

1-[2-(hydroxymethyl)indolizin-3-yl]pyrrolidin-2-one

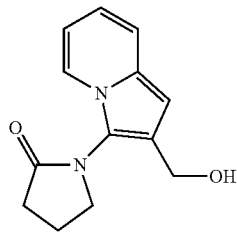 [SMILES: O=C1CCCN1c1c(CO)cc2ccccn12]

Prepared similarly to intermediate K1, starting from ethyl 3-(2-oxopyrrolidin-1-yl)indolizine-2-carboxylate H20 (0.315 g, 1.16 mmol), stirring for 1 h, and the reaction was quenched by drop-wise addition of a saturated solution of potassium and sodium tartrate tetrahydrate; the crude was purified by flash chromatography on silica gel Biotage SNAP cartridge (cyclohexane:EtOAc=100:0 to 0:100) to afford title compound as a brown oil (0.057 g, 0.27 mmol, 21% yield). MS/ESI$^+$ 231.2 [MH]$^+$, Rt=0.61 min (Method A).

Intermediate K21

[3-(pent-1-yn-1-yl)indolizin-2-yl]methanol

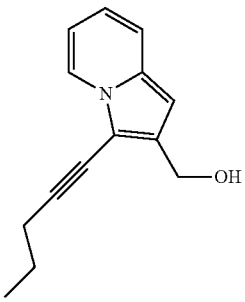 [SMILES: CCCC#Cc1c(CO)cc2ccccn12]

Prepared similarly to intermediate K1, starting from 3-(pent-1-yn-1-yl)indolizine-2-carboxylate 1121 (0.260 g, 1.02 mmol), stirring for 1 h, and the reaction was quenched by drop-wise addition of a saturated solution of potassium and sodium tartrate tetrahydrate; the crude title compound was used without any additional purification (0.217 g, 1.02 mmol, quantitative yield). MS/ESI$^+$ 214.2 [MH]$^+$, Rt=1.09 min (Method A).

Intermediate K22

[3-(3-{[tris(propan-2-yl)silyl]oxy}prop-1-yn-1-yl)indolizin-2-yl]methanol

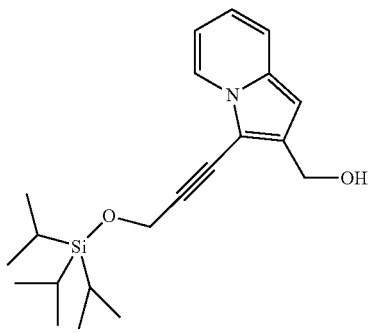 [SMILES: CC(C)[Si](OCC#Cc1c(CO)cc2ccccn12)(C(C)C)C(C)C]

Prepared similarly to intermediate K1, starting from ethyl 3-(3-{[tris(propan-2-yl)silyl]oxy}prop-1-yn-1-yl)indolizine-2-carboxylate H23 (0.501 g, 1.25 mmol), stirring for 1 h, and the reaction was quenched by drop-wise addition of a saturated solution of potassium and sodium tartrate tetrahydrate; the crude title compound was used without any additional purification (0.393 g, 1.10 mmol, 88% yield). MS/ESI$^+$ 358.1 [MH]$^+$, Rt=1.55 min (Method A).

Intermediate K23 indolizin-2-ylmethanol

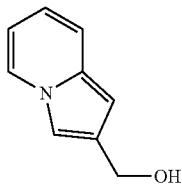 [SMILES: OCc1cc2ccccn2c1]

Prepared similarly to intermediate K1, starting from ethyl indolizine-2-carboxylate B1 (0.500 g, 2.642 mmol), stirring for 1 h, and purified by flash chromatography on silica gel Biotage SNAP cartridge (DCM to DCM:MeOH=95:5) to afford title compound as a white solid (0.334 g, 2.269 mmol, 86% yield). MS/ESI$^+$ 148.0 [MH]$^+$, Rt=0.30 min. (Method A).

Intermediate K24

(1-phenylindolizin-2-yl)methanol

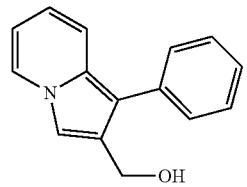 [SMILES: OCc1cn2ccccc2c1-c1ccccc1]

Prepared similarly to intermediate K1, starting from ethyl 1-phenylindolizine-2-carboxylate H24 (0.475 g, 1.79 mmol), stirring for 2 h, and purified by flash chromatography on silica gel Biotage SNAP cartridge (DCM:cyclohexane=90:10 to 100% DCM) to afford title compound as a yellow solid (0.230 g, 1.03 mmol, 57% yield). MS/ESI$^+$ 224.1 [MH]$^+$, Rt=0.97 min (Method A).

Intermediate K25

[1-(3-fluorophenyl)indolizin-2-yl]methanol

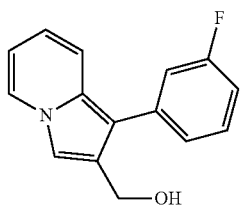 [SMILES: OCc1cn2ccccc2c1-c1cccc(F)c1]

Prepared similarly to intermediate K1, starting from ethyl 1-(3-fluorophenyl)indolizine-2-carboxylate H25 (0.585 g, 2.06 mmol), stirring for 2 h, and purified by flash chromatography on silica gel Biotage SNAP cartridge (DCM:cyclohexane=90:10 to 100% DCM) to afford title compound as a blue oil (0.330 g, 1.36 mmol, 66.3% yield). MS/ESI$^+$ 242.1 [MH]$^+$, Rt=1.02 min (Method A).

Intermediate K26

[1-(2-methylphenyl)indolizin-2-yl]methanol

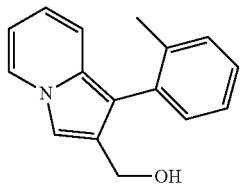 [SMILES: Cc1ccccc1-c1c(CO)cn2ccccc12]

Prepared similarly to intermediate K1, starting from ethyl 1-(2-methylphenyl)indolizine-2-carboxylate H26 (0.547 g, 1.95 mmol), stirring for 2 h, and purified by flash chromatography on silica gel Biotage SNAP cartridge (DCM:cyclohexane=90:10 to 100% DCM) to afford title compound as a yellow oil (0.230 g, 0.96 mmol, 50% yield). MS/ESI$^+$ 238.1 [MH]$^+$, Rt=0.99 min (Method A).

Intermediate K27

[1-(pyridin-2-yl)indolizin-2-yl]methanol

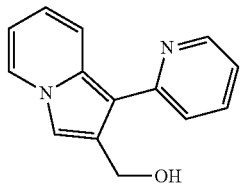 [SMILES: OCc1cn2ccccc2c1-c1ccccn1]

Prepared similarly to intermediate K1, starting from ethyl 1-(pyridin-2-yl)indolizine-2-carboxylate H27 (0.446 g, 1.67 mmol), stirring for 15 min, and the crude title compound obtained after work-up was used without any additional purification (0.358 g, 1.59 mmol, 96% yield). MS/ESI⁺ 225.1 [MH]⁺, Rt=0.38 min (Method A).

Intermediate K28

[7-(pyridin-2-yl)pyrrolo[1,2-b]pyridazin-6-yl]methanol

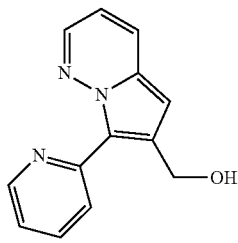 [SMILES: OCc1cc2cccnn2c1-c1ccccn1]

To a solution of methyl 7-(pyridin-2-yl)pyrrolo[1,2-b]pyridazine-6-carboxylate H28 (0.120 g, 0.47 mmol) in DCM (3.7 mL) cooled at −78° C. under nitrogen, a solution of 1 M DIBALH in toluene (0.95 mL, 0.95 mmol) was added drop-wise over 10 min and the reaction was stirred at −78° C. for 1 h. Additional 1M DIBAL in toluene (0.23 mL, 0.23 mmol) was added drop-wise over 10 min. and the reaction was stirred at −78° C. for further 1 h. The reaction mixture was quenched by drop-wise addition of saturated ammonium chloride solution and gradually warmed up to room temperature. The mixture was extracted with DCM and the combined organic layers were filtered through a phase separator tube, dried over sodium sulfate and concentrated in vacuo. The residue was purified by flash chromatography on Biotage silica gel cartridge (cyclohexane:EtOAc=80:20 to 50:50) to afford title compound as a pale yellow solid (0.078 g, 0.35 mmol, 74% yield). MS/ESI⁺ 226.1 [MH]⁺, Rt=0.39 min (Method A).

Intermediates K29-45, K47, K50-52, K54-66 and K-68-71 found in the table below may be prepared from suitable intermediates reported below following similar procedures as for compound K1.

| Intermediate | Name and Molecular Structure | | Reagent | Analytical data |
|---|---|---|---|---|
| K29 | [7-chloro-3-(pyridin-2-yl)-indolizin-2-yl]methanol | | H29 | MS/ESI⁺ 259.1 [MH]⁺, Rt = 0.85 min (Method A) |
| K30 | [7-methyl-3-(pyridin-2-yl)-indolizin-2-yl]methanol | | H30 | MS/ESI⁺ 239.2 [MH]⁺, Rt = 0.63 min (Method A) |
| K31 | [3-(2-methylpyridin-4-yl)-indolizin-2-yl]methanol | | H31 | MS/ESI⁺ 239.2 [MH]⁺, Rt = 0.40 min (Method A) |

-continued

| Intermediate | Name and Molecular Structure | Reagent | Analytical data |
|---|---|---|---|
| K32 | {3-[5-(morpholin-4-ylmethyl)pyridin-2-yl]-indolizin-2-yl}methanol | H32 | MS/ESI+ 324.3 [MH]+, Rt = 0.42 min (Method A) |
| K33 | (3-{5-[(dimethylamino)methyl]-pyridin-2-yl}indolizin-2-yl)methanol | H33 | MS/ESI+ 282.2 [MH]+, Rt = 0.40 min (Method A) |
| K34 | {3-[6-(morpholin-4-ylmethyl)pyridin-2-yl]-indolizin-2-yl}methanol | H34 | MS/ESI+ 324.3 [MH]+, Rt = 0.46 min (Method A) |
| K35 | {3-[4-(morpholin-4-ylmethyl)pyridin-2-yl]-indolizin-2-yl}methanol | H35 | MS/ESI+ 324.2 [MH]+, Rt = 0.44 min (Method A) |

-continued

| Intermediate | Name and Molecular Structure | Reagent | Analytical data |
|---|---|---|---|
| K36 | (3-{4-[(dimethylamino)methyl]-pyridin-2-yl}indolizin-2-yl)methanol | H36 | MS/ESI⁺ 282.3 [MH]⁺, Rt = 0.43 min (Method A) |
| K37 | {3-[5-(pyrrolidin-1-ylmethyl)pyridin-2-yl]-indolizin-2-yl}methanol | H37 | MS/ESI⁺ 308.2 [MH]⁺, Rt = 0.44 min (Method A) |
| K38 | (3-{5-[(4-methylpiperazin-1-yl)methyl]pyridin-2-yl}-indolizin-2-yl)methanol | H38 | MS/ESI⁺ 337.4 [MH]⁺, Rt = 0.38-0.40 min (Method A) |
| K39 | (3-{6-[(4-methylpiperazin-1-yl)methyl]pyridin-2-yl}-indolizin-2-yl)methanol | H39 | MS/ESI⁺ 337.4 [MH]⁺, Rt = 0.44 min (Method A) |

-continued

| Intermediate | Name and Molecular Structure | Reagent | Analytical data |
|---|---|---|---|
| K40 | (3-{4-[(4-methylpiperazin-1-yl)methyl]pyridin-2-yl}-indolizin-2-yl)methanol | H40 | MS/ESI⁺ 337.5 [MH]⁺, Rt = 0.36 min (Method A) |
| K41 | (3-{5-[(2,2,3,3,11,11,12,12-octamethyl-4,10-dioxa-7-aza-3,11-disilatridecan-7-yl)methyl]pyridin-2-yl}indolizin-2-yl)methanol | H41 | MS/ESI⁺ 570.5 [MH]⁺, Rt = 1.16 min (Method A) |
| K42 | {3-[3-(1-methylpyrrolidin-2-yl)phenyl]indolizin-2-yl}-methanol | H42 | MS/ESI⁺ 307.3 [MH]⁺, Rt = 0.53 min (Method A) |
| K43 | (3-{5-[2-(morpholin-4-yl)ethoxy]pyridin-2-yl}-indolizin-2-yl)methanol | H43 | MS/ESI⁺ 354.1 [MH]⁺, Rt = 0.82 min (Method C) |

-continued

| Intermediate | Name and Molecular Structure | Reagent | Analytical data |
|---|---|---|---|
| K44 | [3-(6-methoxypyridin-3-yl)indolizin-2-yl]methanol | H44 | MS/ESI+ 255.0 [MH]+, Rt = 0.88 min (Method A) |
| K45 | [3-(2-methoxypyridin-4-yl)indolizin-2-yl]methanol | H45 | MS/ESI+ 255.2 [MH]+, Rt = 0.80 min (Method A) |
| K47 | [3-(pyridin-2-yl)-1-(trifluoromethyl)indolizin-2-yl]methanol | H48 | MS/ESI+ 293.2 [MH]+, Rt = 1.00 min (Method A) |
| K50 | [3-(1,3-thiazol-4-yl)indolizin-2-yl]methanol | H52 | MS/ESI+ 231.1 [MH]+, Rt = 0.82 min (Method A) |
| K51 | {3-[2-(morpholin-4-ylmethyl)-1,3-thiazol-4-yl]indolizin-2-yl}methanol | H53 | MS/ESI+ 330.2 [MH]+, Rt = 0.49 min (Method A) |
| K52 | {3-[3-(dimethylamino)prop-1-yn-1-yl]indolizin-2-yl}methanol | H54 | MS/ESI+ 228.8 [MH]+, Rt = 0.39 min (Method A) |

| Intermediate | Name and Molecular Structure | | Reagent | Analytical data |
|---|---|---|---|---|
| K54 | 1-[2-(dimethylamino)ethyl]-4-[2-(hydroxymethyl)indolizin-3-yl]-1,2-dihydropyridin-2-one | 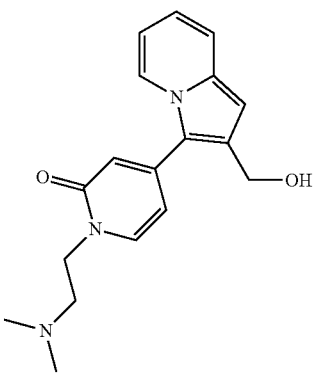 [SMILES: CN(C)CCn1ccc(-c2c(CO)cc3ccccn23)cc1=O] | H56 | MS/ESI⁺ 312.4 [MH]⁺, Rt = 0.45 min (Method A) |
| K55 | 6-[2-(hydroxymethyl)indolizin-3-yl]-2-[2-(pyrrolidin-1-yl)ethyl]-2,3-dihydropyridazin-3-one | 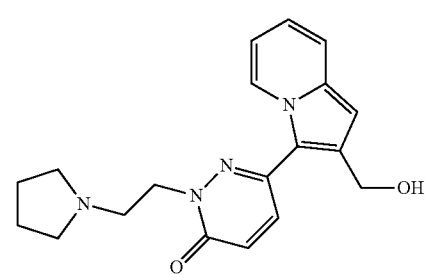 [SMILES: O=c1ccc(-c2c(CO)cc3ccccn23)nn1CCN1CCCC1] | H60 | MS/ESI⁺ 339.3 [MH]⁺, Rt = 0.41-0.44 min (Method A) |
| K56 | 6-[2-(hydroxymethyl)indolizin-3-yl]-2-[2-(4-methylpiperazin-1-yl)ethyl]-2,3-dihydropyridazin-3-one | 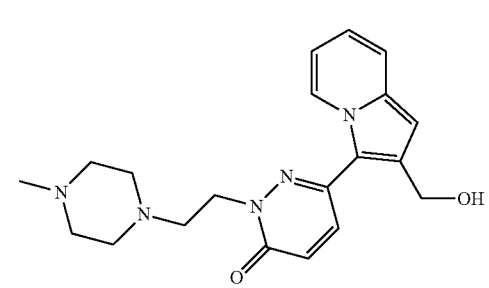 [SMILES: CN1CCN(CCn2nc(-c3c(CO)cc4ccccn34)ccc2=O)CC1] | H61 | MS/ESI⁺ 368.4 [MH]⁺, Rt = 0.43 min (Method A) |
| K57 | 6-[2-(hydroxymethyl)indolizin-3-yl]-2-[2-(morpholin-4-yl)ethyl]-2,3-dihydropyridazin-3-one | 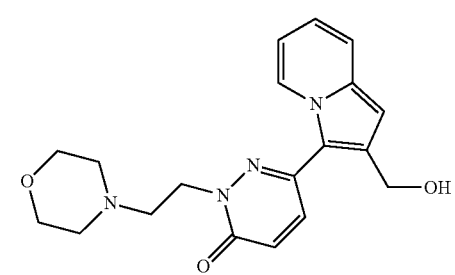 [SMILES: O=c1ccc(-c2c(CO)cc3ccccn23)nn1CCN1CCOCC1] | H62 | MS/ESI⁺ 355.3 [MH]⁺, Rt = 0.42 min (Method A) |

-continued

| Intermediate | Name and Molecular Structure | Reagent | Analytical data |
|---|---|---|---|
| K58 | (3-{6-[2-(4-methylpiperazin-1-yl)ethoxy]pyridazin-3-yl}-indolizin-2-yl)methanol | H63 | MS/ESI+ 368.3 [MH]+, Rt = 0.41-0.43 min (Method A) |
| K59 | (3-{6-[2-(dimethylamino)ethoxy]-pyridazin-3-yl}indolizin-2-yl)methanol | H64 | MS/ESI+ 313.3 [MH]+, Rt = 0.46 min (Method A) |
| K60 | (3-{6-[(1-methylpiperidin-4-yl)oxy]pyridazin-3-yl}-indolizin-2-yl)methanol | H65 | MS/ESI+ 339.3 [MH]+, Rt = 0.45-0.47 min (Method A) |

-continued

| Intermediate | Name and Molecular Structure | | Reagent | Analytical data |
|---|---|---|---|---|
| K61 | (3-{6-[2-(1-methylpiperidin-4-yl)ethoxy]pyridazin-3-yl}-indolizin-2-yl)methanol | 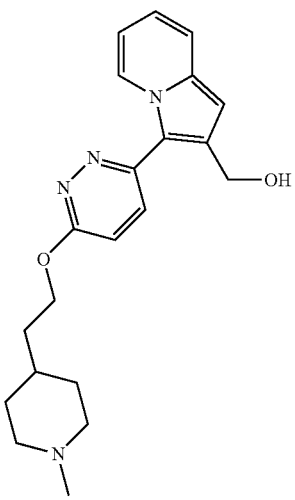 [SMILES: CN1CCC(CCOc2ccc(-c3c(CO)cc4ccccn34)nn2)CC1] | H66 | MS/ESI+ 367.4 [MH]+, Rt = 0.53 min (Method A) |
| K62 | [3-(morpholin-4-ylmethyl)indolizin-2-yl]-methanol | 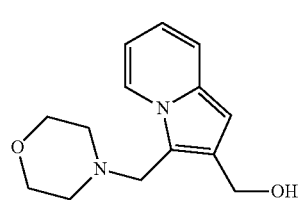 [SMILES: OCc1cc2ccccn2c1CN1CCOCC1] | H67 | MS/ESI+ 160.2 found, Rt = 0.75 min (Method C) |
| K63 | [3-({2-methyl-2,9-diazaspiro[5.5]undecan-9-yl}methyl)indolizin-2-yl]-methanol | 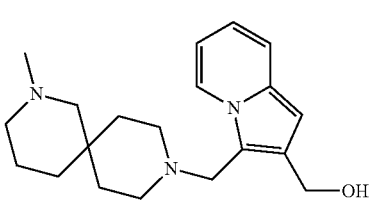 [SMILES: CN1CCCC2(CCN(Cc3c(CO)cc4ccccn34)CC2)C1] | H68 | 1H NMR (400 MHz, DMSO-d6) δ ppm 8.09-8.13 (m, 1 H), 7.33-7.38 (m, 1 H), 6.63-6.69 (m, 1 H), 6.51-6.57 (m, 1 H), 6.35 (s, 1 H), 4.91 (t, 1 H), 4.55 (d, 2 H), 3.73 (s, 2 H), 2.25-2.37 (m, 4 H), 2.11-2.23 (m, 2 H), 2.08 (s, 3 H), 1.98-2.10 (m, 2 H), 1.16-1.51 (m, 8 H) |
| K64 | tert-butyl 9-{[2-(hydroxymethyl)indolizin-3-yl]methyl}-3,9-diazaspiro[5.5]undecane-3-carboxylate | 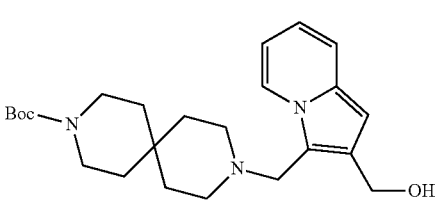 [SMILES: CC(C)(C)OC(=O)N1CCC2(CCN(Cc3c(CO)cc4ccccn34)CC2)CC1] | H69 | MS/ESI+ 414.5 [MH]+, Rt = 0.67 min (Method A) |
| K65 | tert-butyl 2-{[2-(hydroxymethyl)indolizin-3-yl]methyl}-2,7-diazaspiro[3.5]nonane-7-carboxylate | 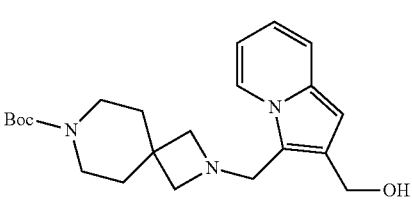 [SMILES: CC(C)(C)OC(=O)N1CCC2(CC1)CN(Cc1c(CO)cc3ccccn13)C2] | H70 | MS/ESI+ 386.5 [MH]+, Rt = 0.60 min (Method A) |
| K66 | tert-butyl (3aR,6aS)-5-{[2-(hydroxymethyl)indolizin-3-yl]methyl}-octahydropyrrolo-[3,4-c]pyrrole-2-carboxylate | 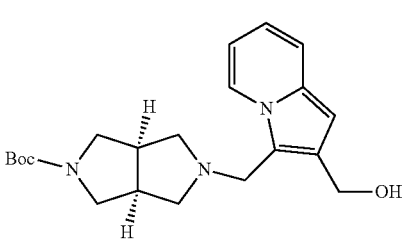 [SMILES: CC(C)(C)OC(=O)N1C[C@H]2CN(Cc3c(CO)cc4ccccn34)C[C@H]2C1] | H71 | MS/ESI+ 372.3 [MH]+, Rt = 1.09 min (Method C) |

-continued

| Intermediate | Name and Molecular Structure | Reagent | Analytical data |
|---|---|---|---|
| K68 | (3-{1-[2-(dimethylamino)ethyl]-1H-pyrazol-3-yl}-indolizin-2-yl)methanol | H75 | MS/ESI+ 285.3 [MH]+, Rt = 0.44 min (Method A) |
| K69 | (3-{1-[2-(4-methylpiperazin-1-yl)ethyl]-1H-pyrazol-3-yl}indolizin-2-yl)methanol | H76 | MS/ESI+ 340.3 [MH]+, Rt = 0.46 min (Method A) |
| K70 | (3-{1-[2-(2,2,3,3,11,11,12,12-octamethyl-4,10-dioxa-7-aza-3,11-disilatridecan-7-yl)ethyl]-1H-pyrazol-3-yl}indolizin-2-yl)methanol | H77 | MS/ESI+ 573.5 [MH]+, Rt = 1.11 min (Method A) |

-continued

| Intermediate | Name and Molecular Structure | Reagent | Analytical data |
|---|---|---|---|
| K71 | (3-{1-[2-(morpholin-4-yl)-ethyl]-1H-pyrazol-3-yl}-indolizin-2-yl)methanol | H78 | MS/ESI⁺ 327.3 [MH]⁺, Rt = 0.50 min (Method A) |

Intermediate K46

2-[2-(hydroxymethyl)indolizin-3-yl]benzonitrile

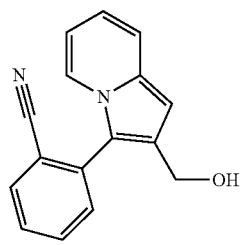 [SMILES: N#Cc1ccccc1-c1c(CO)cc2ccccn12]

Intermediate K48

3-{3-[(dimethylamino)methyl]phenyl}-2-(hydroxymethyl)indolizine-1-carbonitrile

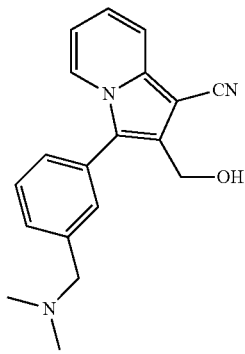 [SMILES: CN(C)Cc1cccc(-c2c(CO)c(C#N)c3ccccn23)c1]

To a stirred solution of ethyl 3-(2-cyanophenyl)indolizine-2-carboxylate H46 (0.240 g, 0.827 mmol) in THF (12 mL), 2M LiBH$_4$ solution in THF (0.83 mL, 1.654 mmol) and MeOH (0.4 mL) were added and the reaction was stirred at 50° C. for 2 h. Additional 2M LiBH$_4$ solution in THF (0.83 mL, 1.654 mmol) was added and the solution was stirred at the same temperature overnight. The reaction mixture was diluted with EtOAc and washed with H$_2$O. The organic phase was concentrated under reduced pressure and the crude was purified by flash chromatography on Biotage silica gel SNAP cartridge (cyclohexane to cyclohexane: EtOAc=60:40) to afford title compound (0.140 g, 0.56 mmol, 68% yield). MS/ESI⁺ 249.2 [MH]⁺, Rt=0.89 min (Method A).

Prepared similarly to intermediate K28, starting from ethyl 1-cyano-3-{3-[(dimethylamino)methyl]phenyl}indolizine-2-carboxylate H50 (2.7 g, 7.77 mmol) and the reaction was quenched by drop-wise addition of a saturated solution of potassium and sodium tartrate tetrahydrate, to afford crude title compound which was used without any additional purification (theoretical 7.77 mmol, yield considered to be quantitative). MS/ESI⁺ 306.3 [MH]⁺, Rt=0.97 min (Method J).

Intermediate K49

(7-{3-[(dimethylamino)methyl]phenyl}pyrrolo[1,2-b]pyridazin-6-yl)methanol

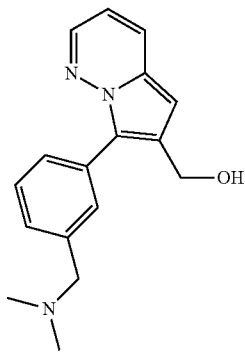 [SMILES: CN(C)Cc1cccc(-c2c(CO)cc3cccnn23)c1]

Prepared similarly to intermediate K28, starting from methyl 7-{3-[(dimethylamino)methyl]phenyl}pyrrolo[1,2-b]pyridazine-6-carboxylate H51 (0.713 g, 2.3 mmol), and purified by flash chromatography on silica-NH Biotage SNAP cartridge (DCM to DCM:MeOH=98:2) to afford title compound (0.530 g, 1.88 mmol, 82% yield). MS/ESI$^+$ 282.3 [MH]$^+$, Rt=0.42-0.44 min (Method A).

Intermediate K53

1-[2-(hydroxymethyl)indolizin-3-yl]-4-methylpiperazin-2-one

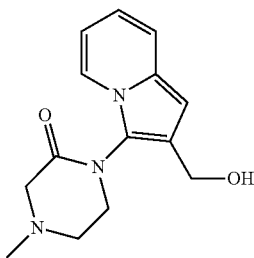 [SMILES: CN1CCN(c2c(CO)cc3ccccn23)C(=O)C1]

Step 1: 3-(4-methyl-2-oxopiperazin-1-yl)indolizine-2-carboxylic acid K53a

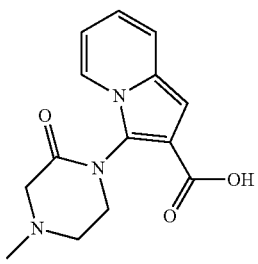 [SMILES: CN1CCN(c2c(C(=O)O)cc3ccccn23)C(=O)C1]

Ethyl 3-(4-methyl-2-oxopiperazin-1-yl)indolizine-2-carboxylate H55 (0.694 g, 2.3 mmol) was dissolved in THF (11.4 mL) and water (5.5 mL), lithium hydroxide (0.110 g, 4.6 mmol) was added and the mixture was heated at 60° C. for 24 h. The organic solvent was removed under reduced pressure and the aqueous residue was acidified with 1N HCl and extracted with DCM; the combined organic layers were dried over sodium sulfate and evaporated. The aqueous phase was evaporated and the residue was taken-up with DCM and MeOH and filtered; the filtered solution was evaporated under reduce pressure. The two fractions were combined to afford title compound as a brown solid (0.598 g). MS/ESI$^+$ 274.2 [MH]$^+$, Rt=0.35 min (Method A).

Step 2: 1-[2-(hydroxymethyl)indolizin-3-yl]-4-methylpiperazin-2-one K53

NaBH$_4$ (0.166 g, 4.4 mmol) was added to dry THF (4 mL), and the mixture was cooled at 10° C. before BF$_3$.Et$_2$O (0.70 mL, 5.72 mmol) was added drop-wise. Then a solution of 3-(4-methyl-2-oxopiperazin-1-yl)indolizine-2-carboxylic acid K53a (0.598 g) in THF (2.6 mL) was carefully added, and the mixture was allowed to stir at room temperature for 4 h. The reaction was quenched with methanol; 10% aqueous HCl was added and the mixture was heated at 60° C. for 1 h. The pH of reaction mixture was adjusted to neutral with 50% aqueous NaOH and the volatiles were evaporated under reduced pressure. The aqueous residue was extracted with DCM and the combined organic layers were dried over sodium sulfate and concentrated in vacuo. The crude was purified by flash chromatography on Biotage silica-NH cartridge (DCM to DCM:MeOH=99:1) to afford title compound as an orange oil (0.122 g) which was used without any additional purification. MS/ESI$^+$ 260.2 [MH]$^+$, Rt=0.31 min (Method A).

Intermediate K67

2-(hydroxymethyl)-3-(morpholin-4-ylmethyl)indolizine-1-carbonitrile

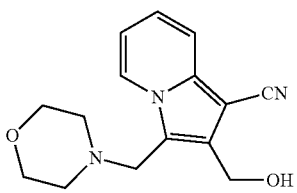 [SMILES: N#Cc1c(CO)c(CN2CCOCC2)n2ccccc12]

To a solution of ethyl 1-cyano-3-(morpholin-4-ylmethyl)indolizine-2-carboxylate H72 (0.382 g, 1.21 mmol) in THF (24 mL) cooled at 0° C. under nitrogen, a solution of LiAlH$_4$ 1M in THF (0.30 mL, 0.3 mmol) was added drop-wise and the reaction was stirred at 0° C. for 30 min. Additional LiAlH$_4$ 1M in THF (0.12 mL, 0.12 mmol) was added drop-wise and the reaction was stirred at 0° C. for 30 min. A new portion of LiAlH$_4$ 1M in THF (0.12 mL, 0.12 mmol) was added drop-wise and the reaction was stirred at 0° C. for further 30 min. The reaction mixture was quenched by portion-wise addition of sodium sulfate decahydrate, the mixture was filtered and the filtrate was concentrated in vacuo. The crude was purified by flash chromatography on Biotage silica-NH SNAP cartridge (DCM to DCM:MeOH=98:2) to afford title compound as a pale yellow oil (0.145 g, 0.53 mmol, 44% yield).

1H NMR (400 MHz, CHLOROFORM-d) δ ppm 8.18-8.23 (m, 1 H), 7.62-7.67 (m, 1 H), 7.08-7.13 (m, 1 H), 6.80-6.86 (m, 1 H), 4.88 (s, 2 H), 3.85 (s, 2 H), 3.66-3.72 (m, 4 H), 2.47-2.53 (m, 4 H).

Intermediate L1

3-phenylindolizine-2-carbaldehyde

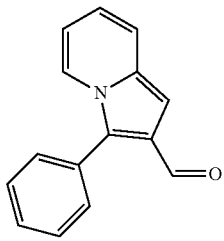 [SMILES: O=Cc1cc2ccccn2c1-c1ccccc1]

To a solution of (3-phenylindolizin-2-yl)methanol K1 (0.227 g, 1.016 mmol) in DCM (5 mL), MnO₂ (1.061 g, 12.20 mmol) was added and the mixture was heated at 50° C. for 2 h. The mixture was diluted with DCM and filtered through a Celite® pad. The filtrate was evaporated to dryness to afford title compound as a yellow oil (0.189 g, 0.854 mmol, 85% yield). MS/ESI⁺ 222.1 [MH]⁺, Rt=1.11 min (Method A).

Intermediate L2

3-(pyridin-2-yl)indolizine-2-carbaldehyde

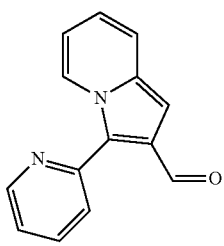

Prepared similarly to intermediate L1 starting from [3-(pyridin-2-yl)indolizin-2-yl]methanol K2 (0.185 g, 0.825 mmol) and MnO₂ (1.08 g, 12.37 mmol) was added and the mixture was heated at 50° C. for 4 h. The mixture was diluted with DCM and filtered through a Celite® pad. The filtrate was evaporated to dryness to afford title compound as a yellow solid (0.170 g, 0.765 mmol, 93% yield). MS/ESI⁺ 223.1 [MH]⁺, Rt=0.84 min (Method A).

Intermediate L3

3-(2-fluorophenyl)indolizine-2-carbaldehyde

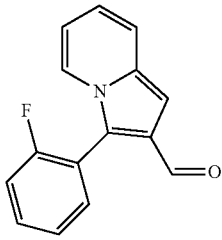 [SMILES: O=Cc1cc2ccccn2c1-c1ccccc1F]

Prepared similarly to intermediate L1, starting from [3-(2-fluorophenyl)indolizin-2-yl]methanol K4 (0.202 g, 0.837 mmol) and MnO₂ (1.114 g, 12.813 mmol), at 50° C. for 4 h, to afford title compound as a brown oil (0.169 g, 0.706 mmol, 84% yield). MS/ESI⁺ 240.1 [MH]⁺, Rt=1.11 min (Method A).

Intermediate L4

3-(pyridin-3-yl)indolizine-2-carbaldehyde

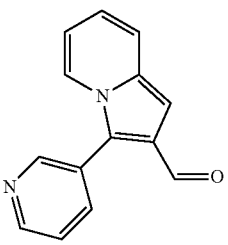 [SMILES: O=Cc1cc2ccccn2c1-c1cccnc1]

Prepared similarly to intermediate L1, starting from [3-(pyridin-3-yl)indolizin-2-yl]methanol K6 (0.200 g, 0.892 mmol) and MnO₂ (0.930 g, 10.70 mmol), at 50° C. for 2 h, to afford title compound as a yellow solid (0.168 g, 0.756 mmol, 85% yield). MS/ESI⁺ 223.1 [MH]⁺, Rt=0.67 min (Method A).

Intermediate L5

3-(pyrazin-2-yl)indolizine-2-carbaldehyde

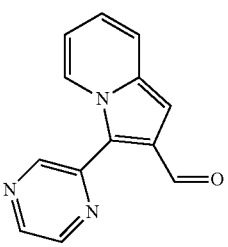 [SMILES: O=Cc1cc2ccccn2c1-c1cnccn1]

Prepared similarly to intermediate L1, starting from [3-(pyrazin-2-yl)indolizin-2-yl]methanol K7 (0.042 g, 0.186 mmol) and MnO₂ (0.194 g, 2.232 mmol), at 50° C. for 2 h, to afford title compound as a yellow solid (0.037 g, 0.165 mmol, 89% yield). MS/ESI⁺ 224.0 [MH]⁺, Rt=0.79 min (Method A).

Intermediate L6

3-(pyridin-4-yl)indolizine-2-carbaldehyde

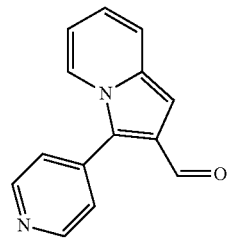 [SMILES: O=Cc1cc2ccccn2c1-c1ccncc1]

Prepared similarly to intermediate L1, starting from [3-(pyridin-4-yl)indolizin-2-yl]methanol K8 (0.130 g, 0.580 mmol) and MnO₂ (0.762 g, 8.70 mmol), at 50° C. for 4 h; after work-up the crude was purified by flash chromatography on 10 g Biotage silica gel SNAP cartridge (DCM to DCM:MeOH=90:10) to afford title compound (0.100 g, 0.450 mmol, 78% yield). MS/ESI⁺ 223.1 [MH]⁺, Rt=0.51 min (Method A).

Intermediate L7

6-methyl-3-(pyridin-2-yl)indolizine-2-carbaldehyde

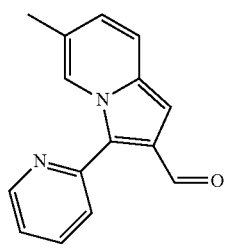 [SMILES: Cc1ccc2cc(C=O)c(-c3ccccn3)n2c1]

Prepared similarly to intermediate L1, starting from [6-methyl-3-(pyridin-2-yl)indolizin-2-yl]methanol K9 (0.136 g, 0.57 mmol) and MnO₂ (0.744 g, 8.56 mmol), at 50° C. for 1 h to afford title compound as a yellow solid (0.127 g, 0.53 mmol, 94% yield). MS/ESI⁺ 237.1 [MH]⁺, Rt=0.93 min (Method A).

Intermediate L8

3-(pyridin-2-yl)-6-(trifluoromethyl)indolizine-2-carbaldehyde

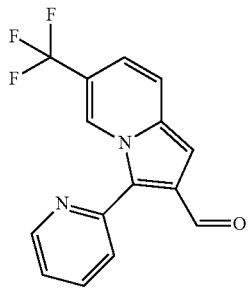 [SMILES: O=Cc1cc2ccc(C(F)(F)F)cn2c1-c1ccccn1]

Prepared similarly to intermediate L1, starting from [3-(pyridin-2-yl)-6-(trifluoromethyl)indolizin-2-yl]methanol K10 (0.197 g, 0.674 mmol) and MnO₂ (0.879 g, 10.11 mmol), at 50° C. for 2 h to afford title compound as a yellow solid (0.150 g, 0.517 mmol, 77% yield). MS/ESI⁺ 291.3 [MH]⁺, Rt=1.12 min. (Method A).

Intermediate L9

8-fluoro-3-(pyridin-2-yl)indolizine-2-carbaldehyde

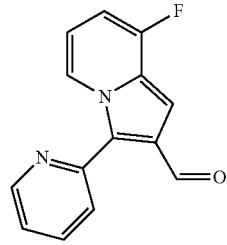 [SMILES: O=Cc1cc2c(F)cccn2c1-c1ccccn1]

Prepared similarly to intermediate L1, starting from [8-fluoro-3-(pyridin-2-yl)indolizin-2-yl]methanol K11 (0.120 g, 0.49 mmol) and MnO₂ (0.521 g, 6.00 mmol), at 50° C. for 3 h, to afford title compound as a yellow solid (0.103 g, 0.43 mmol, 85% yield). MS/ESI⁺ 241.1 [MH]⁺, Rt=0.93 min (Method A).

Intermediate L10

1-methyl-3-(pyridin-2-yl)indolizine-2-carbaldehyde

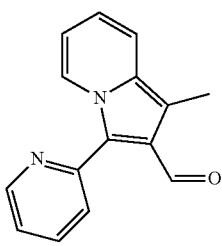 [SMILES: Cc1c(C=O)c(-c2ccccn2)n2ccccc12]

To a stirred solution of oxalyl chloride (0.033 mL) in DCM (1.5 mL) at −78° C. and under nitrogen atmosphere, DMSO (0.055 mL) was slowly added. The mixture was stirred for 10 min then a solution of [1-methyl-3-(pyridin-2-yl)indolizin-2-yl]methanol K12 (0.061 g, 0.256 mmol) in DCM (0.5 mL) was slowly added. The reaction mixture was stirred for 0.5 h then TEA (0.107 mL, 0.768 mmol) was added drop-wise and the mixture was stirred for further 2 h at −78° C. Aqueous saturated sodium bicarbonate was added and the mixture was extracted with DCM. The organic phase was washed with saturated sodium bicarbonate, brine, dried over sodium sulfate and the solvent removed under reduced pressure to afford title compound which was used without any additional purification (0.046 g, 0.195 mmol, 76% yield). MS/ESI$^+$ 237.1 [MH]$^+$, Rt=0.94 min (Method A).

Intermediate L11

3-[5-(morpholin-4-ylmethyl)thiophen-2-yl]indolizine-2-carbaldehyde

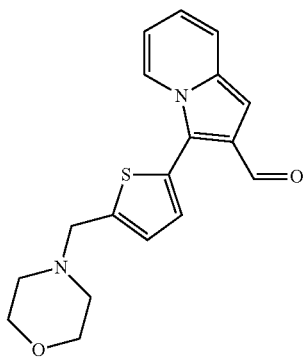 [SMILES: O=Cc1cc2ccccn2c1-c1ccc(CN2CCOCC2)s1]

Prepared similarly to intermediate L1, starting from {3-[5-(morpholin-4-ylmethyl)thiophen-2-yl]indolizin-2-yl}methanol K13 (0.364 g, 1.11 mmol) and MnO$_2$ (1.447 g, 16.65 mmol), at 50° C. for 4 h, to afford title compound as an orange oil (0.337 g, 1.03 mmol, 93% yield). MS/ESI$^+$ 327.2 [MH]$^+$, Rt=0.54 min (Method A).

Intermediate L12

3-[4-(morpholin-4-ylmethyl)phenyl]indolizine-2-carbaldehyde

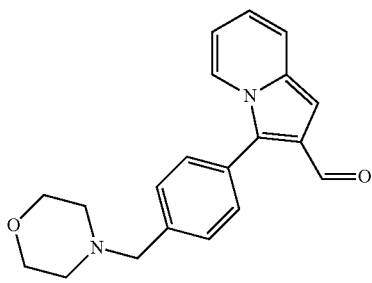 [SMILES: O=Cc1cc2ccccn2c1-c1ccc(CN2CCOCC2)cc1]

Prepared similarly to intermediate L1, starting from {3-[4-(morpholin-4-ylmethyl)phenyl]indolizin-2-yl}methanol K14 (0.271 g, 0.84 mmol) and MnO$_2$ (1.095 g, 12.6 mmol), at 50° C. for 4 h, to afford title compound as a dark yellow oil (0.240 g, 0.75 mmol, 89% yield). MS/ESI$^+$ 321.2 [MH]$^+$, Rt=0.54 min (Method A).

Intermediate L13

3-{4-[(dimethylamino)methyl]phenyl}indolizine-2-carbaldehyde

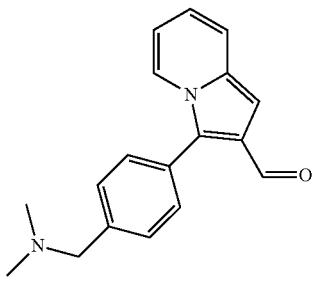 [SMILES: CN(C)Cc1ccc(-c2c(C=O)cc3ccccn23)cc1]

Prepared similarly to intermediate L1, starting from (3-{4-[(dimethylamino)methyl]phenyl}indolizin-2-yl)methanol K15 (0.235 g, 0.83 mmol) and MnO$_2$ (1.082 g, 12.45 mmol), at 50° C. for 4 h, to afford title compound as an orange oil (0.196 g, 0.70 mmol, 84% yield). MS/ESI$^+$ 279.2 [MH]$^+$, Rt=0.53 min (Method A).

Intermediate L14

3-{3-[(dimethylamino)methyl]phenyl}indolizine-2-carbaldehyde

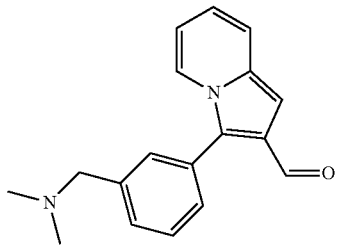 [SMILES: CN(C)Cc1cccc(-c2c(C=O)cc3ccccn23)c1]

Prepared similarly to intermediate L1, starting from (3-{3-[(dimethylamino)methyl]phenyl}indolizin-2-yl)methanol K16 (0.285 g, 1.02 mmol) and MnO$_2$ (1.330 g, 15.3 mmol), at 50° C. for 4 h, to afford title compound as an orange oil (0.199 g, 0.71 mmol, 70% yield). MS/ESI$^+$ 279.2 [MH]$^+$, Rt=0.55 min (Method A).

Intermediate L15

3-(3,6-dihydro-2H-pyran-4-yl)indolizine-2-carbaldehyde

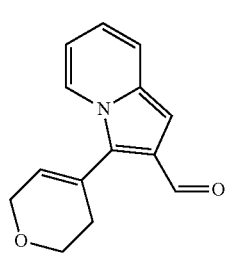 [SMILES: O=Cc1cc2ccccn2c1C1=CCOCC1]

Prepared similarly to intermediate L1, starting from [3-(3,6-dihydro-2H-pyran-4-yl)indolizin-2-yl]methanol K17 (0.078 g, 0.34 mmol) and MnO$_2$ (0.440 g, 5.06 mmol), at 50° C. for 4 h, to afford title compound as a yellow solid (0.057 g, 0.25 mmol, 74% yield). MS/ESI$^+$ 228.1 [MH]$^+$, Rt=0.89 min (Method A).

Intermediate L16 tert-butyl 4-(2-formylindolizin-3-yl)-1,2,3,6-tetrahydropyridine-1-carboxylate

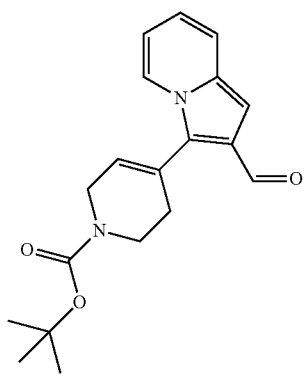 [SMILES: CC(C)(C)OC(=O)N1CC=C(c2c(C=O)cc3ccccn23)CC1]

Prepared similarly to intermediate L1, starting from tert-butyl 4-[2-(hydroxymethyl)indolizin-3-yl]-1,2,3,6-tetrahydropyridine-1-carboxylate K18 (0.193 g, 0.58 mmol) and MnO$_2$ (0.888 g, 10.21 mmol), at 50° C. for 4 h, to afford title compound as a yellow solid (0.135 g, 0.41 mmol, 71% yield). MS/ESI$^+$ 327.3 [MH]$^+$, Rt=1.17 min (Method A).

Intermediate L17

3-(1,3-thiazol-5-yl)indolizine-2-carbaldehyde

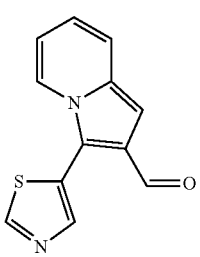 [SMILES: O=Cc1cc2ccccn2c1-c1cncs1]

Prepared similarly to intermediate L1, starting from [3-(1,3-thiazol-5-yl)indolizin-2-yl]methanol K19 (0.143 g, 0.62 mmol) and MnO$_2$ (0.808 g, 9.3 mmol), at 50° C. for 4 h, to afford title compound as an orange solid (0.097 g, 0.42 mmol, 68% yield). MS/ESI$^+$ 229.1 [MH]$^+$, Rt=0.83 min (Method A).

Intermediate L18

3-(2-oxopyrrolidin-1-yl)indolizine-2-carbaldehyde

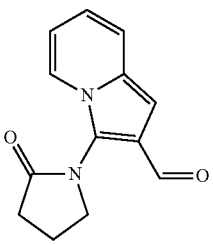 [SMILES: O=Cc1cc2ccccn2c1N1CCCC1=O]

Prepared similarly to intermediate L1, starting from 1-[2-(hydroxymethyl)indolizin-3-yl]pyrrolidin-2-one K20 (0.057 g, 0.25 mmol) and MnO$_2$ (0.326 g, 3.75 mmol), at 50° C. for 4 h, to afford title compound as a brown oil (0.036 g, 0.16 mmol, 63% yield). MS/ESI$^+$ 229.1 [MH]$^+$, Rt=0.70 min (Method A).

Intermediate L19

3-(pent-1-yn-1-yl)indolizine-2-carbaldehyde

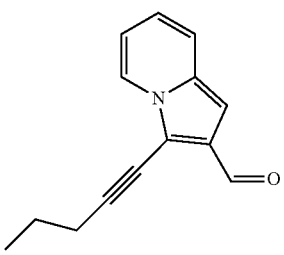 [SMILES: CCCC#Cc1c(C=O)cc2ccccn12]

Prepared similarly to intermediate L1, starting from {[3-(pent-1-yn-1-yl)indolizin-2-yl]methanol K21 (theoretical 1.02 mmol) and MnO$_2$ (1.330 g, 15.3 mmol), at 50° C. for 4 h. The crude was purified by flash chromatography on Biotage silica SNAP cartridge (cyclohexane to cyclohexane:EtOAc=90:10) to afford title compound as a yellow solid (0.158 g, 0.74 mmol, 73%). MS/ESI+ 212.1 [MH]+, Rt=1.22 min (Method A).

Intermediate L20

3-(3-{[tris(propan-2-yl)silyl]oxy}prop-1-yn-1-yl)indolizine-2-carbaldehyde

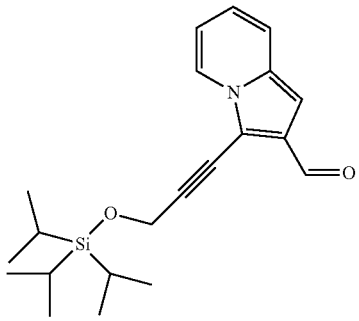 [SMILES: CC(C)[Si](OCC#Cc1c(C=O)cc2ccccn12)(C(C)C)C(C)C]

Prepared similarly to intermediate L1, starting from [3-(3-{[tris(propan-2-yl)silyl]oxy}prop-1-yn-1-yl)indolizin-2-yl]methanol K22 (0.392 g, 1.09 mmol) and MnO2 (1.09 g, 16.35 mmol), at 50° C. for 4 h, to afford title compound as a yellow dark oil (0.332 g, 0.93 mmol, 86% yield). MS/ESI+ 356.1 [MH]+, Rt=1.66 min (Method A).

Intermediate L21

7-(pyridin-2-yl)pyrrolo[1,2-b]pyridazine-6-carbaldehyde

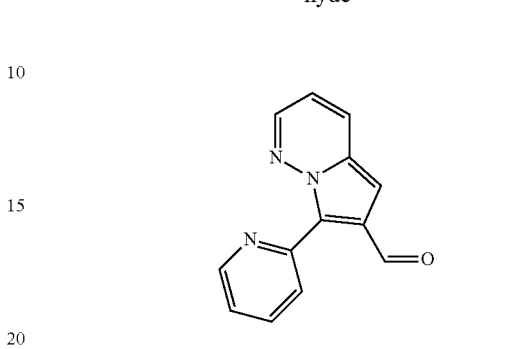

Prepared similarly to intermediate L1, starting from [7-(pyridin-2-yl)pyrrolo[1,2-b]pyridazin-6-yl]methanol K28 (0.078 g, 0.35 mmol) and MnO2 (0.456 g, 5.25 mmol), at 50° C. for 1 h to afford title compound as a yellow solid (0.072 g, 0.32 mmol, 92% yield). MS/ESI+ 224.2 [MH]+, Rt=0.63 min (Method A).

Intermediates L22-40 and L42-65 found in the table below may be prepared from suitable intermediates reported below following similar procedures as for compound L1.

| Intermediate | Name and Molecular Structure | | Reagent | Analytical data |
|---|---|---|---|---|
| L22 | 7-chloro-3-(pyridin-2-yl)indolizine-2-carbaldehyde | | K29 | MS/ESI+ 257.1 [MH]+, Rt = 1.04 min (Method A) |
| L23 | 7-methyl-3-(pyridin-2-yl)indolizine-2-carbaldehyde | | K30 | MS/ESI+ 237.2 [MH]+, Rt = 0.96 min (Method A) |
| L24 | 3-(2-methylpyridin-4-yl)indolizine-2-carbaldehyde | | K31 | MS/ESI+ 237.1 [MH]+, Rt = 0.47 min (Method A) |

-continued

| Intermediate | Name and Molecular Structure | Reagent | Analytical data |
| --- | --- | --- | --- |
| L25 | 3-[5-(morpholin-4-ylmethyl)pyridin-2-yl]indolizine-2-carbaldehyde | K32 | MS/ESI⁺ 322.2 [MH]⁺, Rt = 0.45 min (Method A) |
| L26 | 3-{5-[(dimethylamino)methyl]pyridin-2-yl}indolizine-2-carbaldehyde | K33 | MS/ESI⁺ 280.2 [MH]⁺, Rt = 0.43 min (Method A) |
| L27 | 3-[6-(morpholin-4-ylmethyl)pyridin-2-yl]indolizine-2-carbaldehyde | K34 | MS/ESI⁺ 322.3 [MH]⁺, Rt = 0.48 min (Method A) |
| L28 | 3-[4-(morpholin-4-ylmethyl)pyridin-2-yl]indolizine-2-carbaldehyde | K35 | MS/ESI⁺ 322.2 [MH]⁺, Rt = 0.48 min (Method A) |

-continued

| Intermediate | Name and Molecular Structure | Reagent | Analytical data |
|---|---|---|---|
| L29 | 3-{4-[(dimethylamino)methyl]pyridin-2-yl}indolizine-2-carbaldehyde | K36 | MS/ESI+ 280.4 [MH]+, Rt = 0.45 min (Method A) |
| L30 | 3-[5-(pyrrolidin-1-ylmethyl)pyridin-2-yl]indolizine-2-carbaldehyde | K37 | MS/ESI+ 306.2 [MH]+, Rt = 0.47 min (Method A) |
| L31 | 3-{5-[(4-methylpiperazin-1-yl)methyl]pyridin-2-yl}indolizine-2-carbaldehyde | K38 | MS/ESI+ 335.4 [MH]+, Rt = 0.48 min (Method A) |
| L32 | 3-{6-[(4-methylpiperazin-1-yl)methyl]pyridin-2-yl}indolizine-2-carbaldehyde | K39 | MS/ESI+ 335.4 [MH]+, Rt = 0.49 min (Method A) |

-continued

| Intermediate | Name and Molecular Structure | | Reagent | Analytical data |
|---|---|---|---|---|
| L33 | 3-{4-[(4-methylpiperazin-1-yl)methyl]pyridin-2-yl}indolizine-2-carbaldehyde | 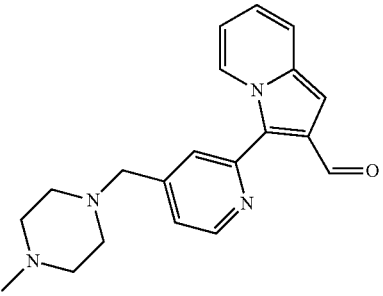 [SMILES: CN1CCN(Cc2ccnc(-c3c(C=O)cc4ccccn34)c2)CC1] | K40 | MS/ESI⁺ 335.4 [MH]⁺, Rt = 0.47 min (Method A) |
| L34 | 3-{5-[(2,2,3,3,11,11,12,12-octamethyl-4,10-dioxa-7-aza-3,11-disilatridecan-7-yl)methyl]pyridin-2-yl}indolizine-2-carbaldehyde | 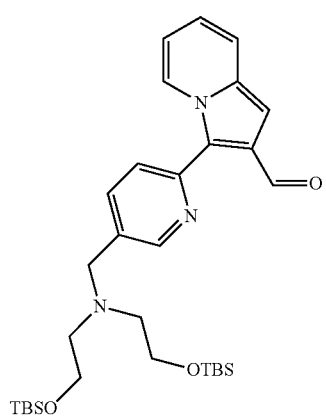 [SMILES: CC(C)(C)[Si](C)(C)OCCN(CCO[Si](C)(C)C(C)(C)C)Cc1ccc(-c2c(C=O)cc3ccccn23)nc1] | K41 | MS/ESI⁺ 568.5 [MH]⁺, Rt = 1.21 min (Method A) |
| L35 | 3-[3-(1-methylpyrrolidin-2-yl)phenyl]indolizine-2-carbaldehyde | 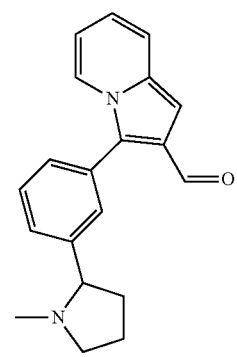 [SMILES: CN1CCCC1c1cccc(-c2c(C=O)cc3ccccn23)c1] | K42 | MS/ESI⁺ 305.3 [MH]⁺, Rt = 0.55 min (Method A) |
| L36 | 3-{5-[2-(morpholin-4-yl)ethoxy]pyridin-2-yl}indolizine-2-carbaldehyde | 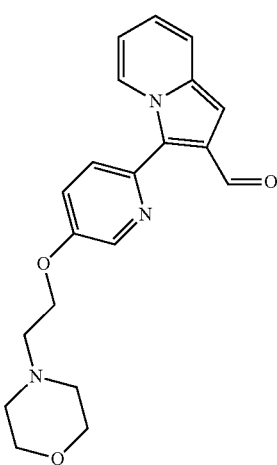 [SMILES: O=Cc1cc2ccccn2c1-c1ccc(OCCN2CCOCC2)cn1] | K43 | MS/ESI⁺ 352.2 [MH]⁺, Rt = 0.88 min (Method C) |

-continued

| Intermediate | Name and Molecular Structure | Reagent | Analytical data |
|---|---|---|---|
| L37 | 3-(6-methoxypyridin-3-yl)indolizine-2-carbaldehyde | K44 | MS/ESI+ 253.2 [MH]+, Rt = 1.00 min (Method A) |
| L38 | 3-(2-methoxypyridin-4-yl)indolizine-2-carbaldehyde | K45 | MS/ESI+ 253.2 [MH]+, Rt = 0.99 min (Method A) |
| L39 | 2-(2-formylindolizin-3-yl)benzonitrile | K46 | MS/ESI+ 247.1 [MH]+, Rt = 0.97 min (Method A). |
| L40 | 3-(pyridin-2-yl)-1-(trifluoromethyl)indolizine-2-carbaldehyde | K47 | MS/ESI+ 291.2 [MH]+, Rt = 1.07 min (Method A) |
| L42 | 3-{3-[(dimethylamino)methyl]phenyl}-2-formylindolizine-1-carbonitrile | K48 | MS/ESI+ 304.3 [MH]+, Rt = 1.02 min (Method J) |

-continued

| Intermediate | Name and Molecular Structure | Reagent | Analytical data |
|---|---|---|---|
| L43 | 7-{3-[(dimethylamino)methyl]phenyl}-pyrrolo[1,2-b]pyridazine-6-carbaldehyde | K49 | MS/ESI⁺ 280.3 [MH]⁺, Rt = 0.43-0.47 min (Method A) |
| L44 | 3-(1,3-thiazol-4-yl)indolizine-2-carbaldehyde | K50 | MS/ESI⁺ 229.1 [MH]⁺, Rt = 0.89 min (Method A) |
| L45 | 3-[2-(morpholin-4-ylmethyl)-1,3-thiazol-4-yl]indolizine-2-carbaldehyde | K51 | MS/ESI⁺ 328.3 [MH]⁺, Rt = 0.63 min (Method A) |
| L46 | 3-[3-(dimethylamino)prop-1-yn-1-yl]indolizine-2-carbaldehyde | K52 | MS/ESI⁺ 226.9 [MH]⁺, Rt = 0.43 min (Method A) |
| L47 | 3-(4-methyl-2-oxopiperazin-1-yl)indolizine-2-carbaldehyde | K53 | MS/ESI⁺ 258.2 [MH]⁺, Rt = 0.35 min (Method A) |

-continued

| Intermediate | Name and Molecular Structure | | Reagent | Analytical data |
|---|---|---|---|---|
| L48 | 3-{1-[2-(dimethylamino)ethyl]-2-oxo-1,2-dihydropyridin-4-yl}indolizine-2-carbaldehyde | 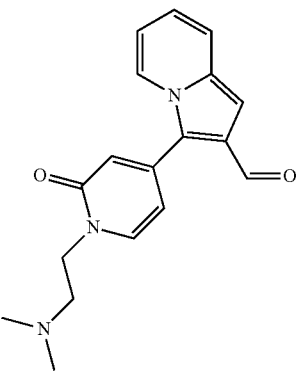 [SMILES: CN(C)CCn1ccc(-c2c(C=O)cc3ccccn23)cc1=O] | K54 | MS/ESI$^+$ 310.3 [MH]$^+$, Rt = 0.48 min (Method A) |
| L49 | 3-{6-oxo-1-[2-(pyrrolidin-1-yl)ethyl]-1,6-dihydropyridazin-3-yl}indolizine-2-carbaldehyde | 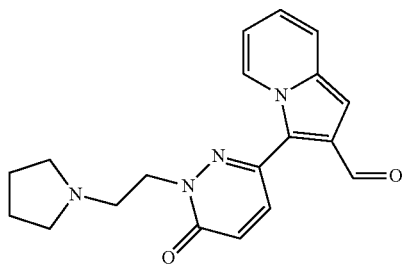 [SMILES: O=Cc1cc2ccccn2c1-c1ccc(=O)n(CCN2CCCC2)n1] | K55 | MS/ESI$^+$ 337.3 [MH]$^+$, Rt = 0.46 min (Method A) |
| L50 | 3-{1-[2-(4-methylpiperazin-1-yl)ethyl]-6-oxo-1,6-dihydropyridazin-3-yl}indolizine-2-carbaldehyde | 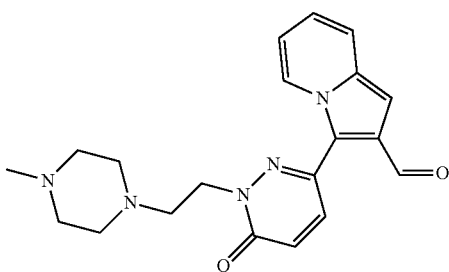 [SMILES: CN1CCN(CCn2nc(-c3c(C=O)cc4ccccn34)ccc2=O)CC1] | K56 | MS/ESI$^+$ 366.3 [MH]$^+$, Rt = 0.43-0.46 min (Method A) |
| L51 | 3-{1-[2-(morpholin-4-yl)ethyl]-6-oxo-1,6-dihydropyridazin-3-yl}indolizine-2-carbaldehyde | 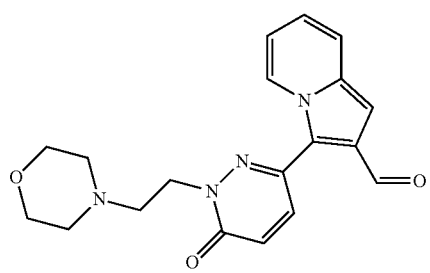 [SMILES: O=Cc1cc2ccccn2c1-c1ccc(=O)n(CCN2CCOCC2)n1] | K57 | MS/ESI$^+$ 353.3 [MH]$^+$, Rt = 0.41-0.44 min (Method A) |

| Intermediate | Name and Molecular Structure | | Reagent | Analytical data |
|---|---|---|---|---|
| L52 | 3-{6-[2-(4-methylpiperazin-1-yl)ethoxy]pyridazin-3-yl}indolizine-2-carbaldehyde | 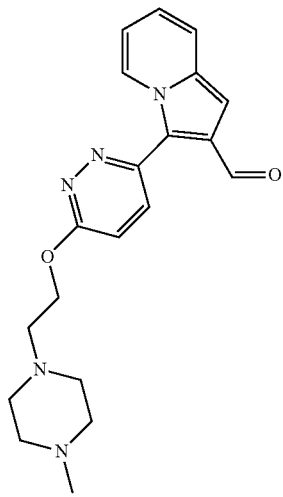 [SMILES: CN1CCN(CCOc2ccc(-c3c(C=O)cc4ccccn34)nn2)CC1] | K58 | MS/ESI+ 366.4 [MH]+, Rt = 0.74 min (Method J) |
| L53 | 3-{6-[2-(dimethylamino)ethoxy]pyridazin-3-yl}indolizine-2-carbaldehyde | 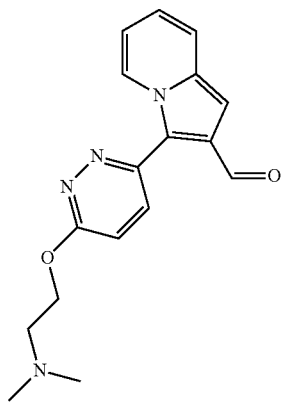 [SMILES: CN(C)CCOc1ccc(-c2c(C=O)cc3ccccn23)nn1] | K59 | MS/ESI+ 311.4 [MH]+, Rt = 0.48 min (Method A) |
| L54 | 3-{6-[(1-methylpiperidin-4-yl)oxy]pyridazin-3-yl}indolizine-2-carbaldehyde | 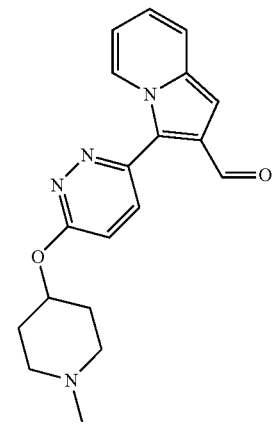 [SMILES: CN1CCC(Oc2ccc(-c3c(C=O)cc4ccccn34)nn2)CC1] | K60 | MS/ESI+ 337.3 [MH]+, Rt = 0.51 min (Method A) |

-continued

| Intermediate | Name and Molecular Structure | Reagent | Analytical data |
|---|---|---|---|
| L55 | 3-{6-[2-(1-methylpiperidin-4-yl)ethoxy]pyridazin-3-yl}indolizine-2-carbaldehyde | K61 | MS/ESI+ 365.3 [MH]+, Rt = 0.57 min (Method A) |
| L56 | 3-(morpholin-4-ylmethyl)indolizine-2-carbaldehyde | K62 | MS/ESI+ 245.3 [MH]+, Rt = 0.86 min (Method C) |
| L57 | 3-({2-methyl-2,9-diazaspiro[5.5]undecan-9-yl}methyl)indolizine-2-carbaldehyde | K63 | MS/ESI+ 326.0 [MH]+, Rt = 1.30 min (Method J) |
| L58 | tert-butyl 9-[(2-formylindolizin-3-yl)methyl]-3,9-diazaspiro[5.5]undecane-3-carboxylate | K64 | MS/ESI+ 412.5 [MH]+, Rt = 0.70 min (Method A) |
| L59 | tert-butyl 2-[(2-formylindolizin-3-yl)methyl]-2,7-diazaspiro[3.5]nonane-7-carboxylate | K65 | MS/ESI+ 384.4 [MH]+, Rt = 0.64 min (Method A) |
| L60 | tert-butyl (3aR,6aS)-5-[(2-formylindolizin-3-yl)methyl]-octahydropyrrolo[3,4-c]pyrrole-2-carboxylate | K66 | MS/ESI+ 370.4 [MH]+, Rt = 1.18 min (Method C) |

| Intermediate | Name and Molecular Structure | | Reagent | Analytical data |
|---|---|---|---|---|
| L61 | 2-formyl-3-(morpholin-4-ylmethyl)indolizine-1-carbonitrile | 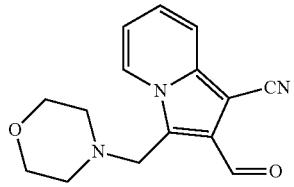 [SMILES: N#Cc1c(C=O)c(CN2CCOCC2)n2ccccc12] | K67 | MS/ESI⁺ 270.2 [MH]⁺, Rt = 0.41-0.42 min (Method A) |
| L62 | 3-{1-[2-(dimethylamino)ethyl]-1H-pyrazol-3-yl}indolizine-2-carbaldehyde | 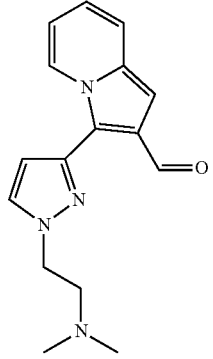 [SMILES: CN(C)CCn1ccc(-c2c(C=O)cc3ccccn23)n1] | K68 | MS/ESI⁺ 283.3 [MH]⁺, Rt = 0.47 min (Method A) |
| L63 | 3-{1-[2-(4-methylpiperazin-1-yl)ethyl]-1H-pyrazol-3-yl}indolizine-2-carbaldehyde | 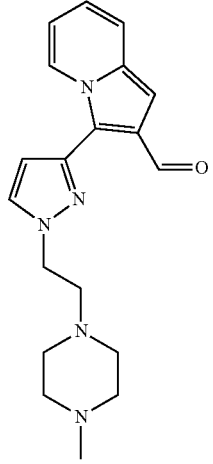 [SMILES: CN1CCN(CCn2ccc(-c3c(C=O)cc4ccccn34)n2)CC1] | K69 | MS/ESI⁺ 338.3 [MH]⁺, Rt = 0.49 min (Method A) |
| L64 | 3-{1-[2-(2,2,3,3,11,11,12,12-octamethyl-4,10-dioxa-7-aza-3,11-disilatridecan-7-yl)ethyl]-1H-pyrazol-3-yl}indolizine-2-carbaldehyde | 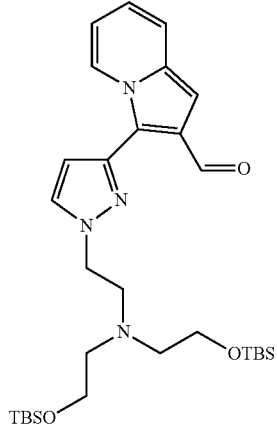 [SMILES: CC(C)(C)[Si](C)(C)OCCN(CCO[Si](C)(C)C(C)(C)C)CCn1ccc(-c2c(C=O)cc3ccccn23)n1] | K70 | MS/ESI⁺ 571.5 [MH]⁺, Rt = 1.15 min (Method A) |

| Intermediate | Name and Molecular Structure | | Reagent | Analytical data |
|---|---|---|---|---|
| L65 | 3-{1-[2-(morpholin-4-yl)ethyl]-1H-pyrazol-3-yl}indolizine-2-carbaldehyde | | K71 | MS/ESI+ 325.3 [MH]+, Rt = 0.52 min (Method A) |

Intermediate L41

2-formyl-3-(pyridin-2-yl)indolizine-1-carbonitrile

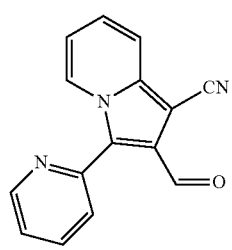 [SMILES: N#Cc1c(C=O)c(-c2ccccn2)n2ccccc12]

To a solution of ethyl 1-cyano-3-(pyridin-2-yl)indolizine-2-carboxylate H49 (0.100 g, 0.34 mmol) in DCM (3.5 mL) cooled at −78° C. under nitrogen, a solution of DIBALH 1M in toluene (1.02 mL, 1.02 mmol) was added drop-wise over 10 min and the reaction was stirred at −78° C. for 10 min. The reaction mixture was quenched by portion-wise addition of sodium sulphate decahydrate, the mixture was filtered through a celite pad and the organic phase was concentrated in vacuo. The crude mixture was dissolved in DCM (3 ml), MnO2 (0.295 g, 3.4 mmol) was added and the reaction was heated at 50° C. for 3 h. The mixture was diluted with DCM and filtered through a celite pad. The filtrate was evaporated to dryness and the crude was purified by flash chromatography on Biotage silica gel cartridge (DCM:EtOAc=98:2 to 95:5) to afford title compound as a yellow solid (0.033 g, 0.13 mmol, 40% yield). MS/ESI+ 248.2 [MH]+, Rt=0.83 min (Method A).

Intermediate M1

1-(3-phenylindolizin-2-yl)ethan-1-ol

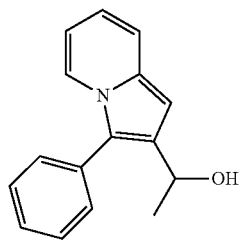 [SMILES: CC(O)c1cc2ccccn2c1-c1ccccc1]

To a solution of 3-phenylindolizine-2-carbaldehyde L1 (0.188 g, 0.850 mmol) in THF (8 mL) cooled to 0° C., 3M MeMgBr solution in Et2O (0.420 mL, 1.27 mmol) was added drop-wise and the reaction was stirred at that temperature for 30 min. The mixture was quenched with 1 mL of MeOH, then diluted with EtOAc and washed with a mixture of aqueous saturated NH4Cl and water. The aqueous phase was extracted with EtOAc and the combined organic layers were washed with brine and dried over sodium sulfate. The solvent was evaporated and the crude was purified by flash chromatography on silica gel Biotage SNAP cartridge (cyclohexane:EtOAc=95:5 to 60:40) to afford title compound as a green-brown oil (0.190 g, 0.80 mmol, 94% yield). MS/ESI+ 238.1 [MH]+, Rt=1.07 min (Method A).

Intermediate M2

1-[3-(pyridin-2-yl)indolizin-2-yl]ethan-1-ol

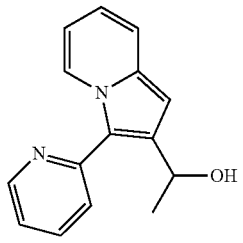 [SMILES: CC(O)c1cc2ccccn2c1-c1ccccn1]

Prepared similarly intermediate M1, starting from 3-(pyridin-2-yl)indolizine-2-carbaldehyde L2 (0.990 g, 4.45 mmol), stirring at 0° C. for 30 min, and purified by flash chromatography on Biotage silica gel cartridge (cyclohexane to cyclohexane:EtOAc=65:35) to afford title compound as a yellow oil (1.02 g, 4.28 mmol, 96% yield). MS/ESI$^+$ 239.2 [MH]$^+$, Rt=0.64 min (Method A).

Intermediate M3

1-[3-(2-fluorophenyl)indolizin-2-yl]ethan-1-ol

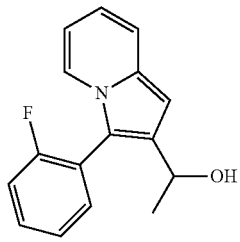 [SMILES: CC(O)c1cc2ccccn2c1-c1ccccc1F]

Prepared similarly to intermediate M1, starting from 3-(2-fluorophenyl)-indolizine-2-carbaldehyde L3 (0.169 g, 0.706 mmol), stirring at 0° C. for 30 min, and purified by flash chromatography on Biotage silica gel SNAP cartridge (cyclohexane:EtOAc=95:5 to 60:40) to afford title compound as a yellow oil (0.171 g, 0.669 mmol, 95% yield). MS/ESI$^+$ 256.2 [MH]$^+$, Rt=1.09 min (Method A).

Intermediate M4

1-[3-(pyridin-3-yl)indolizin-2-yl]ethan-1-ol

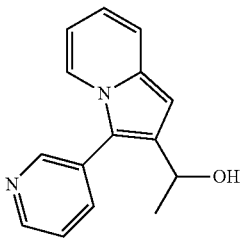

Prepared similarly to intermediate M1, starting from 3-(pyridin-3-yl)indolizine-2-carbaldehyde L4 (0.167 g, 0.751 mmol) and purified by flash chromatography on Biotage silica gel SNAP cartridge (cyclohexane:EtOAc=50:50 to 100% EtOAc) to afford title compound as a pale yellow oil (0.179 g, 0.751 mmol, quantitative yield). MS/ESI$^+$ 239.1 [MH]$^+$, Rt=0.50 min (Method A).

Intermediate M5

1-[3-(pyrazin-2-yl)indolizin-2-yl]ethan-1-ol

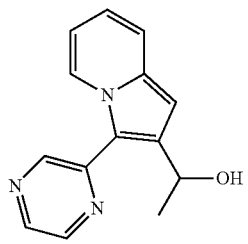 [SMILES: CC(O)c1cc2ccccn2c1-c1cnccn1]

Prepared similarly to intermediate M1, starting from 3-(pyrazin-2-yl)indolizine-2-carbaldehyde L5 (0.037 g, 0.166 mmol) and purified by flash chromatography on Biotage silica gel SNAP cartridge (DCM to DCM:EtOAc=30:70) to afford title compound as a yellow oil (0.033 g, 0.138 mmol, 83% yield). MS/ESI$^+$ 240.1 [MH]$^+$, Rt=0.78 min (Method A).

Intermediate M6

1-[3-(pyridin-4-yl)indolizin-2-yl]ethan-1-ol

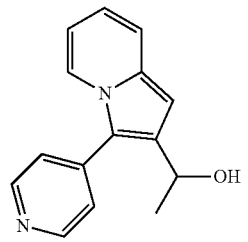

Prepared similarly to intermediate M1, starting from 3-(pyridin-4-yl)indolizine-2-carbaldehyde L6 (0.100 g, 0.450 mmol), stirring at 0° C. for 1 h, and purified by flash chromatography on Biotage silica-NH SNAP cartridge (cyclohexane to cyclohexane:EtOAc=50:50) to afford title compound as a yellow oil (0.100 g, 0.420 mmol, 93% yield). MS/ESI$^+$ 239.2 [MH]$^+$, Rt=0.43 min (Method A).

Intermediate M7

1-[6-methyl-3-(pyridin-2-yl)indolizin-2-yl]ethan-1-ol

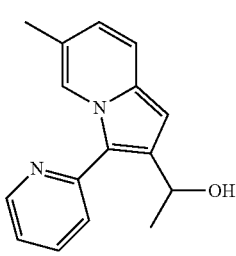 [SMILES: Cc1ccc2cc(C(C)O)c(-c3ccccn3)n2c1]

Prepared similarly to intermediate M1, starting from 6-methyl-3-(pyridin-2-yl)indolizine-2-carbaldehyde L7 (0.127 g, 0.53 mmol), stirring at 0° C. for 1 h, and purified by flash chromatography on Biotage silica SNAP cartridge (cyclohexane:EtOAc=80:20 to 70:30) to afford title compound as a yellow solid (0.092 g, 0.36 mmol, 70% yield). MS/ESI$^+$ 253.1 [MH]$^+$, Rt=0.72 min (Method A).

Intermediate M8

1-[3-(pyridin-2-yl)-6-(trifluoromethyl)indolizin-2-yl]ethan-1-ol

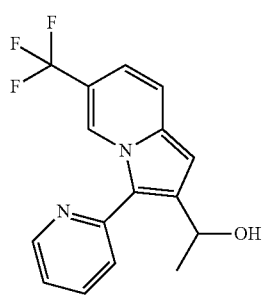 [SMILES: CC(O)c1cc2ccc(C(F)(F)F)cn2c1-c1ccccn1]

Prepared similarly to intermediate M1, starting from 3-(pyridin-2-yl)-6-(trifluoromethyl)indolizine-2-carbaldehyde L8 (0.150 g, 0.517 mmol), stirring at 0° C. for 1 h, and purified by flash chromatography on Biotage silica gel cartridge (cyclohexane to cyclohexane:EtOAc=70:30) to afford title compound as a yellow oil (0.145 g, 0.473 mmol, 92% yield). MS/ESI$^+$ 307.3 [MH]$^+$, Rt=1.06 min (Method A).

Intermediate M9

1-[8-fluoro-3-(pyridin-2-yl)indolizin-2-yl]ethan-1-ol

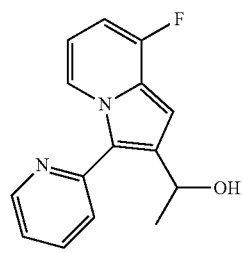 [SMILES: CC(O)c1cc2c(F)cccn2c1-c1ccccn1]

Prepared similarly to intermediate M1, starting from 8-fluoro-3-(pyridin-2-yl)indolizine-2-carbaldehyde L9 (0.103 g, 0.43 mmol), stirring at 0° C. for 10 min, and purified by flash chromatography on Biotage silica gel SNAP cartridge (cyclohexane:EtOAc=70:30 to 50:50) to afford title compound as a pale yellow oil (0.094 g, 0.37 mmol, 85% yield). MS/ESI$^+$ 257.1 [MH]$^+$, Rt=0.78 min (Method A).

Intermediate M10

1-[1-methyl-3-(pyridin-2-yl)indolizin-2-yl]ethan-1-ol

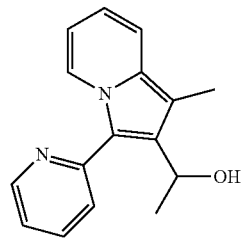 [SMILES: Cc1c(C(C)O)c(-c2ccccn2)n2ccccc12]

Prepared similarly to intermediate M1, starting from 1-methyl-3-(pyridin-2-yl)indolizine-2-carbaldehyde L10 (0.071 g, 0.30 mmol), stirring at 0° C. for 30 min, and purified by flash chromatography on Biotage silica gel cartridge (cyclohexane:EtOAc=70:30 to 50:50) to afford title compound as a yellow oil (0.052 g, 0.21 mmol, 68% yield). MS/ESI$^+$ 253.1 [MH]$^+$, Rt=0.63 min (Method A).

Intermediate M11

1-{3-[5-(morpholin-4-ylmethyl)thiophen-2-yl]indolizin-2-yl}ethan-1-ol

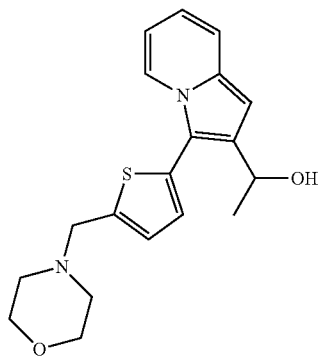 [SMILES: CC(O)c1cc2ccccn2c1-c1ccc(CN2CCOCC2)s1]

Prepared similarly to intermediate M1, starting from 3-[5-(morpholin-4-ylmethyl)thiophen-2-yl]indolizine-2-carbaldehyde L11 (0.337 g, 1.03 mmol), stirring at 0° C. for 1 h, and purified by flash chromatography on Biotage silica-NH SNAP cartridge (cyclohexane to cyclohexane:EtOAc=50:50) to afford title compound as a yellow oil (0.324 g, 0.94 mmol, 92% yield). MS/ESI$^+$ 343.3 [MH]$^+$, Rt=0.55 min (Method A).

Intermediate M12

1-{3-[4-(morpholin-4-ylmethyl)phenyl]indolizin-2-yl}ethan-1-ol

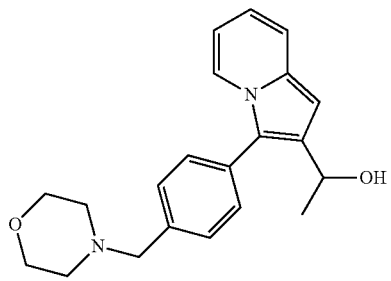 [SMILES: CC(O)c1cc2ccccn2c1-c1ccc(CN2CCOCC2)cc1]

Prepared similarly to intermediate M1, starting from 3-[4-(morpholin-4-ylmethyl)phenyl]indolizine-2-carbaldehyde L12 (0.240 g, 0.75 mmol), stirring at 0° C. for 1 h, and purified by flash chromatography on Biotage silica-NH cartridge (cyclohexane to cyclohexane:EtOAc=50:50) to afford title compound as a yellow oil (0.203 g, 0.60 mmol, 80% yield). MS/ESI$^+$ 337.3 [MH]$^+$, Rt=0.54 min (Method A).

Intermediate M13

1-(3-{4-[(dimethylamino)methyl]phenyl}indolizin-2-yl)ethan-1-ol

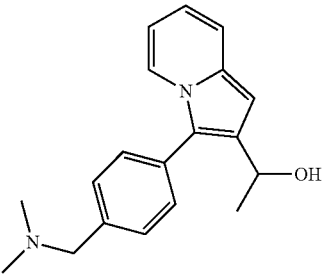 [SMILES: CC(O)c1cc2ccccn2c1-c1ccc(CN(C)C)cc1]

Prepared similarly to intermediate M1, starting from 3-{4-[(dimethylamino)methyl]phenyl}indolizine-2-carbaldehyde L13 (0.196 g, 0.70 mmol), stirring at 0° C. for 1 h, and purified by flash chromatography on Biotage silica-NH cartridge (cyclohexane to cyclohexane:EtOAc=50:50) to afford title compound as a yellow oil (0.186 g, 0.63 mmol, 90% yield). MS/ESI$^+$ 295.2 [MH]$^+$, Rt=0.53 min (Method A).

Intermediate M14

1-(3-{3-[(dimethylamino)methyl]phenyl}indolizin-2-yl)ethan-1-ol

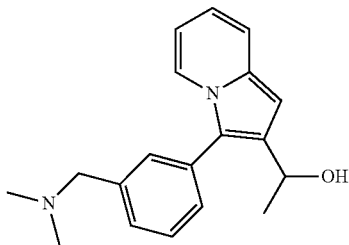 [SMILES: CC(O)c1cc2ccccn2c1-c1cccc(CN(C)C)c1]

Prepared similarly to intermediate M1, starting from 3-{3-[(dimethylamino)methyl]phenyl}indolizine-2-carbaldehyde L14 (0.199 g, 0.71 mmol), stirring at 0° C. for 1 h, and purified by flash chromatography on Biotage silica-NH cartridge (cyclohexane to cyclohexane:EtOAc=50:50) to afford title compound as a yellow oil (0.197 g, 0.67 mmol, 94% yield). MS/ESI$^+$ 295.3 [MH]$^+$, Rt=0.56 min (Method A).

Intermediate M15

1-[3-(3,6-dihydro-2H-pyran-4-yl)indolizin-2-yl]ethan-1-ol

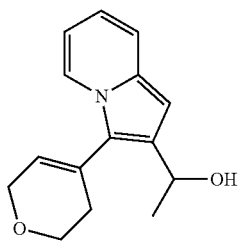 [SMILES: CC(O)c1cc2ccccn2c1C1=CCOCC1]

Prepared similarly to intermediate M1, starting from 3-(3,6-dihydro-2H-pyran-4-yl)indolizine-2-carbaldehyde L15 (0.057 g, 0.25 mmol), and purified by flash chromatography on Biotage silica gel SNAP cartridge (cyclohexane to cyclohexane:EtOAc=70:30) to afford title compound as a yellow oil (0.043 g, 0.177 mmol, 71% yield). MS/ESI$^+$ 244.2 [MH]$^+$, Rt=0.85 min (Method A).

Intermediate M16 tert-butyl 4-[2-(1-hydroxyethyl)indolizin-3-yl]-1,2,3,6-tetrahydropyridine-1-carboxylate

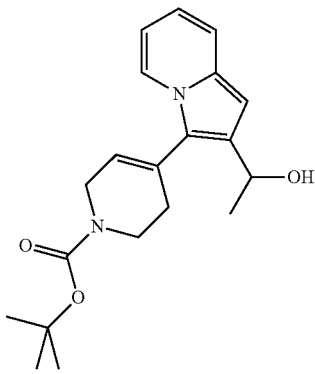 [SMILES: CC(O)c1cc2ccccn2c1C1=CCN(C(=O)OC(C)(C)C)CC1]

Prepared similarly to intermediate M1, starting from tert-butyl 4-(2-formylindolizin-3-yl)-1,2,3,6-tetrahydropyridine-1-carboxylate L16 (0.134 g, 0.41 mmol), and purified by flash chromatography on Biotage silica gel SNAP cartridge (cyclohexane to cyclohexane:EtOAc=70:30) to afford title compound as a yellow oil (0.100 g, 0.29 mmol, 71%). MS/ESI$^+$ 343.3 [MH]$^+$, Rt=1.13 min (Method A).

Intermediate M17

1-[3-(1,3-thiazol-5-yl)indolizin-2-yl]ethan-1-ol

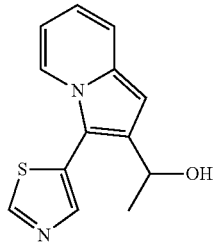 [SMILES: CC(O)c1cc2ccccn2c1-c1cncs1]

Prepared similarly to intermediate M1, starting from 3-(1,3-thiazol-5-yl)indolizine-2-carbaldehyde L17 (0.097 g, 0.42 mmol), stirring at 0° C. for 1 h, and purified by flash chromatography on Biotage silica gel SNAP cartridge (cyclohexane to cyclohexane:EtOAc=50:50) to afford title compound as a yellow oil (0.104 g, 0.42 mmol, quantitative yield). MS/ESI$^+$ 245.1 [MH]$^+$, Rt=0.81 min (Method A).

Intermediate M18

1-[2-(1-hydroxyethyl)indolizin-3-yl]pyrrolidin-2-one

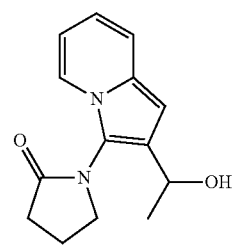 [SMILES: CC(O)c1cc2ccccn2c1N1CCCC1=O]

Prepared similarly to intermediate M1, starting from 3-(2-oxopyrrolidin-1-yl)indolizine-2-carbaldehyde L18 (0.036 g, 0.15 mmol), stirring at 0° C. for 1 h; additional 3M MeMgBr solution in Et$_2$O (0.08 mL, 0.24 mmol) was added and the reaction mixture was stirred at 0° C. for further 5 h. After work-up the residue was purified by flash chromatography on silica gel cartridge (cyclohexane:EtOAc=100:0 to 0:100) to afford title compound as a dark oil (0.028 g, 0.11 mmol, 76% yield). MS/ESI$^+$ 244.9 [MH]$^+$, Rt=0.65 min (Method A).

Intermediate M19

1-[3-(pent-1-yn-1-yl)indolizin-2-yl]ethan-1-ol

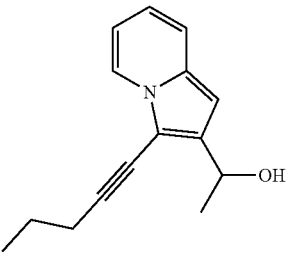 [SMILES: CCCC#Cc1c(C(C)O)cc2ccccn12]

Prepared similarly to intermediate M1, starting from 3-(pent-1-yn-1-yl)indolizine-2-carbaldehyde L19 (0.156 g, 0.74 mmol), and the crude title compound was used without any additional purification (0.168 g, 0.74 mmol, quantitative yield). MS/ESI+ 228.2 [MH]+, Rt=1.15 min (Method A).

Intermediate M20

1-[3-(3-{[tris(propan-2-yl)silyl]oxy}prop-1-yn-1-yl)indolizin-2-yl]ethan-1-ol

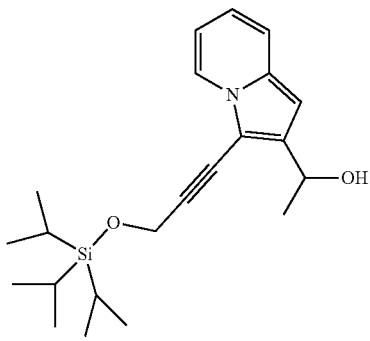 [SMILES: CC(O)c1cc2ccccn2c1C#CCO[Si](C(C)C)(C(C)C)C(C)C]

Prepared similarly to intermediate M1, starting from 3-(3-{[tris(propan-2-yl)silyl]oxy}prop-1-yn-1-yl)indolizine-2-carbaldehyde L20 (0.330 g, 0.93 mmol), stirring at 0° C. for 4 h, and the title compound was used without any additional purification (0.328 g, 0.88 mmol, 95% yield). MS/ESI+ 372.1 [MH]+, Rt=1.60 min (Method A).

Intermediate M21

1-[7-(pyridin-2-yl)pyrrolo[1,2-b]pyridazin-6-yl]ethan-1-ol

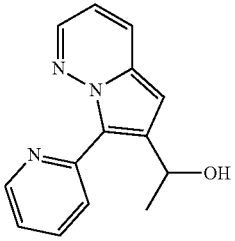 [SMILES: CC(O)c1cc2cccnn2c1-c1ccccn1]

Prepared similarly to intermediate M1, starting from 7-(pyridin-2-yl)pyrrolo[1,2-b]pyridazine-6-carbaldehyde L21 (0.072 g, 0.32 mmol), stirring at 0° C. for 15 min, and purified by flash chromatography on Biotage silica gel cartridge (cyclohexane:EtOAc=90:10 to 70:30) to afford title compound as a pale yellow oil (0.060 g, 0.25 mmol, 78% yield). MS/ESI+ 240.0 [MH]+, Rt=0.47 min (Method A).

Intermediates M22-39 and M41-66 found in the table below may be prepared from suitable intermediates reported below following similar procedures as for compound M1.

| Intermediate | Name and Molecular Structure | | Reagent | Analytical data |
|---|---|---|---|---|
| M22 | 1-[7-chloro-3-(pyridin-2-yl)indolizin-2-yl]ethan-1-ol | Cl ... OH | L22 | MS/ESI+ 273.1 [MH]+, Rt = 0.88 min (Method A) |
| M23 | 1-[7-methyl-3-(pyridin-2-yl)indolizin-2-yl]ethan-1-ol | ... OH | L23 | MS/ESI+ 253.3 [MH]+, Rt = 0.69 min (Method A) |

| Intermediate | Name and Molecular Structure | Reagent | Analytical data |
|---|---|---|---|
| M24 | 1-[3-(2-methylpyridin-4-yl)indolizin-2-yl]ethan-1-ol | L24 | MS/ESI+ 253.2 [MH]+, Rt = 0.44 min (Method A) |
| M25 | 1-{3-[5-(morpholin-4-ylmethyl)pyridin-2-yl]indolizin-2-yl}ethan-1-ol | L25 | MS/ESI+ 338.3 [MH]+, Rt = 0.46 min (Method A) |
| M26 | 1-(3-{5-[(dimethylamino)methyl]pyridin-2-yl}indolizin-2-yl)ethan-1-ol | L26 | MS/ESI+ 296.2 [MH]+, Rt = 0.46 min (Method A) |
| M27 | 1-{3-[6-(morpholin-4-ylmethyl)pyridin-2-yl]indolizin-2-yl}ethan-1-ol | L27 | MS/ESI+ 338.3 [MH]+, Rt = 0.50 min (Method A) |

| Intermediate | Name and Molecular Structure | Reagent | Analytical data |
|---|---|---|---|
| M28 | 1-{3-[4-(morpholin-4-ylmethyl)pyridin-2-yl]indolizin-2-yl}ethan-1-ol | L28 | MS/ESI+ 338.3 [MH]+, Rt = 0.48 min (Method A) |
| M29 | 1-(3-{4-[(dimethylamino)methyl]pyridin-2-yl}indolizin-2-yl)ethan-1-ol | L29 | MS/ESI+ 296.3 [MH]+, Rt = 0.46 min (Method A) |
| M30 | 1-{3-[5-(pyrrolidin-1-ylmethyl)pyridin-2-yl]indolizin-2-yl}ethan-1-ol | L30 | MS/ESI+ 304.1 [MH—H$_2$O]+, Rt = 0.48 min (Method A) |
| M31 | 1-(3-{5-[(4-methylpiperazin-1-yl)methyl]pyridin-2-yl}indolizin-2-yl)ethan-1-ol | L31 | MS/ESI+ 351.4 [MH]+, Rt = 0.45 min (Method A) |

-continued

| Intermediate | Name and Molecular Structure | Reagent | Analytical data |
|---|---|---|---|
| M32 | 1-(3-{6-[(4-methylpiperazin-1-yl)methyl]pyridin-2-yl}indolizin-2-yl)ethan-1-ol | L32 | MS/ESI⁺ 351.4 [MH]⁺, Rt = 0.48 min (Method A) |
| M33 | 1-(3-{4-[(4-methylpiperazin-1-yl)methyl]pyridin-2-yl}indolizin-2-yl)ethan-1-ol | L33 | MS/ESI⁺ 351.4 [MH]⁺, Rt = 0.43 min (Method A) |
| M34 | 1-(3-{5-[(2,2,3,3,11,11,12,12-octamethyl-4,10-dioxa-7-aza-3,11-disilatridecan-7-yl)methyl]pyridin-2-yl}indolizin-2-yl)ethan-1-ol | L34 | MS/ESI⁺ 584.6 [MH]⁺, Rt = 1.15 min (Method A) |
| M35 | 1-{3-[3-(1-methylpyrrolidin-2-yl)phenyl]indolizin-2-yl}ethan-1-ol | L35 | MS/ESI⁺ 321.3 [MH]⁺, Rt = 0.56 min (Method A) |

| Intermediate | Name and Molecular Structure | | Reagent | Analytical data |
|---|---|---|---|---|
| M36 | 1-(3-{5-[2-(morpholin-4-yl)ethoxy]pyridin-2-yl}indolizin-2-yl)ethan-1-ol | 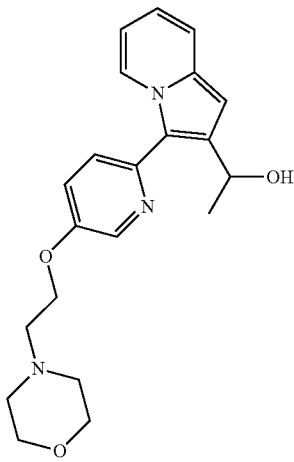 [SMILES: CC(O)c1cc2ccccn2c1-c1ccc(OCCN2CCOCC2)cn1] | L36 | MS/ESI+ 368.1 [MH]+, Rt = 0.87 min (Method C) |
| M37 | 1-[3-(6-methoxypyridin-3-yl)indolizin-2-yl]ethan-1-ol | 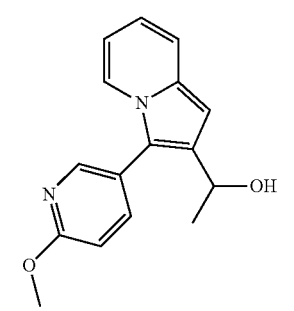 [SMILES: COc1ccc(-c2c(C(C)O)cc3ccccn23)cn1] | L37 | MS/ESI+ 269.3 [MH]+, Rt = 0.96 min (Method A) |
| M38 | 1-[3-(2-methoxypyridin-4-yl)indolizin-2-yl]ethan-1-ol | 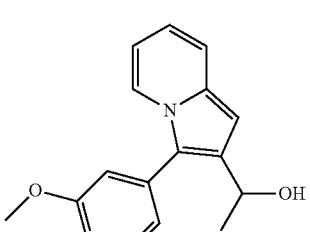 | L38 | MS/ESI+ 269.3 [MH]+, Rt = 0.90 min (Method A) |
| M39 | 2-[2-(1-hydroxyethyl)indolizin-3-yl]benzonitrile | 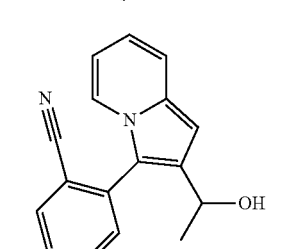 | L39 | MS/ESI+ 263.1 [MH]+, Rt = 0.92 and 0.97 min (mixture of isomers) (Method A) |
| M41 | 1-[3-(pyridin-2-yl)-1-(trifluoromethyl)indolizin-2-yl]ethan-1-ol | 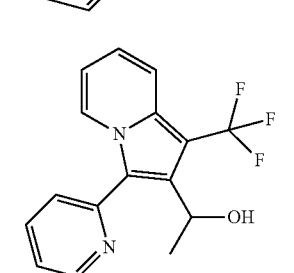 | L40 | MS/ESI+ 307.4 [MH]+, Rt = 1.01 min (Method A) |

| Intermediate | Name and Molecular Structure | | Reagent | Analytical data |
|---|---|---|---|---|
| M42 | 2-(1-hydroxyethyl)-3-(pyridin-2-yl)indolizine-1-carbonitrile | 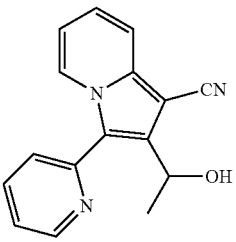 [SMILES: CC(O)c1c(C#N)c2ccccn2c1-c1ccccn1] | L41 | MS/ESI$^+$ 264.2 [MH]$^+$, Rt = 0.79 min (Method A) |
| M43 | 3-{3-[(dimethylamino)methyl]phenyl}-2-(1-hydroxyethyl)indolizine-1-carbonitrile | 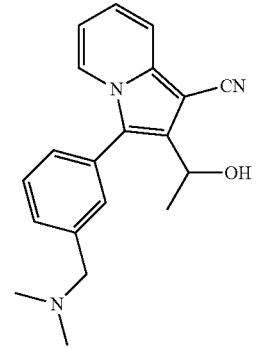 [SMILES: CC(O)c1c(C#N)c2ccccn2c1-c1cccc(CN(C)C)c1] | L42 | MS/ESI$^+$ 320.4 [MH]$^+$, Rt = 1.02 min (Method J) |
| M44 | 1-(7-{3-[(dimethylamino)methyl]phenyl}-pyrrolo[1,2-b]pyridazin-6-yl)ethan-1-ol | 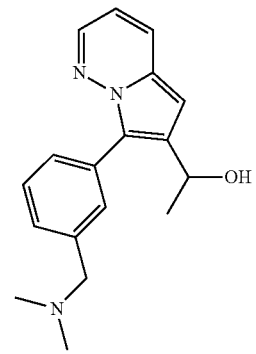 [SMILES: CC(O)c1cc2cccnn2c1-c1cccc(CN(C)C)c1] | L43 | MS/ESI$^+$ 296.3 [MH]$^+$, Rt = 0.46-0.48 min (Method A) |
| M45 | 1-[3-(1,3-thiazol-4-yl)indolizin-2-yl]ethan-1-ol | 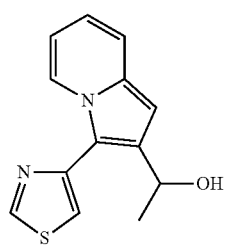 [SMILES: CC(O)c1cc2ccccn2c1-c1cscn1] | L44 | MS/ES$^+$ 245.1 [MH]$^+$, Rt = 0.88 min (Method A) |
| M46 | 1-{3-[2-(morpholin-4-ylmethyl)-1,3-thiazol-4-yl]indolizin-2-yl}ethan-1-ol | 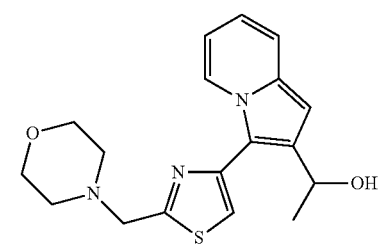 [SMILES: CC(O)c1cc2ccccn2c1-c1csc(CN2CCOCC2)n1] | L45 | MS/ESI$^+$ 344.2 [MH]$^+$, Rt = 0.54 min (Method A) |

| Intermediate | Name and Molecular Structure | | Reagent | Analytical data |
|---|---|---|---|---|
| M47 | 1-{3-[3-(dimethylamino)prop-1-yn-1-yl]indolizin-2-yl}ethan-1-ol | 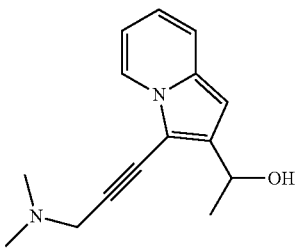 [SMILES: CC(O)c1cc2ccccn2c1C#CCN(C)C] | L46 | MS/ESI+ 243.8 [MH]+, Rt = 0.44 min (Method A) |
| M48 | 1-[2-(1-hydroxyethyl)indolizin-3-yl]-4-methylpiperazin-2-one | 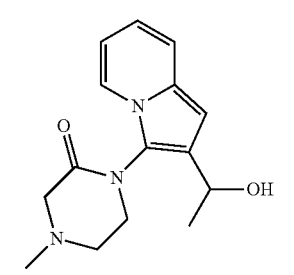 [SMILES: CC(O)c1cc2ccccn2c1N1CCN(C)CC1=O] | L47 | MS/ESI+ 274.3 [MH]+, Rt = 0.34-0.37 min (Method A) |
| M49 | 1-[2-(dimethylamino)ethyl]-4-[2-(1-hydroxyethyl)indolizin-3-yl]-1,2-dihydropyridin-2-one | 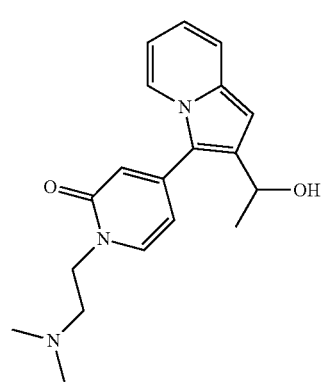 [SMILES: CC(O)c1cc2ccccn2c1-c1ccn(CCN(C)C)c(=O)c1] | L48 | MS/ESI+ 326.3 [MH]+, Rt = 0.46 min (Method A) |
| M50 | 6-[2-(1-hydroxyethyl)indolizin-3-yl]-2-[2-(pyrrolidin-1-yl)ethyl]-2,3-dihydropyridazin-3-one | 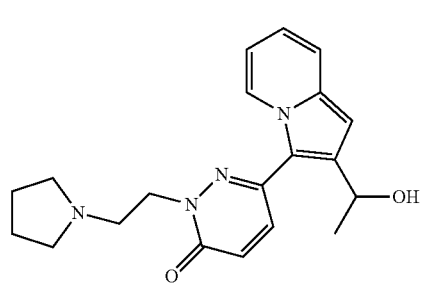 [SMILES: CC(O)c1cc2ccccn2c1-c1ccc(=O)n(CCN2CCCC2)n1] | L49 | MS/ESI+ 353.3 [MH]+, Rt = 0.47 min (Method A) |
| M51 | 6-[2-(1-hydroxyethyl)indolizin-3-yl]-2-[2-(4-methylpiperazin-1-yl)ethyl]-2,3-dihydropyridazin-3-one | 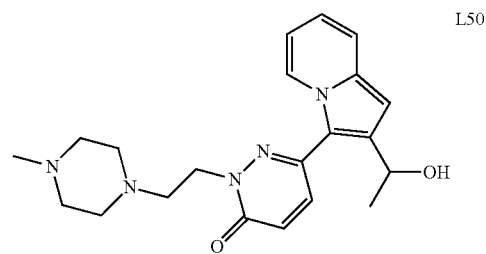 | L50 | MS/ESI+ 382.4 [MH]+, Rt = 0.44-0.47 min (Method A) |

-continued

| Intermediate | Name and Molecular Structure | Reagent | Analytical data |
|---|---|---|---|
| M52 | 6-[2-(1-hydroxyethyl)indolizin-3-yl]-2-[2-(morpholin-4-yl)ethyl]-2,3-dihydropyridazin-3-one | L51 | MS/ESI⁺ 369.3 [MH]⁺, Rt = 0.42-0.46 min (Method A) |
| M53 | 1-(3-{6-[2-(4-methylpiperazin-1-yl)ethoxy]pyridazin-3-yl}indolizin-2-yl)ethan-1-ol | L52 | MS/ESI⁺ 382.4 [MH]⁺, Rt = 0.47 min (Method A) |
| M54 | 1-(3-{6-[2-(dimethylamino)ethoxy]pyridazin-3-yl}indolizin-2-yl)ethan-1-ol | L53 | MS/ESI⁺ 327.3 [MH]⁺, Rt = 0.44-0.47 min (Method A) |

-continued

| Intermediate | Name and Molecular Structure | | Reagent | Analytical data |
|---|---|---|---|---|
| M55 | 1-(3-{6-[(1-methylpiperidin-4-yl)oxy]pyridazin-3-yl}indolizin-2-yl)ethan-1-ol | 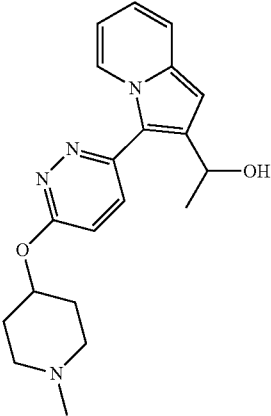 [SMILES: CC(O)c1cc2ccccn2c1-c1ccc(OC2CCN(C)CC2)nn1] | L54 | MS/ESI+ 353.4 [MH]+, Rt = 0.51 (Method A) |
| M56 | 1-(3-{6-[2-(1-methylpiperidin-4-yl)ethoxy]pyridazin-3-yl}indolizin-2-yl)ethan-1-ol | 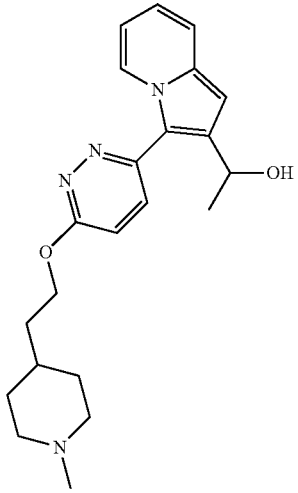 [SMILES: CC(O)c1cc2ccccn2c1-c1ccc(OCCC2CCN(C)CC2)nn1] | L55 | MS/ESI+ 381.4 [MH]+, Rt = 0.57 (Method A) |
| M57 | 1-[3-(morpholin-4-ylmethyl)indolizin-2-yl]ethan-1-ol | 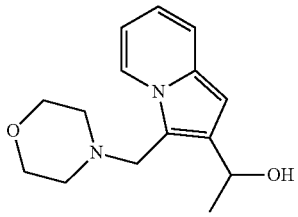 | L56 | MS/ESI+ 174.2 found, Rt = 0.83 min (Method C) |
| M58 | 1-[3-({2-methyl-2,9-diazaspiro[5.5]undecan-9-yl}methyl)indolizin-2-yl]ethan-1-ol | 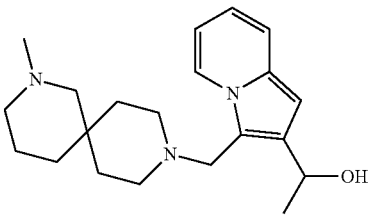 [SMILES: CC(O)c1cc2ccccn2c1CN1CCC2(CCCN(C)C2)CC1] | L57 | MS/ESI+ 342.5 [MH]+, Rt = 1.25 min (Method J) |

| Intermediate | Name and Molecular Structure | Reagent | Analytical data |
|---|---|---|---|
| M59 | tert-butyl 9-{[2-(1-hydroxyethyl)indolizin-3-yl]methyl}-3,9-diazaspiro[5.5]undecane-3-carboxylate | L58 | MS/ESI+ 428.5 [MH]+, Rt = 0.72 min (Method A) |
| M60 | tert-butyl 2-{[2-(1-hydroxyethyl)indolizin-3-yl]methyl}-2,7-diazaspiro[3.5]nonane-7-carboxylate | L59 | MS/ESI+ 400.4 [MH]+, Rt = 0.69 min (Method A) |
| M61 | tert-butyl (3aR,6aS)-5-{[2-(1-hydroxyethyl)indolizin-3-yl]methyl}-octahydropyrrolo[3,4-c]pyrrole-2-carboxylate | L60 | MS/ESI+ 386.4 [MH]+, Rt = 1.15 min (Method C) |
| M62 | 2-(1-hydroxyethyl)-3-(morpholin-4-ylmethyl)indolizine-1-carbonitrile (A/1734/55/1) | L61 | MS/ESI+ 286.3 [MH]+, Rt = 0.39 min (Method A) |
| M63 | 1-(3-{1-[2-(dimethylamino)ethyl]-1H-pyrazol-3-yl}indolizin-2-yl)ethan-1-ol | L62 | MS/ESI+ 299.3 [MH]+, Rt = 0.48 min (Method A) |

-continued

| Intermediate | Name and Molecular Structure | Reagent | Analytical data |
|---|---|---|---|
| M64 | 1-(3-{1-[2-(4-methylpiperazin-1-yl)ethyl]-1H-pyrazol-3-yl}indolizin-2-yl)ethan-1-ol | L63 | MS/ESI+ 354.4 [MH]+, Rt = 0.50 min (Method A) |
| M65 | 1-(3-{1-[2-(2,2,3,3,11,11,12,12-octamethyl-4,10-dioxa-7-aza-3,11-disilatridecan-7-yl)ethyl]-1H-pyrazol-3-yl}indolizin-2-yl)ethan-1-ol | L64 | MS/ESI+ 587.6 [MH]+, Rt = 1.15 min (Method A) |
| M66 | 1-(3-{1-[2-(morpholin-4-yl)ethyl]-1H-pyrazol-3-yl}indolizin-2-yl)ethan-1-ol | L65 | MS/ESI+ 341.3 [MH]+, Rt = 0.51-0.52 min (Method A) |

Intermediate M40

1-{3-[5-(morpholine-4-carbonyl)pyridin-2-yl]indolizin-2-yl}ethan-1-ol

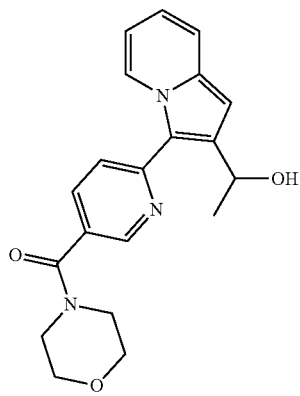 [SMILES: CC(O)c1cc2ccccn2c1-c1ccc(C(=O)N2CCOCC2)cn1]

To a solution of 1-{3-[5-(morpholine-4-carbonyl)pyridin-2-yl]indolizin-2-yl}ethan-1-one 13 (0.140 g, 0.401 mmol) in MeOH (4.5 mL), cooled to 0° C., NaBH$_4$ (0.030 g, 0.802 mmol) was added in two portions. After the addition was complete, the solution was stirred at 0° C. for 30 min and then concentrated under reduced pressure. The residue was diluted with water and extracted with EtOAc. The organic layer was dried over Na$_2$SO$_4$ and the solvent was removed to afford title compound which was used without purification (0.140 g, 0.398 mmol, 99% yield). MS/ESI$^+$ 352.3 [MH]$^+$, Rt=0.76 min (Method A).

Intermediate N1

2-(azidomethyl)-3-phenylindolizine

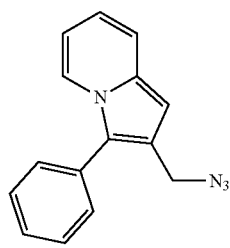 [SMILES: [N-]=[N+]=NCc1cc2ccccn2c1-c1ccccc1]

To a solution of (3-phenylindolizin-2-yl)methanol K1 (0.150 g, 0.672 mmol, in THF (10 mL) under nitrogen, DPPA (0.289 mL, 1.344 mmol) was added followed by DBU (0.201 mL, 1.344 mmol) and the mixture was stirred at r.t. overnight. The solvent was removed under vacuum and the residue was partitioned between EtOAc and water. The aqueous phase was extracted with EtOAc and the combined organic layers were washed with brine and dried over sodium sulfate, filtered and evaporated. In a different flask, to a solution of (3-phenylindolizin-2-yl)methanol K1 (0.050 g, 0.224 mmol, in THF (4 mL) under nitrogen, DPPA (0.096 mL, 0.448 mmol) was added followed by DBU (0.067 mL, 0.448 mmol) and the reaction was stirred at r.t. overnight. The mixture was diluted with EtOAc, washed with water and brine, dried over sodium sulfate, filtered and evaporated. The two batches were combined and purified by flash chromatography on silica gel Biotage SNAP cartridge (cyclohexane to cyclohexane:EtOAc=95:5) to afford title compound as a yellow oil (0.166 g, 0.668 mmol, 75% yield). MS/ESI$^+$ 249.1 [MH]$^+$, Rt=1.33 min (Method A).

Intermediate N2

2-(azidomethyl)-3-(pyridin-2-yl)indolizine

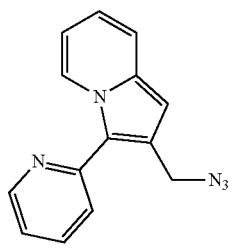 [SMILES: [N-]=[N+]=NCc1cc2ccccn2c1-c1ccccn1]

To a solution of [3-(pyridin-2-yl)indolizin-2-yl]methanol K2 (0.245 g, 1.09 mmol) in THF (10 mL) under nitrogen, DPPA (0.471 mL, 2.18 mmol) was added followed by DBU (0.326 mL, 2.18 mmol) at 0° C. and the mixture was stirred at RT overnight. The solvent was removed under vacuum and the residue was partitioned between EtOAc and water. The aqueous phase was extracted with EtOAc and the combined organic layers were washed with brine and dried over sodium sulfate. The solvent was removed and the crude was purified by flash chromatography on silica gel Biotage SNAP cartridge (cyclohexane to cyclohexane:EtOAc=90:10) to afford title compound as a pale yellow oil (0.272 g, 1.09 mmol, quantitative yield). MS/ESI$^+$ 250.2 [MH]$^+$, Rt=1.07 min (Method A).

Intermediate N3

2-(azidomethyl)-3-(3-fluorophenyl)indolizine

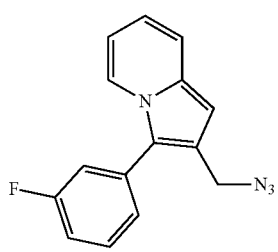 [SMILES: [N-]=[N+]=NCc1cc2ccccn2c1-c1cccc(F)c1]

Prepared similarly to intermediate N2, starting from [3-(3-fluorophenyl)indolizin-2-yl]methanol K3 (0.250 g, 1.04 mmol) and purified by flash chromatography on silica gel Biotage cartridge (cyclohexane to cyclohexane:EtOAc=95:5) to afford title compound as a yellow oil (0.250 g, 0.939 mmol, 90% yield). MS/ESI$^+$ 267.2 [MH]$^+$, Rt=1.32 min (Method A).

Intermediate N4

2-(azidomethyl)-3-(2-fluorophenyl)indolizine

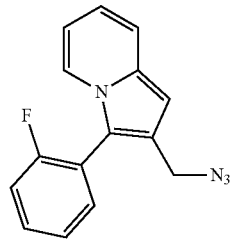

Prepared similarly to intermediate N2, starting from [3-(2-fluorophenyl)indolizin-2-yl]methanol K4 (0.293 g, 1.21 mmol) and purified by flash chromatography on silica gel Biotage SNAP cartridge (cyclohexane to cyclohexane:EtOAc=95:5) to afford title compound as a pale yellow oil (0.279 g, 1.05 mmol, 86% yield). MS/ESI$^+$ 267.1 [MH]$^+$, Rt=1.28 min (Method A).

Intermediate N5

2-(azidomethyl)-3-(2-methylphenyl)indolizine

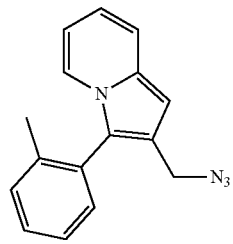 [SMILES: Cc1ccccc1-c1c(CN=[N+]=[N-])cc2ccccn12]

Prepared similarly to intermediate N2, starting from [3-(2-methylphenyl)indolizin-2-yl]methanol K5 (0.278 g, 1.17 mmol) and purified by flash chromatography on silica gel Biotage cartridge (cyclohexane to cyclohexane:EtOAc=95:5) to afford title compound as a pale yellow oil (0.262 g, 1.00 mmol, 85% yield). MS/ESI$^+$ 263.2 [MH]$^+$, Rt=1.37 min (Method A).

Intermediate N6

2-(azidomethyl)-1-phenylindolizine

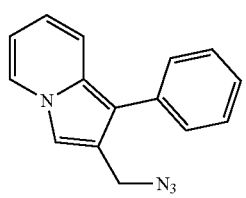

Prepared similarly to intermediate N2, starting from (1-phenylindolizin-2-yl)methanol K24 (0.180 g, 0.80 mmol), stirring for 1.5 h, and the crude was used without purification. MS/ESI$^+$ 249.1 [MH]$^+$, Rt=1.29 min (Method A).

Intermediate N7

2-(azidomethyl)-1-(3-fluorophenyl)indolizine

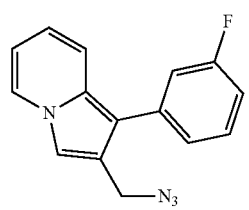 [SMILES: [N-]=[N+]=NCc1cn2ccccc2c1-c1cccc(F)c1]

Prepared similarly to intermediate N2, starting from [1-(3-fluorophenyl)indolizin-2-yl]methanol K25 (0.165 g, 0.68 mmol), stirring for 1.5 h, and the crude was used without purification. MS/ESI$^+$ 267.1 [MH]$^+$, Rt=1.30 min (Method A).

Intermediate N8

2-(azidomethyl)-1-(2-methylphenyl)indolizine

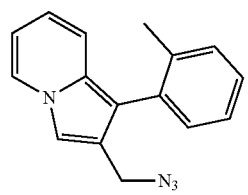 [SMILES: Cc1ccccc1-c1c(CN=[N+]=[N-])cn2ccccc12]

Prepared similarly to intermediate N2, starting from [1-(2-methylphenyl)indolizin-2-yl]methanol K26 (0.100 g, 0.42 mmol), stirring for 1.5 h, and the crude was used without purification. MS/ESI$^+$ 263.1 [MH]$^+$, Rt=1.34 min (Method A).

Intermediate N9

2-(azidomethyl)-1-(pyridin-2-yl)indolizine

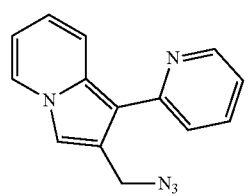 [SMILES: [N-]=[N+]=NCc1cn2ccccc2c1-c1ccccn1]

Prepared similarly to intermediate N2, starting from [1-(pyridin-2-yl)indolizin-2-yl]methanol K27 (0.200 g, 0.90 mmol), stirring for 1.5 h, and the crude was used without purification. MS/ESI$^+$ 250.1 [MH]$^+$, Rt=0.55 min (Method A).

Intermediate O1

2-(1-azidoethyl)-3-phenylindolizine

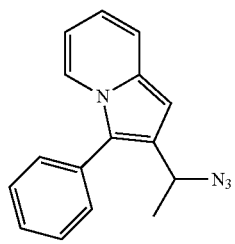 [SMILES: CC(N=[N+]=[N-])c1cc2ccccn2c1-c1ccccc1]

To a solution of 1-(3-phenylindolizin-2-yl)ethan-1-ol M1 (0.078 g, 0.329 mmol) in THF (3 mL) under nitrogen, DPPA (0.142 mL, 0.657 mmol) was added followed by DBU (0.098 mL, 0.657 mmol) and the mixture was stirred at RT overnight. The solvent was removed under reduced pressure and the residue was partitioned between EtOAc and water. The aqueous phase was extracted with EtOAc and the combined organic layers were washed with brine and dried over sodium sulfate. The solvent was removed and the crude was purified by flash chromatography on silica gel Biotage SNAP cartridge (cyclohexane to cyclohexane:EtOAc=98:2) to afford title compound as a pale green oil (0.050 g, 0.191 mmol, 56% yield). MS/ESI$^+$ 263.1 [MH]$^+$, Rt=1.38 min (Method A).

Intermediate O2

2-(1-azidoethyl)-3-(pyridin-2-yl)indolizine

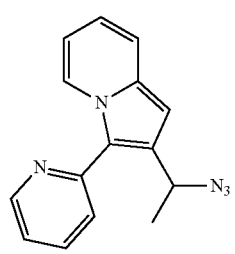 [SMILES: CC(N=[N+]=[N-])c1cc2ccccn2c1-c1ccccn1]

Prepared similarly to intermediate O1, starting from 1-[3-(pyridin-2-yl)indolizin-2-yl]ethan-1-ol M2 (0.085 g, 0.357 mmol), and the crude was purified by flash chromatography on silica gel Biotage SNAP cartridge (cyclohexane to cyclohexane:EtOAc=90:10) to afford title compound as a pale yellow oil (0.085 g, 0.323 mmol, 90% yield). MS/ESI$^+$ 264.1 [MH]$^+$, Rt=1.16 min (Method A).

Intermediate O3

2-(1-azidoethyl)-3-(pyridin-3-yl)indolizine

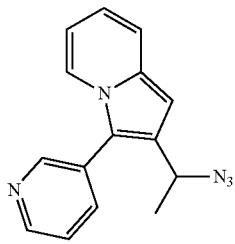 [SMILES: CC(N=[N+]=[N-])c1cc2ccccn2c1-c1cccnc1]

Prepared similarly to intermediate O1, starting from 1-[3-(pyridin-3-yl)indolizin-2-yl]ethan-1-ol M4 (0.175 g, 0.734 mmol), and purified by flash chromatography on silica gel Biotage SNAP cartridge (cyclohexane:EtOAc=90:10 to 60:40) to afford title compound as a pale green oil (0.141 g, 0.535 mmol, 73% yield). MS/ESI$^+$ 264.1 [MH]$^+$, Rt=0.97 min (Method A).

Intermediate O4

2-(1-azidoethyl)-3-(pyrazin-2-yl)indolizine

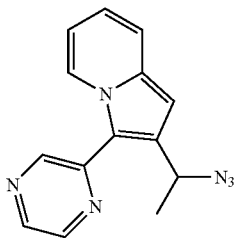 [SMILES: CC(N=[N+]=[N-])c1cc2ccccn2c1-c1cnccn1]

Prepared similarly to intermediate O1, starting from 1-[3-(pyrazin-2-yl)indolizin-2-yl]ethan-1-ol M5 (0.033 g, 0.138 mmol); after stirring at r.t. overnight, the addition of a further equivalent of both DPPA and DBU was required, and the stirring was continued for additional 24 h. After work-up the crude was purified by flash chromatography on silica gel Biotage SNAP cartridge (cyclohexane:EtOAc=90:10 to 80:20) to afford title compound as a yellow oil (0.030 g, 0.114 mmol, 82% yield). MS/ESI$^+$ 265.1 [MH]$^+$, Rt=1.11 min (Method A).

Intermediate O5

2-(1-azidoethyl)-8-fluoro-3-(pyridin-2-yl)indolizine

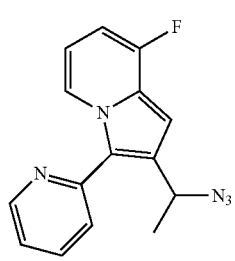 [SMILES: CC(N=[N+]=[N-])c1cc2c(F)cccn2c1-c1ccccn1]

Prepared similarly to intermediate O1, starting from 1-[8-fluoro-3-(pyridin-2-yl)indolizin-2-yl]ethan-1-ol M9 (0.094 g, 0.37 mmol), stirring at RT for 6 h, and the crude title compound was used without any additional purification. MS/ESI⁺ 282.1 [MH]⁺, Rt=1.23 min (Method A).

Intermediate O6

2-(1-azidoethyl)-3-(3,6-dihydro-2H-pyran-4-yl)indolizine

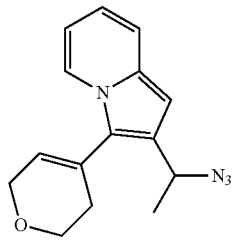 [SMILES: CC(N=[N+]=[N-])c1cc2ccccn2c1C1=CCOCC1]

Prepared similarly to intermediate O1, starting from 1-[3-(3,6-dihydro-2H-pyran-4-yl)indolizin-2-yl]ethan-1-ol M15 (0.043 g, 0.177 mmol), and purified by flash chromatography on silica gel Biotage SNAP cartridge (cyclohexane to cyclohexane:EtOAc=80:20) to afford title compound as a yellow oil (0.047 g, 0.177 mmol, quantitative yield). MS/ESI⁺ 269.2 [MH]⁺, Rt=1.22 min (Method A).

Intermediate O7 tert-butyl 4-[2-(1-azidoethyl)indolizin-3-yl]-1,2,3,6-tetrahydropyridine-1-carboxylate

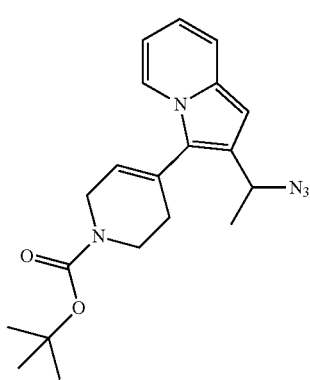 [SMILES: CC(N=[N+]=[N-])c1cc2ccccn2c1C1=CCN(C(=O)OC(C)(C)C)CC1]

Prepared similarly to intermediate O1, starting from tert-butyl 4-[2-(1-hydroxyethyl)indolizin-3-yl]-1,2,3,6-tetrahydropyridine-1-carboxylate M16 (0.099 g, 0.29 mmol); after stirring at r.t. overnight additional 0.6 eq of DPPA and 0.6 eq of DBU were added and the stirring was continued for further 24 h. After work-up, the crude was purified by flash chromatography on silica gel Biotage SNAP cartridge (cyclohexane to cyclohexane:EtOAc=95:5) to afford title compound as a yellow oil (0.106 g, 0.29 mmol, quantitative yield). MS/ESI⁺ 368.3 [MH]⁺, Rt=1.43 min (Method A).

Intermediate O8

2-(1-azidoethyl)-3-(pent-1-yn-1-yl)indolizine

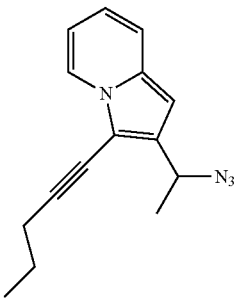 [SMILES: CCCC#Cc1c(C(C)N=[N+]=[N-])cc2ccccn12]

Prepared similarly to intermediate O1, starting from 1-[3-(pent-1-yn-1-yl)indolizin-2-yl]ethan-1-ol M19 (0.168 g, 0.74 mmol, and purified by flash chromatography on Biotage silica gel SNAP cartridge (cyclohexane to cyclohexane:EtOAc=95:5) to afford title compound as a yellow oil (0.130 g, 0.51 mmol, 70% yield). MS/ESI⁺ 253.0 [MH]⁺, Rt=1.46 min (Method A).

Intermediate O9

2-(1-azidoethyl)-3-(3-{[tris(propan-2-yl)silyl]oxy}prop-1-yn-1-yl)indolizine

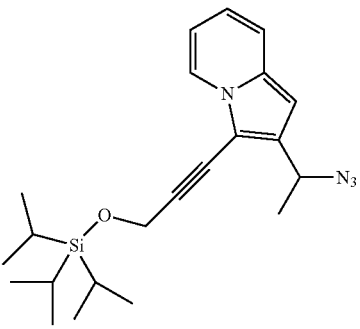 [SMILES: CC(N=[N+]=[N-])c1cc2ccccn2c1C#CCO[Si](C(C)C)(C(C)C)C(C)C]

Prepared similarly to intermediate O1, starting from 1-[3-(3-{[tris(propan-2-yl)silyl]oxy}prop-1-yn-1-yl)indolizin-2-yl]ethan-1-ol M20 (0.328 g, 0.88 mmol), and used without purification (0.349 g, 0.88 mmol, quantitative yield). MS/ESI⁺ 397.2 [MH]⁺, Rt=1.78 min (Method A).

Intermediate P1

(3-phenylindolizin-2-yl)methanamine

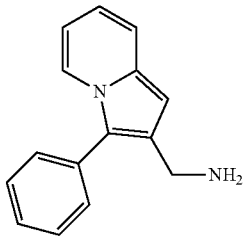

To a solution of 2-(azidomethyl)-3-phenylindolizine N1 (0.166 g, 0.668 mmol) in THF (10 mL) under nitrogen, PPh$_3$ (0.350 g, 1.336 mmol) was added and the mixture was stirred at RT for 2 h. Additional PPh$_3$ (0.088 g, 0.334 mmol) was added and the reaction was stirred at r.t. overnight. Water was added and the reaction was stirred at RT for 3 h. The solvent was removed under reduced pressure and the residue was dissolved in MeOH and purified on SCX cartridge (2 g), washing with MeOH. The product was eluted with 1M ammonia in MeOH and the volatiles were removed under reduced pressure to afford title compound as brown oil (0.148 g, 0.665 mmol, quantitative yield). MS/ESI$^+$ 223.2 [MH]$^+$, Rt=0.55 min (Method A).

Intermediate P2

[3-(pyridin-2-yl)indolizin-2-yl]methanamine

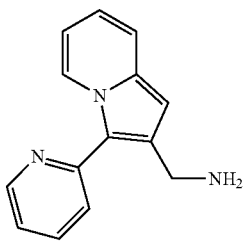

To a solution of 2-(azidomethyl)-3-(pyridin-2-yl)indolizine N2 (0.272 g, 1.09 mmol) in THF (10 mL) under nitrogen, PPh$_3$ (0.572 g, 2.18 mmol) was added and the mixture was stirred at RT overnight. Water was added and the reaction was stirred at RT for 3 h. The solvent was removed under reduced pressure and the residue was dissolved in MeOH and purified on SCX cartridge (5 g), washing with MeOH. The product was eluted with 1M ammonia in MeOH and the volatiles were removed under reduced pressure to afford title compound as yellow oil (0.204 g, 0.914 mmol, 84% yield). MS/ESI$^+$ 224.2 [MH]$^+$, Rt=0.42 m (Method A).

Intermediate P3

[3-(3-fluorophenyl)indolizin-2-yl]methanamine

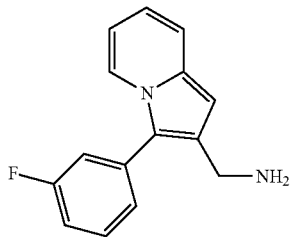 [SMILES: NCc1cc2ccccn2c1-c1cccc(F)c1]

Prepared similarly to intermediate P2, starting from 2-(azidomethyl)-3-(3-fluorophenyl)indolizine N3 (0.248 g, 0.931 mmol), to give title compound as a yellow oil (0.217 g, 0.903 mmol, 97% yield). MS/ESI$^+$ 241.1 [MH]$^+$, Rt=0.58 min (Method A).

Intermediate P4

[3-(2-fluorophenyl)indolizin-2-yl]methanamine

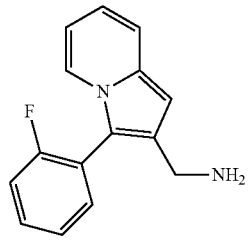 [SMILES: NCc1cc2ccccn2c1-c1ccccc1F]

Prepared similarly to intermediate P2, starting from 2-(azidomethyl)-3-(2-fluorophenyl)indolizine N4 (0.277 g, 1.04 mmol,) to give title compound as yellow oil (0.250 g, 1.04 mmol, quantitative yield). MS/ESI$^+$ 241.1 [MH]$^+$, Rt=0.55 min (Method A).

Intermediate P5

[3-(2-methylphenyl)indolizin-2-yl]methanamine

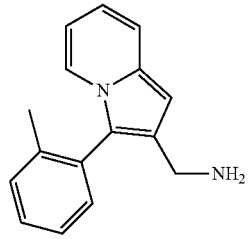 [SMILES: Cc1ccccc1-c1c(CN)cc2ccccn12]

Prepared similarly to intermediate P2, starting from 2-(azidomethyl)-3-(2-methylphenyl)indolizine N5 (0.260 g, 0.991 mmol), to give title compound as yellow oil (0.226 g, 0.956 mmol, 96% yield). MS/ESI$^+$ 237.0 [MH]$^+$, Rt=0.70 min (Method B).

Intermediate P6

(1-phenylindolizin-2-yl)methanamine

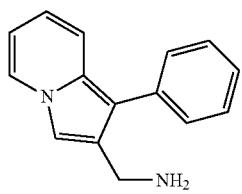 [SMILES: NCc1cn2ccccc2c1-c1ccccc1]

Prepared similarly to intermediate P2, starting from crude 2-(azidomethyl)-1-phenylindolizine N6 (0.80 mmol), to give title compound as blue oil (0.170 g, 0.76 mmol, 96% yield). MS/ESI⁺ 223.1 [MH]⁺, Rt=0.56 min (Method A).

Intermediate P7

[1-(3-fluorophenyl)indolizin-2-yl]methanamine

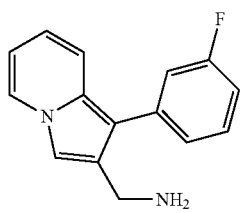 [SMILES: NCc1cn2ccccc2c1-c1cccc(F)c1]

Prepared similarly to intermediate P2, starting from crude 2-(azidomethyl)-1-(3-fluorophenyl)indolizine N7 (0.68 mmol) to give title compound as a green oil (0.124 g, 0.51 mmol, 75% yield). MS/ESI⁺ 241.1 [MH]⁺, Rt=0.59 min (Method A).

Intermediate P8

[1-(2-methylphenyl)indolizin-2-yl]methanamine

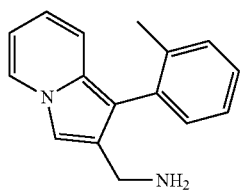 [SMILES: Cc1ccccc1-c1c(CN)cn2ccccc12]

Prepared similarly to intermediate P2, starting from crude 2-(azidomethyl)-1-(2-methylphenyl)indolizine N8 (0.42 mmol) to give title compound as an orange oil (0.093 g, 0.39 mmol, 93% yield). MS/ESI⁺ 237.1 [MH]⁺, Rt=0.62 min (Method A).

Intermediate P9

[1-(pyridin-2-yl)indolizin-2-yl]methanamine

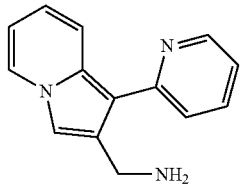 [SMILES: NCc1cn2ccccc2c1-c1ccccn1]

Prepared similarly to intermediate P2, starting from 2-(azidomethyl)-1-(pyridin-2-yl)indolizine N9 (0.90 mmol) to afford title compound (0.088 g, 0.39 mmol, 44% yield). MS/ESI⁺ 224.1 [MH]⁺, Rt=0.40 min (Method A).

Intermediate P10 indolizin-2-ylmethanamine

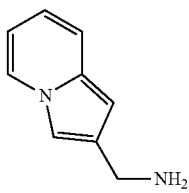 [SMILES: NCc1cc2ccccn2c1]

To a solution of indolizine-2-carbonitrile B5 (0.241 g, 1.7 mmol) in anhydrous THF (17 mL), 1M LiAlH₄ in THF (2.55 mL, 2.55 mmol) was added at −25° C. and the resulting solution was stirred at the same temperature for 2 h. The reaction was quenched by drop-wise addition of water (97 μl), followed by aqueous 15% NaOH (97 μl) and water (291 μl), and gradually warmed up to room temperature. The mixture was filtered and the filtrate was concentrated under reduced pressure; the residue was combined with the crude batch described above and purified by flash chromatography on Biotage silica-NH SNAP cartridge (DCM to DCM:MeOH=99:1.0) affording title compound as a light pink solid (0.139 g, 0.95 mmol, 46% yield). MS/ESI⁺ 147.0 [MH]⁺, Rt=0.27 min (Method A).

Intermediate Q1:
1-(3-phenylindolizin-2-yl)ethan-1-amine

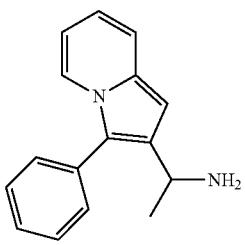 [SMILES: CC(N)c1cc2ccccn2c1-c1ccccc1]

To a solution of 2-(1-azidoethyl)-3-phenylindolizine O1 (0.050 g, 1.191 mmol) in THF (3 mL) under nitrogen, PPh₃ (0.100 g, 0.382 mmol) was added and the mixture was stirred at RT overnight. Water was added and the reaction was stirred at RT for 1 h. Additional PPh₃ (0.050 g, 0.191 mmol) was added and the mixture was stirred at RT for 5 h and then heated at 50° C. for 1 h. The solvent was removed under vacuum and the residue was dissolved in MeOH and purified on a SCX cartridge (2 g), washing with MeOH. The product was eluted with 1M ammonia in MeOH and the volatiles were removed under reduced pressure to afford title compound as a pale yellow oil (0.041 g, 0.174 mmol, 91% yield). MS/ESI⁺ 237.1 [MH]⁺, Rt=0.60 min (Method A).

Intermediate Q2

1-[3-(pyridin-2-yl)indolizin-2-yl]ethan-1-amine

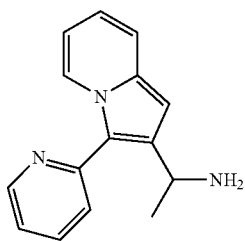 [SMILES: CC(N)c1cc2ccccn2c1-c1ccccn1]

To a solution of 3-(pyridin-2-yl)indolizine-2-carbonitrile J1 (0.800 g, 3.6 mmol) in THF (10.8 mL) cooled at 0° C., a solution of 3M MeMgBr in Et₂O (4.25 mL, 12.7 mmol) was added and the resulting mixture was heated under microwave irradiation at 100° C. for 45 min. After cooling to RT the mixture was carefully added to a freshly prepared solution of NaBH₄ (0.272 g, 7.2 mmol) in MeOH (18 mL) and the reaction was stirred at RT for 30 min. The mixture was evaporated to dryness. In a different flask to a solution of 3-(pyridin-2-yl)indolizine-2-carbonitrile J1 (0.100 g, 0.45 mmol) in THF (1.35 mL) cooled at 0° C., a solution of 3M MeMgBr in Et₂O (0.525 mL, 1.575 mmol) was added and the resulting mixture was heated under microwave irradiation at 100° C. for 45 min. After cooling to RT the mixture was carefully added to a freshly prepared solution of NaBH₄ (0.034 g, 0.9 mmol) in MeOH (2.25 mL) and the reaction was stirred at RT for 30 min. The mixture was evaporated to dryness. The two crudes were combined and purified by flash chromatography on Biotage silica-NH cartridge (DCM to DCM:MeOH=98.5:1.5) to afford title compound as a yellow oil (0.779 g, 3.3 mmol, 81% yield). MS/ESI⁺ 238.1 [MH]⁺, Rt=0.47 min (Method A).

Intermediate Q3

1-[3-(pyridin-3-yl)indolizin-2-yl]ethan-1-amine

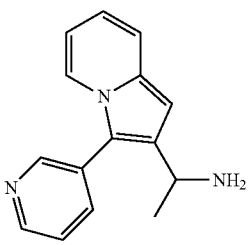 [SMILES: CC(N)c1cc2ccccn2c1-c1cccnc1]

To a solution of 2-(1-azidoethyl)-3-(pyridin-3-yl)indolizine O3 (0.140 g, 0.532 mmol) in THF (5 mL) under nitrogen, PPh₃ (0.279 g, 1.06 mmol) was added and the mixture was stirred at RT overnight. Additional PPh₃ (0.140 g, 0.532 mmol) was added and the mixture was stirred at RT for 1 h. Water was added and the reaction was heated at 50° C. for 1 h. The solvent was removed under vacuum and the residue was dissolved in DCM/MeOH and purified on a SXC cartridge (5 g), washing with MeOH. The product was eluted with 1M ammonia in MeOH and the volatiles were removed under reduced pressure to afford title compound as a brown oil which was used for the next step without any further purifications (0.130 g). MS/ESI⁺ 238.1 [MH]⁺, Rt=0.37 min (Method A).

Intermediate Q4

1-[3-(pyrazin-2-yl)indolizin-2-yl]ethan-1-amine

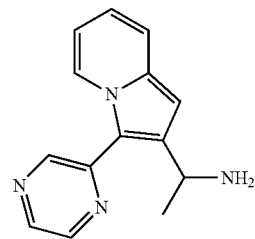 [SMILES: CC(N)c1cc2ccccn2c1-c1cnccn1]

To a solution of 2-(1-azidoethyl)-3-(pyrazin-2-yl)indolizine O4 (0.030 g, 0.114 mmol) in THF (2.5 mL) under nitrogen, PPh₃ (0.060 g, 0.227 mmol) was added and the mixture was stirred at RT overnight. Water was added and the reaction was heated at 50° C. for 2 h. The solvent was removed under vacuum and the residue was dissolved in DCM/MeOH and purified on a SCX cartridge (1 g), washing with MeOH. The product was eluted with 1M NH₃ in MeOH and the volatiles were removed under reduced pressure to afford title compound as a brown oil which was used without any additional purification (0.030 g). MS/ESI⁺ 239.1 [MH]⁺, Rt=0.43 min (Method A).

Intermediate Q5

1-[8-fluoro-3-(pyridin-2-yl)indolizin-2-yl]ethan-1-amine

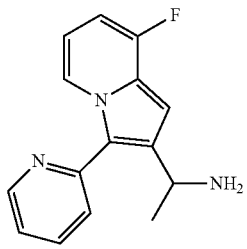 [SMILES: CC(N)c1cc2c(F)cccn2c1-c1ccccn1]

To a solution of 2-(1-azidoethyl)-8-fluoro-3-(pyridin-2-yl)indolizine O5 (0.104 g, 0.37 mmol) in THF (4.8 mL) under nitrogen, PPh₃ (0.194 g, 0.74 mmol) was added and the mixture was stirred at RT overnight. Water was added and the reaction was stirred at RT for 2 h. The solvent was removed under vacuum and the residue was dissolved in MeOH and charged on a SCX cartridge (5 g), washing with MeOH. The product was eluted with 1M ammonia in MeOH and the volatiles were removed under reduced pressure to afford title compound (0.084 g, 0.32 mmol, 88% yield), which was used without further purifications. MS/ESI⁺ 256.1 [MH]⁺, Rt=0.51 min (Method A).

Intermediate Q6

1-[3-(3,6-dihydro-2H-pyran-4-yl)indolizin-2-yl]ethan-1-amine

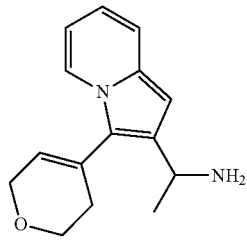 [SMILES: CC(N)c1cc2ccccn2c1C1=CCOCC1]

Prepared similarly to compound Q4, starting from 2-(1-azidoethyl)-3-(3,6-dihydro-2H-pyran-4-yl)indolizine O6 (0.047 g, 0.177 mmol), and heating at 50° C. for 1 h after the addition of water, to afford title compound as a yellow oil (0.033 g, 0.137 mmol, yield 78%). MS/ESI⁺ 256.1 [MH–NH₃]⁺, Rt=0.49 min (Method A).

Intermediate Q7 tert-butyl 4-[2-(1-aminoethyl)indolizin-3-yl]-1,2,3,6-tetrahydropyridine-1-carboxylate

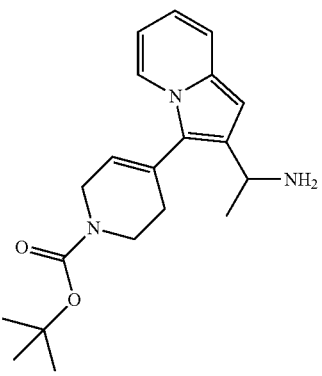 [SMILES: CC(N)c1cc2ccccn2c1C1=CCN(C(=O)OC(C)(C)C)CC1]

Prepared similarly to compound Q4, starting from tert-butyl 4-[2-(1-azidoethyl)indolizin-3-yl]-1,2,3,6-tetrahydropyridine-1-carboxylate P7 (0.106 g, 0.29 mmol), and heating at 50° C. for 1 h after the addition of water, to afford title compound as a yellow oil (0.041 g, 0.12 mmol, 41% yield). MS/ESI⁺ 325.1 [MH–NH₃]⁺, Rt=0.70 min (Method A).

Intermediate Q8

1-[3-(pent-1-yn-1-yl)indolizin-2-yl]ethan-1-amine

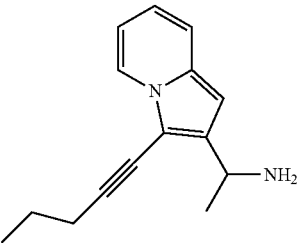 [SMILES: CCCC#Cc1c(C(C)N)cc2ccccn12]

To a solution of 2-(1-azidoethyl)-3-(pent-1-yn-1-yl)indolizine O8 (0.129 g, 0.51 mmol), in THF (4.8 mL) under nitrogen, PPh₃ (0.267 g, 1.02 mmol) was added and the mixture was stirred at RT overnight. Water was added and the reaction was heated at 50° C. for 1 h. The solvent was removed under reduced pressure and the residue was purified by flash chromatography on Biotage silica-NH SNAP cartridge (DCM to DCM:AcOEt=95:5) to afford crude title compound which was used without any additional purification. MS/ESI⁺ 210.2 [MH–NH₃]⁺, Rt=0.65 min (Method A).

Intermediate Q9

1-[3-(3-{[tris(propan-2-yl)silyl]oxy}prop-1-yn-1-yl)indolizin-2-yl]ethan-1-amine

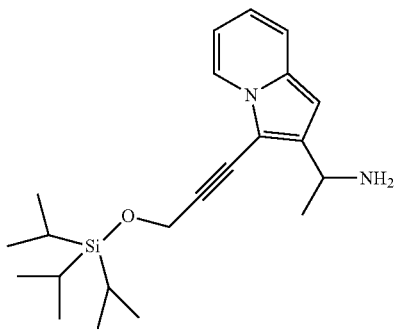 [SMILES: CC(N)c1cc2ccccn2c1C#CCO[Si](C(C)C)(C(C)C)C(C)C]

Prepared similarly to compound Q8, starting from 2-(1-azidoethyl)-3-(3-{[tris(propan-2-yl)silyl]oxy}prop-1-yn-1-yl)indolizine O9 (0.349 g, 0.88 mmol), heating at 50° C. for 5 h after the addition of water. The crude residue was purified by flash chromatography on Biotage silica-NH SNAP cartridge (DCM) followed by flash chromatography on Biotage silica-NH SNAP cartridge (cyclohexane:EtOAc=95:5 to 50:50) to afford title compound as a brown oil (0.089 g, 0.24 mmol, 27% yield). MS/ESI⁺ 371.4 [MH]⁺, Rt=1.02 min (Method A).

Intermediate Q10

1-[3-(pyridin-4-yl)indolizin-2-yl]ethan-1-amine

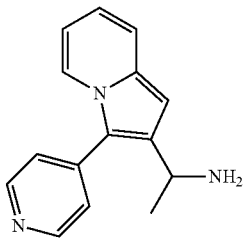 [SMILES: CC(N)c1cc2ccccn2c1-c1ccncc1]

To a suspension of 3-(pyridin-4-yl)indolizine-2-carbonitrile J2 (0.094 mg, 0.424 mmol) in THF (2 mL) cooled at 0° C., 3M MeMgBr solution in Et$_2$O (0.495 mL, 1.485 mmol) was added drop-wise and the resulting mixture was heated under MW irradiation at 100° C. for 1 h. After cooling to RT the mixture was added to a freshly prepared suspension of NaBH$_4$ (0.032 g, 0.848 mmol) in MeOH (2 mL) cooled at 0° C. and the reaction was stirred at the same temperature for 30 min. The solvent was removed under reduced pressure and the crude was purified by flash chromatography on Biotage silica-NH SNAP cartridge (DCM to DCM:MeOH=95:5) to yield title compound as a yellow oil (0.064 g, 0.270 mmol, 64% yield). MS/ESI$^+$ 238.1 [MH]$^+$, Rt=0.28 min (Method A).

Intermediate Q11

1-[3-(thiophen-2-yl)indolizin-2-yl]ethan-1-amine

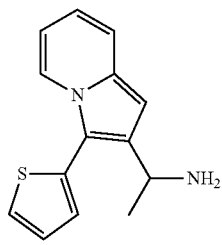 [SMILES: CC(N)c1cc2ccccn2c1-c1cccs1]

To a solution of 3-(thiophen-2-yl)indolizine-2-carbonitrile J3 (0.072) in THF (0.96 mL) cooled at 0° C., a solution of 3M MeMgBr in Et$_2$O (0.37 mL, 1.12 mmol) was added and the resulting mixture was heated under microwave irradiation at 100° C. for 1 h. After cooling to RT the resulting mixture was carefully added to a freshly prepared solution of NaBH$_4$ (0.0242 g, 0.64 mmol) in MeOH (1.6 ml) and the mixture was stirred for 30 minutes at RT. The solvent was evaporated and the crude was purified by flash chromatography on Biotage silica-NH SNAP cartridge (cyclohexane:EtOAc=70:30 to 50:50) to afford title compound that was used in the next step without further purification (0.058 g). MS/ESI$^+$ 243.0 [MH]$^+$, Rt=0.58 min (Method A).

Intermediate Q12

1-[3-(thiophen-3-yl)indolizin-2-yl]ethan-1-amine

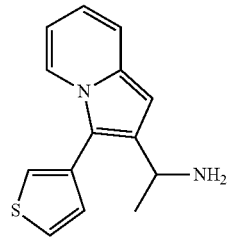 [SMILES: CC(N)c1cc2ccccn2c1-c1ccsc1]

Prepared similarly to intermediate Q11, starting from 3-(thiophen-3-yl)indolizine-2-carbonitrile J4 (0.095 g), stirring at r.t. for 15 min after the addition to NaBH$_4$ solution. The crude was purified by flash chromatography on Biotage silica-NH cartridge (DCM to DCM:MeOH=98:2) to afford title compound which was used in the next step without further purifications (0.067 g). MS/ESI$^+$ 243. [MH]$^+$, Rt=0.58 min (Method A).

Intermediate Q13

1-[5-methyl-3-(pyridin-2-yl)indolizin-2-yl]ethan-1-amine

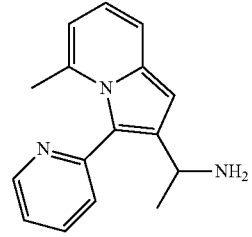 [SMILES: Cc1cccc2cc(C(C)N)c(-c3ccccn3)n12]

Prepared similarly to intermediate Q11, starting from 5-methyl-3-(pyridin-2-yl)indolizine-2-carbonitrile J5 (0.083 g, 0.35 mmol). The crude was purified by flash chromatography on Biotage silica-NH cartridge (DCM to DCM:MeOH=98:2) to afford title compound as a yellow oil (0.045 g, 0.18 mmol, 51% yield). MS/ESI$^+$ 252.1 [MH]$^+$, Rt=0.43 min (Method A).

Intermediate Q14

1-[8-methyl-3-(pyridin-2-yl)indolizin-2-yl]ethan-1-amine

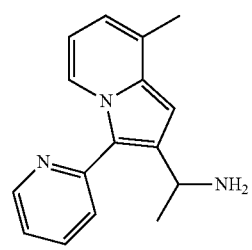 [SMILES: Cc1cccn2c(-c3ccccn3)c(C(C)N)cc12]

Prepared similarly to intermediate Q11, starting from 8-methyl-3-(pyridin-2-yl)indolizine-2-carbonitrile J6 (0.083 g, 0.35 mmol). The crude was purified by flash chromatography on Biotage silica-NH cartridge (DCM to DCM:MeOH=98:2) to afford title compound as a yellow oil (0.051 g, 0.20 mmol, 58% yield). MS/ESI$^+$ 252.1 [MH]$^+$, Rt=0.55 min (Method A).

Intermediate Q15

1-[3-(pyridin-2-yl)indolizin-2-yl]propan-1-amine

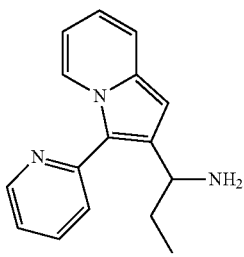 [SMILES: CCC(N)c1cc2ccccn2c1-c1ccccn1]

To a solution of 3-(pyridin-2-yl)indolizine-2-carbonitrile J1 (0.150 g, 0.68 mmol) in THF (2.04 mL) cooled at 0° C., a solution of 1M EtMgBr in THF (2.39 mL, 2.39 mmol) was added and the resulting mixture was heated under MW irradiation at 100° C. for 1 h. Additional 1M EtMgBr in THF (1.5 mL, 1.5 mmol) was added and the resulting mixture was heated under microwave irradiation at 100° C. for 45 min. The resulting mixture was carefully added to a freshly prepared solution of NaBH$_4$ (0.051 g, 1.36 mmol) in MeOH (3.4 mL) at RT. After stirring for 1 h the mixture was evaporated to dryness and the crude was purified by flash chromatography on Biotage silica-NH SNAP cartridge (DCM to DCM:MeOH=99:1) to afford title compound as an orange oil (0.102 g, 0.40 mmol, 60% yield). MS/ESI$^+$ 252.1 [MH]$^+$, Rt=0.53 min (Method A).

Intermediate AA1

3-(4-amino-6-chloropyrimidin-5-yl)prop-2-yn-1-ol

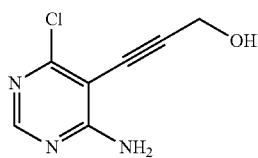 [SMILES: Nc1ncnc(Cl)c1C#CCO]

A mixture of 6-chloro-5-iodopyrimidin-4-amine (prepared accordingly to the procedure reported in *Tetrahedron Letters*, 2010, 51, 27, 3597-3598, which is incorporated herein by reference in its entirety, 0.200 g, 0.78 mmol), 3-trimethylsiloxy-1-propyne (0.500 g, 3.94 mmol), CuI (0.052 g, 0.273 mmol) and diethylamine (0.95 mL, 8.57 mmol) in DMF (3.3 mL) was degassed and then Pd(PPh$_3$)$_2$Cl$_2$ (0.097 g, 0.14 mmol) was added. The reaction was stirred at room temperature for 2 h, then diluted with EtOAc and filtered through a Celite® pad. The filtrate was washed with water and brine, then dried over sodium sulfate, filtered and concentrated. The crude was purified by flash chromatography on Biotage silica-NH SNAP cartridge (cyclohexane:EtOAc=100:0 to 0:100) to afford title compound as a yellow solid (0.078 g, 0.42 mmol, 54% yield). MS/ESI$^+$ 184.0 [MH]$^+$, Rt=0.46 min (Method A).

Intermediate AA2

6-chloro-5-(3-{[tris(propan-2-yl)silyl]oxy}prop-1-yn-1-yl)pyrimidin-4-amine

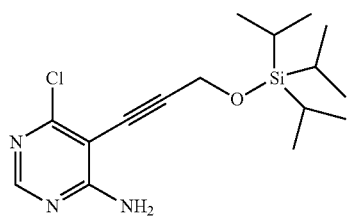 [SMILES: CC(C)[Si](OCC#Cc1c(N)ncnc1Cl)(C(C)C)C(C)C]

To a stirred mixture of 3-(4-amino-6-chloropyrimidin-5-yl)prop-2-yn-1-ol AA1 (0.078 g, 0.42 mmol) and imidazole (0.071 g, 1.05 mmol) in DMF (0.5 mL) triisopropylsilyl chloride (0.083 g, 0.43 mmol) was added at RT and the reaction was stirred overnight. The mixture was diluted with EtOAc and washed with a saturated solution of NH$_4$Cl; the organic phase was dried over sodium sulfate, filtered and concentrated. The crude was purified by flash chromatography on Biotage silica gel SNAP cartridge (cyclohexane to cyclohexane:EtOAc=70:30) to afford title compound as a white solid (0.075 g, 0.22 mmol, 53% yield). MS/ESI$^+$ 340.2 [MH]$^+$, Rt=1.45 min (Method A).

Intermediate AA3

4-amino-6-chloropyrimidine-5-carboxylic acid

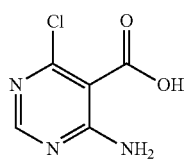 [SMILES: Nc1ncnc(Cl)c1C(=O)O]

To a solution of commercially available 4-amino-6-chloropyrimidine-5-carbaldehyde (0.500 g, 3.17 mmol) in THF (10 mL), sulfamic acid (0.493 g, 5.07 mmol) was added at RT and the mixture was cooled to 0° C. A solution of sodium chlorite (0.860 g, 9.51 mmol) in water (5 mL) was added and the reaction mixture was allowed to warm to RT and stirred for 30 min. The mixture was then concentrated in vacuo and the crude was purified on a Biotage C18 cartridge (H$_2$O:MeOH=99:1 to 1:99) to afford title compound as a white solid (0.400 g, 2.3 mmol, 73% yield). MS/ESI$^+$ 173.9 [MH]$^+$, Rt=0.39 min (Method A).

Intermediate AA4

4-amino-6-chloro-N-methylpyrimidine-5-carboxamide

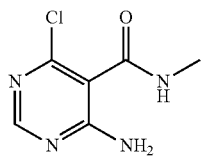

To a solution of 4-amino-6-chloropyrimidine-5-carboxylic acid AA3 J3 (0.030 g, 0.173 mmol) in DCM (2 mL), SOCl$_2$ (0.251 mL, 3.457 mmol) was added and the mixture was heated to reflux for 1 h. Additional SOCl$_2$ (0.251 mL, 3.457 mmol) was added and the mixture was heated to reflux for further 30 min. The volatiles were removed under vacuum and the residue was suspended in DCM (3 mL). 2M MeNH$_2$ in THF (0.260 mL, 0.519 mmol) was added and the mixture was stirred at RT for 15 min. The solvent was removed under reduced pressure and the crude was used for the next step without any additional purification. MS/ESI$^+$ 187.0 [MH]$^+$, Rt=0.29 min (Method A).

Intermediate AA5

4-amino-6-chloropyrimidine-5-carboxamide

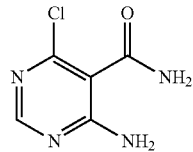 [SMILES: NC(=O)c1c(N)ncnc1Cl]

To a suspension of 4-amino-6-chloropyrimidine-5-carboxylic acid AA3 R3 (0.025 g, 0.144 mmol) in DCM (2 mL), SOCl$_2$ (0.104 mL, 1.44 mmol) was added and the mixture was stirred at RT for 30 minutes. Additional SOCl$_2$ (0.104 mL, 1.44 mmol) was added and the mixture was heated to reflux for 1 h. The volatiles were removed under vacuum and the residue was suspended in DCM (3 mL); aqueous concentrated 30% ammonium hydroxide (0.200 mL, 1.54 mmol) was added and the mixture was stirred at RT for 1 h. The volatiles were removed under vacuum and the crude solid was used without any additional work-up and purification as a mixture with some starting material. MS/ESI$^+$ 173.0 [MH]$^+$, Rt=0.24 min (Method A).

Intermediate AA6

3-{4-amino-1H-pyrazolo[3,4-d]pyrimidin-3-yl}-5-fluorophenol

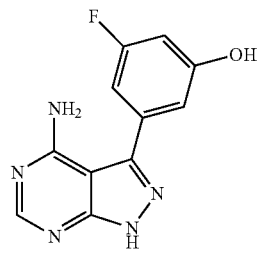 [SMILES: Nc1ncnc2[nH]nc(-c3cc(O)cc(F)c3)c12]

3-Iodo-1H-pyrazolo[3,4-d]pyrimidin-4-amine (1.00 g, 3.83 mmol), (3-fluoro-5-hydroxyphenyl)boronic acid (0.896 g, 5.7 mmol), PdCl$_2$(dppf) (0.700 g, 0.95 mmol) and K$_3$PO$_4$ (1.625 g, 7.66 mmol) were dissolved in a mixture of DMF (10 ml) and water (6 mL) and the reaction was heated at 120° C. for 20 h. The mixture was diluted with EtOAc and 2M HCl and the resulting suspension was filtered. The phases were separated and the organic layer was extracted twice with 2M HCl. The combined aqueous layers were basified with a saturated aqueous solution of Na$_2$CO$_3$ to pH 10 and extracted with EtOAc.

The organic phase was dried over sodium sulfate and the solvent was evaporated to afford title compound as a crude (yield considered to be quantitative) which was used in the next step without any additional purification. MS/ESI$^+$ 246.2 [MH]$^+$, Rt=0.40 min (Method A).

Intermediate AA7

3-{3-[(tert-butyldimethylsilyl)oxy]-5-fluorophenyl}-1H-pyrazolo[3,4-d]pyrimidin-4-amine

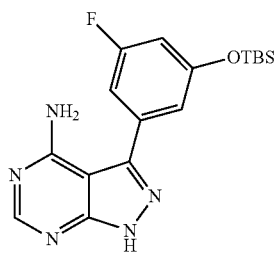 [SMILES: CC(C)(C)[Si](C)(C)Oc1cc(F)cc(-c2n[nH]c3ncnc(N)c23)c1]

To a solution of crude 3-{4-amino-1H-pyrazolo[3,4-d]pyrimidin-3-yl}-5-fluorophenol AA6 (theoretical 3.83 mmol) in DMF (13 ml), imidazole (1.30 g, 19.15 mmol) and tert-butyl(chloro)dimethylsilane (2.88 g, 19.15 mmol) were added and the mixture was stirred at RT for 1 h. The mixture was diluted with EtOAc and washed with a saturated solution of NH$_4$Cl, then with brine. The organic phase was dried over sodium sulfate and the solvent was removed under reduced pressure; the residue was purified by flash chromatography on silica gel Biotage column (cyclohexane:EtOAc=50:50 to 20:80) affording title compound as a white solid (0.220 g, 0.61 mmol). MS/ESI$^+$ 360.3 [MH]$^+$, Rt=1.07 min (Method A).

Intermediate S1

N-(3-bromo-5-fluorophenyl)methanesulfonamide

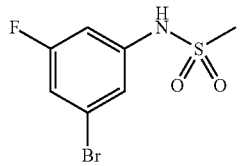

A solution of commercially available 3-bromo-5-fluoroaniline (0.500 g, 2.64 mmol) in pyridine (9.4 mL) was cooled to 0° C. and methanesulfonyl chloride (0.265 mL, 3.43 mmol) was added drop-wise; the resulting solution was allowed to warm to room temperature and stirred for 2 h. The solvent was removed under reduced pressure and the crude was partitioned between EtOAc and aqueous 1N HCl. The organic phase was dried over sodium sulfate and the solvent was removed; the crude was purified by flash chromatography on Biotage silica gel SNAP cartridge (cyclohexane to cyclohexane:EtOAc=50:50) to afford title compound as a white solid (0.543 g, 2.03 mmol, 77% yield). MS/ESI$^+$ not detectable [MH]$^+$, Rt=0.91 min (Method A).

$^1$H NMR (400 MHz, DMSO-d$_6$) δ ppm 10.29 (s, 1 H), 7.23-7.30 (m, 1 H), 7.19 (s, 1 H), 6.99-7.06 (m, 1 H), 3.12 (s, 3 H).

Intermediate S2

3-bromo-5-fluorobenzene-1-sulfonyl chloride

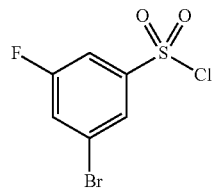 [SMILES: O=S(=O)(Cl)c1cc(F)cc(Br)c1]

To a solution of 3-bromo-5-fluoroaniline (0.500 g, 2.63 mmol) in glacial acetic acid (0.70 mL) cooled in an ice bath, concentrated hydrochloric acid (2.15 mL) was added. Then, a solution of sodium nitrite (0.199 g, 2.89 mmol) in water (0.45 mL) was slowly added maintaining the temperature around 0° C. After completion of the addition, the reaction mixture was further stirred for 20 min. The resulting solution was slowly added to a freshly prepared mixture of aqueous ~40% sodium bisulfite solution (1.915 mL, 7.36 mmol), copper chloride (0.052 g, 0.526 mmol), glacial acetic acid (5.0 mL) and concentrated hydrochloric acid (1 mL) at room temperature and the reaction was stirred at RT for 2.5 h. The mixture was then cooled to 0° C., additional sodium nitrite (0.5 eq) was added and the stirring was continued at r.t. for 1 h. The mixture was extracted with EtOAc and the organic layer was dried over anhydrous sodium sulfate and then concentrated under reduced pressure to afford title compound which was used without any additional purification (0.450 g, 1.65 mmol, 63% yield).

$^1$H NMR (400 MHz, DMSO-d$_6$) δ ppm 7.54-7.58 (m, 1 H), 7.50-7.54 (m, 1 H), 7.30-7.36 (m, 1 H).

Intermediate S3

3-bromo-5-fluorobenzene-1-sulfonamide

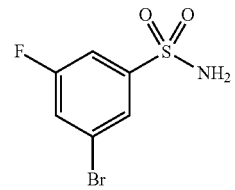 [SMILES: NS(=O)(=O)c1cc(F)cc(Br)c1]

Aqueous 30% NH$_4$OH (17 mL) was added to a solution of 3-bromo-5-fluorobenzene-1-sulfonyl chloride S2 (0.450 g, 1.65 mmol) in dioxane (14 mL) and the reaction was allowed to proceed overnight at RT. Water was added and the mixture was extracted twice with EtOAc and twice with DCM. The combined organic layers were dried over sodium sulfate and the solvent was evaporated to afford title compound as orange solid (0.320 g, 1.26, 76% yield), which was used without any further purification. MS/ESI$^-$ 252.0-254.0 [M–H]$^-$, Rt=0.76 min. (254.1-256.1) (Method A).

Intermediate T1

N-[3-fluoro-5-(tetramethyl-1,3,2-dioxaborolan-2-yl)phenyl]methanesulfonamide

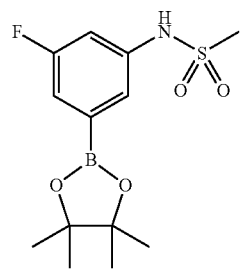 [SMILES: CC1(C)OB(c2cc(F)cc(NS(C)(=O)=O)c2)OC1(C)C]

A mixture of N-(3-bromo-5-fluorophenyl)methanesulfonamide S1 (0.100 g, 0.37 mmol), bis(pinacolato) diboron (0.190 g, 0.74 mmol), KOAc (0.145 g, 1.48 mmol) and [1,1'-bis(diphenylphosphino)ferrocene]dichloropalladium (II) (0.027 g, 0.037 mmol) in dioxane (3.7 mL) was stirred at 90° C. for 2 h. The solvent was removed and the residue was purified by flash chromatography on Biotage silica gel SNAP cartridge (cyclohexane to cyclohexane:EtOAc=70:30) to afford an unclean product. In a different flask a mixture of N-(3-bromo-5-fluorophenyl)methanesulfonamide S1 (0.315 g, 1.18 mmol), bis(pinacolato) diboron (0.599 g, 2.36 mmol), potassium acetate (0.463 g, 4.72 mmol) and [1,1'-bis(diphenylphosphino)ferrocene]dichloropalladium(II) (0.086 g, 0.118 mmol) in anhydrous dioxane (11.8 mL) was stirred at 90° C. for 1 h. The solvent was removed under reduced pressure and the residue was combined with the unclean product obtained in the batch described above. This crude was purified by flash chromatography on Biotage silica gel cartridge (cyclohexane to cyclohexane:EtOAc=70:30) to afford title compound (0.438 g, 1.39 mmol, 89% yield).

¹H NMR (400 MHz, DMSO-d₆) δ ppm 10.01 (s, 1 H), 7.33 (d, J=1.5 Hz, 1 H), 7.11-7.18 (m, 1 H), 7.04-7.10 (m, 1 H), 3.02 (s, 3 H), 1.29 (s, 12 H).

Intermediate T2

3-fluoro-5-(tetramethyl-1,3,2-dioxaborolan-2-yl)benzene-1-sulfonamide

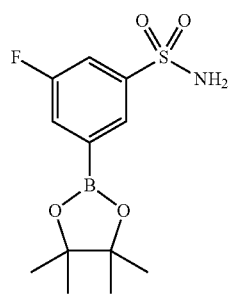 [SMILES: CC1(C)OB(c2cc(F)cc(S(N)(=O)=O)c2)OC1(C)C]

A mixture of 3-bromo-5-fluorobenzene-1-sulfonamide S3 (0.050 g, 0.197 mmol), bis(pinacolato) diboron (0.100 g, 0.394 mmol), KOAc (0.077 g, 0.788 mmol) and [1,1'-bis(diphenylphosphino)ferrocene]dichloropalladium(II) (14.4 mg, 0.0197 mmol) in dioxane (2 mL) was stirred at 90° C. for 3 h. Then the solvent was removed under reduced pressure and the residue was purified by flash chromatography on 10 g Biotage silica gel SNAP cartridge (cyclohexane to cyclohexane:EtOAc=70:30) to afford an impure product. In a different flask, a mixture of 3-bromo-5-fluorobenzene-1-sulfonamide S3 (0.170 g, 0.669 mmol), bis(pinacolato) diboron (0.340 g, 1.338 mmol), KOAc (0.263 g, 2.676 mmol) and [1,1'-bis(diphenylphosphino)ferrocene]dichloropalladium(II) (0.049 g, 0.0669 mmol) in anhydrous dioxane (7 mL) was stirred at 90° C. for 1.5 h. Then the solvent was removed and the crude was purified by flash chromatography on 25 g Biotage silica gel SNAP cartridge (cyclohexane to cyclohexane:EtOAc=90:10) to afford an impure product. The two batches were combined and purified by flash chromatography on 50 g Biotage silica gel SNAP cartridge (cyclohexane to cyclohexane:EtOAc=75:25) to afford title compound (0.070 g, 0.232 mmol, 27% yield).

¹H NMR (400 MHz, DMSO-d₆) δ ppm 7.98 (s, 1 H), 7.69-7.75 (m, 1 H), 7.56-7.62 (m, 1 H), 7.52 (s, 2 H), 1.34 (s, 12 H).

Intermediate T3

3-fluoro-5-(tetramethyl-1,3,2-dioxaborolan-2-yl)aniline

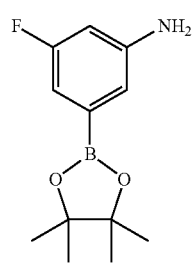

A mixture of 3-bromo-5-fluoroaniline (0.200 g, 1.05 mmol), bis(pinacolato) diboron 0. (535 g, 2.11 mmol), KOAc (0.361 g, 3.68 mmol) and [1,1'-bis(diphenylphosphino)ferrocene]dichloropalladium(II) (0.077 g, 0.105 mmol) in dioxane (10 mL) was purged with N₂ and heated in a sealed tube at 90° C. overnight. The solvent was removed and the crude was purified by flash chromatography on Biotage silica gel SNAP cartridge (cyclohexane to cyclohexane:EtOAc=80:20) to afford title compound (0.270 g) which was used without any additional purification. MS/ESI⁺ 238.2 [MH]⁺, Rt=1.02 min (Method A).

Intermediate T4

3-hydroxy-5-(tetramethyl-1,3,2-dioxaborolan-2-yl)benzonitrile

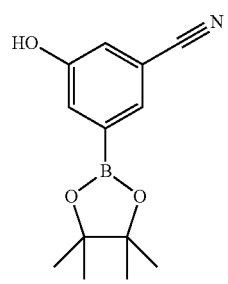 [SMILES: CC1(C)OB(c2cc(O)cc(C#N)c2)OC1(C)C]

A microwave vial was charged with 3-chloro-5-hydroxybenzonitrile (0.300 g, 1.95 mmol), Pd₂(dba)₃ (0.055 g, 0.06 mmol), tricyclohexylphosphine (0.066 g, 0.234 mmol), KOAc (0.288 g, 2.93 mmol) and bis(pinacolato) diboron (0.546 g, 2.15 mmol), DME (3 mL) was added and the mixture was purged with N₂ and heated under microwave irradiation at 150° C. for 1 h. After cooling to room temperature the mixture was diluted with water and extracted with Et₂O. The combined organic layers were concentrated in vacuo and purified by flash chromatography on 50 g silica gel Biotage cartridge (cyclohexane to cyclohexane:EtOAc=80:20) to afford title compound as white solid (0.340 g, 1.39 mmol, 71% yield). This compound was used without any additional purification.

¹H NMR (400 MHz, DMSO-d₆) δ ppm 10.23 (s, 1 H), 7.36-7.40 (m, 2 H), 7.24-7.28 (m, 1 H), 1.31 (s, 12 H).

Intermediate T5

3-fluoro-5-(tetramethyl-1,3,2-dioxaborolan-2-yl)benzonitrile

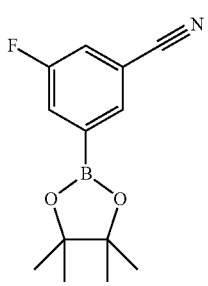 [SMILES: CC1(C)OB(c2cc(F)cc(C#N)c2)OC1(C)C]

A mixture of 3-bromo-5-fluorobenzonitrile (0.300 g, 1.5 mmol), bis(pinacolato)diboron (0.762 g, 3 mmol), KOAc (0.589 g, 6.0 mmol) and [1,1'-bis(diphenylphosphino)ferrocene]dichloropalladium(II) (0.110 g, 0.15 mmol) in dioxane (15 mL) was stirred at 90° C. for 2 h. The solvent was removed and the residue was purified by flash chromatography on Biotage silica 50 g cartridge (cyclohexane to cyclohexane:EtOAc=70:30) to afford title compound (0.360 g, 1.46 mmol, 97% yield).

$^1$H NMR (400 MHz, DMSO-$d_6$) δ ppm 7.98-8.03 (m, 1 H), 7.81-7.85 (m, 1 H), 7.68-7.73 (M, 1 H), 1.33 (s, 12 H).

Intermediate T6

5-[3-fluoro-5-(tetramethyl-1,3,2-dioxaborolan-2-yl)phenyl]-1H-1,2,3,4-tetrazole

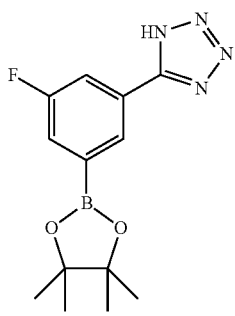 [SMILES: CC1(C)OB(c2cc(F)cc(-c3nnn[nH]3)c2)OC1(C)C]

To a solution of 3-fluoro-5-(tetramethyl-1,3,2-dioxaborolan-2-yl)benzonitrile T5 (0.200 g, 0.809 mmol) in DME (1.5 mL), azidotrimethylsilane (0.186 g, 1.618 mmol) and dibutyltin oxide (0.020 g, 0.0809 mmol) were added and reaction was heated under MW irradiation for 10 min at 150° C. After cooling to room temperature the mixture was concentrated under reduced and the residue was partitioned between Et$_2$O and aqueous 2N NaOH; the organic phase was extracted with aqueous 2N NaOH and the combined aqueous layers were washed with Et$_2$O, acidified to pH 3-4 with aqueous 6N HCl and extracted with DCM. The combined organic layers were dried over sodium sulfate, filtered and concentrated to afford title compound as white solid (0.150 g, 0.517 mmol, 64% yield). $^1$H NMR (400 MHz, DMSO-$d_6$) δ ppm 8.21 (s, 1 H), 7.94-8.00 (m, 1 H), 7.53-7.60 (m, 1 H), 1.35 (s, 12 H).

Intermediate U1 tert-butyl 4-(2-{1-[(6-amino-5-cyanopyrimidin-4-yl)amino]ethyl}indolizin-3-yl)-1,2,3,6-tetrahydropyridine-1-carboxylate

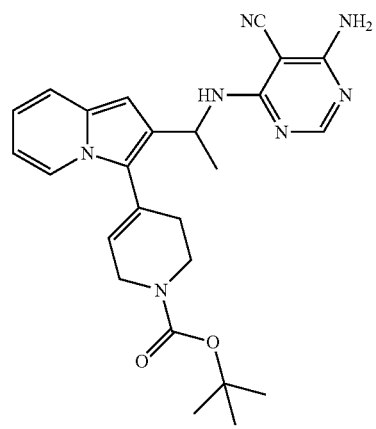 [SMILES: CC(Nc1ncnc(N)c1C#N)c1cc2ccccn2c1C1=CCN(C(=O)OC(C)(C)C)CC1]

To a solution of tert-butyl 4-[2-(1-aminoethyl)indolizin-3-yl]-1,2,3,6-tetrahydropyridine-1-carboxylate Q7 (0.039 g, 0.11 mmol) in t-BuOH (1.5 mL), 4-amino-6-chloropyrimidine-5-carbonitrile (0.017 g, 0.11 mmol) was added followed by DIPEA (0.038 mL, 0.22 mmol) and the resulting mixture was heated to reflux for 3 h. The solvent was removed and the crude was partitioned between DCM/MeOH≈4/1 and water; the organic phase was dried over sodium sulfate, the solvent was removed under reduced pressure and the crude was purified by flash chromatography on Biotage silica-NH SNAP cartridge (cyclohexane to cyclohexane:AcOEt=50:50) to afford title compound as a yellow oil (0.045 g, 0.098 mmol, 89% yield). MS/ESI$^+$ 460.4 [MH]$^+$, Rt=1.14 min (Method A).

Intermediate U2

4-amino-6-({1-[3-(3-{[tris(propan-2-yl)silyl]oxy}prop-1-yn-1-yl)indolizin-2-yl]ethyl}amino)pyrimidine-5-carbonitrile

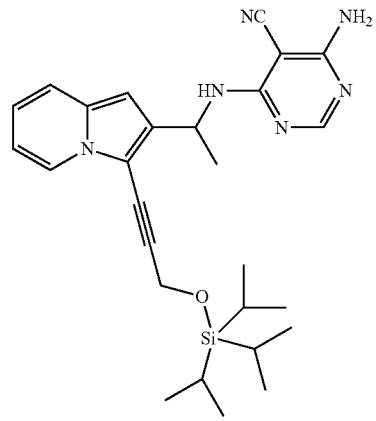 [SMILES: CC(Nc1ncnc(N)c1C#N)c1cc2ccccn2c1C#CCO[Si](C(C)C)(C(C)C)C(C)C]

Prepared similarly to intermediate U1 using 1-[3-(3-{[tris(propan-2-yl)silyl]oxy}prop-1-yn-1-yl)indolizin-2-yl]

ethan-1-amine Q9 (0.089 g, 0.24 mmol) and 4-amino-6-chloropyrimidine-5-carbonitrile (0.037 g, 0.24 mmol), and purified by flash chromatography on Biotage silica-NH SNAP cartridge (cyclohexane to cyclohexane:EtOAc=85:25) to afford title compound as a yellow solid (0.062 g, 0.13 mmol, 53% yield). MS/ESI⁺ 489.4 [MH]⁺, Rt=1.61 min (Method A).

Intermediate V

4-N-{1-[3-(pyridin-2-yl)indolizin-2-yl]ethyl}-5-(3-{[tris(propan-2-yl)silyl]oxy}prop-1-yn-1-yl)pyrimidine-4,6-diamine

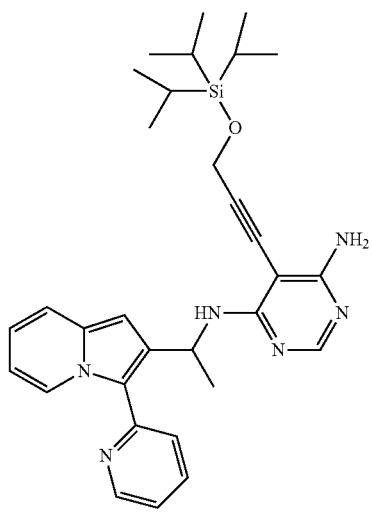 [SMILES: CC(Nc1ncnc(N)c1C#CCO[Si](C(C)C)(C(C)C)C(C)C)c1cc2ccccn2c1-c1ccccn1]

To a solution of 1-[3-(pyridin-2-yl)indolizin-2-yl]ethan-1-amine Q2 (0.052 g, 0.22 mmol) in n-BuOH (3 mL), 6-chloro-5-(3-{[tris(propan-2-yl)silyl]oxy}prop-1-yn-1-yl)pyrimidin-4-amine AA2 J2 (0.075 g, 0.22 mmol) was added followed by DIPEA (0.077 mL, 0.44 mmol) and the resulting mixture was heated to reflux for 48 h. The solvent was removed and the crude was partitioned between DCM and water, the organic phase was dried over sodium sulfate, the solvent was removed under reduced pressure and the crude was purified by flash chromatography on Biotage silica-NH SNAP cartridge (cyclohexane:EtOAc=70:30) to afford title compound as yellow oil (0.057 g, 0.106 mmol, 48% yield). MS/ESI⁺ 541.4 [MH]⁺, Rt=1.16 min (Method A).

Intermediate W1

3-iodo-1-[1-(3-phenylindolizin-2-yl)ethyl]-1H-pyrazolo[3,4-d]pyrimidin-4-amine

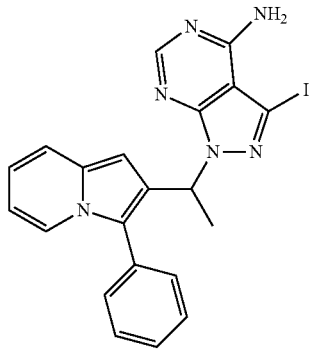 [SMILES: CC(c1cc2ccccn2c1-c1ccccc1)n1nc(I)c2c(N)ncnc21]

To a mixture of 1-(3-phenylindolizin-2-yl)ethan-1-ol M1 (0.190 g, 0.80 mmol), 3-iodo-1H-pyrazolo[3,4-d]pyrimidin-4-amine (0.252 g, 0.96 mmol) and PPh₃ (0.273 g, 1.04 mmol) in dry THF (9 mL), a solution of DIAD (0.19 mL, 0.96 mmol) in THF (5 mL) was added drop-wise at RT and the reaction was stirred for 2 h. The solvent was removed and the residue was purified by flash chromatography on silica gel Biotage SNAP cartridge (cyclohexane:EtOAc=95:5 to 100% EtOAc) to afford title compound as a light-brown solid (0.110 g, 0.23 mmol, 29% yield). MS/ESI⁺ 481.2 [MH]⁺, Rt 1.17 min (Method A).

Intermediate W2

3-iodo-1-{1-[3-(pyridin-2-yl)indolizin-2-yl]ethyl}-1H-pyrazolo[3,4-d]pyrimidin-4-amine

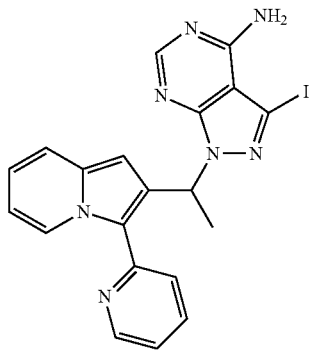 [SMILES: CC(c1cc2ccccn2c1-c1ccccn1)n1nc(I)c2c(N)ncnc21]

To a mixture of 1-[3-(pyridin-2-yl)indolizin-2-yl]ethan-1-ol M2 (1.02 g, 4.28 mmol), 3-iodo-1H-pyrazolo[3,4-d]pyrimidin-4-amine (1.34 g, 5.14 mmol) and PPh₃ (1.46 g, 5.56 mmol) in dry THF (70 mL), a solution of DIAD (1.01 mL, 5.14 mmol) in THF (10 mL) was added drop-wise at r.t. and the reaction was stirred for 2 h. The solvent was removed and the residue was purified by flash chromatography on Biotage silica-NH cartridge (DCM to DCM:EtOAc=95:5) to afford title compound (0.950 g, 1.97 mmol, 46% yield). MS/ESI⁺ 482.1 [MH]⁺, Rt 0.81 min (Method A).

Intermediate W3

1-{1-[3-(2-fluorophenyl)indolizin-2-yl]ethyl}-3-iodo-1H-pyrazolo[3,4-d]pyrimidin-4-amine

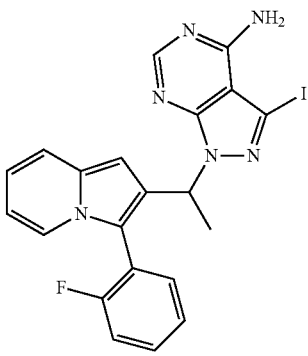 [SMILES: CC(c1cc2ccccn2c1-c1ccccc1F)n1nc(I)c2c(N)ncnc21]

Prepared similarly to intermediate W1, starting from 1-[3-(2-fluorophenyl)indolizin-2-yl]ethan-1-ol M3 (0.171 g, 0.669 mmol), stirring at RT for 2 h, and purified by flash chromatography on silica gel Biotage SNAP cartridge (cyclohexane:EtOAc=95:5 to 100% EtOAc) to afford title compound as a light-brown solid (0.114 g). MS/ESI$^+$ 499.2 [MH]$^+$, Rt 1.11 min (Method A).

Intermediate W4

3-iodo-1-{1-[3-(pyridin-4-yl)indolizin-2-yl]ethyl}-1H-pyrazolo[3,4-d]pyrimidin-4-amine

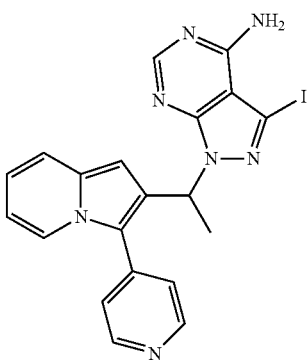 [SMILES: CC(c1cc2ccccn2c1-c1ccncc1)n1nc(I)c2c(N)ncnc21]

Prepared similarly to intermediate W1, starting from 1-[3-(pyridin-4-yl)indolizin-2-yl]ethan-1-ol M6 (0.300 g, 1.26 mmol), stirring at RT for 2 h, and purified by flash chromatography on Biotage silica-NH gel SNAP cartridge (DCM to DCM:MeOH 98:2) to afford title compound (0.216 g, 0.45 mmol, 36% yield). MS/ESI$^+$ 482.2 [MH]$^+$, Rt 0.64 min (Method A).

Intermediate W5

3-iodo-1-{1-[6-methyl-3-(pyridin-2-yl)indolizin-2-yl]ethyl}-1H-pyrazolo[3,4-d]pyrimidin-4-amine

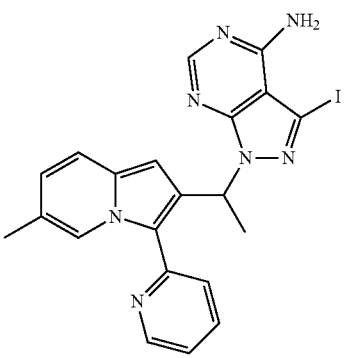 [SMILES: Cc1ccc2cc(C(C)n3nc(I)c4c(N)ncnc43)c(-c3ccccn3)n2c1]

Prepared similarly to intermediate W1 starting from 1-[6-methyl-3-(pyridin-2-yl)indolizin-2-yl]ethan-1-ol M7 (0.092 g, 0.36 mmol), stirring at RT for 2 h, and purified by flash chromatography on Biotage silica-NH cartridge (DCM to DCM:MeOH=95:5) to afford a crude title compound which was used without any additional purification (0.130 g). MS/ESI$^+$ 496.2 [MH]$^+$, Rt 0.89 min (Method A).

Intermediate W6

3-iodo-1-{1-[3-(pyridin-2-yl)-6-(trifluoromethyl)indolizin-2-yl]ethyl}-1H-pyrazolo[3,4-d]pyrimidin-4-amine

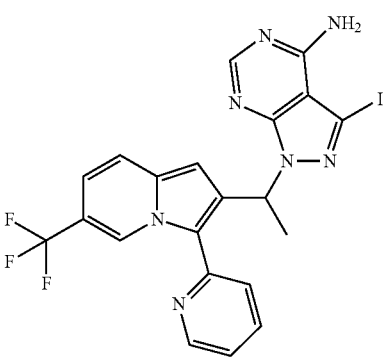 [SMILES: CC(c1cc2ccc(C(F)(F)F)cn2c1-c1ccccn1)n1nc(I)c2c(N)ncnc21]

Prepared similarly to intermediate W1 starting from 1-[3-(pyridin-2-yl)-6-(trifluoromethyl)indolizin-2-yl]ethan-1-ol M8 (0.145 g, 0.473 mmol), stirring at RT for 1 h and purified by flash chromatography on Biotage silica-NH cartridge (DCM to DCM:MeOH=98:2). The residue was purified on SCX cartridge (1 g) washing with MeOH and the product was eluted with 1M ammonia in MeOH to afford title compound (0.085 g, 0.155 mmol, 33% yield). MS/ESI$^+$ 550.1 [MH]$^+$, Rt 1.13 min (Method A).

Intermediate W7

3-iodo-1-{1-[1-methyl-3-(pyridin-2-yl)indolizin-2-yl]ethyl}-1H-pyrazolo[3,4-d]pyrimidin-4-amine

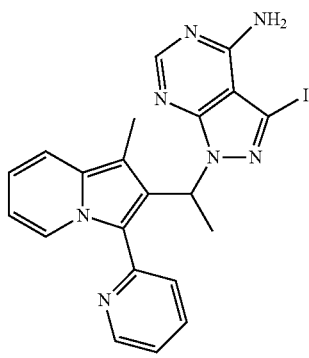 [SMILES: Cc1c(C(C)n2nc(I)c3c(N)ncnc32)c(-c2ccccn2)n2ccccc12]

Prepared similarly to intermediate W1, starting from [1-[1-methyl-3-(pyridin-2-yl)indolizin-2-yl]ethan-1-ol M10 (0.052 g, 0.21 mmol), stirring at RT overnight, and purified by flash chromatography on Biotage silica-NH cartridge (cyclohexane:EtOAc=80:20 to 60:40) to afford crude title compound which was used in the next step without any additional purification (0.106 g). MS/ESI$^+$ 496.2 [MH]$^+$, Rt 0.81 min (Method A).

Intermediate W8

3-iodo-1-(1-{3-[5-(morpholin-4-ylmethyl)thiophen-2-yl]indolizin-2-yl}ethyl)-1H-pyrazolo[3,4-d]pyrimidin-4-amine

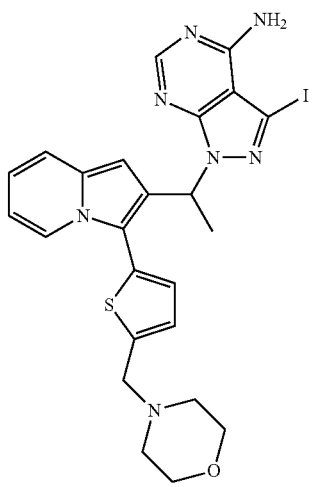 [SMILES: CC(c1cc2ccccn2c1-c1ccc(CN2CCOCC2)s1)n1nc(I)c2c(N)ncnc21]

Prepared similarly to intermediate W1, starting from 1-{3-[5-(morpholin-4-ylmethyl)thiophen-2-yl]indolizin-2-yl}ethan-1-ol M11 (0.324 g, 0.94 mmol), 3-iodo-1H-pyrazolo[3,4-d]pyrimidin-4-amine (0.319 g, 1.22 mmol), PPh$_3$ (0.370 g, 1.41 mmol) and DIAD (0.252 mL, 1.22 mmol), stirring at RT for 4 h, and purified by flash chromatography on Biotage silica-NH cartridge (DCM to DCM:EtOAc=90:10) to afford crude title compound as a yellow oil (0.325 g). MS/ESI$^+$ 586.2 [MH]$^+$, Rt 1.24 min (Method C).

Intermediate W9

3-iodo-1-(1-{3-[4-(morpholin-4-ylmethyl)phenyl]indolizin-2-yl}ethyl)-1H-pyrazolo[3,4-d]pyrimidin-4-amine

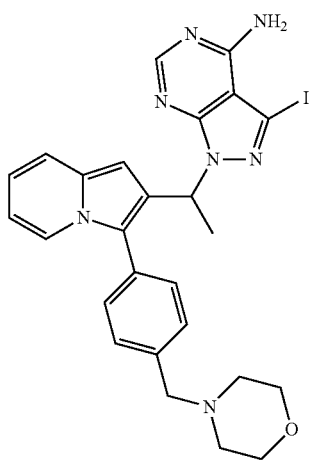 [SMILES: CC(c1cc2ccccn2c1-c1ccc(CN2CCOCC2)cc1)n1nc(I)c2c(N)ncnc21]

Prepared similarly to intermediate W1, starting from 1-{3-[4-(morpholin-4-ylmethyl)phenyl]indolizin-2-yl}ethan-1-ol M12 (0.203 g, 0.60 mmol), 3-iodo-1H-pyrazolo[3,4-d]pyrimidin-4-amine (0.203 g, 0.78 mmol), PPh$_3$ (0.236 g, 0.90 mmol) and DIAD (0.153 mL, 0.78 mmol), stirring at RT for 4 h, and purified by flash chromatography on Biotage silica-NH cartridge (DCM to DCM:EtOAc=90:10) to afford crude title compound as a yellow oil (0.320 g). MS/ESI$^+$ 580.3 [MH]$^+$, Rt 0.66 min (Method A).

Intermediate W10

1-[1-(3-{4-[(dimethylamino)methyl]phenyl}indolizin-2-yl)ethyl]-3-iodo-1H-pyrazolo[3,4-d]pyrimidin-4-amine

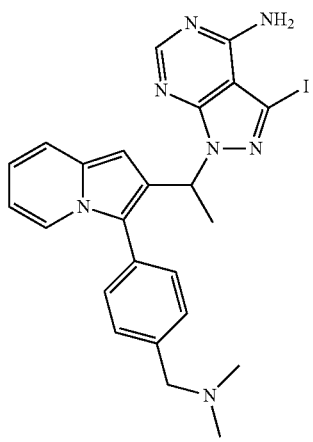 [SMILES: CC(c1cc2ccccn2c1-c1ccc(CN(C)C)cc1)n1nc(I)c2c(N)ncnc21]

Prepared similarly to intermediate W1, starting from 1-(3-{4-[(dimethylamino)methyl]phenyl}indolizin-2-yl)ethan-1-ol M13 (0.186 g, 0.63 mmol), 3-iodo-1H-pyrazolo[3,4-d]pyrimidin-4-amine (0.214 g, 0.82 mmol), PPh$_3$ (0.248 g, 0.94 mmol) and DIAD (0.161 mL, 0.82 mmol), stirring at r.t. for 1 h, and purified by flash chromatography on 5 g silica-NH cartridge (DCM to DCM:EtOAc=90:10) to afford title compound as a yellow oil (0.188 g). MS/ESI⁺ 538.3 [MH]⁺, Rt 0.66 min (Method A).

Intermediate W11

1-[1-(3-{3-[(dimethylamino)methyl]phenyl}indolizin-2-yl)ethyl]-3-iodo-1H-pyrazolo[3,4-d]pyrimidin-4-amine

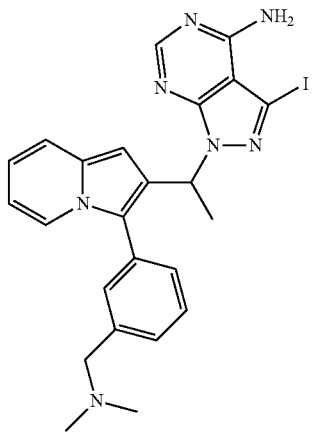 [SMILES: CC(c1cc2ccccn2c1-c1cccc(CN(C)C)c1)n1nc(I)c2c(N)ncnc21]

Prepared similarly to intermediate W1, starting from 1-(3-{3-[(dimethylamino)methyl]phenyl}indolizin-2-yl)ethan-1-ol M14 (0.197 g, 0.67 mmol), 3-iodo-1H-pyrazolo[3,4-d]pyrimidin-4-amine (0.227 g, 0.87 mmol), PPh₃ (0.264 g, 1.0 mmol) and DIAD (0.171 mL, 0.87 mmol), stirring at RT for 2 h, and purified by flash chromatography on silica-NH Biotage SNAP cartridge (DCM to DCM:EtOAc=90:10); the compound was further purified on SCX cartridge (1 g), eluting with 1M ammonia in MeOH to afford title compound as a brown solid (0.091 g). MS/ESI⁺ 538.3 [MH]⁺, Rt 1.07 min (Method C).

Intermediate W12

3-iodo-1-{1-[3-(1,3-thiazol-5-yl)indolizin-2-yl]ethyl}-1H-pyrazolo[3,4-d]pyrimidin-4-amine

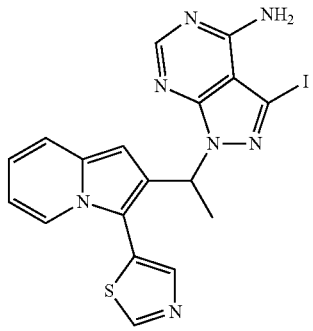 [SMILES: CC(c1cc2ccccn2c1-c1cncs1)n1nc(I)c2c(N)ncnc21]

Prepared similarly to intermediate W1, starting from 1-[3-(1,3-thiazol-5-yl)indolizin-2-yl]ethan-1-ol M17 (0.104 g, 0.42 mmol), 3-iodo-1H-pyrazolo[3,4-d]pyrimidin-4-amine (0.142 g, 0.546 mmol), PPh₃ (0.165 g, 0.63 mmol) and DIAD (0.107 mL, 0.546 mmol), stirring at RT for 4 h, and purified by flash chromatography on Biotage silica-NH SNAP cartridge (DCM to DCM:EtOAc=90:10); a further purification on SCX cartridge, eluting with 1M ammonia in MeOH was required to afford title compound as a brown solid (0.042 g, 0.086 mmol, 20% yield). MS/ESI⁺ 488.1 [MH]⁺, Rt 0.93 min (Method A).

Intermediate W13

1-[2-(1-{4-amino-3-iodo-1H-pyrazolo[3,4-d]pyrimidin-1-yl}ethyl)indolizin-3-yl]pyrrolidin-2-one

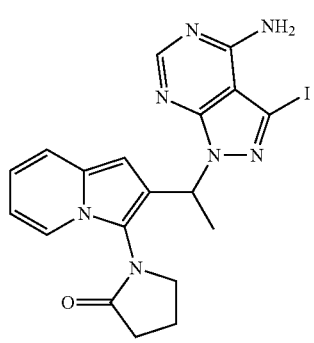 [SMILES: CC(c1cc2ccccn2c1N1CCCC1=O)n1nc(I)c2c(N)ncnc21]

Prepared similarly to intermediate W1, starting from 1-[2-(1-hydroxyethyl)indolizin-3-yl]pyrrolidin-2-one M18 (0.028 g, 0.11 mmol), 3-iodo-1H-pyrazolo[3,4-d]pyrimidin-4-amine (0.037 g, 0.143 mmol), PPh₃ (0.043 g, 0.165 mmol) and DIAD (0.028 mL, 0.143 mmol), stirring at RT for 4 h, and purified by flash chromatography on 5 g silica-NH cartridge (DCM to DCM:EtOAc=90:10) to afford title compound as a brown oil (0.034 g). MS/ESI⁺ 488.2 [MH]⁺, Rt 0.80 min (Method A).

Intermediate W14 tert-butyl 4-[2-(1-{4-amino-3-iodo-1H-pyrazolo[3,4-d]pyrimidin-1-yl}ethyl)indolizin-3-yl]-1,2,3,6-tetrahydropyridine-1-carboxylate

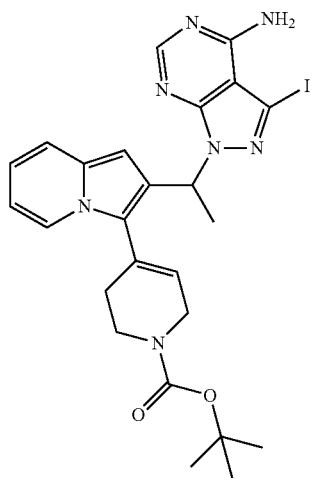 [SMILES: CC(c1cc2ccccn2c1C1=CCN(C(=O)OC(C)(C)C)CC1)n1nc(I)c2c(N)ncnc21]

Prepared similarly to intermediate W1, starting from tert-butyl 4-[2-(1-hydroxyethyl)indolizin-3-yl]-1,2,3,6-tetrahydropyridine-1-carboxylate M16 (0.066 g, 0.19 mmol), 3-iodo-1H-pyrazolo[3,4-d]pyrimidin-4-amine (0.065 g, 0.247 mmol), PPh₃ (0.075 g, 0.285 mmol) and DIAD (0.049 mL, 0.247 mmol), stirring at r.t. for 3 h, and purified by flash chromatography on silica-NH Biotage SNAP cartridge (DCM to DCM:EtOAc=90:10) to afford crude title compound as a yellow oil which was used without any additional purification. MS/ESI⁺ 586.3 [MH]⁺, Rt 1.23 min (Method A).

Intermediate W15

3-iodo-1-{1-[7-(pyridin-2-yl)pyrrolo[1,2-b]pyridazin-6-yl]ethyl}-1H-pyrazolo[3,4-d]pyrimidin-4-amine

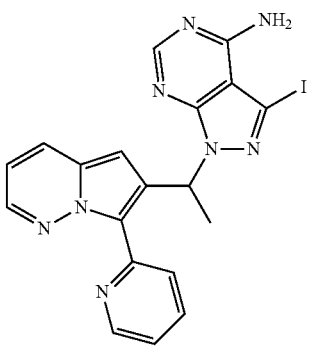 [SMILES: CC(c1cc2cccnn2c1-c1ccccn1)n1nc(I)c2c(N)ncnc21]

Prepared similarly to intermediate W1, starting from 1-[7-(pyridin-2-yl)pyrrolo[1,2-b]pyridazin-6-yl]ethan-1-ol M21 (0.060 g, 0.25 mmol), stirring at RT for 16 h, and purified by flash chromatography on Biotage silica-NH SNAP cartridge (cyclohexane:EtOAc=80:20 to 50:50) to afford crude title compound which was used without any additional purification (0.060 g). MS/ESI⁺ 483.2 [MH]⁺, Rt 0.65 min (Method A).

Intermediate W16

3-iodo-1-{[3-(pyridin-2-yl)indolizin-2-yl]methyl}-1H-pyrazolo[3,4-d]pyrimidin-4-amine

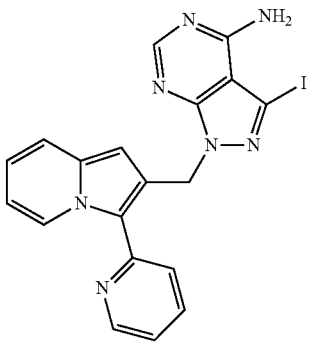 [SMILES: Nc1ncnc2c1c(I)nn2Cc1cc2ccccn2c1-c1ccccn1]

Prepared similarly to intermediate W1, starting from [3-(pyridin-2-yl)indolizin-2-yl]methanol K2 (0.060 g, 0.268 mmol), stirring at RT for 2 h, and purified by flash chromatography on Biotage silica-NH SNAP cartridge (DCM to DCM:MeOH=95:5) to afford title compound (0.020 g, 0.043 mmol, 16% yield). MS/ESI⁺ 468.0 [MH]⁺, Rt 0.79 min (Method A).

Intermediate W17

3-iodo-1-{[3-(pyridin-3-yl)indolizin-2-yl]methyl}-1H-pyrazolo[3,4-d]pyrimidin-4-amine

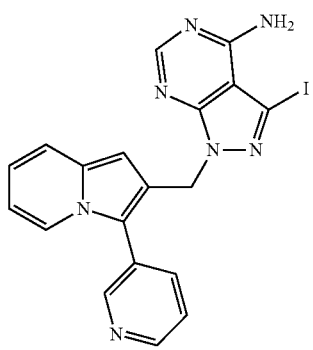 [SMILES: Nc1ncnc2c1c(I)nn2Cc1cc2ccccn2c1-c1cccnc1]

Prepared similarly to intermediate W1, starting from [3-(pyridin-3-yl)indolizin-2-yl]methanol K6 (0.120 g, 0.53 mmol), stirring at RT overnight, and purified by flash chromatography on Biotage silica-NH SNAP cartridge (cyclohexane:EtOAc=50:50 to 100% EtOAc) to afford title compound as a pale yellow oil (0.035 g, 0.075 mmol, 14% yield). MS/ESI⁺ 468.2 [MH]⁺, Rt 0.71 min (Method A).

Intermediate W18

3-iodo-1-{[3-(pyridin-4-yl)indolizin-2-yl]methyl}-1H-pyrazolo[3,4-d]pyrimidin-4-amine

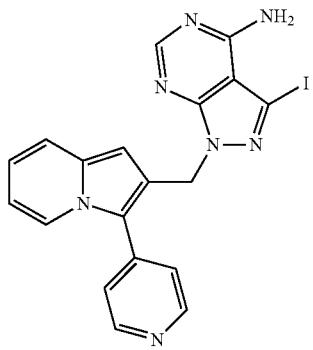 [SMILES: Nc1ncnc2c1c(I)nn2Cc1cc2ccccn2c1-c1ccncc1]

Prepared similarly to intermediate W1, starting from [3-(pyridin-4-yl)indolizin-2-yl]methanol K8 (0.070 g, 0.312 mmol), stirring at RT for 2 h, and purified by flash chromatography on Biotage silica gel SNAP cartridge (EtOAc to EtOAc:MeOH 70:30) to afford title compound (0.055 g, 0.118 mmol, 38% yield). MS/ESI⁺ 468.2 [MH]⁺, Rt 0.57 min (Method A).

Intermediate and Compound W19

3-iodo-1-{[7-(pyridin-2-yl)pyrrolo[1,2-b]pyridazin-6-yl]methyl}-1H-pyrazolo[3,4-d]pyrimidin-4-amine

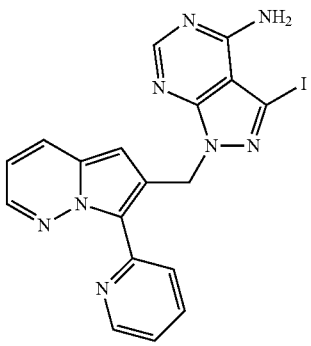 [SMILES: Nc1ncnc2c1c(I)nn2Cc1cc2cccnn2c1-c1ccccn1]

Prepared similarly to intermediate W1, starting from [7-(pyridin-2-yl)pyrrolo[1,2-b]pyridazin-6-yl]methanol K28 (0.050 g, 0.22 mmol), stirring at RT overnight, and purified by flash chromatography on Biotage silica-NH SNAP cartridge (cyclohexane:EtOAc=80:20 to 50:50) to afford title compound as a pale yellow solid (0.026 g, 0.055 mmol, 25% yield). MS/ESI$^+$ 469.1 [MH]$^+$, Rt 0.61 min (Method A).

$^1$H NMR (400 MHz, CHLOROFORM-d) δ ppm 8.71-8.78 (m, 1 H), 8.49 (d, J=8.0 Hz, 1 H), 8.36 (s, 1 H), 8.12-8.17 (m, 1 H), 7.80-7.89 (m, 1 H), 7.66-8.71 (m, 1 H), 7.20-7.26 (m, 1 H), 6.61 (dd, J=9.2, 4.4 Hz, 1 H), 6.18-6.24 (m, 3 H), 6.01 (br. s., 2 H).

Intermediates W20-34, W35a, W36a, W37-47 and W49-63 found in the table below may be prepared from suitable intermediates reported below following similar procedures as for compound W1.

| Intermediate | Name and Molecular Structure | | Reagent | Analytical data |
|---|---|---|---|---|
| W20 | 1-{1-[7-chloro-3-(pyridin-2-yl)indolizin-2-yl]ethyl}-3-iodo-1H-pyrazolo[3,4-d]pyrimidin-4-amine | | M22 | MS/ESI$^+$ 516.2 [MH]$^+$, Rt 1.02 min (Method A) |
| W21 | 3-iodo-1-{1-[7-methyl-3-(pyridin-2-yl)indolizin-2-yl]ethyl}-1H-pyrazolo[3,4-d]pyrimidin-4-amine | | M23 | MS/ESI$^+$ 496.2 [MH]$^+$, Rt 0.88 min (Method A) |
| W22 | 3-iodo-1-{1-[3-(2-methylpyridin-4-yl)indolizin-2-yl]ethyl}-1H-pyrazolo[3,4-d]pyrimidin-4-amine | | M24 | MS/ESI$^+$ 496.2 [MH]$^+$, Rt 0.63 min (Method A) |

| Intermediate | Name and Molecular Structure | Reagent | Analytical data |
|---|---|---|---|
| W23 | 3-iodo-1-(1-{3-[5-(morpholin-4-ylmethyl)pyridin-2-yl]indolizin-2-yl}ethyl)-1H-pyrazolo[3,4-d]pyrimidin-4-amine | M25 | MS/ESI⁺ 581.2 [MH]⁺, Rt 0.61 min (Method A) |
| W24 | 1-[1-(3-{5-[(dimethylamino)methyl]pyridin-2-yl}indolizin-2-yl)ethyl]-3-iodo-1H-pyrazolo[3,4-d]pyrimidin-4-amine | M26 | MS/ESI⁺ 539.1 [MH]⁺, Rt 0.60 min (Method A) |
| W25 | 3-iodo-1-(1-{3-[6-(morpholin-4-ylmethyl)pyridin-2-yl]indolizin-2-yl}ethyl)-1H-pyrazolo[3,4-d]pyrimidin-4-amine | M27 | MS/ESI⁺ 581.4 [MH]⁺, Rt 0.64 min (Method A) |

-continued

| Intermediate | Name and Molecular Structure | Reagent | Analytical data |
|---|---|---|---|
| W26 | 3-iodo-1-(1-{3-[4-(morpholin-4-ylmethyl)pyridin-2-yl]indolizin-2-yl}ethyl)-1H-pyrazolo[3,4-d]pyrimidin-4-amine | M28 | MS/ESI$^+$ 581.5 [MH]$^+$, Rt 0.62 min (Method A) |
| W27 | 1-[1-(3-{4-[(dimethylamino)methyl]pyridin-2-yl}indolizin-2-yl)ethyl]-3-iodo-1H-pyrazolo[3,4-d]pyrimidin-4-amine | M29 | MS/ESI$^+$ 539.3 [MH]$^+$, Rt 0.59 min (Method A) |
| W28 | 3-iodo-1-(1-{3-[5-(pyrrolidin-1-ylmethyl)pyridin-2-yl]indolizin-2-yl}ethyl)-1H-pyrazolo[3,4-d]pyrimidin-4-amine | M30 | MS/ESI$^+$ 565.2 [MH]$^+$, Rt 0.61 min (Method A) |

-continued

| Intermediate | Name and Molecular Structure | Reagent | Analytical data |
|---|---|---|---|
| W29 | 3-iodo-1-[1-(3-{5-[(4-methylpiperazin-1-yl)methyl]pyridin-2-yl}indolizin-2-yl)ethyl]-1H-pyrazolo[3,4-d]pyrimidin-4-amine | M31 | MS/ESI⁺ 594.4 [MH]⁺, Rt 0.58 min (Method A) |
| W30 | 3-iodo-1-[1-(3-{6-[(4-methylpiperazin-1-yl)methyl]pyridin-2-yl}indolizin-2-yl)ethyl]-1H-pyrazolo[3,4-d]pyrimidin-4-amine | M32 | MS/ESI⁺ 594.4 [MH]⁺, Rt 0.61 min (Method A) |
| W31 | 3-iodo-1-[1-(3-{4-[(4-methylpiperazin-1-yl)methyl]pyridin-2-yl}indolizin-2-yl)ethyl]-1H-pyrazolo[3,4-d]pyrimidin-4-amine | M33 | MS/ESI⁺ 594.3 [MH]⁺, Rt 0.55 min (Method A) |

| Intermediate | Name and Molecular Structure | Reagent | Analytical data |
|---|---|---|---|
| W32 | 3-iodo-1-[1-(3-{5-[(2,2,3,3,11,11,12,12-octamethyl-4,10-dioxa-7-aza-3,11-disilatridecan-7-yl)methyl]pyridin-2-yl}indolizin-2-yl)ethyl]-1H-pyrazolo[3,4-d]pyrimidin-4-amine | M34 | MS/ESI+ 827.6 [MH]+, Rt 1.23 min (Method A) |
| W33 | 3-iodo-1-(1-{3-[3-(1-methylpyrrolidin-2-yl)phenyl]indolizin-2-yl}ethyl)-1H-pyrazolo[3,4-d]pyrimidin-4-amine | M35 | MS/ESI+ 564.4 [MH]+, Rt 0.70 min (Method A) |
| W34 | 3-iodo-1-[1-(3-{5-[2-(morpholin-4-yl)ethoxy]pyridin-2-yl}indolizin-2-yl)ethyl]-1H-pyrazolo[3,4-d]pyrimidin-4-amine | M36 | MS/ESI+ 611.1 [MH]+, Rt 0.97 min (Method C) |

-continued

| Intermediate | Name and Molecular Structure | Reagent | Analytical data |
|---|---|---|---|
| W35a | 3-iodo-1-{1-[3-(6-methoxypyridin-3-yl)indolizin-2-yl]ethyl}-1H-pyrazolo[3,4-d]pyrimidin-4-amine | M37 | MS/ESI+ 512.0 [MH]+, Rt 1.02 min (Method A) |
| W36a | 3-iodo-1-{1-[3-(2-methoxypyridin-4-yl)indolizin-2-yl]ethyl}-1H-pyrazolo[3,4-d]pyrimidin-4-amine | M38 | MS/ESI+ 512.3 [MH]+, Rt 1.03 min (Method A) |
| W37 | 2-[2-(1-{4-amino-3-iodo-1H-pyrazolo[3,4-d]pyrimidin-1-yl}ethyl)indolizin-3-yl]benzonitrile | M39 | MS/ESI+ 506.2 [MH]+, Rt 1.06 and 1.09 min (mixture of isomers) (Method A) |
| W38 | 3-iodo-1-(1-{3-[5-(morpholine-4-carbonyl)pyridin-2-yl]indolizin-2-yl}ethyl)-1H-pyrazolo[3,4-d]pyrimidin-4-amine | M40 | MS/ESI+ 595.2 [MH]+, Rt 0.87 min (Method A) |

-continued

| Intermediate | Name and Molecular Structure | Reagent | Analytical data |
|---|---|---|---|
| W39 | 2-(1-{4-amino-3-iodo-1H-pyrazolo[3,4-d]pyrimidin-1-yl}ethyl)-3-(pyridin-2-yl)indolizine-1-carbonitrile | M42 | MS/ESI+ 507.1 [MH]+, Rt 0.85 min (Method A) |
| W40 | 2-(1-{4-amino-3-iodo-1H-pyrazolo[3,4-d]pyrimidin-1-yl}ethyl)-3-{3-[(dimethylamino)methyl]phenyl}indolizine-1-carbonitrile | M43 | MS/ESI+ 563.2 [MH]+, Rt 0.60 min (Method A) |
| W41 | 1-[1-(7-{3-[(dimethylamino)methyl]phenyl}pyrrolo[1,2-b]pyridazin-6-yl)ethyl]-3-iodo-1H-pyrazolo[3,4-d]pyrimidin-4-amine | M44 | MS/ESI+ 539.3 [MH]+, Rt 0.59 min (Method A) |
| W42 | 3-iodo-1-{1-[3-(1,3-thiazol-4-yl)indolizin-2-yl]ethyl}-1H-pyrazolo[3,4-d]pyrimidin-4-amine | M45 | MS/ESI+ 488.1 [MH]+, Rt 0.98 min (Method A) |

-continued

| Intermediate | Name and Molecular Structure | Reagent | Analytical data |
|---|---|---|---|
| W43 | 3-iodo-1-(1-{3-[2-(morpholin-4-ylmethyl)-1,3-thiazol-4-yl]indolizin-2-yl}ethyl)-1H-pyrazolo[3,4-d]pyrimidin-4-amine | M46 | MS/ESI+ 587.2 [MH]+, Rt 0.70 min (Method A) |
| W44 | 1-(1-{3-[3-(dimethylamino)prop-1-yn-1-yl]indolizin-2-yl}ethyl)-3-iodo-1H-pyrazolo[3,4-d]pyrimidin-4-amine | M47 | MS/ESI+ 486.1 [MH]+, Rt 1.00 min (Method C) |
| W45 | 1-[2-(1-{4-amino-3-iodo-1H-pyrazolo[3,4-d]pyrimidin-1-yl}ethyl)indolizin-3-yl]-4-methylpiperazin-2-one | M48 | MS/ESI+ 517.2 [MH]+, Rt 0.78 min (Method C) |

| Intermediate | Name and Molecular Structure | Reagent | Analytical data |
|---|---|---|---|
| W46 | 4-[2-(1-{4-amino-3-iodo-1H-pyrazolo[3,4-d]pyrimidin-1-yl}ethyl)indolizin-3-yl]-1-[2-(dimethylamino)ethyl]-1,2-dihydropyridin-2-one | M49 | MS/ESI+ 569.3 [MH]+, Rt 0.88 min (Method J) |
| W47 | 6-[2-(1-{4-amino-3-iodo-1H-pyrazolo[3,4-d]pyrimidin-1-yl}ethyl)indolizin-3-yl]-2-[2-(pyrrolidin-1-yl)ethyl]-2,3-dihydropyridazin-3-one | M50 | MS/ESI+ 596.5 [MH]+, Rt 0.61 min (Method A) |
| W49 | 6-[2-(1-{4-amino-3-iodo-1H-pyrazolo[3,4-d]pyrimidin-1-yl}ethyl)indolizin-3-yl]-2-[2-(morpholin-4-yl)ethyl]-2,3-dihydropyridazin-3-one | M52 | MS/ESI+ 612.3 [MH]+, Rt 0.61 min (Method A) |

-continued

| Intermediate | Name and Molecular Structure | Reagent | Analytical data |
|---|---|---|---|
| W50 | 3-iodo-1-[1-(3-{6-[2-(4-methylpiperazin-1-yl)ethoxy]pyridazin-3-yl}indolizin-2-yl)ethyl]-1H-pyrazolo[3,4-d]pyrimidin-4-amine | M53 | MS/ESI+ 625.3 [MH]+, Rt 0.61 min (Method A) |
| W51 | 1-[1-(3-{6-[2-(dimethylamino)ethoxy]pyridazin-3-yl}indolizin-2-yl)ethyl]-3-iodo-1H-pyrazolo[3,4-d]pyrimidin-4-amine | M54 | MS/ESI+ 570.4 [MH]+, Rt 0.61 min (Method A) |
| W52 | 3-iodo-1-[1-(3-{6-[(1-methylpiperidin-4-yl)oxy]pyridazin-3-yl}indolizin-2-yl)ethyl]-1H-pyrazolo[3,4-d]pyrimidin-4-amine) | M55 | MS/ESI+ 596.3 [MH]+, Rt 0.63 min (Method A) |

-continued

| Intermediate | Name and Molecular Structure | Reagent | Analytical data |
| --- | --- | --- | --- |
| W53 | 3-iodo-1-[1-(3-{6-[2-(1-methylpiperidin-4-yl)ethoxy]pyridazin-3-yl}indolizin-2-yl)ethyl]-1H-pyrazolo[3,4-d]pyrimidin-4-amine | M56 | MS/ESI$^+$ 624.4 [MH]$^+$, Rt 0.65 min (Method A) |
| W54 | 3-iodo-1-{1-[3-(morpholin-4-ylmethyl)indolizin-2-yl]ethyl}-1H-pyrazolo[3,4-d]pyrimidin-4-amine | M57 | MS/ESI$^+$ 504.3 [MH]$^+$, Rt 1.05 min (Method C) |
| W55 | 3-iodo-1-{1-[3-({2-methyl-2,9-diazaspiro[5.5]undecan-9-yl}methyl)indolizin-2-yl]ethyl}-1H-pyrazolo[3,4-d]pyrimidin-4-amine | M58 | MS/ESI$^+$ 585.3 [MH]$^+$, Rt 1.41 min (Method J) |

-continued

| Intermediate | Name and Molecular Structure | Reagent | Analytical data |
|---|---|---|---|
| W56 | tert-butyl 9-{[2-(1-{4-amino-3-iodo-1H-pyrazolo[3,4-d]pyrimidin-1-yl}ethyl)indolizin-3-yl]methyl}-3,9-diazaspiro[5.5]undecane-3-carboxylate | M59 | MS/ESI⁺ 671.5 [MH]⁺, Rt 1.51 min (Method J) |
| W57 | tert-butyl 2-{[2-(1-{4-amino-3-iodo-1H-pyrazolo[3,4-d]pyrimidin-1-yl}ethyl)indolizin-3-yl]methyl}-2,7-diazaspiro[3.5]nonane-7-carboxylate | M60 | MS/ESI⁺ 643.4 [MH]⁺, Rt 1.36 min (Method J) |
| W58 | tert-butyl (3aR,6aS)-5-{[2-(1-{4-amino-3-iodo-1H-pyrazolo[3,4-d]pyrimidin-1-yl}ethyl)indolizin-3-yl]methyl}-octahydropyrrolo[3,4-c]pyrrole-2-carboxylate | M61 | MS/ESI⁺ 629.4 [MH]⁺, Rt 1.30 min (Method C) |
| W59 | 2-(1-{4-amino-3-iodo-1H-pyrazolo[3,4-d]pyrimidin-1-yl}ethyl)-3-(morpholin-4-ylmethyl)indolizine-1-carbonitrile | M62 | MS/ESI⁺ 529.3 [MH]⁺, Rt 0.58 min (Method A) |

-continued

| Intermediate | Name and Molecular Structure | Reagent | Analytical data |
|---|---|---|---|
| W60 | 1-[1-(3-{1-[2-(dimethylamino)ethyl]-1H-pyrazol-3-yl}indolizin-2-yl)ethyl]-3-iodo-1H-pyrazolo[3,4-d]pyrimidin-4-amine | M63 | MS/ESI+ 542.3 [MH]+, Rt 0.62 min (Method A) |
| W61 | 3-iodo-1-[1-(3-{1-[2-(4-methylpiperazin-1-yl)ethyl]-1H-pyrazol-3-yl}indolizin-2-yl)ethyl]-1H-pyrazolo[3,4-d]pyrimidin-4-amine | M64 | MS/ESI+ 597.4 [MH]+, Rt 0.63 min (Method A) |
| W62 | 3-iodo-1-[1-(3-{1-[2-(2,2,3,3,11,11,12,12-octamethyl-4,10-dioxa-7-aza-3,11-disilatridecan-7-yl)ethyl]-1H-pyrazol-3-yl}indolizin-2-yl)ethyl]-1H-pyrazolo[3,4-d]pyrimidin-4-amine | M65 | MS/ESI+ 830.6 [MH]+, Rt 1.21 min (Method A) |
| W63 | 3-iodo-1-[1-(3-{1-[2-(morpholin-4-yl)ethyl]-1H-pyrazol-3-yl}indolizin-2-yl)ethyl]-1H-pyrazolo[3,4-d]pyrimidin-4-amine | M66 | MS/ESI+ 584.5 [MH]+, Rt 0.66 min (Method A) |

Intermediate W35

5-[2-(1-{4-amino-3-iodo-1H-pyrazolo[3,4-d]pyrimidin-1-yl}ethyl)indolizin-3-yl]-1-[2-(morpholin-4-yl)ethyl]-1,2-dihydropyridin-2-one

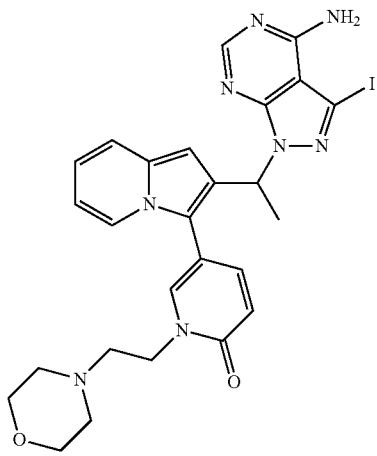 [SMILES: CC(c1cc2ccccn2c1-c1ccc(=O)n(CCN2CCOCC2)c1)n1nc(I)c2c(N)ncnc21]

Step 1: 5-[2-(1-{4-amino-3-iodo-1H-pyrazolo[3,4-d]pyrimidin-1-yl}ethyl)indolizin-3-yl]pyridin-2-ol W35b

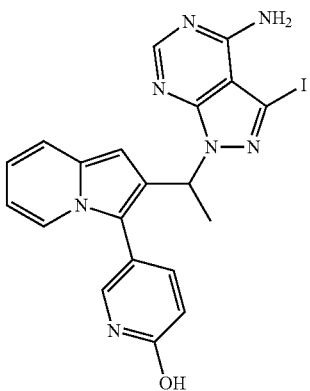 [SMILES: CC(c1cc2ccccn2c1-c1ccc(O)nc1)n1nc(I)c2c(N)ncnc21]

Iodotrimethylsilane (0.583 mL, 4.1 mmol) was added to a solution of 3-iodo-1-{1-[3-(6-methoxypyridin-3-yl)indolizin-2-yl]ethyl}-1H-pyrazolo[3,4-d]pyrimidin-4-amine W35a (0.210 g, 0.41 mmol) in dry acetonitrile (8.3 mL) and the resulting mixture was heated at 50° C. for 3 h. Then, at that temperature, MeOH (8.3 mL) was added and stirring was carried out for further 15 minutes. After cooling to RT, the mixture was diluted with DCM and washed with an aqueous solution of Na$_2$S$_2$O$_5$ and then with brine. The organic phase was concentrated under reduce pressure and the residue was purified by flash chromatography on SNAP C18 cartridge (H$_2$O:MeCN=95:5+0.1% HCOOH to H$_2$O:MeCN=50:50+0.1% HCOOH) to afford title compound as a yellow solid (0.144 g, 0.28 mmol, 68% yield). MS/ESI$^+$ 498.3 [MH]$^+$, Rt 0.79 min (Method A).

Step 2: 5-[2-(1-{4-amino-3-iodo-1H-pyrazolo[3,4-d]pyrimidin-1-yl}ethyl)indolizin-3-yl]-1-[2-(morpholin-4-yl)ethyl]-1,2-dihydropyridin-2-one W35

To a solution of 5-[2-(1-{4-amino-3-iodo-1H-pyrazolo[3,4-d]pyrimidin-1-yl}ethyl)indolizin-3-yl]pyridin-2-ol W35b (0.144 g, 0.28 mmol) in acetone (2.5 mL) K$_2$CO$_3$ (0.178 g, 1.28 mmol) and 4-(2-chloroethyl)morpholine hydrochloride (0.155 g, 0.83 mmol) were added and the resulting mixture was heated to 60° C. overnight. Water was added and the mixture was extracted with DCM/MeOH 4/1; the combined organic layers were concentrated and the crude was purified by flash chromatography on Biotage silica-NH cartridge (DCM to DCM:MeOH=95:5) to afford title compound as a clear semi-solid (0.069 g). MS/ESI$^+$ 611.4 [MH]$^+$, Rt 0.62 min (Method A).

Intermediate W36

4-[2-(1-{4-amino-3-iodo-1H-pyrazolo[3,4-d]pyrimidin-1-yl}ethyl)indolizin-3-yl]-1-[2-(morpholin-4-yl)ethyl]-1,2-dihydropyridin-2-one

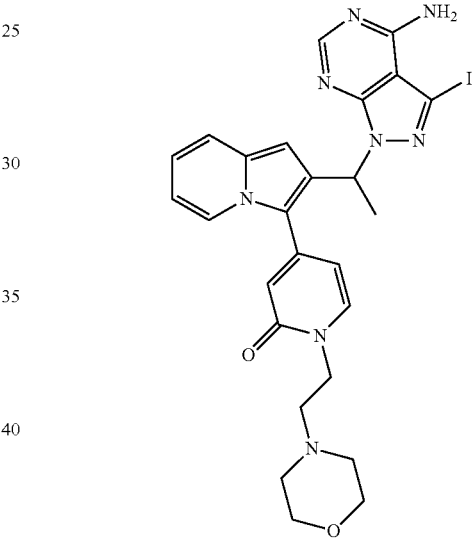

Step 1: 4-[2-(1-{4-amino-3-iodo-1H-pyrazolo[3,4-d]pyrimidin-1-yl}ethyl)indolizin-3-yl]pyridin-2-ol W36b

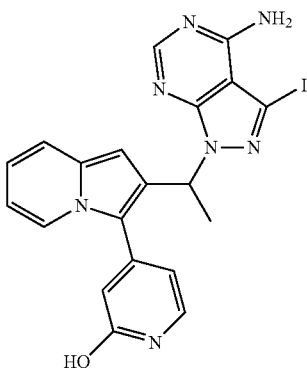 [SMILES: CC(c1cc2ccccn2c1-c1ccnc(O)c1)n1nc(I)c2c(N)ncnc21]

Prepared similarly to intermediate W35b starting from 3-iodo-1-{1-[3-(2-methoxypyridin-4-yl)indolizin-2-yl]ethyl}-1H-pyrazolo[3,4-d]pyrimidin-4-amine W36a (1.27 g) and at 60° C. for 3 h, to afford crude title compound as a brown solid (1.09 g, 2.19 mmol) which was used without any additional purification. MS/ESI+ 498.3 [MH]+, Rt 0.77 min (Method A).

Step 2: 4-[2-(1-{4-amino-3-iodo-1H-pyrazolo[3,4-d]pyrimidin-1-yl}ethyl)indolizin-3-yl]-1-[2-(morpholin-4-yl)ethyl]-1,2-dihydropyridin-2-one W36

Prepared similarly to intermediate W35 Step 2 starting from 4-[2-(1-{4-amino-3-iodo-1H-pyrazolo[3,4-d]pyrimidin-1-yl}ethyl)indolizin-3-yl]pyridin-2-ol W36b (1.09 g, 2.19 mmol) and 4-(2-chloroethyl)morpholine hydrochloride (1.21 g, 6.52 mmol) and purified by flash chromatography on SNAP C18 cartridge (from H$_2$O:MeCN=95:5 with 0.1% HCOOH to H$_2$O:MeCN=50:50 with 0.1% HCOOH). Acetonitrile was evaporated, the aqueous residue was neutralized with sodium bicarbonate and extracted with a mixture of DCM and MeOH 4:1. The organic layer was evaporated to afford title compound as a clear semi-solid (0.380 g, 0.62 mmol, 28% yield). MS/ESI+ 611.3 [MH]+, Rt 0.61 min (Method A).

Intermediate W48

6-[2-(1-{4-amino-3-iodo-1H-pyrazolo[3,4-d]pyrimidin-1-yl}ethyl)indolizin-3-yl]-2-[2-(4-methylpiperazin-1-yl)ethyl]-2,3-dihydropyridazin-3-one

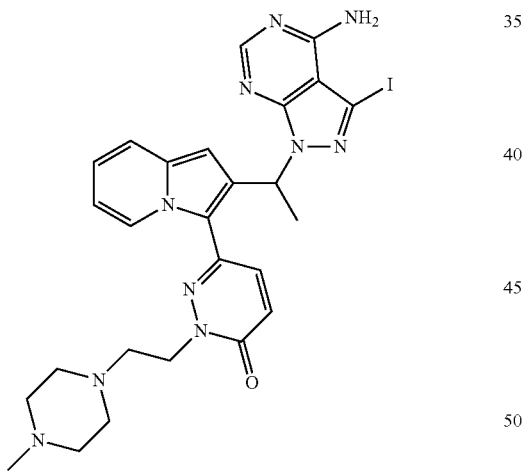

To a mixture of 6-[2-(1-hydroxyethyl)indolizin-3-yl]-2-[2-(4-methylpiperazin-1-yl)ethyl]-2,3-dihydropyridazin-3-one M51 (24 mg), 3-iodo-1H-pyrazolo[3,4-d]pyrimidin-4-amine (16.4 mg, 0.094 mmol) and PPh$_3$ (28.1 mg, 0.10 mmol) in dry THF (1 mL), DIAD (0.01 mL, 0.05 mmol) was added drop-wise at RT and the reaction was stirred for 30 min. Additional DIAD (0.01 mL, 0.05 mmol) was added drop-wise at RT and the reaction was stirred at rt for 30 min. After that time, PPh3 (10 mg, 0.038 mmol) was added followed by DIAD (0.01 mL, 0.05 mmol) and the mixture was stirred at RT for further 30 min. The solvent was removed and the crude was purified by flash chromatography on Biotage silica-NH cartridge (DCM to DCM:MeOH=98:2) to afford title compound (24.5 mg) which was used in the next step without any further purification. MS/ESI+ 625.4 [MH]+, Rt 0.60 min (Method A).

Intermediate X tert-butyl 4-(2-{1-[4-amino-3-(3-fluoro-5-hydroxyphenyl)-1H-pyrazolo[3,4-d]pyrimidin-1-yl]ethyl}indolizin-3-yl)-1,2,3,6-tetrahydropyridine-1-carboxylate

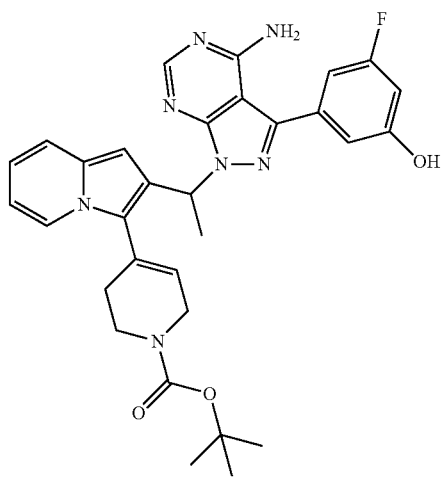 [SMILES: CC(c1cc2ccccn2c1C1=CCN(C(=O)OC(C)(C)C)CC1)n1nc(-c2cc(O)cc(F)c2)c2c(N)ncnc21]

A mixture of crude tert-butyl 4-[2-(1-{4-amino-3-iodo-1H-pyrazolo[3,4-d]pyrimidin-1-yl}ethyl)indolizin-3-yl]-1,2,3,6-tetrahydropyridine-1-carboxylate W14 (0.19 mmol), (3-fluoro-5-hydroxyphenyl)boronic acid (0.032 g, 0.209 mmol) and Pd(PPh$_3$)$_4$ (0.010 g, 0.0095 mmol) DME (7.7 mL), ethanol (1.37 mL) and saturated aqueous sodium carbonate (2.60 mL) was heated at 80° C. for 4 h. The mixture was partitioned between water and DCM, the aqueous phase was extracted with DCM and the combined organic layers were washed with brine and dried over sodium sulfate. The solvent was removed under reduced pressure and the residue was purified by flash chromatography on 5 g silica-NH cartridge (DCM to DCM:MeOH=94:6) to afford title compound as light-yellow oil (0.021 g, 0.037 mmol). MS/ESI+ 570.5 [MH]+, Rt 1.17 min (Method A).

Intermediate Y tert-butyl N-[5-(4-amino-1-{1-[3-(pyridin-2-yl)indolizin-2-yl]ethyl}-1H-pyrazolo[3,4-d]pyrimidin-3-yl)-1,3-thiazol-2-yl]carbamate

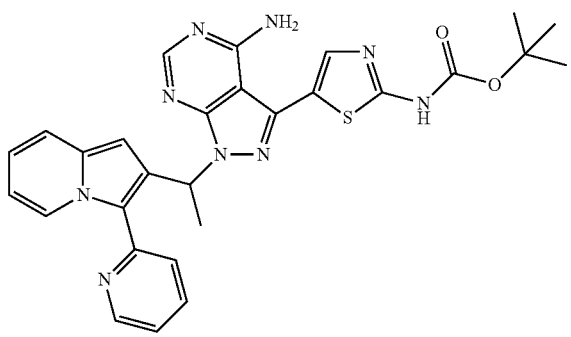 [SMILES: CC(c1cc2ccccn2c1-c1ccccn1)n1nc(-c2cnc(NC(=O)OC(C)(C)C)s2)c2c(N)ncnc21]

A mixture of 3-iodo-1-{1-[3-(pyridin-2-yl)indolizin-2-yl]ethyl}-1H-pyrazolo[3,4-d]pyrimidin-4-amine W2 (0.070 g, 0.145 mmol), tert-butyl 4-(tributylstannyl)thiazol-2-ylcarbamate (0.142 g, 0.291 mmol), Pd(PPh$_3$)$_4$ (0.017 g, 0.0145 mmol) and lithium chloride (6.15 mg, 0.145 mmol) in dioxane (1.5 mL) was purged with N$_2$ and heated at 100° C. for 3 h. The solvent was removed under reduced pressure and the crude was purified by flash chromatography on silica-NH Biotage SNAP cartridge (DCM to DCM:MeOH=95:5) affording title compound as a yellow solid (0.060 g, 0.108 mmol, 75% yield). MS/ESI$^+$ 554.4 [MH]$^+$, Rt=0.97 min (Method A).

Preparation of Compounds

Example 1

9-[(3-phenylindolizin-2-yl)methyl]-9H-purin-6-amine

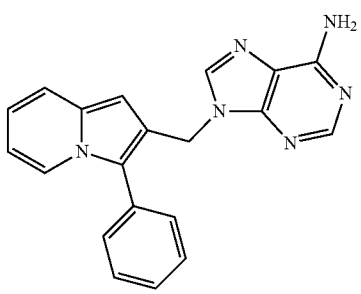 [SMILES: Nc1ncnc2c1ncn2Cc1cc2ccccn2c1-c1ccccc1]

To a mixture of (3-phenylindolizin-2-yl)methanol K1 (0.100 g, 0.449 mmol), adenine (0.073 g, 0.537 mmol) and PPh$_3$ (0.153 g, 0.584 mmol) in dry THF (8 mL), a solution of DIAD (0.106 mL, 0.537 mmol) in THF (1 mL) was added drop-wise at room temperature and the reaction was stirred for 1 h. Additional PPh$_3$ (0.059 g, 0.225 mmol) and DIAD (0.026 mL, 0.135 mmol) were added and the stirring was continued for 40 min. The solvent was removed under reduced pressure, the residue was dissolved in DCM and filtered. The filtrate was evaporated to dryness and purified by flash chromatography on Biotage silica-NH 28 g SNAP cartridge (DCM to DCM:MeOH=98:2). Two fractions containing different isomers were collected. The first eluted fraction was evaporated to afford a residue which was triturated with Et$_2$O. The obtained solid (0.040 g) was further purified by flash chromatography on silica-NH Biotage SNAP cartridge (cyclohexane to cyclohexane:EtOAc=10:90) to yield title compound as a beige solid (0.032 g). MS/ESI$^+$ 341.2 [MH]$^+$, Rt=0.76 min (LC/MS Method A).

$^1$H NMR (400 MHz, DMSO-d$_6$) δ ppm 8.11 (s, 1 H), 8.01 (d, 1 H), 7.99 (s, 1 H), 7.53-7.63 (m, 4 H), 7.44-7.51 (m, 1 H), 7.40 (d, 1 H), 7.17 (br. s, 2 H), 6.69-6.76 (m, 1 H), 6.51-6.59 (m, 1H), 6.30 (s, 1 H), 5.39 (s, 2 H).

Example 2

3-[(3-phenylindolizin-2-yl)methyl]-3H-purin-6-amine

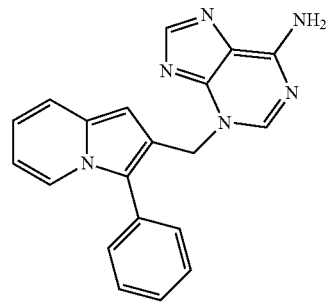 [SMILES: Nc1ncn(Cc2cc3ccccn3c2-c2ccccc2)c2ncnc1-2]

The second eluted fraction obtained from the reaction described in Example 1 was concentrated and further purified by reverse phase semi-preparative MDAP under acidic conditions (Method E), followed by evaporation, and extraction with DCM washing with aqueous sat. NaHCO$_3$, to afford title compound as an off-white solid. MS/ESI$^+$ 341.1 [MH]$^+$, Rt=0.63 min (LC/MS Method A).

$^1$H NMR (400 MHz, DMSO-d$_6$) δ ppm 8.16 (s, 1 H), 7.99 (d, 1 H), 7.76-7.95 (m, 2 H), 7.72 (s, 1 H), 7.63-7.70 (m, 2 H), 7.55-7.63 (m, 2 H), 7.45-7.52 (m, 1 H), 7.39 (d, 1 H), 6.69-6.76 (m, 1 H), 6.51-6.58 (m, 1 H), 6.31 (s, 1 H), 5.57 (s, 2 H)

Example 3

9-{[3-(pyridin-2-yl)indolizin-2-yl]methyl}-9H-purin-6-amine

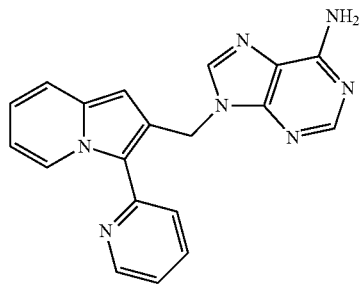 [SMILES: Nc1ncnc2c1ncn2Cc1cc2ccccn2c1-c1ccccn1]

To a mixture of ethyl [3-(pyridin-2-yl)indolizin-2-yl]methanol K2 (0.150, 0.669 mmol), adenine (0.117 g, 0.869 mmol) and PPh₃ (0.263 g, 1.00 mmol) in dry THF (12 mL), a solution of DIAD (0.171 mL, 0.869 mmol) in THF (1 mL) was added drop-wise at r.t. and the reaction was stirred for 2 h. The reaction mixture was filtered and the filtrate was evaporated under reduced pressure. The residue was purified by flash chromatography on silica-NH Biotage SNAP cartridge (cyclohexane:EtOAc=80:20 to 100% EtOAc) to afford title compound as a white solid (0.065 g). MS/ESI⁺ 342.1 [MH]⁺, Rt=0.51 min (Method A).

¹H NMR (500 MHz, DMSO-d₆) δ ppm 8.90 (d, 1 H), 8.77 (d, 1 H), 8.16 (s, 1 H), 8.11 (s, 1 H), 7.96 (td, 1 H), 7.78 (d, J=7.8 Hz, 1 H), 7.44 (d, 1 H), 7.37 (dd, 1 H), 7.21 (s, 2 H), 6.83 (dd, 1 H), 6.65 (t, 1 H), 6.16 (s, 1 H), 5.61 (s, 2 H).

Example 4

9-{[3-(3-fluorophenyl)indolizin-2-yl]methyl}-9H-purin-6-amine

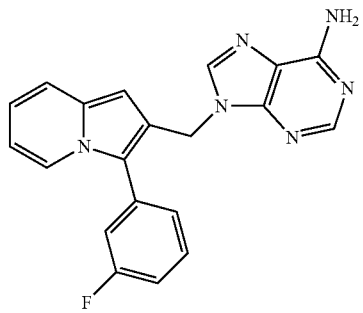 [SMILES: Nc1ncnc2c1ncn2Cc1cc2ccccn2c1-c1cccc(F)c1]

Prepared similarly to Example 3, starting from [3-(3-fluorophenyl)indolizin-2-yl]methanol K3 (0.165 g, 0.684 mmol) and purified by flash chromatography on silica-NH Biotage SNAP cartridge (cyclohexane:EtOAc=90:10 to 100% EtOAc); the first eluted isomer was obtained as an off-white solid (0.047 g). MS/ESI⁺ 359.1 [MH]⁺, Rt=0.79 min (Method A).

¹H NMR (400 MHz, DMSO-d₆) δ ppm 8.12 (s, 1 H), 8.07 (d, 1 H), 8.05 (s, 1 H), 7.58-7.66 (m, 1 H), 7.48-7.54 (m, 1 H), 7.40-7.47 (m, 2 H), 7.27-7.35 (m, 1 H), 7.20 (s, 2 H), 6.74-6.81 (m, 1 H), 6.55-6.63 (m, 1 H), 6.33 (s, 1 H), 5.43 (s, 2 H).

Example 5

3-{[3-(3-fluorophenyl)indolizin-2-yl]methyl}-3H-purin-6-amine

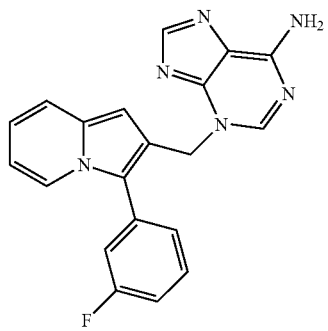 [SMILES: Nc1ncn(Cc2cc3ccccn3c2-c2cccc(F)c2)c2ncnc1-2]

Obtained as the minor isomer form the reaction described in Example 4 and purified by reverse phase semi-preparative MDAP under basic conditions (Method F) to afford an off-white solid. MS/ESI⁺ 359.2 [MH]⁺, Rt=0.89 min (Method C).

¹H NMR (500 MHz, DMSO-d₆) δ ppm 8.23 (s, 1 H), 8.04 (d, 1 H), 7.78-7.96 (m, 2 H), 7.71 (s, 1 H), 7.58-7.68 (m, 2 H), 7.50 (d, 1 H), 7.39 (d, 1 H), 7.30 (td, 1 H), 6.71-6.77 (m, 1 H), 6.57 (t, 1 H), 6.31 (s, 1 H), 5.58 (s, 2 H).

Example 6

9-{[3-(2-fluorophenyl)indolizin-2-yl]methyl}-9H-purin-6-amine

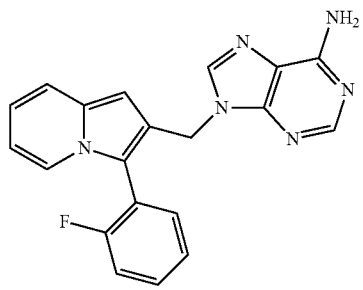

Prepared similarly to compound Example 3, starting from [3-(2-fluorophenyl)indolizin-2-yl]methanol K4 (0.150 g, 0.622 mmol) and purified by flash chromatography on silica-NH (cyclohexane:EtOAc=90:10 to 100% EtOAc) followed by trituration with Et₂O to yield title compound as an off white solid (0.050 g) MS/ESI⁺ 359.2 [MH]⁺, Rt=0.80 min (Method B).

¹H NMR (400 MHz, DMSO-d₆) δ ppm 8.10 (s, 1 H), 8.00 (s, 1 H), 7.64-7.75 (m, 2 H), 7.55-7.63 (m, 1 H), 7.36-7.50 (m, 3 H), 7.18 (s, 2 H), 6.77-6.82 (m, 1 H), 6.58-6.64 (m, 1 H), 6.39 (s, 1 H), 5.36 (s, 2 H).

Example 7

9-{[3-(2-methylphenyl)indolizin-2-yl]methyl}-9H-purin-6-amine

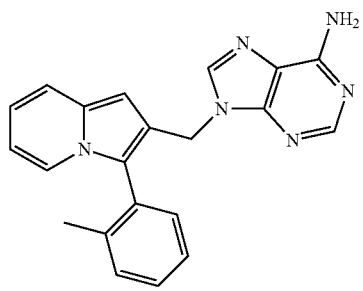 [SMILES: Cc1ccccc1-c1c(Cn2cnc3c(N)ncnc32)cc2ccccn12]

Prepared similarly to Example 3, starting from [3-(2-methylphenyl)indolizin-2-yl]methanol K5 (0.150 g, 0.632 mmol). The crude mixture was purified by reverse phase semi-preparative MDAP under acidic conditions (Method E). The collected fractions containing the main product (slower compound under reverse phase UPLC conditions) were concentrated under reduced pressure, basified with aqueous sat. NaHCO₃ and extracted with DCM. The organic phase was dried over sodium sulfate and the solvent was evaporated. The residue was further purified by flash chromatography on silica-NH Biotage 11 g SNAP cartridge (cyclohexane:EtOAc=90:10 to 10:90) to afford title compound as a white solid (0.044 g). MS/ESI⁺ 355.2 [MH]⁺, Rt=0.82 min (Method A).

1H NMR (500 MHz, DMSO-d₆) δ ppm 8.07 (s, 1 H), 7.85 (s, 1 H), 7.40-7.45 (m, 3 H), 7.32-7.37 (m, 3 H), 7.14 (s, 2 H), 6.69-6.75 (m, 1 H), 6.50-6.55 (m, 1 H), 6.41 (s, 1 H), 5.18-5.29 (m, 2 H), 1.88 (s, 3 H)

Example 8

3-{[3-(2-methylphenyl)indolizin-2-yl]methyl}-3H-purin-6-amine

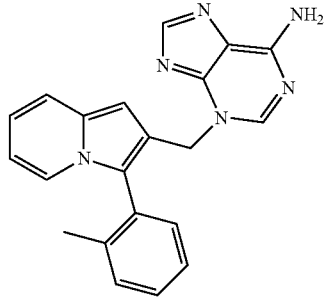 [SMILES: Cc1ccccc1-c1c(Cn2cnc(N)c3ncnc2-3)cc2ccccn12]

Obtained as the minor isomer (faster compound under reverse phase UPLC conditions) from the purification described in Example 7. The collected fractions were concentrated under reduced pressure, basified with sat. NaHCO₃ and extracted with DCM. The organic phase was dried over sodium sulfate and evaporated. The residue was further purified by flash chromatography on silica-NH Biotage cartridge (DCM to DCM:MeOH=95:5) to yield title compound as a white solid (0.021 g). MS/ESI⁺ 355.2 [MH]⁺, Rt=0.65 min (Method A).

¹H NMR (400 MHz, DMSO-d₆) δ ppm 7.99 (s, 1 H), 7.83 (br. s., 2 H), 7.71 (s, 1 H), 7.32-7.50 (m, 6 H), 6.70-6.77 (m, 1 H), 6.51-6.57 (m, 1 H), 6.47 (s, 1 H), 5.44 (s, 2 H), 1.89 (s, 3 H).

Example 9

9-(indolizin-2-ylmethyl)-9H-purin-6-amine

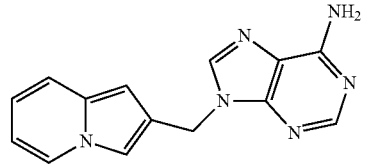 [SMILES: Nc1ncnc2c1ncn2Cc1cc2ccccn2c1]

Prepared similarly to Example 3, starting from indolizin-2-ylmethanol K23 (0.150 g, 1.02 mmol) and purified by flash chromatography on silica-NH 28 g Biotage SNAP cartridge (DCM to DCM:MeOH=95:5) followed by flash chromatography on silica-NH Biotage SNAP cartridge (cyclohexane:EtOAc=80:20 to 100% EtOAc). A further purification by reverse phase semi-preparative MDAP under basic conditions (Method G) was required to obtain title compound as a white solid (0.011 g). MS/ESI⁺ 265.1 [MH]⁺, Rt=0.68 min (Method C).

¹H NMR (500 MHz, DMSO-d₆) δ ppm 8.16 (s, 1 H), 8.14 (dd, 1 H), 8.11 (s, 1 H), 7.44 (s, 1 H), 7.27 (d, 1 H), 7.14 (br. s, 2 H), 6.59-6.62 (m, 1 H), 6.44 (t, 1 H), 6.28 (s, 1 H), 5.36 (s, 2 H).

Example 10

9-[(1-phenylindolizin-2-yl)methyl]-9H-purin-6-amine

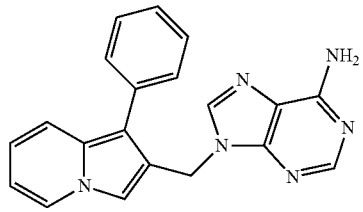 [SMILES: Nc1ncnc2c1ncn2Cc1cn2ccccc2c1-c1ccccc1]

To a mixture of (1-phenylindolizin-2-yl)methanol K24 (0.050 g, 0.22 mmol), adenine (0.0356 g, 0.29 mmol) and PPh₃ (0.075 g, 0.286 mmol) in dry THF (4.5 mL), a solution of DIAD (0.052 mL, 0.26 mmol) in THF (1 mL) was added drop-wise at RT and the reaction was stirred at 50° C. for 48 h. The solvent was removed and the residue was purified by flash chromatography on Biotage silica-NH SNAP cartridge (cyclohexane to cyclohexane:EtOAc=96:4). A further purification by reverse phase semi-preparative MDAP under acidic conditions (Method A), followed by extraction with DCM washing with aqueous sat. NaHCO₃, was required to afford title compound as pale yellow solid (0.003 g). MS/ESI⁺ 341.1 [MH]⁺, Rt=0.75 min (Method A).

¹H NMR (400 MHz, DMSO-d₆) δ ppm 8.22 (d, J=7.0 Hz, 1 H), 8.12 (s, 1 H), 7.95 (s, 1 H) 7.39-7.51 (m, 5 H), 7.27-7.36 (m, 2 H), 7.21 (s, 2 H), 6.72-6.78 (m, 1 H), 6.54-6.59 (m, 1 H), 5.52 (s, 2 H).

Example 11

9-{[1-(3-fluorophenyl)indolizin-2-yl]methyl}-9H-purin-6-amine

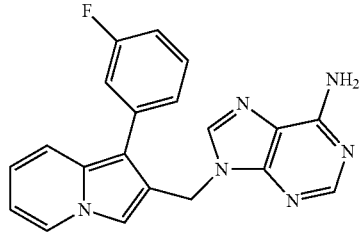 [SMILES: Nc1ncnc2c1ncn2Cc1cn2ccccc2c1-c1cccc(F)c1]

Prepared similarly to Example 10, starting from [1-(3-fluorophenyl)indolizin-2-yl]methanol K25 (0.165 g, 0.68 mmol), and purified by flash chromatography on silica-NH 25 g Biotage cartridge (DCM to DCM:MeOH=98:2). A further purification by flash chromatography on silica NH Biotage SNAP cartridge (cyclohexane:EtOAc=30:70 to 100% EtOAc) was required to afford title compound (0.015 g). MS/ESI+ 359.1 [MH]+, Rt=0.79 min (Method A).

¹H NMR (500 MHz, DMSO-d₆) δ ppm 8.23 (d, 1 H), 8.11 (s, 1 H), 7.98 (s, 1 H), 7.45-7.50 (m, 1 H), 7.44 (d, 1 H), 7.34 (s, 1 H), 7.30 (d, 1 H), 7.25-7.28 (m, 1 H), 7.19 (br. s, 2 H), 7.11 (td, 1 H), 6.75-6.81 (m, 1 H), 6.56-6.61 (m, 1 H), 5.52 (s, 2 H).

Example 12

9-{[1-(2-methylphenyl)indolizin-2-yl]methyl}-9H-purin-6-amine

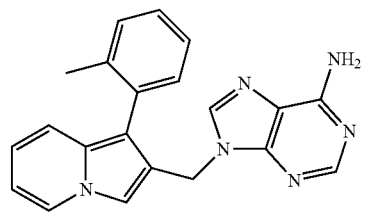 [SMILES: Cc1ccccc1-c1c(Cn2cnc3c(N)ncnc32)cn2ccccc12]

Prepared similarly to Example 10, starting from [1-(2-methylphenyl)indolizin-2-yl]methanol K26 (0.085 g, 0.36 mmol), and purified by flash chromatography on Biotage silica-NH 10 g SNAP cartridge (DCM to DCM:MeOH=97:3). A further purification by flash chromatography on Biotage silica-NH SNAP cartridge (cyclohexane:EtOAc=30:70 to 100% EtOAc) was required to afford title compound (0.007 g). MS/ESI+ 355.2 [MH]+, Rt=0.77 min (Method A).

¹H NMR (400 MHz, DMSO-d₆) δ ppm 8.24 (d, 1 H), 8.08 (s, 1 H), 7.66 (s, 1 H), 7.49 (s, 1 H), 7.15-7.35 (m, 6 H), 6.88 (d, 1 H), 6.64-6.70 (m, 1 H), 6.52-6.57 (m, 1 H), 5.19-5.34 (m, 2 H), 1.99 (s, 3 H).

Example 13

N-[(3-phenylindolizin-2-yl)methyl]-9H-purin-6-amine

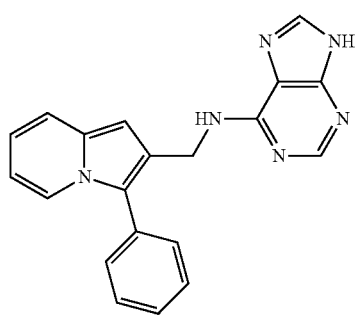 [SMILES: c1ccc(-c2c(CNc3ncnc4[nH]cnc34)cc3ccccn23)cc1]

To a solution of (3-phenylindolizin-2-yl)methanamine P1 (0.070 g, 0.315 mmol) in t-BuOH (4 mL), 6-bromopurine (0.063 g, 0.315 mmol) was added followed by DIPEA (0.110 mL, 0.630 mmol) and the resulting mixture was heated to reflux for 1 h. The solvent was removed under reduced pressure and the crude was partitioned between DCM/MeOH 3/1 and water; the organic phase was dried over sodium sulfate, the solvent was removed under vacuum and the crude was purified by flash chromatography on Biotage silica-NH SNAP cartridge (DCM to DCM:MeOH=95:5) to afford title compound as a pale yellow solid (0.067 g). MS/ESI+ 341.1 [MH]+, Rt=0.76 min (Method A).

¹H NMR (500 MHz, DMSO-d₆) δ ppm 12.06-13.46 (m, 1 H), 8.15-8.18 (m, 1 H), 8.08-8.10 (m, 1 H), 8.04 (d, 1 H), 7.77-7.98 (m, 1 H), 7.59-7.64 (m, 2 H), 7.53-7.59 (m, 2 H), 7.37-7.46 (m, 2 H), 6.67-6.71 (m, 1 H), 6.48-6.54 (m, 2 H), 4.63-4.88 (m, 2 H).

Example 14

N-{[3-(pyridin-2-yl)indolizin-2-yl]methyl}-9H-purin-6-amine

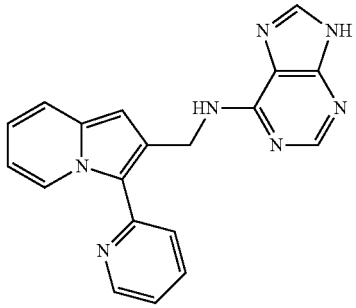 [SMILES: c1ccc(-c2c(CNc3ncnc4[nH]cnc34)cc3ccccn23)nc1]

Prepared similarly to Example 13, starting from [3-(pyridin-2-yl)indolizin-2-yl]methanamine P2 (0.103 g, 0.461 mmol), heating to reflux for 5 h, and purified by flash chromatography on Biotage silica-NH SNAP cartridge (DCM to DCM:MeOH=90:10) to afford title compound as a pale yellow solid (0.110 g). MS/ESI+ 342.2 [MH]+, Rt=0.56 min (Method B).

¹H NMR (400 MHz, DMSO-d₆) δ ppm 12.81 (br. s., 1 H), 9.04 (d, 1 H), 8.73-8.78 (m, 1 H), 8.18 (s, 1 H), 8.12 (s, 1 H), 8.06 (br. s., 1 H), 7.95 (td, 1 H), 7.78 (d, 1 H), 7.46 (d, 1 H), 7.30-7.38 (m, 1 H), 6.79-6.86 (m, 1 H), 6.60-6.67 (m, 1 H), 6.54 (s, 1 H), 4.97 (br. s., 2 H).

Example 15

N-{[3-(3-fluorophenyl)indolizin-2-yl]methyl}-9H-purin-6-amine

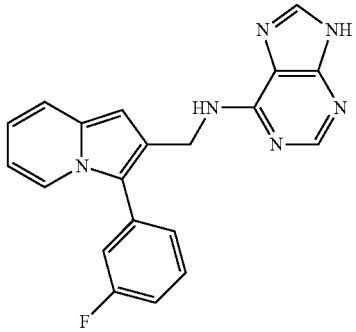 [SMILES: Fc1cccc(-c2c(CNc3ncnc4[nH]cnc34)cc3ccccn23)c1]

Prepared similarly to Example 13, starting from [3-(3-fluorophenyl)indolizin-2-yl]methanamine P3 (0.100 g, 0.416 mmol), heating to reflux for 4 h, and purified by flash chromatography on Biotage silica-NH SNAP cartridge (DCM to DCM:MeOH=95:5) to afford title compound as a pale yellow solid (0.087 g). MS/ESI⁺ 359.2 [MH]⁺, Rt=0.85 min (Method B).

$^1$H NMR (400 MHz, DMSO-$d_6$) δ ppm 12.80 (br. s., 1 H), 8.18 (s, 1 H), 8.06-8.15 (m, 2 H), 7.96 (br. s., 1 H), 7.50-7.66 (m, 2 H), 7.38-7.50 (m, 2 H), 7.23-7.32 (m, 1 H), 6.69-6.77 (m, 1 H), 6.50-6.60 (m, 2 H), 4.79 (br. s., 2 H).

Example 16

N-{[3-(2-fluorophenyl)indolizin-2-yl]methyl}-9H-purin-6-amine

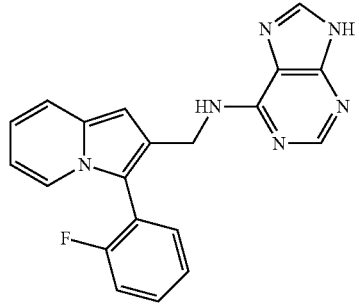 [SMILES: Fc1ccccc1-c1c(CNc2ncnc3[nH]cnc23)cc2ccccn12]

Prepared similarly to Example 13, starting from [3-(2-fluorophenyl)indolizin-2-yl]methanamine P4 (0.115 g, 0.476 mmol), heating to reflux for 2 h, and purified by flash chromatography on Biotage silica-NH SNAP cartridge (DCM to DCM:MeOH=95:5) to afford title compound as an off-white solid (0.115 g) MS/ESI⁺ 359.1 [MH]⁺, Rt=0.77 min (Method A).

$^1$H NMR (400 MHz, DMSO-$d_6$) δ ppm 12.79 (br. s., 1 H), 8.16 (s, 1 H), 8.10 (s, 1 H), 7.89 (br. s., 1 H), 7.65-7.77 (m, 2 H), 7.51-7.61 (m, 1 H), 7.35-7.50 (m, 3 H), 6.72-7.79 (m, 1 H), 6.52-6.61 (m, 2 H), 4.73 (br. s., 2 H).

Example 17

N-[(1-phenylindolizin-2-yl)methyl]-9H-purin-6-amine

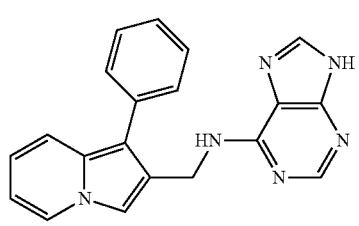 [SMILES: c1ccc(-c2c(CNc3ncnc4[nH]cnc34)cn3ccccc23)cc1]

Prepared similarly to Example 13, starting from (1-phenylindolizin-2-yl)methanamine P6 (0.050 g, 0.224 mmol), heating to reflux for 6 h, and purified by flash chromatography on Biotage silica-NH SNAP cartridge (DCM to DCM:MeOH=94:6) to afford title compound as a pale yellow solid (0.030 g). MS/ESI⁺ 341.1 [MH]⁺, Rt=0.77 min (Method A).

$^1$H NMR (400 MHz, DMSO-$d_6$) δ ppm 12.85 (br. s., 1 H), 8.24 (d, 1 H), 8.19 (s, 1 H), 8.12 (s, 1 H), 7.97 (br. s., 1 H), 7.50-7.55 (m, 3 H), 7.41-7.49 (m, 3 H), 7.25-7.33 (m, 1 H), 6.68-6.75 (m, 1 H), 6.50-6.55 (m, 1 H), 4.86 (br. s., 2 H).

Example 18

N-{[1-(3-fluorophenyl)indolizin-2-yl]methyl}-9H-purin-6-amine

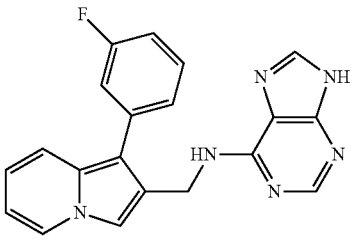 [SMILES: Fc1cccc(-c2c(CNc3ncnc4[nH]cnc34)cn3ccccc23)c1]

Prepared similarly to Example 13, starting from [1-(3-fluorophenyl)indolizin-2-yl]methanamine P7 (0.074 g, 0.31 mmol), heating to reflux for 3 h, and purified by flash chromatography on Biotage silica-NH SNAP cartridge (DCM to DCM:MeOH=97:3) to afford title compound as an off-white solid (0.044 g). MS/ESI⁺ 359.1 [MH]⁺, Rt=0.82 min (Method A).

$^1$H NMR (400 MHz, DMSO-$d_6$) δ ppm 12.92 (br. s., 1 H), 7.93-8.37 (m, 4 H), 7.41-7.57 (m, 3 H), 7.26-7.40 (m, 2 H), 7.05-7.14 (m, 1 H), 6.70-6.81 (m, 1 H), 6.50-6.61 (m, 1 H), 4.74-4.97 (m, 2 H).

Example 19

N-{[1-(2-methylphenyl)indolizin-2-yl]methyl}-9H-purin-6-amine

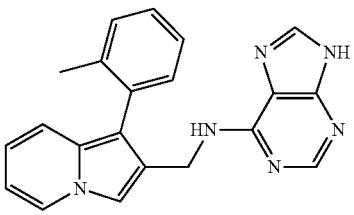 [SMILES: Cc1ccccc1-c1c(CNc2ncnc3[nH]cnc23)cn2ccccc12]

Prepared similarly Example 13, starting from [1-(2-methylphenyl)indolizin-2-yl]methanamine P8 (0.047 g, 0.20 mmol), heating to reflux for 5 h, and purified by flash chromatography on Biotage silica-NH SNAP cartridge (DCM to DCM:MeOH=95:5) to afford title compound as an off-white solid as a mixture of isomers (0.040 g). MS/ESI⁺ 355.2 [MH]⁺, Rt=0.96 min (Method C).

$^1$H NMR (400 MHz, DMSO-$d_6$) δ ppm 11.91-12.94 (m, 1 H), 8.02-8.30 (m, 3 H), 7.74-7.89 (m, 1 H), 7.46-7.71 (m, 1 H), 7.15-7.40 (m, 4 H), 6.83-6.94 (m, 1 H), 6.58-6.70 (m, 1 H), 6.44-6.57 (m, 1 H), 4.45-4.72 (m, 2 H), 2.08-2.14 (m, 3 H).

Example 20

N-{[1-(pyridin-2-yl)indolizin-2-yl]methyl}-9H-purin-6-amine

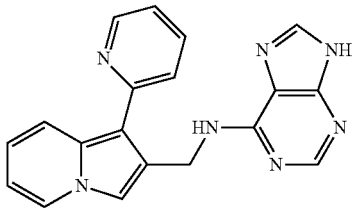 [SMILES: c1ccc(-c2c(CNc3ncnc4[nH]cnc34)cn3ccccc23)nc1]

Prepared similarly to Example 13, starting from [1-(pyridin-2-yl)indolizin-2-yl]methanamine P9 (0.044 g, 0.20 mmol), heating to reflux for 6 h, and purified by flash chromatography on Biotage silica-NH SNAP cartridge (DCM to DCM:MeOH=95:5) to afford title compound as a pale brown solid (0.025 g). MS/ESI$^+$ 342.1 [MH]$^+$, Rt=0.43 min (Method A).

$^1$H NMR (400 MHz, DMSO-d$_6$) δ ppm 12.97 (br. s., 1 H), 8.70 (d, 1 H), 8.03-8.41 (m, 4 H), 7.93 (d, 1 H), 7.86 (t, 1 H), 7.69 (d, 1 H), 7.56 (br. s., 1 H), 7.20-7.26 (m, 1 H), 6.84-6.93 (m, 1 H), 6.59-6.67 (m, 1 H), 5.00 (br. s., 2 H).

Example 21

N-(indolizin-2-ylmethyl)-9H-purin-6-amine

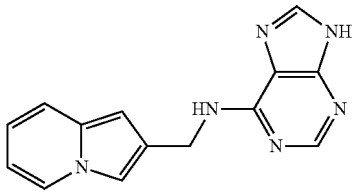 [SMILES: c1ccn2cc(CNc3ncnc4[nH]cnc34)cc2c1]

Prepared similarly to Example 13, starting from indolizin-2-ylmethanamine P10 (0.065 g, 0.44 mmol), heating to reflux for 2 h, and purified by flash chromatography on Biotage silica-NH SNAP cartridge (DCM to DCM:MeOH=98:2) to afford title compound as an off-white solid (0.057 g). MS/ESI$^+$ 264.9 [MH]$^+$, Rt=0.66 min (Method C).

$^1$H NMR (400 MHz, DMSO-d$_6$) δ ppm 12.79 (br. s., 1 H), 8.14-8.28 (m, 2 H), 8.11 (s, 1H), 7.94 (br. s., 1 H), 7.46 (s, 1 H), 7.31 (d, 1 H), 6.58-6.66 (m, 1 H), 6.41-6.49 (m, 1 H), 6.35 (s, 1 H), 4.77 (br. s., 2 H).

Example 22

4-amino-6-{[(3-phenylindolizin-2-yl)methyl]amino}pyrimidine-5-carbonitrile

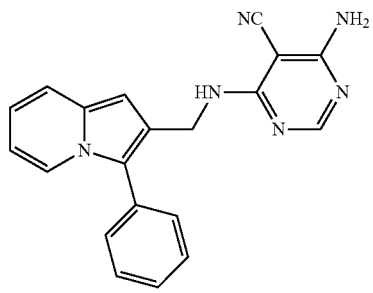 [SMILES: N#Cc1c(N)ncnc1NCc1cc2ccccn2c1-c1ccccc1]

To a solution of (3-phenylindolizin-2-yl)methanamine P1 (0.076 g, 0.342 mmol) in t-BuOH (4 mL), 4-amino-6-chloropyrimidine-5-carbonitrile (0.053 g, 0.342 mmol) was added followed by DIPEA (0.119 mL, 0.742 mmol) and the resulting mixture was heated to reflux for 1 h. The solvent was removed and the crude was partitioned between DCM and water; the organic phase was dried over sodium sulfate, the solvent was removed under reduced pressure and the crude was purified by flash chromatography on 28 g Biotage silica-NH SNAP cartridge (cyclohexane:EtOAc=90:10 to 60:40) to afford title compound as a pale yellow solid (0.065 g). MS/ESI$^+$ 341.1 [MH]$^+$, Rt=0.99 min (Method A).

$^1$H NMR (400 MHz, DMSO-d$_6$) δ ppm 8.01-8.05 (m, 1 H), 8.00 (s, 1 H), 7.76 (t, 1 H), 7.53-7.61 (m, 4 H), 7.40-7.48 (m, 2 H), 7.21 (br. s., 2 H), 6.67-6.75 (m, 1 H), 6.49-6.55 (m, 1 H), 6.47 (s, 1 H), 4.63 (d, 2 H).

Example 23

4-amino-6-({[3-(pyridin-2-yl)indolizin-2-yl]methyl}amino)pyrimidine-5-carbonitrile

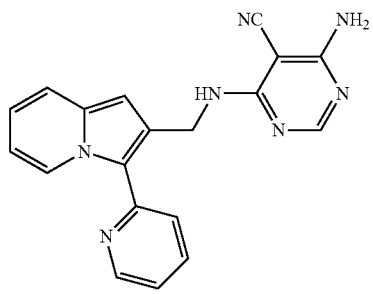 [SMILES: N#Cc1c(N)ncnc1NCc1cc2ccccn2c1-c1ccccn1]

Prepared similarly to Example 22, starting from [3-(pyridin-2-yl)indolizin-2-yl]methanamine P2 (0.097 g, 0.434 mmol), heating to reflux for 2 h, and purified by flash chromatography on 28 g Biotage silica-NH SNAP cartridge (DCM to DCM:MeOH=95:5) to afford title compound as a pale yellow solid (0.120 g). MS/ESI$^+$ 342.2 [MH]$^+$, Rt=0.58 min (Method A).

$^1$H NMR (400 MHz, DMSO-d$_6$) δ ppm 8.96 (d, 1 H), 8.71-8.78 (m, 1 H), 7.98-8.06 (m, 2 H), 7.95 (td, 1 H), 7.72 (d, 1 H), 7.50 (d, 1 H), 7.32-7.37 (m, 1 H), 7.25 (br. s., 2 H), 6.81-6.87 (m, 1 H), 6.61-6.67 (m, 1 H), 6.48 (s, 1 H), 4.79 (d, 2 H).

Example 24

4-amino-6-({[3-(3-fluorophenyl)indolizin-2-yl]methyl}amino)pyrimidine-5-carbonitrile

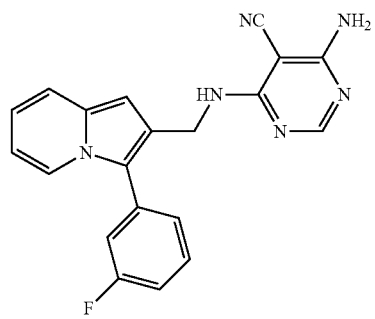 [SMILES: N#Cc1c(N)ncnc1NCc1cc2ccccn2c1-c1cccc(F)c1]

Prepared similarly to Example 22, starting from [3-(3-fluorophenyl)indolizin-2-yl]methanamine P3 (0.101 g, 0.421 mmol), heating to reflux for 1 h, and purified by flash chromatography on 28 g Biotage silica-NH SNAP cartridge (cyclohexane:EtOAc=90:10 to 60:40) to afford title compound as a pale yellow solid (0.100 g). MS/ESI⁺ 359.2 [MH]⁺, Rt=1.01 min (Method B).

$^1$H NMR (400 MHz, DMSO-$d_6$) δ ppm 8.07 (d, 1 H), 7.99 (s, 1 H), 7.80 (t, 1 H), 7.55-7.64 (m, 1 H), 7.39-7.51 (m, 3 H), 7.24-7.31 (m, 1 H), 7.22 (br. s., 2 H), 6.71-6.78 (m, 1 H), 6.52-6.57 (m, 1 H), 6.49 (s, 1 H), 4.64 (d, 2 H).

Example 25

4-amino-6-({[3-(2-fluorophenyl)indolizin-2-yl]methyl}amino)pyrimidine-5-carbonitrile

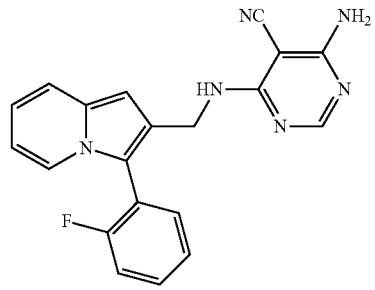 [SMILES: N#Cc1c(N)ncnc1NCc1cc2ccccn2c1-c1ccccc1F]

Prepared similarly to Example 22, starting from [3-(2-fluorophenyl)indolizin-2-yl]methanamine P4 (0.130 g, 0.541 mmol), heating to reflux for 2 h, and purified by flash chromatography on 28 g Biotage silica-NH SNAP cartridge (DCM to DCM:MeOH=98:2) to afford title compound as an off-white solid (0.140 g). MS/ESI⁺ 359.1 [MH]⁺, Rt=0.98 min (Method A).

$^1$H NMR (400 MHz, DMSO-$d_6$) δ ppm 7.96 (s, 1 H), 7.74 (t, 1 H), 7.61-7.71 (m, 2 H), 7.51-7.60 (m, 1 H), 7.36-7.50 (m, 3 H), 7.20 (br. s., 2 H), 6.73-6.79 (m, 1 H), 6.53-6.60 (m, 1 H), 6.51 (s, 1 H), 4.51-4.65 (m, 2 H).

Example 26

4-amino-6-({[3-(2-methylphenyl)indolizin-2-yl]methyl}amino)pyrimidine-5-carbonitrile

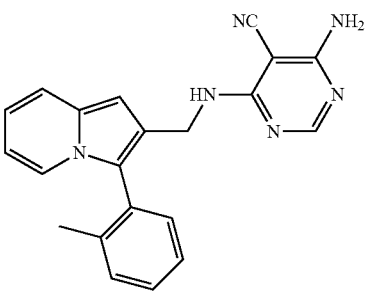 [SMILES: Cc1ccccc1-c1c(CNc2ncnc(N)c2C#N)cc2ccccn12]

Prepared similarly to Example 22, starting from [3-(2-methylphenyl)indolizin-2-yl]methanamine P5 (0.129 g, 0.546 mmol), heating to reflux for 2 h, and purified by flash chromatography on 28 g Biotage silica-NH SNAP cartridge (DCM to DCM:MeOH=95:5) to afford title compound as an off-white solid (0.132 g). MS/ESI⁺ 355.2 [MH]⁺, Rt=1.05 min (Method A).

$^1$H NMR (400 MHz, DMSO-$d_6$) δ ppm 7.94 (s, 1 H), 7.63 (t, 1 H), 7.29-7.47 (m, 6 H), 7.17 (br. s., 2 H), 6.67-6.73 (m, 1 H), 6.45-6.52 (m, 2 H), 4.42-4.55 (m, 2 H), 1.97 (s, 3 H).

Example 27

4-amino-6-{[(1-phenylindolizin-2-yl)methyl]amino}pyrimidine-5-carbonitrile

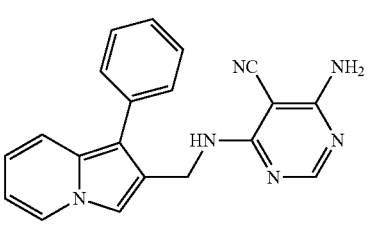 [SMILES: N#Cc1c(N)ncnc1NCc1cn2ccccc2c1-c1ccccc1]

Prepared similarly to Example 22, starting from (1-phenylindolizin-2-yl)methanamine P6 (0.050 g, 0.224 mmol), heating to reflux for 1 h, and purified by flash chromatography on Biotage silica-NH SNAP cartridge (cyclohexane:EtOAc=70:30 to 50:50) to afford title compound as an off-white solid (0.037 g). MS/ESI⁺ 341.2 [MH]⁺, Rt=0.99 min (Method A).

$^1$H NMR (400 MHz, DMSO-d6) δ ppm 8.27 (d, 1 H), 8.00 (s, 1 H), 7.79 (t, 1 H), 7.44-7.49 (m, 5 H), 7.39-7.43 (m, 1 H), 7.19-7.33 (m, 3 H), 6.68-6.74 (m, 1 H), 6.51-6.56 (m, 1 H), 4.72 (d, 2 H).

Example 28

4-amino-6-({[1-(3-fluorophenyl)indolizin-2-yl]methyl}amino)pyrimidine-5-carbonitrile

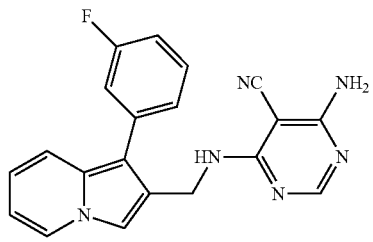 [SMILES: N#Cc1c(N)ncnc1NCc1cn2ccccc2c1-c1cccc(F)c1]

Prepared similarly to Example 22, starting from [1-(3-fluorophenyl)indolizin-2-yl]methanamine P7 (0.055 g, 0.23 mmol), heating to reflux for 2 h, and purified by flash chromatography on Biotage silica-NH SNAP cartridge (DCM to DCM:MeOH=99.5:0.5) to afford title compound as an off-white solid (0.033 g). MS/ESI$^+$ 359.1 [MH]$^+$, Rt 1.02 min (Method A).

$^1$H NMR (400 MHz, DMSO-d$_6$) δ ppm 8.30 (d, 1 H), 8.01 (s, 1 H), 7.81 (t, 1 H), 7.43-7.53 (m, 3 H), 7.26-7.34 (m, 2 H), 7.24 (br. s, 2 H), 7.07-7.15 (m, 1 H), 6.74-6.80 (m, 1 H), 6.55-6.61 (m, 1 H), 4.73 (d, 2 H).

Example 29

4-amino-6-({[1-(2-methylphenyl)indolizin-2-yl]methyl}amino)pyrimidine-5-carbonitrile

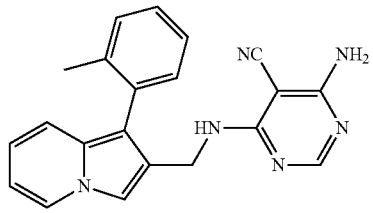 [SMILES: Cc1ccccc1-c1c(CNc2ncnc(N)c2C#N)cn2ccccc12]

Prepared similarly to Example 22, starting from [1-(2-methylphenyl)indolizin-2-yl]methanamine P8 (0.046 g, 0.19 mmol), heating to reflux for 2 h, and purified by flash chromatography on 11 g Biotage silica-NH cartridge (cyclohexane:EtOAc=80:20 to 50:50) to afford title compound as an off-white solid (0.024 g). MS/ESI$^+$ 355.2 [MH]$^+$, Rt 0.96 min (Method C).

$^1$H NMR (400 MHz, DMSO-d$_6$) δ ppm 8.23-8.29 (m, 1 H), 7.96 (s, 1 H), 7.59 (t, 1 H), 7.49 (s, 1 H), 7.33 (d, 1 H), 7.22-7.30 (m, 3 H), 7.19 (br. s., 2 H), 6.87 (d, 1 H), 6.60-6.67 (m, 1 H), 6.48-6.54 (m, 1 H), 4.48 (d, 2 H), 2.10 (s, 3 H).

Example 30

4-amino-6-({[1-(pyridin-2-yl)indolizin-2-yl]methyl}amino)pyrimidine-5-carbonitrile

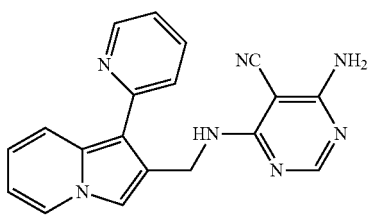 [SMILES: N#Cc1c(N)ncnc1NCc1cn2ccccc2c1-c1ccccn1]

Prepared similarly to Example 22, starting from [1-(pyridin-2-yl)indolizin-2-yl]methanamine P9 (0.044 g, 0.20 mmol), heating to reflux for 1 h, and purified by flash chromatography on 11 g Biotage silica-NH cartridge (cyclohexane:EtOAc=70:30 to 40:60) to afford title compound as a pale brown solid (0.0416 g). MS/ESI$^+$ 342.1 [MH]$^+$, Rt 0.49 min (Method A).

$^1$H NMR (400 MHz, DMSO-d$_6$) δ ppm 8.61-8.71 (m, 2 H), 8.34 (d, 1 H), 8.05 (s, 1 H), 7.81-7.92 (m, 2 H), 7.69 (d, 1 H), 7.59 (s, 1 H), 7.19-7.32 (m, 3 H), 6.88-6.95 (m, 1 H), 6.63-6.70 (m, 1 H), 4.80 (d, 2 H).

Example 31

4-amino-6-[(indolizin-2-ylmethyl)amino]pyrimidine-5-carbonitrile

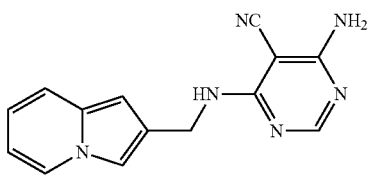 [SMILES: N#Cc1c(N)ncnc1NCc1cc2ccccn2c1]

Prepared similarly to Example 22, starting from indolizin-2-ylmethanamine P10 (0.065 g, 0.44 mmol), heating to reflux for 2 h, and purified by flash chromatography on 28 g Biotage silica-NH SNAP cartridge (DCM to DCM:MeOH=99.9:0.1) to afford title compound as an off-white solid (0.040 g). MS/ESI$^+$ 265.1 [MH]$^+$, Rt 0.78 min (Method C).

$^1$H NMR (400 MHz, DMSO-d$_6$) δ ppm 8.17-8.21 (m, 1 H), 8.04 (s, 1 H), 7.79 (t, 1 H), 7.41 (s, 1 H), 7.32 (d, 1 H), 7.22 (br. s., 2 H), 6.60-6.66 (m, 1 H), 6.43-6.49 (m, 1 H), 6.30 (s, 1 H), 4.62 (d, 2 H).

Example 32

4-amino-6-{[1-(3-phenylindolizin-2-yl)ethyl]amino}pyrimidine-5-carbonitrile

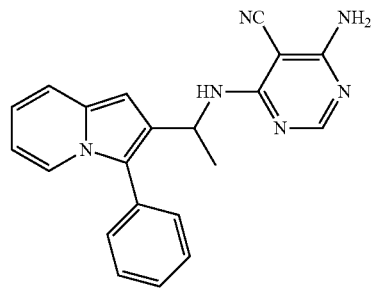 [SMILES: CC(Nc1ncnc(N)c1C#N)c1cc2ccccn2c1-c1ccccc1]

Prepared similarly to Example 22, starting from 1-(3-phenylindolizin-2-yl)ethan-1-amine Q1 (0.041 g, 0.174 mmol), heating to reflux for 2 h, and purified by flash chromatography on Biotage silica-NH cartridge (cyclohexane:EtOAc=90:10 to 60:40). A further purification by trituration with Et$_2$O was required to afford title compound as a white solid (0.035 g). MS/ESI$^+$ 355.2 [MH]$^+$, Rt 1.05 min (Method A).

$^1$H NMR (400 MHz, DMSO-d$_6$) δ ppm 7.88-7.94 (m, 2 H), 7.39-7.58 (m, 6 H), 7.27 (d, 1 H), 7.17 (br. s., 2 H), 6.68-6.76 (m, 2 H), 6.47-6.55 (m, 1 H), 5.44-5.54 (m, 1 H), 1.45 (d, 3 H).

Example 33

4-amino-6-({1-[3-(pyridin-2-yl)indolizin-2-yl]ethyl}amino)pyrimidine-5-carbonitrile

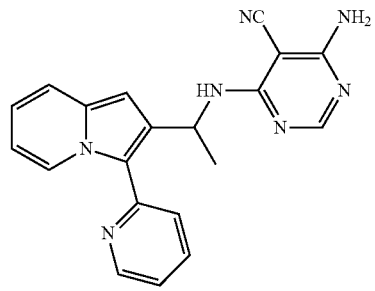 [SMILES: CC(Nc1ncnc(N)c1C#N)c1cc2ccccn2c1-c1ccccn1]

Prepared similarly to Example 22, starting from 1-[3-(pyridin-2-yl)indolizin-2-yl]ethan-1-amine Q2 (0.050 g, 0.211 mmol), heating to reflux for 2 h, and purified by flash chromatography on Biotage silica-NH SNAP cartridge (cyclohexane:EtOAc=80:20 to 30:70) to afford title compound as a yellow solid (0.049 g). MS/ESI$^+$ 365.1 [MH]$^+$, Rt 0.64 min (Method A).

$^1$H NMR (400 MHz, DMSO-d$_6$) δ ppm 8.74-8.79 (m, 1 H), 8.67 (d, 1 H), 8.10 (d, 1 H), 7.90-8.00 (m, 2 H), 7.77 (d, 1 H), 7.52 (d, 1 H), 7.34-7.40 (m, 1 H), 7.21 (br. s., 2 H), 6.80-6.88 (m, 1 H), 6.71 (s, 1 H), 6.59-6.67 (m, 1 H), 5.68-5.79 (m, 1 H), 1.39 (d, 3 H).

Example 34

4-amino-6-({1-[3-(pyridin-3-yl)indolizin-2-yl]ethyl}amino)pyrimidine-5-carbonitrile

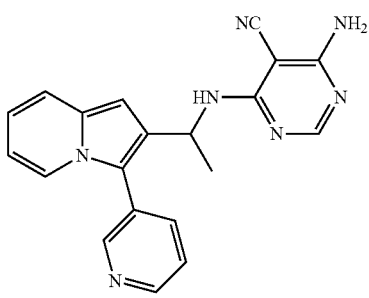 [SMILES: CC(Nc1ncnc(N)c1C#N)c1cc2ccccn2c1-c1cccnc1]

Prepared similarly to Example 22, starting from 1-[3-(pyridin-3-yl)indolizin-2-yl]ethan-1-amine Q3 (0.062 g), heating to reflux for 3 h, and purified by flash chromatography on Biotage silica-NH cartridge (DCM:EtOAc=80:20 to 30:70) to afford title compound as a pale yellow solid (0.045 g). MS/ESI$^+$ 356.1 [MH]$^+$, Rt 0.66 min (Method A).

$^1$H NMR (400 MHz, DMSO-d$_6$) δ ppm 8.68 (d, 1 H), 8.62 (dd, 1 H), 7.93-7.98 (m, 1 H), 7.91 (d, 1 H), 7.87 (s, 1 H), 7.52-7.58 (m, 1 H), 7.49 (d, 1 H), 7.36 (d, 1 H), 7.15 (br. s., 2 H), 6.72-6.80 (m, 2 H), 6.50-6.57 (m, 1 H), 5.39-5.49 (m, 1 H), 1.49 (d, 3 H).

Example 35

4-amino-6-({1-[3-(pyrazin-2-yl)indolizin-2-yl]ethyl}amino)pyrimidine-5-carbonitrile

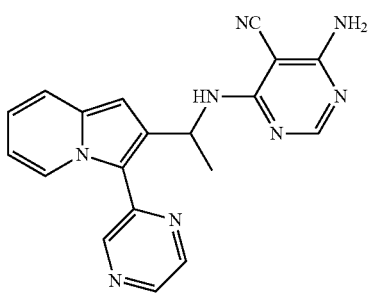 [SMILES: CC(Nc1ncnc(N)c1C#N)c1cc2ccccn2c1-c1cnccn1]

Prepared similarly to Example 22, starting from crude 1-[3-(pyrazin-2-yl)indolizin-2-yl]ethan-1-amine Q4 (0.114 mmol), heating to reflux for 4 h, and purified by flash chromatography on Biotage silica-NH cartridge (DCM to DCM:EtOAc=30:70) to afford title compound as a pale yellow solid (0.024 g). MS/ESI$^+$ 357.1 [MH]$^+$, Rt 0.81 min (Method A).

$^1$H NMR (400 MHz, DMSO-d$_6$) δ ppm 8.93 (d, 1 H), 8.73-8.80 (m, 2 H), 8.54 (d, 1 H), 7.87 (s, 1 H), 7.67 (d, 1 H), 7.56 (d, 1 H), 7.20 (br. s., 2 H), 6.86-6.93 (m, 1 H), 6.79 (s, 1 H), 6.63-6.69 (m, 1 H), 5.69-5.78 (m, 1 H), 1.52 (d, 3 H).

Example 36

4-amino-6-({1-[3-(pyridin-4-yl)indolizin-2-yl]ethyl}amino)pyrimidine-5-carbonitrile

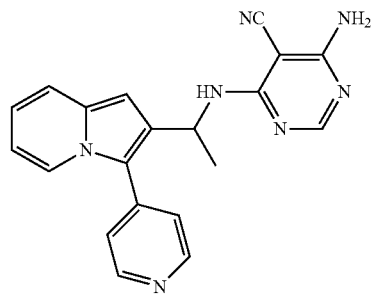 [SMILES: CC(Nc1ncnc(N)c1C#N)c1cc2ccccn2c1-c1ccncc1]

Prepared similarly to Example 22, starting from 1-[3-(pyridin-4-yl)indolizin-2-yl]ethan-1-amine Q10 (0.062 g, 0.261 mmol), heating to reflux for 2 h, and purified by flash chromatography on Biotage silica-NH SNAP cartridge (DCM:EtOAc=80:20 to 30:70) followed by trituration with Et$_2$O to afford title compound as a pale yellow solid (0.036 g). MS/ESI$^+$ 356.1 [MH]$^+$, Rt 0.52 min (Method A).

$^1$H NMR (400 MHz, DMSO-d$_6$) δ ppm 8.65-6.72 (m, 2 H), 8.11 (d, 1 H), 7.90 (s, 1 H), 7.54-7.60 (m, 2 H), 7.49 (d, 1 H), 7.40 (d, 1 H), 7.15 (br. s., 2 H), 6.74-6.83 (m, 2 H), 6.53-6.60 (m, 1 H), 5.48-5.61 (m, 1 H), 1.47 (d, 3 H).

Example 37

4-amino-6-({1-[3-(thiophen-2-yl)indolizin-2-yl]ethyl}amino)pyrimidine-5-carbonitrile

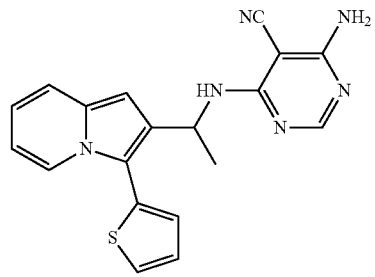 [SMILES: CC(Nc1ncnc(N)c1C#N)c1cc2ccccn2c1-c1cccs1]

Prepared similarly to Example 22, starting from 1-[3-(thiophen-2-yl)indolizin-2-yl]ethan-1-amine Q11 (0.058 g), heating to reflux for 2 h, and purified by flash chromatography on Biotage silica-NH SNAP cartridge (cyclohexane:EtOAc=80:20). A further purification by reverse phase semi-preparative MDAP under acidic conditions (Method A) followed by dissolution in DCM and washing with sat. NaHCO$_3$ was required to afford title compound as a pale yellow solid (0.020 g). MS/ESI$^+$ 361.1 [MH]$^+$, Rt 1.04 min (Method A).

$^1$H NMR (400 MHz, DMSO-d$_6$) δ ppm 7.97-8.03 (m, 1 H), 7.92 (s, 1 H), 7.75 (dd, 1 H), 7.44-7.49 (m, 1 H), 7.26-7.30 (m, 2 H), 7.23-7.26 (m, 1 H), 7.15 (br. s., 2 H), 6.73-6.79 (m, 1 H), 6.68 (s, 1 H), 6.55-6.61 (m, 1 H), 5.49-5.59 (m, 1 H), 1.46 (d, 3 H).

Example 38

4-amino-6-({1-[3-(thiophen-3-yl)indolizin-2-yl]ethyl}amino)pyrimidine-5-carbonitrile

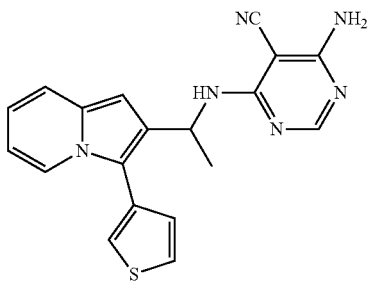 [SMILES: CC(Nc1ncnc(N)c1C#N)c1cc2ccccn2c1-c1ccsc1]

Prepared similarly to Example 22, starting from 1-[3-(thiophen-3-yl)indolizin-2-yl]ethan-1-amine Q12 (0.061 g), heating to reflux for 2 h, and purified by flash chromatography on 11 g Biotage silica-NH SNAP cartridge (cyclohexane:EtOAc=80:20). A further purification by reverse phase semi-preparative MDAP under acidic conditions (Method E) followed by dissolution in DCM and washing with sat. NaHCO$_3$ was required to afford title compound as a pale green solid (0.030 g). MS/ESI$^+$ 361.1 [MH]$^+$, Rt 1.04 min. (Method A).

$^1$H NMR (400 MHz, DMSO-d$_6$) δ ppm 7.96 (s, 1 H), 7.91-7.95 (m, 1 H), 7.74-7.77 (m, 2 H), 7.45 (d, 1 H), 7.34-7.37 (m, 1 H), 7.27 (d, 1 H), 7.17 (br. s., 2 H), 6.67-6.74 (m, 2H), 6.51-6.56 (m, 1 H), 5.48-5.58 (m, 1 H), 1.45 (d, 3 H).

Example 39

4-amino-6-({1-[8-fluoro-3-(pyridin-2-yl)indolizin-2-yl]ethyl}amino)pyrimidine-5-carbonitrile

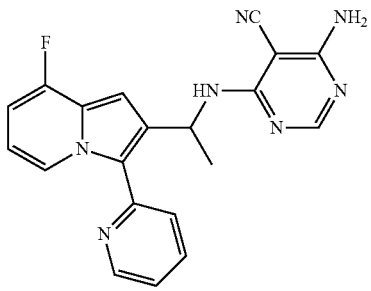 [SMILES: CC(Nc1ncnc(N)c1C#N)c1cc2c(F)cccn2c1-c1ccccn1]

Prepared similarly to Example 22, starting from 1-[8-fluoro-3-(pyridin-2-yl)indolizin-2-yl]ethan-1-amine Q5 (0.084 g, 0.33 mmol), heating to reflux for 1 h, and purified by flash chromatography on 11 g Biotage silica-NH SNAP cartridge (DCM to DCM:MeOH=98:2); a further flash chromatography on 10 g Biotage silica SNAP cartridge (cyclohexane:EtOAc=60:40 to 40:60) to afford title compound (0.052 g). MS/ESI$^+$ 374.2 [MH]$^+$, Rt 0.76 min (Method A).

$^1$H NMR (400 MHz, DMSO-d$_6$) δ ppm 8.74-8.80 (m, 1 H), 8.48 (d, 1 H), 7.92-8.03 (m, 3 H), 7.81 (d, 1 H), 7.38-7.44 (m, 1 H), 7.23 (br. s., 2 H), 6.91 (s, 1 H), 6.68-6.75 (m, 1 H), 6.57-6.64 (m, 1 H), 5.69-5.76 (m, 1 H), 1.42 (d, 3 H).

Example 40

4-amino-6-({1-[5-methyl-3-(pyridin-2-yl)indolizin-2-yl]ethyl}amino)pyrimidine-5-carbonitrile

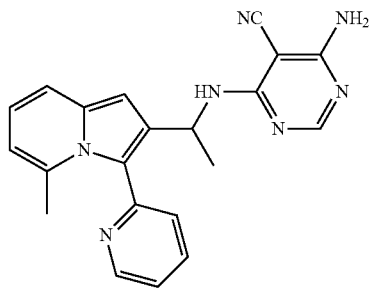 [SMILES: Cc1cccc2cc(C(C)Nc3ncnc(N)c3C#N)c(-c3ccccn3)n12]

Prepared similarly to Example 22, starting from 1-[5-methyl-3-(pyridin-2-yl)indolizin-2-yl]ethan-1-amine Q13 (0.045 g, 0.18 mmol), heating to reflux for 2 h, and purified by flash chromatography on 11 g Biotage silica-NH SNAP cartridge (cyclohexane:EtOAc=80:20 to 50:50) to afford title compound as a pale white solid (0.036 g). MS/ESI$^+$ 370.1 [MH]$^+$, Rt 0.91 min (Method C)

$^1$H NMR (400 MHz, DMSO-d$_6$) δ ppm 8.55-8.74 (m, 1 H), 7.50-8.02 (m, 4 H), 7.02-7.48 (m, 4 H), 6.64-6.77 (m, 2 H), 6.40 (d, 1 H), 5.31-5.43 (m, 1 H), 1.95 (s, 3 H), 1.10-1.40 (m, 3 H).

Example 41

4-amino-6-({1-[8-methyl-3-(pyridin-2-yl)indolizin-2-yl]ethyl}amino)pyrimidine-5-carbonitrile

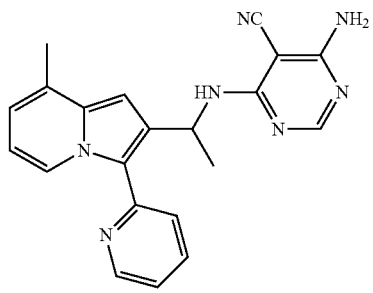 [SMILES: Cc1cccn2c(-c3ccccn3)c(C(C)Nc3ncnc(N)c3C#N)cc12]

Prepared similarly to Example 22, starting from 1-[8-methyl-3-(pyridin-2-yl)indolizin-2-yl]ethan-1-amine Q14 (0.050 g, 0.20 mmol), heating to reflux for 1 h, and purified by flash chromatography on Biotage silica-NH SNAP cartridge (DCM to DCM:MeOH=98:2); a further purification by flash chromatography on 11 g Biotage silica-NH SNAP cartridge (cyclohexane:EtOAc=50:50) was required to afford title compound as a pale yellow solid (0.019 g). MS/ESI$^+$ 370.2 [MH]$^+$, Rt 0.70 min (Method A).

$^1$H NMR (400 MHz, DMSO-d$_6$) δ ppm 8.74-8.79 (m, 1 H), 8.51 (d, 1 H), 8.16 (d, 1 H), 7.90-8.00 (m, 2 H), 7.76 (d, 1 H), 7.35-7.40 (m, 1 H), 7.22 (br. s., 2 H), 6.72 (s, 1 H), 6.68 (d, 1 H), 6.55-6.60 (m, 1 H), 5.68-5.78 (m, 1 H), 2.40 (s, 3 H), 1.38 (d, 3 H).

Example 42

4-amino-6-({1-[3-(3,6-dihydro-2H-pyran-4-yl)indolizin-2-yl]ethyl}amino)pyrimidine-5-carbonitrile

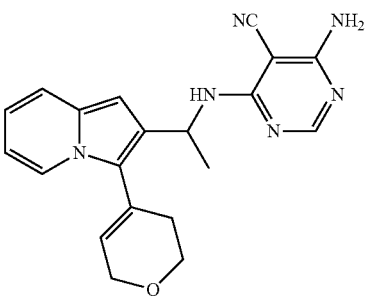 [SMILES: CC(Nc1ncnc(N)c1C#N)c1cc2ccccn2c1C1=CCOCC1]

Prepared similarly to Example 22, starting from 1-[3-(3,6-dihydro-2H-pyran-4-yl)indolizin-2-yl]ethan-1-amine Q6 (0.033 g, 0.13 mmol), heating to reflux for 3 h, and purified by flash chromatography on Biotage silica-NH SNAP cartridge (cyclohexane:EtOAc=90:10 to 50:50) followed by reverse phase semi-preparative MDAP under basic conditions (Method F) to afford title compound as a white solid (0.0055 g). MS/ESI$^+$ 361.2 [MH]$^+$, Rt 0.92 min (Method C).

$^1$H NMR (400 MHz, DMSO-d$_6$) δ ppm 7.98 (s, 1 H), 7.88 (d, 1 H), 7.38 (d, 1 H), 7.25 (d, 1 H), 7.14 (br. s., 2 H), 6.60-6.69 (m, 1 H), 6.46-6.56 (m, 2 H), 5.91 (br. s., 1 H), 5.53-5.63 (m, 1 H), 4.18-4.23 (m, 2 H), 3.76-3.88 (m, 2 H), 2.24-2.31 (m, 2 H), 1.50 (d, 3 H).

Example 43

4-amino-6-({1-[3-(pent-1-yn-1-yl)indolizin-2-yl]ethyl}amino)pyrimidine-5-carbonitrile

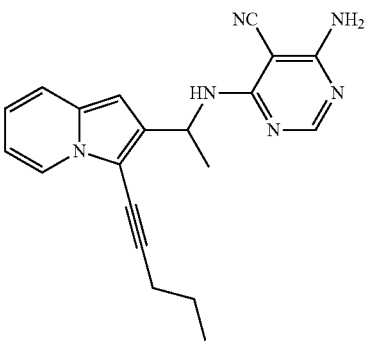 [SMILES: CCCC#Cc1c(C(C)Nc2ncnc(N)c2C#N)cc2ccccn12]

Prepared similarly to Example 22, starting from crude 1-[3-(pent-1-yn-1-yl)indolizin-2-yl]ethan-1-amine Q8 (0.20 mmol) and 4-amino-6-chloropyrimidine-5-carbonitrile (0.031 g, 0.20 mmol), heating to reflux for 3 h, and purified by reverse phase semi-preparative MDAP under basic conditions (Method F) to afford title compound as a white solid (0.030 g). MS/ESI$^+$ 345.3 [MH]$^+$, Rt 1.18 min (Method C).

$^1$H NMR (400 MHz, DMSO-d$_6$) δ ppm 8.13 (d, 1 H), 8.00 (s, 1 H), 7.45 (d, 1 H), 7.35 (d, 1 H), 7.21 (br. s., 2 H), 6.77-6.85 (m, 1 H), 6.68-6.76 (m, 1 H), 6.44 (s, 1 H), 5.63-5.72 (m, 1 H), 2.48-2.57 (m, 2 H), 1.51-1.64 (m, 5 H), 1.02 (t, 3 H).

Example 44

4-amino-6-({1-[3-(pyridin-2-yl)indolizin-2-yl]propyl}amino)pyrimidine-5-carbonitrile

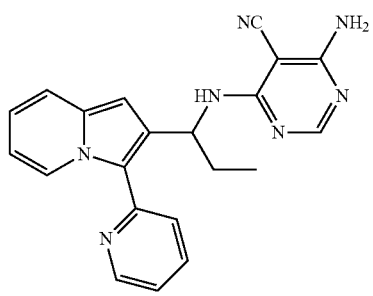 [SMILES: CCC(Nc1ncnc(N)c1C#N)c1cc2ccccn2c1-c1ccccn1]

Prepared similarly to Example 22, starting from 1-[3-(pyridin-2-yl)indolizin-2-yl]propan-1-amine Q15 (0.102 g, 0.40 mmol), heating to reflux for 3 h, and purified by flash chromatography on Biotage silica-NH cartridge (Cy:AcOEt=8:2 to Cy:AcOEt=1:1) to afford the compound as a yellow solid (0.0463 g). MS/ESI$^+$ 370.2 [MH]$^+$, Rt 0.73 min (Method A).

$^1$H NMR (400 MHz, DMSO-d$_6$) δ ppm 8.76-8.80 (m, 1 H), 8.62 (d, 1 H), 8.29 (d, 1 H), 7.92-8.02 (m, 2 H), 7.86 (d, 1 H), 7.51 (d, 1 H), 7.36-7.42 (m, 1 H), 7.20 (br. s., 2 H), 6.80-6.87 (m, 1 H), 6.69 (s, 1 H), 6.59-6.66 (m, 1 H), 5.48-5.57 (m, 1 H), 1.73-1.86 (m, 1 H), 1.53-1.67 (m, 1 H), 0.71 (t, 3 H).

Example 45

4-amino-6-({1-[3-(1,2,3,6-tetrahydropyridin-4-yl)indolizin-2-yl]ethyl}amino)pyrimidine-5-carbonitrile

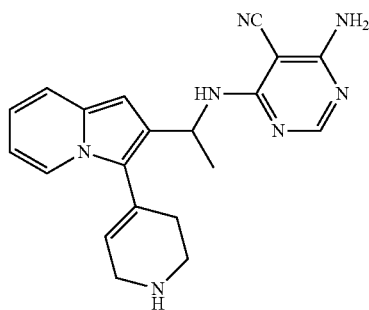 [SMILES: CC(Nc1ncnc(N)c1C#N)c1cc2ccccn2c1C1=CCNCC1]

To a solution of tert-butyl 4-(2-{1-[(6-amino-5-cyanopyrimidin-4-yl)amino]ethyl}indolizin-3-yl)-1,2,3,6-tetrahydropyridine-1-carboxylate U1 (0.045 g, 0.098 mmol) in DCM (0.5 mL), trifluoroacetic acid (0.045 mL, 0.59 mmol) was slowly added at 0° C. and the reaction was stirred at r.t. for 1 h. The mixture was partitioned between DCM and aqueous sat. NaHCO$_3$ and the aqueous phase was extracted with DCM; the combined organic layers were washed with brine, dried over anhydrous MgSO$_4$ and concentrated. The crude was purified by flash chromatography on silica-NH cartridge (cyclohexane to cyclohexane AcOEt=50:50) followed by reverse phase flash chromatography on C18 cartridge (H$_2$O:CH$_3$CN=95:5 to 70:30, with 0.1% HCOOH) to afford title compound as a brown solid (0.0067 g). MS/ESI$^+$ 360.3 [MH]$^+$, Rt 0.53 min (Method A).

$^1$H NMR (400 MHz, DMSO-d$_6$) δ ppm 7.99 (s, 1 H), 7.85 (d, 1 H), 7.36 (d, 1 H), 7.08-7.27 (m, 3 H), 6.59-6.67 (m, 1 H), 6.47-6.53 (m, 2 H), 5.85 (br. s., 1 H), 5.51-5.62 (m, 1 H), 3.26-3.41 (m, 2 H), 2.84-2.98 (m, 2 H), 2.16 (br. s., 2 H), 1.49 (d, 3 H).

Example 46

4-amino-6-({1-[3-(3-hydroxyprop-1-yn-1-yl)indolizin-2-yl]ethyl}amino)pyrimidine-5-carbonitrile

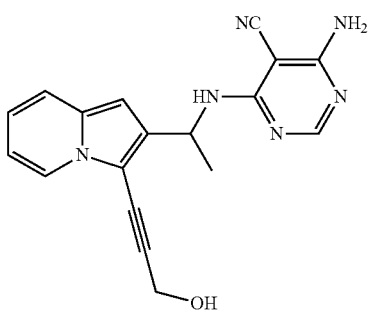 [SMILES: CC(Nc1ncnc(N)c1C#N)c1cc2ccccn2c1C#CCO]

To a solution of 4-amino-6-({1-[3-(3-{[tris(propan-2-yl)silyl]oxy}prop-1-yn-1-yl)indolizin-2-yl]ethyl}amino)pyrimidine-5-carbonitrile U2 (0.062 g, 0.13 mmol) in THF (0.65 mL), tetrabutylammonium fluoride 1M in THF (0.14 mL, 0.14 mmol) was added the resulting mixture was stirred at room temperature for 30 min and then quenched with saturated aqueous NH$_4$Cl. The mixture was extracted with DCM and the combined organic layers were dried, filtered and concentrated. The residue was purified by flash chromatography on Biotage silica-NH SNAP cartridge (cyclohexane:EtOAc=100:0 to 0:100) to afford title compound as a yellow solid (0.017 g). MS/ESI$^+$ 333.2 [MH]$^+$, Rt 0.83 min (Method C).

$^1$H NMR (400 MHz, DMSO-d$_6$) δ ppm 8.20 (d, 1 H), 7.99 (s, 1 H), 7.47 (d, 1 H), 7.40 (d, 1 H), 7.20 (br. s., 2 H), 6.81-6.89 (m, 1 H), 6.71-6.78 (m, 1 H), 6.45 (s, 1 H), 5.60-5.72 (m, 1 H), 5.33 (t, 1 H), 4.38-4.50 (m, 2 H), 1.54 (d, 3 H).

Example 47

4-amino-6-({1-[3-(pyridin-2-yl)indolizin-2-yl]ethyl}amino)pyrimidine-5-carbaldehyde

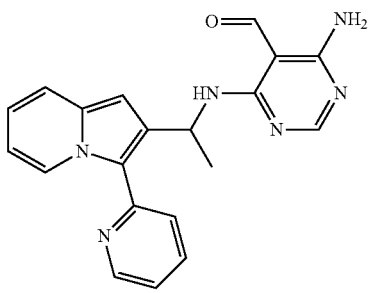 [SMILES: CC(Nc1ncnc(N)c1C=O)c1cc2ccccn2c1-c1ccccn1]

To a solution of 1-[3-(pyridin-2-yl)indolizin-2-yl]ethan-1-amine Q2 (0.150 g, 0.63 mmol) in t-BuOH (6.7 mL), 4-amino-6-chloro-5-pyrimidinecarbaldehyde (0.100 g, 0.63 mmol) was added followed by DIPEA (0.219 mL, 1.26 mmol) and the resulting mixture was heated to reflux for 2 h. The solvent was removed under reduced pressure and the crude was purified by flash chromatography on Biotage silica-NH SNAP cartridge (DCM to DCM:MeOH=99:1) to afford title compound as a yellow solid (0.106 g). MS/ESI$^+$ 359.1 [MH]$^+$, Rt 0.61 min (Method A).

$^1$H NMR (400 MHz, DMSO-d$_6$) δ ppm 10.01 (s, 1 H), 9.38 (d, 1 H), 8.69-8.79 (m, 2 H), 7.96 (s, 1 H), 7.90 (td, 1 H), 7.46-7.75 (m, 4 H), 7.30-7.36 (m, 1 H), 6.82-6.90 (m, 1 H), 6.60-6.70 (m, 2 H), 5.68-5.77 (m, 1 H), 1.52 (d, 3 H).

Example 48

5-bromo-4-N-{1-[3-(pyridin-2-yl)indolizin-2-yl]ethyl}pyrimidine-4,6-diamine

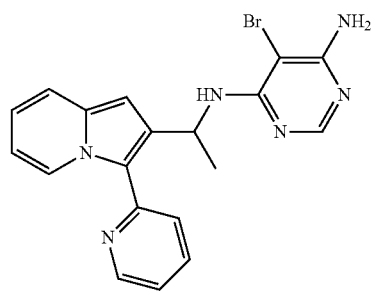 [SMILES: CC(Nc1ncnc(N)c1Br)c1cc2ccccn2c1-c1ccccn1]

Prepared similarly to Example 47, starting from 1-[3-(pyridin-2-yl)indolizin-2-yl]ethan-1-amine Q2 (0.171 g, 0.72 mmol) and 5-bromo-6-chloropyrimidin-4-amine (0.150 g, 0.72 mmol), heating to reflux for 6 days, and purified by flash chromatography on 28 g Biotage silica-NH SNAP cartridge (DCM to DCM:MeOH=99.5:0.5) followed by flash chromatography on Biotage silica-NH SNAP cartridge (cyclohexane:EtOAc=90:10 to 80:20) to afford title compound as a white solid (0.144 g). MS/ESI$^+$ 408.9-410.9 [MH]$^+$, Rt 0.63 min (Method A).

$^1$H NMR (400 MHz, DMSO-d$_6$) δ ppm 8.73-7.77 (m, 1 H), 8.67 (d, 1 H), 7.92 (td, 1 H), 7.82 (s, 1 H), 7.74 (d, 1 H), 7.49 (d, 1 H), 7.32-7.37 (m, 1 H), 6.77-6.86 (m, 1 H), 6.68 (s, 1 H), 6.57-6.64 (m, 1 H), 6.43 (br. s., 2 H), 5.58-5.68 (m, 1 H), 1.40 (d, 3 H).

Example 49

4-N-{1-[3-(pyridin-2-yl)indolizin-2-yl]ethyl}-5-(trifluoromethyl)pyrimidine-4,6-diamine

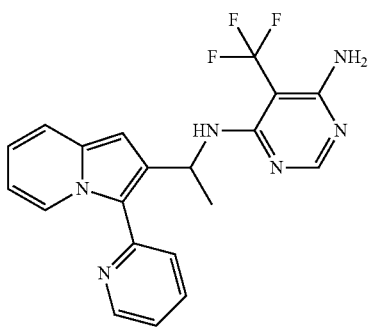 [SMILES: CC(Nc1ncnc(N)c1C(F)(F)F)c1cc2ccccn2c1-c1ccccn1]

Prepared similarly to Example 47, starting from 1-[3-(pyridin-2-yl)indolizin-2-yl]ethan-1-amine Q2 (0.036 g, 0.15 mmol) and 6-chloro-5-(trifluoromethyl)pyrimidin-4-amine (prepared accordingly to the procedure reported in the patent WO2011/146882, which is incorporated herein by reference in its entirety) (0.030 g, 0.15 mmol), heating to reflux for 10 h, and purified by flash chromatography on 11 g Biotage silica-NH SNAP cartridge (cyclohexane:EtOAc=70:30). A further purification by flash chromatography on Biotage silica-NH cartridge (DCM to DCM:MeOH=99:1), was required to afford title compound (0.007 g). MS/ESI$^+$ 399.2 [MH]$^+$, Rt 0.74 min (Method A).

$^1$H NMR (400 MHz, DMSO-d$_6$) δ ppm 8.64-8.73 (m, 2 H), 7.90-7.96 (m, 2 H), 7.74 (d, 1 H), 7.50 (d, 1 H), 7.33-7.39 (m, 1 H), 7.01-7.07 (m, 1 H), 6.80-6.86 (m, 1 H), 6.69 (br. s., 2 H), 6.59-6.66 (m, 2 H), 5.76-5.85 (m, 1 H), 1.37 (d, 3 H).

Example 50

5-methyl-4-N-{1-[3-(pyridin-2-yl)indolizin-2-yl]ethyl}pyrimidine-4,6-diamine

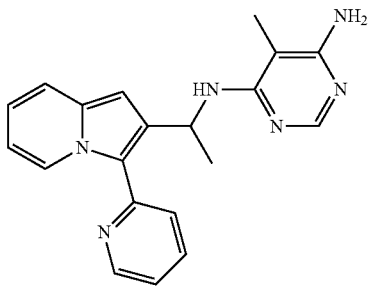 [SMILES: Cc1c(N)ncnc1NC(C)c1cc2ccccn2c1-c1ccccn1]

To a solution of 1-[3-(pyridin-2-yl)indolizin-2-yl]ethan-1-amine Q2 (0.100 g, 0.42 mmol) in t-BuOH (4.5 mL), 6-chloro-5-methylpyrimidin-4-amine (0.060 g, 0.42 mmol) was added followed by DIPEA (0.146 mL, 0.84 mmol) and the resulting mixture was heated to reflux for 24 h. Additional 1-[3-(pyridin-2-yl)indolizin-2-yl]ethan-1-amine Q2 (0.100 g, 0.42 mmol) was added over 48 h heating to reflux. The solvent was removed and the crude was dissolved in n-BuOH (4.5 mL); DIPEA (0.146 mL, 0.84 mmol) was added and the reaction was heated to 130° C. for 10 days. An additional experiment was performed: to a solution of 1-[3-(pyridin-2-yl)indolizin-2-yl]ethan-1-amine Q2 (0.059 g, 0.25 mmol) in n-BuOH (2.7 mL), 6-chloro-5-methylpyrimidin-4-amine (0.036 g, 0.25 mmol) was added followed by DIPEA (0.087 mL, 0.50 mmol) and the resulting mixture was heated under MW irradiation for 2 h at 120° C. and for 2 h at 150° C. Then the mixture was heated under thermal conditions at 130° C. for 24 h. Additional 1-[3-(pyridin-2-yl)indolizin-2-yl]ethan-1-amine Q2 (0.059 g, 0.25 mmol) was added over 10 days continuing the heating at 130° C. The two reaction mixtures were combined, the solvent was removed and the crude was partitioned between DCM/MeOH 4/1 and water. The organic phase was dried over sodium sulfate, the solvent was removed under reduced pressure and the crude was purified by flash chromatography on Biotage silica-NH cartridge (cyclohexane:EtOAc=50:50 to 40:60); two further purifications by flash chromatography on Biotage silica cartridge (DCM to DCM:MeOH=98:2) were required to afford title compound as a dark yellow solid (0.0207 g). MS/ESI$^+$ 345.2 [MH]$^+$, Rt 0.56 min (Method A).

$^1$H NMR (400 MHz, DMSO-d$_6$) δ ppm 8.78 (d, 1 H), 8.69-8.74 (m, 1 H), 7.80-7.92 (m, 2H), 7.77 (s, 1 H), 7.46 (d, 1 H), 7.27-7.35 (m, 1 H), 6.76-6.83 (m, 1 H), 6.67 (s, 1 H), 6.54-6.61 (m, 1 H), 6.24-6.33 (m, 1 H), 5.85 (br. s., 2 H), 5.60-5.70 (m, 1 H), 1.80 (s, 3 H), 1.41 (d, 3 H).

Example 51

4-amino-N-methyl-6-({1-[3-(pyridin-2-yl)indolizin-2-yl]ethyl}amino)pyrimidine-5-carboxamide

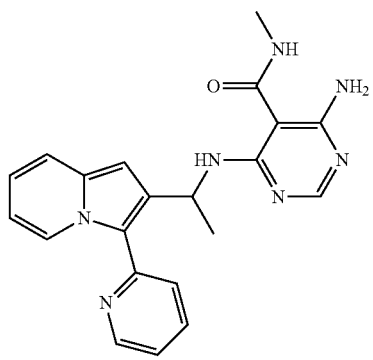 [SMILES: CNC(=O)c1c(N)ncnc1NC(C)c1cc2ccccn2c1-c1ccccn1]

To a suspension of 1-[3-(pyridin-2-yl)indolizin-2-yl]ethan-1-amine Q2 (0.040 g, 0.172 mmol) and crude 4-amino-6-chloro-N-methylpyrimidine-5-carboxamide AA4 (0.173 mmol) in t-BuOH (3 mL), DIPEA (0.090 mL, 0.516 mmol) was added and the resulting mixture was heated at 100° C. overnight. Additional DIPEA (0.090 mL, 0.516 mmol) was added and the mixture was stirred at the same temperature for 100 h. The solvent was removed and the crude was partitioned between DCM and water. The organic phase was dried over sodium sulfate, the solvent was removed under reduced pressure and the crude was purified by flash chromatography on Biotage silica-NH cartridge (DCM:EtOAc=80:20 to 100% EtOAc) to afford title compound as a brown amorphous solid (0.010 g). MS/ESI$^+$ 388.3 [MH]$^+$, Rt 0.55 min (Method A).

$^1$H NMR (400 MHz, DMSO-d$_6$) δ ppm 8.79 (d, 1 H), 8.74 (d, 1 H), 7.80-7.97 (m, 3 H), 7.74 (d, 1 H), 7.64 (d, 1 H), 7.53 (d, 1 H), 7.32-7.37 (m, 1 H), 6.81-6.89 (m, 1 H), 6.57-6.68 (m, 2 H), 6.43 (s, 2 H), 5.52-5.62 (m, 1 H), 2.70 (d, 3 H), 1.45 (d, 3 H).

Example 52

4-amino-6-({1-[3-(pyridin-2-yl)indolizin-2-yl]ethyl}amino)pyrimidine-5-carboxamide

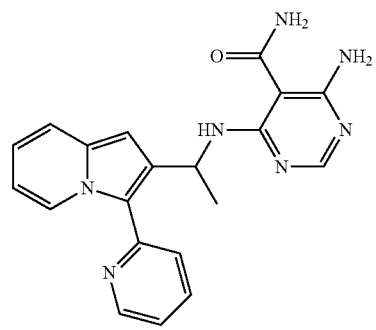 [SMILES: CC(Nc1ncnc(N)c1C(N)=O)c1cc2ccccn2c1-c1ccccn1]

To a solution of 1-[3-(pyridin-2-yl)indolizin-2-yl]ethan-1-amine Q2 (0.034 g, 0.144 mmol) in t-BuOH (1.6 mL), crude 4-amino-6-chloropyrimidine-5-carboxamide AA5 (containing some 4-amino-6-chloropyrimidine-5-carboxylic acid (0.144 mmol) was added followed by DIPEA (0.050 mL, 0.29 mmol) and the resulting mixture was heated to reflux for 4 h. The solvent was removed and the crude was partitioned between DCM/MeOH≈4/1 and water. The organic phase was dried over sodium sulfate, the solvent was removed under reduced pressure and the crude was purified by semi-preparative MDAP under acidic conditions (Method E) to afford two fractions. The first eluted fraction afforded title compound as a yellow solid (0.0055 g). MS/ESI$^+$ 374.1 [MH]$^+$, Rt 0.50 min (Method A).

$^1$H NMR (400 MHz, DMSO-d$_6$) δ ppm 8.79 (d, 1 H), 8.73 (d, 1 H), 7.86-7.97 (m, 3 H), 7.64 (d, 1 H), 7.51 (d, 1 H), 7.40 (s, 2 H), 7.31-7.36 (m, 1 H), 6.81-6.87 (m, 1 H), 6.59-6.67 (m, 2 H), 6.49 (s, 2 H), 5.51-6.60 (m, 1 H), 1.46 (d, 3 H).

Example 53

4-amino-6-({1-[3-(pyridin-2-yl)indolizin-2-yl]ethyl}amino)pyrimidine-5-carboxylic acid formate

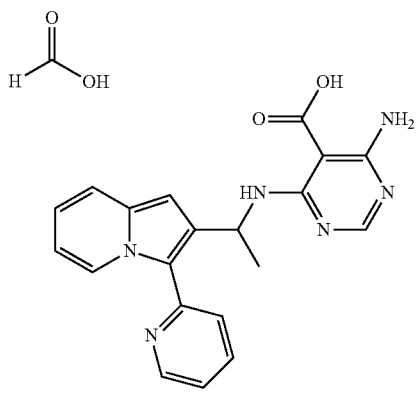 [SMILES: O=CO ; CC(Nc1ncnc(N)c1C(=O)O)c1cc2ccccn2c1-c1ccccn1]

The second fraction eluted from the purification by semi-preparative MDAP under acidic conditions (Method E) of the reaction mixture described in Example 52 was evaporated to dryness to afford title compound as a brown solid (0.0035 g) MS/ESI⁺ 375.1 [MH]⁺, Rt 0.63 min (Method A).

¹H NMR (500 MHz, DMSO-$d_6$) δ ppm 13.27 (br. s, 1 H), 9.98 (br. s, 1 H), 8.80 (d, 1 H), 8.72 (d, 1 H), 7.84-7.92 (m, 2 H), 7.62 (d, 1 H), 7.51 (d, 1 H), 7.29-7.35 (m, 1 H), 6.80-6.87 (m, 1 H), 6.58-6.66 (m, 2 H), 7.36 (br. s, 2 H), 5.52-5.68 (m, 1 H), 1.47 (d, 3 H). Presence of ~31% mol of formic acid

Example 54

3-amino-N-{1-[3-(pyridin-2-yl)indolizin-2-yl]ethyl}pyrazine-2-carboxamide

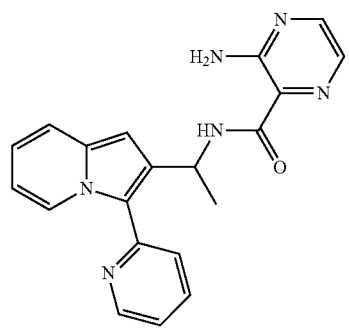 [SMILES: CC(NC(=O)c1nccnc1N)c1cc2ccccn2c1-c1ccccn1]

A mixture of 3-amino-2-pyrazinecarboxylic acid (0.032 g, 0.232 mmol), HOBt (0.037 g) and EDC HCl (0.053 g, 0.274 mmol) in DMF (2 mL) was stirred at r.t. for 20 min. DIPEA (0.055 mL, 0.316 mmol) was added followed by a solution of 1-[3-(pyridin-2-yl)indolizin-2-yl]ethan-1-amine Q2 (0.050 g, 0.211 mmol) in DMF (0.5 mL) and the reaction was stirred at RT for 1 h. The mixture was partitioned between DCM and water and the aqueous phase was extracted with DCM. The combined organic layers were washed with brine and dried over sodium sulfate. The crude was purified by flash chromatography on Biotage silica-NH SNAP cartridge (cyclohexane to cyclohexane:EtOAc=80:20). The obtained material was treated with pentane, evaporated and triturated with Et₂O to afford title compound as a light yellow solid (0.037 g). MS/ESI⁺ 359.1 [MH]⁺, Rt 0.81 min (Method A).

¹H NMR (400 MHz, DMSO-$d_6$) δ ppm 9.01 (d, 1 H), 8.70-8.78 (m, 2 H), 8.21 (d, 1 H), 7.97 (td, 1 H), 7.83 (d, 1 H), 7.73 (d, 1 H), 7.39-7.62 (m, 3 H), 7.34-7.39 (m, 1 H), 6.81-6.87 (m, 1 H), 6.77 (s, 1 H), 6.58-6.66 (m, 1 H), 5.42-5.53 (m, 1 H), 1.52 (d, 3 H).

Example 55

3-amino-N-{[1-(pyridin-2-yl)indolizin-2-yl]methyl}pyrazine-2-carboxamide

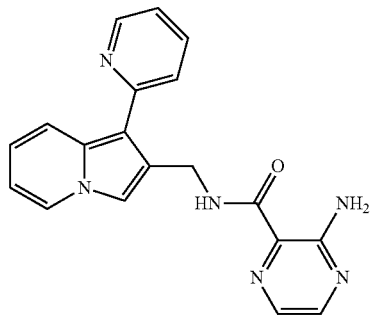 [SMILES: Nc1nccnc1C(=O)NCc1cn2ccccc2c1-c1ccccn1]

Prepared similarly to Example 54, starting from [1-(pyridin-2-yl)indolizin-2-yl]methanamine P9 (0.086 g, 0.385 mmol) and purified by flash chromatography on Biotage silica-NH SNAP cartridge (cyclohexane to cyclohexane:EtOAc=50:50) to afford title compound as a light yellow solid (0.079 g). MS/ESI⁺ 345.1 [MH]⁺, Rt 0.54 min (Method A).

¹H NMR (400 MHz, DMSO-$d_6$) δ ppm 9.60 (t, 1 H), 8.65-8.71 (m, 1 H), 8.34 (d, 1 H), 8.21 (d, 1 H), 7.79-7.93 (m, 3 H), 7.33-7.74 (m, 4 H), 7.19-7.25 (m, 1 H), 6.86-6.93 (m, 1 H), 6.62-6.69 (m, 1 H), 4.73 (d, 2 H).

Example 56

[4-amino-6-({1-[3-(pyridin-2-yl)indolizin-2-yl]ethyl}amino)pyrimidin-5-yl]methanol

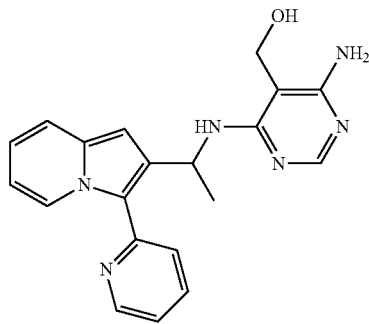 [SMILES: CC(Nc1ncnc(N)c1CO)c1cc2ccccn2c1-c1ccccn1]

To a solution of 4-amino-6-({1-[3-(pyridin-2-yl)indolizin-2-yl]ethyl}amino)pyrimidine-5-carbaldehyde of Example 47 (0.031 g) in MeOH (0.44 mL), NaBH₄ (0.005 g, 0.13 mmol) was added at 0° C. and the mixture was stirred for 1 h. The solvent was removed under reduced pressure and the crude was purified by flash chromatography on Biotage silica-NH SNAP cartridge (DCM to DCM:MeOH=97:3) to afford title compound as a white foamy solid (0.021 g). MS/ESI⁺ 359.1 [MH]⁺, Rt 0.81 min (Method A).

¹H NMR (400 MHz, DMSO-$d_6$) δ ppm 8.82 (d, 1 H), 8.71-8.75 (m, 1 H), 7.90 (td, 1 H), 7.83 (s, 1 H), 7.75 (d, 1 H), 7.49 (d, 1 H), 7.30-7.36 (m, 1 H), 6.79-6.86 (m, 1 H), 6.67 (s, 1 H), 6.57-6.64 (m, 1 H), 6.54 (d, 1 H), 5.94 (s, 2 H), 5.55-5.65 (m, 1 H), 4.94 (t, 1 H), 4.30-4.44 (m, 2 H), 1.45 (d, 3 H).

Example 57

5-(morpholin-4-ylmethyl)-4-N-{1-[3-(pyridin-2-yl)indolizin-2-yl]ethyl}pyrimidine-4,6-diamine

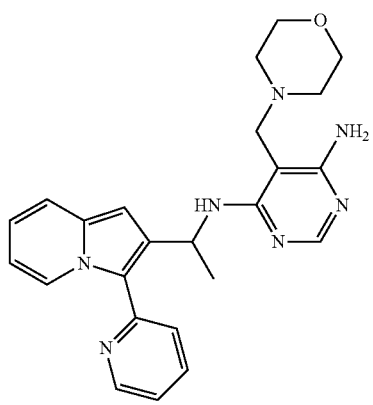 [SMILES: CC(Nc1ncnc(N)c1CN1CCOCC1)c1cc2ccccn2c1-c1ccccn1]

To a suspension of 4-amino-6-({1-[3-(pyridin-2-yl)indolizin-2-yl]ethyl}amino)pyrimidine-5-carbaldehyde of Example 47 (0.065 g) in DCM (4 mL), morpholine (0.024 mL, 0.272 mL) was added followed by a catalytic amount of acetic acid (pH≈6), and the resulting solution was stirred at r.t. for 20 minutes. Na(OAc)$_3$BH (0.077 g, 0.363 mmol) was added and the reaction was stirred at r.t overnight. The mixture was diluted with DCM and washed with aqueous sat. Na$_2$CO$_3$; the organic phase was dried over sodium sulfate and the solvent was removed. The crude was purified by flash chromatography on silica-NH Biotage SNAP cartridge (DCM:EtOAc=70:30 to 100% EtOAc) followed by flash chromatography on silica-NH cartridge (DCM:MeOH=99:1). A further purification by preparative TLC on silica NH (DCM:MeOH=97:3) was required to afford title compound as a pale yellow solid (0.007 g). MS/ESI$^+$ 430.1 [MH]$^+$, Rt 0.95 min (Method C).

$^1$H NMR (400 MHz, DMSO-d$_6$) δ ppm 8.84 (d, 1 H), 8.70-8.74 (m, 1 H), 7.84-7.90 (m, 2 H), 7.65 (d, 1 H), 7.50 (d, 1 H), 7.47-7.59 (m, 1 H), 7.28-7.34 (m, 1 H), 6.80-6.87 (m, 1 H), 6.68 (s, 1 H), 6.58-6.64 (m, 2 H), 6.16 (br. s., 2 H), 5.43-5.60 (m, 1 H), 3.41-3.52 (m, 4 H), 3.31 (s, 2 H), 2.22-2.42 (m, 4 H), 1.47 (d, 3 H).

Example 58

5-[(1E)-(hydroxyimino)methyl]-4-N-{1-[3-(pyridin-2-yl)indolizin-2-yl]ethyl}pyrimidine-4,6-diamine

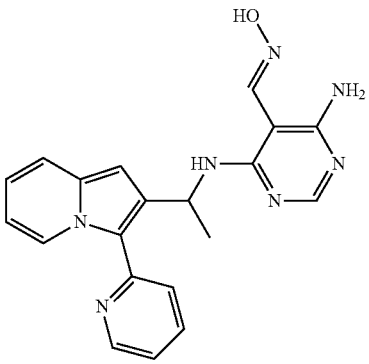 [SMILES: CC(Nc1ncnc(N)c1/C=N/O)c1cc2ccccn2c1-c1ccccn1]

To a solution of 4-amino-6-({1-[3-(pyridin-2-yl)indolizin-2-yl]ethyl}amino)pyrimidine-5-carbaldehyde of Example 47 (0.050 g) in EtOH (2 mL), pyridine (0.013 mL, 0.156 mmol) was added followed by hydroxylamine hydrochloride (0.011 g, 0.156 mmol) and the resulting mixture was stirred at r.t. overnight. The volatiles were removed under reduced pressure and the crude was partitioned between DCM and water. The organic layer was washed with brine and dried over sodium sulfate, the solvent removed under reduced pressure, the residue was dissolved in CH$_3$CN and dried under vacuum to afford title compound as a yellow solid (0.024 g). MS/ESI$^+$ 374.2 [MH]$^+$, Rt 0.57 min (Method A).

$^1$H NMR (400 MHz, DMSO-d$_6$) δ ppm 10.96 (s, 1 H), 8.80 (d, 1 H), 8.69-8.73 (m, 1 H), 8.51 (s, 1 H), 8.41 (d, 1 H), 7.83-7.90 (m, 2 H), 7.63 (d, 1 H), 7.50 (d, 1 H), 7.32 (dd, 1 H), 6.80-6.90 (m, 3 H), 6.57-6.66 (m, 2 H), 5.69 (t, 1H), 1.50 (d, 3 H).

Example 59

3-[4-amino-6-({1-[3-(pyridin-2-yl)indolizin-2-yl]ethyl}amino)pyrimidin-5-yl]prop-2-yn-1-ol

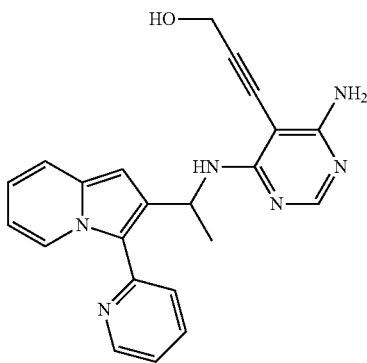 [SMILES: CC(Nc1ncnc(N)c1C#CCO)c1cc2ccccn2c1-c1ccccn1]

To a solution of 4-N-{1-[3-(pyridin-2-yl)indolizin-2-yl]ethyl}-5-(3-{[tris(propan-2-yl)silyl]oxy}prop-1-yn-1-yl)pyrimidine-4,6-diamine V (0.057 g, 0.10 mmol) in THF (0.5 mL), tetrabutylammonium fluoride 1M in THF (0.110 mL, 0.110 mmol) was added and the resulting mixture was stirred at room temperature for 30 minutes. The reaction was quenched with saturated aqueous NH₄Cl and extracted with DCM; the combined organic layers were dried over sodium sulfate, filtered and concentrated. The residue was dissolved in MeOH and charged on SCX cartridge (2 g), washing with MeOH. The product was eluted with 1M NH₃ in MeOH and the volatiles were removed under reduced pressure. The residue was purified by flash chromatography on 11 g Biotage silica-NH SNAP cartridge (DCM to DCM: MeOH=95:5) to afford title compound as a yellow solid (0.022 g). MS/ESI⁺ 385.3 [MH]⁺, Rt 0.56 min (Method A).

¹H NMR (400 MHz, DMSO-d₆) δ ppm 8.73-8.77 (m, 1 H), 8.70 (d, 1 H), 7.84-7.95 (m, 2 H), 7.72 (d, 1 H), 7.50 (d, 1 H), 7.31-7.37 (m, 1 H), 6.79-6.86 (m, 1 H), 6.58-6.72 (m, 3 H), 6.42 (br. s., 2 H), 5.59-5.71 (m, 1 H), 5.19 (t, 1 H), 4.36 (d, 2 H), 1.39 (d, 3 H).

Example 60

3-phenyl-1-{1-[3-(pyridin-2-yl)indolizin-2-yl]ethyl}-1H-pyrazolo[3,4-d]pyrimidin-4-amine

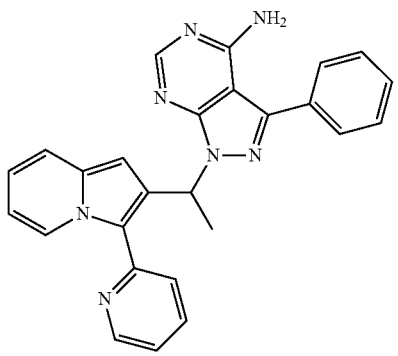 [SMILES: CC(c1cc2ccccn2c1-c1ccccn1)n1nc(-c2ccccc2)c2c(N)ncnc21]

A mixture of 3-iodo-1-{1-[3-(pyridin-2-yl)indolizin-2-yl]ethyl}-1H-pyrazolo[3,4-d]pyrimidin-4-amine W2 (0.030 g, 0.062 mmol), phenylboronic acid (8.4 mg, 0.062 mmol) and Pd(PPh₃)₄ (3.6 mg, 0.0031 mmol) in DME (4.5 mL), ethanol (0.65 mL) and saturated aqueous Na₂CO₃ (1.2 mL) was stirred at 80° C. overnight. The mixture was quenched with water and extracted with DCM; the combined organic layers were dried over sodium sulfate, filtered and concentrated. The residue was purified by flash chromatography on Biotage silica-NH SNAP cartridge (DCM to DCM: EtOAc=90:10) to afford title compound (8.0 mg). MS/ESI⁺ 432.3 [MH]⁺, Rt 0.86 min (Method A).

¹H NMR (400 MHz, DMSO-d6) δ ppm 8.70-8.74 (m, 1 H), 8.62 (dd, 1 H), 8.18 (s, 1 H), 7.91 (td, 1 H), 7.73-7.77 (m, 1 H), 7.65-7.69 (m, 2 H), 7.53-7.58 (m, 2 H), 7.46-7.52 (m, 2 H), 7.33-7.38 (m, 1 H), 6.73-6.82 (m, 1 H), 6.70 (s, 1 H), 6.56-6.61 (m, 1 H), 6.50 (q, 1 H), 6.09-7.13 (m, 2H), 1.92 (d, 3 H).

Example 61

3-(4-amino-1-{1-[3-(pyridin-2-yl)indolizin-2-yl]ethyl}-1H-pyrazolo[3,4-d]pyrimidin-3-yl)phenol

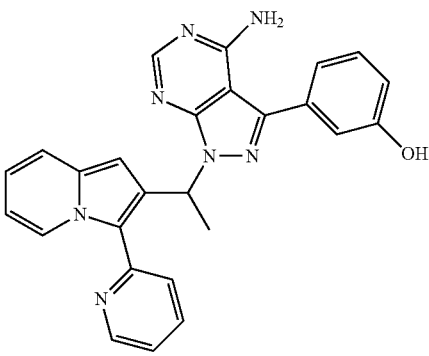 [SMILES: CC(c1cc2ccccn2c1-c1ccccn1)n1nc(-c2cccc(O)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.030, 0.063 mmol), 3-hydroxyphenylboronic acid (9.5 mg, 0.068 mmol) and Pd(PPh₃)₄ (3.6 mg, 0.0031 mmol), in DME (6.2 mL), EtOH (0.93 mL) and saturated aqueous Na₂CO₃ (1.76 mL), heating at 80° C. for 2 h. After work-up, the crude was purified by flash chromatography on Biotage silica-NH cartridge (DCM MeOH=99:1 to 95:5) to afford title compound (0.010 g). MS/ESI⁺ 432.3 [MH]⁺, Rt 0.86 min (Method A).

¹H NMR (400 MHz, DMSO-d₆) δ ppm 9.73 (s, 1 H), 8.71-8.75 (m, 1 H), 8.64 (d, 1 H), 8.18 (s, 1 H), 7.93 (td, 1 H), 7.76 (d, 1 H), 7.50 (d, 1 H), 7.31-7.40 (m, 2 H), 7.06-7.11 (m, 2 H), 6.86-6.90 (m, 1 H), 6.78-6.84 (m, 1 H), 6.69 (s, 1 H), 6.57-6.62 (m, 1 H), 6.49 (q, 1 H), 5.70-7.45 (m, 2H), 1.92 (d, 3 H).

Example 62

3-(3-fluoro-5-methoxyphenyl)-1-{1-[3-(pyridin-2-yl)indolizin-2-yl]ethyl}-1H-pyrazolo[3,4-d]pyrimidin-4-amine

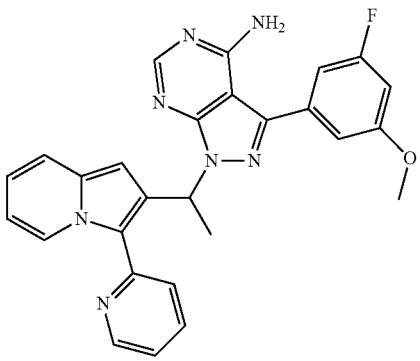 [SMILES: COc1cc(F)cc(-c2nn(C(C)c3cc4ccccn4c3-c3ccccn3)c3ncnc(N)c23)c1]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.030 g, 0.063 mmol), (3-fluoro-5-methoxyphenyl)boronic acid (0.012 g, 0.069 mmol) and Pd(PPh₃)₄ (4.0 mg, 0.0031 mmol), in DME (6.3 mL), EtOH (1 mL) and saturated aqueous Na₂CO₃ (1.7 mL), heating at 80° C. overnight. After work-up, the crude was purified by flash chromatography on silica Biotage cartridge (DCM to DCM:EtOAc=10:90). A further purification by reverse phase semi-preparative MDAP under acidic conditions (Method E) was required, followed by evaporation and filtration through a silica-NH cartridge eluting with DCM:MeOH=95:5 to afford title compound as a pale yellow solid (0.007 g). MS/ESI$^+$ 480.3 [MH]$^+$, Rt 0.96 min (Method A).

$^1$H NMR (400 MHz, DMSO-d$_6$) δ ppm 8.70-8.74 (m, 1 H), 8.61 (d, 1 H), 8.17 (s, 1 H), 7.91 (td, 1 H), 7.74 (d, 1 H), 7.49 (d, 1 H), 7.30-7.39 (m, 1 H), 6.98-7.05 (m, 2 H), 6.90-6.99 (m, 1 H), 6.77-6.82 (m, 1 H), 6.69 (s, 1 H), 6.54-6.63 (m, 1 H), 6.53-7.30 (m, 2H), 6.49 (q, 1 H), 3.85 (s, 3 H), 1.91 (d, 3 H)

Example 63

N-[3-(4-amino-1-{1-[3-(pyridin-2-yl)indolizin-2-yl]ethyl}-1H-pyrazolo[3,4-d]pyrimidin-3-yl)phenyl]acetamide

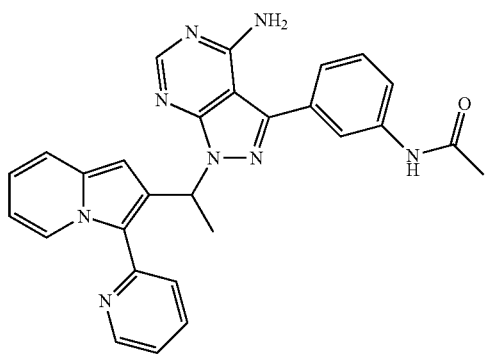 [SMILES: CC(=O)Nc1cccc(-c2nn(C(C)c3cc4ccccn4c3-c3ccccn3)c3ncnc(N)c23)c1]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.030 g, 0.063 mmol), 3-acetamidophenylboronic acid (0.012 g, 0.068 mmol) and Pd(PPh$_3$)$_4$ (3.6 mg, 0.0031 mmol), in DME (4.5 mL), EtOH (0.65 mL) and saturated aqueous Na$_2$CO$_3$ (1.2 mL), heating at 80° C. overnight. After work-up, the crude was purified by flash chromatography on Biotage silica-NH cartridge (DCM to DCM:MeOH=95:5) to afford title compound (5.0 mg). MS/ESI$^+$ 489.3 [MH]$^+$, Rt 0.74 min (Method A).

$^1$H NMR (400 MHz, DMSO-d$_6$) δ ppm 10.18 (s, 1 H), 8.71-8.75 (m, 1 H), 8.64 (d, 1 H), 8.19 (s, 1 H), 7.89-7.97 (m, 2 H), 7.77 (d, 1 H), 7.61-7.66 (m, 1 H), 7.45-7.53 (m, 2 H), 7.33-7.40 (m, 2 H), 6.77-6.85 (m, 1 H), 6.69 (s, 1 H), 6.57-6.63 (m, 1 H), 6.51 (q, 1 H), 6.00-8.00 (m, 2H), 2.10 (s, 3 H), 1.94 (d, 3 H).

Example 64

[3-(4-amino-1-{1-[3-(pyridin-2-yl)indolizin-2-yl]ethyl}-1H-pyrazolo[3,4-d]pyrimidin-3-yl)phenyl]methanol

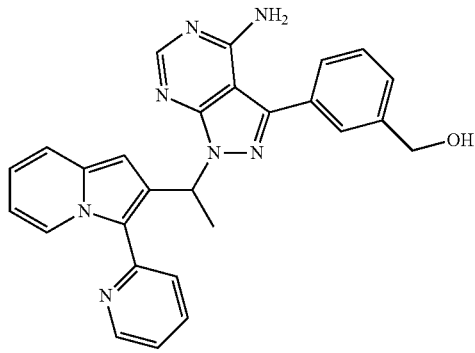 [SMILES: CC(c1cc2ccccn2c1-c1ccccn1)n1nc(-c2cccc(CO)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.060 g, 0.125 mmol), 3-(hydroxymethyl)phenylboronic acid (0.023 g, 0.150 mmol) and Pd(PPh$_3$)$_4$ (7.2 mg, 0.0062 mmol), in DME (9 mL), EtOH (1.3 mL) and saturated aqueous Na$_2$CO$_3$ (2.4 mL), heating at 80° C. overnight. After work-up, the crude was purified by flash chromatography on Biotage silica-NH cartridge (DCM to DCM:MeOH=90:10). A further purification by filtration on SCX cartridge, eluting with 1M ammonia in MeOH, was required to afford title compound (9.0 mg). MS/ESI$^+$ 462.3 [MH]$^+$, Rt 0.71 min (Method A).

$^1$H NMR (400 MHz, DMSO-d$_6$) δ ppm 8.72-9.76 (m, 1 H), 8.64 (d, 1 H), 8.19 (s, 1 H), 7.89-7.98 (m, 1 H), 7.77 (d, 1 H), 7.64 (s, 1 H), 7.48-7.55 (m, 3 H), 7.42-7.47 (m, 1 H), 7.33-7.40 (m, 1 H), 6.78-6.85 (m, 1 H), 6.70 (s, 1 H), 6.57-6.63 (m, 1 H), 6.52 (q, 1 H), 6.00-7.18 (m, 2H), 5.30 (t, 1 H), 4.62 (d, 2 H), 1.94 (d, 3 H).

Example 65

3-(4-amino-1-{1-[3-(pyridin-2-yl)indolizin-2-yl]ethyl}-1H-pyrazolo[3,4-d]pyrimidin-3-yl)-5-(trifluoromethyl)phenol

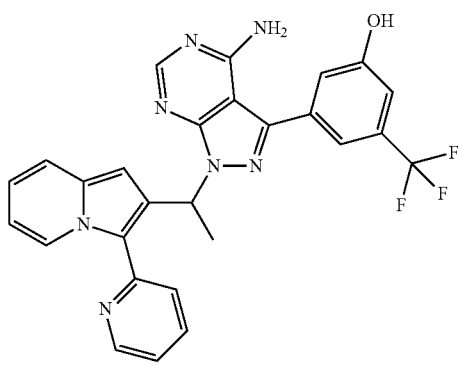 [SMILES: CC(c1cc2ccccn2c1-c1ccccn1)n1nc(-c2cc(O)cc(C(F)(F)F)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.060 g, 0.125 mmol), [3-hydroxy-5-(trifluoromethyl)phenyl]boronic acid (0.031 g, 0.150 mmol) and Pd(PPh₃)₄ (7.2 mg, 0.0062 mmol), in DME (9 mL), EtOH (1.3 mL) and saturated aqueous Na₂CO₃ (2.4 mL), heating at 80° C. overnight. After work-up, the crude was purified by flash chromatography on Biotage silica-NH cartridge (DCM to DCM:MeOH=70:30). A further purification by filtration on SCX cartridge, eluting with 1M ammonia in MeOH, was required to afford title compound (0.023 g). MS/ESI⁺ 516.0 [MH]⁺, Rt 0.94 min (Method A).

¹H NMR (400 MHz, DMSO-d₆) δ ppm 10.39 (br. s., 1 H), 8.70-8.74 (m, 1 H), 8.60-8.64 (m, 1 H), 8.20 (s, 1 H), 7.91 (td, 1 H), 7.75 (d, 1 H), 7.50 (d, 1 H), 7.30-7.40 (m, 3 H), 7.14 (s, 1 H), 6.77-6.85 (m, 1 H), 6.68 (s, 1 H), 6.56-7.30 (m, 2H), 6.57-6.63 (m, 1 H), 6.52 (q, 1 H), 1.94 (d, 3 H).

Example 66

3-(3-fluorophenyl)-1-{1-[3-(pyridin-2-yl)indolizin-2-yl]ethyl}-1H-pyrazolo[3,4-d]pyrimidin-4-amine

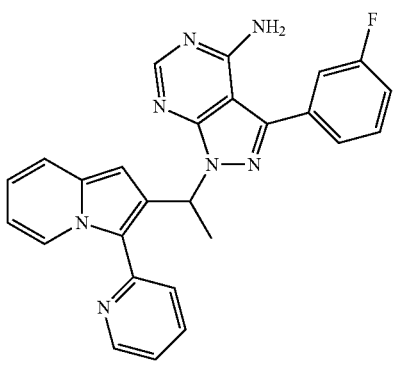 [SMILES: CC(c1cc2ccccn2c1-c1ccccn1)n1nc(-c2cccc(F)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.060 g, 0.125 mmol), 3-fluorophenylboronic acid (0.021 g, 0.150 mmol) and Pd(PPh₃)₄ (7.2 mg, 0.0062 mmol), in DME (9 mL), EtOH (1.3 mL) and saturated aqueous Na₂CO₃ (2.4 mL), heating at 80° C. overnight. After work-up, the crude was purified by flash chromatography on Biotage silica-NH cartridge (DCM to DCM:MeOH=98:2). A further purification by flash chromatography on silica-NH cartridge (DCM:EtOAc=90:10) was required to afford title compound (0.015 g). MS/ESI⁺ 450.3 [MH]⁺, Rt 0.92 min (Method A).

¹H NMR (400 MHz, DMSO-d₆) δ ppm 8.71-8.76 (m, 1 H), 8.63 (d, 1 H), 8.20 (s, 1 H), 7.93 (td, 1 H), 7.76 (d, 1 H), 7.57-7.64 (m, 1 H), 7.48-7.55 (m, 2 H), 7.43-7.48 (m, 1 H), 7.30-7.39 (m, 2 H), 6.78-6.84 (m, 1 H), 6.72 (s, 1 H), 6.57-6.64 (m, 1 H), 6.52 (q, 1 H), 6.25-7.30 (m, 2H), 1.94 (d, 3 H).

Example 67

N-[3-(4-amino-1-{1-[3-(pyridin-2-yl)indolizin-2-yl]ethyl}-1H-pyrazolo[3,4-d]pyrimidin-3-yl)phenyl]methanesulfonamide

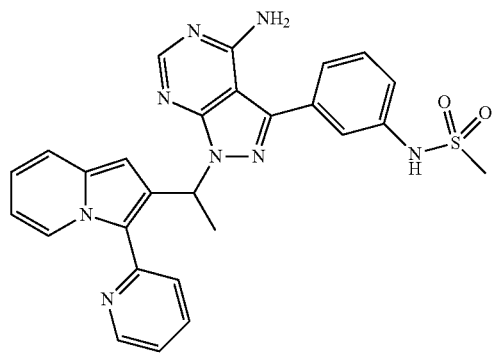 [SMILES: CC(c1cc2ccccn2c1-c1ccccn1)n1nc(-c2cccc(NS(C)(=O)=O)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.060 g, 0.125 mmol), (3-methanesulfonamidophenyl)boronic acid (0.032 g, 0.150 mmol) and Pd(PPh₃)₄ (7.2 mg, 0.0062 mmol), in DME (9 mL), EtOH (1.3 mL) and saturated aqueous Na₂CO₃ (2.4 mL), heating at 80° C. overnight. After work-up, the crude was purified by flash chromatography on Biotage silica-NH SNAP cartridge (DCM to DCM:MeOH=95:5). The obtained product was diluted with MeOH and the precipitate was collected by filtration; the filtrate solution was charged on SCX (1 g) cartridge washing with MeOH and the product was eluted with 1M ammonia in MeOH. This material was combined with the collected solid and evaporated, treated with CH₃CN and water and evaporated to afford title compound as a white solid (9 mg). MS/ESI⁺ 535.3 [MH]⁺, Rt 0.77 min (Method A).

¹H NMR (400 MHz, DMSO-d₆) δ ppm 9.93 (br. s., 1 H), 8.71-8.76 (m, 1 H), 8.63 (d, 1 H), 8.19 (s, 1 H), 7.90-7.96 (m, 1 H), 7.77 (d, 1 H), 7.46-7.57 (m, 3 H), 7.42 (d, 1 H), 7.31-7.40 (m, 2 H), 6.78-6.85 (m, 1 H), 6.71 (s, 1 H), 6.58-6.63 (m, 1 H), 6.51 (q, 1 H), 5.80-8.00 (m, 2H), 3.08 (s, 3 H), 1.94 (d, 3 H).

Example 68

1-{1-[3-(pyridin-2-yl)indolizin-2-yl]ethyl}-3-(pyridin-3-yl)-1H-pyrazolo[3,4-d]pyrimidin-4-amine

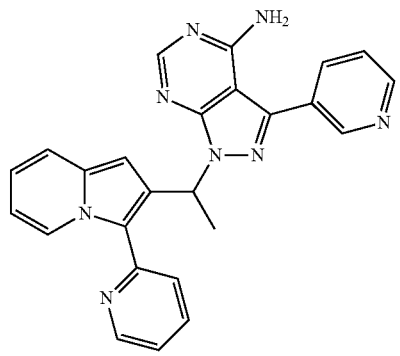 [SMILES: CC(c1cc2ccccn2c1-c1ccccn1)n1nc(-c2cccnc2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.060 g, 0.125 mmol), 3-pyridinylboronic acid (0.018 g, 0.150 mmol) and Pd(PPh$_3$)$_4$ (7.2 mg, 0.0062 mmol), in DME (9 mL), EtOH (1.3 mL) and saturated aqueous Na$_2$CO$_3$ (2.4 mL), heating at 80° C. overnight. After work-up, the crude was purified by flash chromatography on Biotage silica-NH SNAP cartridge (DCM to DCM:MeOH=90:10) to afford title compound (0.033 g). MS/ESI$^+$ 433.3 [MH]$^+$, Rt 0.65 min (Method A).

$^1$H NMR (400 MHz, DMSO-d$_6$) δ ppm 8.83-8.85 (m, 1 H), 8.70-8.74 (m, 1 H), 8.65-8.69 (m, 1 H), 8.60-8.64 (m, 1 H), 8.19 (s, 1 H), 8.01-8.06 (m, 1 H), 7.89-7.95 (m, 1 H), 7.75 (d, 1 H), 7.53-7.59 (m, 1 H), 7.49 (d, 1 H), 7.33-7.38 (m, 1 H), 6.77-6.83 (m, 1 H), 6.72 (s, 1 H), 6.64-7.25 (m, 2H), 6.56-6.62 (m, 1 H), 6.51 (q, 1 H), 1.93 (d, 3 H).

Example 69

5-(4-amino-1-{1-[3-(pyridin-2-yl)indolizin-2-yl]ethyl}-1H-pyrazolo[3,4-d]pyrimidin-3-yl)pyridin-3-ol

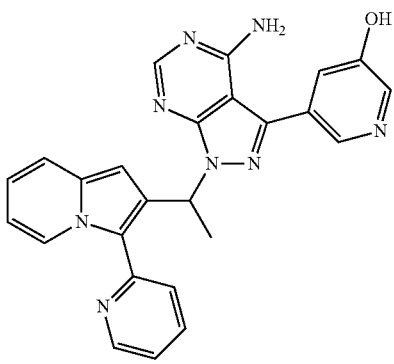 [SMILES: CC(c1cc2ccccn2c1-c1ccccn1)n1nc(-c2cncc(O)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.050 g, 0.104 mmol), 5-(tetramethyl-1,3,2-dioxaborolan-2-yl)pyridin-3-ol (0.028 g, 0.125 mmol) and Pd(PPh$_3$)$_4$ (6.0 mg, 0.0052 mmol), in DME (5 mL), EtOH (0.8 mL) and saturated aqueous Na$_2$CO$_3$ (1.2 mL), heating at 80° C. for 3 h. After work-up, the crude was purified by flash chromatography on Biotage silica-NH SNAP cartridge (DCM to DCM:MeOH=70:30) to afford title compound (0.0135 g). MS/ESI$^+$ 449.3 [MH]$^+$, Rt 0.63 min (Method A).

$^1$H NMR (400 MHz, DMSO-d$_6$) δ ppm 10.23 (br. s., 1 H), 8.71-8.76 (m, 1 H), 8.63 (d, 1 H), 8.31 (d, 1 H), 8.16-8.27 (m, 2 H), 7.93 (td, 1 H), 7.76 (d, 1 H), 7.50 (d, 1 H), 7.34-7.42 (m, 2 H), 6.94 (br. s., 2 H), 6.79-6.85 (m, 1 H), 6.71 (s, 1 H), 6.57-6.64 (m, 1 H), 6.52 (q, 1 H), 1.93 (d, 3 H).

Example 70

4-(4-amino-1-{1-[3-(pyridin-2-yl)indolizin-2-yl]ethyl}-1H-pyrazolo[3,4-d]pyrimidin-3-yl)-2-fluorophenol

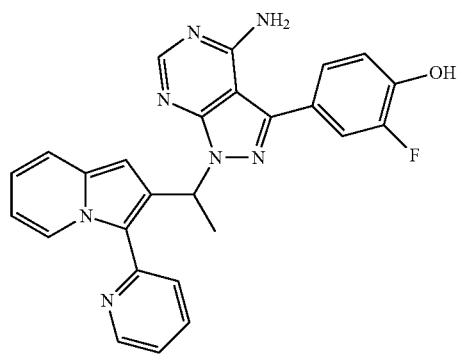 [SMILES: CC(c1cc2ccccn2c1-c1ccccn1)n1nc(-c2ccc(O)c(F)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.050 g, 0.104 mmol), (3-fluoro-4-hydroxyphenyl)boronic acid (0.019 g, 0.125 mmol) and Pd(PPh$_3$)$_4$ (6.0 mg, 0.0052 mmol), in DME (8 mL), EtOH (1.2 mL) and saturated aqueous Na$_2$CO$_3$ (2.2 mL), heating at 80° C. overnight. After work-up, the crude was purified by flash chromatography Biotage silica-NH SNAP cartridge (DCM to DCM:MeOH=70:30) to afford title compound (0.015 g). MS/ESI$^+$ 466.0 [MH]$^+$, Rt 0.75 min (Method A).

$^1$H NMR (400 MHz, DMSO-d$_6$) δ ppm 10.20 (br. s., 1 H), 8.71-8.77 (m, 1 H), 8.64 (d, 1 H), 8.17 (s, 1 H), 7.89-7.97 (m, 1 H), 7.76 (d, 1 H), 7.50 (d, 1 H), 7.24-7.44 (m, 3 H), 7.07-7.16 (m, 1 H), 6.77-6.86 (m, 1 H), 6.71 (s, 1 H), 6.56-6.64 (m, 1 H), 6.44-6.53 (m, 1 H), 6.25-7.22 (m, 2H), 1.92 (d, 3 H).

Example 71

5-(4-amino-1-{1-[3-(pyridin-2-yl)indolizin-2-yl]ethyl}-1H-pyrazolo[3,4-d]pyrimidin-3-yl)-2-fluorophenol

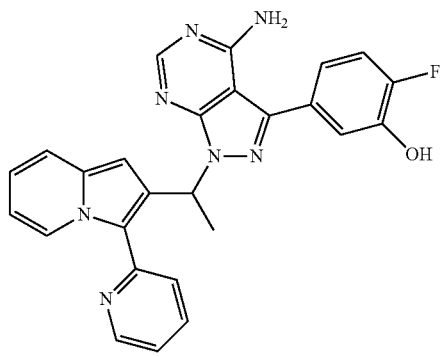 [SMILES: CC(c1cc2ccccn2c1-c1ccccn1)n1nc(-c2ccc(F)c(O)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.050 g, 0.104 mmol), (4-fluoro-3-hydroxyphenyl)boronic acid (0.019 g, 0.125 mmol) and Pd(PPh₃)₄ (6.0 mg, 0.0052 mmol), in DME (8 mL), EtOH (1.2 mL) and saturated aqueous Na₂CO₃ (2.2 mL), heating at 80° C. overnight. After work-up, the crude was purified by flash chromatography on Biotage silica-NH SNAP cartridge (DCM to DCM:MeOH=85:25) to afford title compound (0.012 g). MS/ESI⁺ 466.4 [MH]⁺, Rt 0.78 min (Method A).

¹H NMR (400 MHz, DMSO-d₆) δ ppm 10.15 (br. s., 1 H), 8.72-8.75 (m, 1 H), 8.64 (d, 1 H), 8.18 (s, 1 H), 7.92 (td, 1 H), 7.75 (d, 1 H), 7.50 (d, 1 H), 7.22-7.40 (m, 3 H), 7.04-7.09 (m, 1 H), 6.78-6.86 (m, 1 H), 6.69 (s, 1 H), 6.57-6.64 (m, 1 H), 6.49 (q, 1 H), 6.00-7.60 (m, 2H), 1.92 (d, 3 H).

Example 72

3-(4-amino-1-{1-[3-(pyridin-2-yl)indolizin-2-yl]ethyl}-1H-pyrazolo[3,4-d]pyrimidin-3-yl)-5-chlorophenol

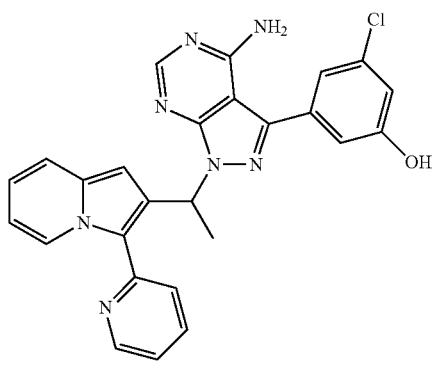

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.050 g, 0.104 mmol), (3-chloro-5-hydroxyphenyl)boronic acid (0.021 g, 0.125 mmol) and Pd(PPh₃)₄ (6.0 mg, 0.0052 mmol), in DME (8 mL), EtOH (1.2 mL) and saturated aqueous Na₂CO₃ (2.2 mL), heating at 80° C. overnight. After work-up, the crude was purified by flash chromatography on Biotage silica-NH SNAP cartridge (DCM to DCM:MeOH=90:10) to afford title compound (0.019 g). MS/ESI⁺ 482.0 [MH]⁺, Rt 0.87 min (Method A).

¹H NMR (400 MHz, DMSO-d₆) δ ppm 10.20 (br. s., 1 H), 8.71-8.75 (m, 1 H), 8.61-8.65 (m, 1 H), 8.19 (s, 1 H), 7.92 (td, 1 H), 7.75 (d, 1 H), 7.50 (d, 1 H), 7.34-7.39 (m, 1 H), 7.08-7.11 (m, 1 H), 7.00-7.04 (m, 1 H), 6.89-6.93 (m, 1 H), 6.78-6.85 (m, 1 H), 6.68 (s, 1 H), 6.57-6.64 (m, 1 H), 6.51 (q, 1 H), 6.41-7.45 (m, 2H), 1.92 (d, 3 H). NH₂ not clearly visible: broad signal in aromatic region (2 H).

Example 73

3-(4-amino-1-{1-[3-(pyridin-2-yl)indolizin-2-yl]ethyl}-1H-pyrazolo[3,4-d]pyrimidin-3-yl)benzene-1-sulfonamide

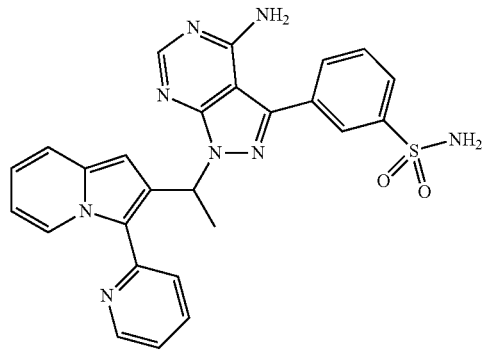 [SMILES: CC(c1cc2ccccn2c1-c1ccccn1)n1nc(-c2cccc(S(N)(=O)=O)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.060 g, 0.125 mmol), (3-sulfamoylphenyl)boronic acid (0.029 g, 0.144 mmol) and Pd(PPh₃)₄ (6.9 mg, 0.0060 mmol), in DME (12 mL), EtOH (1.8 mL) and saturated aqueous Na₂CO₃ (3.75 mL), heating at 80° C. overnight. After work-up, the crude was purified by flash chromatography on silica gel Biotage SNAP cartridge (DCM to DCM:MeOH=95:5) to afford title compound (0.015 g). MS/ESI⁺ 511.2 [MH]⁺, Rt 0.72 min (Method A).

¹H NMR (400 MHz, DMSO-d₆) δ ppm 8.71-8.74 (m, 1 H), 8.62 (d, 1 H), 8.20 (s, 1 H), 8.12-8.16 (m, 1 H), 7.89-7.97 (m, 2 H), 7.87 (d, 1 H), 7.71-7.80 (m, 2 H), 7.45-7.53 (m, 3 H), 7.33-7.40 (m, 1 H), 6.78-6.84 (m, 1 H), 6.68 (s, 1 H), 6.56-6.64 (m, 1 H), 6.53 (q, 1 H), 6.40-7.33 (m, 2H), 1.94 (d, 3 H).

Example 74

N-[3-(4-amino-1-{1-[3-(pyridin-2-yl)indolizin-2-yl]ethyl}-1H-pyrazolo[3,4-d]pyrimidin-3-yl)-5-fluorophenyl]methanesulfonamide

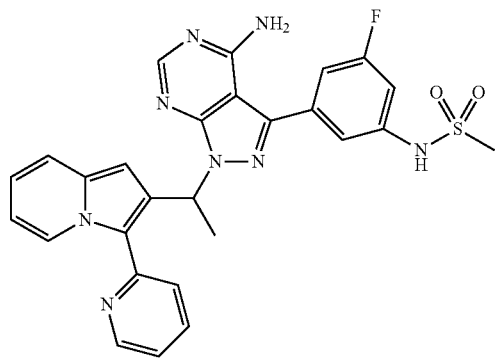 [SMILES: CC(c1cc2ccccn2c1-c1ccccn1)n1nc(-c2cc(F)cc(NS(C)(=O)=O)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.050 g, 0.104 mmol), N-[3-fluoro-5-(tetramethyl-1,3,2-dioxaborolan-2-yl)phenyl]methanesulfonamide T1 (0.052 g, 0.166 mmol) and Pd(PPh$_3$)$_4$ (6.0 mg, 0.0052 mmol), in DME (5 mL), EtOH (0.8 mL) and saturated aqueous Na$_2$CO$_3$ (1.2 mL), heating at 80° C. for 2 h. After work-up, the crude was purified by flash chromatography on silica-NH Biotage SNAP cartridge (DCM to DCM:MeOH=90:10) to afford title compound as a white solid (0.034 g). MS/ESI$^+$ 543.2 [MH]$^+$, Rt 0.84 min (Method A).

$^1$H NMR (400 MHz, DMSO-d$_6$) δ ppm 10.20 (br. s., 1 H), 8.70-8.73 (m, 1 H), 8.61 (d, 1 H), 8.18 (s, 1 H), 7.91 (td, 1 H), 7.74 (d, 1 H), 7.48 (d, 1 H), 7.32-7.38 (m, 1 H), 7.28-7.31 (m, 1 H), 7.06-7.17 (m, 2 H), 6.77-6.83 (m, 1 H), 6.69 (s, 1 H), 6.55-6.62 (m, 1 H), 6.49 (q, 1 H), 6.40-7.53 (m, 2H), 3.11 (s, 3 H), 1.92 (d, 3 H).

Example 75

3-(4-amino-1-{1-[3-(pyridin-2-yl)indolizin-2-yl]ethyl}-1H-pyrazolo[3,4-d]pyrimidin-3-yl)-5-fluorobenzene-1-sulfonamide

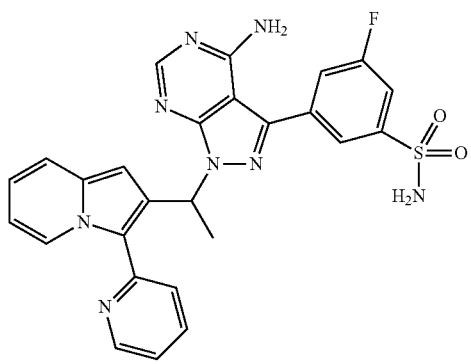 [SMILES: CC(c1cc2ccccn2c1-c1ccccn1)n1nc(-c2cc(F)cc(S(N)(=O)=O)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.050 g, 0.104 mmol), 3-fluoro-5-(tetramethyl-1,3,2-dioxaborolan-2-yl)benzene-1-sulfonamide T2 (0.050 g, 0.145 mmol) and Pd(PPh$_3$)$_4$ (6.0 mg, 0.0052 mmol), in DME (5 mL), EtOH (0.8 mL) and saturated aqueous Na$_2$CO$_3$ (1.2 mL), heating at 80° C. overnight. After work-up, the crude was purified by flash chromatography on 11 g silica-NH Biotage SNAP cartridge (DCM to DCM:MeOH=90:10) to afford title compound (0.014 g). MS/ESI$^+$ 529.2 [MH]$^+$, Rt 0.79 min. (Method A).

$^1$H NMR (400 MHz, DMSO-d$_6$) δ ppm 8.70-8.74 (m, 1 H), 8.59-8.63 (m, 1 H), 8.20 (s, 1 H), 7.96-7.99 (m, 1 H), 7.92 (td, 1 H), 7.75 (d, 1 H), 7.63-7.70 (m, 2 H), 7.61 (s, 2 H), 7.48 (d, 1 H), 7.33-7.39 (m, 1 H), 7.07 (br. s, 2 H), 6.78-6.84 (m, 1 H), 6.67 (s, 1 H), 6.56-6.62 (m, 1 H), 6.53 (q, 1 H), 1.94 (d, 3 H).

Example 76

3-(3-amino-5-fluorophenyl)-1-{1-[3-(pyridin-2-yl)indolizin-2-yl]ethyl}-1H-pyrazolo[3,4-d]pyrimidin-4-amine

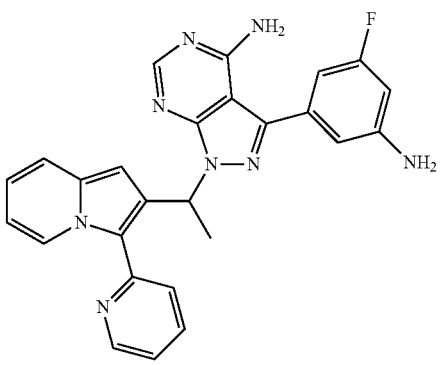 [SMILES: CC(c1cc2ccccn2c1-c1ccccn1)n1nc(-c2cc(N)cc(F)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.050 g, 0.104 mmol), 3-fluoro-5-(tetramethyl-1,3,2-dioxaborolan-2-yl)aniline T3 (0.030 g, 0.125 mmol) and Pd(PPh$_3$)$_4$ (6.0 mg, 0.0052 mmol), in DME (5 mL), EtOH (0.8 mL) and saturated aqueous Na$_2$CO$_3$ (1.2 mL), heating at 80° C. for 3 h. Additional 3-fluoro-5-(tetramethyl-1,3,2-dioxaborolan-2-yl)aniline T3 (10 mg) and Pd(PPh$_3$)$_4$ (6.0 mg, 0.0052 mmol) were added and the heating was continued for 1 h. After work-up, the crude was purified by flash chromatography on 11 g silica-NH Biotage SNAP cartridge (DCM to DCM:EtOAc=95:5) to afford title compound (0.011 g). MS/ESI$^+$ 465.3 [MH]$^+$, Rt 0.79 min (Method A).

$^1$H NMR (400 MHz, DMSO-d$_6$) δ ppm 8.72-8.76 (m, 1 H), 8.64 (d, 1 H), 8.18 (s, 1 H), 7.90-7.96 (m, 1 H), 7.75 (d, 1 H), 7.50 (d, 1 H), 7.34-7.39 (m, 1 H), 6.79-6.84 (m, 1 H), 6.67-6.72 (m, 2 H), 6.57-6.63 (m, 1 H), 6.41-6.54 (m, 3 H), 6.25-7.32 (m, 2H), 5.71 (s, 2 H), 1.92 (d, 3 H).

Example 77

3-(4-amino-1-{1-[3-(pyridin-2-yl)indolizin-2-yl]ethyl}-1H-pyrazolo[3,4-d]pyrimidin-3-yl)-5-hydroxybenzonitrile

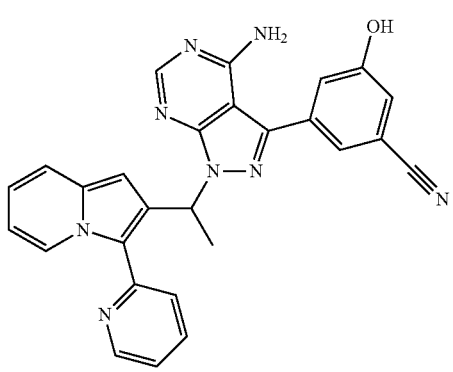 [SMILES: CC(c1cc2ccccn2c1-c1ccccn1)n1nc(-c2cc(O)cc(C#N)c2)c2c(N)ncnc21]

Prepared similarly to Example 60, starting from 3-iodo-1-{1-[3-(pyridin-2-yl)indolizin-2-yl]ethyl}-1H-pyrazolo[3,4-d]pyrimidin-4-amine W2 (0.060 g, 0.125 mmol), 3-hydroxy-5-(tetramethyl-1,3,2-dioxaborolan-2-yl)benzonitrile T4 (0.037 g, 0.150 mmol) and Pd(PPh$_3$)$_4$ (7.2 mg, 0.0063 mmol), in DME (9.5 mL), EtOH (2.9 mL) and saturated aqueous Na$_2$CO$_3$ (1.4 mL), heating at 80° C. overnight. After work-up, the crude was purified by flash chromatography on silica-NH Biotage SNAP cartridge (DCM to DCM:MeOH=90:10) to afford title compound (0.017 g). MS/ESI$^+$ 473.3 [MH]$^+$, Rt 0.81 min (Method A).

$^1$H NMR (400 MHz, DMSO-d$_6$) δ ppm 10.47 (s, 1 H), 8.71-8.75 (m, 1 H), 8.63 (d, 1 H), 8.19 (s, 1 H), 7.92 (td, 1 H), 7.75 (d, 1 H), 7.50 (d, 1 H), 7.44-7.47 (m, 1 H), 7.33-7.40 (m, 2 H), 7.22-7.26 (m, 1 H), 7.01 (br. s., 2 H), 6.79-6.85 (m, 1 H), 6.70 (s, 1 H), 6.57-6.64 (m, 1 H), 6.52 (q, 1 H), 1.93 (d, 3 H)

Example 78

3-[3-fluoro-5-(1H-1,2,3,4-tetrazol-5-yl)phenyl]-1-{1-[3-(pyridin-2-yl)indolizin-2-yl]ethyl}-1H-pyrazolo[3,4-d]pyrimidin-4-amine:ammonia 2:1

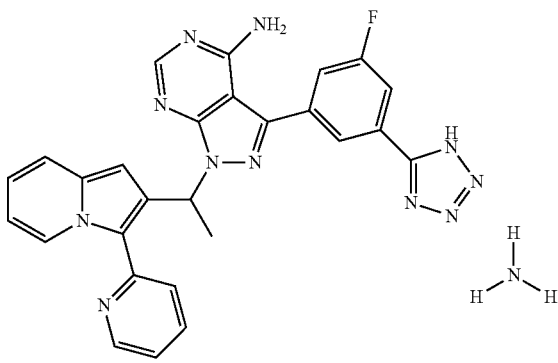

3-Iodo-1-{1-[3-(pyridin-2-yl)indolizin-2-yl]ethyl}-1H-pyrazolo[3,4-d]pyrimidin-4-amine W2 (0.100 g, 0.208 mmol) was split in two batches (0.050 g, 0.104 mmol each one). Both the batches were reacted with 5-[3-fluoro-5-(tetramethyl-1,3,2-dioxaborolan-2-yl)phenyl]-1H-1,2,3,4-tetrazole T6 (0.036 g, 0.125 mmol each one) and Pd(PPh$_3$)$_4$ (6.0 mg, 0.0052 mmol each one) in DME (5.0 mL each one), ethanol (0.8 mL each one) and saturated aqueous sodium carbonate (1.2 mL each one), at 80° C. overnight. Water was added and the mixtures were acidified to pH 5-6 with aqueous 1N HCl and extracted with DCM. The combined organic layers were dried over sodium sulfate, filtered and concentrated. One batch was purified by flash chromatography on 10 g silica gel Biotage SNAP cartridge (DCM to DCM:MeOH 90:10 with 0.01% formic acid). The obtained compound was mixed with the second crude and purified by flash chromatography on 10 g Biotage silica gel SNAP cartridge (DCM to DCM:MeOH=70:30). A further purification by reverse phase semi-preparative MDAP under basic conditions (Method F) was performed to obtain title compound (7.0 mg). MS/ESI$^+$ 518.4 [MH]$^+$, Rt 0.85 min (Method A).

$^1$H NMR (400 MHz, DMSO-d$_6$) δ ppm 8.73 (d, 1 H), 8.62 (d, 1 H), 8.20 (s, 1 H), 8.16 (t, 1 H), 7.93 (td, 1 H), 7.83-7.89 (m, 1 H), 7.76 (d, 1 H), 7.45-7.53 (m, 2 H), 7.33-7.38 (m, 1 H), 6.76-6.83 (m, 1 H), 6.70 (s, 1 H), 6.56-6.62 (m, 1 H), 6.53 (q, 1 H), 6.41-7.54 (m, 2H), 1.94 (d, 3 H).

Example 79

3-(4-amino-1-{1-[3-(pyridin-2-yl)indolizin-2-yl]ethyl}-1H-pyrazolo[3,4-d]pyrimidin-3-yl)-5-fluorophenol

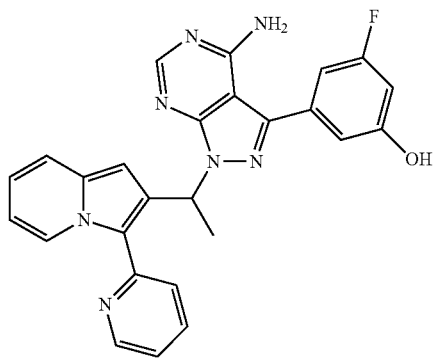 [SMILES: CC(c1cc2ccccn2c1-c1ccccn1)n1nc(-c2cc(O)cc(F)c2)c2c(N)ncnc21]

3-Iodo-1-{1-[3-(pyridin-2-yl)indolizin-2-yl]ethyl}-1H-pyrazolo[3,4-d]pyrimidin-4-amine W2 (0.465 g, 0.96 mmol) was equally divided in five vials. Each one was reacted with (3-fluoro-5-hydroxyphenyl)boronic acid (0.0374 g, 0.24 mmol), Pd(PPh$_3$)$_4$ (0.011 g, 0.0094 mmol), DME (18.7 ml), ethanol (2.8 ml) and saturated aqueous sodium carbonate (5.3 ml) at 80° C. overnight. Then they were collected and quenched in water and finally extracted with DCM. The combined organic layers were dried over sodium sulfate, filtered and concentrated. The residue was purified by flash chromatography on Biotage silica-NH SNAP cartridge (DCM:MeOH=98:2 to 94:6) to afford title compound (0.265 g). MS/ESI$^+$ 466.3 [MH]$^+$, Rt 0.81 min (Method A).

$^1$H NMR (400 MHz, DMSO-d$_6$) δ ppm 10.17 (br. s., 1 H), 8.69-8.75 (m, 1 H), 8.59-8.65 (m, 1 H), 8.17 (s, 1 H), 7.91 (td, 1 H), 7.74 (d, 1 H), 7.49 (d, 1 H), 7.32-7.38 (m, 1 H), 6.89-6.93 (m, 1 H), 6.77-6.89 (m, 2 H), 6.63-6.70 (m, 2 H), 6.56-6.62 (m, 1 H), 6.49 (q, 1 H), 6.40-7.46 (m, 2H), 1.91 (d, 3 H).

Example 80 (Enantiomer 1) and Example 81 (Enantiomer 2)

3-(4-amino-1-{1-[3-(pyridin-2-yl)indolizin-2-yl]ethyl}-1H-pyrazolo[3,4-d]pyrimidin-3-yl)-5-fluorophenol single enantiomers

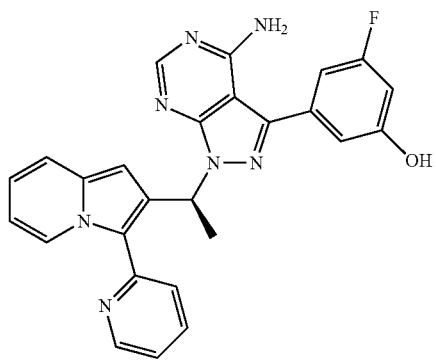

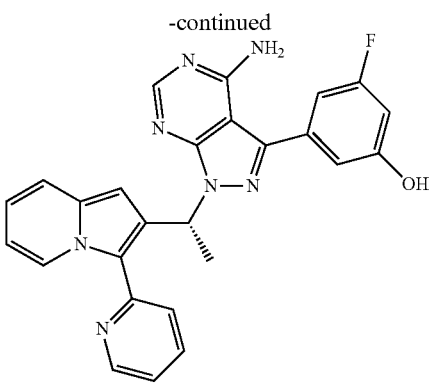

Racemate 3-(4-amino-1-{1-[3-(pyridin-2-yl)indolizin-2-yl]ethyl}-1H-pyrazolo[3,4-d]pyrimidin-3-yl)-5-fluorophenol described in Example 79 (0.260 g) was dissolved in EtOH/MeOH 1/1 (38 mL) and submitted to chiral resolution by Chiral preparative liquid chromatography. Conditions: Column: Chiralpak AD-H (25×2.0 cm); Mobile phase: n-Hexane/(Ethanol+0.1% isopropylamine) 80/20 v/v; UV detection: 220 nM; Flow Rate: 13 mL/min; Injection: 20.4 mg.

Compound 80 was obtained as the first eluted enantiomer as a yellow solid (0.095 g). MS/ESI$^+$ 466.3 [MH]$^+$, Rt 0.82 min (Method A). Chiral HPLC Method H: Rt.=8.2 min, ee>99%

$^1$H NMR (400 MHz, DMSO-d$_6$) δ ppm 10.21 (br. s., 1 H), 8.69-8.75 (m, 1 H), 8.60-8.66 (m, 1 H), 8.18 (s, 1 H), 7.92 (td, 1 H), 7.75 (d, 1 H), 7.50 (d, 1 H), 7.32-7.39 (m, 1 H), 6.90-6.94 (m, 1 H), 6.78-6.90 (m, 2 H), 6.64-6.71 (m, 2 H), 6.56-6.62 (m, 1 H), 6.49 (q, 1 H), 6.40-7.46 (m, 2H), 1.91 (d, 3 H).

Compound 81 was obtained as the second eluted enantiomer as a yellow solid (0.095 g). MS/ESI$^+$ 466.4 [MH]$^+$, Rt 0.82 min (Method A). Chiral HPLC Method H: Rt.=13.2 min, ee>99%

$^1$H NMR (400 MHz, DMSO-d$_6$) δ ppm 10.21 (br. s., 1 H), 8.70-8.75 (m, 1 H), 8.60-8.66 (m, 1 H), 8.18 (s, 1 H), 7.92 (td, 1 H), 7.75 (d, 1 H), 7.50 (d, 1 H), 7.32-7.39 (m, 1 H), 6.90-6.94 (m, 1 H), 6.77-6.89 (m, 2 H), 6.64-6.71 (m, 2 H), 6.56-6.63 (m, 1 H), 6.49 (q, 1 H), 6.40-7.46 (m, 2H), 1.91 (d, 3 H).

Example 82

3-(4-amino-1-{1-[3-(pyridin-4-yl)indolizin-2-yl]ethyl}-1H-pyrazolo[3,4-d]pyrimidin-3-yl)-5-fluorophenol

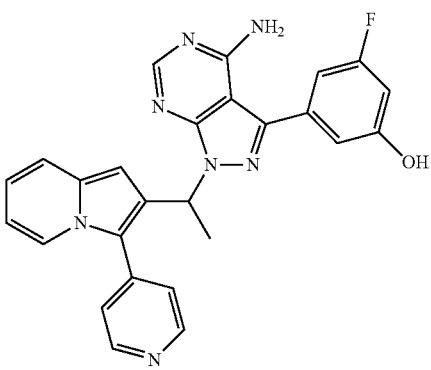 [SMILES: CC(c1cc2ccccn2c1-c1ccncc1)n1nc(-c2cc(O)cc(F)c2)c2c(N)ncnc21]

3-Iodo-1-{1-[3-(pyridin-4-yl)indolizin-2-yl]ethyl}-1H-pyrazolo[3,4-d]pyrimidin-4-amine W4 (0.216 g, 0.45 mmol) was split in two vials (0.108 g each one); each one was reacted with (3-fluoro-5-hydroxyphenyl)boronic acid (0.0455 g, 0.29 mmol each one), Pd(PPh$_3$)$_4$ (0.013 g, 0.011 mmol each one), DME (15.4 mL each one), ethanol (2.3 mL each one) and saturated aqueous sodium carbonate (4.2 mL each one) at 80° C. overnight. Then, they were collected and quenched with water and extracted with DCM. The combined organic layers were dried over sodium sulfate, filtered and concentrated. The residue was purified by flash chromatography on 28 g Biotage silica-NH SNAP cartridge (DCM to DCM:MeOH=90:10) to afford title compound (0.100 g). MS/ESI$^+$ 466.3 [MH]$^+$, Rt 0.68 min (Method A).

$^1$H NMR (400 MHz, DMSO-d$_6$) δ ppm 10.18 (br. s., 1 H), 8.62-8.68 (m, 2 H), 8.19 (s, 1 H), 8.07 (d, 1 H), 7.48-7.55 (m, 3 H), 6.89-6.93 (m, 1 H), 6.77-6.88 (m, 2 H), 6.76 (s, 1 H), 6.64-6.70 (m, 1 H), 6.55-6.62 (m, 1 H), 6.30 (q, 1 H), 6.20-7.46 (m, 2H), 1.90 (d, 3 H)

Example 83 (Enantiomer 1) and Example 84 (Enantiomer 2)

3-(4-amino-1-{1-[3-(pyridin-4-yl)indolizin-2-yl]ethyl}-1H-pyrazolo[3,4-d]pyrimidin-3-yl)-5-fluorophenol single enantiomers

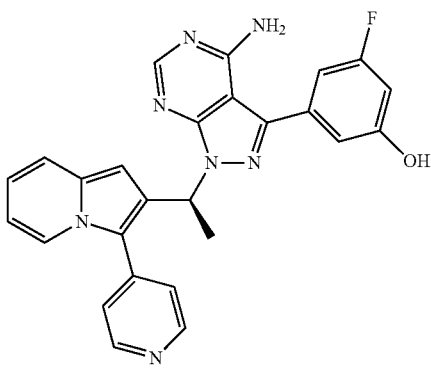

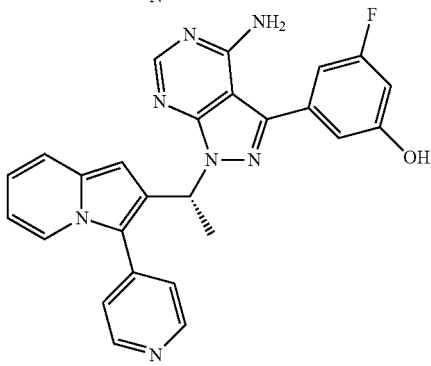

Racemate 3-(4-amino-1-{1-[3-(pyridin-4-yl)indolizin-2-yl]ethyl}-1H-pyrazolo[3,4-d]pyrimidin-3-yl)-5-fluorophenol described in Example 82 (0.100 g) was dissolved in EtOH (60 mL) and submitted to chiral resolution by Chiral preparative liquid chromatography. Conditions: Column: Chiralpak IC (25×2.0 cm), 5 μm; Mobile phase: n-Hexane/(2-Propanol+0.1% isopropylamine) 60/40% v/v; UV detection: 220 nM; Flow Rate: 16 mL/min; Injection: 8.3 mg.

Compound 83 was obtained as the first eluted enantiomer as a pale yellow powder (0.030 g). MS/ESI+ 466.4 [MH]+, Rt 0.68 min (Method A). Chiral HPLC Method I: Rt=6.8 min, 95.2% ee.

$^1$H NMR (400 MHz, DMSO-d$_6$) δ ppm 10.19 (br. s., 2 H), 8.62-8.69 (m, 2 H), 8.19 (s, 1 H), 8.07 (d, 1 H), 7.48-7.55 (m, 3 H), 6.89-6.93 (m, 1 H), 6.77-6.88 (m, 2 H), 6.76 (s, 1 H), 6.64-6.71 (m, 1 H), 6.55-6.62 (m, 1 H), 6.30 (q, 1 H), 6.20-7.47 (m, 2H), 1.89 (d, 3 H).

Compound 84 was obtained as the second eluted enantiomer as a pale yellow powder (0.032 g). MS/ESI+ 466.3 [MH]+, Rt 0.69 min (Method A). Chiral HPLC Method I: Rt=8.7 min, 97.8% ee.

$^1$H NMR (400 MHz, DMSO-d$_6$) δ ppm 10.19 (br. s., 1 H), 8.62-8.68 (m, 2 H), 8.19 (s, 1 H), 8.06 (d, 1 H), 7.48-7.55 (m, 3 H), 6.88-6.93 (m, 1 H), 6.77-6.88 (m, 2 H), 6.76 (s, 1 H), 6.64-6.71 (m, 1 H), 6.55-6.62 (m, 1 H), 6.30 (q, 1 H), 6.20-7.47 (m, 2H), 1.89 (d, 3 H).

Example 85

3-{4-amino-1-[1-(3-phenylindolizin-2-yl)ethyl]-1H-pyrazolo[3,4-d]pyrimidin-3-yl}-5-fluorophenol

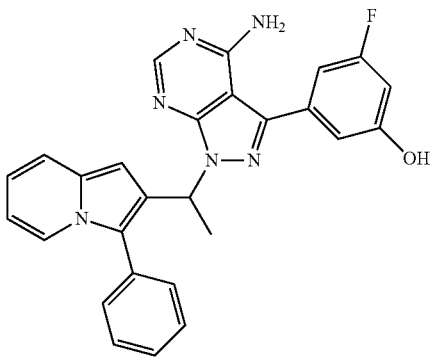 [SMILES: CC(c1cc2ccccn2c1-c1ccccc1)n1nc(-c2cc(O)cc(F)c2)c2c(N)ncnc21]

A mixture of 3-iodo-1-[1-(3-phenylindolizin-2-yl)ethyl]-1H-pyrazolo[3,4-d]pyrimidin-4-amine W1 (0.110 g, 0.23 mmol), (3-fluoro-5-hydroxyphenyl)boronic acid (0.040 g, 0.25 mmol) and Pd(PPh$_3$)$_4$ (14.4 mg, 0.012 mmol), in DME (9.5 mL), EtOH (1.66 mL) and saturated aqueous Na$_2$CO$_3$ (3.2 mL) was heated at 80° C. for 2 h. The mixture was partitioned between water and DCM, the aqueous phase was extracted with DCM and the combined organic layers were washed with brine and dried over sodium sulfate. The solvent was removed under reduced pressure and the residue was purified by flash chromatography on 28 g silica-NH Biotage SNAP cartridge (DCM:MeOH=99:1 to 80:20) to afford title compound as a white solid (0.077 g). MS/ESI+ 465.3 [MH]+, Rt 1.09 min (Method A).

$^1$H NMR (400 MHz, DMSO-d$_6$) δ ppm 10.17 (br. s., 1 H), 8.16 (s, 1 H), 7.83 (d, 1 H), 7.38-7.54 (m, 6 H), 6.91 (br. s., 1 H), 6.81-6.89 (m, 1 H), 6.62-6.74 (m, 3 H), 6.46-6.53 (m, 1 H), 6.26-7.37 (m, 2H), 6.21 (q, 1 H), 1.84 (d, 3 H).

Example 86

3-(4-amino-1-{1-[3-(2-fluorophenyl)indolizin-2-yl]ethyl}-1H-pyrazolo[3,4-d]pyrimidin-3-yl)-5-fluorophenol

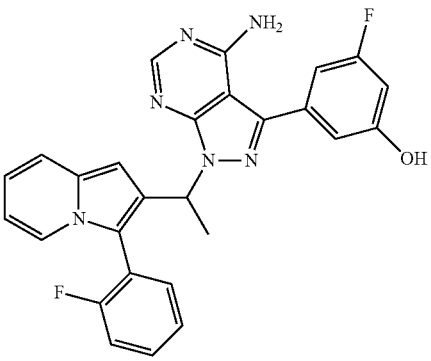 [SMILES: CC(c1cc2ccccn2c1-c1ccccc1F)n1nc(-c2cc(O)cc(F)c2)c2c(N)ncnc21]

Prepared similarly to Example 85, starting from 1-{1-[3-(2-fluorophenyl)indolizin-2-yl]ethyl}-3-iodo-1H-pyrazolo[3,4-d]pyrimidin-4-amine W3 (0.114 g), (3-fluoro-5-hydroxyphenyl)boronic acid (0.039 g, 0.251 mmol) and Pd(PPh$_3$)$_4$ (0.013 g, 0.0114 mmol), in DME (9.4 mL), EtOH (1.6 mL) and saturated aqueous Na$_2$CO$_3$ (3.2 mL), heating at 80° C. for 3 h. After work-up the crude was purified by flash chromatography on silica-NH Biotage SNAP cartridge (DCM:MeOH=98:2 to 80:20) to afford title compound as a white solid (0.020 g). MS/ESI+ 483.0 [MH]+, Rt 1.03 min (Method A).

$^1$H NMR (400 MHz, DMSO-d$_6$) δ ppm 10.12-10.18 (m, 1 H), 8.02-8.18 (m, 1 H), 7.16-7.62 (m, 6 H), 6.49-6.95 (m, 6 H), 6.09-6.25 (m, 1 H), 6.00-7.5 (m, 2H), 1.76-1.95 (M, 3 H)

Example 87

3-(4-amino-1-{1-[6-methyl-3-(pyridin-2-yl)indolizin-2-yl]ethyl}-1H-pyrazolo[3,4-d]pyrimidin-3-yl)-5-fluorophenol

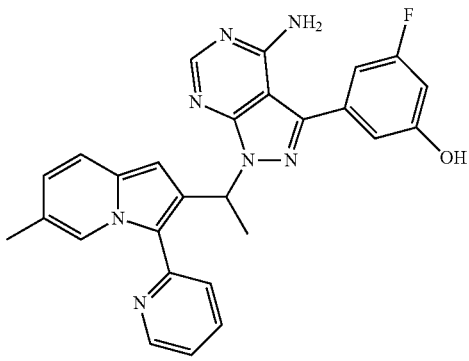 [SMILES: Cc1ccc2cc(C(C)n3nc(-c4cc(O)cc(F)c4)c4c(N)ncnc43)c(-c3ccccn3)n2c1]

Prepared similarly to Example 85, starting from crude 3-iodo-1-{1-[6-methyl-3-(pyridin-2-yl)indolizin-2-yl]ethyl}-1H-pyrazolo[3,4-d]pyrimidin-4-amine W5 (0.130 g), (3-fluoro-5-hydroxyphenyl)boronic acid (0.041 g, 0.26 mmol) and Pd(PPh$_3$)$_4$ (0.015 g, 0.013 mmol), in DME (15 mL), EtOH (2.6 mL) and saturated aqueous Na₂CO₃ (4 mL), heating at 80° C. overnight. After work-up the crude was purified by flash chromatography on 11 g silica-NH Biotage SNAP cartridge (DCM to DCM:MeOH=90:10) to afford title compound as an off-white solid (0.012 g). MS/ESI⁺ 480.3 [MH]⁺, Rt 0.88 min (Method A).

¹H NMR (400 MHz, DMSO-d₆) δ ppm 10.19 (s, 1 H), 8.70-8.74 (m, 1 H), 8.39 (s, 1 H), 8.16 (s, 1 H), 7.89 (td, 1 H), 7.70 (d, 1 H), 7.41 (d, 1 H), 7.31-7.37 (m, 1 H), 6.89-6.92 (m, 1 H), 6.82-6.88 (m, 1 H), 6.60-6.71 (m, 3 H), 6.45 (q, 1 H), 6.22-7.30 (m, 2H), 2.15 (s, 3 H), 1.88 (d, 3 H).

Example 88

3-(4-amino-1-{1-[3-(pyridin-2-yl)-6-(trifluoromethyl)indolizin-2-yl]ethyl}-1H-pyrazolo[3,4-d]pyrimidin-3-yl)-5-fluorophenol

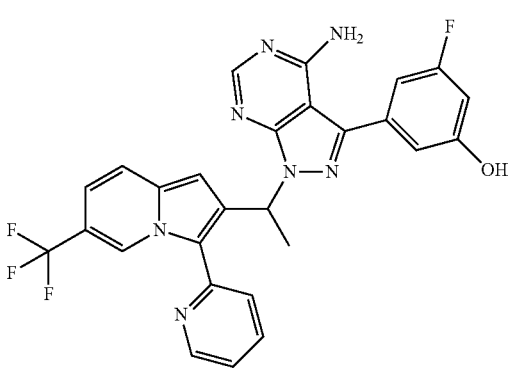 [SMILES: CC(c1cc2ccc(C(F)(F)F)cn2c1-c1ccccn1)n1nc(-c2cc(O)cc(F)c2)c2c(N)ncnc21]

Prepared similarly to Example 85, starting from 3-iodo-1-{1-[3-(pyridin-2-yl)-6-(trifluoromethyl)indolizin-2-yl]ethyl}-1H-pyrazolo[3,4-d]pyrimidin-4-amine W6 (0.085 g, 0.155 mmol), (3-fluoro-5-hydroxyphenyl)boronic acid (0.029 g, 0.186 mmol) and Pd(PPh₃)₄ (9 mg, 0.008 mmol), in DME (7.0 mL), EtOH (1.1 mL) and saturated aqueous Na₂CO₃ (1.7 mL), heating at 80° C. for 3 h. Additional (3-fluoro-5-hydroxyphenyl)boronic acid (0.029 g, 0.186 mmol) and Pd(PPh₃)₄ (9 mg, 0.008 mmol) were added and the heating was continued overnight. After work-up the crude was purified by flash chromatography on 11 g silica-NH Biotage SNAP cartridge (DCM to DCM:MeOH=95:5) to afford title compound as an off-white solid (20.5 mg). MS/ESI⁺ 534.3 [MH]⁺, Rt 1.09 min (Method A).

¹H NMR (400 MHz, DMSO-d₆) δ ppm 10.22 (br. s., 1 H), 9.09 (br. s., 1 H), 8.75-8.81 (m, 1 H), 8.20 (s, 1 H), 7.97 (td, 1 H), 7.85 (d, 1 H), 7.75 (d, 1 H), 7.40-7.46 (m, 1 H), 6.98-7.04 (m, 1 H), 6.90-6.95 (m, 2 H), 6.84-6.90 (m, 1 H), 6.65-6.71 (m, 1 H), 6.51 (q, 1 H), 6.40-7.40 (m, 2H), 1.94 (d, 3 H).

Example 89

3-(4-amino-1-{1-[1-methyl-3-(pyridin-2-yl)indolizin-2-yl]ethyl}-1H-pyrazolo[3,4-d]pyrimidin-3-yl)-5-fluorophenol

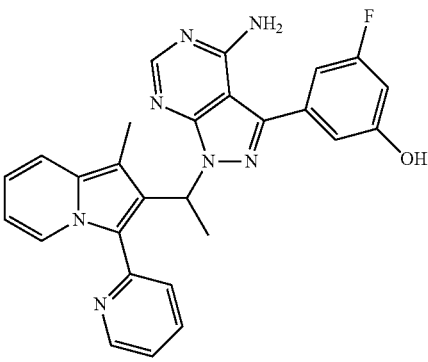 [SMILES: Cc1c(C(C)n2nc(-c3cc(O)cc(F)c3)c3c(N)ncnc32)c(-c2ccccn2)n2ccccc12]

Prepared similarly to Example 85, starting from crude 3-iodo-1-{1-[1-methyl-3-(pyridin-2-yl)indolizin-2-yl]ethyl}-1H-pyrazolo[3,4-d]pyrimidin-4-amine W7 (0.106 g), (3-fluoro-5-hydroxyphenyl)boronic acid (0.0233 g, 0.15 mmol) and Pd(PPh₃)₄ (6.6 mg, 0.005 mmol), in DME (7.0 mL), EtOH (1.3 mL) and saturated aqueous Na₂CO₃ (2 mL), heating at 80° C. overnight. After work-up the crude was purified by flash chromatography on silica-NH Biotage SNAP cartridge (DCM:MeOH=99:1 to 95:5) to afford title compound (4.0 mg). MS/ESI⁺ 480.0 [MH]⁺, Rt 81 min (Method A).

¹H NMR (400 MHz, DMSO-d₆) δ ppm 10.20 (br. s., 1 H), 8.74-8.78 (m, 1 H), 8.32 (d, 1 H), 8.11 (s, 1 H), 7.95 (td, 1 H), 7.81 (d, 1 H), 7.46 (d, 1 H), 7.37-7.43 (m, 1 H), 6.92-6.96 (m, 1 H), 6.83-6.89 (m, 1 H), 6.71-6.77 (m, 1 H), 6.63-6.71 (m, 1 H), 6.48-6.56 (m, 1 H), 6.38-6.46 (m, 1 H), 6.36-7.36 (m, 2H), 2.39 (s, 3 H), 1.94 (d, 3 H).

Example 90

3-[4-amino-1-(1-{3-[5-(morpholin-4-ylmethyl)thiophen-2-yl]indolizin-2-yl}ethyl)-1H-pyrazolo[3,4-d]pyrimidin-3-yl]-5-fluorophenol

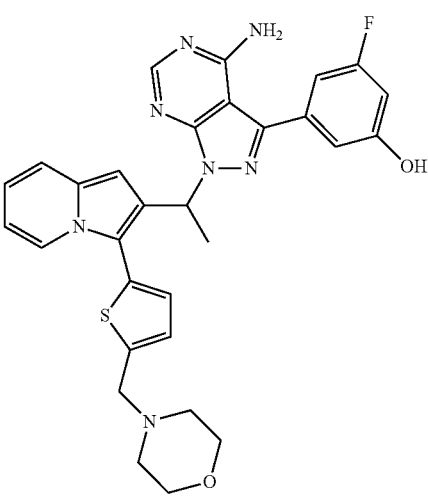 [SMILES: CC(c1cc2ccccn2c1-c1ccc(CN2CCOCC2)s1)n1nc(-c2cc(O)cc(F)c2)c2c(N)ncnc21]

Prepared similarly to Example 85, starting from crude 3-iodo-1-(1-{3-[5-(morpholin-4-ylmethyl)thiophen-2-yl]indolizin-2-yl}ethyl)-1H-pyrazolo[3,4-d]pyrimidin-4-amine W8 (0.325 g), (3-fluoro-5-hydroxyphenyl)boronic acid (0.095 g, 0.61 mmol) and Pd(PPh$_3$)$_4$ (0.032 g, 0.027 mmol), in DME (20 mL), EtOH (3.8 mL) and saturated aqueous Na$_2$CO$_3$ (7.6 mL), heating at 80° C. for 4 h. After work-up the crude was purified by flash chromatography on Biotage silica-NH SNAP cartridge (DCM to DCM:MeOH=94:6) to afford title compound as a white solid (0.074 g). MS/ESI$^+$ 570.2 [MH]$^+$, Rt 1.02 min (Method C).

$^1$H NMR (400 MHz, DMSO-d$_6$) δ ppm 10.15 (s, 1 H), 8.13 (s, 1 H), 7.94 (d, 1 H), 7.46 (d, 1 H), 7.03 (d, 1 H), 6.99 (d, 1 H), 6.87-6.91 (m, 1 H), 6.80-6.86 (m, 1 H), 6.71-6.78 (m, 1 H), 6.61-6.68 (m, 2 H), 6.56-6.61 (m, 1 H), 6.50-7.43 (m, 2H), 6.30 (q, 1 H), 3.63-3.73 (m, 2 H), 3.52-3.61 (m, 4 H), 2.35-3.45 (m, 4 H), 1.85 (d, 3 H).

Example 91

3-[4-amino-1-(1-{3-[4-(morpholin-4-ylmethyl)phenyl]indolizin-2-yl}ethyl)-1H-pyrazolo[3,4-d]pyrimidin-3-yl]-5-fluorophenol

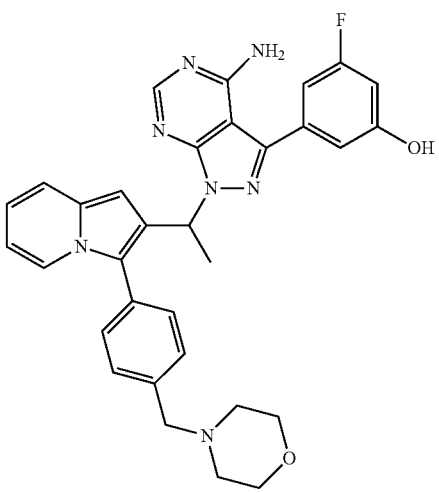 [SMILES: CC(c1cc2ccccn2c1-c1ccc(CN2CCOCC2)cc1)n1nc(-c2cc(O)cc(F)c2)c2c(N)ncnc21]

Prepared similarly to Example 85, starting from 3-iodo-1-(1-{3-[4-(morpholin-4-ylmethyl)phenyl]indolizin-2-yl}ethyl)-1H-pyrazolo[3,4-d]pyrimidin-4-amine W9 (0.320 g, (3-fluoro-5-hydroxyphenyl)boronic acid (0.094 g, 0.60 mmol) and Pd(PPh$_3$)$_4$ (0.032 g, 0.027 mmol), in DME (21 mL), EtOH (3.9 mL) and saturated aqueous Na$_2$CO$_3$ (7.5 mL), heating at 80° C. for 4 h. After work-up the crude was purified by flash chromatography on 11 g Biotage silica-NH SNAP cartridge (DCM to DCM:MeOH=95:5) to afford title compound as a pale yellow solid (0.057 g). MS/ESI$^+$ 564.0 [MH]$^+$, Rt 3.89 min (Method D).

$^1$H NMR (400 MHz, DMSO-d$_6$) δ ppm 10.18 (br. s., 1 H), 8.14 (s, 1 H), 7.81 (d, 1 H), 7.45 (d, 1 H), 7.30-7.40 (m, 4 H), 6.86-6.89 (m, 1 H), 6.79-6.85 (m, 1 H), 6.63-6.73 (m, 3 H), 6.46-6.51 (m, 1 H), 6.32-7.30 (m, 2H), 6.25 (q, 1 H), 3.57-3.66 (m, 4 H), 3.50 (s, 2 H), 2.33-2.42 (m, 4 H), 1.84 (d, 3 H).

Example 92

3-{4-amino-1-[1-(3-{4-[(dimethylamino)methyl]phenyl}indolizin-2-yl)ethyl]-1H-pyrazolo[3,4-d]pyrimidin-3-yl}-5-fluorophenol

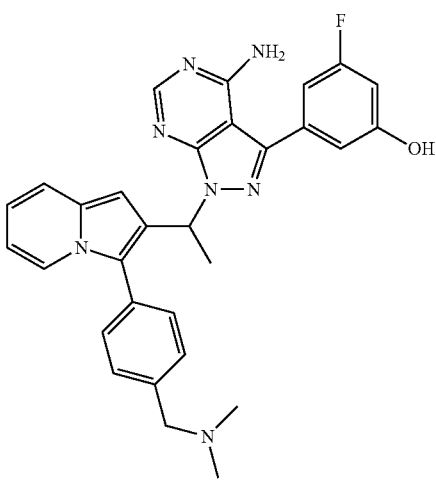 [SMILES: CC(c1cc2ccccn2c1-c1ccc(CN(C)C)cc1)n1nc(-c2cc(O)cc(F)c2)c2c(N)ncnc21]

Prepared similarly to Example 85, starting from 1-[1-(3-{4-[(dimethylamino)methyl]phenyl}indolizin-2-yl)ethyl]-3-iodo-1H-pyrazolo[3,4-d]pyrimidin-4-amine W10 (0.188 g, (3-fluoro-5-hydroxyphenyl)boronic acid (0.060 g, 0.38 mmol) and Pd(PPh$_3$)$_4$ (0.020 g, 0.017 mmol), in DME (13 mL), EtOH (2.4 mL) and saturated aqueous Na$_2$CO$_3$ (4.8 mL), heating at 80° C. for 4 h. After work-up the crude was purified by flash chromatography on 11 g Biotage silica-NH SNAP cartridge (DCM to DCM:MeOH=95:5). A further purification by reverse phase semi-preparative MDAP under basic conditions (Method F) was required to afford title compound as a yellow solid (0.022 g). MS/ESI$^+$ 522.3 [MH]$^+$, Rt 1.04 min (Method C).

$^1$H NMR (400 MHz, DMSO-d$_6$) δ ppm 10.38 (br. s., 1 H), 8.14 (s, 1 H), 7.83 (d, 1 H), 7.44 (d, 1 H), 7.34-7.39 (m, 4 H), 6.87 (br. s., 1 H), 6.76-6.82 (m, 1 H), 6.59-6.73 (m, 3 H), 6.46-6.52 (m, 1 H), 6.23 (q, 1 H), 6.17-7.30 (m, 2H), 3.43 (s, 2 H), 2.18 (s, 6 H), 1.83 (d, 3 H).

Example 93

3-{4-amino-1-[1-(3-{3-[(dimethylamino)methyl]phenyl}indolizin-2-yl)ethyl]-1H-pyrazolo[3,4-d]pyrimidin-3-yl}-5-fluorophenol

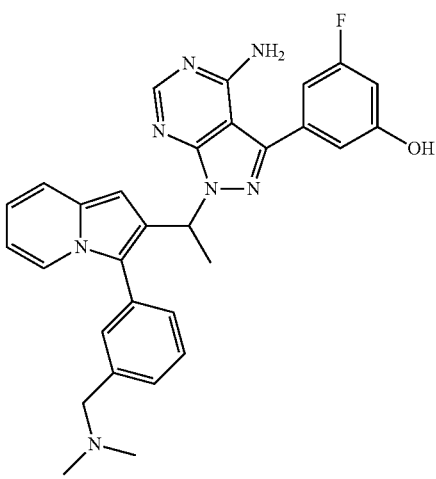 [SMILES: CC(c1cc2ccccn2c1-c1cccc(CN(C)C)c1)n1nc(-c2cc(O)cc(F)c2)c2c(N)ncnc21]

Prepared similarly to Example 85, starting from 1-[1-(3-{3-[(dimethylamino)methyl]phenyl}indolizin-2-yl)ethyl]-3-iodo-1H-pyrazolo[3,4-d]pyrimidin-4-amine W11 (0.091 g), (3-fluoro-5-hydroxyphenyl)boronic acid (0.029 g, 0.187 mmol) and Pd(PPh$_3$)$_4$ (0.010 g, 0.009 mmol), in DME (6.3 mL), EtOH (1.2 mL) and saturated aqueous Na$_2$CO$_3$ (2.3 mL), heating at 80° C. for 4 h. After work-up the crude was purified by flash chromatography on 11 g Biotage silica-NH SNAP cartridge (DCM to DCM:MeOH=95:5). A further purification by reverse phase semi-preparative MDAP under basic conditions (Method F) was required to afford title compound as a white solid (0.032 g). MS/ESI$^+$ 522.3 [MH]$^+$, Rt 1.07 min (Method C).

$^1$H NMR (400 MHz, DMSO-d$_6$) δ ppm 10.19 (s, 1 H), 8.15 (s, 1 H), 7.82 (d, 1 H), 7.40-7.49 (m, 2 H), 7.28-7.36 (m, 2 H), 7.23 (br. s., 1 H), 6.88-6.92 (m, 1 H), 6.82-6.87 (m, 1 H), 6.64-6.74 (m, 3 H), 6.48-6.54 (m, 1 H), 6.20 (q, 1 H), 5.16-7.49 (m, 2H), 3.39 (br. s., 2 H), 2.14 (s, 6 H), 1.84 (d, 3 H).

Example 94

3-(4-amino-1-{1-[3-(1,3-thiazol-5-yl)indolizin-2-yl]ethyl}-1H-pyrazolo[3,4-d]pyrimidin-3-yl)-5-fluorophenol

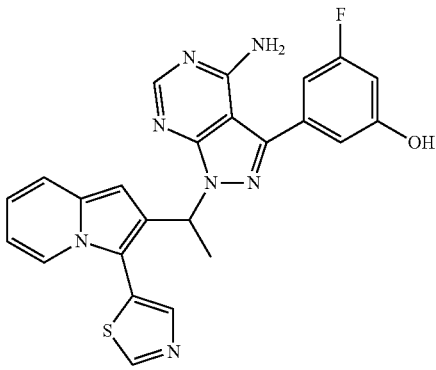 [SMILES: CC(c1cc2ccccn2c1-c1cncs1)n1nc(-c2cc(O)cc(F)c2)c2c(N)ncnc21]

Prepared similarly to Example 85, starting from 3-iodo-1-{1-[3-(1,3-thiazol-5-yl)indolizin-2-yl]ethyl}-1H-pyrazolo[3,4-d]pyrimidin-4-amine W12 (0.042 g, 0.086 mmol), (3-fluoro-5-hydroxyphenyl)boronic acid (0.015 g, 0.095 mmol) and Pd(PPh$_3$)$_4$ (5.0 mg, 0.0043 mmol), in DME (3.5 mL), EtOH (0.62 mL) and saturated aqueous Na$_2$CO$_3$ (1.2 mL), heating at 80° C. for 4 h. After work-up the crude was purified by flash chromatography on 28 g Biotage silica-NH SNAP cartridge (DCM to DCM:MeOH=94:6) to afford title compound as a white solid (0.016 g). MS/ESI$^+$ 472.3 [MH]$^+$, Rt 0.90 min (Method A).

$^1$H NMR (400 MHz, DMSO-d$_6$) δ ppm 10.20 (br. s., 1 H), 9.29 (s, 1 H), 8.15 (s, 1 H), 8.02 (s, 1 H), 7.89 (d, 1 H), 7.51 (d, 1 H), 6.89-6.92 (m, 1 H), 6.78-6.88 (m, 2 H), 6.72 (s, 1 H), 6.59-6.69 (m, 2 H), 6.22 (q, 1 H), 6.12-7.72 (m, 2H), 1.88 (d, 3 H).

Example 95

1-(2-{1-[4-amino-3-(3-fluoro-5-hydroxyphenyl)-1H-pyrazolo[3,4-d]pyrimidin-1-yl]ethyl}indolizin-3-yl)pyrrolidin-2-one

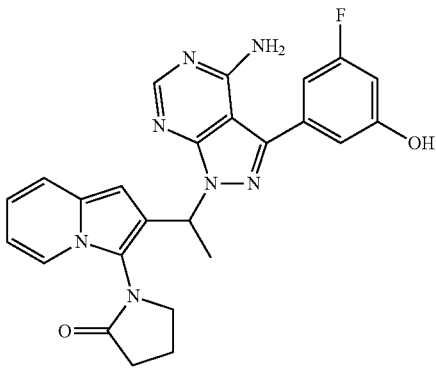 [SMILES: CC(c1cc2ccccn2c1N1CCCC1=O)n1nc(-c2cc(O)cc(F)c2)c2c(N)ncnc21]

Prepared similarly to Example 85, starting from 1-[2-(1-{4-amino-3-iodo-1H-pyrazolo[3,4-d]pyrimidin-1-yl}ethyl)indolizin-3-yl]pyrrolidin-2-one W13 (0.034 mmol), (3-fluoro-5-hydroxyphenyl)boronic acid (0.012 g, 0.076 mmol) and Pd(PPh₃)₄ (4.0 mg, 0.003 mmol), in DME (2.8 mL), EtOH (0.50 mL) and saturated aqueous Na₂CO₃ (0.95 mL), heating at 80° C. for 4 h; additional (3-fluoro-5-hydroxyphenyl)boronic acid (0.012 g, 0.076 mmol) and Pd(PPh₃)₄ (0.004 g, 0.003 mmol) were added and the mixture was heated at the same temperature overnight. After work-up the crude was purified by flash chromatography on 2 g silica-NH cartridge (DCM to DCM:MeOH=94:6). A further purification by reverse phase semi-preparative MDAP under basic conditions (Method F) was required to afford title compound as a pink solid (mixture of diastereoisomers, ratio 65/35 by 1H NMR). (0.004 g). MS/ESI⁺ 472.3 [MH]⁺, Rt 0.78 min (Method C).

¹H NMR (500 MHz, DMSO-d₆) δ ppm 10.38 (br. s., 1 H), 8.27 (s, 1 H), 7.86 (d, 1 H), 7.41-7.45 (m, 1 H), 6.82-6.88 (m, 1 H), 6.70-6.81 (m, 2H), 6.53-6.64 (m, 3 H), 6.39-7.50 (m, 2 H), 6.11 (q, 1 H), 3.57-3.63 (m, 1 H), 2.90-2.97 (m, 1 H), 2.38-2.56 (m, 2 H), 2.12-2.20 (m, 1 H), 1.84-1.94 (m, 4 H). Spectrum referred to the most abundant isomer.

Example 96

3-(4-amino-1-{1-[7-(pyridin-2-yl)pyrrolo[1,2-b]pyridazin-6-yl]ethyl}-1H-pyrazolo[3,4-d]pyrimidin-3-yl)-5-fluorophenol

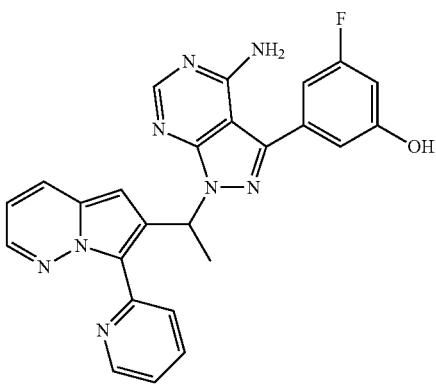 [SMILES: CC(c1cc2cccnn2c1-c1ccccn1)n1nc(-c2cc(O)cc(F)c2)c2c(N)ncnc21]

Prepared similarly to Example 85, starting from crude 3-iodo-1-{1-[7-(pyridin-2-yl)pyrrolo[1,2-b]pyridazin-6-yl]ethyl}-1H-pyrazolo[3,4-d]pyrimidin-4-amine W15 (0.060 g), (3-fluoro-5-hydroxyphenyl)boronic acid (0.027 g, 0.17 mmol) and Pd(PPh₃)₄ (7.0 mg, 0.006 mmol), in DME (12 mL), EtOH (1.8 mL) and saturated aqueous Na₂CO₃ (3.42 mL), heating at 80° C. for 2 h. After work-up the crude was purified by flash chromatography on silica-NH Biotage SNAP cartridge (DCM to DCM:MeOH=97:3); a further purification by flash chromatography on 10 g silica gel Biotage SNAP cartridge (DCM to DCM:MeOH=97:3) was required to afford title compound (0.010 g). MS/ESI⁺ 467.2 [MH]⁺, Rt 0.73 min (Method A).

¹H NMR (400 MHz, DMSO-d₆) δ ppm 10.21 (s, 1 H), 8.71-8.75 (m, 1 H), 8.25-8.32 (m, 2 H), 8.13 (s, 1 H), 8.00-8.04 (m, 1 H), 7.92 (td, 1 H), 7.31-7.36 (m, 1 H), 7.04 (q, 1 H), 6.88-6.98 (m, 2 H), 6.79 (dd, 1 H), 6.65-6.71 (m, 1 H), 6.59 (s, 1 H), 6.40-7.50 (m, 2H), 1.95 (d, 3 H).

Example 97

3-(4-amino-1-{[3-(pyridin-2-yl)indolizin-2-yl]methyl}-1H-pyrazolo[3,4-d]pyrimidin-3-yl)-5-fluorophenol

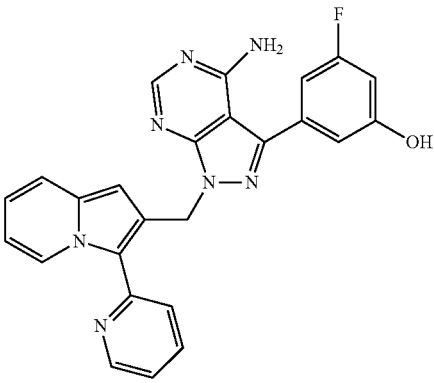 [SMILES: Nc1ncnc2c1c(-c1cc(O)cc(F)c1)nn2Cc1cc2ccccn2c1-c1ccccn1]

Prepared similarly to Example 85, starting from 3-iodo-1-{[3-(pyridin-2-yl)indolizin-2-yl]methyl}-1H-pyrazolo[3,4-d]pyrimidin-4-amine W16 (0.020 g, 0.043 mmol), (3-fluoro-5-hydroxyphenyl)boronic acid (7.3 mg, 0.047 mmol) and Pd(PPh₃)₄ (2.5 mg, 0.0022 mmol), in DME (4.5 mL), EtOH (0.65 mL) and saturated aqueous Na₂CO₃ (1.2 mL), heating at 80° C. overnight. Additional (3-fluoro-5-hydroxyphenyl)boronic acid (7.3 mg, 0.047 mmol) and Pd(PPh₃)₄ (2.5 mg, 0.0022 mmol) were added and the heating was continued for further 2 h. After work-up, the crude was purified by flash chromatography on silica-NH Biotage SNAP cartridge (DCM to DCM:MeOH=85:15) to afford title compound (0.012 g). MS/ESI⁺ 452.2 [MH]⁺, Rt 0.78 min (Method A).

¹H NMR (400 MHz, DMSO-d₆) δ ppm 10.17 (br. s., 1 H), 8.91-8.95 (m, 1 H), 8.75-8.80 (m, 1 H), 8.28 (s, 1 H), 7.93-8.03 (m, 2 H), 7.44 (d, 1 H), 7.36-7.42 (m, 1 H), 6.90-6.93 (m, 1 H), 6.79-6.89 (m, 2 H), 6.61-6.70 (m, 2 H), 6.35-7.46 (m, 2H), 6.26 (s, 1 H), 5.79 (s, 2 H).

Example 98

3-(4-amino-1-{[3-(pyridin-3-yl)indolizin-2-yl]methyl}-1H-pyrazolo[3,4-d]pyrimidin-3-yl)-5-fluorophenol

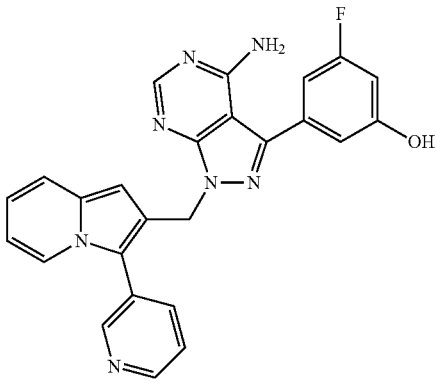 [SMILES: Nc1ncnc2c1c(-c1cc(O)cc(F)c1)nn2Cc1cc2ccccn2c1-c1cccnc1]

Prepared similarly to Example 85, starting from 3-iodo-1-{[3-(pyridin-3-yl)indolizin-2-yl]methyl}-1H-pyrazolo[3,4-d]pyrimidin-4-amine W17 (0.035 g, 0.075 mmol), (3-fluoro-5-hydroxyphenyl)boronic acid (0.015 g, 0.097 mmol) and Pd(PPh$_3$)$_4$ (4.3 mg, 0.0037 mmol), in DME (7.5 mL), EtOH (1.2 mL) and saturated aqueous Na$_2$CO$_3$ (2.1 mL), heating at 80° C. overnight. After work-up the crude was purified by flash chromatography on Biotage silica-NH SNAP cartridge (DCM to DCM:MeOH=80:20) to afford title compound (0.011 g). MS/ESI$^+$ 452.3 [MH]$^+$, Rt 0.74 min (Method A).

$^1$H NMR (400 MHz, DMSO-d$_6$) δ ppm 10.18 (br. s., 1 H), 8.84 (d, 1 H), 8.63-8.66 (m, 1 H), 8.26 (s, 1 H), 8.04-8.09 (m, 1 H), 8.01 (d, 1 H), 7.54-7.59 (m, 1 H), 7.44 (d, 1 H), 6.88-6.91 (m, 1 H), 6.81-6.87 (m, 1 H), 6.74-6.80 (m, 1 H), 6.63-6.70 (m, 1 H), 6.54-6.60 (m, 1 H), 6.45 (s, 1 H), 6.20-7.53 (m, 2H), 5.59 (s, 2 H).

Example 99

3-(4-amino-1-{[3-(pyridin-4-yl)indolizin-2-yl]methyl}-1H-pyrazolo[3,4-d]pyrimidin-3-yl)-5-fluorophenol

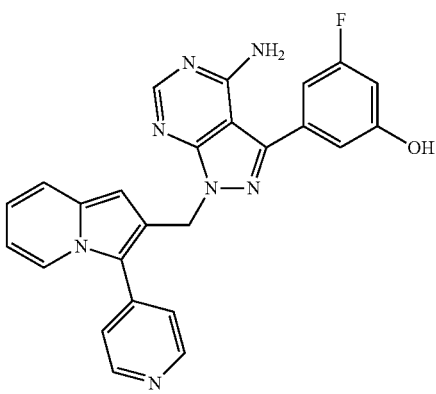 [SMILES: Nc1ncnc2c1c(-c1cc(O)cc(F)c1)nn2Cc1cc2ccccn2c1-c1ccncc1]

Prepared similarly to Example 85, starting from 3-iodo-1-{[3-(pyridin-4-yl)indolizin-2-yl]methyl}-1H-pyrazolo[3,4-d]pyrimidin-4-amine W18 (0.055 g, 0.118 mmol), (3-fluoro-5-hydroxyphenyl)boronic acid (0.020 g, 0.130 mmol) and Pd(PPh$_3$)$_4$ (6.8 mg, 0.006 mmol), in DME (8 mL), EtOH (1.2 mL) and saturated aqueous Na$_2$CO$_3$ (2.2 mL), heating at 80° C. overnight. Additional (3-fluoro-5-hydroxyphenyl)boronic acid (1 eq) and Pd(PPh$_3$)$_4$ (6.8 mg, 0.006 mmol) were added and the heating was continued for further 2 h. After work-up the crude was purified by flash chromatography on g Biotage silica-NH SNAP cartridge (DCM to DCM:MeOH=90:10); a further purification on SCX cartridge (1 g), eluting with 1M ammonia in MeOH was required to afford title compound (0.009 g). MS/ESI$^+$ 452.3 [MH]$^+$, Rt 0.61 min (Method A).

$^1$H NMR (400 MHz, DMSO-d$_6$) δ ppm 10.19 (br. s., 1 H), 8.70-8.76 (m, 2 H), 8.21-8.31 (m, 2 H), 7.71-7.77 (m, 2 H), 7.43-7.49 (m 1 H), 6.89-6.93 (m, 1 H), 6.77-6.88 (m, 2 H), 6.59-6.70 (m, 1 H), 6.40 (s, 1 H), 6.00-7.70 (m, 2H), 5.66 (s, 2 H).

Example 100

3-(4-amino-1-{[7-(pyridin-2-yl)pyrrolo[1,2-b]pyridazin-6-yl]methyl}-1H-pyrazolo[3,4-d]pyrimidin-3-yl)-5-fluorophenol

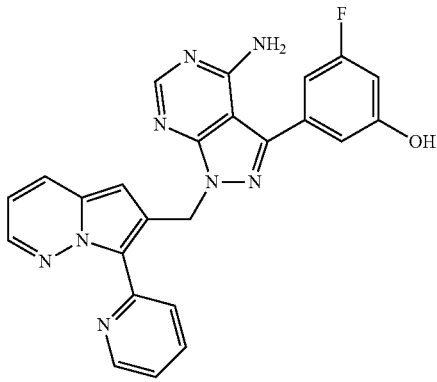 [SMILES: Nc1ncnc2c1c(-c1cc(O)cc(F)c1)nn2Cc1cc2cccnn2c1-c1ccccn1]

Prepared similarly to Example 85, 3-iodo-1-{[7-(pyridin-2-yl)pyrrolo[1,2-b]pyridazin-6-yl]methyl}-1H-pyrazolo[3,4-d]pyrimidin-4-amine W19 (0.026 g, 0.05 mmol), (3-fluoro-5-hydroxyphenyl)boronic acid (0.0113 g, 0.072 mmol) and Pd(PPh$_3$)$_4$ (2.9 mg, 0.0025 mmol), in DME (5 mL), EtOH (0.75 mL) and saturated aqueous Na$_2$CO$_3$ (1.42 mL), heating at 80° C. for 3 h. After work-up the crude was purified by flash chromatography on 10 g Biotage silica gel SNAP cartridge (DCM to DCM:MeOH=95:5) to afford title compound (0.012 g). MS/ESI$^+$ 453.3 [MH]$^+$, Rt 0.66 min (Method A).

$^1$H NMR (400 MHz, DMSO-d$_6$) δ ppm 10.20 (s, 1 H), 8.74-8.77 (m, 1 H), 8.50 (d, 1 H), 8.30-8.34 (m, 1 H), 8.23 (s, 1 H), 7.93-8.00 (m, 2 H), 7.32-7.38 (m, 1 H), 6.90-6.95 (m, 1 H), 6.85-6.91 (m, 1 H), 6.81 (dd, 1 H), 6.63-6.69 (m, 1 H), 6.20-7.77 (m, 2 H), 6.12 (s, 1 H), 6.06 (s, 2 H).

Example 101

3-(4-amino-1-{1-[3-(1,2,3,6-tetrahydropyridin-4-yl)indolizin-2-yl]ethyl}-1H-pyrazolo[3,4-d]pyrimidin-3-yl)-5-fluorophenol

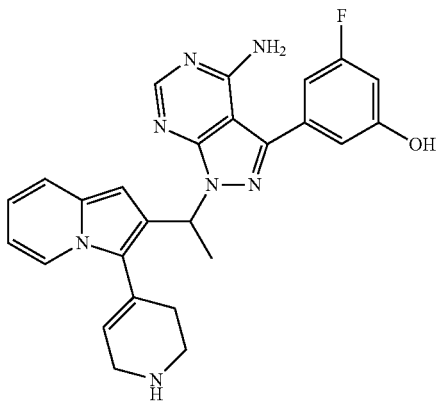 [SMILES: CC(c1cc2ccccn2c1C1=CCNCC1)n1nc(-c2cc(O)cc(F)c2)c2c(N)ncnc21]

To a solution of tert-butyl 4-(2-{1-[4-amino-3-(3-fluoro-5-hydroxyphenyl)-1H-pyrazolo[3,4-d]pyrimidin-1-yl]

ethyl}indolizin-3-yl)-1,2,3,6-tetrahydropyridine-1-carboxylate X (0.021 g, 0.037 mmol) in DCM (0.5 mL), trifluoroacetic acid (0.017 mL, 0.22 mmol) was slowly added at 0° C. and the solution was stirred at room temperature for 3 days. The mixture was partitioned between saturated aqueous NaHCO$_3$ solution and DCM, the aqueous phase was further extracted with a mixture of DCM:MeOH (5:1), and the combined organic layers were washed with brine, dried over anhydrous MgSO$_4$ and concentrated. The crude was purified by reverse phase flash chromatography on 1 g C-18 cartridge (H$_2$O+0.1% formic acid:H$_3$CN+0.1% formic acid=95:5 to 50:50). A further purification by reverse phase semi-preparative MDAP under basic condition (Method F) was required to afford title compound as an orange solid (2 mg). MS/ESI$^+$ 570.2 [MH]$^+$, Rt 1.17 min (Method C).

$^1$H NMR (400 MHz, METHANOL-d$_4$) δ ppm 8.27 (s, 1 H), 7.83 (d, 1 H), 7.33 (d, 1 H), 6.87-6.90 (m, 1 H), 6.80-6.85 (m, 1 H), 6.59-6.66 (m, 3 H), 6.46 (t, 1 H), 6.37 (q, 1 H), 5.73-5.78 (m, 1 H), 3.35-3.38 (m, 2 H), 2.90-2.98 (m, 1 H), 2.80-2.90 (m, 1 H), 2.25-2.35 (m, 1 H), 1.94-2.05 (m, 4 H).

OH, NH and NH$_2$ not visible because of the chemical exchange with MeOH.

Example 102

3-(4-amino-1-{1-[3-(pyridin-2-yl)indolizin-2-yl]ethyl}-1H-pyrazolo[3,4-d]pyrimidin-3-yl)prop-2-yn-1-ol

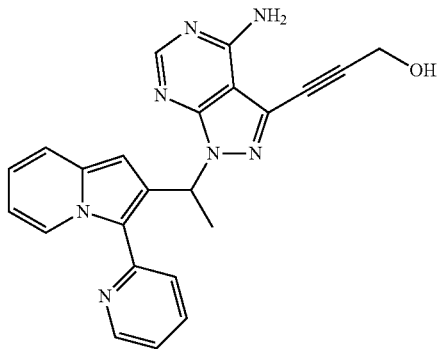 [SMILES: CC(c1cc2ccccn2c1-c1ccccn1)n1nc(C#CCO)c2c(N)ncnc21]

A mixture of 3-iodo-1-{1-[3-(pyridin-2-yl)indolizin-2-yl]ethyl}-1H-pyrazolo[3,4-d]pyrimidin-4-amine W2 (0.060 g, 0.125 mmol), propargyl alcohol (0.036 mL, 0.625 mmol), CuI (8.3 mg, 0.044 mmol) and diethylamine (0.13 mL, 1.25 mmol) in DMF (0.5 mL) was degassed, then Pd(PPh$_3$)$_2$Cl$_2$ (0.015 g, 0.021 mmol) was added and the reaction was stirred at room temperature for 2 h. The mixture was diluted with EtOAc and filtered through a celite pad; the filtrate was washed with water and brine, dried over anhydrous sodium sulfate, filtered and concentrated. The crude was purified by flash chromatography on 11 g Biotage silica-NH SNAP cartridge (DCM to DCM:MeOH 90:10). A further purification on SCX (1 g) cartridge eluting with 1M ammonia in MeOH was required to afford title compound (9.7 mg). MS/ESI$^+$ 410.3 [MH]$^+$, Rt 0.67 min (Method A).

$^1$H NMR (400 MHz, DMSO-d$_6$) δ ppm 8.71-8.75 (m, 1 H), 8.64 (d, 1 H), 8.15 (s, 1 H), 7.93 (td, 1 H), 7.72 (d, 1 H), 7.51 (d, 1 H), 7.34-7.39 (m, 1 H), 6.79-6.86 (m, 1 H), 6.57-6.66 (m, 2 H), 6.44 (q, 1 H), 6.00-8.00 (m, 2H), 5.45 (t, 1 H), 4.40 (d, 2 H), 1.87 (d, 3 H).

Example 103

5-(4-amino-1-{1-[3-(pyridin-2-yl)indolizin-2-yl]ethyl}-1H-pyrazolo[3,4-d]pyrimidin-3-yl)-1,3-thiazol-2-amine

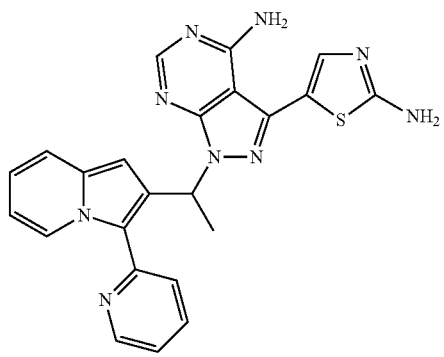 [SMILES: CC(c1cc2ccccn2c1-c1ccccn1)n1nc(-c2cnc(N)s2)c2c(N)ncnc21]

To a solution of tert-butyl N-[5-(4-amino-1-{1-[3-(pyridin-2-yl)indolizin-2-yl]ethyl}-1H-pyrazolo[3,4-d]pyrimidin-3-yl)-1,3-thiazol-2-yl]carbamate Y (0.060 g, 0.108 mmol) in DCM (2 mL), TFA (0.050 mL, 0.650 mmol) was slowly added at 0° C. and the reaction was then stirred at RT for 3 h. Additional TFA (0.648 mmol) was added and the reaction mixture was stirred at RT overnight. The volatiles were removed under reduced pressure and the crude was purified by reverse phase flash chromatography on 12 g Biotage C18 SNAP cartridge (H$_2$O+0.1% formic acid:acetonitrile+0.1% formic=95:5 to 70:30) to afford title compound (0.014 g). MS/ESI$^+$ 454.3 [MH]$^+$, Rt 0.59 min (Method A).

$^1$H NMR (400 MHz, DMSO-d$_6$) δ ppm 8.72-8.76 (m, 1H,) 8.64 (d, 1 H), 8.15 (s, 1 H), 7.94 (td, 1 H), 7.75 (d, 1 H), 7.49 (d, 1 H), 7.35-7.40 (m, 1 H), 7.29 (s, 1 H), 7.27 (br. s, 2 H), 6.99 (br. s., 2 H), 6.78-6.85 (m, 1 H), 6.65 (s, 1 H), 6.57-6.63 (m, 1 H), 6.42 (q, 1 H), 1.88 (d, 3 H).

Examples 104-116, 118-123, 125-142, 146-148 and 150 found in the table below may be prepared from suitable intermediates reported below following similar procedures as for Example 85.

| Example | Name and Molecular Structure | Reagent | Analytical data |
|---|---|---|---|
| 104 | 3-(4-amino-1-{1-[7-chloro-3-(pyridin-2-yl)indolizin-2-yl]ethyl}-1H-pyrazolo[3,4-d]pyrimidin-3-yl)-5-fluorophenol | W20 and (3-fluoro-5-hydroxyphenyl)boronic acid | MS/ESI$^+$ 500.3 [MH]$^+$, Rt 1.01 min (Method A). 1H NMR (400 MHz, DMSO-d6) δ ppm 10.23 (br. s., 1 H), 8.71-8.75 (m, 1 H), 8.65 (d, 1 H), 8.18 (s, 1 H), 7.94 (td, 1 H), 7.78 (d, 1 H), 7.67 (d, 1 H), 7.36-7.41 (m, 1 H), 6.90-6.92 (m, 1 H), 6.84-6.89 (m, 1 H), 6.72 (s, 1 H), 6.61-6.70 (m, 2 H), 6.47 (q, 1 H), 6.00-8.00 (m, 2 H), 1.91 (d, 3 H). |
| 105 | 3-(4-amino-1-{1-[7-methyl-3-(pyridin-2-yl)indolizin-2-yl]ethyl}-1H-pyrazolo[3,4-d]pyrimidin-3-yl)-5-fluorophenol | W21 and (3-fluoro-5-hydroxyphenyl)boronic acid | MS/ESI$^+$ 480.3 [MH]$^+$, Rt 0.87 min (Method A). $^1$H NMR (400 MHz, DMSO-d6) δ ppm 10.19 (br. s., 1 H), 8.67-8.73 (m, 1 H), 8.58 (d, 1 H,) 8.17 (s, 1 H), 7.89 (td, 1 H), 7.68-7.75 (m, 1 H), 7.29-7.35 (m, 1 H), 7.22-7.26 (m, 1 H), 6.89-6.93 (m, 1 H), 6.82-6.89 (m, 1 H), 6.63-6.69 (m, 1 H), 6.54 (s, 1 H), 6.42-6.51 (m, 2 H), 6.15-7.50 (m, 2 H), 2.23 (s, 3 H), 1.90 (d, 3 H). |
| 106 | 3-(4-amino-1-{1-[3-(2-methylpyridin-4-yl)indolizin-2-yl]ethyl}-1H-pyrazolo[3,4-d]pyrimidin-3-yl)-5-fluorophenol | W22 and (3-fluoro-5-hydroxyphenyl)boronic acid | MS/ESI$^+$ 480.2 [MH]$^+$, Rt 0.67 min (Method A). $^1$H NMR (400 MHz, DMSO-d$_6$) δ ppm 10.16 (br. s., 1 H), 8.46-8.50 (m, 1 H), 8.21 (s, 1 H), 8.00-8.04 (m, 1 H), 7.48-7.52 (m, 1 H), 7.25-7.30 (m, 2 H), 6.86-6.90 (m, 1 H), 6.75-6.85 (m, 3 H), 6.65 (dt, 1 H), 6.53-6.59 (m, 1 H), 6.27 (q, 1 H), 6.00-7.55 (m, 2 H), 2.45 (s, 3 H), 1.86 (d, 3 H). |

-continued

| Example | Name and Molecular Structure | | Reagent | Analytical data |
|---|---|---|---|---|
| 107 | 5-(4-amino-1-{1-[3-(2-methylpyridin-4-yl)indolizin-2-yl]ethyl}-1H-pyrazolo[3,4-d]pyrimidin-3-yl)pyridin-3-ol | 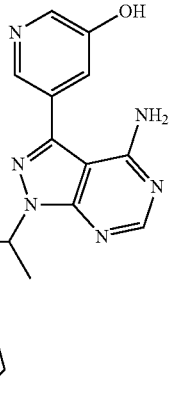 | W22 and 5-(tetramethyl-1,3,2-dioxaborolan-2-yl)pyridin-3-ol | MS/ESI+ 463.3 [MH]+, Rt 0.67 min (Method C) 1H NMR (400 MHz, DMSO-d6) δ ppm 10.14 (bs, 1 H), 8.46-8.49 (m, 1 H), 8.26 (d, 1 H), 8.22 (s, 1 H), 8.20 (d, 1 H), 8.00-8.04 (m, 1 H), 7.47-7.52 (m, 1 H), 7.34-7.36 (m, 1 H), 7.26-7.29 (m, 2 H), 6.75-6.80 (m, 2 H), 6.54-6.58 (m, 1 H), 6.25-6.32 (m, 1 H), 6.20-7.55 (m, 2 H), 2.45 (s, 3 H), 1.87 (d, 3 H). |
| 108 | 3-[4-amino-1-(1-{3-[5-(morpholin-4-ylmethyl)pyridin-2-yl]indolizin-2-yl}ethyl)-1H-pyrazolo[3,4-d]pyrimidin-3-yl]-5-fluorophenol | 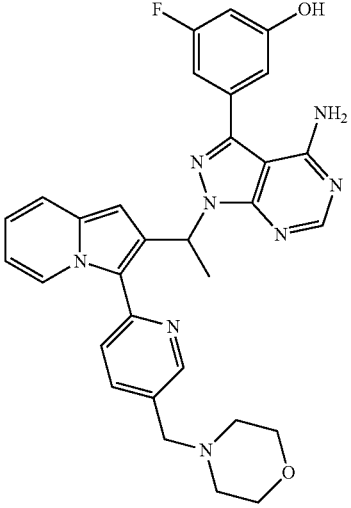 [SMILES: CC(c1cc2ccccn2c1-c1ccc(CN2CCOCC2)cn1)n1nc(-c2cc(O)cc(F)c2)c2c(N)ncnc21] | W23 and (3-fluoro-5-hydroxyphenyl)-boronic acid | MS/ESI+ 565.3 [MH]+, Rt 0.64 min (Method A) 1H NMR (400 MHz, DMSO-d6) δ ppm 10.18 (s, 1 H), 8.57-8.63 (m, 2 H), 8.18 (s, 1 H), 7.74-7.80 (m, 1 H), 7.65-7.71 (m, 1 H), 7.48-7.53 (m, 1 H), 6.87-6.91 (m, 1 H), 6.77-6.86 (m, 2 H), 6.71 (s, 1 H), 6.67 (dt, 1 H), 6.57-6.63 (m, 1 H), 6.53 (q, 1 H), 6.10-7.44 (m, 2 H), 3.58-3.67 (m, 4 H), 3.51-3.59 (m, 2 H), 2.36-2.46 (m, 4 H), 1.92 (d, 3 H). |
| 109 | 3-{4-amino-1-[1-(3-{5-[(dimethylamino)-methyl]pyridin-2-yl}indolizin-2-yl)ethyl]-1H-pyrazolo[3,4-d]pyrimidin-3-yl}-5-fluorophenol | 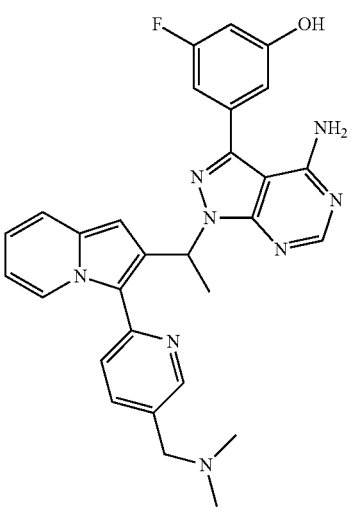 [SMILES: CC(c1cc2ccccn2c1-c1ccc(CN(C)C)cn1)n1nc(-c2cc(O)cc(F)c2)c2c(N)ncnc21] | W24 and (3-fluoro-5-hydroxyphenyl)-boronic acid | MS/ESI+ 523.3 [MH]+, Rt 0.63 min (Method A) 1H NMR (400 MHz, DMSO-d6) δ ppm 10.20 (br. s., 2 H), 8.58-8.64 (m, 2 H), 8.17 (s, 1 H), 7.79 (dd, 1 H), 7.68-7.73 (m, 1 H), 7.48-7.53 (m, 1 H), 6.89-6.92 (m, 1 H), 6.78-6.87 (m, 2 H), 6.70 (s, 1 H), 6.64-6.69 (m, 1 H), 6.57-6.62 (m, 1 H), 6.52 (q, 1 H), 6.00-7.50 (m, 2 H), 3.48 (s, 2 H), 2.21 (s, 6 H), 1.92 (d, 3 H). |

-continued

| Example | Name and Molecular Structure | | Reagent | Analytical data |
|---|---|---|---|---|
| 110 | 3-[4-amino-1-(1-{3-[6-(morpholin-4-ylmethyl)pyridin-2-yl]indolizin-2-yl}ethyl)-1H-pyrazolo[3,4-d]-pyrimidin-3-yl]-5-fluorophenol | 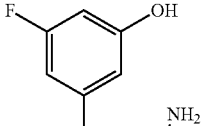 | W25 and (3-fluoro-5-hydroxyphenyl)-boronic acid | MS/ESI$^+$ 565.4 [MH]$^+$, Rt 0.66 min (Method A) $^1$H NMR (400 MHz, DMSO-d6) δ ppm 10.21 (br. s., 1 H), 8.59-8.65 (m, 1 H), 8.14 (s, 1 H), 7.87 (t, 1 H), 7.60 (d, 1 H), 7.47-7.52 (m, 1 H), 7.38 (d, 1 H), 6.88-6.92 (m, 1 H), 6.77-6.87 (m, 2 H), 6.70 (s, 1 H), 6.63-6.69 (m, 1 H), 6.57-6.62 (m, 1 H), 6.51 (q, 1 H), 6.00-7.70 (m, 2 H), 3.57-3.68 (m, 6 H), 2.40-2.47 (m, 4 H), 1.92 (d, 3 H). |
| 111 | 3-[4-amino-1-(1-{3-[4-(morpholin-4-ylmethyl)pyridin-2-yl]indolizin-2-yl}ethyl)-1H-pyrazolo[3,4-d]-pyrimidin-3-yl]-5-fluorophenol | 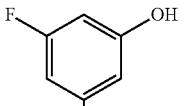 | W26 and (3-fluoro-5-hydroxyphenyl)-boronic acid | MS/ESI$^+$ 565.5 [MH]$^+$, Rt 0.66 min (Method A) $^1$H NMR (400 MHz, DMSO-d$_6$) δ ppm 10.18 (br. s., 1 H), 8.62-8.67 (m, 2 H), 8.18 (s, 1 H), 7.48-7.54 (m, 2 H), 77.26-7.30 (m, 1 H), 6.88-6.91 (m, 1 H), 6.78-6.86 (m, 2 H), 6.76 (s, 1 H), 6.65 (dt, 1 H), 6.57-6.62 (m, 1 H), 6.44 (q, 1 H), 6.00-7.48 (m, 2 H), 3.45-3.58 (m, 6 H), 2.32-2.42 (m, 4 H), 1.90 (d, 3 H). |
| 112 | 3-{4-amino-1-[1-(3-{4-[(dimethylamino)-methyl]pyridin-2-yl}indolizin-2-yl)-ethyl]-1H-pyrazolo[3,4-d]pyrimidin-3-yl}-5-fluorophenol | 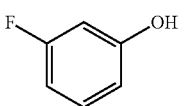 | W27 and (3-fluoro-5-hydroxyphenyl)-boronic acid | MS/ESI$^+$ 523.5 [MH]$^+$, Rt 0.64 min (Method A) $^1$H NMR (400 MHz, DMSO-d$_6$) δ ppm 10.18 (br.s., 1 H), 8.59-8.66 (m, 2 H), 8.19 (s, 1 H), 7.47-7.54 (m, 2 H), 7.24-7.29 (m, 1 H), 6.87-6.91 (m, 1 H), 6.77-6.86 (m, 2 H), 6.75 (s, 1 H), 6.65 (dt, 1 H), 6.56-6.62 (m, 1 H), 6.39-6.47 (m, 1 H), 6.00-7.70 (m, 2 H), 3.41 (s, 2 H), 2.16 (s, 6 H), 1.89 (d, 3 H). |

| Example | Name and Molecular Structure | | Reagent | Analytical data |
|---|---|---|---|---|
| 113 | 3-[4-amino-1-(1-{3-[5-(pyrrolidin-1-ylmethyl)pyridin-2-yl]indolizin-2-yl}ethyl)-1H-pyrazolo[3,4-d]pyrimidin-3-yl]-5-fluorophenol | 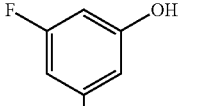 | W28 and (3-fluoro-5-hydroxyphenyl)-boronic acid | MS/ESI+ 549.4 [MH]+, Rt 0.65 min (Method A) 1H NMR (400 MHz, DMSO-d6) δ ppm 10.18 (br. s., 1 H), 8.57-8.62 (m, 2 H), 8.16 (s, 1 H), 7.78 (dd, 1 H), 7.67 (d, 1 H), 7.46-7.51 (m, 1 H), 6.87-6.91 (m, 1 H), 6.76-6.86 (m, 2 H), 6.63-6.70 (m, 2 H), 6.55-6.61 (m, 1 H), 6.50 (q, 1 H), 6.00-7.30 (m, 2 H), 3.60-3.69 (m, 2 H), 2.42-2.52 (m, 4 H), 1.90 (d, 3 H), 1.68-1.77 (m, 4 H). |
| 114 | 3-{4-amino-1-[1-(3-{5-[(4-methylpiperazin-1-yl)methyl]pyridin-2-yl}indolizin-2-yl)ethyl]-1H-pyrazolo-[3,4-d]pyrimidin-3-yl}-5-fluorophenol | 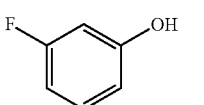 | W29 and (3-fluoro-5-hydroxyphenyl)-boronic acid | MS/ESI+ 578.4 [MH]+, Rt 0.62 min (Method A) 1H NMR (400 MHz, DMSO-d6) δ ppm 10.16 (br. s, 1 H), 8.54-8.61 (m, 2 H), 8.15 (s, 1 H), 7.72 (dd, 1 H), 7.64 (d, 1 H), 7.47-7.52 (m, 1 H), 6.86-6.90 (m, 1 H), 6.76-6.85 (m, 2 H), 6.69 (s, 1 H), 6.65 (dt, 1 H), 6.55-6.61 (m, 1 H), 6.51 (q, 1 H), 6.10-7.30 (m, 2 H), 3.48-3.58 (m, 2 H), 2.22-2.49 (m, 8 H), 2.16 (s, 3 H), 1.90 (d, 3 H). |
| 115 | 3-{4-amino-1-[1-(3-{6-[(4-methylpiperazin-1-yl)methyl]pyridin-2-yl}indolizin-2-yl)ethyl]-1H-pyrazolo-[3,4-d]pyrimidin-3-yl}-5-fluorophenol | 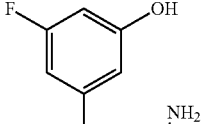 | W30 and (3-fluoro-5-hydroxyphenyl)-boronic acid | MS/ESI+ 578.5 [MH]+, Rt 0.63 min (Method A) 1H NMR (400 MHz, DMSO-d6) δ ppm 10.17 (br.s., 1 H), 8.59-8.65 (m, 1 H), 8.14 (s, 1 H), 7.81-7.88 (m, 1 H), 7.58 (d, 1 H), 7.47-7.51 (m, 1 H), 7.33 (d, 1 H), 6.87-6.92 (m, 1 H), 6.76-6.87 (m, 2 H), 6.69 (s, 1 H), 6.65 (dt, 1 H), 6.55-6.61 (m, 1 H), 6.50 (q, 1 H), 6.10-7.40 (m, 2 H), 3.57-3.66 (m, 2 H), 2.19-2.47 (m, 8 H), 2.15 (s, 3 H), 1.92 (d, 3 H). |

| Example | Name and Molecular Structure | | Reagent | Analytical data |
|---|---|---|---|---|
| 116 | 3-{4-amino-1-[1-(3-{4-[(4-methylpiperazin-1-yl)methyl]pyridin-2-yl}indolizin-2-yl)ethyl]-1H-pyrazolo-[3,4-d]pyrimidin-3-yl}-5-fluorophenol | 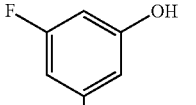 | W31 and (3-fluoro-5-hydroxyphenyl)-boronic acid | MS/ESI+ 578.5 [MH]+, Rt 0.60 min (Method A) 1H NMR (400 MHz, DMSO-d6) δ ppm 10.18 (br.s., 1 H), 8.60-8.67 (m, 2 H), 8.18 (s, 1 H), 7.46-7.54 (m, 2 H), 7.22-7.28 (m, 1 H), 6.88-6.91 (m, 1 H), 6.78-6.86 (m, 2 H), 6.76 (s, 1 H), 6.62-6.68 (m, 1H), 6.56-6.62 (m, 1 H), 6.44 (q, 1 H), 6.10-7.45 (m, 2 H), 3.42-3.54 (m, 2 H), 2.16-2.45 (m, 8 H), 2.11 (s, 3 H), 1.89 (d, 3 H). |
| 118 | 3-[4-amino-1-(1-{3-[3-(1-methylpyrrolidin-2-yl)phenyl]indolizin-2-yl}ethyl)-1H-pyrazolo[3,4-d]pyrimidin-3-yl]-5-fluorophenol | 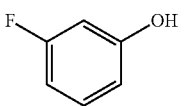 | W33 and (3-fluoro-5-hydroxyphenyl)-boronic acid | MS/ESI+ 548.4 [MH]+, Rt 0.70 min (Method A) (mixture of diastereoisomers) 1H NMR (500 MHz, DMSO-d6) δ ppm 1.48-1.78 (m, 3 H), 1.79-1.87 (m, 3 H), 2.00-2.11 (m, 3 H), 2.10-2.17 (m, 1 H), 2.17-2.25 (m, 1 H), 2.98-3.07 (m, 1 H), 3.07-3.18 (m, 1 H), 6.07-7.68 (m, 2 H), 6.13-6.23 (m, 1 H), 6.47-6.55 (m, 1 H), 6.61-6.74 (m, 3 H), 6.80-6.87 (m, 1 H), 6.87-6.93 (m, 1 H), 7.27-7.39 (m, 3 H), 7.40-7.49 (m, 2 H), 7.77-7.86 (m, 1 H), 8.13 (s, 1 H), 10.17 (s, 1 H). |

| Example | Name and Molecular Structure | | Reagent | Analytical data |
|---|---|---|---|---|
| 119 | 3-{4-amino-1-[1-(3-{5-[2-(morpholin-4-yl)ethoxy]pyridin-2-yl}indolizin-2-yl)ethyl]-1H-pyrazolo[3,4-d]pyrimidin-3-yl}-5-fluorophenol | 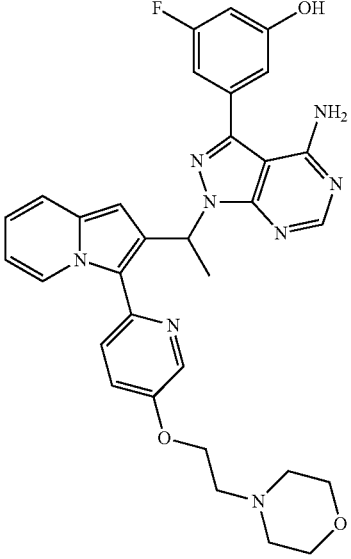 [SMILES: CC(c1cc2ccccn2c1-c1ccc(OCCN2CCOCC2)cn1)n1nc(-c2cc(O)cc(F)c2)c2c(N)ncnc21] | W34 and (3-fluoro-5-hydroxyphenyl)-boronic acid | MS/ESI$^+$ 595.2 [MH]$^+$, Rt 0.90 min (Method C) $^1$H NMR (400 MHz, DMSO-d6) δ ppm 10.19 (br. s., 1 H), 8.37-8.45 (m, 2 H), 8.18 (s, 1 H), 7.65 (d, 1 H), 7.51 (dd, 1 H), 7.43-7.48 (m, 1 H), 6.91 (s, 1 H), 6.82-6.87 (m, 1 H), 6.72-6.78 (m, 1 H), 6.63-6.69 (m, 2 H), 6.52-6.57 (m, 1 H), 6.41 (q, 1 H), 6.00-8.00 (m, 2 H), 4.20-4.27 (m, 2 H), 3.57-3.65 (m, 4 H), 2.72-2.79 (m, 2 H), 2.51-2.56 (m, 4 H), 1.89 (d, 3 H). |
| 120 | 5-(2-{1-[4-amino-3-(3-fluoro-5-hydroxyphenyl)-1H-pyrazolo[3,4-d]pyrimidin-1-yl]ethyl}-indolizin-3-yl)-1-[2-(morpholin-4-yl)ethyl]-1,2-dihydropyridin-2-one | 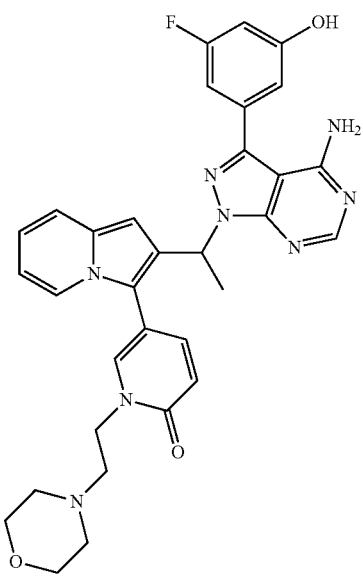 [SMILES: CC(c1cc2ccccn2c1-c1ccc(=O)n(CCN2CCOCC2)c1)n1nc(-c2cc(O)cc(F)c2)c2c(N)ncnc21] | W35 and (3-fluoro-5-hydroxyphenyl)-boronic acid | MS/ESI$^+$ 595.2 [MH]$^+$, Rt 0.85 min (Method C) $^1$H NMR (400 MHz, DMSO-d6) δ ppm 10.20 (br. s., 1 H), 8.19 (s, 1 H), 7.76-7.83 (m, 2 H), 7.41-7.48 (m, 1 H), 7.28-7.37 (m, 1 H), 6.88-6.92 (m, 1 H), 6.82-6.87 (m, 1 H), 6.70-6.75 (m, 1 H), 6.63-6.69 (m, 2 H), 6.50-6.56 (m, 1 H), 6.42 (d, 1 H), 6.22 (q, 1 H), 6.00-8.00 (m, 2 H), 3.91-4.06 (m, 2 H), 3.44-3.55 (m, 4 H), 2.54-2.64 (m, 2 H), 2.35-2.46 (m, 4 H), 1.89 (d, 3 H). |

| Example | Name and Molecular Structure | Reagent | Analytical data |
|---|---|---|---|
| 121 | 4-(2-{1-[4-amino-3-(3-fluoro-5-hydroxyphenyl)-1H-pyrazolo[3,4-d]pyrimidin-1-yl]ethyl}-indolizin-3-yl)-1-[2-(morpholin-4-yl)ethyl]-1,2-dihydropyridin-2-one | W36 and (3-fluoro-5-hydroxyphenyl)-boronic acid | MS/ESI+ 595.3 [MH]+, Rt 0.79 min (Method C) |
| 122 | 4-(2-{1-[4-amino-3-(5-hydroxypyridin-3-yl)-1H-pyrazolo[3,4-d]pyrimidin-1-yl]ethyl}indolizin-3-yl)-1-[2-(morpholin-4-yl)ethyl]-1,2-dihydropyridin-2-one | W36 and 5-(tetramethyl-1,3,2-dioxaborolan-2-yl)pyridin-3-ol | MS/ESI+ 578.4 [MH]+, Rt 0.60 min (Method J) $^1$H NMR (400 MHz, DMSO-d6) δ ppm 10.24 (bs, 1 H), 8.28-8.31 (m, 1 H), 8.20 (d, 1 H), 8.17 (s, 1 H), 8.04 (d, 1 H), 7.73 (d, 1 H), 7.45-7.50 (m, 1 H), 7.35-7.41 (m, 1 H), 6.73-6.82 (m, 1 H), 6.70 (s, 1 H), 6.56-6.64 (m, 1 H), 6.43-6.47 (m, 1 H), 6.27-6.39 (m, 2 H), 6.02-7.95 (m, 2 H), 3.98-4.06 (m, 2 H), 3.54-3.62 (m, 4 H), 2.54-2.62 (m, 2 H), 2.42-2.48 (m, 4 H), 1.89 (d, 3 H). |

-continued

| Example | Name and Molecular Structure | | Reagent | Analytical data |
|---|---|---|---|---|
| 123 | 2-(2-{1-[4-amino-3-(3-fluoro-5-hydroxyphenyl)-1H-pyrazolo[3,4-d]pyrimidin-1-yl]-ethyl}indolizin-3-yl)benzonitrile | 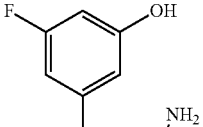 | W37 and (3-fluoro-5-hydroxyphenyl)-boronic acid | MS/ESI⁺ 490.3 [MH]⁺, Rt 0.96 and 0.97 min (Method A) (mixture of isomers ≈ 45/55 by ¹H NMR) ¹H NMR (500 MHz, DMSO-d₆) δ ppm 1.86-1.98 (m, 3 H), 6.71 (br. s, 2 H), 6.09-6.24 (m, 1 H), 6.45-6.98 (m, 6 H), 7.20-7.94 (m, 6 H), 7.96-8.10 (m, 1 H), 10.16 (br. s., 1 H). |
| 125 | 3-[4-amino-1-(1-{3-[5-(morpholine-4-carbonyl)pyridin-2-yl]indolizin-2-yl}ethyl)-1H-pyrazolo[3,4-d]-pyrimidin-3-yl]-5-fluorophenol | 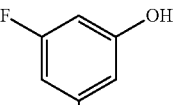 | W38 and (3-fluoro-5-hydroxyphenyl)-boronic acid | MS/ESI⁺ 579.3 [MH]⁺, Rt 0.86 min (Method A) ¹H NMR (400 MHz, DMSO-d₆) δ ppm 10.16 (br. s., 1 H), 8.66-8.78 (m, 2 H), 8.17 (s, 1 H), 7.87 (dd, 1 H), 7.75-7.80 (m, 1 H), 7.49-7.55 (m, 1 H), 6.76-6.90 (m, 3 H), 6.73 (s, 1 H), 6.60-6.69 (m, 2 H), 6.56 (q, 1 H), 6.00-8.00 (m, 2 H), 3.32-3.76 (m, 8 H), 1.92 (d, 3 H). |
| 126 | 2-{1-[4-amino-3-(3-fluoro-5-hydroxyphenyl)-1H-pyrazolo[3,4-d]pyrimidin-1-yl]-ethyl}-3-(pyridin-2-yl)indolizine-1-carbonitrile | 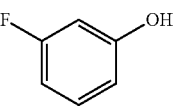 | W39 and (3-fluoro-5-hydroxyphenyl)-boronic acid | MS/ESI⁺ 491.3 [MH]⁺, Rt 0.85 min (Method A) 1H NMR (400 MHz, DMSO-d6) δ ppm 10.19 (s, 1 H), 8.75-8.80 (m, 1 H), 8.52 (d, 1 H), 8.12 (s, 1 H), 7.99 (td, 1 H), 7.76 (d, 1 H), 7.70 (d, 1 H), 7.47-7.53 (m, 1 H), 7.28-7.34 (m, 1 H), 6.92-6.97 (m, 3 H), 6.66 (dt, 1 H), 6.42 (q, 1 H), 6.00-7.95 (m, 2 H), 2.01 (d, 3 H). |

| Example | Name and Molecular Structure | Reagent | Analytical data |
|---|---|---|---|
| 127 | 2-{1-[4-amino-3-(3-fluoro-5-hydroxyphenyl)-1H-pyrazolo[3,4-d]pyrimidin-1-yl]-ethyl}-3-{3-[(dimethylamino)-methyl]phenyl}indolizine-1-carbonitrile | W40 and (3-fluoro-5-hydroxyphenyl)-boronic acid | MS/ESI$^+$ 547.0 [MH]$^+$, Rt 0.64 min (Method A) |
| 128 | 3-{4-amino-1-[1-(7-{3-[(dimethylamino)-methyl]phenyl}pyrrolo[1,2-b]pyridazin-6-yl)-ethyl]-1H-pyrazolo[3,4-d]pyrimidin-3-yl}-5-fluorophenol | W41 and (3-fluoro-5-hydroxyphenyl)-boronic acid | MS/ESI$^+$ 523.5 [MH]$^+$, Rt 0.62 min (Method A) 1H NMR (400 MHz, DMSO-d6) δ ppm 10.16 (br. s., 1 H), 8.17 (s, 1 H), 8.08 (dd, 1 H), 7.98 (dd, 1 H), 7.41-7.46 (m, 1 H), 7.35-7.41 (m, 1 H), 7.30-7.33 (m, 1 H), 7.25-7.29 (m, 1 H), 6.88-6.91 (m, 1 H), 6.81-6.86 (m, 2 H), 6.63-6.70 (m, 2 H), 6.27-6.33 (m, 1 H), 6.26-7.95 (m, 2 H), 3.30-3.38 (m, 2 H), 2.11 (s, 6 H), 1.85 (d, 3 H). |
| 129 | 3-(4-amino-1-{1-[3-(1,3-thiazol-4-yl)indolizin-2-yl]-ethyl}-1H-pyrazolo[3,4-d]pyrimidin-3-yl)-5-fluorophenol | W42 and (3-fluoro-5-hydroxyphenyl)-boronic acid | MS/ESI$^+$ 472.3 [MH]$^+$, Rt 0.95 min (Method A). $^1$H NMR (400 MHz, DMSO-d$_6$) δ ppm 10.19 (br. s., 1 H), 9.35 (d, 1 H), 8.34-8.42 (m, 1 H), 8.19 (s, 1 H), 8.16 (d, 1 H), 7.44-7.50 (m, 1 H), 6.92-6.95 (m, 1 H), 6.83-6.90 (m, 1 H), 6.73-6.80 (m, 1 H), 6.63-6.70 (m, 2 H), 6.58-6.62 (m, 1 H), 6.48 (q, 1 H), 6.30-7.30 (m, 2 H), 1.91 (d, 3 H). |

| Example | Name and Molecular Structure | | Reagent | Analytical data |
|---|---|---|---|---|
| 130 | 3-[4-amino-1-(1-{3-[2-(morpholin-4-ylmethyl)-1,3-thiazol-4-yl]indolizin-2-yl}ethyl)-1H-pyrazolo-[3,4-d]pyrimidin-3-yl]-5-fluorophenol | 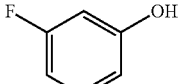 | W43 and (3-fluoro-5-hydroxyphenyl)-boronic acid | MS/ESI⁺ 571.3 [MH]⁺, Rt 0.73 min (Method A). ¹H NMR (400 MHz, DMSO-d6) δ ppm 10.17 (s, 1 H), 8.31 (d, 1 H), 8.17 (s, 1 H), 7.96 (s, 1 H), 7.47 (d, 1 H), 6.87-6.91 (m, 1 H), 6.80-6.86 (m, 1 H), 6.73-6.79 (m, 1 H), 6.63-6.68 (m, 2 H), 6.56-6.62 (m, 1 H), 6.47 (q, 1 H), 6.00-7.80 (m, 2 H), 3.81-3.92 (m, 2 H), 3.59-3.65 (m, 4 H), 2.48-2.54 (m, 4 H), 1.90 (d, 3 H). |
| 131 | 3-[4-amino-1-(1-{3-[3-(dimethylamino)prop-1-yn-1-yl]indolizin-2-yl}ethyl)-1H-pyrazolo[3,4-d]-pyrimidin-3-yl]-5-fluorophenol | 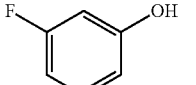 | W44 and (3-fluoro-5-hydroxyphenyl)-boronic acid | MS/ESI⁺ 470.2 [MH]⁺, Rt 0.97 min (Method C). ¹H NMR (400 MHz, DMSO-d6) δ ppm 10.17 (s, 1 H), 8.25 (s, 1 H), 8.12-8.16 (m, 1 H), 7.49 (d, 1 H), 6.91-6.95 (m, 1 H), 6.84-6.90 (m, 2 H), 6.75-6.81 (m, 1 H), 6.64-6.70 (m, 1 H), 6.47 (s, 1 H), 6.39 (q, 1 H), 6.20-7.50 (m, 2 H), 3.44-3.55 (m, 2 H), 2.20 (s, 6 H), 1.95 (d, 3 H). |
| 132 | 1-(2-{1-[4-amino-3-(3-fluoro-5-hydroxyphenyl)-1H-pyrazolo[3,4-d]pyrimidin-1-yl]ethyl}indolizin-3-yl)-4-methylpiperazin-2-one | 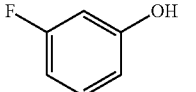 | W45 and (3-fluoro-5-hydroxyphenyl)-boronic acid | MS/ESI⁺ 501.3 [MH]⁺, Rt 0.74 and 0.77 min (Method C) mixture of isomers ≈ 65/35 by ¹H NMR) ¹H NMR (500 MHz, DMSO-d₆) δ ppm 10.10-10.23 (m, 1 H), 8.25 (s, 1 H), 7.62-7.75 (m, 1 H), 7.40-7.47 (m, 1 H), 6.80-6.96 (m, 2 H), 6.71-6.78 (m, 1 H), 6.52-6.69 (m, 3 H), 6.05-6.29 (m, 1 H), 5.92-8.00 (m, 2 H), 3.30-3.77 (m, 2 H), 3.04-3.28 (m, 2 H), 2.71-2.85 (m, 1 H), 2.47-2.59 (m, 1 H), 2.24-2.34 (m, 3 H), 1.81-1.95 (m, 3 H). |

| Example | Name and Molecular Structure | | Reagent | Analytical data |
|---|---|---|---|---|
| 133 | 4-(2-{1-[4-amino-3-(3-fluoro-5-hydroxyphenyl)-1H-pyrazolo[3,4-d]pyrimidin-1-yl]-ethyl}indolizin-3-yl)-1-[2-(dimethylamino)-ethyl]-1,2-dihydropyridin-2-one | 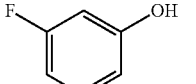 | W46 and (3-fluoro-5-hydroxyphenyl)-boronic acid | MS/ESI$^+$ 553.4 [MH]$^+$, Rt 0.80 min (Method J). $^1$H NMR (400 MHz, DMSO-d6) δ ppm 10.21 (br. s., 1 H), 8.16 (s, 1 H), 8.04 (d, 1 H), 7.72 (d, 1 H), 7.44-7.50 (m, 1 H), 6.90-6.92 (m, 1 H), 6.84-6.89 (m, 1 H), 6.75-6.81 (m, 1 H), 6.63-6.70 (m, 2 H), 6.57-6.62 (m, 1 H), 6.45 (d, 1 H), 6.28-6.37 (m, 2 H), 6.00-7.40 (m, 2 H), 3.99 (t, 2 H), 2.52-2.56 (m, 2 H), 2.22 (s, 6 H), 1.89 (d, 3 H). |
| 134 | 6-(2-{1-[4-amino-3-(3-fluoro-5-hydroxyphenyl)-1H-pyrazolo[3,4-d]pyrimidin-1-yl]-ethyl}indolizin-3-yl)-2-[2-(pyrrolidin-1-yl)-ethyl]-2,3-dihydropyridazin-3-one | 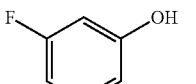 | W47 and (3-fluoro-5-hydroxyphenyl)-boronic acid | MS/ESI$^+$ 580.4 [MH]$^+$, Rt 0.65 min (Method A). $^1$H NMR (400 MHz, DMSO-d6) δ ppm 10.17 (br.s, 1H), 8.28-8.33 (m, 1H), 8.18 (s, 1 H), 7.73 (d, 1 H), 7.49-7.55 (m, 1 H), 6.97 (d, 1 H), 6.88-6.91 (m, 1 H), 6.79-6.87 (m, 2 H), 6.59-6.73 (m, 3 H), 6.39 (q, 1 H), 6.10-7.45 (m, 2 H), 4.10-4.26 (m, 2 H), 2.73-2.84 (m, 2 H), 2.43-2.55 (m, 4 H), 1.93 (d, 3 H), 1.62-1.73 (m, 4 H). |

-continued

| Example | Name and Molecular Structure | | Reagent | Analytical data |
|---|---|---|---|---|
| 135 | 6-(2-{1-[4-amino-3-(3-fluoro-5-hydroxyphenyl)-1H-pyrazolo[3,4-d]pyrimidin-1-yl]-ethyl}indolizin-3-yl)-2-[2-(4-methylpiperazin-1-yl)ethyl]-2,3-dihydropyridazin-3-one | 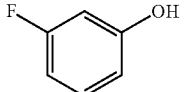 | W48 and (3-fluoro-5-hydroxyphenyl)-boronic acid | MS/ESI+ 609.7 [MH]+, Rt 0.63 min (Method A). 1H NMR (400 MHz, DMSO-d6) δ ppm 10.23 (br. s., 1 H), 8.26-8.31 (m, 1 H), 8.17 (s, 1 H), 7.72 (d, 1 H), 7.50-7.55 (m, 1 H), 6.97 (d, 1 H), 6.80-6.91 (m, 3 H), 6.59-6.73 (m, 3 H), 6.39 (q, 1 H), 6.00-8.00 (m, 2 H), 4.10-4.27 (m, 2 H), 2.62-2.72 (m, 2 H), 2.36-2.49 (m, 4 H), 2.20-2.33 (m, 4 H), 2.12 (s, 3 H), 1.93 (d, 3 H). |
| 136 | 6-(2-{1-[4-amino-3-(3-fluoro-5-hydroxyphenyl)-1H-pyrazolo[3,4-d]pyrimidin-1-yl]-ethyl}indolizin-3-yl)-2-[2-(morpholin-4-yl)ethyl]-2,3-dihydropyridazin-3-one | 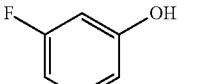 | W49 and (3-fluoro-5-hydroxyphenyl)-boronic acid | MS/ESI+ 596.3 [MH]+, Rt 0.65 min (Method A) 1H NMR (400 MHz, DMSO-d6) δ ppm 10.19 (bs, 1 H), 8.26-8.30 (m, 1 H), 8.17 (s, 1 H), 7.73 (d, 1 H), 7.50-7.55 (m, 1 H), 6.98 (d, 1 H), 6.89-6.92 (m, 1 H), 6.81-6.88 (m, 2 H), 6.60-6.74 (m, 3 H), 6.39 (q, 1 H), 6.00-7.40 (m, 2 H), 4.12-4.30 (m, 2 H), 3.50-3.58 (m, 4 H), 2.65-2.73 (m, 2 H), 2.37-2.47 (m, 4 H), 1.93 (d, 3 H). |

| Example | Name and Molecular Structure | Reagent | Analytical data |
|---|---|---|---|
| 137 | 3-{4-amino-1-[1-(3-{6-[2-(4-methylpiperazin-1-yl)ethoxy]pyridazin-3-yl}indolizin-2-yl)-ethyl]-1H-pyrazolo[3,4-d]pyrimidin-3-yl}-5-fluorophenol | W50 and (3-fluoro-5-hydroxyphenyl)-boronic acid | MS/ESI+ 609.5 [MH]+, Rt 0.63 min (Method A). 1H NMR (400 MHz, DMSO-d6) δ ppm 10.19 (br. s., 1 H), 8.39-8.43 (m, 1 H), 8.15 (s, 1 H), 7.94 (d, J = 8 Hz, 1 H), 7.51-7.55 (m, 1 H), 7.28 (d, 1 H), 6.88-6.91 (m, 1 H), 6.81-6.87 (m, 2 H), 6.73 (s, 1 H), 6.67 (dt, 1 H), 6.60-6.64 (m, 1 H), 6.40 (q, 1 H), 6.00-7.90 (m, 2 H), 4.58-4.65 (m, 2 H), 2.79 (t, 2 H), 2.29-2.60 (m, 8 H), 2.17 (s, 3 H), 1.94 (d, 3 H). |
| 138 | 3-{4-amino-1-[1-(3-{6-[2-(dimethylamino)-ethoxy]pyridazin-3-yl}indolizin-2-yl)-ethyl]-1H-pyrazolo[3,4-d]pyrimidin-3-yl}-5-fluorophenol | W51 and (3-fluoro-5-hydroxyphenyl)-boronic acid | MS/ESI+ 554.4 [MH]+, Rt 0.65 min (Method A). 1H NMR (400 MHz, DMSO-d6) δ ppm 10.23 (br. s., 1 H), 8.38-8.42 (m, 1 H), 8.14 (s, 1 H), 7.94 (d, 1 H), 7.50-7.54 (m, 1 H), 7.27 (d, 1 H), 6.88-6.90 (m, 1 H), 6.80-6.86 (m, 2 H), 6.72 (s, 1 H), 6.66 (dt, 1 H), 6.59-6.64 (m, 1 H), 6.39 (q, 1 H), 6.30-8.37 (m, 2 H), 4.57-4.61 (m, 2 H), 2.72 (t, 2 H), 2.26 (s, 6 H), 1.93 (d, 3 H). |

| Example | Name and Molecular Structure | Reagent | Analytical data |
|---|---|---|---|
| 139 | 3-{4-amino-1-[1-(3-{6-[(1-methylpiperidin-4-yl)oxy]pyridazin-3-yl}indolizin-2-yl)ethyl]-1H-pyrazolo-[3,4-d]pyrimidin-3-yl}-5-fluorophenol | W52 and (3-fluoro-5-hydroxyphenyl)-boronic acid | MS/ESI+ 580.5 [MH]+, Rt 0.66 min (Method A). 1H NMR (400 MHz, DMSO-d6) δ ppm 10.16 (s, 1 H), 8.37-8.40 (m, 1 H), 8.12 (s, 1 H), 7.90 (d, 1 H), 7.49-7.53 (m, 1 H), 7.19 (d, 1 H), 6.86-6.89 (m, 1 H), 6.78-6.85 (m, 2 H), 6.71 (s, 1 H), 6.65 (dt, 1 H), 6.57-6.62 (m, 1 H), 6.36-6.42 (m, 1H), 5.90-7.86 (m, 2 H), 5.19-5.27 (m, 1 H), 2.65-2.73 (m, 2 H), 2.15-2.26 (m, 5 H), 2.02-2.13 (m, 2 H), 1.92 (d, 3 H), 1.70-1.82 (m, 2 H). |
| 140 | 3-{4-amino-1-[1-(3-{6-[2-(1-methylpiperidin-4-yl)ethoxy]pyridazin-3-yl}indolizin-2-yl)-ethyl]-1H-pyrazolo[3,4-d]pyrimidin-3-yl}-5-fluorophenol | W53 and (3-fluoro-5-hydroxyphenyl)-boronic acid | MS/ESI+ 608.6 [MH]+, Rt 0.68 min (Method A). 1H NMR (400 MHz, DMSO-d6) δ ppm 10.22 (s, 1 H), 8.40 (d, 1H), 8.14 (s, 1 H), 7.93 (d, 1H), 7.50-7.54 (m, 1 H), 7.25 (d, 1 H), 6.87-6.90 (m, 1 H), 6.79-6.86 (m, 2 H), 6.72 (s, 1 H), 6.58-6.69 (m, 2 H), 6.38 (q, 1 H), 6.00-7.80 (m, 2 H), 4.49-4.59 (m, 2 H), 2.72-2.79 (m, 2 H), 2.14 (s, 3 H), 1.93 (d, 3 H), 1.66-1.89 (m, 6 H), 1.39-1.51 (m, 1 H), 1.18-1.31 (m, 2 H). |

| Example | Name and Molecular Structure | Reagent | Analytical data |
|---|---|---|---|
| 141 | 3-(4-amino-1-{1-[3-(morpholin-4-ylmethyl)indolizin-2-yl]ethyl}-1H-pyrazolo[3,4-d]pyrimidin-3-yl)-5-fluorophenol | W54 and (3-fluoro-5-hydroxyphenyl)-boronic acid | MS/ESI+ 488.4 [MH]+, Rt 0.92 min (Method J). 1H NMR (400 MHz, DMSO-d6) δ ppm 10.16 (br. s., 1 H), 8.28 (s, 1 H), 8.11-8.15 (m, 1 H), 7.37-7.42 (m, 1 H), 6.85-6.88 (m, 1 H), 6.79-6.84 (m, 1 H), 6.61-6.72 (m, 2 H), 6.54-6.61 (m, 2 H), 6.36 (q, 1 H), 6.00-7.30 m, 2 H), 3.73-3.88 (m, 2 H), 3.34-3.50 (m, 4 H), 2.12-2.23 (m, 4 H), 1.90 (d, 3 H). |
| 142 | 3-(4-amino-1-{1-[3-({2-methyl-2,9-diazaspiro[5.5]-undecan-9-yl}methyl)indolizin-2-yl]ethyl}-1H-pyrazolo[3,4-d]-pyrimidin-3-yl)-5-fluorophenol | W55 and (3-fluoro-5-hydroxyphenyl)-boronic acid | MS/ESI+ 569.5 [MH]+, Rt 1.18 min (Method J). 1H NMR (400 MHz, DMSO-d6) δ ppm 10.12 (br.s., 1 H), 8.28 (s, 1 H), 8.07-8.11 (m, 1 H), 7.37-7.41 (m, 1 H), 6.83-6.87 (m, 1 H), 6.77-6.82 (m, 1 H), 6.61-6.70 (m, 2 H), 6.60 (s, 1 H), 6.52-6.57 (m, 1 H), 6.36 (q, 1 H), 6.00-7.70 (m, 2 H), 3.66-3.85 (m, 2 H), 2.06 (s, 3 H), 1.90 (d, 3 H), 1.83-2.24 (m, 8 H), 1.05-1.45 (m, 8 H). |
| 146 | 2-{1-[4-amino-3-(3-fluoro-5-hydroxyphenyl)-1H-pyrazolo[3,4-d]pyrimidin-1-yl]-ethyl}-3-(morpholin-4-ylmethyl)indolizine-1-carbonitrile | W59 and (3-fluoro-5-hydroxyphenyl)-boronic acid | MS/ESI+ 513.4 [MH]+, Rt 0.64 min (Method A) 1H NMR (400 MHz, DMSO-d6) δ ppm 10.19 (s, 1 H), 8.44 (d, 1H), 8.26 (s, 1 H), 7.57-7.63 (m, 1 H), 7.20-7.26 (m, 1 H), 6.89-6.99 (m, 3 H), 6.64 (dt, 1 H), 6.42 (q, 1 H), 6.00-7.66 (m, 2 H), 3.84-4.00 (m, 2 H), 3.37-3.48 (m, 4 H), 2.19-2.28 (m, 4 H), 2.05 (d, 3 H). |

-continued

| Example | Name and Molecular Structure | Reagent | Analytical data |
|---|---|---|---|
| 147 | 3-{4-amino-1-[1-(3-{1-[2-(dimethylamino)-ethyl]-1H-pyrazol-3-yl}indolizin-2-yl)-ethyl]-1H-pyrazolo[3,4-d]pyrimidin-3-yl}-5-fluorophenol | W60 and (3-fluoro-5-hydroxyphenyl)-boronic acid | MS/ESI+ 526.4 [MH]+, Rt 0.65 min (Method A) 1H NMR (400 MHz, DMSO-d6) δ ppm 10.24 (br. s., 1 H), 8.72-8.75 (m, 1 H), 8.21 (s, 1 H), 7.94 (d, 1 H), 7.42-7.45 (m, 1 H), 6.93-6.96 (m, 1 H), 6.86-6.91 (m, 1 H), 6.77 (d, 1 H), 6.70-6.75 (m, 1 H), 6.66 (dt, 1 H), 6.57-6.62 (m, 2 H), 6.50 (q, 1 H), 6.45-7.40 (m, 2 H), 4.30 (t, 2 H), 2.73 (t, 2 H), 2.20 (s, 6 H), 1.89 (d, 3 H) |
| 148 | 3-{4-amino-1-[1-(3-{1-[2-(4-methylpiperazin-1-yl)ethyl]-1H-pyrazol-3-yl}indolizin-2-yl)-ethyl]-1H-pyrazolo[3,4-d]pyrimidin-3-yl}-5-fluorophenol | W61 and (3-fluoro-5-hydroxyphenyl)-boronic acid | MS/ESI+ 580.9 [MH]+, Rt 0.66 min (Method A) 1H NMR (400 MHz, DMSO-d6) δ ppm 10.20 (br. s., 1 H), 8.70-8.74 (m, 1 H), 8.21 (s, 1 H), 7.94 (d, 1 H), 7.41-7.46 (m, 1 H), 6.93-6.96 (m, 1 H), 6.87-6.92 (m, 1 H), 6.77 (d, 1 H), 6.70-6.75 (m, 1 H), 6.67 (dt, 1 H), 6.56-6.62 (m, 2 H), 6.50 (q, 1 H), 6.10-7.30 (m, 2 H), 4.32 (t, 2 H), 2.79 (t, 2 H), 2.39-2.51 (m, 4 H), 2.23-2.37 (m, 4 H), 2.13 (s, 3 H), 1.89 (d, 3 H). |
| 150 | 3-{4-amino-1-[1-(3-{1-[2-(morpholin-4-yl)ethyl]-1H-pyrazol-3-yl}indolizin-2-yl)ethyl]-1H-pyrazolo-[3,4-d]pyrimidin-3-yl}-5-fluorophenol | W63 and (3-fluoro-5-hydroxyphenyl)-boronic acid | MS/ESI+ 568.4 [MH]+, Rt 0.70 min (Method A) 1H NMR (400 MHz, METHANOL-d4) δ ppm 8.31-8.35 (m, 1 H), 8.22 (s, 1 H), 7.76 (d, 1 H), 7.38-7.43 (m, 1 H), 6.92-6.94 (m, 1 H), 6.87-6.91 (m, 1 H), 6.70-6.75 (m, 2 H), 6.66 (dt, 1 H), 6.50-6.59 (m, 3 H), 4.29-4.35 (m, 2 H), 3.68-3.72 (m, 4 H), 2.84 (t, 2 H), 2.51-2.55 (m, 4 H), 1.98 (d, 3 H). |

Example 117

3-(4-amino-1-{1-[3-(5-{[bis(2-hydroxyethyl)amino]methyl}pyridin-2-yl)indolizin-2-yl]ethyl}-1H-pyrazolo[3,4-d]pyrimidin-3-yl)-5-fluorophenol

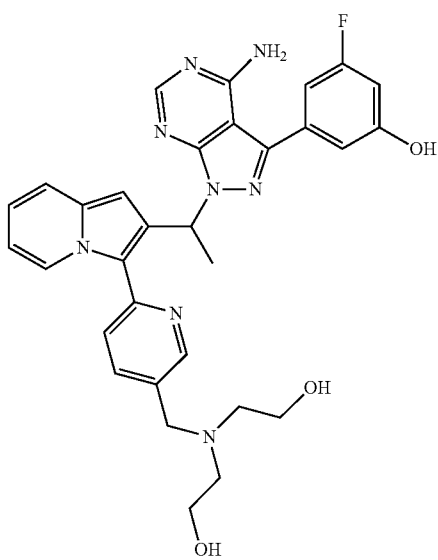 [SMILES: CC(c1cc2ccccn2c1-c1ccc(CN(CCO)CCO)cn1)n1nc(-c2cc(O)cc(F)c2)c2c(N)ncnc21]

A mixture of crude 3-iodo-1-[1-(3-{5-[(2,2,3,3,11,11,12,12-octamethyl-4,10-dioxa-7-aza-3,11-disilatridecan-7-yl)methyl]pyridin-2-yl}indolizin-2-yl)ethyl]-1H-pyrazolo[3,4-d]pyrimidin-4-amine W32 (0.214), (3-fluoro-5-hydroxyphenyl)boronic acid (0.044 g, 0.285 mmol) and Pd(PPh$_3$)$_4$ (0.015 g, 0.013 mmol), in DME (9.3 ml), EtOH (1.7 mL) and saturated aqueous Na$_2$CO$_3$ (3.5 ml) was heated at 80° C. for 3 h. The mixture was partitioned between water and DCM and the aqueous phase was extracted with DCM; the combined organic layers were washed with brine and dried over sodium sulfate, and the solvent was removed under reduced pressure. The residue was dissolved in a 1M solution of aqueous HCl in EtOH (prepared from aqueous 37% HCl in EtOH) (3.5 mL) and the mixture was stirred at r.t. for 3 h. The volatiles were removed under reduced pressure and the crude was dissolved in MeOH, charged on a SCX cartridge (1 g) washing with MeOH, and then eluted with 1M NH$_3$ in MeOH. The basic fractions were evaporated and the residue was purified by flash chromatography on silica gel cartridge (DCM to DCM:MeOH=85:15) to afford title compound as a yellow solid (0.040 g). MS/ESI$^+$ 583.3 [MH]$^+$, Rt 0.62 min (Method A). 1H NMR (400 MHz, DMSO-d6) δ ppm 10.18 (s, 1 H), 8.65-8.68 (m, 1 H), 8.60 (d, 1 H), 8.17 (s, 1 H), 7.87 (dd, 1 H), 7.70 (d, 1 H), 7.46-7.50 (m, 1 H), 6.90-6.93 (m, 1 H), 6.83-6.89 (m, 1 H), 6.76-6.82 (m, 1 H), 6.64-6.69 (m, 2 H), 6.55-6.61 (m, 1 H), 6.49 (q, 1 H), 6.20-7.30 (m, 2 H), 4.43 (t, 2 H), 3.76 (s, 2 H), 3.46-3.56 (m, 4 H), 2.60 (t, 4 H), 1.90 (d, 3 H).

Example 124

3-(4-amino-1-{1-[3-(pyridin-2-yl)-1-(trifluoromethyl)indolizin-2-yl]ethyl}-1H-pyrazolo[3,4-d]pyrimidin-3-yl)-5-fluorophenol

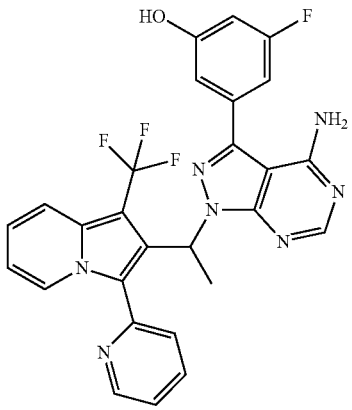 [SMILES: CC(c1c(C(F)(F)F)c2ccccn2c1-c1ccccn1)n1nc(-c2cc(O)cc(F)c2)c2c(N)ncnc21]

Step 1: 3-{3-[(tert-butyldimethylsilyl)oxy]-5-fluorophenyl}-1-{1-[3-(pyridin-2-yl)-1-(trifluoromethyl)indolizin-2-yl]ethyl}-1H-pyrazolo[3,4-d]pyrimidin-4-amine 124a

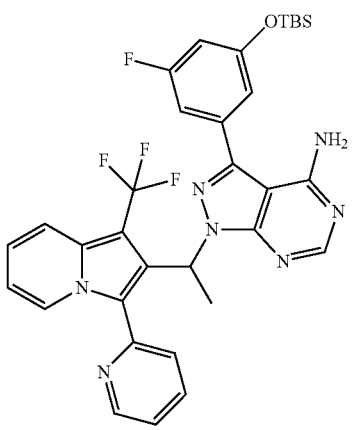 [SMILES: CC(c1c(C(F)(F)F)c2ccccn2c1-c1ccccn1)n1nc(-c2cc(F)cc(O[Si](C)(C)C(C)(C)C)c2)c2c(N)ncnc21]

To a mixture of 1-[3-(pyridin-2-yl)-1-(trifluoromethyl)indolizin-2-yl]ethan-1-ol M41 (0.065 g, 0.21 mmol), 3-{3-[(tert-butyldimethylsilyl)oxy]-5-fluorophenyl}-1H-pyrazolo[3,4-d]pyrimidin-4-amine AA7 (0.091 g, 0.25 mmol) and PPh3 (0.072 g, 0.27 mmol) in dry THF (3 mL), a solution of DIAD (0.049 ml, 0.25 mmol) in THF (1 mL) was added drop-wise and the reaction was stirred at RT for 1 h. The solvent was removed and the crude was purified by flash chromatography on Biotage silica gel cartridge (DCM to DCM:MeOH=95:5) to afford crude title compound (0.100 g) which was used without any additional purification. MS/ESI$^+$ 648.4 [MH]$^+$, Rt 1.56 (Method A).

Step 2: 3-(4-amino-1-{1-[3-(pyridin-2-yl)-1-(trifluoromethyl)indolizin-2-yl]ethyl}-1H-pyrazolo[3,4-d]pyrimidin-3-yl)-5-fluorophenol 124

To a solution of crude 3-{3-[(tert-butyldimethylsilyl)oxy]-5-fluorophenyl}-1-{1-[3-(pyridin-2-yl)-1-(trifluoromethyl)indolizin-2-yl]ethyl}-1H-pyrazolo[3,4-d]pyrimidin-4-amine 124a (0.100 g) in THF (1.7 ml), a solution of tetrabutylammonium fluoride 1M in THF (0.23 ml, 0.23 mmol) was added and the resulting mixture was stirred at RT for 30 minutes, then diluted with DCM and quenched with a saturated aqueous solution of NH₄Cl. The phases were separated, the organic layer was dried over sodium sulfate, filtered and concentrated. The crude was purified by flash chromatography on Biotage silica gel cartridge (DCM to DCM:MeOH=98:3). The obtained product was further purified by preparative TLC (DCM:MeOH=95:5) to obtain title compound (4.5 mg). MS/ESI⁺ 534.3 [MH]⁺, Rt 1.00 (Method A).

1H NMR (400 MHz, DMSO-d6) δ ppm 10.23 (br. s., 1 H), 8.58-8.61 (m, 1 H), 8.12 (s, 1 H), 7.74-7.83 (m, 2 H), 7.64-7.69 (m, 1 H), 7.47-7.51 (m, 1 H), 7.29-7.34 (m, 1 H), 7.13-7.18 (m, 1 H), 6.73-6.81 (m, 2 H), 6.67-6.72 (m, 1 H), 6.64 (dt, 1 H), 6.31 (q, 1 H), 6.00-7.73 (m, 2 H), 1.91 (d, 3 H).

Example 143

3-(4-amino-1-{1-[3-({9-methyl-3,9-diazaspiro[5.5]undecan-3-yl}methyl)indolizin-2-yl]ethyl}-1H-pyrazolo[3,4-d]pyrimidin-3-yl)-5-fluorophenol

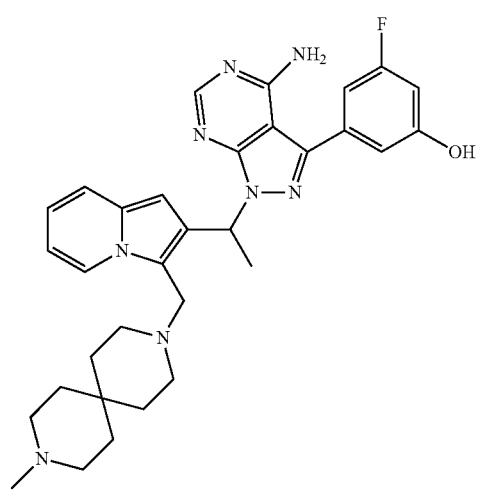 [SMILES: CC(c1cc2ccccn2c1CN1CCC2(CCN(C)CC2)CC1)n1nc(-c2cc(O)cc(F)c2)c2c(N)ncnc21]

Step 1: tert-butyl 9-[(2-{1-[4-amino-3-(3-fluoro-5-hydroxyphenyl)-1H-pyrazolo[3,4-d]pyrimidin-1-yl]ethyl}indolizin-3-yl)methyl]-3,9-diazaspiro[5.5]undecane-3-carboxylate 143a

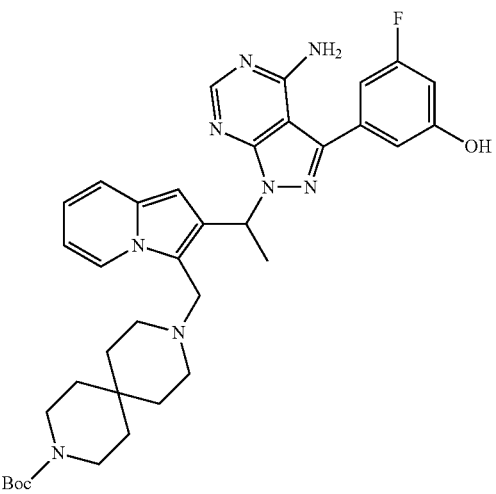 [SMILES: CC(c1cc2ccccn2c1CN1CCC2(CC1)CCN(C(=O)OC(C)(C)C)CC2)n1nc(-c2cc(O)cc(F)c2)c2c(N)ncnc21]

Prepared similarly to Example 85, starting from crude tert-butyl 9-{[2-(1-{4-amino-3-iodo-1H-pyrazolo[3,4-d]pyrimidin-1-yl}ethyl)indolizin-3-yl]methyl}-3,9-diazaspiro[5.5]undecane-3-carboxylate W56 (0.370 g), (3-fluoro-5-hydroxyphenyl)boronic acid (0.129 g, 0.828 mmol) and Pd(PPh₃)₄ (0.032 g, 0.028 mmol), in DME (18 ml), EtOH (3 mL) and saturated aqueous Na₂CO₃ (5.5 ml), heating at 80° C. overnight; after work-up the crude was purified by flash chromatography on Biotage silica-NH SNAP cartridge (DCM to DCM:MeOH=95:5) to afford title compound (0.017 g, 0.026 mmol). MS/ESI⁺ 655.5 [MH]⁺, Rt 1.46 min (Method J).

Step 2: 3-(4-amino-1-{1-[3-({9-methyl-3,9-diazaspiro[5.5]undecan-3-yl}methyl)indolizin-2-yl]ethyl}-1H-pyrazolo[3,4-d]pyrimidin-3-yl)-5-fluorophenol 143

A mixture of tert-butyl 9-[(2-{1-[4-amino-3-(3-fluoro-5-hydroxyphenyl)-1H-pyrazolo[3,4-d]pyrimidin-1-yl]ethyl}indolizin-3-yl)methyl]-3,9-diazaspiro[5.5]undecane-3-carboxylate 143a (17 mg, 0.026 mmol) and 1M in THF LiAlH4 (0.156 mL, 0.156 mmol) in dry THF (8 mL) was stirred at 65° C. under nitrogen for 2 h. The reaction was cooled to 0° C., sodium sulphate decahydrate was added and the mixture was stirred at RT for 0.5 h, then the solid was filtered off and the filtrate was evaporated. The resulting crude was purified by chromatography on silica NH cartridge (DCM to DCM:MeOH=90:10) to afford title compound as a white solid (5 mg). MS/ESI⁺ 569.6 [MH]⁺, Rt 1.09 min (Method J).

1H NMR (500 MHz, DMSO-d6) δ ppm 10.20 (br. s., 1 H), 8.29 (s, 1 H), 8.08 (d, 1 H), 7.39 (d, 1 H), 6.75-6.87 (m, 2 H), 6.60-6.71 (m, 3 H), 6.55 (t, 1 H), 6.36 (q, 1 H), 6.85 (br. s, 2 H), 3.82 (d, 1 H), 3.67 (d, 1 H), 2.12-2.22 (m, 4 H), 2.09 (s, 3 H), 1.90 (d, 3 H), 1.85-2.03 (m, 4 H), 1.10-1.29 (m, 8 H).

Example 144

3-(4-amino-1-{1-[3-({7-methyl-2,7-diazaspiro[3.5]nonan-2-yl}methyl)indolizin-2-yl]ethyl}-1H-pyrazolo[3,4-d]pyrimidin-3-yl)-5-fluorophenol

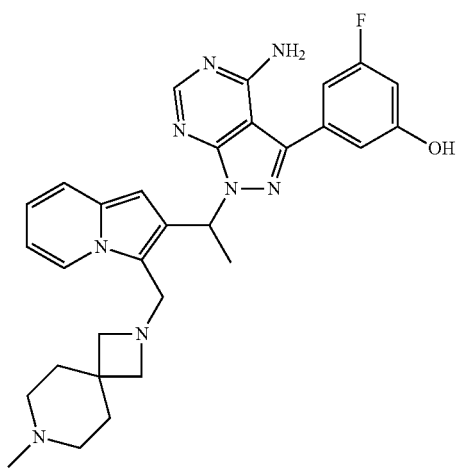 [SMILES: CC(c1cc2ccccn2c1CN1CC2(CCN(C)CC2)C1)n1nc(-c2cc(O)cc(F)c2)c2c(N)ncnc21]

Step 1: tert-butyl 2-[(2-{1-[4-amino-3-(3-fluoro-5-hydroxyphenyl)-1H-pyrazolo[3,4-d]pyrimidin-1-yl]ethyl}indolizin-3-yl)methyl]-2,7-diazaspiro[3.5]nonane-7-carboxylate 144a

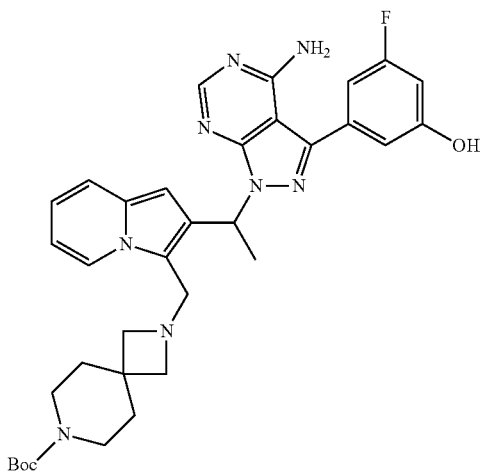 [SMILES: CC(c1cc2ccccn2c1CN1CC2(CCN(C(=O)OC(C)(C)C)CC2)C1)n1nc(-c2cc(O)cc(F)c2)c2c(N)ncnc21]

Prepared similarly to Example 85, starting from crude tert-butyl 2-{[2-(1-{4-amino-3-iodo-1H-pyrazolo[3,4-d]pyrimidin-1-yl}ethyl)indolizin-3-yl]methyl}-2,7-diazaspiro[3.5]nonane-7-carboxylate W57 (0.056 g), (3-fluoro-5-hydroxyphenyl)boronic acid (0.027 g, 0.174 mmol) and Pd(PPh$_3$)$_4$ (0.010 g, 0.0087 mmol), in DME (4 ml), EtOH (0.5 mL) and saturated aqueous Na$_2$CO$_3$ (1.4 ml), heating at 80° C. overnight; after work-up the crude was purified by flash chromatography on Biotage silica-NH SNAP cartridge (DCM to DCM:MeOH=85:15) to afford title compound as a pale brown solid (0.024 g, 0.038 mmol). MS/ESI$^+$ 627.6 [MH]$^+$, Rt 0.77 min (Method A).

Step 2: 3-(4-amino-1-{1-[3-({7-methyl-2,7-diazaspiro[3.5]nonan-2-yl}methyl)indolizin-2-yl]ethyl}-1H-pyrazolo[3,4-d]pyrimidin-3-yl)-5-fluorophenol 144

Prepared similarly to Example 143 Step 2, starting from tert-butyl 2-[(2-{1-[4-amino-3-(3-fluoro-5-hydroxyphenyl)-1H-pyrazolo[3,4-d]pyrimidin-1-yl]ethyl}indolizin-3-yl)methyl]-2,7-diazaspiro[3.5]nonane-7-carboxylate 144a (24 mg, 0.038 mmol), heating at 65° C. overnight, and purified by chromatography on silica-NH cartridge (DCM to DCM:MeOH=90:10) to afford title compound as a white solid (6 mg). MS/ESI$^+$ 541.5 [MH]$^+$, Rt 0.88 min (Method J).

1H NMR (500 MHz, DMSO-d6) δ ppm 10.15 (br. s., 1 H), 8.30 (s, 1 H), 8.11 (d, 1 H), 7.39 (d, 1 H), 6.85-6.91 (m, 1 H), 6.78-6.83 (m, 1 H), 6.60-6.71 (m, 3 H), 6.51-6.57 (m, 1 H), 6.41 (q, 1 H), 6.32-8.39 (m, 2 H), 3.69-4.07 (m, 2 H), 2.52-2.63 (m, 4 H), 1.80-2.22 (m, 10 H), 1.36-1.51 (m, 4 H).

Example 145

3-{1-[1-(3-{[(3aR,6aS)-5-methyl-octahydropyrrolo[3,4-c]pyrrol-2-yl]methyl}indolizin-2-yl)ethyl]-4-amino-1H-pyrazolo[3,4-d]pyrimidin-3-yl}-5-fluorophenol

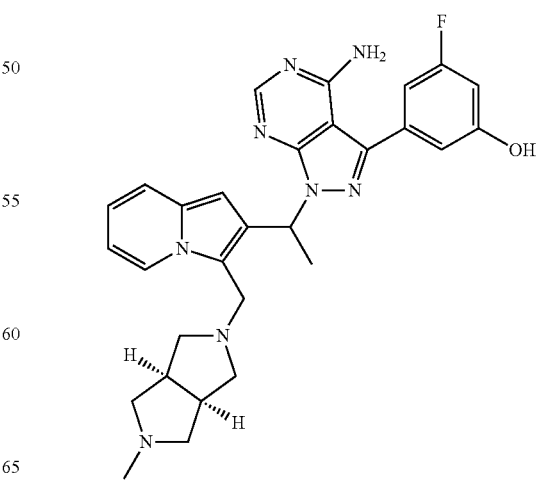

Step 1: tert-butyl (3aR,6aS)-5-[(2-{1-[4-amino-3-(3-fluoro-5-hydroxyphenyl)-1H-pyrazolo[3,4-d]pyrimidin-1-yl]ethyl}indolizin-3-yl)methyl]-octahydropyrrolo[3,4-c]pyrrole-2-carboxylate 145a

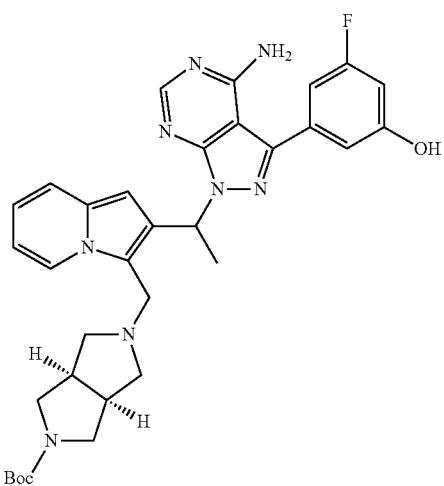 [SMILES: CC(c1cc2ccccn2c1CN1C[C@@H]2CN(C(=O)OC(C)(C)C)C[C@@H]2C1)n1nc(-c2cc(O)cc(F)c2)c2c(N)ncnc21]

Prepared similarly to Example 85, starting from crude tert-butyl (3aR,6aS)-5-{[2-(1-{4-amino-3-iodo-1H-pyrazolo[3,4-d]pyrimidin-1-yl}ethyl)indolizin-3-yl]methyl}-octahydropyrrolo[3,4-c]pyrrole-2-carboxylate W58 (0.152 g), (3-fluoro-5-hydroxyphenyl)boronic acid (0.041 g, 0.266 mmol) and Pd(PPh$_3$)$_4$ (0.014 g, 0.012 mmol), in DME (8.6 ml), EtOH (1.6 mL) and saturated aqueous Na$_2$CO$_3$ (3.3 ml), heating at 80° C. for 3 h; after work-up the crude was purified by flash chromatography on Biotage silica-NH SNAP cartridge (DCM to DCM:MeOH=90:10) to afford title compound as a yellow solid (0.032 g). MS/ESI$^+$ 613.3 [MH]$^+$, Rt 1.23 min (Method C).

Step 2: 3-{1-[1-(3-{[(3aR,6aS)-5-methyl-octahydropyrrolo[3,4-c]pyrrol-2-yl]methyl}indolizin-2-yl)ethyl]-4-amino-1H-pyrazolo[3,4-d]pyrimidin-3-yl}-5-fluorophenol 145

Prepared similarly to Example 143 Step 2, starting from tert-butyl (3aR,6aS)-5-[(2-{1-[4-amino-3-(3-fluoro-5-hydroxyphenyl)-1H-pyrazolo[3,4-d]pyrimidin-1-yl]ethyl}indolizin-3-yl)methyl]-octahydropyrrolo[3,4-c]pyrrole-2-carboxylate 145a (18 mg, 0.029 mmol), heating at 65° C. overnight, and purified by chromatography on silica-NH cartridge (DCM:MeOH=99:1 to 90:10) to afford title compound as a vitreous solid (2.8 mg). MS/ESI$^+$ 527.3 [MH]$^+$, Rt 0.99 min (Method C).

1H NMR (400 MHz, METHANOL-d4) δ ppm 8.28 (s, 1 H), 8.17 (d, 1 H), 7.34 (d, 1 H), 6.86-6.89 (m, 1 H), 6.80-6.85 (m, 1 H), 6.59-6.71 (m, 3 H), 6.42-6.53 (m, 2 H), 3.84-4.09 (m, 2 H), 2.74-2.88 (m, 2 H), 2.52-2.69 (m, 2 H), 2.28-2.39 (m, 2 H), 2.27 (s, 3 H), 2.18-2.24 (m, 1 H), 1.99 (d, 3 H), 1.96-2.16 (m, 3 H).

Example 149

3-(4-amino-1-{1-[3-(1-{2-[bis(2-hydroxyethyl)amino]ethyl}-1H-pyrazol-3-yl)indolizin-2-yl]ethyl}-1H-pyrazolo[3,4-d]pyrimidin-3-yl)-5-fluorophenol

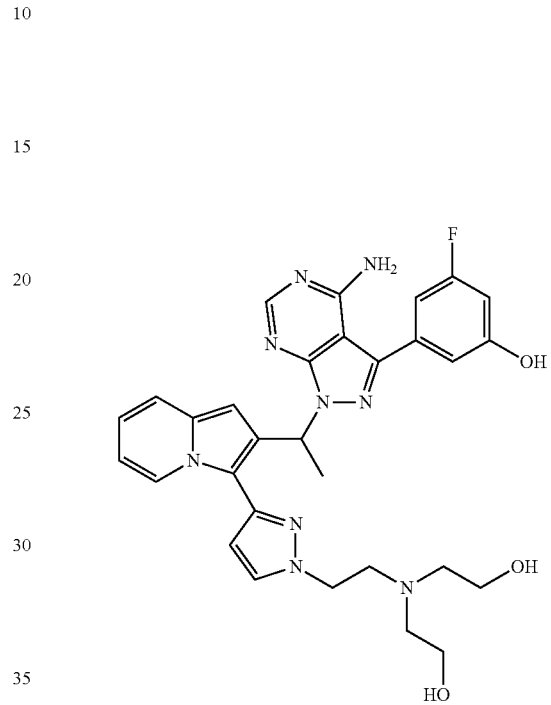

Prepared similarly to Example 117, starting from 3-iodo-1-[1-(3-{1-[2-(2,2,3,3,11,11,12,12-octamethyl-4,10-dioxa-7-aza-3,11-disilatridecan-7-yl)ethyl]-1H-pyrazol-3-yl}indolizin-2-yl)ethyl]-1H-pyrazolo[3,4-d]pyrimidin-4-amine W62 (0.180 g) and (3-fluoro-5-hydroxyphenyl)boronic acid (39.7 mg, 0.25 mmol). After work-up the crude was dissolved in MeOH and charged on a SCX cartridge (10 g) washing with MeOH, and then eluted with 1M NH$_3$ in MeOH. The basic fractions were evaporated and the residue was purified by flash chromatography on silica gel cartridge (DCM to DCM:MeOH=90:10) to afford title compound as a yellow solid (8.7 mg). MS/ESI$^+$ 586.5 [MH]$^+$, Rt 0.63 min (Method A).

1H NMR (400 MHz, DMSO-d6) δ ppm 8.69-8.73 (m, 1H), 8.22 (s, 1H), 7.97 (d, 1 H), 7.41-7.45 (m, 1H), 6.94-6.97 (m, 1 H), 6.87-6.92 (m, 1 H), 6.78 (d, 1 H), 6.69-6.75 (m, 1 H), 6.66 (dt, 1 H), 6.56-6.62 (m, 2 H), 6.50 (q, 1 H), 6.46-7.30 (m, 2 H), 4.19-4.43 (m, 4 H), 3.39 (t, 4 H), 2.99 (t, 2 H), 2.60 (t, 4 H), 1.88 (d, 3 H).

Example 93a (Enantiomer 1) and Example 93b (Enantiomer 2)

3-{4-amino-1-[1-(3-{3-[(dimethylamino)methyl]phenyl}indolizin-2-yl)ethyl]-1H-pyrazolo[3,4-d]pyrimidin-3-yl}-5-fluorophenol

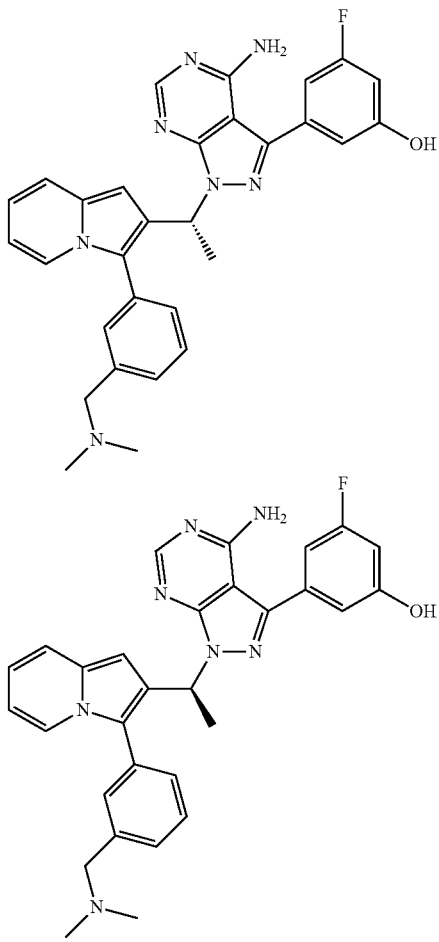

Racemate 3-{4-amino-1-[1-(3-{3-[(dimethylamino)methyl]phenyl}indolizin-2-yl)ethyl]-1H-pyrazolo[3,4-d]pyrimidin-3-yl}-5-fluorophenol described in Example 93 (0.330 g) was dissolved in EtOH/MeOH 1/1 (140 ml) and submitted to chiral resolution by Chiral preparative liquid chromatography. Conditions: Column: Chiralpak AD-H (25×3.0 cm), 5 µm; Mobile phase: n-Hexane/(Ethanol+0.1% isopropylamine) 85/15% v/v; UV detection: 220 nm; Flow Rate: 34 mL/min; Injection: 10.8 mg.

Compound 93a was obtained as the first eluted enantiomer as a pale brown solid (0.105 g). MS/ESI⁺ 522.3 [MH]⁺, Rt 0.70 min (Method A). Chiral HPLC Method K: Rt=7.3 min, 100% ee.

1H NMR (400 MHz, DMSO-d6) δ ppm 10.16 (br. s., 1 H), 8.14 (s, 1 H), 7.78-7.83 (m, 1 H), 7.40-7.48 (m, 2 H), 7.28-7.34 (m, 2 H), 7.22 (s, 1 H), 6.88-6.92 (m, 1 H), 6.80-6.87 (m, 1 H), 6.62-6.74 (m, 3 H), 6.54-8.10 (m, 2 H), 6.47-6.53 (m, 1 H), 6.20 (q, 1 H), 3.32-3.40 (m, 2 H), 2.12 (s, 6 H), 1.83 (d, 3 H).

Compound 93b was obtained as the second eluted enantiomer as a pale brown solid (0.103 g). MS/ESI⁺ 522.3 [MH]⁺, Rt 0.69 min (Method A). Chiral HPLC Method K: Rt=10.5 min, 100% ee.

1H NMR (400 MHz, DMSO-d6) δ ppm 10.15 (br. s., 1 H), 8.14 (s, 1 H), 7.78-7.83 (m, 1 H), 7.40-7.48 (m, 2 H), 7.28-7.34 (m, 2 H), 7.22 (s, 1 H), 6.88-6.92 (m, 1 H), 6.80-6.87 (m, 1 H), 6.62-6.74 (m, 3 H), 6.54-8.10 (m, 2 H), 6.47-6.53 (m, 1 H), 6.20 (q, 1 H), 3.32-3.40 (m, 2 H), 2.12 (s, 6 H), 1.83 (d, 3 H).

Example 108a (Enantiomer 1) and Example 108b (Enantiomer 2)

3-[4-amino-1-(1-{3-[5-(morpholin-4-ylmethyl)pyridin-2-yl]indolizin-2-yl}ethyl)-1H-pyrazolo[3,4-d]pyrimidin-3-yl]-5-fluorophenol

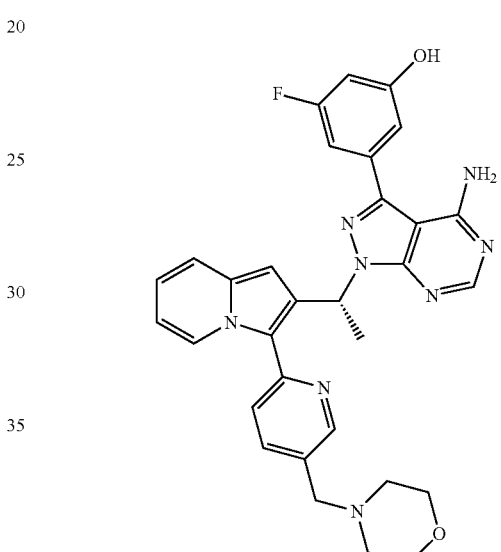

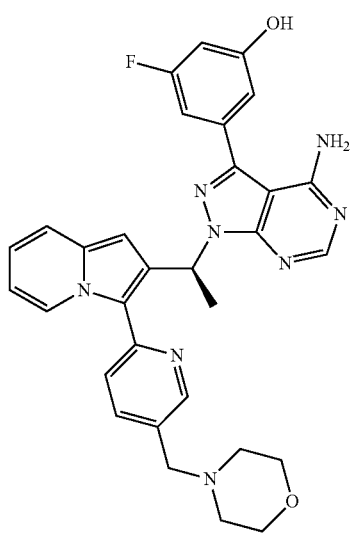

Racemate 3-[4-amino-1-(1-{3-[5-(morpholin-4-ylmethyl)pyridin-2-yl]indolizin-2-yl}ethyl)-1H-pyrazolo[3,4-d]pyrimidin-3-yl]-5-fluorophenol described in Example 108 (0.063 g) was dissolved in EtOH (8 ml) and submitted to chiral resolution by Chiral preparative liquid chromatography. Conditions: Column: Chiralpak AD-H (25×2 cm), 5 um; Mobile phase: n-Hexane/(Ethanol+0.1% isopropylamine) 70/30% v/v; UV detection: 220 nm; Flow Rate: 14 mL/min; Injection: 9 mg.

Compound 108a was obtained as the first eluted enantiomer (23 mg) MS/ESI⁺ 565.4 [MH]⁺, Rt 0.65 min (Method A). Chiral HPLC Method L: Rt=12.8 min, 100% ee.

¹H NMR (400 MHz, DMSO-d₆) δ ppm 10.18 (br. s., 1 H), 8.57-8.62 (m, 2 H), 8.17 (s, 1 H), 7.77 (dd, 1 H), 7.68 (d, 1 H), 7.48-7.53 (m, 1 H), 6.86-6.90 (m, 1 H), 6.77-6.86 (m, 2 H), 6.71 (s, 1 H), 6.66 (dt, 1 H), 6.57-6.63 (m, 1 H), 6.52 (q, 1 H), 6.10-7.44 (m, 2 H), 3.59-3.65 (m, 4 H), 3.51-3.59 (m, 2 H), 2.36-2.44 (m, 4 H), 1.92 (d, 3 H). Compound 108b was obtained as the second eluted enantiomer (19 mg). MS/ESI⁺ 565.4 [MH]⁺, Rt 0.64 min (Method A). Chiral HPLC Method L: Rt=16.0 min, 97.6% ee.

¹H NMR (400 MHz, DMSO-d₆) δ ppm 10.20 (br. s., 1 H), 8.57-8.62 (m, 2 H), 8.17 (s, 1 H), 7.77 (dd, 1 H), 7.68 (d, 1 H), 7.48-7.53 (m, 1 H), 6.86-6.90 (m, 1 H), 6.77-6.86 (m, 2 H), 6.71 (s, 1 H), 6.66 (dt, 1 H), 6.57-6.63 (m, 1 H), 6.52 (q, 1 H), 6.10-7.44 (m, 2 H), 3.59-3.66 (m, 4 H), 3.51-3.59 (m, 2 H), 2.36-2.45 (m, 4 H), 1.92 (d, 3 H).

Example 114a (Enantiomer 1) and Example 114b (Enantiomer 2)

3-{4-amino-1-[1-(3-{5-[(4-methylpiperazin-1-yl)methyl]pyridin-2-yl}indolizin-2-yl)ethyl]-1H-pyrazolo[3,4-d]pyrimidin-3-yl}-5-fluorophenol

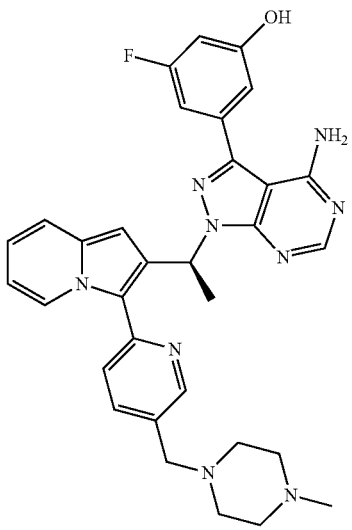

Racemate 3-{4-amino-1-[1-(3-{5-[(4-methylpiperazin-1-yl)methyl]pyridin-2-yl}indolizin-2-yl)ethyl]-1H-pyrazolo[3,4-d]pyrimidin-3-yl}-5-fluorophenol described in Example 114 (0.266 g) was dissolved in 10 ml Ethanol+4 ml n-Hexane and submitted to chiral resolution by Chiral preparative liquid chromatography. Conditions: Column: Chiralpak AD-H (25×2.0 cm), 5 μm; Mobile phase: n-Hexane/(Ethanol+0.1% isopropylamine) 80/20% v/v; UV detection: 220 nm; Flow Rate: 18 mL/min; Injection: 28.5 mg.

Compound 114a was obtained as the first eluted enantiomer as a yellow solid (0.091 g). MS/ESI⁺ 578.4 [MH]⁺, Rt 0.64 min (Method A). Chiral HPLC Method M: Rt=8.8 min, 100% ee.

1H NMR (400 MHz, DMSO-d6) δ ppm 10.18 (br. s., 1 H), 8.54-8.60 (m, 2 H), 8.15 (s, 1 H), 7.72 (dd, 1 H), 7.64 (d, 1 H), 7.47-7.51 (m, 1 H), 6.86-6.89 (m, 1 H), 6.76-6.84 (m, 2 H), 6.69 (s, 1 H), 6.64 (dt, 1 H), 6.55-6.60 (m, 1 H), 6.51 (q, 1 H), 6.10-7.30 (m, 2 H), 3.48-3.58 (m, 2 H), 2.22-2.49 (m, 8 H), 2.16 (s, 3 H), 1.90 (d, 3 H).

Compound 114b was obtained as the second eluted enantiomer as a yellow solid (0.091 g). MS/ESI⁺ 578.4 [MH]⁺, Rt 0.64 min (Method A). Chiral HPLC Method M: Rt=15.3 min, 100% ee.

1H NMR (400 MHz, DMSO-d6) δ ppm 10.17 (br. s., 1 H), 8.54-8.60 (m, 2 H), 8.15 (s, 1 H), 7.72 (dd, 1 H), 7.64 (d, 1 H), 7.47-7.51 (m, 1 H), 6.86-6.89 (m, 1 H), 6.76-6.84 (m, 2 H), 6.69 (s, 1 H), 6.64 (dt, 1 H), 6.55-6.60 (m, 1 H), 6.51 (q, 1 H), 6.10-7.30 (m, 2 H), 3.48-3.58 (m, 2 H), 2.22-2.49 (m, 8 H), 2.16 (s, 3 H), 1.90 (d, 3 H).

Example 117a (Enantiomer 1) and Example 117b (Enantiomer 2)

3-(4-amino-1-{1-[3-(5-{[bis(2-hydroxyethyl)amino]methyl}pyridin-2-yl)indolizin-2-yl]ethyl}-1H-pyrazolo[3,4-d]pyrimidin-3-yl)-5-fluorophenol

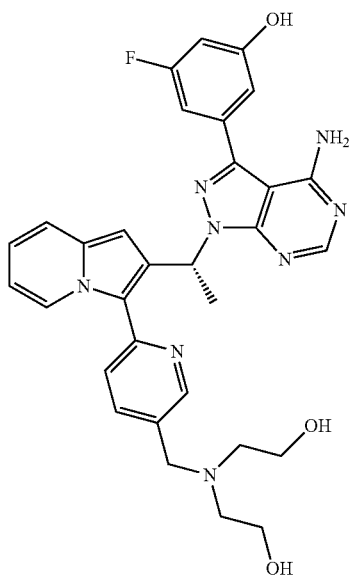

Racemate 3-(4-amino-1-{1-[3-(5-{[bis(2-hydroxyethyl)amino]methyl}pyridin-2-yl)indolizin-2-yl]ethyl}-1H-pyrazolo[3,4-d]pyrimidin-3-yl)-5-fluorophenol described in Example 117 (0.030 g) was dissolved in 3 ml of (Ethanol/n-Hexane 1/1) and submitted to chiral resolution by Chiral preparative liquid chromatography. Conditions: Column: Chiralpak AD-H (25×2.0 cm), 5 μm; Mobile phase: n-Hexane/(Ethanol/Methanol 1/1+0.1% isopropylamine) 75/25% v/v; UV detection: 220 nm; Flow Rate: 17 mL/min; Injection: 8 mg.

Compound 117a was obtained as the first eluted enantiomer (0.012 g). MS/ESI$^+$ 583.4 [MH]$^+$, Rt 0.60 min (Method A). Chiral HPLC Method N: Rt=5.3 min, 100% ee.

1H NMR (400 MHz, DMSO-d6) δ ppm 9.75-10.50 (m, 1 H), 8.65-8.68 (m, 1 H), 8.58-8.62 (m, 1 H), 8.17 (s, 1 H), 7.87 (dd, 1 H), 7.70 (d, 1 H), 7.46-7.50 (m, 1 H), 6.88-6.91 (m, 1 H), 6.76-6.86 (m, 2 H), 6.62-6.68 (m, 2 H), 6.55-6.61 (m, 1 H), 6.49 (q, 1 H), 6.20-7.30 (m, 2 H), 4.45 (br. s., 2 H), 3.76 (s, 2 H), 3.51 (t, 4 H), 2.60 (t, 4 H), 1.90 (d, 3 H).

Compound 117b was obtained as the second eluted enantiomer (0.012 g). MS/ESI$^+$ 583.4 [MH]$^+$, Rt 0.60 min (Method A). Chiral HPLC Method N: Rt=7.7 min, 100% ee.

1H NMR (400 MHz, DMSO-d6) δ ppm 10.17 (s, 1 H), 8.65-8.68 (m, 1 H), 8.58-8.62 (m, 1 H), 8.17 (s, 1 H), 7.87 (dd, 1 H), 7.70 (d, 1 H), 7.46-7.50 (m, 1 H), 6.90-6.93 (m, 1 H), 6.84-6.89 (m, 1 H), 6.76-6.82 (m, 1 H), 6.64-6.69 (m, 2 H), 6.55-6.61 (m, 1 H), 6.49 (q, 1 H), 6.20-7.30 (m, 2 H), 4.43 (t, 2 H), 3.76 (s, 2 H), 3.47-3.55 (m, 4 H), 2.60 (t, 4 H), 1.90 (d, 3 H).

Example 121a (Enantiomer 1) and Example 121b (Enantiomer 2)

4-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one

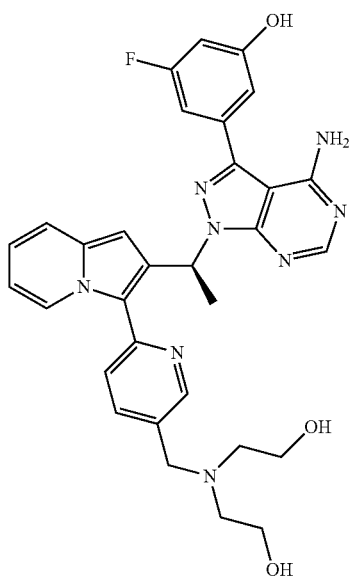

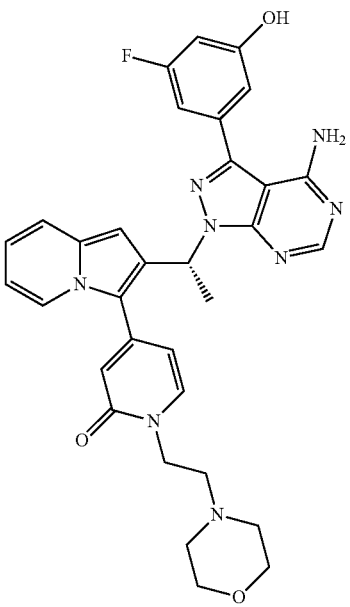

-continued

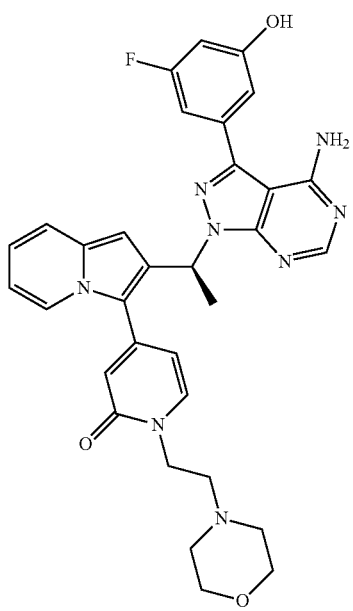

Racemate 4-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one described in Example 121 (0.225 g) was dissolved in 50 ml of (Ethanol/n-Hexane 1/1) and submitted to chiral resolution by Chiral preparative liquid chromatography. Conditions: Column: Chiralpak IC (25×2.0 cm), 5 μm; Mobile phase: n-Hexane/(Ethanol+0.1% isopropylamine) 75/25% v/v; UV detection: 220 nm; Flow Rate: 19 mL/min; Injection: 22 mg.

Compound 121a was obtained as the first eluted enantiomer (0.074 g). MS/ESI$^+$ 595.4 [MH]$^+$, Rt 0.67 min (Method J). Chiral HPLC Method O: Rt=14.9 min, 98% ee.

1H NMR (400 MHz, DMSO-d6) δ ppm 10.17 (br.s., 1 H), 8.16 (s, 1 H), 8.02-8.06 (m, 1 H), 7.73 (d, 1 H), 7.45-7.50 (m, 1 H), 6.89-6.92 (m, 1 H), 6.84-6.89 (m, 1 H), 6.75-6.81 (m, 1 H), 6.63-6.71 (m, 2 H), 6.57-6.63 (m, 1 H), 6.42-6.46 (m, 1 H), 6.29-6.37 (m, 2 H), 6.00-7.40 (m, 2 H), 3.98-4.05 (m, 2 H), 3.54-3.62 (m, 4 H), 2.55-2.61 (m, 2 H), 2.43-2.50 (m, 4 H), 1.89 (d, 3 H).

Compound 121b was obtained as the second eluted enantiomer (0.076 g). MS/ESI$^+$ 595.4 [MH]$^+$, Rt 0.64 min (Method J). Chiral HPLC Method O: Rt=17.9 min, 98% ee.

1H NMR (400 MHz, DMSO-d6) δ ppm 10.19 (br.s., 1 H), 8.16 (s, 1 H), 8.02-8.06 (m, 1 H), 7.73 (d, 1 H), 7.45-7.50 (m, 1 H), 6.89-6.92 (m, 1 H), 6.84-6.89 (m, 1 H), 6.75-6.81 (m, 1 H), 6.63-6.71 (m, 2 H), 6.57-6.63 (m, 1 H), 6.42-6.46 (m, 1 H), 6.29-6.37 (m, 2 H), 6.00-7.40 (m, 2 H), 3.98-4.06 (m, 2 H), 3.54-3.62 (m, 4 H), 2.55-2.62 (m, 2 H), 2.43-2.50 (m, 4 H), 1.89 (d, 3 H).

Example 127a (Enantiomer 1) and Example 127b (Enantiomer 2)

2-{1-[4-amino-3-(3-fluoro-5-hydroxyphenyl)-1H-pyrazolo[3,4-d]pyrimidin-1-yl]ethyl}-3-{3-[(dimethylamino)methyl]phenyl}indolizine-1-carbonitrile

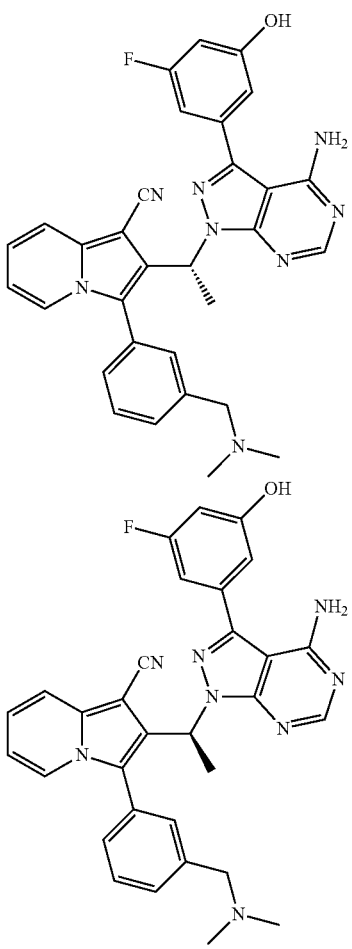

Racemate 2-{1-[4-amino-3-(3-fluoro-5-hydroxyphenyl)-1H-pyrazolo[3,4-d]pyrimidin-1-yl]ethyl}-3-{3-[(dimethylamino)methyl]phenyl}indolizine-1-carbonitrile described in Example 127 (0.146 g) was dissolved in 7 ml Ethanol/n-Hexane 1/1 and submitted to chiral resolution by Chiral preparative liquid chromatography. Conditions: Column: Chiralpak AD-H (25×2.0 cm), 5 μm; Mobile phase: n-Hexane/(Ethanol+0.1% isopropylamine) 75/25% v/v; UV detection: 220 nm; Flow Rate: 17 mL/min; Injection: 10.4 mg.

Compound 127a was obtained as the first eluted enantiomer (53.7 mg). MS/ESI$^+$ 547.4 [MH]$^+$, Rt 0.64 min (Method A). Chiral HPLC Method P: Rt=5.7 min, 100% ee.

1H NMR (400 MHz, DMSO-d6) δ ppm 10.19 (br. s., 1 H), 8.12 (s, 1 H), 7.89 (d, 1 H), 7.67 (d, 1 H), 7.43-7.49 (m, 1 H), 7.37-7.42 (m, 1 H), 7.27-7.33 (m, 1 H), 7.17-7.26 (m, 2 H), 6.84-6.92 (m, 3 H), 6.64 (dt, 1 H), 6.17 (q, 1 H), 6.10-7.80 (m, 2 H), 3.30-3.40 (m, 2 H), 2.10 (s, 6 H), 1.93 (d, 3 H).

Compound 127b was obtained as the second eluted enantiomer (52.8 mg). MS/ESI$^+$ 547.3 [MH]$^+$, Rt 0.64 min (Method A). Chiral HPLC Method P: Rt=7.5 min, 99.6% ee.

1H NMR (400 MHz, DMSO-d6) δ ppm 10.19 (br. s., 1 H), 8.12 (s, 1 H), 7.89 (d, 1 H), 7.67 (d, 1 H), 7.43-7.49 (m, 1 H), 7.37-7.42 (m, 1 H), 7.27-7.33 (m, 1 H), 7.17-7.26 (m, 2 H), 6.84-6.92 (m, 3 H), 6.64 (dt, 1 H), 6.17 (q, 1 H), 6.10-7.80 (m, 2 H), 3.30-3.40 (m, 2 H), 2.10 (s, 6 H), 1.93 (d, 3 H).

Example 133a (Enantiomer 1) and Example 133b (Enantiomer 2)

4-(2-{1-[4-amino-3-(3-fluoro-5-hydroxyphenyl)-1H-pyrazolo[3,4-d]pyrimidin-1-yl]ethyl}indolizin-3-yl)-1-[2-(dimethylamino)ethyl]-1,2-dihydropyridin-2-one

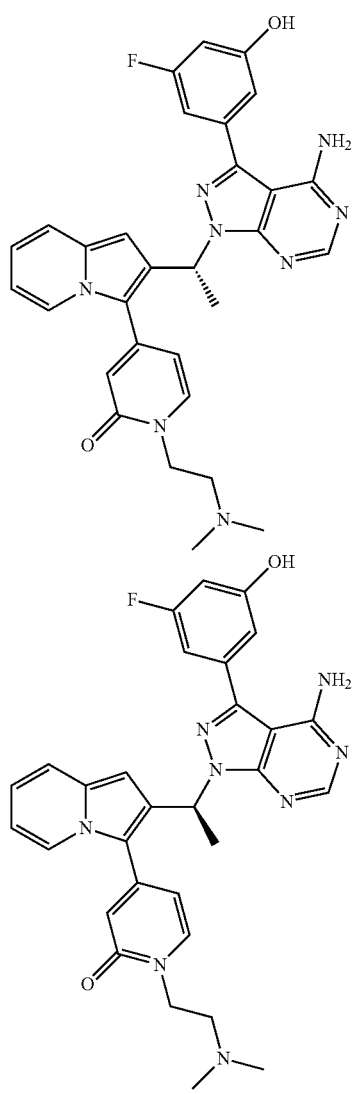

Racemate 4-(2-{1-[4-amino-3-(3-fluoro-5-hydroxyphenyl)-1H-pyrazolo[3,4-d]pyrimidin-1-yl]ethyl}indolizin-3-yl)-1-[2-(dimethylamino)ethyl]-1,2-dihydropyridin-2-one described in Example 133 (55.0 mg) was dissolved in 11 ml of ethanol and submitted to chiral resolution by Chiral preparative liquid chromatography. Conditions: Column: Chiralpak IC (25×2.0 cm), 5 μm; Mobile phase: n-Hexane/(Ethanol+0.1% isopropylamine) 70/30% v/v; UV detection: 220 nm; Flow Rate: 15 mL/min; Injection: 5 mg.

Compound 133a was obtained as the first eluted enantiomer (17.3 mg). MS/ESI$^+$ 553.5 [MH]$^+$, Rt 0.63 min (Method A). Chiral HPLC Method Q: Rt=7.7 min, 100% ee.

1H NMR (400 MHz, DMSO-d6) δ ppm 10.17 (br. s., 1 H), 8.16 (s, 1 H), 8.04 (d, 1 H), 7.72 (d, 1 H), 7.45-7.49 (m, 1 H), 6.90-6.92 (m, 1 H), 6.84-6.89 (m, 1 H), 6.75-6.81 (m, 1 H), 6.63-6.70 (m, 2 H), 6.57-6.62 (m, 1 H), 6.45 (d, 1 H), 6.28-6.36 (m, 2 H), 6.00-7.40 (m, 2 H), 3.99 (t, 2 H), 2.51-2.55 (m, 2 H), 2.22 (s, 6 H), 1.89 (d, 3 H).

Compound 133b was obtained as the second eluted enantiomer (19.7 mg). MS/ESI$^+$ 553.5 [MH]$^+$, Rt 0.63 min (Method A). Chiral HPLC Method Q: Rt=8.9 min, 96.8% ee.

1H NMR (400 MHz, DMSO-d6) δ ppm 10.19 (br. s., 1 H), 8.16 (s, 1 H), 8.04 (d, 1 H), 7.72 (d, 1 H), 7.45-7.49 (m, 1 H), 6.90-6.92 (m, 1 H), 6.84-6.89 (m, 1 H), 6.75-6.81 (m, 1 H), 6.63-6.70 (m, 2 H), 6.57-6.62 (m, 1 H), 6.45 (d, 1 H), 6.28-6.36 (m, 2 H), 6.00-7.40 (m, 2 H), 3.99 (t, 2 H), 2.51-2.55 (m, 2 H), 2.22 (s, 6 H), 1.89 (d, 3 H).

Pharmacological Activity of the Compounds of the Invention

In vitro Determination of the PI3K Enzyme Inhibitory Activity in the Cell Free Assay Human recombinant proteins PI3Kα, PI3Kβ, PI3Kγ and PI3Kδ were purchased from Millipore Ltd (Billerica, Mass.). Compounds were dissolved at 0.5 mM in DMSO and were tested at different concentrations for their activity against PI3Ks using the ADP-Glo™ Kinase Assay (Promega, Madison Wis.) according to the manufacturer's instructions.

Briefly, the kinase reactions were performed in 384-well white plates (Greiner Bio-One GmbH, Frickenhausen). Each well was loaded with 0.1 μl of test compounds and 2.5 μl of 2× reaction buffer (40 mM Tris pH7.5, 0.5 mM EGTA, 0.5 mM Na$_3$VO$_4$, 5 mM β-glycerophosphate, 0.1 mg/ml BSA, 1 mM DTT), containing 50 μM PI and PS substrates (L-α-phosphatidylinositol sodium salt and L-α-phosphatidyl-L-serine, Sigma-Aldrich, St. Louis Mo.) and the PI3K recombinant proteins (PI3Kγ 0.25 ng/μl, PI3Kδ 1 ng/μl, PI3Kα 0.125 ng/μl, PI3Kβ 1 ng/μl).

The reactions were started by adding 2.5 μl of 2×ATP solution to each well (final concentrations: PI3Kγ ATP 30 μM; PI3Kδ ATP 80 μM; PI3KαATP 50 μM; PI3Kβ ATP 100 μM) and incubated for 60 min at room temperature. Subsequently, each kinase reaction was incubated for 40 min with 5 μl ADP-Glo™ Reagent, allowing depletion of unconsumed ATP. Then, the Kinase Detection Reagent (10 μl) was added in each well to convert ADP to ATP and to allow the newly synthesized ATP to be measured using a luciferase/luciferin reaction. Following 60 min incubation, the luminescence signal was measured using a Wallac EnVision® multilabel reader (PerkinElmer, Waltham Mass.).

Curve fitting and IC50 calculation were carried out using a four-parameter logistic model in XLfit (IDBS, Guilford, UK) for Microsoft Excel (Microsoft, Redmont, Wash.).

Representative compounds according to the invention showed IC50<1 μM, some even lower than 10 nM, particularly in the PI3Kdelta inhibitory assay herein above described. The results for individual compounds are provided below in Table 1

TABLE 1

Results of the in vitro determination of the PI3K enzyme inhibitory activity in the cell free assay.

| Compound of Example N. | PI3K alpha inhibition | PI3K beta inhibition | PI3K delta inhibition | PI3K gamma inhibition |
|---|---|---|---|---|
| 1 | + | + | + | + |
| 2 | + | + | + | + |
| 3 | + | + | + | + |
| 4 | + | + | ++ | + |
| 5 | + | + | + | + |
| 6 | + | + | + | + |
| 7 | + | + | + | + |
| 8 | + | + | + | + |
| 9 | + | + | + | + |
| 10 | + | + | + | + |
| 11 | + | + | + | + |
| 12 | + | + | + | + |
| 13 | + | + | + | + |
| 14 | + | + | + | + |
| 15 | + | + | + | + |
| 16 | + | + | + | + |
| 17 | + | + | + | + |
| 18 | + | + | ++ | + |
| 19 | + | + | + | + |
| 20 | + | + | ++ | + |
| 21 | + | ++ | ++ | + |
| 22 | + | + | ++ | + |
| 23 | + | + | ++ | + |
| 24 | + | + | ++ | + |
| 25 | + | + | ++ | + |
| 26 | + | + | ++ | + |
| 27 | + | + | + | + |
| 28 | + | + | ++ | + |
| 29 | + | + | ++ | + |
| 30 | + | + | ++ | + |
| 31 | + | + | ++ | + |
| 32 | + | + | ++ | + |
| 33 | + | ++ | ++ | + |
| 34 | + | ++ | ++ | ++ |
| 35 | + | ++ | ++ | + |
| 36 | + | ++ | ++ | ++ |
| 37 | + | + | ++ | + |
| 38 | + | + | ++ | + |
| 39 | + | ++ | +++ | + |
| 40 | + | + | +++ | + |
| 41 | + | + | ++ | + |
| 42 | + | ++ | ++ | + |
| 43 | + | ++ | ++ | + |
| 44 | + | + | ++ | ++ |
| 45 | + | ++ | ++ | + |
| 46 | + | ++ | ++ | ++ |
| 47 | + | ++ | ++ | + |
| 48 | + | + | ++ | + |
| 49 | + | + | ++ | + |
| 50 | + | + | ++ | + |
| 51 | + | + | ++ | + |
| 52 | + | + | ++ | + |
| 53 | + | + | + | + |
| 54 | + | + | + | + |
| 55 | + | + | + | + |
| 56 | + | + | + | + |
| 57 | + | + | + | + |
| 58 | + | ++ | +++ | + |
| 59 | + | + | ++ | + |
| 60 | + | + | ++ | + |
| 61 | + | ++ | ++ | ++ |
| 62 | + | + | ++ | + |
| 63 | + | + | + | + |
| 64 | + | + | ++ | + |
| 65 | + | ++ | +++ | ++ |
| 66 | + | ++ | ++ | + |
| 67 | + | + | ++ | + |
| 68 | + | + | ++ | + |
| 69 | + | ++ | +++ | ++ |
| 70 | + | + | ++ | ++ |
| 71 | + | + | ++ | ++ |
| 72 | + | ++ | +++ | ++ |
| 73 | + | + | ++ | + |
| 74 | + | + | ++ | + |
| 75 | + | + | + | + |
| 76 | + | ++ | ++ | + |
| 77 | + | ++ | +++ | ++ |
| 78 | + | + | + | + |
| 79 | ++ | ++ | +++ | ++ |
| 80 | ++ | ++ | +++ | ++ |
| 81 | + | + | ++ | + |
| 82 | + | ++ | +++ | ++ |
| 83 | ++ | ++ | +++ | ++ |
| 84 | + | + | ++ | + |
| 85 | + | ++ | ++ | + |
| 86 | + | + | ++ | ++ |
| 87 | + | ++ | ++ | + |
| 88 | + | + | ++ | + |
| 89 | ++ | ++ | ++ | ++ |
| 90 | ++ | ++ | +++ | ++ |
| 91 | + | + | ++ | + |
| 92 | + | ++ | ++ | + |
| 93 | ++ | ++ | ++ | ++ |
| 93a | ++ | ++ | +++ | + |
| 93b | + | ++ | ++ | + |
| 94 | ++ | ++ | +++ | ++ |
| 95 | ++ | ++ | +++ | ++ |
| 96 | + | ++ | +++ | + |
| 97 | ++ | ++ | +++ | ++ |
| 98 | ++ | ++ | ++ | ++ |
| 99 | ++ | ++ | +++ | ++ |
| 100 | + | ++ | +++ | ++ |
| 101 | + | ++ | ++ | + |
| 102 | + | + | ++ | + |
| 103 | + | ++ | ++ | ++ |
| 104 | ++ | ++ | +++ | ++ |
| 105 | + | + | ++ | + |
| 106 | + | ++ | +++ | ++ |
| 107 | + | ++ | +++ | ++ |
| 108 | + | ++ | +++ | + |
| 108a | + | ++ | +++ | + |
| 108b | + | ++ | +++ | + |
| 109 | + | ++ | ++ | + |
| 110 | + | ++ | +++ | + |
| 111 | + | ++ | +++ | ++ |
| 112 | ++ | ++ | +++ | ++ |
| 113 | + | ++ | +++ | + |
| 114 | + | ++ | +++ | + |
| 114a | ++ | ++ | +++ | ++ |
| 114b | ++ | ++ | +++ | ++ |
| 115 | ++ | ++ | ++ | ++ |
| 116 | ++ | ++ | +++ | ++ |
| 117 | + | ++ | +++ | + |
| 117a | ++ | ++ | +++ | + |
| 117b | ++ | ++ | +++ | + |
| 118 | + | ++ | ++ | + |
| 119 | + | ++ | +++ | + |
| 120 | + | + | +++ | ++ |
| 121 | + | ++ | +++ | ++ |
| 121a | + | + | ++ | + |
| 121b | ++ | ++ | +++ | ++ |
| 122 | + | ++ | +++ | + |
| 123 | + | ++ | +++ | + |
| 124 | + | ++ | +++ | + |
| 125 | ++ | ++ | +++ | ++ |
| 126 | ++ | ++ | +++ | ++ |
| 127 | + | ++ | +++ | + |
| 127a | ++ | ++ | +++ | ++ |
| 127b | + | + | +++ | + |
| 128 | + | ++ | ++ | + |
| 129 | ++ | ++ | ++ | ++ |
| 130 | + | ++ | +++ | ++ |
| 131 | ++ | ++ | ++ | ++ |
| 132 | ++ | ++ | +++ | ++ |
| 133 | + | ++ | +++ | ++ |
| 133a | + | + | ++ | + |
| 133b | ++ | ++ | +++ | ++ |
| 134 | + | ++ | +++ | + |

TABLE 1-continued

Results of the in vitro determination of the PI3K enzyme inhibitory activity in the cell free assay.

| Compound of Example N. | PI3K alpha inhibition | PI3K beta inhibition | PI3K delta inhibition | PI3K gamma inhibition |
|---|---|---|---|---|
| 135 | + | ++ | ++ | + |
| 136 | ++ | ++ | ++ | + |
| 137 | + | ++ | +++ | + |
| 138 | ++ | ++ | +++ | ++ |
| 139 | + | ++ | ++ | + |
| 140 | + | ++ | ++ | + |
| 141 | ++ | ++ | +++ | ++ |
| 142 | + | + | ++ | ++ |
| 143 | ++ | ++ | +++ | ++ |
| 144 | ++ | ++ | ++ | ++ |
| 145 | ++ | ++ | ++ | ++ |
| 146 | | | | |
| 147 | ++ | ++ | +++ | + |
| 148 | ++ | ++ | +++ | ++ |
| 149 | + | ++ | +++ | ++ |
| 150 | + | ++ | +++ | ++ |

Wherein the compounds are classified in term of potency with respect to their inhibitory activity on PI3K-alpha, -beta, -gamma and -delta according to the following:
+++: IC50<10 nM
++: 1050 in the range 10-1000 nM
+: IC50>1000 nM Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I)

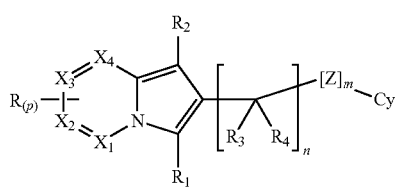

(I)

wherein
$X_1$, $X_2$, $X_3$ and $X_4$ are all CH groups;
each R, when present, is —$OR_5$, —$SR_5$, —$S(O)_q$—$R_7$, halogen, —$NR_{10}R_{11}$, ($C_1$-$C_6$) alkyl, ($C_1$-$C_6$) haloalkyl, ($C_1$-$C_6$) hydroxyalkyl, ($C_1$-$C_6$) aminoalkyl, ($C_3$-$C_7$) cycloalkyl, ($C_2$-$C_6$) alkenyl, ($C_5$-$C_7$) cycloalkenyl, ($C_2$-$C_6$) alkynyl, ($C_2$-$C_6$) hydroxyalkynyl, aryl, heteroaryl, or ($C_3$-$C_6$) heterocycloalkyl, each of which may be optionally and independently substituted with one or more groups selected from the group consisting of halogen, —OH, ($C_1$-$C_6$) alkyl, ($C_1$-$C_6$) haloalkyl, ($C_1$-$C_6$) hydroxyalkyl, ($C_1$-$C_6$) aminoalkyl, ($C_3$-$C_7$) cycloalkyl, ($C_2$-$C_6$) alkenyl, ($C_5$-$C_7$) cycloalkenyl, ($C_2$-$C_6$) alkynyl, and ($C_2$-$C_6$) hydroxyalkynyl;

$R_1$ is —H, —$OR_6$, —$SR_6$, —$S(O)_q$—$R_8$, halogen, —$NR_{12}R_{13}$, —CN, —$C(O)NR_{12}R_{13}$, —$C(O)OR_{16}$, ($C_1$-$C_6$) alkyl, ($C_1$-$C_6$) haloalkyl, ($C_1$-$C_6$) hydroxyalkyl, ($C_1$-$C_6$) aminoalkyl, ($C_3$-$C_7$) cycloalkyl, ($C_2$-$C_6$) alkenyl, ($C_5$-$C_7$) cycloalkenyl, ($C_2$-$C_6$) alkynyl, ($C_2$-$C_6$) hydroxyalkynyl, aryl, heteroaryl, or ($C_3$-$C_6$) heterocycloalkyl, each of which may be optionally and independently substituted with one or more groups selected from the group consisting of halogen, —$NR_{22}R_{23}$, —$(CH_2)_nNR_{22}R_{23}$, ($C_1$-$C_6$) alkyl, ($C_1$-$C_6$) alkoxyl, (C1-C6) aminoalkoxyl ($C_3$-$C_6$) heterocycloalkyloxyl, ($C_3$-$C_6$) heterocycloalkyl ($C_1$-$C_6$) alkoxyl, ($C_1$-$C_6$) haloalkyl, ($C_1$-$C_6$) hydroxyalkyl, ($C_2$-$C_6$) alkenyl, ($C_2$-$C_6$) alkynyl, and ($C_2$-$C_6$) hydroxyalkynyl;

$R_2$ is —H, —$OR_9$, —$SR_9$, —$S(O)_q$—R—, halogen, —$NR_{14}R_{15}$, —CN, —$C(O)NR_{14}R_{15}$, —$C(O)OR_{18}$, —($C_1$-$C_6$) alkyl, —($C_1$-$C_6$) haloalkyl, —($C_1$-$C_6$) hydroxyalkyl, ($C_1$-$C_6$) aminoalkyl, ($C_3$-$C_7$) cycloalkyl, ($C_5$-$C_7$) cycloalkenyl, ($C_2$-$C_6$) alkenyl, ($C_2$-$C_6$) alkynyl,($C_2$-$C_6$) hydroxyalkynyl, aryl, heteroaryl, or ($C_3$-$C_6$) heterocycloalkyl each of which may be optionally and independently substituted with one or more groups selected from the group consisting of halogen; —$NR_{24}R_{25}$, —$(CH_2)_nNR_{24}R_{25}$, ($C_1$-$C_6$) alkyl, ($C_1$-$C_6$) haloalkyl,($C_1$-$C_6$) hydroxyalkyl, ($C_2$-$C_6$) alkenyl, ($C_2$-$C_6$) alkynyl, and ($C_2$-$C_6$) hydroxyalkynyl;

$R_3$ and $R_4$, are the same or different and are each independently —H, ($C_1$-$C_6$) alkyl, or ($C_1$-$C_6$) haloalkyl;

Cy is 3H-purin-3-yl, 9H-purin-9-yl, 9H-purin-6-yl, 1H-pyrazolo[3,4-d]pyrimidin-1-yl, 6-oxo-5H,6H,7H-pyrrolo[2,3-d]pyrimidin-4-yl, pyrimidin-4-yl, pyrimidin-2-yl, pyrazin-2-yl, or 1,3,5-triazin-2-yl, each of which may be optionally and independently substituted by one or more substituents selected from the group consisting of halogen, —OH, —$NR_{19}R_{20}$, —$CH_2NR_{19}R_{20}$; —CN, —CH(O), —CH=NOH, —$C(O)NR_{19}R_{20}$, —$C(O)OR_{21}$, ($C_1$-$C_6$) alkyl, ($C_1$-$C_6$) haloalkyl, ($C_1$-$C_6$) hydroxyalkyl, ($C_2$-$C_6$) alkenyl, ($C_2$-$C_6$) alkynyl, ($C_2$-$C_6$) hydroxyalkynyl, aryl, heteroaryl, and ($C_3$-$C_6$) heterocycloalkyl wherein each substituent may be optionally and independently substituted with one or more groups selected from the group consisting of —OH, halogen, —CN, —$S(O)_2NR^IR^{III}$, —$NR^{III}S(O)_2R^{II}$, —$NR^IR^{III}$, ($C_1$-$C_6$) alkyl, ($C_1$-$C_6$) haloalkyl, ($C_1$-$C_6$) hydroxyalkyl, ($C_1$-$C_6$)alkoxy, aryl, heteroaryl, and ($C_3$-$C_6$) heterocycloalkyl;

wherein $R^I$ $R^{II}$ and $R^{III}$ are the same or different and are each independently —H, ($C_1$-$C_6$) alkyl or alkanoyl;

$R_5$, $R_6$, $R_9$, $R_{16}$, $R_{18}$, and $R_{21}$ are the same or different and are each independently —H, ($C_1$-$C_6$) alkyl, ($C_1$-$C_6$) haloalkyl, ($C_1$-$C_6$) hydroxyalkyl, ($C_1$-$C_6$) aminoalkyl, alkanoyl, or aryl alkanoyl;

$R_7$, $R_8$ and $R_{17}$ are the same or different and are each independently $NR_{12}R_{13}$, ($C_1$-$C_6$) alkyl, ($C_1$-$C_6$) haloalkyl, ($C_1$-$C_6$) hydroxyalkyl, ($C_1$-$C_6$) aminoalkyl, aryl, heteroaryl or($C_3$-$C_6$) heterocycloalkyl, each of which may be optionally and independently substituted with one or more groups selected from the group consisting of halogen, —$NR_{22}R_{23}$, —$CH_2NR_{22}R_{23}$, ($C_1$-$C_6$) alkyl, ($C_1$-$C_6$) haloalkyl, ($C_1$-$C_6$) hydroxyalkyl, ($C_2$-$C_6$) alkenyl,($C_2$-$C_6$) alkynyl, and ($C_2$-$C_6$) hydroxyalkynyl;

$R_{10}$, $R_{11}$, $R_{12}$, $R_{13}$, $R_{14}$, $R_{15}$, $R_{19}$, $R_{20}$, $R_{22}$, $R_{23}$, $R_{24}$ and $R_{25}$ are the same or different and are each independently —H, ($C_1$-$C_6$) alkyl, ($C_1$-$C_6$) hydroxyalkyl, or alkanoyl or, taken together with the nitrogen atom to which they are bonded, anyone of $R_{10}$ and $R_{11}$, $R_{12}$ and $R_{13}$, $R_{14}$ and $R_{15}$, $R_{19}$ and $R_{20}$, $R_{22}$ and $R_{23}$, abd $R_{24}$ and $R_{25}$ may form an optionally substituted 5 to 6 membered heterocycle wherein at least one ring carbon atom in said heterocycle may be replaced by at least one member selected from the group consisting of O, S, N, NH and an oxo substituent;

Z, when present, is —O—, —NH—, —C(O)—, —NHC(O)—, —C(O)NH—, —S—, —S(O)—, or —S(O)$_2$—;

m is zero or 1;

n is 1 or 2;

p is zero or an integer ranging from 1 to 3; and q is an integer ranging from 1 to 2, or a pharmaceutically acceptable salt thereof.

2. A compound or pharmaceutically acceptable salt according to claim 1, which is a mixture of diastereoisomers.

3. A compound or pharmaceutically acceptable salt according to claim 1, wherein:
$R_3$ is H or ($C_1$-$C_6$) alkyl; and
$R_4$ is H.

4. A compound or pharmaceutically acceptable salt according to claim 1, wherein:
$R_3$ is ($C_1$-$C_6$) alkyl;
$R_4$ is H.

5. A compound or pharmaceutically acceptable salt according to claim 1, wherein:
$R_3$ is methyl;
$R_4$ is H; and
Cy is 1H-pyrazolo[3,4-d]pyrimidin-1-yl, which may be optionally substituted by one or more substituents selected from the group consisting of —NR$_{19}$R$_{20}$ and aryl wherein said substituents may be optionally substituted by one or more groups selected from the group consisting of —OH and halogen.

6. A compound or pharmaceutically acceptable salt according to claim 5, wherein:
$R_1$ is 4-morpholinomethyl, 2-methyl-2,9-diazaspiro[5.5]undecan-9-yl}methyl, 9-methyl-3,9-diazaspiro[5.5]undecan-3-yl}methyl, 7-methyl-2,7-diazaspiro[3.5]nonan-2-yl}methyl, or 5-methyl-octahydropyrrolo[3,4-c]pyrrol-2-yl]methyl;
$R_3$ is methyl;
$R_4$ is H; and
CY is 1H-pyrazolo[3,4-d]pyrimidin-1-yl (I-4), which is substituted in position 4 by —NH$_2$ and in position 3 by 3-fluoro-5-hydroxyphenyl.

7. A compound or pharmaceutically acceptable salt according to claim 1, wherein:
R is $C_1$-$C_6$ alkyl, $C_1$-$C_6$ haloalkyl, or halogen;
$R_1$ is hydrogen, $C_2$-$C_6$ alkynyl, $C_2$-$C_6$ aminoalkynyl, $C_2$-$C_6$ hydroxyalkynyl, aryl, heteroaryl, $C_3$-$C_6$ heterocycloalkyl, —(CH$_2$)$_n$N$_{22}$N$_{23}$, wherein each aryl and heteroaryl may be optionally substituted by one or two groups independently selected from the group consisting of halogen, cyano, ($C_1$-$C_6$) alkyl, —C(O)NR$_{12}$R$_{13}$, ($C_3$-$C_6$) heterocycloalkyl, —NR$_{22}$R$_{23}$, —(CH$_2$)nR$_{22}$R$_{23}$, ($C_3$-$C_6$) heterocycloalkoxyl, and ($C_3$-$C_6$) heterocycloalkyl ($C_1$-$C_6$) alkoxyl;
$R_2$ is hydrogen, cyano, ($C_1$-$C_6$) haloalkyl, aryl, or heteroaryl;
$R_3$ is H or ($C_1$-$C_6$) alkyl;
$R_4$ is H;
Cy is 9H-purine-6-amine-9-yl, 3H-purine-6-amine-3-yl, 9H-purin-6-yl, 4-amino-5-cyanopyrimidin-6-yl, 4-amino-5-formylpyrimidin-6-yl, 4-amino-5-bromopyrimidin-6-yl, 4-amino-5-trifluoromethylpyrimidin-6-yl, 4-amino-5-methylpyrimidin-6-yl, 4-amino-5-(N-methtylcarbamoyl)pyrimidin-6-yl, 4-amino-5-carbamoylpyrimidin-6-yl, 4-amino-5-carboxypyrimidin-6-yl, 2-amino-3-pyrazinyl, 4-amino-5-hydroxymethylpyrimidin-6-yl, 4-amino-5-(4-morpholinomethyl)pyrimidin-6-yl, 4-amino-5-(hydroxyiminomethyl)pyrimidin-6-yl, 4-amino-5-(3-hydroxypropyn-1-yl)pyrimidin-6-yl, 4-amino-3-(3-fluoro-5-methoxyphenyl)-1H-pyrazolo[3,4-d]pyrimidin-1-yl, 4-amino-3-(3-acetylaminophenyl)-1H-pyrazolo[3,4-d]pyrimidin-1-yl, 4-amino-3-(3-hydroxymethylphenyl)-1H-pyrazolo[3,4-d]pyrimidin-1-yl, 4-amino-3-(5-hydroxy-3-trifluoromethylphenyl)-1H-pyrazolo[3,4-d]pyrimidin-1-yl, 4-amino-3-(3-fluorophenyl)-1H-pyrazolo[3,4-d]pyrimidin-1-yl, 4-amino-3-(3-methanesulphonylaminophenyl)-1H-pyrazolo[3,4-d]pyrimidin-1-yl, 4-amino-3-(3-pyridyl)-1H-pyrazolo[3,4-d]pyrimidin-1-yl, 4-amino-3-(5-hydroxy-3-pyridyl)-1H-pyrazolo[3,4-d]pyrimidin-1-yl, 4-amino-3-(3-fluoro-4-hydroxyphenyl)-1H-pyrazolo[3,4-d]pyrimidin-1-yl, 4-amino-3-(4-fluoro-3-hydroxyphenyl)-1H-pyrazolo[3,4-d]pyrimidin-1-yl, 4-amino-3-(3-chloro-5-hydroxyphenyl)-1H-pyrazolo[3,4-d]pyrimidin-1-yl, 4-amino-3-(3-aminosulphonylphenyl)-1H-pyrazolo[3,4-d]pyrimidin-1-yl, 4-amino-3-(3-sulphonylamino-5-fluorophenyl)-1H-pyrazolo[3,4-d]pyrimidin-1-yl, 4-amino-3-(3-aminosulphonyl-5-fluorophenyl)-1H-pyrazolo[3,4-d]pyrimidin-1-yl, 4-amino-3-(3-amino-5-fluorophenyl)-1H-pyrazolo[3,4-d]pyrimidin-1-yl, 4-amino-3-(3-cyano-5-hydroxyphenyl)-1H-pyrazolo[3,4-d]pyrimidin-1-yl, 4-amino-3-(3-fluoro-5-(1H-1,2,3,4-tetrazol-5-yl)phenyl)-1H-pyrazolo[3,4-d]pyrimidin-1-yl, 4-amino-3-(3-fluoro-5-hydroxyphenyl)-1H-pyrazolo[3,4-d]pyrimidin-1-yl, 4-amino-3-(3-hydroxypropyn-1-yl)-1H-pyrazolo[3,4-d]pyrimidin-1-yl, or 4-amino-3-(2-aminothiazol-5-yl)-1H-pyrazolo[3,4-d]pyrimidin-1-yl.

m is 1;

n is 1;

p is 0 or 1; and

Z is absent or is —NH— or —NHC(O)—.

8. A compound or pharmaceutically acceptable salt according to claim 7, wherein:
R is methyl, trifluoromethyl, or halogen selected from the group consisting of fluoro, chloro and bromo;
$R_1$ is hydrogen, 3-pent-1-yn-1-yl, 3-dimethylaminoprop-1-yn-1-yl, 3-hydroxyprop-1-yn-1-yl, phenyl, heteroaryl selected from the group consisting of pyridyl, pyrazinyl, thienyl and thiazolyl, 3,6-dihydro-2H-pyran-4-yl, 1,2,3,6-tetrahydropyridin-4-yl, pyrrolidin-1-yl-2-one, 4-methylpiperazin-1-yl-2-one, 4-morpholinomethyl, 2-methyl-2,9-diazaspiro[5.5]undecan-9-ylmethyl, 9-methyl-3,9-diazaspiro[5.5]undecan-3-yl}methyl, 7-methyl-2,7-diazaspiro[3.5]nonan-2-yl}methyl, and 5-methyl-octahydropyrrolo[3,4-c]pyrrol-2-yl]methyl, wherein each phenyl and heteroaryl may be optionally substituted by one or two groups independently selected from the group consisting of chlorine, fluorine, cyano, methyl, 4-morpholinocarbonyl, 1-methylpyrrolidin-1-yl, dimenthlamino, 2-dimethylaminomethyl, N,N-bis(2-hydroxyethyl)amino, 4-morpholinomethyl, 2-(4-morpholino)ethyl, 1-pyrrolidinomethyl, (4-methylpiperazin-1-yl)methyl, 1-methylpiperidin-4-yl-oxyl, 2-(4-methylpiperazin-1yl)ethoxyl, 2-(4-morpholino)ethoxyl, 2-dimethylaminoethoxyl and 2-(1-methylpiperidin-4-yl)ethoxyl;
R$_2$ is hydrogen, cyano, trifluoromethyl, phenyl which is optionally substituted by fluoro or methyl, or pyridinyl;
R$_3$ is H, methyl, or ethyl;
R$_4$ is H;
Cy is 9H-purine-6-amine-9-yl, 3H-purine-6-amine-3-yl, 9H-purin-6-yl, 4-amino-5-cyanopyrimidin-6-yl, 4-amino-5-formylpyrimidin-6-yl, 4-amino-5-bromopyrimidin-6-yl, 4-amino-5-trifluoromethylpyrimidin-6-yl, 4-amino-5-methylpyrimidin-6-yl, 4-amino-5-(N-methtylcarbamoyl)pyrimidin-6-yl, 4-amino-5-carbamoylpyrimidin-6-yl, 4-amino-5-carboxypyrimidin-6-yl, 2-amino-3-pyrazinyl, 4-amino-5-hydroxymethylpyrimidin-6-yl, 4-amino-5-(4-morpholinomethyl)pyrimidin-6-yl, 4-amino-5-(hydroxyiminomethyl)pyrimidin-6-yl, 4-amino-5-(3-hydroxypropyn-1-yl)pyrimidin-6-yl, 4-amino-3-(3-fluoro-5-methoxyphenyl)-1H-pyrazolo[3,4-d]pyrimidin-1-yl, 4-amino-3-(3-acetylaminophenyl)-1H-pyrazolo[3,4-d]pyrimidin-1-yl, 4-amino-3-(3-hydroxymethylphenyl)-1H-pyrazolo[3,4-d]pyrimidin-1-yl, 4-amino-3-(5-hydroxy-3-trifluoromethylphenyl)-1H-pyrazolo[3,4-d]pyrimidin-1-yl, 4-amino-3-(3-fluorophenyl)-1H-pyrazolo[3,4-d]pyrimidin-1-yl, 4-amino-3-(3-methanesulphonylaminophenyl)-1H-pyrazolo[3,4-d]pyrimidin-1-yl, 4-amino-3-(3-pyridyl)-1H-pyrazolo[3,4-d]pyrimidin-1-yl, 4-amino-3-(5-hydroxy-3-pyridyl)-1H-pyrazolo[3,4-d]pyrimidin-1-yl, 4-amino-3-(3-fluoro-4-hydroxyphenyl)-1H-pyrazolo[3,4-d]pyrimidin-1-yl, 4-amino-3-(4-fluoro-3-hydroxyphenyl)-1H-pyrazolo[3,4-d]pyrimidin-1-yl, 4-amino-3-(3-chloro-5-hydroxyphenyl)-1H-pyrazolo[3,4-d]pyrimidin-1-yl, 4-amino-3-(3-aminosulphonylphenyl)-1H-pyrazolo[3,4-d]pyrimidin-1-yl, 4-amino-3-(3-sulphonylamino-5-fluorophenyl)-1H-pyrazolo[3,4-d]pyrimidin-1-yl, 4-amino-3-(3-aminosulphonyl-5-fluorophenyl)-1H-pyrazolo[3,4-d]pyrimidin-1-yl, 4-amino-3-(3-amino-5-fluorophenyl)-1H-pyrazolo[3,4-d]pyrimidin-1-yl, 4-amino-3-(3-cyano-5-hydroxyphenyl)-1H-pyrazolo[3,4-d]pyrimidin-1-yl, 4-amino-3-(3-fluoro-5-(1H-1,2,3,4-tetrazol-5-yl)phenyl)-1H-pyrazolo[3,4-d]pyrimidin-1-yl, 4-amino-3-(3-fluoro-5-hydroxyphenyl)-1H-pyrazolo[3,4-d]pyrimidin-1-yl, 4-amino-3-(3-hydroxypropyn-1-yl)-1H-pyrazolo[3,4-d]pyrimidin-1-yl, or 4-amino-3-(2-aminothiazol-5-yl)-1H-pyrazolo[3,4-d]pyrimidin-1-yl.
m is 1;
n is 1;
p is 0 or 1; and
Z is absent or is —NH— or —NHC(O)—.

9. A compound, which is selected from the group consisting of:
9-[(3-phenylindolizin-2-yl)methyl]-9H-purin-6-amine,
3-[(3-phenylindolizin-2-yl)methyl]-3H-purin-6-amine,
9-{[3-(pyridin-2-yl)indolizin-2-yl]methyl}-9H-purin-6-amine,
9-{[3-(3-fluorophenyl)indolizin-2-yl]methyl}-9H-purin-6-amine,
3-{[3-(3-fluorophenyl)indolizin-2-yl]methyl}-3H-purin-6-amine,
9-{[3-(2-fluorophenyl)indolizin-2-yl]methyl}-9H-purin-6-amine,
9-{[3-(2-methylphenyl)indolizin-2-yl]methyl}-9H-purin-6-amine,
3-{[3-(2-methylphenyl)indolizin-2-yl]methyl}-3H-purin-6-amine,
9-(indolizin-2-ylmethyl)-9H-purin-6-amine,
9-[(1-phenylindolizin-2-yl)methyl]-9H-purin-6-amine,
9-{[1-(3-fluorophenyl)indolizin-2-yl]methyl}-9H-purin-6-amine,
9-{[1-(2-methylphenyl)indolizin-2-yl]methyl}-9H-purin-6-amine,
N-[(3-phenylindolizin-2-yl)methyl]-9H-purin-6-amine,
N-{[3-(pyridin-2-yl)indolizin-2-yl]methyl}-9H-purin-6-amine,
N-{[3-(3-fluorophenyl)indolizin-2-yl]methyl}-9H-purin-6-amine,
N-{[3-(2-fluorophenyl)indolizin-2-yl]methyl}-9H-purin-6-amine,
N-[(1-phenylindolizin-2-yl)methyl]-9H-purin-6-amine,
N-{[1-(3-fluorophenyl)indolizin-2-yl]methyl}-9H-purin-6-amine,
N-{[1-(2-methylphenyl)indolizin-2-yl]methyl}-9H-purin-6-amine,
N-{[1-(pyridin-2-yl)indolizin-2-yl]methyl}-9H-purin-6-amine,
N-(indolizin-2-ylmethyl)-9H-purin-6-amine,
4-amino-6-{[(3-phenylindolizin-2-yl)methyl]amino}pyrimidine-5-carbonitrile,
4-amino-6-({[3-(pyridin-2-yl)indolizin-2-yl]methyl}amino)pyrimidine-5-carbonitrile,
4-amino-6-({[3-(3-fluorophenyl)indolizin-2-yl]methyl}amino)pyrimidine-5-carbonitrile,
4-amino-6-({[3-(2-fluorophenyl)indolizin-2-yl]methyl}amino)pyrimidine-5-carbonitrile,
4-amino-6-({[3-(2-methylphenyl)indolizin-2-yl]methyl}amino)pyrimidine-5-carbonitrile,
4-amino-6-{[(1-phenylindolizin-2-yl)methyl]amino}pyrimidine-5-carbonitrile,
4-amino-6-({[1-(3-fluorophenyl)indolizin-2-yl]methyl}amino)pyrimidine-5-carbonitrile,
4-amino-6-({[1-(2-methylphenyl)indolizin-2-yl]methyl}amino)pyrimidine-5-carbonitrile,
4-amino-6-({[1-(pyridin-2-yl)indolizin-2-yl]methyl}amino)pyrimidine-5-carbonitrile,
4-amino-6-[(indolizin-2-ylmethyl)amino]pyrimidine-5-carbonitrile,
4-amino-6-{[1-(3-phenylindolizin-2-yl)ethyl]amino}pyrimidine-5-carbonitrile,
4-amino-6-({1-[3-(pyridin-2-yl)indolizin-2-yl]ethyl}amino)pyrimidine-5-carbonitrile,
4-amino-6-({1-[3-(pyridin-3-yl)indolizin-2-yl]ethyl}amino)pyrimidine-5-carbonitrile,
4-amino-6-({1-[3-(pyrazin-2-yl)indolizin-2-yl]ethyl}amino)pyrimidine-5-carbonitrile,
4-amino-6-({1-[3-(pyridin-4-yl)indolizin-2-yl]ethyl}amino)pyrimidine-5-carbonitrile,
4-amino-6-({1-[3-(thiophen-2-yl)indolizin-2-yl]ethyl}amino)pyrimidine-5-carbonitrile,
4-amino-6-({1-[3-(thiophen-3-yl)indolizin-2-yl]ethyl}amino)pyrimidine-5-carbonitrile,
4-amino-6-({1-[8-fluoro-3-(pyridin-2-yl)indolizin-2-yl]ethyl}amino)pyrimidine-5-carbonitrile,
4-amino-6-({1-[5-methyl-3-(pyridin-2-yl)indolizin-2-yl]ethyl}amino)pyrimidine-5-carbonitrile,
4-amino-6-({1-[8-methyl-3-(pyridin-2-yl)indolizin-2-yl]ethyl}amino)pyrimidine-5-carbonitrile,
4-amino-6-({1-[3-(3,6-dihydro-2H-pyran-4-yl)indolizin-2-yl]ethyl}amino)pyrimidine-5-carbonitrile,
4-amino-6-({1-[3-(pent-1-yn-1-yl)indolizin-2-yl]ethyl}amino)pyrimidine-5-carbonitrile,
4-amino-6-({1-[3-(pyridin-2-yl)indolizin-2-yl]propyl}amino)pyrimidine-5-carbonitrile, 4-amino-6-({1-[3-(1,2,3,6-tetrahydropyridin-4-yl)indolizin-2-yl]ethyl}amino)pyrimidine-5-carbonitrile,
4-amino-6-({1-[3-(3-hydroxyprop-1-yn-1-yl)indolizin-2-yl]ethyl}amino)pyrimidine-5-carbonitrile,
4-amino-6-({1-[3-(pyridin-2-yl)indolizin-2-yl]ethyl}amino)pyrimidine-5-carbaldehyde,
5-bromo-4-N-{1-[3-(pyridin-2-yl)indolizin-2-yl]ethyl}pyrimidine-4,6-diamine,
4-N-{1-[3-(pyridin-2-yl)indolizin-2-yl]ethyl}-5-(trifluoromethyl)pyrimidine-4,6-diamine,
5-methyl-4-N-{1-[3-(pyridin-2-yl)indolizin-2-yl]ethyl}pyrimidine-4,6-diamine,
4-amino-N-methyl-6-({1-[3-(pyridin-2-yl)indolizin-2-yl]ethyl}amino)pyrimidine-5-carboxamide,
4-amino-6-({1-[3-(pyridin-2-yl)indolizin-2-yl]ethyl}amino)pyrimidine-5-carboxamide,
4-amino-6-({1-[3-(pyridin-2-yl)indolizin-2-yl]ethyl}amino)pyrimidine-5-carboxylic acid,
3-amino-N-{1-[3-(pyridin-2-yl)indolizin-2-yl]ethyl}pyrazine-2-carboxamide,
3-amino-N-{[1-(pyridin-2-yl)indolizin-2-yl]methyl}pyrazine-2-carboxamide,
[4-amino-6-({1-[3-(pyridin-2-yl)indolizin-2-yl]ethyl}amino)pyrimidin-5-yl]methanol,
5-(morpholin-4-ylmethyl)-4-N-{1-[3-(pyridin-2-yl)indolizin-2-yl]ethyl}pyrimidine-4,6-diamine,
5-[(1E)-(hydroxyimino)methyl]-4-N-{1-[3-(pyridin-2-yl)indolizin-2-yl]ethyl}pyrimidine-4,6-diamine,
3-[4-amino-6-({1-[3-(pyridin-2-yl)indolizin-2-yl]ethyl}amino)pyrimidin-5-yl]prop-2-yn-1-ol,
3-phenyl-1-{1-[3-(pyridin-2-yl)indolizin-2-yl]ethyl}-1H-pyrazolo[3,4-d]pyrimidin-4-amine,
3-(4-amino-1-{1-[3-(pyridin-2-yl)indolizin-2-yl]ethyl}-1H-pyrazolo[3,4-d]pyrimidin-3-yl)phenol,
3-(3-fluoro-5-methoxyphenyl)-1-{1-[3-(pyridin-2-yl)indolizin-2-yl]ethyl}-1H-pyrazolo[3,4-d]pyrimidin-4-amine,
N-[3-(4-amino-1-{1-[3-(pyridin-2-yl)indolizin-2-yl]ethyl}-1H-pyrazolo[3,4-d]pyrimidin-3-yl)phenyl]acetamide,
[3-(4-amino-1-{1-[3-(pyridin-2-yl)indolizin-2-yl]ethyl}-1H-pyrazolo[3,4-d]pyrimidin-3-yl)phenyl]methanol,
3-(4-amino-1-{1-[3-(pyridin-2-yl)indolizin-2-yl]ethyl}-1H-pyrazolo[3,4-d]pyrimidin-3-yl)-5-(trifluoromethyl)phenol,
3-(3-fluorophenyl)-1-{1-[3-(pyridin-2-yl)indolizin-2-yl]ethyl}-1H-pyrazolo[3,4-d]pyrimidin-4-amine,
N-[3-(4-amino-1-{1-[3-(pyridin-2-yl)indolizin-2-yl]ethyl}-1H-pyrazolo[3,4-d]pyrimidin-3-yl)phenyl]methanesulfonamide,
1-{1-[3-(pyridin-2-yl)indolizin-2-yl]ethyl}-3-(pyridin-3-yl)-1H-pyrazolo[3,4-d]pyrimidin-4-amine,
5-(4-amino-1-{1-[3-(pyridin-2-yl)indolizin-2-yl]ethyl}-1H-pyrazolo[3,4-d]pyrimidin-3-yl)pyridin-3-ol,
4-(4-amino-1-{1-[3-(pyridin-2-yl)indolizin-2-yl]ethyl}-1H-pyrazolo[3,4-d]pyrimidin-3-yl)-2-fluorophenol,
5-(4-amino-1-{1-[3-(pyridin-2-yl)indolizin-2-yl]ethyl}-1H-pyrazolo[3,4-d]pyrimidin-3-yl)-2-fluorophenol,
3-(4-amino-1-{1-[3-(pyridin-2-yl)indolizin-2-yl]ethyl}-1H-pyrazolo[3,4-d]pyrimidin-3-yl)-5-chlorophenol,
3-(4-amino-1-{1-[3-(pyridin-2-yl)indolizin-2-yl]ethyl}-1H-pyrazolo[3,4-d]pyrimidin-3-yl)benzene-1-sulfonamide,
N-[3-(4-amino-1-{1-[3-(pyridin-2-yl)indolizin-2-yl]ethyl}-1H-pyrazolo[3,4-d]pyrimidin-3-yl)-5-fluorophenyl]methanesulfonamide,
3-(4-amino-1-{1-[3-(pyridin-2-yl)indolizin-2-yl]ethyl}-1H-pyrazolo[3,4-d]pyrimidin-3-yl)-5-fluorobenzene-1-sulfonamide,
3-(3-amino-5-fluorophenyl)-1-{1-[3-(pyridin-2-yl)indolizin-2-yl]ethyl}-1H-pyrazolo[3,4-d]pyrimidin-4-amine,
3-(4-amino-1-{1-[3-(pyridin-2-yl)indolizin-2-yl]ethyl}-1H-pyrazolo[3,4-d]pyrimidin-3-yl)-5-hydroxybenzonitrile,
3-[3-fluoro-5-(1H-1,2,3,4-tetrazol-5-yl)phenyl]-1-{1-[3-(pyridin-2-yl)indolizin-2-yl]ethyl}-1H-pyrazolo[3,4-d]pyrimidin-4-amine,
3-(4-amino-1-{1-[3-(pyridin-2-yl)indolizin-2-yl]ethyl}-1H-pyrazolo[3,4-d]pyrimidin-3-yl)-5-fluorophenol,
3-(4-amino-1-{1-[3-(pyridin-2-yl)indolizin-2-yl]ethyl}-1H-pyrazolo[3,4-d]pyrimidin-3-yl)-5-fluorophenol enantiomer 1,
3-(4-amino-1-{1-[3-(pyridin-2-yl)indolizin-2-yl]ethyl}-1H-pyrazolo[3,4-d]pyrimidin-3-yl)-5-fluorophenol enantiomer 2,
3-(4-amino-1-{1-[3-(pyridin-4-yl)indolizin-2-yl]ethyl}-1H-pyrazolo[3,4-d]pyrimidin-3-yl)-5-fluorophenol,
3-{4-amino-1-[1-(3-phenylindolizin-2-yl)ethyl]-1H-pyrazolo[3,4-d]pyrimidin-3-yl}-5-fluorophenol,
3-(4-amino-1-{1-[3-(2-fluorophenyl)indolizin-2-yl]ethyl}-1H-pyrazolo[3,4-d]pyrimidin-3-yl)-5-fluorophenol,
3-(4-amino-1-{1-[6-methyl-3-(pyridin-2-yl)indolizin-2-yl]ethyl}-1H-pyrazolo[3,4-d]pyrimidin-3-yl)-5-fluorophenol,
3-(4-amino-1-{1-[3-(pyridin-2-yl)-6-(trifluoromethyl)indolizin-2-yl]ethyl}-1H-pyrazolo[3,4-d]pyrimidin-3-yl)-5-fluorophenol,
3-(4-amino-1-{1-[1-methyl-3-(pyridin-2-yl)indolizin-2-yl]ethyl}-1H-pyrazolo[3,4-d]pyrimidin-3-yl)-5-fluorophenol,
3-[4-amino-1-(1-{3-[5-(morpholin-4-ylmethyl)thiophen-2-yl]indolizin-2-yl}ethyl)-1H-pyrazolo[3,4-d]pyrimidin-3-yl]-5-fluorophenol,
3-[4-amino-1-(1-{3-[4-(morpholin-4-ylmethyl)phenyl]indolizin-2-yl}ethyl)-1H-indazol-3-yl]-5-fluorophenol,
3-[4-amino-1-[1-(3-{4-[(dimethylamino)methyl]phenyl}indolizin-2-yl)ethyl]-1H-pyrazolo[3,4-d]pyrimidin-3-yl]-5-fluorophenol,
3-{4-amino-1-[1-(3-{3-[(dimethylamino)methyl]phenyl}indolizin-2-yl)ethyl]-1H-pyrazolo[3,4-d]pyrimidin-3-yl}-5-fluorophenol,
3-{4-amino-1-[1-(3-{3-[(dimethylamino)methyl]phenyl}indolizin-2-yl)ethyl]-1H-pyrazolo[3,4-d]pyrimidin-3-yl}-5-fluorophenol enantiomer 1,
3-{4-amino-1-[1-(3-{3-[(dimethylamino)methyl]phenyl}indolizin-2-yl)ethyl]-1H-pyrazolo[3,4-d]pyrimidin-3-yl}-5-fluorophenol enantiomer 2,
3-(4-amino-1-{1-[3-(1,3-thiazol-5-yl)indolizin-2-yl]ethyl}-1H-pyrazolo[3,4-d]pyrimidin-3-yl)-5-fluorophenol,
1-(2-{1-[4-amino-3-(3-fluoro-5-hydroxyphenyl)-1H-pyrazolo[3,4-d]pyrimidin-1-yl]ethyl}indolizin-3-yl)pyrrolidin-2-one,
3-(4-amino-1-{1-[7-(pyridin-2-yl)pyrrolo[1,2-b]pyridazin-6-yl]ethyl}-1H-pyrazolo[3,4-d]pyrimidin-3-yl)-5-fluorophenol,
3-(4-amino-1-{[3-(pyridin-2-yl)indolizin-2-yl]methyl}-1H-pyrazolo[3,4-d]pyrimidin-3-yl)-5-fluorophenol,
3-(4-amino-1-{[3-(pyridin-3-yl)indolizin-2-yl]methyl}-1H-pyrazolo[3,4-d]pyrimidin-3-yl)-5-fluorophenol, 3-(4-amino-1-{[3-(pyridin-4-yl)indolizin-2-yl]methyl}-1H-pyrazolo[3,4-d]pyrimidin-3-yl)-5-fluorophenol,
3-(4-amino-1-{[7-(pyridin-2-yl)pyrrolo[1,2-b]pyridazin-6-yl]methyl}-1H-pyrazolo[3,4-d]pyrimidin-3-yl)-5-fluorophenol,
3-(4-amino-1-{1-[3-(1,2,3,6-tetrahydropyridin-4-yl)indolizin-2-yl]ethyl}-1H-pyrazolo[3,4-d]pyrimidin-3-yl)-5-fluorophenol,
3-(4-amino-1-{1-[3-(pyridin-2-yl)indolizin-2-yl]ethyl}-1H-pyrazolo[3,4-d]pyrimidin-3-yl)prop-2-yn-1-ol,
5-(4-amino-1-{1-[3-(pyridin-2-yl)indolizin-2-yl]ethyl}-1H-pyrazolo[3,4-d]pyrimidin-3-yl)-1,3-thiazol-2-amine,
3-(4-amino-1-{1-[7-chloro-3-(pyridin-2-yl)indolizin-2-yl]ethyl}-1H-pyrazolo[3,4-d]pyrimidin-3-yl)-5-fluorophenol,
3-(4-amino-1-{1-[7-methyl-3-(pyridin-2-yl)indolizin-2-yl]ethyl}-1H-pyrazolo[3,4-d]pyrimidin-3-yl)-5-fluorophenol,
3-(4-amino-1-{1-[3-(2-methylpyridin-4-yl)indolizin-2-yl]ethyl}-1H-pyrazolo[3,4-d]pyrimidin-3-yl)-5-fluorophenol,
5-(4-amino-1-{1-[3-(2-methylpyridin-4-yl)indolizin-2-yl]ethyl}-1H-pyrazolo[3,4-d]pyrimidin-3-yl)pyridin-3-ol,
3-[4-amino-1-(1-{3-[5-(morpholin-4-ylmethyl)pyridin-2-yl]indolizin-2-yl}ethyl)-1H-pyrazolo[3,4-d]pyrimidin-3-yl]-5-fluorophenol,
3-[4-amino-1-(1-{3-[5-(morpholin-4-ylmethyl)pyridin-2-yl]indolizin-2-yl}ethyl)-1H-pyrazolo[3,4-d]pyrimidin-3-yl]-5-fluorophenol enantiomer 1,
3-[4-amino-1-(1-{3-[5-(morpholin-4-ylmethyl)pyridin-2-yl]indolizin-2-yl}ethyl)-1H-pyrazolo[3,4-d]pyrimidin-3-yl]-5-fluorophenol enantiomer 2,
3-{4-amino-1-[1-(3-{5-[(dimethylamino)methyl]pyridin-2-yl}indolizin-2-yl)ethyl]-1H-pyrazolo[3,4-d]pyrimidin-3-yl}-5-fluorophenol,
3-[4-amino-1-(1-{3-[6-(morpholin-4-ylmethyl)pyridin-2-yl]indolizin-2-yl}ethyl)-1H-pyrazolo[3,4-d]pyrimidin-3-yl]-5-fluorophenol,
3-[4-amino-1-(1-{3-[4-(morpholin-4-ylmethyl)pyridin-2-yl]indolizin-2-yl}ethyl)-1H-pyrazolo[3,4-d]pyrimidin-3-yl]-5-fluorophenol,
3-{4-amino-1-[1-(3-{4-[(dimethylamino)methyl]pyridin-2-yl}indolizin-2-yl)ethyl]-1H-pyrazolo[3,4-d]pyrimidin-3-yl}-5-fluorophenol,
3-[4-amino-1-(1-{3-[5-(pyrrolidin-1-ylmethyl)pyridin-2-yl]indolizin-2-yl}ethyl)-1H-pyrazolo[3,4-d]pyrimidin-3-yl]-5-fluorophenol,
3-{4-amino-1-[1-(3-{5-[(4-methylpiperazin-1-yl)methyl]pyridin-2-yl}indolizin-2-yl)ethyl]-1H-pyrazolo[3,4-d]pyrimidin-3-yl}-5-fluorophenol,
3-{4-amino-1-[1-(3-{5-[(4-methylpiperazin-1-yl)methyl]pyridin-2-yl}indolizin-2-yl)ethyl]-1H-pyrazolo[3,4-d]pyrimidin-3-yl}-5-fluorophenol enantiomer 1,
3-{4-amino-1-[1-(3-{5-[(4-methylpiperazin-1-yl)methyl]pyridin-2-yl}indolizin-2-yl)ethyl]-1H-pyrazolo[3,4-d]pyrimidin-3-yl}-5-fluorophenol enantiomer 2,
3-{4-amino-1-[1-(3-{6-[(4-methylpiperazin-1-yl)methyl]pyridin-2-yl}indolizin-2-yl)ethyl]-1H-pyrazolo[3,4-d]pyrimidin-3-yl}-5-fluoropyrimidin-3-yl}-5-fluorophenol,
3-{4-amino-1-[1-(3-{4-[(4-methylpiperazin-1-yl)methyl]pyridin-2-yl}indolizin-2-yl)ethyl]-1H-pyrazolo[3,4-d]pyrimidin-3-yl}-5-fluorophenol,
3-(4-amino-1-{1-[3-(5-{[bis(2-hydroxyethyl)amino]methyl}pyridin-2-yl)indolizin-2-yl]ethyl}-1H-pyrazolo[3,4-d]pyrimidin-3-yl)-5-fluorophenol,
3-(4-amino-1-{1-[3-(5-{[bis(2-hydroxyethyl)amino]methyl}pyridin-2-yl)indolizin-2-yl]ethyl}-1H-pyrazolo[3,4-d]pyrimidin-3-yl)-5-fluorophenol enantiomer 1,
3-(4-amino-1-{1-[3-(5-{[bis(2-hydroxyethyl)amino]methyl}pyridin-2-yl)indolizin-2-yl]ethyl}-1H-pyrazolo[3,4-d]pyrimidin-3-yl)-5-fluorophenol enantiomer 2,
3-[4-amino-1-(1-{3-[3-(1-methylpyrrolidin-2-yl)phenyl]indolizin-2-yl}ethyl)-1H-pyrazolo[3,4-d]pyrimidin-3-yl]-5-fluorophenol,
3-{4-amino-1-[1-(3-{5-[2-(morpholin-4-yl)ethoxy]pyridin-2-yl}indolizin-2-yl)ethyl]-1H-pyrazolo[3,4-d]pyrimidin-3-yl}-5-fluorophenol,
5-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one,
4-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one,
4-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one enantiomer 1,
4-(2-{1-[4-amino-3-(3-fluoro-5-hydroxyphenyl)-1H-pyrazolo[3,4-d]pyrimidin-1-yl]ethyl}indolizin-3-yl)-1-[2-(morpholin-4-yl)ethyl]-1,2-dihydropyridin-2-one enantiomer 2,
4-(2-{1-[4-amino-3-(5-hydroxypyridin-3-yl)-1H-pyrazolo[3,4-d]pyrimidin-1-yl]ethyl}indolizin-3-yl)-1-[2-(morpholin-4-yl)ethyl]-1,2-dihydropyridin-2-one;
2-(2-{1-[4-amino-3-(3-fluoro-5-hydroxyphenyl)-1H-pyrazolo[3,4-d]pyrimidin-1-yl]ethyl}indolizin-3-yl)benzonitrile,
3-(4-amino-1-{1-[3-(pyridin-2-yl)-1-(trifluoromethyl)indolizin-2-yl]ethyl}-1H-pyrazolo[3,4-d]pyrimidin-3-yl)-5-fluorophenol,
3-[4-amino-1-(1-{3-[5-(morpholine-4-carbonyl)pyridin-2-yl]indolizin-2-yl}ethyl)-1H-pyrazolo[3,4-d]pyrimidin-3-yl]-5-fluorophenol,
2-{1-[4-amino-3-(3-fluoro-5-hydroxyphenyl)-1H-pyrazolo[3,4-d]pyrimidin-1-yl]ethyl}-3-(pyridin-2-yl)indolizine-1-carbonitrile,
2-{1-[4-amino-3-(3-fluoro-5-hydroxyphenyl)-1H-pyrazolo[3,4-d]pyrimidin-1-yl]ethyl}-3-{3-[(dimethylamino)methyl]phenyl}indolizine-1-carbonitrile,
2-{1-[4-amino-3-(3-fluoro-5-hydroxyphenyl)-1H-pyrazolo[3,4-d]pyrimidin-1-yl]ethyl}-3-{3-[(dimethylamino)methyl]phenyl}indolizine-1-carbonitrile enantiomer 1,
2-{1-[4-amino-3-(3-fluoro-5-hydroxyphenyl)-1H-pyrazolo[3,4-d]pyrimidin-1-yl]ethyl}-3-{3-[(dimethylamino)methyl]phenyl}indolizine-1-carbonitrile enantiomer 2,
3-{4-amino-1-[1-(7-{3-[(dimethylamino)methyl]phenyl}pyrrolo[1,2-b]pyridazin-6-yl)ethyl]-1H-pyrazolo[3,4-d]pyrimidin-3-yl}-5-fluorophenol,
3-(4-amino-1-{1-[3-(1,3-thiazol-4-yl)indolizin-2-yl]ethyl}-1H-pyrazolo[3,4-d]pyrimidin-3-yl)-5-fluorophenol,
3-[4-amino-1-(1-{3-[2-(morpholin-4-ylmethyl)-1,3-thiazol-4-yl]indolizin-2-yl}ethyl)-1H-pyrazolo[3,4-d]pyrimidin-3-yl]-5-fluorophenol,
3-(4-amino-1-(1-{3-[3-(dimethylamino)prop-1-yn-1-yl]indolizin-2-yl}ethyl)-1H-pyrazolo[3,4-d]pyrimidin-3-yl]-5-fluorophenol, 1-(2-{1-[4-amino-3-(3-fluoro-5-hydroxyphenyl)-1H-pyrazolo[3,4-d]pyrimidin-1-yl]ethyl}indolizin-3-yl)-4-methylpiperazin-2-one, 4-(2-{1-[4-amino-3-(3-fluoro-5-hydroxyphenyl)-1H-pyrazolo[3,4-d]pyrimidin-1-yl]ethyl}indolizin-3-yl)-1-[2-(dimethylamino)ethyl]-1,2-dihydropyridin-2-one, 4-(2-{1-[4-amino-3-(3-fluoro-5-hydroxyphenyl)-1H-pyrazolo[3,4-d]pyrimidin-1-yl]ethyl}indolizin-3-yl)-1-[2-(dimethylamino)ethyl]-1,2-dihydropyridin-2-one enantiomer 1, 4-(2-{1-[4-amino-3-(3-fluoro-5-hydroxyphenyl)-1H-pyrazolo[3,4-d]pyrimidin-1-yl]ethyl}indolizin-3-yl)-1-[2-(dimethylamino)ethyl]-1,2-dihydropyridin-2-one enantiomer 2, 6-(2-{1-[4-amino-3-(3-fluoro-5-hydroxyphenyl)-1H-pyrazolo[3,4-d]pyrimidin-1-yl]ethyl}indolizin-3-yl)-2-[2-(pyrrolidin-1-yl)ethyl]-2,3-dihydropyridazin-3-one, 6-(2-{1-[4-amino-3-(3-fluoro-5-hydroxyphenyl)-1H-pyrazolo[3,4-d]pyrimidin-1-yl]ethyl}indolizin-3-yl)-2-[2-(4-methylpiperazin-1-yl)ethyl]-2,3-dihydropyridazin-3-one, 6-(2-{1-[4-amino-3-(3-fluoro-5-hydroxyphenyl)-1H-pyrazolo[3,4-d]pyrimidin-1-yl]ethyl}indolizin-3-yl)-2-[2-(morpholin-4-yl)ethyl]-2,3-dihydropyridazin-3-one, 3-{4-amino-1-[1-(3-{6-[2-(4-methylpiperazin-1-yl)ethoxy]pyridazin-3-yl}indolizin-2-yl)ethyl]-1H-pyrazolo[3,4-d]pyrimidin-3-yl}-5-fluorophenol, 3-{4-amino-1-[1-(3-{6-[2-(dimethylamino)ethoxy]pyridazin-3-yl}indolizin-2-yl)ethyl]-1H-pyrazolo[3,4-d]pyrimidin-3-yl}-5-fluorophenol, 3-{4-amino-1-[1-(3-{6-[(1-methylpiperidin-4-yl)oxy]pyridazin-3-yl}indolizin-2-yl)ethyl]-1H-pyrazolo[3,4-d]pyrimidin-3-yl}-5-fluorophenol, 3-{4-amino-1-[1-(3-{6-[2-(1-methylpiperidin-4-yl)ethoxy]pyridazin-3-yl}indolizin-2-yl)ethyl]-1H-pyrazolo[3,4-d]pyrimidin-3-yl}-5-fluorophenol, 3-(4-amino-1-{1-[3-(morpholin-4-ylmethyl)indolizin-2-yl]ethyl}-1H-pyrazolo[3,4-d]pyrimidin-3-yl)-5-fluorophenol, 3-(4-amino-1-{1-[3-({2-methyl-2,9-diazaspiro[5.5]undecan-9-yl}methyl)indolizin-2-yl]ethyl}-1H-pyrazolo[3,4-d]pyrimidin-3-yl)-5-fluorophenol, 3-(4-amino-1-{1-[3-({9-methyl-3,9-diazaspiro[5.5]undecan-3-yl}methyl)indolizin-2-yl]ethyl}-1H-pyrazolo[3,4-d]pyrimidin-3-yl)-5-fluorophenol, 3-(4-amino-1-{1-[3-({7-methyl-2,7-diazaspiro[3.5]nonan-2-yl}methyl)indolizin-2-yl]ethyl}-1H-pyrazolo[3,4-d]pyrimidin-3-yl)-5-fluorophenol, 3-{1-[1-(3-{[(3aR,6aS)-5-methyl-octahydropyrrolo[3,4-c]pyrrol-2-yl]methyl}indolizin-2-yl)ethyl]-4-amino-1H-pyrazolo[3,4-d]pyrimidin-3-yl}-5-fluorophenol, 2-{1-[4-amino-3-(3-fluoro-5-hydroxyphenyl)-1H-pyrazolo[3,4-d]pyrimidin-1-yl]ethyl}-3-(morpholin-4-ylmethyl)indolizine-1-carbonitrile, 3-{4-amino-1-[1-(3-{1-[2-(dimethylamino)ethyl]-1H-pyrazol-3-yl}indolizin-2-yl)ethyl]-1H-pyrazolo[3,4-d]pyrimidin-3-yl}-5-fluorophenol, 3-{4-amino-1-[1-(3-{1-[2-(4-methylpiperazin-1-yl)ethyl]-1H-pyrazol-3-yl}indolizin-2-yl)ethyl]-1H-pyrazolo[3,4-d]pyrimidin-3-yl}-5-fluorophenol, 3-(4-amino-1-{1-[3-(1-{2-[bis(2-hydroxyethyl)amino]ethyl}-1H-pyrazol-3-yl)indolizin-2-yl]ethyl}-1H-pyrazolo[3,4-d]pyrimidin-3-yl)-5-fluorophenol, and 3-{4-amino-1-[1-(3-{1-[2-(morpholin-4-yl)ethyl]-1H-pyrazol-3-yl}indolizin-2-yl)ethyl]-1H-pyrazolo[3,4-d]pyrimidin-3-yl}-5-fluorophenol, or a pharmaceutically acceptable salt of said compound.

10. A pharmaceutical composition, comprising a compound or pharmaceutically acceptable salt according to claim 1 in admixture with one or more pharmaceutically acceptable carriers or excipients.

11. A pharmaceutical composition according to claim 10, further comprising one or more additional active agents.

12. A method for the treatment of rheumatoid arthritis, comprising administering, to a subject in need thereof, an effective amount of a compound or pharmaceutically acceptable salt according to claim 1.

13. A method for treating asthma, chronic obstructive pulmonary disease, or idiopathic pulmonary fibrosis, comprising administering, to a subject in need thereof, an effective amount of a compound or pharmaceutically acceptable salt according to claim 1.

14. A method for the treatment of rheumatoid arthritis, comprising administering, to a subject in need thereof, an effective amount of a compound or pharmaceutically acceptable salt according to claim 9.

15. A method for treating asthma, chronic obstructive pulmonary disease, or idiopathic pulmonary fibrosis, comprising administering, to a subject in need thereof, an effective amount of a compound or pharmaceutically acceptable salt according to claim 9.

16. A method for treating asthma, comprising administering, to a subject in need thereof, an effective amount of a compound or pharmaceutically acceptable salt according to claim 1.

17. A method for treating asthma, comprising administering, to a subject in need thereof, an effective amount of a compound or pharmaceutically acceptable salt according to claim 9.

18. A method for treating chronic obstructive pulmonary disease, comprising administering, to a subject in need thereof, an effective amount of a compound or pharmaceutically acceptable salt according to claim 1.

19. A method for treating chronic obstructive pulmonary disease, comprising administering, to a subject in need thereof, an effective amount of a compound or pharmaceutically acceptable salt according to claim 9.

20. A method for treating idiopathic pulmonary fibrosis, comprising administering, to a subject in need thereof, an effective amount of a compound or pharmaceutically acceptable salt according to claim 1.

21. A method for treating idiopathic pulmonary fibrosis, comprising administering, to a subject in need thereof, an effective amount of a compound or pharmaceutically acceptable salt according to claim 9.

* * * * *